US007754458B2

(12) United States Patent
Wiesmann et al.

(10) Patent No.: US 7,754,458 B2
(45) Date of Patent: Jul. 13, 2010

(54) CRYSTAL STRUCTURE OF THE COMPLEX OF HEPATOCYTE GROWTH FACTOR BETA CHAIN WITH MET RECEPTOR AND METHODS OF USE

(75) Inventors: Christian Wiesmann, Brisbane, CA (US); Jennifer Stamos, Belmont, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 12/015,993

(22) Filed: Jan. 17, 2008

(65) Prior Publication Data

US 2008/0293923 A1 Nov. 27, 2008

Related U.S. Application Data

(63) Continuation of application No. 11/124,607, filed on May 6, 2005, now abandoned.

(60) Provisional application No. 60/568,865, filed on May 6, 2004.

(51) Int. Cl.
*C12N 9/00* (2006.01)
*G01N 31/00* (2006.01)
(52) U.S. Cl. .......................................... 435/183; 436/4
(58) Field of Classification Search ....................... None
See application file for complete search history.

(56) References Cited

U.S. PATENT DOCUMENTS

| RE30,985 | E | 6/1982 | Cartaya |
| 4,560,655 | A | 12/1985 | Baker |
| 4,767,704 | A | 8/1988 | Cleveland et al. |
| 4,927,762 | A | 5/1990 | Darfler |
| 5,122,469 | A | 6/1992 | Mather et al. |
| 5,849,296 | A | 12/1998 | Navia et al. |
| 5,849,689 | A | 12/1998 | Chamow et al. |
| 5,879,910 | A | 3/1999 | Godowski et al. |
| 6,099,841 | A | 8/2000 | Hillan et al. |
| 6,133,231 | A | 10/2000 | Ferrara et al. |
| 6,207,152 | B1 | 3/2001 | Schwall et al. |
| 6,468,529 | B1 | 10/2002 | Schwall et al. |
| 6,689,595 | B1 | 2/2004 | Benson |
| 6,795,776 | B1 | 9/2004 | Weinmann et al. |
| 2002/0136721 | A1 | 9/2002 | Schwall et al. |
| 2002/0165155 | A1 | 11/2002 | Schaffer et al. |
| 2004/0005686 | A1 | 1/2004 | Kurumbail et al. |
| 2004/0009569 | A1 | 1/2004 | Barford et al. |
| 2006/0003931 | A1 | 1/2006 | Eigenbrot et al. |
| 2006/0069019 | A1 | 3/2006 | Wiesmann et al. |

FOREIGN PATENT DOCUMENTS

| EP | 1 243 596 A2 | 9/2002 |
| EP | 1 243 596 A3 | 9/2002 |
| WO | WO-87/00195 A1 | 1/1987 |
| WO | WO-90/03430 A1 | 4/1990 |
| WO | WO-2005/108424 A1 | 11/2005 |
| WO | WO-2006/001911 A2 | 1/2006 |
| WO | WO-2006/001911 A3 | 1/2006 |

OTHER PUBLICATIONS

Benevenuti et al., Nature Protocols, published on-line Jun. 28, 2007, 2(7):1633-1651.*
Angeloni, D. et al. (2004). "The Soluble Sema Domain of the RON Receptor Inhibits Macrophage-Stimulating Protein-Induced Receptor Activation," *J. Biol. Chem.* 279(5):3726-3732.
Antipenko, A. et al. (2003). "Structure of the Semaphoria-3A Receptor Binding Module," *Neuron* 39:589-598.
Appendix A: Figure of the Overlay of 1SI5 and 1RTF Using .pdb Output Files from DaliLite Created from Swisspdbview v3.7, www.expasy.org/spdbv/_<http://www.expasy.org/spdbv/> (Date Unknown), one page.
Appendix A: Sequence Alignment of NCBI:P14210 (Weidner et al.) against SEQ ID No. 1, <http://us.expasy.org/cgi-bin/sim.pl?prot>, last visited Feb. 15, 2007, four pages and http://www.ncbi.nlm.nih.gov/entrez/viewer.fcgi?db=protein&val=123116>, last visited Feb. 15, 2007, 17 pages.
Appendix B: Sequence Alignment of NCBI:P08581 (Park et al.) against SEQ ID No. 3, <http://us.expasy.org/cgi-bin/sim.pl?prot>, last visited Feb. 15, 2007, five pages and <http://www.ncbi.nlm.nih.gov/entrez/viewer.fcgi?db=protein&val=125484>, last visited Feb. 15, 2007, 18 pages.
Barnes, D. et al. (1980). "Methods for Growth of Cultured Cells in Serum-Free Medium," *Anal. Biochem.* 102:255-270.
Benevenuti, M. et al. (2007, e-pub. Jun. 28, 2007). "Crystallization of Soluble Proteins in Vapor Diffusion for X-Ray Crystallography," *Nature Protocols* 2(7):1633-1651.
Berman, H. et al. (2000). "The Protein Data Bank," *Nucl. Acid Res.* 28:235-242.
Birchmeier, C. et al. (2003). "Met, Metastasis, Motility and More," *Nature Rev. Mol. Cell Biol.* 4:915-925.
Bohm, H. (1992). "The Computer Program LUDI: A Method for the deNovo Design of Enzyme Inhibitors," *J. Computer-Aided Molec. Design* 6:61-78.
Boose, J. et al. (1989). "The Single-Chain Form of Tissue-Type Plasminogen Activator Has Catalytic Activity: Studies with a Mutant Enzyme That Lacks the Cleavage Site," *Biochemistry* 28:635-643.
Bork, P. et al. (1999). "Domains in Plexins: Links to Integrins and Transcription Factors," *Trends Biochem. Sci.* 24:261-263.
Bottaro, D. et al. (1991). "Identification of the Hepatocyte Growth Factor Receptor as the c-Met Proto-Oncogene Product," *Science* 251:802-804.
Broze, Jr. G. (2001). "Protein Z-Dependent Regulation of Coagulation," *Thromb. Haemost.* 86:8-13.
Chan, A. (1991). "Identification of a Competitive HGF Antagonist Encoded by an Alternative Transcript," *Science* 254:1382-1385.
Cioce, V. et al. (1996). "Hepatocyte Growth Factor (HGF)/NK1 is a Naturally Occuring HGF/Scatter Factor Variant with Partial Agonist/Antagonist Activity," *J. Biol. Chem.* 271:13110-13115.

(Continued)

*Primary Examiner*—Suzanne M. Noakes
(74) *Attorney, Agent, or Firm*—Morrison & Foerster LLP

(57) ABSTRACT

The disclosure provides a crystal structure of a complex of the HGF β-chain with am extracellular fragment of the Met receptor, as well as use of the crystal structure in the design, identification, and selection of ligands that modulate the Met Receptor and the interaction of HGF with the Met receptor.

3 Claims, 8 Drawing Sheets

OTHER PUBLICATIONS

Cohen, G. (1997). Align: A Pgrogram to Superimpose Protein Coordinates, Accounting for Insertions and Deletions, *J. Appl. Crystallog.* 30:1160-1161.

Collaborative Computational Project N. (1994). "The CCP4 Suite: Programs for Protein Crystallography," *Acta Cryst.* D50:760-763.

Comoglio, P. (2001). "Scatter Factors and Invasive Growth," *Seminars in Cancer Biology* 11:153-165.

Comoglio, P. et al. (1999). Plasminogen-Related Growth Factor and Semaphorin Receptors: A Gene Superfamily Controlling Invasive Growth, *Experimental Cell Research* 253:88-99.

Congreve, M. et al. (2003). "Detection of Ligands from a Dynamic Combinatorial Library by X-Ray Crystallography," *Angew. Chem. Int. Ed.* 42:4479-4482.

Cooper, C. et al. (1984). "Molecular Cloning of a New Transforming Gene From a Chemically Transformed Human Cell Line," *Nature* 311:29-33.

Cudney, R. (1999). "Protein Crystallization and Dumb Luck," *The Rigaku Journal* 16(1):1-7.

Danilkovitch, A. et al. (1999). "Interaction of Macrophage-Stimulating Protein with its Receptor," *J. Biol. Chem.* 274:22937-29943.

Danilkovitch-Miagkova, A. et al. (2002). "Dysregulation of Met Receptor Tyrosine Kinase Activity in Invasive Tumors," *J. Clin. Invest.* 109:863-867.

Database PDB, XP-002342317, retrieved from EB1, Hinxton, UK, Database Accession No. 1SHY, pp. 1-94. (Feb. 26, 2004).

Database PDB, XP-002342318, retrieved from EB1, Hinxton, UK, Database Accession No. 1UX3, pp. 1-72. (Feb. 18, 2004).

Date, L. et al. (1997). "HGF/NK4 is a Specific Antagonist for Pleiotrophic Actions of Hepatocyte Growth Factor," *FEBS Letters* 520:1-8.

De Vos, A. et al. (1992). "Human Growth Hormone and Extracellular Domain of Its Receptor: Crystal Structure of the Complex," *Science* 255:306-312.

Dennis, M. et al. (2000). "Peptide Exosite Inhibitors of Factor VIIa as Anticoagulants," *Nature* 404:465-470.

Derksen, P. et al. (2002). "Cell Surface Proteoglycan Syndecan-1 Mediates Hepatocyte Growth Factor Binding and Promotes Met Signaling in Multiple Myeloma," *Blood* 99(4):1405-1410.

Di Cera, E. et al. (1995). "The $Na_+$ Binding Site of Thrombin," *J. Biol. Chem.* 270:22089-22092.

Dickinson, C. et al. (1996). "Identification of Surface Residues Mediating Tissue Factor Binding and Catalytic Function of the Serine Protease Factor VIIa," *Proc. Natl. Acad. Sci. USA* 93:14379-14384.

Donate, L.E. et al. (1994). "Molecular Evolution and Domain Structure of Plasminogen-Related Growth Factors (HGF/SF and HGF1/MSP)," *Protein Science* 3(12):2378-2394.

Drain, J. et al. (2001). "Haptoglobin-Related Protein Mediates Trypanosome Lytic Facotr Binding to Trypanosomes," *J. Biol. Chem.* 276:30254-30260.

Drenth, J. (1999). "Crystallizing a Protein," Chapter I *in Principles of Protein X-Ray Crystallography*, Second Edition, Springer-Verlag: New York, NY, pp. 1-21.

EMBL-European Bioinformatics Institute. (Dec. 2004). DaliLite Results for PDB Entries 1SI5 and 1RTF <http://www.ebi.ac.uk/cgi-bin/dalilite/result?tool=dalilite&jobid=dalilite-20070223-12053067 <http://www.ebi.ac.uk/cgi-bin/dalilite/result?tool=dalilite&jobid=dalilite-20070223-12053067>>, last visited Feb. 23, 2007, two pages.

Freer, S. et al. (1970). "Chymotrypsinogen: 2.5-Å Crystal Structure, Comparison with α-Chymotrypsin, and Implications for Zymogen Activation," *Biochemistry* 9(9):1997-2009.

Gherardi, E. et al. (Oct. 14, 2003). "Functional Map and Domain Structure of MET, the Product of the C-Met Protooncogene and Receptor for Hepatocyte Growth Factor/Scatter Factor," *Proc. Natl. Acad. Sci. USA* 100(21):12039-12044.

Giegé, R. et al. (1994). "Crystallogenesis of Biological Macromolecules: Facts and Perspectives," *Acta Cryst. D.* D50:339-350.

Gillet, V. et al. (1993). "Sprout: A Program for Structure Generation," *J. Computer-Aided Mol. Design* 7:127-153.

Goodsell, D. et al. (1990). "Automated Docking of Substrates to Proteins by Simulated Annealing," *Proteins: Structure, Function, and Genetics* 8:195-202.

Ham, R. et al. (1979). "Media and Growth Requirements," *in Methods in Enzymology* 58:44-93.

Hartmann, G. et al. (1992). "A Functional Domain in the Heavy Chain of Scatter Factor/Heptocyte Gwoeth Factor Binds the c-Met Receptor and Induces Cell Dissociation by not Mitogenesis," *Proc. Natl. Acad. Sci. USA* 89:11574-11578.

Hartmann, G. et al. (1998). "Engineered Mutants of HGF/SF with Reduced Binding to Heparan Sulphate Proteoglycans, Decreased Clearance and Enhanced Activity in vivo," *Curr. Biol.* 8:125-134.

Hedstrom, L. (2002). "Serine Protease Mechanism and Specificity," *Chem. Rev.* 102:4501-4523.

Hubbard, S. (1999). "Src Autoinhibition: Let Us Count the Ways," *Nature Struct. Biol.* 6:711-714.

Huber, R. et al. (1978). "Structural Basis of the Activation and Action of Trypsin," *Acc. Chem. Res.* 11:114-122.

Huff, J. et al. (1993). "The Protooncogene c-*sea* Encodes a Transmembrane Protein-Tyrosine Kinase Related to the Met/Hepatocyte Growth Factor/Scatter Factor Receptor," *Proc. Natl. Acad. Sci. USA* 90:6140-6144.

International Search Report mailed Sep. 8, 2005, for PCT Application No. PCT/US2005/016025, filed May 6, 2005, six pages.

International Search Report mailed Jun. 22, 2006, for PCT Application No. PCT/US2005/016039, filed May 6, 2005, five pages.

Jankowski, K. et al. (2003). "Both Hepatocyte Growth Factor (HGF) and Stomal-Derived Factor-1 Regulate the Metastatic Behavior of Human Thabdomyosarcoma Cells, But Only HGF Enhances Their Resistance to Radiochemotherapy," *Cancer Res.* 63:7926-7935.

Jones, T. et al. (1991). "Improved Methods for Building Protein Models in Electron Density Maps and the Location of Errors in These Models," *Acta Cryst.* A47:110-119.

Kataoka, H. et al. (2003). "Roles of Hepatocyte Growth Factor (HGF) Activator and HGF Activator Inhibitor in the Pericellular Activation of HGF/Scatter Factor," *Cancer Metastasis Rev.* 22:223-236.

Kirchhofer, D. et al. (Sep. 17, 2004). "Structural and Functional Basis of the Serine Protease-Like Hepatocyte Growth Factor Beta-Chain in met Binding and Signaling," *Journal of Biological Chemistry* 279(38):39915-39924.

Komada, M. et al. (1993). "Proteolytic Processing of the Hepatocyte Growth Factor/Scatter Factor Receptor by Furin," *FEBS Letters* 328(1.2):25-29.

Kong-Beltran, M. et al. (2004). "The Sema Domain of Met is Necessary for Recpetor Dimerization and Activation," *Cancer Cell* 6:75-84.

Kundrot, C.E. (2004). "Which Strategy for a Protein Crystallization Project?" *Cellular Molecular Life Science* 61:525-536.

Kunkel, T. (1985). "Rapid and Efficient Site-Specific Mutagenesis Without Phenotypic Selection," *Proc. Natl. Acad. Sci. USA* 82:488-492.

Kuntz, I. et al. (1982). "A Geometric Approach to Macromolecule-Ligand Interactions," *J. Mol. Biol.* 161:269-288.

Kurosky, A. et al. (1980). "Covalent Structure of Human Haptoglobin: A Serine Protease Homolog," *Proc. Natl. Acad. Sci. USA* 77:3388-3392.

Lamba, D. et al. (1996). "The 2.3 Å Crystal Structure of the Catalytic Domain of Recombinant Two-Chain Human Tissue-Type Plasminogen Activator," *The Journal of Molecular Biology* 258:117-135.

Laskowski, R. et al. (1993). "Procheck—A Program to Check the Stereochemical Quality of Protein Structures," *J. Appl. Cryst.* 26:283-291.

Lattman, E. (1985). "Use of the Rotation and Translation Functions," *in Methods in Enzymology*, 115:55-77.

Lietha, D. et al. (Oct. 15, 2001). "Crystal Structures of NK1-Heparin Complexes Reveal the Basis for NK1 Activity and Enable Engineering of Potent Agonists of the MET Receptor," *EMBO Journal* 20(20):5543-5555.

Lijnen, H. et al. (1990). "Plasminogen Activation with Single-Chain Urokinase-Type Plasminogen Activator (scu-PA). Studies with Active Site Mutagenized Plasminogen ($Ser^{740} \rightarrow Ala$) and Plasmin-Ressistant scu-PA ($Lys^{158} \rightarrow Glu$)," *J. Biol. Chem.* 265:5232-5236.

Lokker, N. et al. (1992). "Structure-Function Analysis of Hepatocyte Growth Factor: Identification of Variants that Lack Mitogenic Activity yet Retain High Affinity Receptor Binding," *EMBO Journal* 11:2503-2510.

Lokker, N. et al. (1994). "Mutational Analysis and Molecular Modeling of the N-Terminal Kringle-Containing Domain of Hepatocyte Growth Factor Identifies Amino Acid Side Chains Important for Interaction with the c-Met Receptor," *Protein Engr.* 7:895-903.

Love, C.A. et al. (Oct. 2003). "The Ligand-Binding Face of the Semaphorins Revealed by the High-Resolution Crystal Structure of SEMA4D," *Nature Structural Biology* 10(10):843-848.

Ma, P. et al. (2003). "C-Met: Structure, Functions and Potential for Therapeutic Inhibition," *Cancer Metastasis Rev.* 22:309-325.

Malkowski, M. et al. (1997). "The Co-Crystal Structure of Unliganded Bovine α-Thrombin and Prethrombin-2: Movement of the Tyr-Pro-Pro-Trp Segment and Active Site Residues Upon Ligand Binding," *Protein Science* 6:1438-1448.

Mark, M. et al. (1992). "Expression and Characterization of Hepatocyte Growth Factor Receptor-IgG Fusion Proteins. Effects of Mutations in the Potential Proteolytic Cleavage Site on Processing and Ligand Binding," *J. Biol. Chem.* 267:26166-26171.

Mather, J. (1980). "Establishment and Characterization of Two Distinct Mouse Testicular Epithelial Cell Lines," *Biol. Reprod.* 23:243-252.

Matsumoto, K. et al. (1991). "Deletion of Kringle Domains or the N-Terminal Hairpin Structure inHepatocyte Growth Factor Results in Marked Decreases in Related Biological Activities," *Biochemical and Biophysical Research Communications* 181(2):691-699.

Matsumoto, K. et al. (1998). "Cooperative Interaction Between α- and β-chains of Hepatocyte Growth Factor on c-Met Recpetor Confers Ligand-Induced Receptor Tyrosine Phosphorylation and Multiple Biological Response," *J. Biol. Chem.* 273:22913-22920.

Maulik, G. et al. (2002). "Role of the Hepatocyte Growth Factor Receptor, c-Met, in Oncogenesis and Potential for Therapeutic Inhibition," *Cytokine & Growth Factor Rev.* 13:41-59.

McPherson, A. (1990). "Current Approaches to Macromolecular Crystallization," *European Journal of Biochemistry* 189:1-23.

McRee, D. (1999). "XtalView/Xfit—A Versatile Program for Manipulating Atomic Coordinates and Electron Density," *Journal of Structural Biology* 125:156-165.

Meng, E. et al. (1992). "Automated Docking with Grid-Based Energy Evaluation," *J. Comp. Chem.* 13:505-524.

Miller, M. et al. (1998). "Mode of Receptor Binding and Activation by Plasminogen-Related Growth Factors," *FEBS Letters* 429:1-3.

Miranker, A. et al. (1991). "Functionality Maps of Binding Sites: A Multiple Copy Simultaneous Search Method," *Proteins, Structure, Function and Genetics* 11:29-34.

Montesano, R. et al. (1991). "Identification of a Fibroblast-Derived Epithelial Morphogen as Hepatocyte Growth Factor," *Cell* 67:901-908.

Murshudov, G. et al. (1997). "Refinement of Macromolecular Structures by the Maximum-Likelihood Method," *Acta Cryst.* D53:240-255.

Naka, D. et al. (1992). "Activation of Hepatocyte Growth Factor by Proteolytic Conversion of Single Chain Form to a Heterodimer," *J. Biol. Chem.* 267(28):20114-20119.

Nakamura, T. et al. (Nov. 1989). "Molecular Cloning and Expression of Human Hepatocyte Growth Factor," *Nature* 342:440-443.

Naldini, L. et al. (1992). "Extracellular Proteolytic Cleavage by Urokinase is Required for Activation of Hepatocyte Growth Factor/Scatter Factor," *EMBO Journal* 11(13):4825-4833.

Nardone, H. et al. (2003). "c-Met Expression in Tall Cell Variant Papillary Carcinoma of the Thyroid," *Cancer* 98:1386-1393.

Navaza, J. (1994). "AmoRe: An Automated Package for Molecular Replacement," *Acta Cryst.* A50:157-163.

Nicolaou, K. et al. (1994). "Calicheamicin $\theta^1$1: A Rationally Designed Molecule with Extremley Potent and Selective DNA Cleaving Properties and Apoptosis Inducing Activity," *Agnew Chem. Int. Ed. Engl.* 33(2):183-186.

Nienaber, V. et al. (2000). "Discovering Novel Ligands for Macromolecules using X-Ray Crystallographic Screening," *Nat. Biotechnol.* 18:1105-1108.

Nishibata, Y. et al. (1993). "Confirmation of Usefulness of a Structure Construction Program Based on Three-Dimensional Receptor Structure for Rational Lead Generation," *J. Med. Chem.* 36:2921-2928.

Noren, C. et al. (1989). "A General Method for Site-Specific Incorporation of Unnatural Amino Acids into Proteins," *Science* 244:182-188.

Ohta, K. et al. (1995). "Plexin: A Novel Neuronal Cell Surface Molecule That Mediates Cell Adhesion via a Homophilic Binding Mechanism in the Presence of Calcium Ions," *Neuron* 14:1189-1199.

Okigaki, M. et al. (1992). "Functional Characterization of Human Hepatocyte Growth Factor Mutants Obtained by Deletion of Structural Domains," *Biochemistry* 31:9555-9561.

Otwinowski, Z. et al. (1997). "Processing of X-Ray Diffraction Data Collected in Oscillation Mode," *in Methods in Enzymology*, 276:307-326.

Park, M. et al. (Sep. 1987). "Sequence of *MET* Protooncongene cDNA has Features Characteristic of the Tyrosine Kinase Family of Growth-Factor Receptors," *Proc. Natl. Acad. Sci. USA* 84:6379-6383.

Parry, M. et al. (1998). "The Ternary Microplasmin-staphylokinase-microplasmin Complex is a Proteinase-cofactor-substrate Complex in Action," *Nat. Struct. Biol.* 5(10):917-923.

PDB. (Jan. 11, 1997). Structural Coordinates for 1RTF (Lamda et al.) <http://www.rcsb.org/pdb/explore/explore.do?structureid=1RTF>, last visited Mar. 1, 2007, two pages and <http:/www.rcsb.org/pdb/files/1rtf.pdb>, last visited Feb. 23, 2007, 47 pages.

Peek, M. et al. (2002). "Unusual Proteolytic Activation of Pro-hepatocyte Growth Factor by Plasma Kallikrein and Coagulation Factor XIa," *J. Biol. Chem.* 277(49):47804-47809.

Peisach, E. et al. (Aug. 24, 1999). "Crystal Structure of the Proenzyme Domain of Plasminogen," *Biochemistry* 38(34):11180-11188.

Perona, J. et al. (1995). "Structural Basis of Substrate Specificity in the Serine Protease," *Protein Science* 4:337-360.

Prat, M. et al. (1998). "Agonistic Monoclonal Antibodies Against the Met Receptor Dissect the Biological Responses to HGF," *J. Cell Science* 111:237-247.

Rawlings, N. et al. (2002). "MEROPS: The Protease Database," *Nucl. Acid Res.* 30(1):343-346.

Renatus, M. et al. (1997). "Lysine 156 Promotes the Anamalous Proenzyme Activity of tPA: X-ray Crystal Structure of Single-Chain Human tPA," *EMBO Journal* 16(16):4797-4805.

Ronsin, C. et al. (1993). "A Novel Putative Receptor Protein Tyrosine Kinase of the Met Family," *Oncogene* 8:1195-1202.

Rosen, E. et al. (1994). "Scatter Factor and the c-Met Receptor: A Paradigm for Mesenchymal/Epithelial Interation," *J. Cell Biol.* 127(6):1783-1787.

Shuker, S. et al. (1996). "Discovering High-Affinity Ligands for Proteins: SAR by NMR," *Science* 274:1531-1534.

Siebenlist, U. et al. (1980). "*E. coli* RNA Polymerase Interacts Homologously with Two Different Promoters," *Cell* 20:269-281.

Sonnenberg, E. et al. (1993). "Scatter Factor.Hepatocyte Growth Factor and Its Receptor, the c-Met Tyrosine Kinase, Can Mediate a Signal Exchange Between Mesenchyme and Epithelia during Mouse Development," *J. Cell Biol.* 123(1):223-235.

Stamos, J. et al. (Jun. 15, 2004). "The Crystal Structure of HGF Beta-Chain in Complex with the Sema Domain of the Met Receptor," <http://www.ebi.ac.uk/Thornton-srv/Databases/cgi-bin/pdbsum/GetPage.pl?pdbcode=1shy>, (Database Accession No. 1SHY) one page.

Stamos, J. et al. (Jun. 16, 2004). "Crystal Structure of the HGF Beta-Chain in Complex with the Sema Domain of the Met Receptor," *EMBO Journal* 23(12):2325-2335.

Stubbs, M. et al. (1993). "A Player of Many Parts: The Spotlight Falls on Thrombin's Structure," *Thromb. Res.* 69:1-58.

Trusolino, L. et al. (2002). "Scatter-Factor and Semaphorin Receptors: Cell Signaling for Invasive Growth," *Nature Rev. Cancer* 2:289-300.

Tsiang, M. et al. (1995). "Functional Mapping of the Surface Residues of Human Thrombin," *J. Biol. Chem.* 270:16854-16863.

Ultsch, M. et al. (1998). "Crystal Structure of the NK1 Fragment of Human Hepatocyte Growth Factor at 2.0 Å Resolution," *Structure* 15:1383-1393.

Urlaub, G. et al. (1980). "Isolation of Chinese Hamster Cell Mutants Deficient in Dihydrofolate Reductase Activity," *Proc. Natl. Acad. Sci. USA* 77:4216-4220.

Vijayalakshmi, J. et al. (1994). "The Isomorphic Strctures of Prethrombin2, Hirugen-, and PPACK-Thrombin: Changes Accompanying Activation and Exosite Binding to Thrombin," *Protein Science* 3:2254-2271.

Wang, D. et al. (1985). "Bovine Chymotrypsinogen A X-Ray Crystal Structure Analysis and Refinement of a New Crystal Form at 1.8 Å Resolution," *J. Mol. Biol.* 185:595-624.

Wang, M. et al. (1997). "Macrophage Stimulating Protein (MSP) Binds to its Receptor via the MSP β Cahin," *J. Biol. Chem.* 272:16999-17004.

Weidner, K.M. et al. (Aug. 1991). "Evidence for the Identity of Human Scatter Factor and Human Hepatocyte Growth Factor," *Proc. Natl. Acad. Sci. USA* 88:7001-7005.

Winberg, M. et al. (1998). "Plexin A is a Neuronal Semaphorin Receptor that Controls Axon Guidance," *Cell* 95:903-916.

Xiong, J. et al. (2002). "Crystal Strucutre of the Extracellular Segment of Integrin αVβ3 in Complex with an Arg-Gly-Asp Ligand," *Science* 296:151-155.

Zhang, Y. et al. (2003). "HGF/SF-Met Signaling in the Control of Branching Morphogenesis and Invasion," *J. Cell Biochem.* 88:408-417.

* cited by examiner

SEQUENCE LISTING

```
<160> NUMBER OF SEQ ID NOS: 14

<210> SEQ ID NO 1
<211> LENGTH: 234
<212> TYPE: PRT
<213> ORGANISM: Homo sapiens

<400> SEQUENCE: 1

Val Val Asn Gly Ile Pro Thr Arg Thr Asn Ile Gly Trp Met Val Ser
1               5                   10                  15

Leu Arg Tyr Arg Asn Lys His Ile Cys Gly Gly Ser Leu Ile Lys Glu
                20                  25                  30

Ser Trp Val Leu Thr Ala Arg Gln Cys Phe Pro Ser Arg Asp Leu Lys
            35                  40                  45

Asp Tyr Glu Ala Trp Leu Gly Ile His Asp Val His Gly Arg Gly Asp
        50                  55                  60

Glu Lys Cys Lys Gln Val Leu Asn Val Ser Gln Leu Val Tyr Gly Pro
65                  70                  75                  80

Glu Gly Ser Asp Leu Val Leu Met Lys Leu Ala Arg Pro Ala Val Leu
                85                  90                  95

Asp Asp Phe Val Ser Thr Ile Asp Leu Pro Asn Tyr Gly Ser Thr Ile
                100                 105                 110

Pro Glu Lys Thr Ser Cys Ser Val Tyr Gly Trp Gly Tyr Thr Gly Leu
            115                 120                 125

Ile Asn Tyr Asp Gly Leu Leu Arg Val Ala His Leu Tyr Ile Met Gly
        130                 135                 140
```

```
Asn Glu Lys Cys Ser Gln His His Arg Gly Lys Val Thr Leu Asn Glu
145                 150                 155                 160

Ser Glu Ile Cys Ala Gly Ala Glu Lys Ile Gly Ser Gly Pro Cys Glu
            165                 170                 175

Gly Asp Tyr Gly Gly Pro Leu Val Cys Glu Gln His Lys Met Arg Met
                180                 185                 190

Val Leu Gly Val Ile Val Pro Gly Arg Gly Cys Ala Ile Pro Asn Arg
        195                 200                 205

Pro Gly Ile Phe Val Arg Val Ala Tyr Tyr Ala Lys Trp Ile His Lys
    210                 215                 220

Ile Ile Leu Thr Tyr Lys Val Pro Gln Ser
225                 230
```

`<210> SEQ ID NO 2`
`<211> LENGTH: 1390`
`<212> TYPE: PRT`
`<213> ORGANISM: Homo sapiens`

`<400> SEQUENCE: 2`

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
    275                 280                 285
```

```
His Ser Tyr Met Glu Met Pro Leu Glu Cys Ile Leu Thr Glu Lys Arg
    290                 295                 300

Lys Lys Arg Ser Thr Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
                340                 345                 350

Ser Ala Glu Pro Met Asp Arg Ser Ala Met Cys Ala Phe Pro Ile Lys
                355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
                420                 425                 430

Gln Phe Ser Glu Val Leu Leu Thr Ser Ile Ser Thr Phe Ile Lys Gly
                435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
                500                 505                 510

Ile Pro Leu Asn Gly Leu Gly Cys Arg His Phe Gln Ser Cys Ser Gln
    515                 520                 525

Cys Leu Ser Ala Pro Pro Phe Val Gln Cys Gly Trp Cys His Asp Lys
530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
            595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
                675                 680                 685

His Ile Ser Ile Gly Gly Lys Thr Cys Thr Leu Lys Ser Val Ser Asn
    690                 695                 700
```

-continued

```
Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
        755                 760                 765

Ser Val Ser Val Pro Arg Met Val Ile Asn Val His Glu Ala Gly Arg
    770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
        835                 840                 845

Met Ile Ser Met Gly Asn Glu Asn Val Leu Glu Ile Lys Gly Asn Asp
    850                 855                 860

Ile Asp Pro Glu Ala Val Lys Gly Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
        915                 920                 925

Gln Asn Phe Thr Gly Leu Ile Ala Gly Val Val Ser Ile Ser Thr Ala
    930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
                965                 970                 975

Thr Pro His Leu Asp Arg Leu Val Ser Ala Arg Ser Val Ser Pro Thr
            980                 985                 990

Thr Glu Met Val Ser Asn Glu Ser  Val Asp Tyr Arg Ala Thr Phe Pro
        995                 1000                1005

Glu Asp Gln Phe Pro Asn Ser  Ser Gln Asn Gly Ser  Cys Arg Gln
   1010                1015                1020

Val Gln Tyr Pro Leu Thr Asp Met Ser Pro Ile Leu  Thr Ser Gly
   1025               1030                1035

Asp Ser Asp Ile Ser Ser Pro  Leu Leu Gln Asn Thr  Val His Ile
   1040                1045                1050

Asp Leu Ser Ala Leu Asn Pro  Glu Leu Val Gln Ala  Val Gln His
   1055                1060                1065

Val Val Ile Gly Pro Ser Ser  Leu Ile Val His Phe  Asn Glu Val
   1070                1075                1080

Ile Gly Arg Gly His Phe Gly Cys Val Tyr His Gly  Thr Leu Leu
   1085                1090                1095

Asp Asn Asp Gly Lys Lys Ile  His Cys Ala Val Lys  Ser Leu Asn
   1100                1105                1110

Arg Ile Thr Asp Ile Gly Glu  Val Ser Gln Phe Leu  Thr Glu Gly
```

```
                1115                1120                1125

Ile Ile Met Lys Asp Phe Ser His Pro Asn Val Leu Ser Leu Leu
    1130                1135                1140

Gly Ile Cys Leu Arg Ser Glu Gly Ser Pro Leu Val Val Leu Pro
    1145                1150                1155

Tyr Met Lys His Gly Asp Leu Arg Asn Phe Ile Arg Asn Glu Thr
    1160                1165                1170

His Asn Pro Thr Val Lys Asp Leu Ile Gly Phe Gly Leu Gln Val
    1175                1180                1185

Ala Lys Gly Met Lys Tyr Leu Ala Ser Lys Lys Phe Val His Arg
    1190                1195                1200

Asp Leu Ala Ala Arg Asn Cys Met Leu Asp Glu Lys Phe Thr Val
    1205                1210                1215

Lys Val Ala Asp Phe Gly Leu Ala Arg Asp Met Tyr Asp Lys Glu
    1220                1225                1230

Tyr Tyr Ser Val His Asn Lys Thr Gly Ala Lys Leu Pro Val Lys
    1235                1240                1245

Trp Met Ala Leu Glu Ser Leu Gln Thr Gln Lys Phe Thr Thr Lys
    1250                1255                1260

Ser Asp Val Trp Ser Phe Gly Val Val Leu Trp Glu Leu Met Thr
    1265                1270                1275

Arg Gly Ala Pro Pro Tyr Pro Asp Val Asn Thr Phe Asp Ile Thr
    1280                1285                1290

Val Tyr Leu Leu Gln Gly Arg Arg Leu Leu Gln Pro Glu Tyr Cys
    1295                1300                1305

Pro Asp Pro Leu Tyr Glu Val Met Leu Lys Cys Trp His Pro Lys
    1310                1315                1320

Ala Glu Met Arg Pro Ser Phe Ser Glu Leu Val Ser Arg Ile Ser
    1325                1330                1335

Ala Ile Phe Ser Thr Phe Ile Gly Glu His Tyr Val His Val Asn
    1340                1345                1350

Ala Thr Tyr Val Asn Val Lys Cys Val Ala Pro Tyr Pro Ser Leu
    1355                1360                1365

Leu Ser Ser Glu Asp Asn Ala Asp Asp Glu Val Asp Thr Arg Pro
    1370                1375                1380

Ala Ser Phe Trp Glu Thr Ser
    1385                1390

<210> SEQ ID NO 3
<211> LENGTH: 543
<212> TYPE: PRT
<213> ORGANISM: Homo sapiens

<400> SEQUENCE: 3

Glu Cys Lys Glu Ala Leu Ala Lys Ser Glu Met Asn Val Asn Met Lys
1               5                   10                  15

Tyr Gln Leu Pro Asn Phe Thr Ala Glu Thr Pro Ile Gln Asn Val Ile
                20                  25                  30

Leu His Glu His His Ile Phe Leu Gly Ala Thr Asn Tyr Ile Tyr Val
            35                  40                  45

Leu Asn Glu Glu Asp Leu Gln Lys Val Ala Glu Tyr Lys Thr Gly Pro
        50                  55                  60

Val Leu Glu His Pro Asp Cys Phe Pro Cys Gln Asp Cys Ser Ser Lys
65                  70                  75                  80
```

```
Ala Asn Leu Ser Gly Gly Val Trp Lys Asp Asn Ile Asn Met Ala Leu
                85                  90                  95

Val Val Asp Thr Tyr Tyr Asp Asp Gln Leu Ile Ser Cys Gly Ser Val
            100                 105                 110

Asn Arg Gly Thr Cys Gln Arg His Val Phe Pro His Asn His Thr Ala
        115                 120                 125

Asp Ile Gln Ser Glu Val His Cys Ile Phe Ser Pro Gln Ile Glu Glu
    130                 135                 140

Pro Ser Gln Cys Pro Asp Cys Val Val Ser Ala Leu Gly Ala Lys Val
145                 150                 155                 160

Leu Ser Ser Val Lys Asp Arg Phe Ile Asn Phe Val Gly Asn Thr
            165                 170                 175

Ile Asn Ser Ser Tyr Phe Pro Asp His Pro Leu His Ser Ile Ser Val
        180                 185                 190

Arg Arg Leu Lys Glu Thr Lys Asp Gly Phe Met Phe Leu Thr Asp Gln
    195                 200                 205

Ser Tyr Ile Asp Val Leu Pro Glu Phe Arg Asp Ser Tyr Pro Ile Lys
210                 215                 220

Tyr Val His Ala Phe Glu Ser Asn Asn Phe Ile Tyr Phe Leu Thr Val
225                 230                 235                 240

Gln Arg Glu Thr Leu Asp Ala Gln Thr Phe His Thr Arg Ile Ile Arg
            245                 250                 255

Phe Cys Ser Ile Asn Ser Gly Leu His Ser Tyr Met Glu Met Pro Leu
        260                 265                 270

Glu Cys Ile Leu Thr Glu Leu Val Pro Arg Gly Ser Thr Lys Lys Glu
    275                 280                 285

Val Phe Asn Ile Leu Gln Ala Ala Tyr Val Ser Lys Pro Gly Ala Gln
290                 295                 300

Leu Ala Arg Gln Ile Gly Ala Ser Leu Asn Asp Ile Leu Phe Gly
305                 310                 315                 320

Val Phe Ala Gln Ser Lys Pro Asp Ser Ala Glu Pro Met Asp Arg Ser
            325                 330                 335

Ala Met Cys Ala Phe Pro Ile Lys Tyr Val Asn Asp Phe Phe Asn Lys
        340                 345                 350

Ile Val Asn Lys Asn Asn Val Arg Cys Leu Gln His Phe Tyr Gly Pro
    355                 360                 365

Asn His Glu His Cys Phe Asn Arg Thr Leu Leu Arg Asn Ser Ser Gly
370                 375                 380

Cys Glu Ala Arg Arg Asp Glu Tyr Arg Thr Glu Phe Thr Thr Ala Leu
385                 390                 395                 400

Gln Arg Val Asp Leu Phe Met Gly Gln Phe Ser Glu Val Leu Leu Thr
            405                 410                 415

Ser Ile Ser Thr Phe Ile Lys Gly Asp Leu Thr Ile Ala Asn Leu Gly
        420                 425                 430

Thr Ser Glu Gly Arg Phe Met Gln Val Val Ser Arg Ser Gly Pro
    435                 440                 445

Ser Thr Pro His Val Asn Phe Leu Leu Asp Ser His Pro Val Ser Pro
450                 455                 460

Glu Val Ile Val Glu His Thr Leu Asn Gln Asn Gly Tyr Thr Leu Val
465                 470                 475                 480

Ile Thr Gly Lys Lys Ile Thr Lys Ile Pro Leu Asn Gly Leu Gly Cys
            485                 490                 495

Arg His Phe Gln Ser Cys Ser Gln Cys Leu Ser Ala Pro Pro Phe Val
```

-continued

```
                500             505             510
Gln Cys Gly Trp Cys His Asp Lys Cys Val Arg Ser Glu Glu Cys Leu
        515                 520                 525
Ser Gly Thr Trp Thr Gln Gln Ile Cys Leu Pro Ala Ile Tyr Lys
        530                 535                 540

<210> SEQ ID NO 4
<211> LENGTH: 5
<212> TYPE: PRT
<213> ORGANISM: Homo sapiens

<400> SEQUENCE: 4

Lys Arg Lys Lys Arg
1               5

<210> SEQ ID NO 5
<211> LENGTH: 5
<212> TYPE: PRT
<213> ORGANISM: Artificial Sequence
<220> FEATURE:
<223> OTHER INFORMATION: Thrombin cleavable residues 304-308

<400> SEQUENCE: 5

Leu Val Pro Arg Gly
1               5

<210> SEQ ID NO 6
<211> LENGTH: 25
<212> TYPE: DNA
<213> ORGANISM: Artificial Sequence
<220> FEATURE:
<223> OTHER INFORMATION: Oligonucleotide

<400> SEQUENCE: 6
cctaattatg gatccacaat tcctg                                         25

<210> SEQ ID NO 7
<211> LENGTH: 74
<212> TYPE: PRT
<213> ORGANISM: Homo sapiens

<400> SEQUENCE: 7

Val Ile Ser Cys Ala Lys Thr Lys Gln Leu Arg Val Val Asn Gly Leu
1               5                   10                  15
Gly Ile His Asp Val His Gly Arg Gly Asp Glu Lys Cys Lys Gln Val
                20                  25                  30
Leu Asn Val Ser Gln Leu Val Tyr Gly Pro Val Leu Asp Asp Phe Val
            35                  40                  45
Ser Thr Ile Asp Leu Pro Asn Tyr Gly Cys Thr Ile Pro Glu Lys Thr
        50                  55                  60
Ser Cys Ser Val Tyr Gly Trp Gly Tyr Thr
65                  70

<210> SEQ ID NO 8
<211> LENGTH: 84
<212> TYPE: PRT
<213> ORGANISM: Homo sapiens

<400> SEQUENCE: 8

Val Gln Phe Glu Lys Cys Gly Lys Arg Val Asp Arg Leu Asp Gln Arg
1               5                   10                  15
Arg Ser Lys Leu Arg Val Val Gly Gly Leu Gly Thr Leu Phe Gln Asn
```

```
                    20                  25                  30

Pro Gln His Gly Glu Pro Ser Leu Gln Arg Val Pro Val Ala Lys Met
                35                  40                  45

Val Cys Gly Pro Thr Leu Asn Gln Arg Val Ala Leu Ile Cys Leu Pro
 50                  55                  60

Pro Glu Trp Tyr Val Val Pro Pro Gly Thr Lys Cys Glu Ile Ala Gly
 65                  70                  75                  80

Trp Gly Glu Thr

<210> SEQ ID NO 9
<211> LENGTH: 82
<212> TYPE: PRT
<213> ORGANISM: Homo sapiens

<400> SEQUENCE: 9

Val Ser Pro Ser Phe Asp Cys Gly Lys Pro Arg Val Glu Pro Gln
 1               5                  10                  15

Lys Cys Pro Gly Arg Ile Val Gly Gly Leu Gly Leu His Arg Glu Val
                20                  25                  30

Asn Pro Glu Ser Tyr Ser Gln Glu Ile Gly Val Ser Arg Leu Phe Lys
                35                  40                  45

Gly Pro Ala Ile Asn Asp Lys Val Ile Pro Ala Cys Leu Pro Ser Gln
 50                  55                  60

Asp Phe Met Val Pro Arg Thr Leu Cys His Val Thr Gly Trp Gly
 65                  70                  75                  80

Asp Thr

<210> SEQ ID NO 10
<211> LENGTH: 491
<212> TYPE: PRT
<213> ORGANISM: Homo sapiens

<400> SEQUENCE: 10

Glu Cys Lys Glu Ala Leu Ala Lys Ser Glu Met Asn Val Asn Met Lys
 1               5                  10                  15

Tyr Gln Leu Pro Asn Phe Thr Ala Glu Thr Pro Ile Gln Asn Val Ile
                20                  25                  30

Leu His Glu His His Ile Phe Leu Gly Ala Thr Asn Tyr Ile Tyr Val
                35                  40                  45

Leu Asn Glu Glu Asp Leu Gln Lys Val Ala Glu Tyr Lys Thr Gly Pro
 50                  55                  60

Val Leu Glu His Pro Asp Cys Phe Pro Cys Gln Asp Cys Ser Ser Lys
 65                  70                  75                  80

Ala Asn Leu Ser Gly Gly Val Trp Lys Asp Asn Ile Asn Met Ala Leu
                85                  90                  95

Val Val Asp Thr Tyr Tyr Asp Asp Gln Leu Ile Ser Cys Gly Ser Val
                100                 105                 110

Asn Arg Gly Thr Cys Gln Arg His Val Phe Pro His Asn His Thr Ala
                115                 120                 125

Asp Ile Gln Ser Glu Val His Cys Ile Phe Ser Pro Gln Ile Glu Glu
 130                 135                 140

Pro Ser Gln Cys Pro Asp Cys Val Val Ser Ala Leu Gly Ala Lys Val
 145                 150                 155                 160

Leu Ser Ser Val Lys Asp Arg Phe Ile Asn Phe Phe Val Gly Asn Thr
                165                 170                 175
```

-continued

```
Ile Asn Ser Ser Tyr Phe Pro Asp His Pro Leu His Ser Ile Ser Val
            180                 185                 190

Arg Arg Leu Lys Glu Thr Lys Asp Gly Phe Met Phe Leu Thr Asp Gln
        195                 200                 205

Ser Tyr Ile Asp Val Leu Pro Glu Phe Arg Asp Ser Tyr Pro Ile Lys
    210                 215                 220

Tyr Val His Ala Phe Glu Ser Asn Asn Phe Ile Tyr Phe Leu Thr Val
225                 230                 235                 240

Gln Arg Glu Thr Leu Asp Ala Gln Thr Phe His Thr Arg Ile Ile Arg
                245                 250                 255

Phe Cys Ser Ile Asn Ser Gly Leu His Ser Tyr Met Glu Met Pro Leu
            260                 265                 270

Glu Cys Ile Leu Thr Glu Lys Arg Lys Arg Ser Thr Lys Lys Glu
        275                 280                 285

Val Phe Asn Ile Leu Gln Ala Ala Tyr Val Ser Lys Pro Gly Ala Gln
    290                 295                 300

Leu Ala Arg Gln Ile Gly Ala Ser Leu Asn Asp Asp Ile Leu Phe Gly
305                 310                 315                 320

Val Phe Ala Gln Ser Lys Pro Asp Ser Ala Glu Pro Met Asp Arg Ser
                325                 330                 335

Ala Met Cys Ala Phe Pro Ile Lys Tyr Val Asn Asp Phe Phe Asn Lys
            340                 345                 350

Ile Val Asn Lys Asn Asn Val Arg Cys Leu Gln His Phe Tyr Gly Pro
        355                 360                 365

Asn His Glu His Cys Phe Asn Arg Thr Leu Leu Arg Asn Ser Ser Gly
    370                 375                 380

Cys Glu Ala Arg Arg Asp Glu Tyr Arg Thr Glu Phe Thr Thr Ala Leu
385                 390                 395                 400

Gln Arg Val Asp Leu Phe Met Gly Gln Phe Ser Glu Val Leu Leu Thr
                405                 410                 415

Ser Ile Ser Thr Phe Ile Lys Gly Asp Leu Thr Ile Ala Asn Leu Gly
            420                 425                 430

Thr Ser Glu Gly Arg Phe Met Gln Val Val Ser Arg Ser Gly Pro
        435                 440                 445

Ser Thr Pro His Val Asn Phe Leu Leu Asp Ser His Pro Val Ser Pro
    450                 455                 460

Glu Val Ile Val Glu His Thr Leu Asn Gln Asn Gly Tyr Thr Leu Val
465                 470                 475                 480

Ile Thr Gly Lys Lys Ile Thr Lys Ile Pro Leu
                485                 490

<210> SEQ ID NO 11
<211> LENGTH: 477
<212> TYPE: PRT
<213> ORGANISM: Homo sapiens

<400> SEQUENCE: 11

Phe Ala Pro Ile Pro Arg Ile Thr Trp Glu His Arg Glu Val His Leu
1               5                   10                  15

Val Gln Phe His Glu Pro Asp Ile Tyr Asn Tyr Ser Ala Leu Leu Leu
                20                  25                  30

Ser Glu Asp Lys Asp Thr Leu Tyr Ile Gly Ala Arg Glu Ala Val Phe
            35                  40                  45

Ala Val Asn Ala Leu Asn Ile Ser Glu Lys Gln His Glu Val Tyr Trp
        50                  55                  60
```

-continued

```
Lys Val Ser Glu Asp Lys Lys Ala Lys Cys Ala Glu Lys Gly Lys Ser
 65              70              75              80

Lys Gln Thr Glu Cys Leu Asn Tyr Ile Arg Val Leu Gln Pro Leu Ser
             85              90              95

Ala Thr Ser Leu Tyr Val Cys Gly Thr Asn Ala Phe Gln Pro Ala Cys
            100             105             110

Asp His Leu Asn Leu Thr Ser Phe Lys Phe Leu Gly Lys Asn Glu Asp
            115             120             125

Gly Lys Gly Arg Cys Pro Phe Asp Pro Ala His Ser Tyr Thr Ser Val
130             135             140

Met Val Asp Gly Glu Leu Tyr Ser Gly Thr Ser Tyr Asn Phe Leu Gly
145             150             155             160

Ser Glu Pro Ile Ile Ser Arg Asn Ser Ser His Ser Pro Leu Arg Thr
                165             170             175

Glu Tyr Ala Ile Pro Trp Leu Asn Glu Pro Ser Phe Val Phe Ala Asp
            180             185             190

Val Ile Arg Lys Ser Pro Asp Ser Pro Asp Gly Glu Asp Asp Arg Val
            195             200             205

Tyr Phe Phe Phe Thr Glu Val Ser Val Glu Tyr Phe Val Phe Arg Val
            210             215             220

Leu Ile Pro Arg Ile Ala Arg Val Cys Lys Gly Asp Gln Gly Gly Leu
225             230             235             240

Arg Thr Leu Gln Lys Lys Trp Thr Ser Phe Leu Lys Ala Arg Leu Ile
            245             250             255

Cys Ser Arg Pro Asp Ser Gly Leu Val Phe Asn Val Leu Arg Asp Val
            260             265             270

Phe Val Leu Arg Ser Pro Gly Leu Lys Val Pro Val Phe Tyr Ala Leu
            275             280             285

Phe Thr Pro Gln Leu Asn Asn Val Gly Leu Ser Ala Val Cys Ala Tyr
290             295             300

Asn Leu Ser Thr Ala Glu Glu Val Phe Ser His Gly Lys Tyr Met Gln
305             310             315             320

Ser Thr Thr Val Glu Gln Ser His Thr Lys Trp Val Arg Tyr Asn Gly
            325             330             335

Pro Val Pro Lys Pro Arg Pro Gly Ala Cys Ile Asp Ser Glu Ala Arg
            340             345             350

Ala Ala Asn Tyr Thr Ser Ser Leu Asn Leu Pro Asp Lys Thr Leu Gln
            355             360             365

Phe Val Lys Asp His Pro Leu Met Asp Asp Ser Val Thr Pro Ile Asp
370             375             380

Asn Arg Pro Arg Leu Ile Lys Lys Asp Val Asn Tyr Thr Gln Ile Val
385             390             395             400

Val Asp Arg Thr Gln Ala Leu Asp Gly Thr Val Tyr Asp Val Met Phe
            405             410             415

Val Ser Thr Asp Arg Gly Ala Leu His Lys Ala Ile Ser Leu Glu His
            420             425             430

Ala Val His Ile Ile Glu Glu Thr Gln Leu Phe Gln Asp Phe Glu Pro
            435             440             445

Val Gln Gln Thr Leu Leu Ser Ser Lys Lys Gly Asn Arg Phe Val
450             455             460

Tyr Ala Gly Ser Asn Ser Gly Val Val Gln Ala Pro Leu
465             470             475
```

<210> SEQ ID NO 12
<211> LENGTH: 489
<212> TYPE: PRT
<213> ORGANISM: Murine

<400> SEQUENCE: 12

```
Lys Asn Asn Val Pro Arg Leu Lys Leu Ser Tyr Lys Glu Met Leu Glu
1               5                   10                  15

Ser Asn Asn Val Ile Thr Phe Asn Gly Leu Ala Asn Ser Ser Ser Tyr
                20                  25                  30

His Thr Phe Leu Leu Asp Glu Glu Arg Ser Arg Leu Tyr Val Gly Ala
            35                  40                  45

Lys Asp His Ile Phe Ser Phe Asn Leu Val Asn Ile Lys Asp Phe Gln
        50                  55                  60

Lys Ile Val Trp Pro Val Ser Tyr Thr Arg Arg Asp Glu Cys Lys Trp
65                  70                  75                  80

Ala Gly Lys Asp Ile Leu Lys Glu Cys Ala Asn Phe Ile Lys Val Leu
                85                  90                  95

Glu Ala Tyr Asn Gln Thr His Leu Tyr Ala Cys Gly Thr Gly Ala Phe
                100                 105                 110

His Pro Ile Cys Thr Tyr Ile Glu Val Gly His His Pro Glu Asp Asn
            115                 120                 125

Ile Phe Lys Leu Gln Asp Ser His Phe Glu Asn Gly Arg Gly Lys Ser
        130                 135                 140

Pro Tyr Asp Pro Lys Leu Leu Thr Ala Ser Leu Leu Ile Asp Gly Glu
145                 150                 155                 160

Leu Tyr Ser Gly Thr Ala Ala Asp Phe Met Gly Arg Asp Phe Ala Ile
                165                 170                 175

Phe Arg Thr Leu Gly His His Pro Ile Arg Thr Glu Gln His Asp
                180                 185                 190

Ser Arg Trp Leu Asn Asp Pro Arg Phe Ile Ser Ala His Leu Ile Pro
            195                 200                 205

Glu Ser Asp Asn Pro Glu Asp Asp Lys Val Tyr Phe Phe Arg Glu
        210                 215                 220

Asn Ala Ile Asp Gly Glu His Ser Gly Lys Ala Thr His Ala Arg Ile
225                 230                 235                 240

Gly Gln Ile Cys Lys Asn Asp Phe Gly Gly His Arg Ser Leu Val Asn
                245                 250                 255

Lys Trp Thr Thr Phe Leu Lys Ala Arg Leu Ile Cys Ser Val Pro Gly
                260                 265                 270

Pro Asn Gly Ile Asp Thr His Phe Asp Glu Leu Gln Asp Val Phe Leu
            275                 280                 285

Met Asn Ser Lys Asp Pro Lys Asn Pro Ile Val Tyr Gly Val Phe Thr
        290                 295                 300

Thr Ser Ser Asn Ile Phe Lys Gly Ser Ala Val Cys Met Tyr Ser Met
305                 310                 315                 320

Ser Asp Val Arg Arg Val Phe Leu Gly Pro Tyr Ala His Arg Asp Gly
                325                 330                 335

Pro Asn Tyr Gln Trp Val Pro Tyr Gln Gly Arg Val Pro Tyr Pro Arg
                340                 345                 350

Pro Gly Thr Cys Pro Ser Lys Thr Phe Gly Gly Phe Asp Ser Thr Lys
            355                 360                 365

Asp Leu Pro Asp Asp Val Ile Thr Phe Ala Arg Ser His Pro Ala Met
        370                 375                 380
```

```
Tyr Asn Pro Val Phe Pro Ile Asn Asn Arg Pro Ile Met Ile Lys Thr
385                 390                 395                 400

Asp Val Asn Tyr Gln Phe Thr Gln Ile Val Asp Arg Val Asp Ala
            405                 410                 415

Glu Asp Gly Gln Tyr Asp Val Met Phe Ile Gly Thr Asp Val Gly Thr
            420                 425                 430

Val Leu Lys Val Val Ser Val Pro Lys Glu Thr Trp His Asp Leu Glu
            435                 440                 445

Glu Val Leu Leu Glu Glu Met Thr Val Phe Arg Glu Pro Thr Ala Ile
            450                 455                 460

Ser Ala Met Glu Leu Ser Thr Lys Gln Gln Gln Leu Tyr Ile Gly Ser
465                 470                 475                 480

Thr Ala Gly Val Ala Gln Leu Pro Leu
                485

<210> SEQ ID NO 13
<211> LENGTH: 8
<212> TYPE: PRT
<213> ORGANISM: Artificial Sequence
<220> FEATURE:
<223> OTHER INFORMATION: Poly-His8 Tag

<400> SEQUENCE: 13

His His His His His His His His
1               5

<210> SEQ ID NO 14
<211> LENGTH: 234
<212> TYPE: PRT
<213> ORGANISM: Homo sapiens

<400> SEQUENCE: 14

Val Val Asn Gly Ile Pro Thr Arg Thr Asn Ile Gly Trp Met Val Ser
1               5                   10                  15

Leu Arg Tyr Arg Asn Lys His Ile Cys Gly Gly Ser Leu Ile Lys Glu
            20                  25                  30

Ser Trp Val Leu Thr Ala Arg Gln Cys Phe Pro Ser Arg Asp Leu Lys
        35                  40                  45

Asp Tyr Glu Ala Trp Leu Gly Ile His Asp Val His Gly Arg Gly Asp
    50                  55                  60

Glu Lys Cys Lys Gln Val Leu Asn Val Ser Gln Leu Val Tyr Gly Pro
65                  70                  75                  80

Glu Gly Ser Asp Leu Val Leu Met Lys Leu Ala Arg Pro Ala Val Leu
            85                  90                  95

Asp Asp Phe Val Ser Thr Ile Asp Leu Pro Asn Tyr Gly Cys Thr Ile
            100                 105                 110

Pro Glu Lys Thr Ser Cys Ser Val Tyr Gly Trp Gly Tyr Thr Gly Leu
            115                 120                 125

Ile Asn Tyr Asp Gly Leu Leu Arg Val Ala His Leu Tyr Ile Met Gly
    130                 135                 140

Asn Glu Lys Cys Ser Gln His His Arg Gly Lys Val Thr Leu Asn Glu
145                 150                 155                 160

Ser Glu Ile Cys Ala Gly Ala Glu Lys Ile Gly Ser Gly Pro Cys Glu
                165                 170                 175

Gly Asp Tyr Gly Gly Pro Leu Val Cys Glu Gln His Lys Met Arg Met
            180                 185                 190
```

-continued

```
Val Leu Gly Val Ile Val Pro Gly Arg Gly Cys Ala Ile Pro Asn Arg
        195                 200                 205

Pro Gly Ile Phe Val Arg Val Ala Tyr Tyr Ala Lys Trp Ile His Lys
    210                 215                 220

Ile Ile Leu Thr Tyr Lys Val Pro Gln Ser
225                 230
```

CRYSTAL STRUCTURE OF THE COMPLEX OF HEPATOCYTE GROWTH FACTOR BETA CHAIN WITH MET RECEPTOR AND METHODS OF USE

CROSS REFERENCE TO RELATED APPLICATIONS

This application is a continuation application of U.S. patent application Ser. No. 11/124,607, filed May 6, 2005, which claims the benefit under 35 U.S.C. §119(e) to U.S. Provisional Application Ser. No. 60/568,865, filed May 6, 2004, which applications are hereby incorporated by reference in their entirety.

BACKGROUND

The receptor tyrosine kinase Met, and its ligand, hepatocyte growth factor (HGF, also called scatter factor), have been implicated in promoting invasive growth of many tumor types due to inappropriate activation of Met function (Jankowski et al., 2003; Nardone et al., 2003; Trusolino and Comoglio, 2002; Birchmeier et al., 2003). This activation can arise from a variety of sources, but in each case the Met receptor activates signaling cascades that normally function to organize groups of cells into branching, tubular structures that are present in a variety of organs (Montesano et al., 1992; Sonnenberg et al., 1993; Rosen et al., 1994; Trusolino and Comoglio, 2002; Zhang and Vande Woude, 2003). The Met receptor plays a unique role during development as a master switch, which can stimulate proliferation and motility necessary for the full program of growth and scattering of cells. Its role in the invasiveness of many cancers makes it an attractive target for therapeutics (Ma et al., 2003). However, many questions remain about how the ligand, HGF, binds to Met and induces its tyrosine kinase cascade and thus leads to a biological response.

The Met receptor is part of a larger family of growth factor receptors with identical domain architecture that includes the Ron and Sea receptors (Monsin et al., 1992, Huff et al., 1993). The extracellular portions of Met family members are composed of three domain types. The N-terminal 500 residues fold into a Sema domain, which shares sequence homology with domains found in the Semaphorin and plexin families of neural development proteins (Winburg et al., 1998). As reported recently, Sema domains form a 7-bladed β-propeller structure (Antipenkov et al., 2003, Love et al., 2003). Met undergoes proteolytic cleavage within the Sema domain during normal processing, although the role for this remains unclear since cells that are unable to cleave Met show normal levels of Met activation upon ligand binding (Komada et al., 1993). A PSI domain, a small domain spanning about 50 residues and containing 4 disulfide bonds, follows the Sema domain. In addition to the Met receptor family, PSI domains are also found in the plexins, Semaphorins and integrins, hence its name (Bork et al., 1999). In Met, the PSI domain is connected via 4 IPT domains to the transmembrane helix and the kinase domain in the intracellular portion of the receptor. IPT domains are related to immunoglobulin-like domains and are named after their presence in plexins and transcription factors (Takagi et al., 1995).

HGF is a large growth factor of 728 residues that is produced as an inactive single-chain precursor which is proteolytically processed to form the biologically active disulfide-linked α/β-heterodimer (Nakamura et al., 1989; Hartmann et al., 1992; Kataoka et al., 2003). The α-chain folds into an N-terminal domain (N-domain) followed by 4 Kringle domains. The β-chain starts with residue Val495 and is homologous to the protease domain of chymotrypsin like serine proteases, which, like HGF, are activated by a proteolytic cleavage event (Perona and Craig, 1995; Hedstrom 2002). However, no protease activity has been demonstrated for HGF β-chain (Lokker et al., 1992) consistent with the absence of the key serine and histidine residues that are part of the 'catalytic triad' Asp[c102]-His[c57]-Ser[c195] ([chymotrypsinogen numbering]) required for catalytic activity in serine proteases.

Comparisons of the biologically active, two-chain HGF, and the inactive single-chain HGF precursor on the Met receptor have shown that both forms of HGF bind Met with similar affinity, but only the cleaved, mature form of HGF is able to activate Met (Lokker et al., 1992). In addition, various C-terminally truncated fragments of the α-chain (termed NK1, NK2, or NK4 depending on the number of Kringle domains retained) bind Met; in many cases they act as potent antagonists of Met receptor function (Cioce et al., 1996; Chan et al., 1991; Date et al., 1997). Studies involving the cross-linking of Met receptors by a variety of specific antibodies to its extracellular domain have demonstrated that simple dimerization of Met is sufficient for activation (Prat et al., 1998). Based on these characteristics, the fundamental mechanism for Met dimerization remains unclear.

Currently, there is no detailed structural information about HGF β-chain complexed with Met receptor. A completely solved crystal structure of the HGF β-chain complexed with Met receptor is needed, for example, for assays for Met-ligand (e.g., HGF β-chain) interaction and function, modeling the structure-function relationship of Met and other molecules, diagnostic assays for mutation-induced pathologies, and rational design of agents useful in modulating Met or HGF activity or activation.

SUMMARY

In some embodiments, the present disclosure provides a crystalline form of hepatocyte growth factor beta chain (HGF β) complexed with Met receptor, and the structural coordinates of the crystal. Coordinates of a crystal structure solved by molecular replacement are listed in Table 2. In some embodiments, HGF β comprises an amino acid sequence of SEQ ID NO:1 or conservative substitutions thereof and the Met receptor comprises an amino acid sequence of SEQ ID NO:3 or conservative substitutions thereof.

In some embodiments, the disclosure provides a crystal structure of HGF β complexed with Met receptor, as well as use of the crystal structure to model Met receptor activity when complexed with HGF β. This use of the structure includes: modeling the interaction of ligands with the Met receptor; activation and inhibition of Met receptor; and the rational design of modulators of Met receptor activity. For example, these modulators include ligands that interact with Met receptor and modulate Met receptor activities, such as cell migration, HGF β binding to Met, and Met phosphorylation and signaling.

In other embodiments, the amino acid residues that form the binding site for the Met receptor on HGF β are identified and are useful, for example, in methods to model the structure of HGF binding site and to identify agents that can bind or fit into the binding site. In addition, the amino acid positions that form the binding site for HGF β on Met have been identified and are useful, for example, in methods to model the structure of the Met ligand binding site and to identify other agents that can bind or fit into the binding site.

BRIEF DESCRIPTION OF FIGURES

FIGS. 2A and 2B show ribbon representations with HGF β-chain.

FIG. 2A provides a view onto the 'top' side of the propeller. The numbers in the center refer to the blades. The β-strands in blade 1 are labeled A, B, C, and D. Disordered residues in the represented model are indicated with dotted lines and the dotted line associated numbers refer to the last and first amino acid residues present in the model.

FIG. 2B provides a side view of the same complex of FIG. 2A. Note that the loops on the top face of the propeller are longer than the ones on the bottom face. All figures were made using Pymol (DeLano, 2002).

FIG. 2C provides a surface representation of the Met Sema domain and an associated HGF β-chain represented as a gray ribbon. The left panel of FIG. 2C captures the complex in the same view as FIG. 2A and shows approximate molecular dimensions. The right panel of FIG. 2C is a view towards the bottom of the propeller and indicates a proteolysis site.

FIG. 8A shows the domain structure of Met. FIG. 8B shows a complex of Met with HGF in its uncleaved, immature form. High affinity binding of HGF to Met is established via the N and the K1 domains. FIGS. 8C and 8D show examples of maturation of HGF where the α- and β-chains remain connected via a single disulfide bond (—S—S—) between two cysteines (shown as —C—C—). Maturation of HGF further leads to rearrangements in its activation domain and to an increased affinity of the HGF β-chain to the Sema domain of Met. FIG. 8C shows a 2:1 model where the α- and β-chains of HGF bind to different Met receptor molecules. FIG. 8D shows a 2:2 model where the α- and β-chains of HGF bind to the same Met receptor molecule to form stable 1:1 complexes. Maturation of HGF creates a new binding interface in the β-chain and allows the formation of a weak 2:2 Met:HGF complex. Such complexes may be stabilized via heparin or other co-receptors.

DETAILED DESCRIPTION

Figure 1:
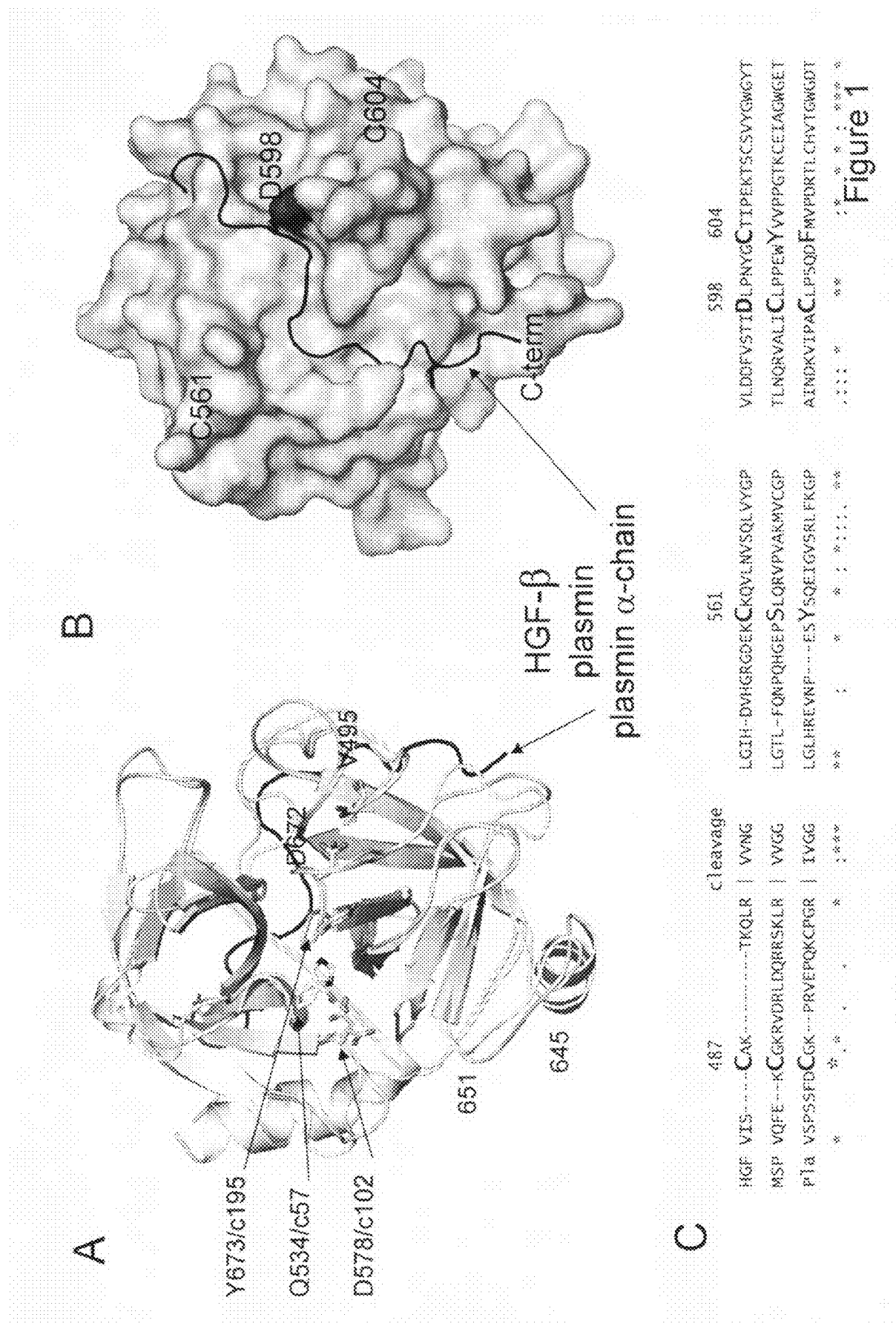
FIG. 1A shows a superposition representation of HGF β-chain (grey) and plasmin. The plasmin α chain is shown as a thin dark line. Selected side-chains of HGF β and plasmin are shown as sticks. They include the residues of the catalytic triad in serine proteases (His[c57], Asp[c102], and Ser[c195]) and the respective residues in the catalytically inactive HGF β-chain (Gln534, Asp578 and Tyr673), the N-terminal Val495 (V495; Val16 in plasmin) and Asp672 (D672; Asp194 in plasmin). After maturation, the N-terminus of Val495 of HGF β is inserted into the core of the protein. The N-terminal amine forms a salt bridge with the side-chain of Asp672 and thus rearranges the loops that carry the catalytic triad. The numbering system with a lower case c is that of the chymotyrpsinogen numbering system.
FIG. 1B shows the same superposition of FIG. 1A rotated 180° around the y-axis. The surface of HGF β-chain is grey. Cysteines 561 (C561) and 604 (C604) in HGF β-chain and the Asp598 (D598) are shown. The α-chain of plasmin follows a groove that is also present on the HGF surface. The distance requirements for the formation of the disulfide bond between the α- and the β-chain analogous to plasmin and MSP are not satisfied. The two cysteines on the plasmin α-chain are shown as stick stubs.
FIG. 1C shows the sequence alignment of selected regions of HGF, MSP, and plasmin. (SEQ ID NOs:7-9) The alignment shows the Cys residues that are present in the α and β chain of HGF. The Cys at position 487 in the α chain of HGF is conserved when compared with MSP and plasmin. However, the Cys residues in the β chain of HGF are not at conserved positions, but are found at positions 561 and 604. A disulfide bond between amino acid residues at 487 in the α chain and the cysteine residue at 604 in the β chain may be formed. However, given the location of cysteine 561 in the three-dimensional structure, this residue could also form a disulfide bond with amino acid residue 487 in the α chain. Asterisks indicate amino acid residues that are conserved when the three sequences are compared and dots indicate amino acids that are conservative substitutions.

A. Abbreviations (Å) Ångström (AA or aa) Amino acid; Amino acids are represented by single letter code or three letter code PSI domain is a small domain, which follows the Sema domain of Met, and spans about 50 residues and contains 4 disulfide bonds trypsin:BPTI (pdb 2PTC) is trypsin complexed with bovine pancreatic trypsin inhibitor MSP is macrophage stimulating protein NK1 is a region of the α-chain of a HGF variant, see U.S. Pat. No. 5,849,689.

B. Definitions

The following definitions are used herein, unless specifically or contextually indicated otherwise:

The term "hepatocyte growth factor" or "HGF", as used herein, refers, unless specifically or contextually indicated otherwise, to any native or variant (whether native or synthetic) HGF polypeptide that is capable of binding to Met and/or activating the HGF/Met signaling pathway under conditions that permit such process to occur, for example, conditions that allow for the formation of the two chain form. The term "wild type HGF sequence" generally refers to an amino acid sequence found in a naturally occurring HGF and includes naturally occurring truncated or secreted forms, variant forms (e.g. alternatively spliced forms) and naturally occurring allelic variants.

"HGF β" or "HGF β-chain", "HGF-beta" or variations thereof, refers to any HGF β chain having the conformation that is adopted by wild type HGF β chain upon conversion of wild type HGF protein from a single chain form to a 2 chain form (i.e., α and β chain). In some embodiments, the conversion results at least in part from cleavage between residue 494 and residue 495 of the wild type HGF protein. In some embodiments, the conformation refers specifically to the conformation of the activation domain of the protease-like domain in the β chain. In some embodiments, the conformation refers even more specifically to the conformation of the active site of the protease-like domain in the HGF β chain. Generally, adoption of the conformation reveals a Met binding site, as described herein. HGF β includes variants of wild type HGF β, for example, a variant comprising an amino acid sequence of SEQ ID NO:1. The HGF β chain may be isolated from a variety of sources such as human tissue or prepared by recombinant or synthetic methods. One embodiment of HGF β chain comprises an amino acid sequence of SEQ ID NO:1 in Table 4. Another embodiment of HGF β chain comprises an amino acid sequence of SEQ ID NO:14 in Table 8.

"HGF β variant" as used herein refers to polypeptide that has a different sequence than a reference polypeptide. In some embodiments, the reference polypeptide is a HGF β polypeptide comprising SEQ ID NO: 1 in Table 4. In some embodiments, a variant has at least 80% amino acid sequence identity with the HGF β amino acid sequence of Table 4 (SEQ ID NO: 1) or Table 8 (SEQ ID NO:14). The variants include those polypeptides that have substitutions, additions or deletions. The variants also include those polypeptides that have at least one conservative amino acid substitutions, preferably all of the substitutions are conservative. In some embodiments, the HGF β variant has about 1-25 conservative amino acid substitutions, more preferably about 1-20 conservative amino acids substitutions, more preferably about 1-10 conservative amino acid substitutions, more preferably about 1-5 conservative amino acid substitutions, and more preferably about 1-2 conservative amino acid substitutions. In some embodiments, the variants have the biological activity of binding to the Met receptor and/or activating it. In other embodiments, the variant can bind to the Met receptor but not activate it.

Ordinarily, a HGF β variant polypeptide will have at least 80% sequence identity, more preferably will have at least 81% sequence identity, more preferably will have at least 82% sequence identity, more preferably will have at least 83% sequence identity, more preferably will have at least 84% sequence identity; more preferably will have at least 85% sequence identity, more preferably will have at least 86% sequence identity, more preferably will have at least 87% sequence identity, more preferably will have at least 88% sequence identity, more preferably will have at least 89% sequence identity, more preferably will have at least 90% sequence identity, more preferably will have at least 91% sequence identity, more preferably will have at least 92% sequence identity, more preferably will have at least 93% sequence identity, more preferably will have at least 94% sequence identity, more preferably will have at least 95% sequence identity, more preferably will have at least 96% sequence identity, more preferably will have at least 96% sequence identity, more preferably will have at least 97% sequence identity, more preferably will have at least 98% sequence identity, more preferably will have at least 99% sequence identity with a HGF β polypeptide having an amino acid sequence comprising SEQ ID NO: 1 or SEQ ID NO:14.

Figure 3:
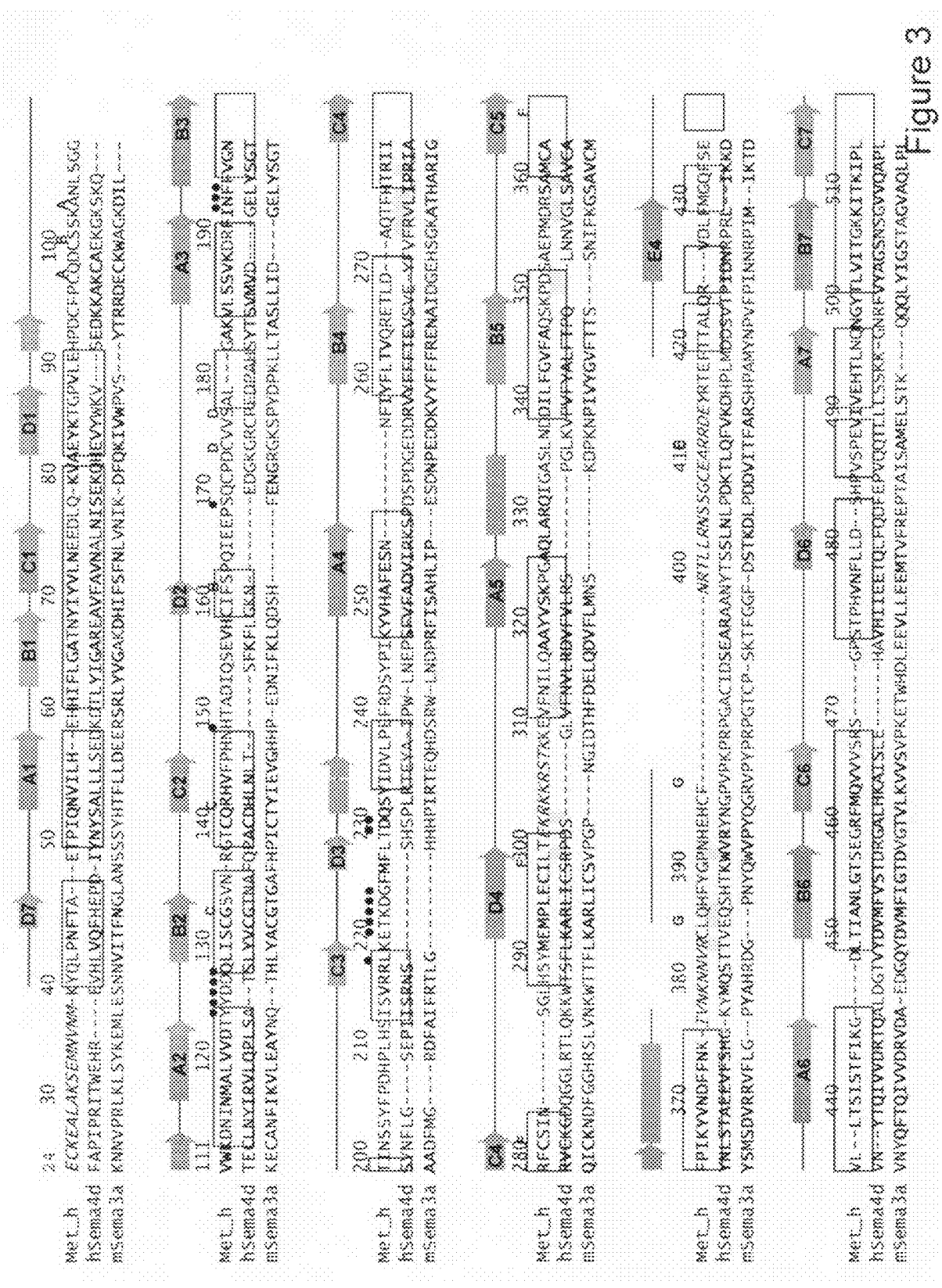
FIG. 3 shows sequence alignment of the Sema domains of human Met receptor (Met_h) (SEQ ID NO:10), human Sema4D (hSema4d) (SEQ ID NO:11), and mouse Sema3A (mSema3a) (SEQ ID NO:12). The secondary structure elements depicted refer to the Met structure. The structural elements identified as A1, B1, C1, etc. refer to β sheets that form the blades 1-7 of the propeller of the human Met receptor. For example, A1, B1, C1 and D1 identify the amino acids that form propellor blade 1 of the Met Sema domain. The amino acids forming other blades of the propeller are also identified. The boxes indicate structural equivalent positions between Met and Sema4D. The coordinates of the Sema3A structure were unavailable. Dots above the amino acid residues indicate these residues contact HGF β. Residues in the dimer interface of Sema4D are shaded. Cysteines engaged in disulfide bonds are marked with letters A to G and those with same letter form a disulfide bond. Residues that are disordered in the represented structure are shown in italics.

The term "Met receptor" or "Met", as used herein, refers to any native or variant (whether native or synthetic) Met polypeptide that is capable of binding to and/or being activated by HGF. The term "wild-type Met receptor" generally refers to a polypeptide comprising an amino acid sequence found in a naturally occurring Met receptor and includes naturally occurring truncated or secreted forms, variant forms (e.g. alternatively spliced forms) and naturally occurring allelic variants. The "Met Sema domain" comprises the N terminal 500 amino acid residues of a wild type Met receptor. A PSI domain follows the Sema domain and comprises 50 amino acid residues and has 4 disulfide bonds. Following the PSI domain are four IPT domains. IPT domains are related to immunoglobulin like domains. An embodiment of the Met receptor comprises an amino acid sequence of SEQ ID NO:2 as shown in Table 5. An embodiment of the extracellular fragment including the Sema domain of the Met receptor comprises an amino acid sequence of SEQ ID NO:3 as shown in Table 6 or comprises an amino acid sequence of SEQ ID NO:10 as shown in FIG. 3.

The term "Met receptor variant", as used herein, refers to a polypeptide that has a different sequence than a reference polypeptide, wherein the reference polypeptide is the Met receptor that comprises an amino acid sequence of SEQ ID NO:2 or the extracellular fragment of the Met receptor that comprises an amino acid sequence of SEQ ID NO:3. Another embodiment of an extracellular fragment of the Met receptor comprises an amino acid sequence of SEQ ID NO:10 as shown in FIG. 3. An extracellular fragment of Met receptor comprising a sequence of SEQ ID NO:3 has amino acid substitutions at positions 304-308 of wild type sequence to insert a thrombin cleavage site. Variants include those polypeptides that have substitutions, deletions, and/or deletions. Variants also include those polypeptides that have at least one conservative amino acid substitution, preferably, all of the substitutions are conservative. In some embodiments, the Met receptor variant has about 1-25 conservative amino acid substitutions, more preferably about 1-20 conservative amino acids substitutions, more preferably about 1-10 conservative amino acid substitutions, more preferably about 1-5 conservative amino acid substitutions, and more preferably about 1-2 conservative amino acid substitutions. In some embodiments, the variant has the biological activity of binding to HGF, but not becoming activated.

Ordinarily, a Met receptor variant will have at least 80% sequence identity to a polypeptide having SEQ ID NO:3 In some embodiments, Met receptor polypeptide variants have at least 80% sequence identity, more preferably 81% sequence identity, more preferably 82% sequence identity, more preferably 83% sequence identity, more preferably 84% sequence identity, more preferably 85% sequence identity, more preferably 86% sequence identity, more preferably 87% sequence identity, more preferably 88% sequence identity, more preferably 89% sequence identity, more preferably 90% sequence identity, more preferably 91% sequence identity, more preferably 92% sequence identity, more preferably 93% sequence identity, more preferably 94% sequence identity, more preferably 95% sequence identity, more preferably 96% sequence identity, more preferably 97% sequence identity, more preferably 98% sequence identity, more preferably 99% sequence identity or greater, to a polypeptide having a sequence of SEQ ID NO:2 or SEQ ID NO:3.

The term "binding site," as used herein, refers to a region of a molecule or molecular complex that, as a result of its shape, distribution of electrostatic charge and/or distribution of non-polar regions, favorably associates with a ligand. Thus, a binding site may include or consist of features such as cavities, surfaces, or interfaces between domains. Ligands that may associate with a binding site include, but are not limited to, cofactors, substrates, receptors, agonists, and antagonists. The term binding site includes a functional binding site and/or a structural binding site. A structural binding site includes "in contact" amino acid residues as determined from examination of a three-dimensional structure. "Contact" can be determined using Van der Waals radii of atoms or by proximity sufficient to exclude solvent, typically water, from the space between the ligand and the molecule or molecular complex. Some of the "in contact" amino acid residues may not cause any change in a biochemical assay, a cell-based assay, or an in vivo assay used to define a functional binding site but may contribute to the formation of a three dimensional structure. A functional binding site includes amino acid residues that are identified as binding site residues based upon loss or gain of function, for example, loss of binding to ligand upon mutation of the residue. In some embodiments, the amino acid residues of a functional binding site are a subset of the amino acid residues of the structural binding site.

The term "HGF β structural binding site" includes all or a portion of a molecule or molecular complex whose shape is sufficiently similar to at least a portion of a binding site on HGF β for Met as to be expected to bind Met or related structural analogs of Met. A structurally equivalent ligand binding site is defined by a root mean square deviation from the structure coordinates of the backbone atoms of the amino acids that make up binding sites in HGF β for Met of at most about 0.70 Å, preferably about 0.5 Å. In some embodiments, a structural binding site for the Met receptor on HGF β comprises, consists essentially of, or consists of at least one amino acid residue corresponding to a residue 513, 516, 533, 534, 536, 537, 539, 578, 619, 647, 649, 656, 668 to 670, 673, 692 to 697, 699, 702, 705 or 707 or mixtures thereof. Numbering of amino acids is that of the native receptor.

The term "Met structural binding site" includes all, or a portion of, a molecule whose shape is sufficiently similar to the binding site on Met for HGF β to be expected to bind HGF β or structural analogs of HGF β. A structurally equivalent "Met binding site" is defined by root mean square deviation from the structure coordinates of the amino acids that make up the binding sites in Met of at most about 0.70 Å, preferably about 0.5 Å. In some embodiments, a structural binding site for HGF β on the Met receptor comprises, consists essentially of, or consists of at least one amino acid residue corresponding to a residue 124-128, 148, 167, 190-192, 218, 220 to 224, 227, 229 to 230, 286 or 414 or mixtures thereof. Numbering of amino acids is that of the native receptor.

The term "a blade of a propeller" refers to a structural feature of the Met receptor. A blade is formed by four anti-parallel strands with strand A in the center of the blade followed by strands B and C, and with strand D forming the outermost strand of the blade. The 7 blades are arranged in a circular fashion, with the N terminal strand forming strand D of the last blade. The AB and CD loops of each blade of the Met Sema domain form the flat bottom face of the propeller and the BC and DA loops form the top face of the propeller. In some embodiments, each of the blades of the propellor of the human Met receptor comprise the amino acid sequence as identified in FIG. 3.

"Crystal" as used herein, refers to one form of a solid state of matter in which atoms are arranged in a pattern that repeats periodically in three-dimensions, typically forming a lattice.

"Complementary or complement" as used herein, means the fit or relationship between two molecules that permits interaction, including for example, space, charge, three-dimensional configuration, and the like.

The term "corresponding" or "corresponds" refers to an amino acid residue or amino acid sequence that is found at the same positions or positions in a sequence when the amino acid position or sequences are aligned with a reference sequence. In some embodiments, the reference sequence is the extracellular fragment of the Met receptor comprising a sequence of SEQ ID NO:3. It will be appreciated that when the amino acid position or sequence is aligned with the reference sequence the numbering of the amino acids may differ from that of the reference sequence or a different numbering system may be utilized.

"Heavy atom derivative", as used herein, means a derivative produced by chemically modifying a crystal with a heavy atom such as Hg, Au, or a halogen.

"Structural homolog" of Met receptor as used herein refers to a protein that contains one or more amino acid substitutions, deletions, additions, or rearrangements with respect to the amino acid sequence of Met receptor, but that, when folded into its native conformation, exhibits or is reasonably expected to exhibit at least a portion of the tertiary (three-dimensional) structure of the Met receptor. In some embodiments, a portion of the three dimensional structure refers to structural domains of the Met receptor including the Sema domain, PSI domain, IPT domains, transmembrane domain and/or intracellular domain, and combinations thereof. For example, structurally homologous molecules of Met receptor include Met receptor variants, preferably variants with one or more conservative amino acid substitutions. In some embodiments, a Met receptor variant has only conservative amino acid substitutions. Homolog tertiary structure can be probed, measured, or confirmed by known analytic or diagnostic methods, for example, X-ray, NMR, circular dichroism, a panel of monoclonal antibodies that recognize native Met receptor, and like techniques. For example, structurally homologous molecules can have substitutions, deletions or additions of one or more contiguous or noncontiguous amino acids, such as a loop or a domain. Structurally homologous molecules also include "modified" Met receptor molecules that have been chemically or enzymatically derivatized at one or more constituent amino acid, including side chain modifications, backbone modifications, and N- and C-terminal modifications including acetylation, hydroxylation, methylation, amidation, and the attachment of carbohydrate or lipid moieties, cofactors, and like modifications.

"Ligand", as used herein, refers to an agent and/or compound that associates with a binding site on a molecule, for example, Met and/or HGF β binding sites, and may be an antagonist or agonist of Met or HGF β activity. Ligands include molecules that mimic HGF β binding to Met and in some embodiments, are not capable of activating HGF β/Met signalling pathway.

"Compound" refers to molecule that associates with the Met or the HGF β or a pharmaceutically acceptable salt, ester, amide, prodrug, isomer, or metabolite, thereof. "Pharmaceutically acceptable salt" refers to a formulation of a compound that does not compromise the biological activity and properties of the compound. Pharmaceutical salts can be obtained by reacting a binding-active compound of the disclosure with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like. "Prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of the present invention which is administered as an ester (the "prodrug") to facilitate transport across a cell membrane where water solubility is detrimental to mobility but which then is metabolically hydrolyzed to the carboxylic acid, the active entity, once inside the cell where water solubility is beneficial. A further example of a prodrug might be a short peptide (polyaminoacid) bonded to an acid group wherein the peptide is metabolized to yield the active moiety.

"Molecular complex", as used herein, refers to a combination of bound substrate or ligand with polypeptide, such as HGF β bound to Met, or a ligand bound to HGF β or Met.

"Machine-readable data storage medium", as used herein, means a data storage material encoded with machine-readable data, wherein a machine programmed with instructions for using such data and is capable of displaying data in the desired format, for example, a graphical three-dimensional representation of molecules or molecular complexes.

"Scalable," as used herein, means the increasing or decreasing of distances between coordinates (configuration of points) by a scalar factor while keeping the angles essentially the same.

"Space group symmetry", as used herein, means the whole symmetry of the crystal that combines the translational symmetry of a crystalline lattice with the point group symmetry. A space group is designated by a capital letter identifying the lattice type (P, A, F, etc.) followed by the point group symbol in which the rotation and reflection elements are extended to include screw axes and glide planes. Note that the point group symmetry for a given space group can be determined by removing the cell centering symbol of the space group and replacing all screw axes by similar rotation axes and replacing all glide planes with mirror planes. The point group symmetry for a space group describes the true symmetry of its reciprocal lattice.

"Unit cell", as used herein, means the atoms in a crystal that are arranged in a regular repeating pattern, in which the smallest repeating unit is called the unit cell. The entire structure can be reconstructed from knowledge of the unit cell, which is characterized by three lengths (a, b and c) and three angles ($\alpha$, $\beta$ and $\gamma$). The quantities a and b are the lengths of the sides of the base of the cell and $\gamma$ is the angle between these two sides. The quantity c is the height of the unit cell. The angles $\alpha$ and $\beta$ describe the angles between the base and the vertical sides of the unit cell.

"X-ray diffraction pattern" means the pattern obtained from X-ray scattering of the periodic assembly of molecules or atoms in a crystal. X-ray crystallography is a technique that exploits the fact that X-rays are diffracted by crystals. X-rays have the proper wavelength (in the Ångström (Å) range, approximately $10^{-8}$ cm) to be scattered by the electron cloud of an atom of comparable size. Based on the diffraction pattern obtained from X-ray scattering of the periodic assembly of molecules or atoms in the crystal, the electron density can be reconstructed. Additional phase information can be extracted either from the diffraction data or from supplementing diffraction experiments to complete the reconstruction (the phase problem in crystallography). A model is then progressively built into the experimental electron density, refined against the data to produce an accurate molecular structure.

X-ray structure coordinates define a unique configuration of points in space. Those of skill in the art understand that a set of structure coordinates for a protein or a protein/ligand complex, or a portion thereof, define a relative set of points that, in turn, define a configuration in three dimensions. A similar or identical configuration can be defined by an entirely different set of coordinates, provided the distances and angles between coordinates remain essentially the same. In addition, a configuration of points can be defined by increasing or decreasing the distances between coordinates by a scalar factor, while keeping the angles essentially the same.

"Crystal structure" generally refers to the three-dimensional or lattice spacing arrangement of repeating atomic or molecular units in a crystalline material. The crystal structure of a crystalline material can be determined by X-ray crystallographic methods, see for example, "Principles of Protein X-Ray Crystallography," by Jan Drenth, Springer Advanced Texts in Chemistry, Springer Verlag; 2nd ed., February 1999, ISBN: 0387985875, and "Introduction to Macromolecular Crystallography," by Alexander McPherson, Wiley-Liss, Oct. 18, 2002, ISBN: 0471251224.

C. Modes for Carrying Out the Invention

The present disclosure thus includes a crystalline form and a crystal structure of hepatocyte growth factor beta-chain (HGF β) complexed with Met receptor (HGF β:Met) and methods of using the HGF β:Met crystal structure and structural coordinates to identify homologous proteins and to design or identify agents that can modulate the function of HGF, Met, and/or HGF β:Met complex. In some embodiments, the crystalline form of HGF β complexed with Met receptor diffracts X-rays for a determination of atomic coordinates to a resolution of 5 Å or better. The present disclosure also includes the three-dimensional configuration of points derived from the structure coordinates of at least a portion of an extracellular fragment of a Met receptor molecule or molecular complex, as well as structurally equivalent configurations, as described below. The three-dimensional configuration includes points derived from structure coordinates representing the locations of a plurality of the amino acids defining the Met binding site for HGF β, the blades of the propeller, and the PSI domain.

In some embodiments, the three-dimensional configuration includes points derived from structure coordinates representing the locations of the backbone atoms of a plurality of amino acids defining the Met or HGF β:Met complex binding site. Alternatively, the three-dimensional configuration includes points derived from structure coordinates representing the locations of the side chain and the backbone atoms (other than hydrogens) of a plurality of the amino acids defining the Met or HGF β:Met complex binding site including the Met binding site for HGF β and the HGF β binding site for Met.

The disclosure also includes the three-dimensional configuration of points identifying other structural features of an extracellular fragment of the Met receptor. Those other structural features include the blades of the propeller structure and PSI domain. A plurality of amino acid residues have been identified as contributing to these structural features of Met receptor. In some embodiments, the amino acid residues comprise those identified as corresponding to structural features as shown in FIG. 3.

Likewise, the disclosure also includes the scalable three-dimensional configuration of points derived from structure coordinates of molecules or molecular complexes that are structurally homologous to HGF β:Met complex or extracellular fragment of the Met receptor including the Sema domain, as well as structurally equivalent configurations. Structurally homologous molecules or molecular complexes are defined below. Advantageously, structurally homologous molecules can be identified using the structure coordinates of the HGF β:Met complex or extracellular fragment of the Met receptor according to a method of the disclosure.

The configurations of points in space derived from structure coordinates according to the disclosure can be visualized as, for example, a holographic image, a stereodiagram, a model, or a computer-displayed image, and the disclosure thus includes such images, diagrams or models.

The crystal structure and structural coordinates can be used in methods, for example, for obtaining structural information of a related molecule, and for identifying and designing agents that modulate Met or HGF β:Met complex activity.

The coordinates of the present disclosure have been deposited in the RCSB Protein Data Bank under accession code: PDBISHY.

1. Met and HGF β Polypeptides, Polynucleotides and Variants Thereof.

The present disclosure includes a description of HGF β and an extracellular fragment of Met including the Sema domain of the Met receptor.

The present disclosure includes a description of hepatocyte growth factor and/or portions thereof. Hepatocyte growth factor comprises a 69 kDa alpha chain and 34 kDa beta chain. HGF is secreted as a single chain precursor form (scHGF). The 69 kDa alpha chain comprise a N terminal finger domain and four kringle domains (K1-K4). A representative amino acid sequence of human HGF β chain is shown in Table 4 (SEQ ID NO: 1). The sequence of Table 4 has one amino acid change from wild type shown in Table 8; the cysteine at amino acid position 604 is changed to a serine. It would be expected that a wild type HGF β would have an equivalent crystal structure. The amino acid numbering of the HGF β chain is based on the numbering of the single chain precursor form. Numbers in brackets or preceded by a lower case c represent a numbering system based on reference to chymotrypsinogen.

The Met receptor is a tyrosine kinase and is part of a larger family of growth factor receptors with domain architecture similar to the Ron and Sea receptors. The extracellular portion of the Met receptor comprises N-terminal 500 amino acids that fold into a Sema domain. A PSI domain follows the Sema domain and comprises about 50 amino acids and has 4 disulfide bonds. The PSI domain is connected to the transmembrane domain and extracellular kinase domain by 4 IPT domains. IPT domains are immunoglobulin-like domains and are located C terminal to the PSI domain. Met becomes activated upon binding of a ligand, such as HGF β, the receptor is phosphorylated and cells expressing activated Met are stimulated to migrate, proliferate and/or differentiate. Crosslinking of Met receptors to form dimers also activates the Met receptor. A representative example of an amino acid sequence of a Met receptor is shown in Table 5 and comprises an amino acid sequence of SEQ ID NO:2. A representative example of a sequence of an extracellular portion of the Met receptor including the Sema domain and the PSI domain is shown in Table 6 and comprises an amino acid sequence of SEQ ID NO:3. The extracellular fragment of the Met receptor having a sequence of SEQ ID NO:3 differs from wild type in that amino acids at positions 304 to 308 have been substituted to include a thrombin cleavage site. Another embodiment of an extracellular fragment of Met is provided in FIG. 3 and comprises an amino acid sequence of SEQ ID NO:10. The numbering system of Met receptor is that of the Swiss Prot database as shown in Table 6.

Native or wild-type HGF, HGFα; HGF β, or Met receptor polypeptides are those polypeptides that have a sequence of a polypeptide obtained from nature. Native or wild-type polypeptides include naturally occurring variants, secreted or truncated forms. Some domains of HGF and/or the Met receptor are known. Several isoforms of HGF are known such as isoform 1, isoform 2, isoform 3, isoform 4, and isoform 5. Representative sequences can be found at GenBank Accession Numbers NM_000601, NM_001010931, NM_001010932, NM_001010933, NM_001010934, and NP_000592.

The present disclosure also includes a polypeptide comprising, consisting essentially of, or consisting of a portion or fragment of the Met receptor. The polypeptide fragment includes amino acid residues from any of amino acid 1 to 25 residues to amino acid position 567 or residues corresponding to those positions. In some embodiments, the polypeptide portion has the ability to bind to ligand HGF. The polypeptide portion may also be fused to heterologous polypeptide, such as a peptide tag. Preferably, the fusion polypeptide retains the ability to bind a ligand, such as HGF.

The disclosure also provides a polypeptide comprising, consisting essentially of, or consisting of a portion or fragment of the Met receptor starting at amino acid residue 124 and ending at any one of amino acid residues 230 to 286 or residues corresponding to these residues. This polypeptide includes the amino acid residues that contact the HGF β ligand and preferably, the polypeptide has the ability to bind to a ligand such as HGF β. The polypeptide portion or fragment may be fused to a heterologous polypeptide. Preferably, the fusion protein can bind to a ligand, such as HGF β.

The present disclosure also includes variants of the Met receptor. Variants include those polypeptides that have amino acid substitutions, deletions, and additions. Amino acid substitutions can be made for example to replace cysteines and eliminate formation of disulfide bonds. Amino acid substitutions can also be made to change proteolytic cleavage sites. The variants also include those polypeptides that have at least one conservative amino acid substitution. In some embodiments a variant only has conservative amino acid substitutions. In some embodiments, the Met receptor variant has about 1-25 conservative amino acid substitutions, more preferably about 1-20 conservative amino acids substitutions, more preferably about 1-10 conservative amino acid substitutions, more preferably about 1-5 conservative amino acid substitutions, and more preferably about 1-2 conservative amino acid substitutions. In some embodiments, a Met receptor variant has at least 90% sequence identity to an extracellular domain fragment of the Met receptor, such as SEQ ID NO:3, and has changes at amino acids other than those associated with the binding site for HGF β on Met, preferably the amino acid changes are only conservative substitutions. Other variants can be made at the Met binding site for HGF β. In other embodiments, the variants of the Met receptor bind HGF β bind with the same or higher affinity than the wild type Met receptor.

Fusion Proteins

A Met receptor, variant or structural homolog or portions thereof, may be fused to a heterologous polypeptide or compound. The heterologous polypeptide is a polypeptide that has a different function than that of the Met receptor. Examples of heterologous polypeptide include polypeptides that may act as carriers, may extend half life, may act as epitope tags, may provide ways to detect or purify the fusion protein. Heterologous polypeptides include KLH, albumin, salvage receptor binding epitopes, immunoglobulin constant regions, and peptide tags. Peptide tags useful for detection or purification include FLAG, gD protein, polyhistidine tags, hemaglutinin from influenza virus, T7 tag, S tag, Strep tag, chloramiphenicol acetyl transferase, biotin, glutathione-S transferase, green fluorescent protein and maltose binding protein. Compounds that can be combined with the Met receptor, variants or structural homolog or portions thereof, include radioactive labels, protecting groups, and carbohydrate or lipid moieties.

Polynucleotides, Vectors and Host Cells

Variants of a Met receptor or extracellular fragment thereof can be prepared by introducing appropriate nucleotide changes into DNA encoding Met or the extracellular fragment, or by synthesis of the desired polypeptide variants. HGF β chain variants can be prepared by introducing appropriate nucleotide changes into DNA encoding HGF β or by synthesis of the desired polypeptide variants. Variants can be made using standard methods.

Amino acid substitutions, include one or more conservative amino acid substitutions. The term "conservative" amino acid substitution as used herein refers to an amino acid substitution which substitutes a functionally equivalent amino acid. Conservative amino acid changes result in silent changes in the amino acid sequence of the resulting polypeptide. For example, one or more amino acids of a similar polarity act as functional equivalents and result in a silent alteration within the amino acid sequence of the peptide. In general, substitutions within a group can be considered conservative with respect to structure and function. However, the skilled artisan will recognize that the role of a particular residue is determined by its context within the three-dimensional structure of the molecule in which it occurs. For example, Cys residues may occur in the oxidized (disulfide) form, which is less polar than the reduced (thiol) form. The long aliphatic portion of the Arg side chain can constitute a feature of its structural or functional role, and this may be best conserved by substitution of a nonpolar, rather than another basic residue. Also, it will be recognized that side chains containing aromatic groups (Trp, Tyr, and Phe) can participate in ionic-aromatic or "cation-pi" interactions. In these cases, substitution of one of these side chains with a member of the acidic or uncharged polar group may be conservative with respect to structure and function. Residues such as Pro, Gly, and Cys (disulfide form) can have direct effects on the main chain conformation, and often may not be substituted without structural distortions.

Amino acid substitutions can be the result of replacing one amino acid with another amino acid having similar structural and/or chemical properties, such as the replacement of a leucine with a serine, i.e., conservative amino acid replacements. Examples of conservative substitutions are shown in Table 9. The variation allowed can be determined by systematically making insertions, deletions or substitutions of amino acids in the sequence and testing the resulting variants for activity exhibited by the native sequence.

TABLE 9

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Polynucleotide sequences encoding the polypeptides described herein can be obtained using standard recombinant techniques. Desired polynucleotide sequences may be isolated and sequenced from appropriate source cells. Alternatively, polynucleotides can be synthesized using nucleotide synthesizer or PCR techniques. Once obtained, sequences encoding the polypeptides or variant polypeptides are inserted into a recombinant vector capable of replicating and expressing heterologous polynucleotides in a host cell. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication (in particular when the vector is inserted into a prokaryotic cell), a selection marker gene, a promoter, a ribosome binding site (RBS), a signal sequence, the heterologous nucleic acid insert and a transcription termination sequence.

In general, plasmid vectors containing replicon and control sequences, which are derived from a species compatible with the host cell are used in connection with these hosts. The vector ordinarily carries a replication site, as well as marking sequences, which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

Either constitutive or inducible promoters can be used in the present invention, in accordance with the needs of a particular situation, which can be ascertained by one skilled in the art. A large number of promoters recognized by a variety of potential host cells are well known. The selected promoter can be operably linked to cistron DNA encoding a polypeptide described herein by removing the promoter from the source DNA via restriction enzyme digestion and inserting the isolated promoter sequence into the vector of choice. Both the native promoter sequence and many heterologous promoters may be used to direct amplification and/or expression of the target genes. However, heterologous promoters are preferred, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the polypeptides or variant polypeptides (Siebenlist et al. (1980) Cell 20: 269) using linkers or adaptors to supply any required restriction sites.

In embodiments, each cistron within a recombinant vector comprises a secretion signal sequence component that directs translocation of the expressed polypeptides across a membrane. In general, the signal sequence may be a component of the vector, or it may be a part of the polypeptide encoding DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP.

Prokaryotic host cells suitable for expressing polypeptides include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla,* or *Paracoccus*. Preferably, gram-negative cells are used. Preferably the host cell should secrete minimal amounts of proteolytic enzymes, and additional protease inhibitors may desirably be incorporated in the cell culture.

Besides prokaryotic host cells, eukaryotic host cell systems are also well established in the art. Examples of invertebrate cells include insect cells such as *Drosophila* S2 and *Spodoptera* Sf9, as well as plants and plant cells. Examples of useful mammalian host cell lines include Chinese hamster ovary (CHO) and COS cells. More specific examples include monkey kidney CV1 line transformed by SV40 (COS-7, ATCC CRL 1651); Chinese hamster ovary cells/–DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); and mouse mammary tumor (MMT 060562, ATCC CCL51).

Polypeptide Production

Host cells are transformed or transfected with the above-described expression vectors and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In preferred embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector, protein expression is induced under conditions suitable for the activation of the promoter. For example, if a PhoA promoter is used for controlling transcription, the transformed host cells may be cultured in a phosphate-limiting medium for induction. A variety of other inducers may be used, according to the vector construct employed, as is known in the art.

Eukaryotic host cells are cultured under conditions suitable for expression of the HGF and/or Met receptor polypeptides. The host cells used to produce the polypeptides may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in one or more of Ham et al., 1979, *Meth. Enz.* 58:44, Barnes et al., 1980, *Anal. Biochem.* 102: 255, U.S. Pat. No. 4,767,704, 4,657,866, 4,927,762, 4,560,655, or 5,122,469, WO 90/103430, WO 87/00195, and U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES™), nucleotides (such as adenosine and thymidine), antibiotics (such as GENTAMYCIN™), trace elements (defined as inorganic compounds usually present at final concentrations in the micromolar range), and glucose or an equivalent energy source. Other supplements may also be included at appropriate concentrations that would be known to those skilled in the art. The culture conditions, such as temperature, pH, and the like, are those previously used with the host cell selected for expression, and will be apparent to the ordinarily skilled artisan.

Polypeptides described herein expressed in a host cell may be secreted into and/or recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated there from. Cells may be removed from the culture and the culture supernatant being filtered and concentrated for further purification of the proteins produced. The expressed polypeptides can be further isolated and identified using commonly known methods such as fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; hydrophobic affinity resins, ligand affinity using a suitable antigen immobilized on a matrix and Western blot assay.

Polypeptides that are produced may be purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

2. Crystals and Crystal Structures

The present disclosure provides crystals of and a crystal structure of HGF β chain cocrystallized with a fragment of the Met receptor. In some embodiments, the Met receptor fragment includes the Sema and PSI domain. The crystals were formed by contacting a mixture of purified HGF β chain and the Met receptor extracellular fragment with a precipitant in a buffer. In some embodiments, the crystal of a HGF β and a Met receptor can be diffracted by X-rays to determine atomic coordinates to a resolution of 5 Å or better. In some embodiments, the precipitant was 12-15% polyethylene glycol 10,000. In some embodiments, the crystals are formed from a HGF β comprising SEQ ID NO:1 and a Met receptor fragment comprising SEQ ID NO:3.

The resulting crystals diffracted to 3.2 Å resolution (Table 1) and have one (1) full complex containing one Met fragment and a single HGF β-chain in the asymmetric unit. The structure was refined to an R-value of 20.9% (Rfree 27.0%) with good geometry. Of the 628 non-glycine and non-proline residues, 97.6% have their main-chain torsion angles in the 'most-favored' or the 'additionally allowed' regions of the Ramachandran plot (Laskowski et al., 1993). The refined model includes residues 495 to 722 of HGF and residues 40 to 301, 311 to 377, 382 to 400, and 414 to 564 of Met. Although a number of glycosylation sites displayed electron density, none of the sugars were modeled into the structure.

In a specific embodiment, the structure of HGF β complexed with a Met receptor extracellular fragment (HGF β:Met) was solved by molecular replacement with the program AMORE (NAVAZC 1994) using the crystal structure of HGF β chain alone as search model (coordinates for HGF β can be found in the RCSB Protein Data Bank under accession code: PDB1UX3). The crystals belonged to space group $P2_1P2_1P$ with cell parameters of a=137.1 Å, b=186.4 Å and c=66.7 Å and contained 1 complex of Met: HGF β chain in the asymmetric unit.

Each of the constituent amino acids in HGF β:Met is defined by a set of structural coordinates as set forth in Table 2. The coordinates and structure factors of the present disclosure have been deposited by the RCSB Protein Data Bank under Accession Code: PDB 1SHY.

The term "structure coordinates" refers to Cartesian coordinates derived from mathematical equations related to the patterns obtained on diffraction of a monochromatic beam of X-rays by the atoms (scattering centers) of a Met receptor or Met: HGF β in crystal form. The diffraction data are used to calculate an electron density map of the repeating unit of the crystal. The electron density maps are then used to establish the positions of the individual atoms of the Met receptor or protein ligand complex.

Slight variations in structure coordinates can be generated by mathematically manipulating the Met receptor or Met: HGF β complex structure coordinates. For example, the structure coordinates as set forth in Table 2 could be manipulated by crystallographic permutations of the structure coordinates, fractionalization of the structure coordinates, integer additions or subtractions to sets of the structure coordinates, inversion of the structure coordinates, or any combination of the above. Alternatively, modifications in the crystal structure due to mutations, additions, substitutions, deletions, and combinations thereof, of amino acids, or other changes in any of the components that make up the crystal, could also yield variations in structure coordinates. Such slight variations in the individual coordinates will have little effect on overall shape. If such variations are within an acceptable standard error as compared to the original coordinates, the resulting three-dimensional shape is considered to be structurally equivalent. Structural equivalence is described in more detail below.

It should be noted that slight variations in individual structure coordinates of the HGF β:Met would not be expected to significantly alter the nature of chemical entities such as ligands that could associate with a binding site or other structural features of HGF β or Met. In this context, the phrase "associating with" refers to a condition of proximity between a ligand, or portions thereof, and a HGF β or Met molecule or portions thereof. The association may be non-covalent, wherein the juxtaposition is energetically favored by hydrogen bonding, van der Waals forces, and/or electrostatic interactions, or it may be covalent.

HGF β Chain Structure

The β-chain of HGF shares close to 40% sequence identity with the protease domain of plasmin, a trypsin-like serine protease. Structurally, these enzymes can be described as globular proteins composed of two antiparallel β-barrel domains (FIG. 1A). Both of the β-barrels share the same general topology and are formed by six antiparallel β-strands, with the N-terminal four strands folding into a Greek key motif, followed by two strands that form a hairpin. HGF, like serine proteases, is expressed as a zymogen-like precursor. For serine proteases, structural studies have shown that insertion of the N-terminus resulting from the maturation process leads to allosteric rearrangements within the binding site for the protease substrate (Perona and Craig, 1995; Hedstrom 2002). In serine proteases, the newly formed N-terminus forms a salt bridge with a nearby aspartate, which leads to the formation of the oxyanion hole via the backbone NH's of two neighboring residues and the creation of a part of the S1 pocket (FIG. 1). The 'activated' form of the HGF β-chain, as seen in the structure presented here, is similar to the mature form of serine proteases: superposition with plasmin (pdb-code 1BML) yields an rmsd of about 1.3 Å for 212 $C_\alpha$ pairs. Superposition between HGF β-chain and plasminogen (pdb-code 1QRZ) reveal differences in their 'activation domain' (Freer et al., 1970) and only 198 $C_\alpha$ pairs can be aligned well.

As with serine proteases, the N-terminal amine of HGF β, Val495, is inserted into the core of the C-terminal β-barrel and forms a salt bridge with the carboxyl group of Asp672, which corresponds to Asp[c194] in plasmin, presumably leading to similar rearrangements, which have been characterized in serine proteases. The region in HGF corresponding to this so-called 'activation domain', i.e., the loops that undergo conformational changes in serine proteases (Freer et al., 1970; Huber and Bode, 1978), form part of the binding surface with Met.

After maturation, the α- and β-chains of HGF remain connected via a disulfide bond. Based on alignments of the kringle domains K1 to K4 of HGF α chain and macrophage stimulating protein (MSP), the two cysteine residues responsible for the formation of this disulfide bond were identified as Cys487 on the α-chain of HGF and Cys604 on the β-chain (Donate et al., 1994). The crystal structure, however, raises the possibility of an alternative cysteine residue as the anchor for the HGF α-chain. The HGF β-chain has two (2) cysteine residues that do not have partners for the formation of disulfide bridges within the β-chain. Neither is conserved in plasmin or MSP and both are located on the periphery of the protein and are at least partially solvent exposed; either could be potential partners for the formation of a disulfide bond with the α-chain while the other remains unpaired. The superposition of the plasmin structure that contains part of the α-chain (FIG. 1B), and the HGF β-chain structure presented here, shows that the distance between the C-terminus of the plasmin α-chain and Cys604 of the HGF β-chain is 27 Å and thus only slightly shorter than the respective distance between the plasmin α-chain C-terminus and Cys561 (33 Å) (FIG. 1B). In addition, the sequence alignment between plasmin, MSP, and HGF (FIG. 1C) shows that the α-chain cysteine forming the disulfide bond in plasmin and MSP is 13 and 15 residues away from the cleavage site in those proteins respectively, but there are only 7 residues in HGF to span the distance from Cys487 to the cleavage site. Therefore, due to distance requirements, the C-terminus of the HGF α-chain cannot follow the same path on the surface of the β-chain as it does in plasmin or MSP. Regardless of the position of the disulfide bond between the alpha and beta chain, the overall structure or the structural model of the Met receptor or Met:HGF β complex is not impacted.

Met Structure

Figure 2:
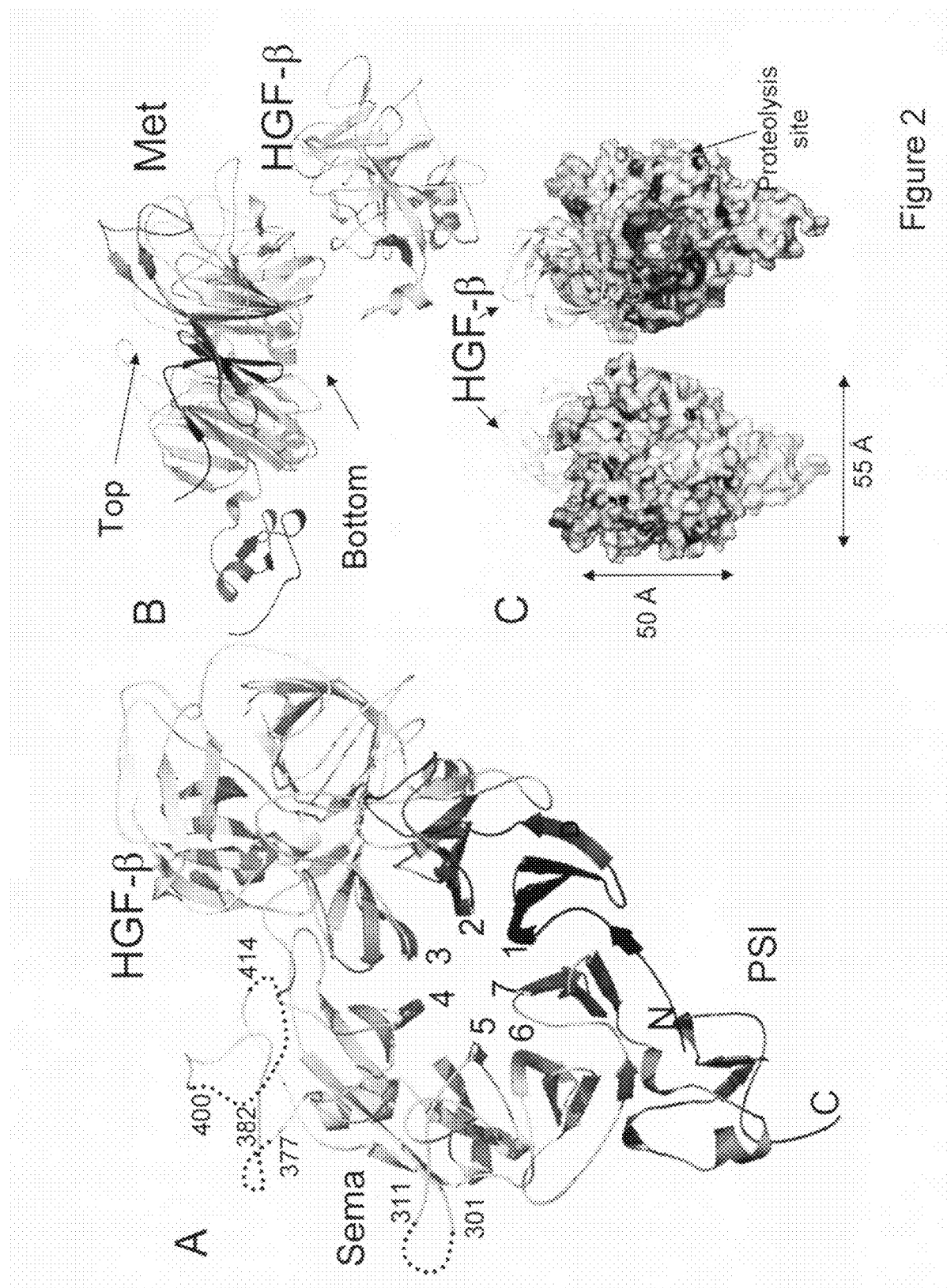
FIGS. 2A-C show representations of the complex of Met and HGF β-chain.

The analysis of crystal structure of the Sema domain of Met shows that it forms 7-bladed β-propeller with a diameter of a little more than 50 Å. The overall shape of the domain resembles a funnel with an inner diameter of about 25 Å between main chain atoms at the wide portion and 10 Å in the narrowest part (FIG. 2). Generally, in β-propellers, each of the blades is formed by 4 antiparallel β-strands with strand A in the center of the propeller followed by strands B and C, and with strand D forming the outermost strand of the blade. The blades are arranged in a circular fashion, with the N-terminal strand forming strand D of the last blade, thus closing the propeller and stabilizing the overall structure (FIG. 2A). The AB and CD loops of each blade of the Met Sema domain form the relatively flat 'bottom' face, and the generally longer BC and DA loops form the 'top' face of the propeller (FIG. 2B). In Met, the position of the 6th and the 7th blade are off-center, with blade 7 being closer to the center of the barrel and blade 6 more distant. This gives the domain an overall oval shape.

Figure 4:
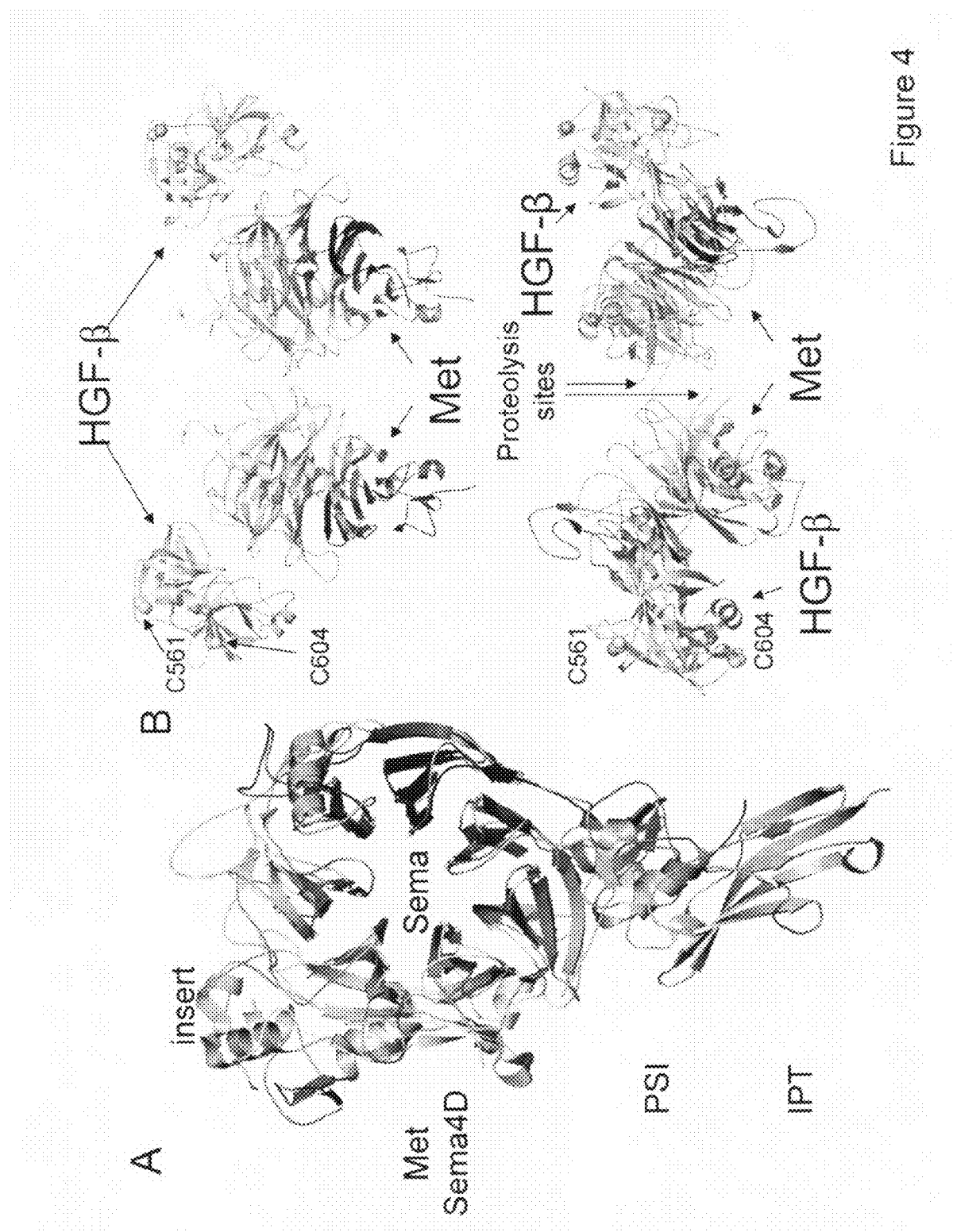
FIG. 4A shows a superposition representation of Met and Sema4D. Note the structural similarities within the β-propellers and the differences in the insertions. The topology of the PSI domains in both structures is identical, but the relative orientation in comparison to the Sema domains is rather different.
FIGS. 4B and 4C shows two different views of a model of a potential Met-dimer based on the dimer of Sema4D and the superposition shown in FIG. 4A. The interface between the two molecules forming the Sema4D dimer is large and buries approximately 2,500 Å$^2$. If this dimerization interface were present on Met, the respective interface in Met would be much smaller due to the different conformation of the loops that correspond to the loops forming the dimer interface in Sema4D. Also shown are two HGF β molecules. Residues shown as spheres represent Cys604 (C604) and Cys561 (C561), which are potential disulfide partners of Cys487 in the α-chain of HGF.

The β-propeller of the Met Sema domain is structurally most closely related to the recently reported crystal structures of Sema4D (Love et al., 2003) and Sema3A (Antipenkov et al., 2003). With the exception of the D-strands in blades 3 and 5, the core of Sema4D and the Met Sema domain align well (FIGS. 3 and 4) and the superposition of residues 40 to 519 with the Sema domain of Sema4D results in an rmsd of 1.6 Å for 303 atom pairs (FIG. 4). The residues that form strand D5 in Sema4A are hydrogen bonded to strand D4 in Met, thus the 4th blade of Met contains an extra strand while blade 5 is missing its strand D. While the core of both proteins align well, the loops contain a number of insertions or deletions and generally adopt very different conformations. For example, the Sema domains of Met and of Sema4D both have an insert of about 20 residues following strand D1. In Met, these residues form a short antiparallel two-stranded β-sheet, while Sema4D has an α-helix (FIGS. 3 and 4). Of the 24 loops that connect the various strands, only 3 have no insertions or deletions when comparing Met with Sema4D or Sema3A (FIG. 3). Interestingly, both the Semaphorins and the Met receptor have their largest insertion between strands C5 and A6; however, these inserts are not related in structure or sequence to each other. In Sema3A, this insert is involved in dimer formation and has been shown to be important for neuropilin binding (Antipenko et al., 2003). In the Met Sema domain, some of the residues within the insert are disordered and not included in our model (see FIG. 2). The function of the insert in Met is not known but its proximity to the HGF β-chain binding site, discussed below, suggests that it might be involved in binding to the α-chain of HGF.

The loop containing the cleavage site between the α- and β-chain of Met connects strand D4 to A5; it is disordered in the electron density. After processing of native Met, the α-chain, which forms the N-terminal 4 blades of the Sema domain, and the α-chain remain connected via at least 2 disulfide bonds. One disulfide bond is formed between residues Cys298 on strand D4 and Cys363 on C5, and the second is formed between Cys282 (D3) and Cys409. This last cysteine is positioned in a disordered region of the insert after blade 4. The electron density does not allow tracing of the main chain in this area but there is sufficient density in the area of the Sγ position to suggest that the disulfide bond is at least partially formed. With the exception of the N-terminal Cys26, which is disordered in the presently disclosed crystal structure and has no potential partner in the construct that was used for crystallization, all cysteine residues are engaged in disulfide bonds. It is unclear if Cys26 remains unpaired in the context of full length Met receptor or if it forms a disulfide bond with another cysteine that resides in the IPT domains. Besides the two disulfide bonds that covalently connect the α- and β-chain of the Sema domain, the domain is stabilized by 5 additional disulfide bridges formed between Cys95-Cys10, Cys98-Cys159, Cys133-Cys141, Cys172-Cys175, and Cys385-Cys397 (FIG. 3).

The surface of the Met Sema domain appears to be mostly negatively charged, especially in the center of the bottom face of the Sema domain (FIG. 2C). This surface, which is formed by a 20 residue insertion after strand D in the first blade and includes the rather irregular area of strand D in the third blade, shows clusters of acidic residues. Monomeric, full length Met was shown to bind to heparin (Gherardi et al., 2003). In the presently disclosed structure there are no dominant positively charged patches within the Met Sema domain; however, two arginines are located in the vicinity of the disordered furin-cleavage site. Together with the 6 positively charged residues that reside in this loop, these arginines could constitute a potential heparin binding site.

The last strand of the Sema domain (C7) is followed immediately by the PSI domain. This domain, with dimensions of about 20×15 Å, contains four (4) disulfide bridges and is not an integral part of the Sema domain but rather an independent structural module. The small core of the domain is formed by a helix and a short two-stranded antiparallel β-sheet that are connected via a disulfide bond and sandwich the side-chain of Trp540. Superposition of this domain with the PSI domain of Sema4D results in an rmsd of 1.6 Å for 41 $C_\alpha$ pairs. The relative orientation between the Sema and the PSI domains in the Met and the Sema4D structures, however, is different and requires a rotation of about 40° for superposition.

Th Interface Between the HGF β-Chain and Met

The HGF β-chain binds to the Sema domain of Met at the bottom face of the propeller, and forms contacts with residues that protrude from blades 2 and 3 (FIGS. 2 and 3). This is unlike other β-propeller containing receptors, such as the integrins, which bind their ligands utilizing the top face of the propeller (Xiong et al., 2002). Other Sema domain containing proteins, such as Sema3A and Sema4D, are also postulated to bind ligands using the top face (Antipenko et al., 2003; Love et al., 2003).

The interface between HGF β-chain and Met buries a total of 1770 Å$^2$ of solvent accessible surface and is dominated by polar or charge-charge interactions. The volume of the cavity of the pocket that is blocked by Met on the surface of HGF β is about 380 cubic angstroms as determined by placing a number of atoms at the entrance of the pocket to close the pocket and using the program GRASP (available from Columbia University at honigts@columbia/edu) to calculate the volume of the resulting cavity.

Of the 20 HGF β residues that have more that 10 Å$^2$ buried in the interface, 6 are positively charged, 3 carry negative charges, and 3 are aromatic. The positively charged amino acids include K516, R533, R647, R695, K649, and R702. The negatively charged amino acids include E656, E670, and D578. The aromatic amino acids include Y513, Y673, and Y619. (See Table 3).

Even more dramatic, of the 18 residues contributing more than 10 Å$^2$ of buried surface to the interface on the Met receptor, 6 carry negative charges, 4 are positively charged and 3 are aromatic. The positively charged amino acid residues include H148, R191, R218, and K223. The negatively charged amino acids include D127, D128, E168, E221, and D224. The aromatic amino acids include Y125, Y126, and F192. The combined buried surface of the hydrophobic residues Ala, Val, Leu, Ile, Met and Phe amounts to a mere 145 Å$^2$, while the charged residues Asp, Glu, Lys, Arg, and His are responsible for more than 1,000 Å$^2$ of buried surface. The resolution of the presently disclosed structure does not permit a detailed discussion of hydrogen bonds; however, the position of the side chains suggest the presence of at least 7 charged interactions between Met and the HGF β-chain. In some embodiments, variants of HGF beta or Met receptor may be designed to preserve and/or strengthen these charge interactions. In other embodiments, small molecules may be designed to mimic the charge-charge interaction of either the HGF β binding site for Met or the Met binding site for HGF β. (See Table 3).

On HGF, the residues analogous to those responsible for substrate binding and catalysis in the related serine proteases form most of the interactions with Met. Serine proteases bind linear peptides to their recognition site and form hydrogen bonds to main chain atoms to position a specific peptide bond for proteolytic cleavage. In contrast, the HGF β-chain binds to a series of protruding polar side chains from Met that comprise amino acid residues from 3 separate loops (FIG. 5B). The first of these loops includes residues 124-128 of Met and connects strands A2 and B2 of Met. This loop contains two tyrosines that are in the core of the binding interface and pack against Arg695 of HGF β. The second loop of Met that contacts HGF β-chain includes residues Asp190, Arg191, and Phe192 and connects A3 and B3. Asp190 of Met forms charged interactions with Arg533 of HGF. The side chain of Arg191 of Met packs against Val692 and Pro693 of HGF with its hydrophobic portion and in the presently disclosed model is in hydrogen bonding distance to the side chains of Glu656 and Asp578 with its guanidinium group. This Asp578 corresponds to aspartic acid [c102] in the catalytic triad of the related serine proteases. Furthermore, the backbone of this loop forms hydrophilic interactions with Gln534, the residue homologous to the histidine [c57] of the protease catalytic triad.

Figure 5:
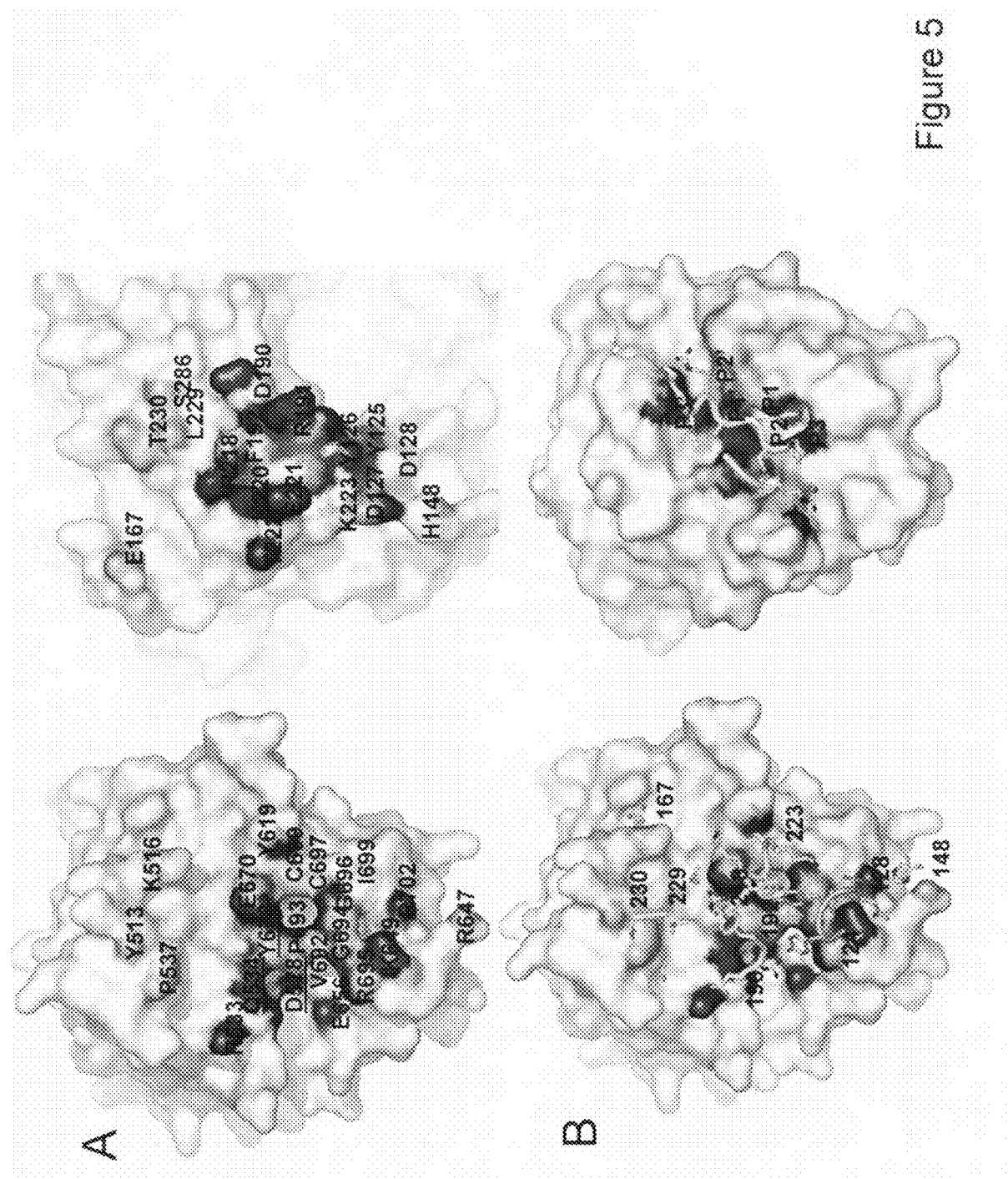
FIG. 5A shows an open-book surface representation view of the Met-HGF complex interface. Atoms of an amino acid residues of HGF β (shown on the left) that are closer than about 4.7 Å to an atom of an amino acid of Met include Y513, K516, R533, Q534, P537, Y673, E670, Y619, D578, R647, P693, C669, V692, C697, E656, G694, G696, R695, I699, K649, and R702. Atoms of an amino acid residues of Met (shown on the right) closer than about 4.7 Å to an atom of an amino acid residues of HGF β include R218, K220, E221, T222, L229, T230, E167, D190, R191, F192, K223, Y126, D127, D128, H148, S286, and Y125. Contact residues are labeled. HGF is on the left side and Met is on the right side. The three underlined amino acid residue numbers indicate the residues that form the catalytic triad in serine proteases.
FIG. 5B shows differences in binding mode between a HGF:Met complex (left) and a trypsin:BPTI (pdb 2PTC) complex (right). Orientations of HGF and trypsin are similar to the view in FIG. 1. Contact residues of Met are shown as sticks. The numbers refer to Met residues. Contact residues of BPTI are also shown as sticks and the "P" number labels refer to BPTI residues.
Figure 6:
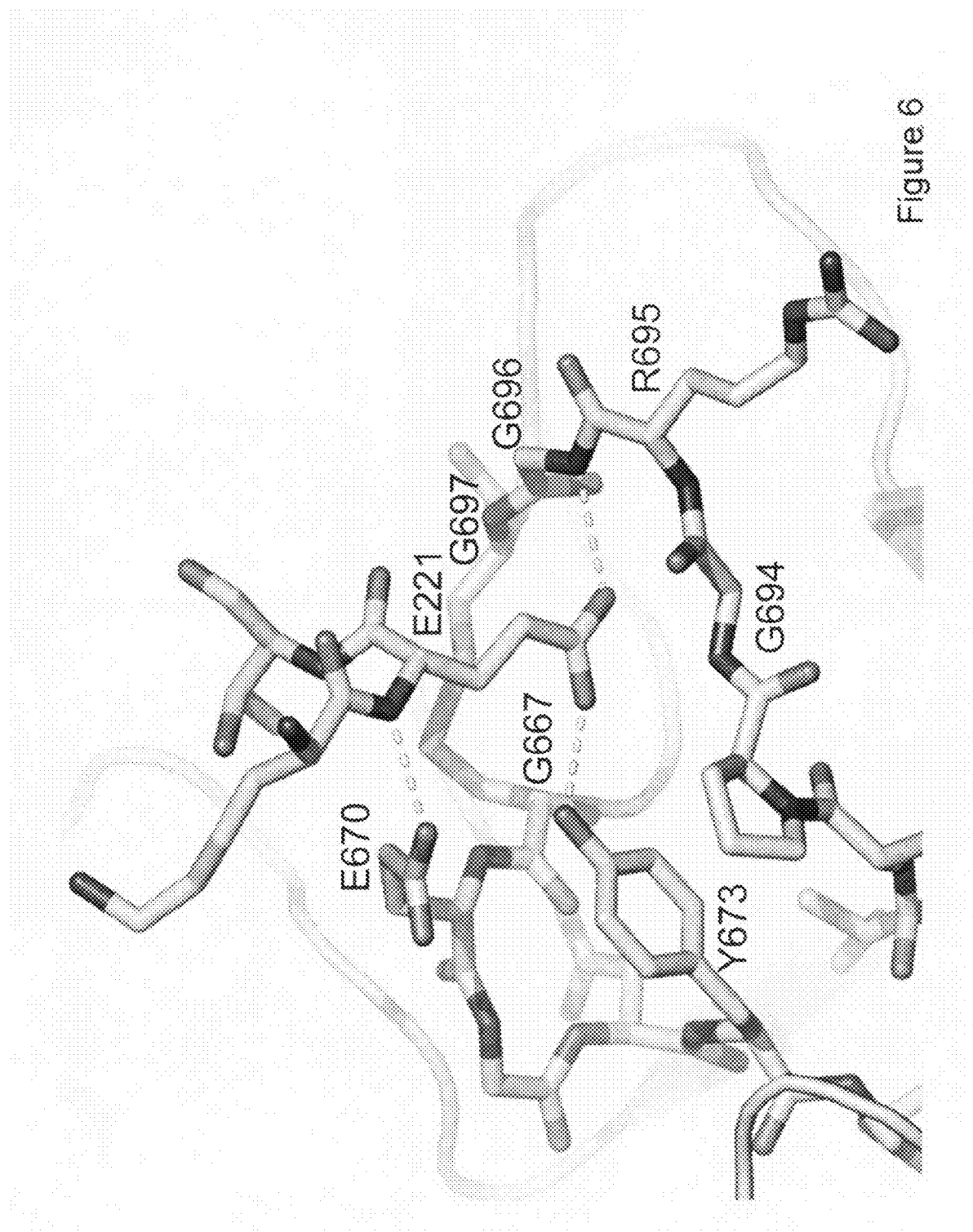
FIG. 6 shows a view of the 'S1-pocket' of HGF β. Selected numbered residues that form the 'S1 pocket' of HGF are shown as sticks with gray carbons. Glu221 (E221) of Met is shown. The dotted lines indicate potential hydrogen bonds between HGF β and Met amino acid residues.

The third segment contributing to the interface also includes strand D in the third blade of the propeller, an area that deviates from the classical 'propeller fold'. Strand D is interrupted and has a short helical insert within its strand. This unusual conformation presents a number of residues towards the surface of the HGF β-chain. The most prominent interaction formed by this loop involves Glu221 which extends its side chain towards what would be the S1 binding site in serine proteases (FIGS. 5 and 6). The carboxylate of Glu221 forms an extensive network of polar interactions with the side chain of Tyr673 (corresponding to the serine [c195] of the catalytic triad in proteases), as well as the backbone amides of Gly694 and Gly696 (FIG. 6); however, unlike in serine proteases, where the S1 pocket is filled by the specificity determining P1 residue, it does not penetrate deeply into the S1 pocket. As a result of the exchange of Ser to Tyr in position 673 [c195], the entrance of the S1 pocket is much smaller than in the related proteases. Thus, Glu221 projects towards the entrance of the S1 pocket from a different angle when compared to a complex between trypsin and bovine pancreatic trypsin inhibitor (BPTI) and does not fill the pocket (FIG. 6). Therefore, a large cavity, presumably filled with a number of water molecules, remains in HGF β-chain.

Comparison of HGF β-Chain Unbound and Bound to Met

The structures of the HGF β-chain bound to Met and HGF β in its unbound state, as disclosed in application U.S. Ser. No. 60/569,301, filed May 6, 2004, which is hereby incorporated by reference, are very similar and superimpose with an rmsd of less than 0.8 Å for 218 $C_\alpha$-pairs. The only significant differences between the two structures involve residues that are close to the Met binding interface. The backbone of residues 645 to 651 is disordered in unliganded HGF β but well defined in the structure of the complex, where it adopts a conformation that is commonly observed in serine proteases (FIG. 1). The side chains of the basic residues Arg647 and Lys649 are not well defined in the electron density but project towards the Met binding interface and, in presently disclosed model, participate in the formation of the complex. Arg695 also undergoes a change in conformation upon Met binding. This residue, located in the center of the receptor binding interface, packs against Tyr125 of Met, and its backbone forms part of the S1 pocket. In the structure of unliganded HGF β, the conformation of the backbone in this area is different, and the side chain of Arg695 projects toward the disordered region of the structure. It is conceivable that the binding event alters the position of Arg695, which in turn allows residues 645 to 651 to adopt a more stable conformation. The tunnel or void identified in the crystal structure of HGF β is also seen in the cocrystal.

3. Structurally Equivalent Crystal Structures

Various computational analyses can be used to determine whether a molecule or portions of the molecule defining structure features are "structurally equivalent," defined in terms of its three-dimensional structure, to all or part of a Met receptor or HGF β:Met complex or its ligand binding sites. Such analyses may be carried out in current software applications, such as the Molecular Similarity application of QUANTA (Molecular Simulations Inc., San Diego, Calif.), Version 4.1, and as described in the accompanying User's Guide.

The Molecular Similarity application permits comparisons between different structures, different conformations of the same structure, and different parts of the same structure. A procedure used in Molecular Similarity to compare structures comprises: 1) loading the structures to be compared; 2) defining the atom equivalences in these structures; 3) performing a fitting operation; and 4) analyzing the results.

One structure is identified as the target (i.e., the fixed structure); all remaining structures are working structures (i.e., moving structures). Since atom equivalency within QUANTA is defined by user input, for the purpose of this disclosure equivalent atoms are defined as protein backbone atoms (N, Cα, C, and O) for all conserved residues between the two structures being compared. A conserved residue is defined as a residue that is structurally or functionally equivalent. Only rigid fitting operations are considered.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in Angstroms, is reported by QUANTA.

Structurally equivalent crystal structures have portions of the two molecules that are substantially identical, within an acceptable margin of error. The margin of error can be calculated by methods known to those of skill in the art In some embodiments, any molecule or molecular complex or any portion thereof, that has a root mean square deviation of conserved residue backbone atoms (N, Cα, C, O) of less than about 0.70 Å, preferably 0.5 Å. For example, structurally equivalent molecules or molecular complexes are those that are defined by the entire set of structure coordinates listed in Table 2±a root mean square deviation from the conserved backbone atoms of those amino acids of not more than 0.70 Å, preferably 0.5 Å. The term "root mean square deviation" means the square root of the arithmetic mean of the squares of the deviations. It is a way to express the deviation or variation from a trend or object. For purposes of this disclosure, the "root mean square deviation" defines the variation in the backbone of a protein from the backbone of HGF β:Met complex (as defined by the structure coordinates of the complex as described herein) or a defining structural feature thereof.

4. Structurally Homologous Molecules, Molecular Complexes, and Crystal Structures Structure coordinates can be used to aid in obtaining structural information about another crystallized molecule or molecular complex. The method of the disclosure allows determination of at least a portion of the three-dimensional structure of molecules or molecular complexes that contain one or more structural features that are similar to structural features of at least a portion of Met receptor or HGF β:Met complex. These molecules are referred to herein as "structurally homologous" to Met receptor or HGF β:Met. Similar structural features can include, for example, regions of amino acid identity, conserved active site or binding site motifs, and similarly arranged secondary structural elements (e.g. binding sites for HGF β, PSI domain, IPT domain, and propellor blades of the Sema domain).

Optionally, structural homology is determined by aligning the residues of the two amino acid sequences to optimize the number of identical amino acids along the lengths of their sequences; gaps in either or both sequences are permitted in making the alignment in order to optimize the number of identical amino acids, although the amino acids in each sequence must nonetheless remain in their proper order. Two amino acid sequences are compared using the BLAST program, version 2.0.9, of the BLAST 2 search algorithm, as described by Tatusova et al. (56), and available at http:www.ncbi.nlm.nih.gov/BLAST/. Preferably, the default values for all BLAST 2 search parameters are used, including matrix BLOSUM62; open gap penalty=11, extension gap penalty=1, gap x_dropoff=50, expect=10, wordsize=3, and filter on. In the comparison of two amino acid sequences using the BLAST search algorithm, structural similarity is referred to as "identity."

In some embodiments, a structurally homologous molecule is a protein that has an amino acid sequence sharing at least 80% identity with a native or recombinant amino acid sequence of Met, preferably an extracellular fragment of the Met receptor comprising a sequence of SEQ ID NO:3 or SEQ ID NO:10. An extracellular fragment of Met receptor comprising a sequence of SEQ ID NO:3 has amino acid substitutions at positions 304-308 to insert a thrombin cleavage site. In some embodiments, a Met receptor has a sequence of SEQ ID NO:3 and the structurally homologous molecule is a variant that has a % sequence identity to SEQ ID NO: 3 of at least 80%, 81%, 82%, 83%, 84%, 85%, 86%, 87%, 88%, 89%, 90%, 91%, 92%, 93%, 94%, 95%, 96%, 97%, 98% or 99% or greater. In some embodiments, the Met receptor variant or structurally homologous molecule has one or more conservative amino acid substitutions, preferably only conservative amino acid substitutions and retains the structure of the binding site for HGF β. In some embodiments, the Met receptor variant has about 1-25 conservative amino acid substitutions, more preferably about 1-20 conservative amino acids substitutions, more preferably about 1-10 conservative amino acid substitutions, more preferably about 1-5 conservative amino acid substitutions, and more preferably about 1-2 conservative amino acid substitutions. Preferably, the variant retains at least one or more domains such as the binding site for HGF β. More preferably, a protein that is structurally homologous to Met includes at least one contiguous stretch of at least 50 amino acids that shares at least 80% amino acid sequence identity with the analogous portion of the native or recombinant Met. Methods for generating structural information about the structurally homologous molecule or molecular complex are well known and include, for example, molecular replacement techniques.

Therefore, in another embodiment this disclosure provides a method of utilizing molecular replacement to obtain structural information about a molecule or molecular complex whose structure is unknown comprising:

(a) generating an X-ray diffraction pattern from a crystallized molecule or molecular complex of unknown or incompletely known structure; and/or (b) applying at least a portion of the structural coordinates of the Met receptor or HGF β:Met complex to the X-ray diffraction pattern to generate a three-dimensional electron density map of the molecule or molecular complex whose structure is unknown or incompletely known.

By using molecular replacement, all or part of the structure coordinates of the Met receptor and/or HGF β:Met complex as provided by this disclosure can be used to determine the unsolved structure of a crystallized molecule or molecular complex more quickly and efficiently than attempting to determine such information ab initio. Coordinates of structural features of the Met receptor can be utilized including the Sema domain, PSI domain and the binding site for HGF β.

Molecular replacement can provide an accurate estimation of the phases for an unknown or incompletely known structure. Phases are one factor in equations that are used to solve crystal structures, and this factor cannot be determined directly. Obtaining accurate values for the phases, by methods other than molecular replacement, can be a time-consuming process that involves iterative cycles of approximations and refinements and greatly hinders the solution of crystal structures. However, when the crystal structure of a protein containing at least a structurally homologous portion has been solved, molecular replacement using the known structure provide a useful estimate of the phases for the unknown or incompletely known structure.

Thus, this method involves generating a preliminary model of a molecule or molecular complex whose structure coordinates are unknown, by orienting and positioning the relevant portion of the Met receptor and/or HGF β:Met complex within the unit cell of the crystal of the unknown molecule or molecular complex. This orientation or positioning is conducted so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure. This map, in turn, can be subjected to established and well-known model building and structure refinement techniques to provide a final, accurate structure of the unknown crystallized molecule or molecular complex (see for example, Lattman, 1985. *Methods in Enzymology* 115:55-77).

Structural information about a portion of any crystallized molecule or molecular complex that is sufficiently structurally homologous to a portion of the Met receptor and/or HGF β:Met can be resolved by this method. In addition to a molecule that shares one or more structural features with the Met receptor, such as the Sema domain, and/or HGF β:Met as described above, a molecule that has similar bioactivity, such as the same catalytic activity, substrate specificity or ligand binding activity as the Met receptor and/or HGF β:Met, may also be sufficiently structurally homologous to a portion of the Met receptor and/or HGF β:Met to permit use of the structure coordinates of HGF β:Met to solve its crystal structure or identify structural features that are similar to those identified in the Met receptor described herein. It will be appreciated that amino acid residues in the structurally homologous molecule identified as corresponding to the Met receptor structural feature may have different amino acid numbering.

In one embodiment of the disclosure, the method of molecular replacement is utilized to obtain structural information about a molecule or molecular complex, wherein the molecule or molecular complex includes at least one HGF β:Met or Met receptor subunit or homolog. In the context of the present disclosure, a "structural homolog" of the Met receptor or HGF β:Met is a protein that contains one or more amino acid substitutions, deletions, additions, or rearrangements with respect to the amino acid sequence of HGF β:Met complex or Met receptor, but that, when folded into its native conformation, exhibits or is reasonably expected to exhibit at least a portion of the tertiary (three-dimensional) structure of at least a portion of the Met receptor and/or HGF β:Met complex. A portion of the Met receptor includes the Sema domain, PSI domain, IPT domains, and binding site for HGF β and combinations thereof.

For example, structurally homologous molecules can contain deletions or additions of one or more contiguous or noncontiguous amino acids, such as a loop or a domain. Structurally homologous molecules also include "modified" extracellular fragment of the Met receptor and/or HGF β:Met molecules that have been chemically or enzymatically derivatized at one or more constituent amino acid, including side chain modifications, backbone modifications, and N- and C-terminal modifications including acetylation, hydroxylation, methylation, amidation, and the attachment of carbohydrate or lipid moieties, cofactors, and like modifications. It will be appreciated that amino acid residues in the structurally homologous molecule identified as corresponding to extracellular fragment of the Met receptor or other structural feature of the Sema domain of the Met receptor may have different amino acid numbering.

A heavy atom derivative of HGF β:Met is also included as a HGF β:Met homolog. The term "heavy atom derivative" refers to derivatives of HGF β:Met produced by chemically modifying a crystal of HGF β or Met or both. In practice, a crystal is soaked in a solution containing heavy metal atom salts, or organometallic compounds, e.g., lead chloride, gold thiomalate, thiomersal or uranyl acetate, which can diffuse through the crystal and bind to the surface of the protein. The location(s) of the bound heavy metal atom(s) can be determined by X-ray diffraction analysis of the soaked crystal. This information, in turn, is used to generate the phase information used to construct three-dimensional structure of the protein (Blundell, et al., 1976, *Protein Crystallography*, Academic Press, San Diego, Calif.).

The structure coordinates of HGF β:Met provided by this disclosure are particularly useful in solving the structure of Met variants. Variants may be prepared, for example, by expression of Met cDNA previously altered in its coding sequence by oligonucleotide-directed mutagenesis as described herein. Variants may also be generated by site-specific incorporation of unnatural amino acids into Met proteins using known biosynthetic methods (Noren, et al., 1989, *Science* 244:182-88). In this method, the codon encoding the amino acid of interest in wild-type Met is replaced by a "blank" nonsense codon, TAG, using oligonucleotide-directed mutagenesis. A suppressor tRNA directed against this codon is then chemically aminoacylated in vitro with the desired unnatural amino acid. The aminoacylated tRNA is then added to an in vitro translation system to yield a mutant Met with the site-specific incorporated unnatural amino acid.

The structure coordinates of HGF β:Met are also particularly useful to solve or model the structure of crystals of HGF β, Met, HGF β variants, Met variants, or Met homologs or HGF β homologs which are co-complexed with a variety of ligands. HGF β is an inhibitor of full length HGF and can be used to identify or design other like inhibitors. This approach enables the determination of the optimal sites for interaction between ligand entities, including candidate HGF β or Met ligands. Potential sites for modification within the various binding sites of the molecule can also be identified. This information provides an additional tool for determining more efficient binding interactions, for example, increased hydrophobic or polar interactions, between Met and a ligand. For example, high-resolution X-ray diffraction data collected from crystals exposed to different types of solvent allows the determination of where each type of solvent molecule resides. Small molecules that bind tightly to those sites can then be designed and synthesized and tested for their Met affinity, such as inhibition activity.

In another embodiment, homology modeling can be conducted using the structural coordinates of HGF β and/or the Met receptor and a program designed to generate models of structures, such as Protein Explorer, Swiss Model, or RASMOL. The programs can provide a structural model of a homolog or variant of HGF β and/or Met by providing the structural coordinates such as provided in Table 2 and an alignment of the sequences.

All of the complexes referred to above may be studied using well-known X-ray diffraction techniques and may be refined versus 1.5-3.5 Å resolution X-ray data to an R-factor of about 0.30 or less using computer software, such as X-PLOR (Yale University, distributed by Molecular Simulations, Inc.)(see for example, Blundell, et al. 1976. *Protein Crystallography*, Academic Press, San Diego, Calif., and *Methods in Enzymology*, Vol. 114 & 115, H. W. Wyckoff et al., eds., Academic Press (1985)). This information may thus be used to optimize known Met modulators, and more importantly, to design new Met modulators.

The disclosure also includes the unique three-dimensional configuration defined by a set of points defined by the structure coordinates for a molecule or molecular complex structurally homologous to an extracellular fragment of the Met receptor or HGF β:Met complex as determined using the method of the present disclosure, structurally equivalent configurations, and magnetic storage media including such set of structure coordinates.

4. Homology modeling

Using homology modeling, a computer model of a HGF β:Met complex or Met receptor homolog can be built or refined without crystallizing the homolog. First, a preliminary model of the homolog is created by sequence alignment with HGF β:Met or an extracellular fragment of Met, secondary structure prediction, the screening of structural libraries, or any combination of those techniques. Computational software may be used to carry out the sequence alignments and the secondary structure predictions. Programs available for such an analysis include Protein Explorer (eg available at molvissdsc.edu.protexpl.frontdoor.htm), Swiss Model (eg available at swissmodel.expasy.org) and RASMOL.Structural incoherences, e.g., structural fragments around insertions and deletions, can be modeled by screening a structural library for peptides of the desired length and with a suitable conformation. For prediction of the side chain conformation, a side chain rotamer library may be employed. If the homolog has been crystallized, the final homology model can be used to solve the crystal structure of the homolog by molecular replacement, as described above. Next, the preliminary model is subjected to energy minimization to yield an energy-minimized model. The energy-minimized model may contain regions where stereochemistry restraints are violated, in which case such regions are remodeled to obtain a final homology model. The homology model is positioned according to the results of molecular replacement, and subjected to further refinement including molecular dynamics calculations.

6. Methods for Identification of Modulators of HGF β:Met

Potent and selective ligands that modulate activity (antagonists and agonists) are identified using the three-dimensional model of the Met binding site for HGF β and/or other structural features produced using the coordinates of a cocrystal of HGF β with Met or a fragment thereof, such as provided in Table 2. Using this model, ligands that interact with the Met binding site for HGF β are identified, and the result of the interactions is modeled. In some embodiments, agents identified as candidate molecules for modulating the activity of HGF, Met and/or HGF β:Met can be screened against known bioassays. For example, the ability of an agent to inhibit the anti-apoptotic effects of Met can be measured using assays known in the art, or for example, the assays disclosed in the Examples. Using the modeling information and the assays described, one can identify agents that possess HGF, Met and/or HGF β:Met—modulating properties.

The methods of the disclosure also include methods of identifying molecules that mimic HGF β binding to a ligand (such as the Met receptor) or Met receptor binding to HGF β or both, but do not activate the HGF/Met signaling pathway. HGF β is an inhibitor of full length HGF and can be used to identify or design other like inhibitors. These molecules can be identified using the three-dimensional model of HGF β:Met complex using the coordinates of Tables 7 and 2.

In another embodiment, a candidate modulator can be identified using a biological assay such as binding to HGF and/or HGF β, modulating Met phosphorylation or modulating HGF induced cell migration. The candidate modulator can then serve as a model to design similar agents and/or to modify the candidate modulator for example, to improve characteristics such as binding to HGF β or Met receptor. Design or modification of candidate modulators can be accomplished using the crystal structure coordinates and available software.

Binding Site and Other Structural Features

Applicants' disclosure provides information inter alia about the shape and structure of the structural binding site of Met for HGF β in the presence or absence of a modulator. Binding sites are of significant utility in fields such as drug discovery. The association of natural ligands or substrates with the binding sites of their corresponding receptors or enzymes is the basis of many biological mechanisms of action. Similarly, many drugs exert their biological effects through association with the binding sites of receptors and enzymes. Such associations may occur with all or any part of the binding site. An understanding of such associations helps lead to the design of drugs having more favorable associations with their target, and thus improved biological effects. Therefore, this information is valuable in designing potential modulators of HGF, Met and/or HGF β:Met binding sites, as discussed in more detail below.

The amino acid constituents of a Met or HGF β:Met binding site as defined herein are positioned in three dimensions. In one aspect, the structure coordinates defining a binding site of Met or HGF β:Met include structure coordinates of all atoms in the constituent amino acids; in another aspect, the structure coordinates of a binding site include structure coordinates of just the backbone atoms of the constituent atoms.

In some embodiments, the HGF β structural binding site for Met, for example, includes the amino acids highlighted in FIG. 5A as well as those identified in Table 3. In some embodiments, the amino acid residues identified in the HGF β binding site for Met comprise, consist essentially of, or consist of at least one or more or all amino acid residue corresponding to residues 513, 516, 533, 534, 537, 578, 619, 647, 649, 656, 669, 670, 673, 692, 693, 694, 695, 696, 697, 699 or 702 or mixtures thereof. In some embodiments, the amino acid residues identified in the HGF β binding site for Met comprise, consist essentially of, or consist of at least one or more or all amino acid residue corresponding to residues Y513, K516, R533, Q 534, P537, D 578, Y619, R647, K 649, E656, C669, E670, Y673, V692, P693, G694, R695, G 696, C697, I699 or R702 or mixtures thereof, or conservative amino acid substitutions thereof. The cocrystallization studies indicate that amino acids residues 645 to 651 are better ordered in the HGF β:Met complex and further indicate that K649 contacts the Met receptor. In other embodiments, the amino acid residues identified in the HGF β binding site for Met comprise, consist essentially of, or consist of at least one or more or all amino acid residue corresponding to residues Y513, K516, R533, Q534, F536, P537, S538, R539, D578, Y619, R647, K649, E656, P668, C669, E670, Y673, V692, P693, G694, R695, C696, C697, I699, R702 or mixtures thereof or conservative amino acid substitutions thereof. These residues may participate in polar or nonpolar interactions with charged residues on Met.

The term "Met structural binding site" includes all or a portion of a molecule or molecular complex whose shape is sufficiently similar to at least a portion of a binding site of Met for HGF β as to be expected to bind HGF β or related structural analogs. A structurally equivalent ligand binding site is defined by a root mean square deviation from the structure coordinates of the backbone atoms of the amino acids that make up binding sites in Met of at most about 0.70 Å, preferably about 0.5 Å. In some embodiments, the Met structural binding site for HGF β, for example, includes the amino acids highlighted in FIG. 5B as well as those identified in Table 3. In some embodiments, a structural binding site for HGF β on the Met receptor comprises, consists essentially of, or consists of at least one or more or all amino acid residues corresponding to residues 124-128, 148, 167, 190-192, 218, 220 to 223, 229 to 230, or 286, 414 or mixtures thereof. In some embodiments, a structural binding site for HGF β on the Met receptor comprises, consists essentially of, or consists of at least one or more or all amino acid residue corresponding to residues T124, Y125, Y126, D127, D128, H148, E167, E168, D190, R191, F192, R218, K220, E221, T222, K223, D224, M227, L229, T230, I284, S286, D414, or mixtures thereof or conservative substitutions thereof. These residues may participate in polar interactions with charged residues on HGF β.

The binding site of HGF β or Met may be defined by those amino acids whose backbone atoms are situated within about 5 Å of one or more constituent atoms of a bound substrate or ligand. In yet another alternative, the binding site for HGF β on Met receptor can be defined by those amino acids whose backbone atoms are situated within a sphere centered on the coordinates representing the alpha carbon atom of amino acid E221 on the Met receptor, the sphere having a radius of about 5-6 Å, for example 5.8 Å.

Other structural features include the blades of the propellor of the Sema domain of the Met receptor and those that define the void in the center of the propellor, as well as the domains of the Met receptor including PSI and IPT domains. Amino acid residues that form these structural features can be found in FIG. 3.

Rational Drug Design

Computational techniques can be used to screen, identify, select, design ligands, and combinations thereof, capable of associating with Met or structurally homologous molecules. Candidate modulators of HGF, HGF β and/or Met may be identified using functional assays, such as binding to HGF β or Met, and novel modulators designed based on the structure of the candidate molecules so identified. Knowledge of the structure coordinates for Met or HGF β:Met permits, for example, the design, the identification of synthetic compounds, and like processes, and the design, the identification of other molecules and like processes, that have a shape complementary to the conformation of the Met and/or HGF β binding sites. In particular, computational techniques can be used to identify or design ligands, such as agonists and/or antagonists, that associate with a Met and/or HGF β binding site. Antagonists may bind to or interfere with all or a portion of an active site of Met, and can be competitive, non-competitive, or uncompetitive inhibitors. Once identified and screened for biological activity, these agonists, antagonists, and combinations thereof, may be used therapeutically and/or prophylactically, for example, to block Met activity and thus prevent the onset and/or further progression of diseases associated with Met activity. Structure-activity data for analogues of ligands that bind to or interfere with Met binding sites and/or HGF β binding sites can also be obtained computationally.

In some embodiments, an antagonist or agonist may be a molecule that mimics either HGF β or the Met receptor such that it binds to either the Met receptor or HGF β or both. HGF β is an inhibitor of full length HGF and can be used to identify or design other like inhibitors. In some embodiments, if the molecule is an antagonist, it binds to either receptor or both but does not activate the Met receptor. As the structural information provided herein indicates that the interaction of the HGF β with the Met receptor includes charge-charge interactions, in some embodiments, agonists or antagonists can be designed to include components that preserve and/or strengthen the charge interactions. Such antagonists or agonists would include components that are able to interact, for example, hydrogen bond with the charged amino acids found in either the HGF β or Met receptor binding site or both. In some embodiments, for HGF β, antagonist or agonist molecules are designed or selected that can interact with at least one or more or all amino acid residues that comprise, consist essentially of, or consist of amino acid residues corresponding to amino acid residues Y513, K516, R533, Y619, R647, R695, K649, R702, E656, E670, Y673, or D578 or mixtures thereof. In some embodiments, for the Met receptor, antagonist or agonist molecules are designed or selected that can interact with at least one or more or all amino acid residues that comprise, consist essentially of, or consist of amino acid residues corresponding to amino acid residues Y125, Y126, H148, R191, R218, K223, D127, D128, E168, F192, E221, or D224 or mixtures thereof. In other embodiments, another criteria that may be utilized in the design of modulators is whether the modulator can fit into the binding site cavity on HGF β that is blocked by Met. The volume of that cavity is about 380 cubic angstroms. The volume of the cavity can be determined by placing atoms in the entrance of the pocket close to the surface and using a program like GRASP to calculate the volume of those atoms.

Data stored in a machine-readable storage medium that is capable of displaying a graphical three-dimensional representation of the structure of Met or a structurally homologous molecule or molecular complex, as identified herein, or portions thereof may thus be advantageously used for drug discovery. The structure coordinates of the ligand are used to generate a three-dimensional image that can be computationally fit to the three-dimensional image of Met, HGF β:Met complex, or a structurally homologous molecule. The three-dimensional molecular structure encoded by the data in the data storage medium can then be computationally evaluated for its ability to associate with ligands. When the molecular structures encoded by the data is displayed in a graphical three-dimensional representation on a computer screen, the protein structure can also be visually inspected for potential association with ligands.

One embodiment of the method of drug design involves evaluating the potential association of a candidate ligand with Met, such as HGF β, or a structurally homologous molecule or homologous complex, particularly with a binding site on the Met receptor. The method of drug design thus includes computationally evaluating the potential of a selected ligand to associate with any of the molecules or molecular complexes set forth above. This method includes the steps of: (a) employing computational means, for example, such as a programmable computer including the appropriate software known in the art or as disclosed herein, to perform a fitting operation between the selected ligand and a ligand binding site or a pocket nearby the ligand binding site of the molecule or molecular complex; and (b) analyzing the results of the fitting operation to quantify the association between the ligand and the ligand binding site. Optionally, the method further comprises analyzing the ability of the selected ligand to interact with charged amino acids in either the HGF β and/or Met receptor binding sites. Other structural features of the Met receptor and/or HGF β: Met complex can also be analyzed in the same manner.

In another embodiment, the method of drug design involves computer-assisted design of ligand that associate with Met, HGF β: Met, its homologs, or portions thereof. Ligands can be designed in a step-wise fashion, one fragment at a time, or may be designed as a whole or de novo. Ligands can be designed based on the structure of molecules that can modulate at least one biological function of HGF β or Met.

In some embodiments, to be a viable drug candidate, the ligand identified or designed according to the method must be capable of structurally associating with at least part of a Met binding site and/or HGF β binding site, and must be able, sterically and energetically, to assume a conformation that allows it to associate with the Met binding site and/or HGF β binding site. Non-covalent molecular interactions important in this association include hydrogen bonding, van der Waals interactions, hydrophobic interactions, and/or electrostatic interactions. In some embodiments, agents may contact at least one amino acid position in the Met binding site for HGF β. Conformational considerations include the overall three-dimensional structure and orientation of the ligand in relation to the ligand binding site, and the spacing between various functional groups of a ligand that directly interact with the Met binding site and/or HGF β binding site or homologs thereof.

Optionally, the potential binding of a ligand to a Met binding site and/or HGF β binding site is analyzed using computer modeling techniques prior to the actual synthesis and testing of the ligand. If these computational experiments suggest insufficient interaction and association between it and the Met binding site, and/or HGF β binding site testing of the ligand is obviated. However, if computer modeling indicates a strong interaction, the molecule may then be synthesized and tested for its ability to bind to or interfere with a Met binding site and/or HGF β binding site. Binding assays to determine if a compound actually modulates with Met activity can also be performed and are well known in the art.

Several methods can be used to screen ligands or fragments for the ability to associate with a Met binding site and/or HGF β binding site. This process may begin by visual inspection of, for example, a Met binding site and/or HGF β binding site on the computer screen based on the Met or HGF β:Met structure coordinates or other coordinates which define a similar shape generated from the machine-readable storage medium. Selected ligands may then be positioned in a variety of orientations, or docked, within the binding site. Docking may be accomplished using software such as QUANTA and SYBYL, followed by energy minimization and molecular dynamics with standard molecular mechanics force fields, such as CHARMM and AMBER.

Specialized computer programs may also assist in the process of selecting ligands. Examples include GRID (Hubbard, S. 1999. *Nature Struct. Biol.* 6:711-4); MCSS (Miranker, et al. 1991. *Proteins* 11:29-34) available from Molecular Simulations, San Diego, Calif.; AUTODOCK (Goodsell, et al. 1990. *Proteins* 8:195-202) available from Scripps Research Institute, La Jolla, Calif.; and DOCK (Kuntz, et al. 1982. *J. Mol. Biol.* 161:269-88) available from University of California, San Francisco, Calif.

For example, an examination of the structure of HGF β shows a tunnel or void formed by amino acid residues 634, 660-670, 673, 691 and 693-706. A molecule with an indole ring can fit within this void as determined by manual docking Met binding ligands can be designed to fit a Met binding site and/or HGF β binding site, optionally as defined by the binding of a known modulator or one identified as modulating the activity of HGF β or Met. Examples of tyrosine kinase inhibitor compounds are disclosed in U.S. Pat. No. 6,696,463. There are many ligand design methods including, without limitation, LUDI (Bohm, 1992. *J. Comput. Aided Molec. Design* 6:61-78) available from Molecular Simulations Inc., San Diego, Calif.; LEGEND (Nishibata, Y., and Itai, A. 1993. *J. Med. Chem.* 36:2921-8) available from Molecular Simulations Inc., San Diego, Calif.; LeapFrog, available from Tripos Associates, St. Louis, Mo.; and SPROUT (Gillet, et al. 1993. *J. Comput. Aided Mol. Design.* 7:127-53) available from the University of Leeds, UK.

Once a compound has been designed or selected by the above methods, the efficiency with which that ligand may bind to or interfere with a Met binding site and/or HGF β binding site may be tested and optimized by computational evaluation. For example, an effective Met binding site ligand and/or HGF β binding site should preferably demonstrate a relatively small difference in energy between its bound and free states (i.e., a small deformation energy of binding). Thus, an efficient Met binding site ligand should preferably be designed with a deformation energy of binding of not greater than about 10 to about 15 kcal/mole, such as about 12 kcal/mole, preferably not greater than about 8 to about 12 kcal/mole, such as about 10 kcal/mole, and more preferably not greater than about 5 to about 10 kcal/mole, such as about 7 kcal/mole. Met binding site and/or HGF β binding site ligands may interact with the binding site in more than one conformation that is similar in overall binding energy. In those cases, the deformation energy of binding is taken to be the difference between the free energy of the ligand and the average energy of the conformations observed when the ligand binds to the protein.

A ligand designed or selected as binding to or interfering with a Met binding site and/or HGF β binding site may be further computationally optimized so that in its bound state it would preferably lack repulsive electrostatic interaction with the target enzyme and with the surrounding water molecules. Such non-complementary electrostatic interactions include repulsive charge-charge, dipole-dipole, and charge-dipole interactions.

Specific computer software is available to evaluate compound deformation energy and electrostatic interactions. Examples of programs designed for such uses include: Gaussian 94, revision C (M. J. Frisch, Gaussian, Inc., Pittsburgh, Pa.); AMBER, version 4.1 (P. A. Kollman, University of California at San Francisco); QUANTA/CHARMM (Molecular Simulations, Inc., San Diego, Calif.); Insight II/Discover (Molecular Simulations, Inc., San Diego, Calif.); DelPhi (Molecular Simulations, Inc., San Diego, Calif.); and AMSOL (Quantum Chemistry Program Exchange, Indiana University). These programs can be implemented, for instance, using a Silicon Graphics workstation, such as an Indigo2 with IMPACT graphics. Other hardware systems and software packages will be known to those skilled in the art.

Another approach encompassed by this disclosure is the computational screening of small molecule databases for ligands or compounds that can bind in whole, or in part, to a Met binding site and/or HGF β binding site. In this screening, the quality of fit of such ligands to the binding site may be judged either by shape complementarity or by estimated interaction energy (Meng, et al., 1992. *J. Comp. Chem.*, 13:505-24). In addition, these small molecule databases can be screened for the ability to interact with the charged amino acids in the Met binding site and/or HGF β binding site as identified herein.

A compound that is identified or designed as a result of any of these methods can be obtained (or synthesized) and tested for its biological activity, for example, binding and/or inhibition of HGF and/or Met activity.

Another method involves assessing agents that are antagonists or agonists of the Met receptor. A method comprises applying at least a portion of the crystallography coordinates of a cocrystal of HGF β and Met, such as provided in Tables 7 and/or 2 to a computer algorithm that generates a three-dimensional model of HGF β: Met complex or the Met receptor suitable for designing molecules that are antagonists or agonists and searching a molecular structure database to identify potential antagonists or agonists. In some embodiments, a portion of the structural coordinates of a cocrystal of HGF β and Met, such as provided in Tables 7 and/or 2 that define a structural feature, for example, binding site for HGF β, may be utilized. The method may further comprise synthesizing or obtaining the agonist or antagonist and contacting the agonist or antagonist with the Met receptor and/or HGF β and selecting the antagonist or agonist that modulates the Met receptor and/or HGF β activity compared to a control without the agonist or antagonists and/or selecting the antagonist or agonist that binds to the Met receptor and/or HGF β. Activities of HGF and/or the Met receptor include phosphorylation of Met, stimulation of cell proliferation, and stimulation of cell migration.

A compound that is identified or designed as a result of any of these methods can be obtained (or synthesized) and tested for its biological activity, for example, binding to HGF β and/or Met receptor and/or modulation of HGF, HGF β and/or Met activity. Other modulators of the Met receptor include, for example, monoclonal antibodies directed against the Met receptor, peptide(s) that can modulate Met receptor function, or small-molecule compounds, such as organic and inorganic molecules, which can be identified with methods of the present disclosure.

7. Machine-Readable Storage Media

Transformation of the structure coordinates for all or a portion of Met or the HGF β:Met complex or one of its ligand binding sites, for structurally homologous molecules as defined below, or for the structural equivalents of any of these molecules or molecular complexes as defined above, into three-dimensional graphical representations of the molecule or complex can be conveniently achieved through the use of commercially-available software.

The disclosure thus further provides a machine-readable storage medium including a data storage material encoded with machine-readable data wherein a machine programmed with instructions for using said data displays a graphical three-dimensional representation of any of the molecule or molecular complexes of this disclosure that have been described above. In a preferred embodiment, the machine-readable data storage medium includes a data storage material encoded with machine-readable data wherein a machine programmed with instructions for using the abovementioned data displays a graphical three-dimensional representation of a molecule or molecular complex including all or any parts of a Met, Met ligand binding site, or Met-like ligand binding site, HGF β, HGF β binding site, or HGFβ:Met complex as defined above. In another preferred embodiment, the machine-readable data storage medium includes a data storage material encoded with machine readable data wherein a machine programmed with instructions for using the data displays a graphical three-dimensional representation of a molecule or molecular complex±a root mean square deviation from the atoms of the amino acids of not more than 0.05 Å.

In an alternative embodiment, the machine-readable data storage medium includes a data storage material encoded with a first set of machine readable data which includes the Fourier transform of structure coordinates, and wherein a machine programmed with instructions for using the data is combined with a second set of machine readable data including the X-ray diffraction pattern of a molecule or molecular complex to determine at least a portion of the structure coordinates corresponding to the second set of machine readable data.

For example, a system for reading a data storage medium may include a computer including a central processing unit ("CPU"), a working memory which may be, for example, RAM (random access memory) or "core" memory, mass storage memory (such as one or more disk drives or CD-ROM drives), one or more display devices (e.g., cathode-ray tube ("CRT") displays, light emitting diode ("LED") displays, liquid crystal displays ("LCDs"), electroluminescent displays, vacuum fluorescent displays, field emission displays ("FEDs"), plasma displays, projection panels, etc.), one or more user input devices (e.g., keyboards, microphones, mice, track balls, touch pads, etc.), one or more input lines, and one or more output lines, all of which are interconnected by a conventional bidirectional system bus. The system may be a stand-alone computer, or may be networked (e.g., through local area networks, wide area networks, intranets, extranets, or the internet) to other systems (e.g., computers, hosts, servers, etc.). The system may also include additional computer controlled devices such as consumer electronics and appliances.

Input hardware may be coupled to the computer by input lines and may be implemented in a variety of ways. Machine-readable data of this disclosure may be inputted via the use of a modem or modems connected by a telephone line or dedicated data line. Alternatively or additionally, the input hardware may include CD-ROM drives or disk drives. In conjunction with a display terminal, a keyboard may also be used as an input device.

Output hardware may be coupled to the computer by output lines and may similarly be implemented by conventional devices. By way of example, the output hardware may include a display device for displaying a graphical representation of a binding site of this disclosure using a program such as QUANTA as described herein. Output hardware might also include a printer, so that hard copy output may be produced, or a disk drive, to store system output for later use.

In operation, a CPU coordinates the use of the various input and output devices, coordinates data accesses from mass storage devices, accesses to and from working memory, and determines the sequence of data processing steps. A number of programs may be used to process the machine-readable data of this disclosure. Such programs are discussed in reference to the computational methods of drug discovery as described herein. References to components of the hardware system are included as appropriate throughout the following description of the data storage medium.

Machine-readable storage devices useful in the present disclosure include, but are not limited to, magnetic devices, electrical devices, optical devices, and combinations thereof. Examples of such data storage devices include, but are not limited to, hard disk devices, CD devices, digital video disk devices, floppy disk devices, removable hard disk devices, magneto-optic disk devices, magnetic tape devices, flash memory devices, bubble memory devices, holographic storage devices, and any other mass storage peripheral device. It should be understood that these storage devices include necessary hardware (e.g., drives, controllers, power supplies, etc.) as well as any necessary media (e.g., disks, flash cards, etc.) to enable the storage of data.

8. Therapeutic Use

HGF, Met, and/or HGF β:Met complex modulator compounds obtained by methods of the invention are useful in a variety of therapeutic settings. For example, Met antagonists designed or identified using the crystal structure of an extracellular fragment of Met or HGF β:Met complex can be used to treat disorders or conditions, where inhibition or prevention of Met binding or activity is indicated.

Likewise, Met agonists designed or identified using the crystal structure of the HGF β:Met complex or an extracellular fragment of Met can be used to treat disorders or conditions, where induction or stimulation of Met activity is indicated.

An indication can be, for example, inhibition or stimulation of Met phosphorylation and the concomitant activation of a complex set of intracellular pathways that lead to cell growth, differentiation, and migration in a variety of cell types. The ability of HGF to stimulate mitogenesis, cell motility, and matrix invasion gives it and the Met receptor a central role in angiogenesis, tumorogenesis and tissue regeneration. Another indication can be, for example, in inhibition or stimulation of embryonic development. Still another indication can be, for example, in inhibition or stimulation of tissue regeneration. Another indication can be, for example, in inhibition of angiogenesis, mitogenesis and/or vasculogenesis. Expression of HGF has been associated with thyroid cancer, colon cancer, lymphoma, prostate cancer, and multiple myeloma. Yet another indication can be, for example, in inhibition or stimulation of the HGF/Met signaling pathway. Still yet another indication can be, for example, in inhibition of invasive tumor growth and metastasis.

Met and/or HGF β:Met complex antagonists are also useful as chemosensitizing agents, useful in combination with other chemotherapeutic drugs, in particular, drugs that induce apoptosis. Examples of other chemotherapeutic drugs that can be used in combination with chemosensitizing Met inhibitors include topoisomerase I inhibitors (e.g., camptothesin or topotecan), topoisomerase II inhibitors (e.g., daunomycin and etoposide), alkylating agents (e.g., cyclophosphamide, melphalan and BCNU), tubulin-directed agents (e.g., taxol and vinblastine), and biological agents (e.g., antibodies such as anti CD20 antibody, IDEC 8, immunotoxins, and cytokines). Examples of other chemotherapeutic drugs that can be used in combination with chemosensitizing HGF β inhibitors include topoisomerase I inhibitors (e.g., camptothecin or topotecan), topoisomerase II inhibitors (e.g., daunomycin and etoposide), alkylating agents (e.g., cyclophosphamide, melphalan and BCNU), tubulin-directed agents (e.g., taxol and vinblastine), and biological agents (e.g., antibodies such as anti CD20 antibody, IDEC 8, anti-VEGF antibody, immunotoxins, and cytokines). Other examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin I and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxy-doxorubicin), epirubicin, esorubic in, idarubicin, marcellomyc in, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carnofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above.

Also included in the definition of "chemotherapeutic agent" above are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

9. Other Uses

The HGF β chain, or variants thereof, form cocrystals with the Met receptor in accord with the methods described herein. The crystals also are useful to store and/or deliver HGF β-chain or Met receptor molecules. HGF β is useful as an inhibitor of full length HGF and can be used to identify or design other like inhibitors. HGF β:Met complex may be useful as a standards in assays including diagnostic assays. Crystals can be prepared and used to store HGF β-chain Met receptor complexes for later use.

A variety of methods are known to those of skill in the art for formation of crystals. In some embodiments, for crystals prepared for storage, the crystal size and structure does not have to be so uniform or homogenous as for X-ray diffraction. In other embodiments, the crystals effectively diffract x-rays to a resolution of 5 Å or better. Typically, a purified polypeptide is contacted with a precipitant in the presence of a buffer. Precipitants include salts, polymers, or organic molecules. Organic precipitants include isopropanol, ethanol, hexanediol, and 2-methyl-2,4-pentanediol. Polymeric precipitants include polyethylene glycol and polyamines. Salts used include ammonium sulfate, sodium citrate, sodium acetate, ammonium dichloride, sodium chloride and magnesium formate. Many buffers can be utilized and are known to those of skill in the art.

In some cases, crystals can be cross-linked to one another. Such cross-linking may enhance the stability of the crystal. Methods of cross-linking crystals are know to those of skill in the art and have been described, for example, in U.S. Pat. No. 5,849,296.

The crystals can be maintained in crystallization solution, they can be dried, or combined with other carriers and/or other ingredients to form compositions and formulations. In some embodiments, the crystals can be combined with a polymeric carrier for stability and sustained release. Formulations of crystals of proteins, such as enzymes, receptors, antibodies, and like molecules, or fragments thereof, can include at least one ingredient or excipient. Ingredient or expedients are known to those of skill in the art and include acidifying agents, aerosol propellants, alcohol denaturants, alkalizing agents, anti-caking agents, antifoaming agents, microbial preservatives, anti-antioxidants, buffering agents, lubricants, chelating agents, colors, desiccants, emulsifying agents, filtering aids, flavors and perfumes, humectants, ointments, plasticizers, solvents (e.g. oils or organic), sorbents, carbon dioxide sorbents, stiffening agents, suppository bases, suspending or viscosity increasing agents, sweetening agents, tablet binders, table or capsule diluents, tablet disintegrants, tablet or capsule lubricants, tonicity agent, flavored or sweetened vehicles, oleaginous vehicles, solid carrier vehicles, water repelling agent, and wetting or solubilizing agents.

In some embodiments, the ingredients enhance storage stability. In other embodiments, the ingredient or excipient is preferably selected from the group consisting of albumin, sucrose, trehalose, lactitol, gelatin, and hydroxypropyl-β-cyclodextran.

All publications, patents, and patent documents are incorporated by reference herein, as though individually incorporated by reference. The disclosure has been described with reference to various specific and preferred embodiments and techniques. However, it should be understood that many variations and modifications can be made while remaining within the spirit and scope of the disclosure.

EXAMPLE 1

Protein Expression and Purification

For crystallization, we used a construct of the Met receptor that contained residues 25 to 567 and an additional C-terminal (His)$_8$-tag. In addition, the cleavage site after residue Arg308, present in the Met receptor family but not in the Sema domain of the Semaphorins or plexins, was replaced with a thrombin cleavable site. This exchange (residues 304 to 308 were exchanged from KRKKR (SEQ ID NO:4) to LVPRG (SEQ ID NO:5)) was introduced since native Met expressed in insect cells was partially cleaved and not homogeneous. Mutation of the cleavage site allowed for the production of homogeneous protein that depending on treatment with thrombin was cleaved or uncleaved. The complex presented here was obtained with the unprocessed, single chain Met.

The HGF β-chain protein used for crystallization begins with residue Val495 (the N-terminal residue obtained after maturation of single chain HGF), and has one alteration from the natural sequence: in full length, mature HGF, the α- and β-chains are covalently tethered by a disulfide bridge putatively formed between Cys487 and Cys604 (Donate et al., 1994). In order to prevent artificial dimerization of HGF β-chains during purification and crystallization, Cys604 was replaced with serine. (SEQ ID NO:1) The complex of the HGF β-chain and the Met fragment was formed in solution, purified using size exclusion chromatography and set up for crystallization trials.

Materials and Methods

The cDNA for the full length Met receptor was kindly provided by D. Wickramasinghe. PCR was carried out on the region encoding residues 25-567 of the Met receptor. A 2-step overlapping PCR scheme was used to introduce the thrombin cleavage site (LVPRG) (SEQ ID NO:5) and remove the native sequence (KRKKR) (SEQ ID NO:4). An N-terminal primer added overlapping sequence with the C-terminus of the insect cell secretion signal present in the pAcGP67A vector (BD Biosciences). A C-terminal primer contained coding sequence for (His)$_8$ and a NotI restriction site added directly onto the C-terminus. For placement into the pAcGP67A vector, an additional PCR was carried out on the coding region for the insect cell secretion signal, with additional overlapping sequence from the N-terminus of our Met construct. A final PCR was done to directly fuse the C-terminus of the secretion signal to the N-terminus of our Met construct. This PCR product, as well as pAcGP67A, were digested with SpeI and NotI. Insert was combined with vector at a 3:1 ratio, ligated, and transformed into XL-1 Blue cells (Stratagene).

Purified plasmid DNA (pAcGP67A plus Met Sema and PSI domain) was transfected into Sf9 insect cells according to the manufacturer's protocol (BD Biosciences). Viral stock was amplified 3 times before use in protein expression. For expression, 1 L of Hi5 insect cells growing in ESF 921 media (Protein Expression, LLC) at a density of 5×10$^5$ cells/mL were infected with 10 mL of viral stock from the 3$^{rd}$ amplification and incubated at 27° C. for 72 hours. Cells were then removed from the supernatant by centrifugation at 3000 g for 15 minutes. 1 mM of NiCl$_2$, 5 mM of CaCl$_2$, and 50 mM Tris pH 8.0 were added to the supernatant. The supernatant was then filtered through a 0.2 µm vacuum filter. Supernatant was applied to a 2 mL Ni-NTA column (Qiagen) by gravity flow, followed by 20 mL of wash buffer (50 mM Tris pH 8.0, 500 mM NaCl, 5 mM imidazole). Protein was eluted with a buffer containing 50 mM Tris 8.0, 300 mM NaCl, 250 mM imidazole. Fractions containing Met were identified by SDS-PAGE analysis and pooled, concentrated to 500 µL, and loaded onto a Superdex S-75 gel filtration column (Amersham Biosciences) equilibrated with 50 mM Tris 8.0, 500 mM NaCl. The final yield for Met (Sema and PSI domain) was approximately 0.25 mg/L of insect cell supernatant.

The amino acid sequence of an extracellular fragment of Met is shown in Table 6. (SEQ ID NO:3). Another embodiment of an extracellular fragment of Met comprises an amino acid sequence of SEQ ID NO:10 and is shown in FIG. 3.

HGF β proteins were expressed in insect cells using baculovirus secretion vector pAcGP67 (Pharmingen, San Diego, Calif.). All constructs contained a His$_6$ tag at the carboxy terminus and were purified to homogeneity (>95% purity) by Ni NTA metal chelate and gel filtration chromatography. For wildtype HGF β, a cDNA fragment encoding the HGF β-chain from residues Val495 [c16] to Ser728 [c250] was cloned by PCR such that Val495 [c16] was inserted immediately after the secretion signal sequence. Site-directed mutagenesis was carried out using QuikChange™ (Stratagene, La Jolla, Calif.) with oligonucleotide 5'CCTAAT-TATGGATCCACAATTCCTG3' (SEQ ID NO:6) to make HGF β containing a Cys604 to Ser mutation (HGF β). The cysteine was not altered in this construct to allow putative disulfide formation between Cys487 and Cys604. Wildtype HGF β (SEQ ID NO:14) refers to the native sequence and HGF β(SEQ ID NO:1) refers to the C604S mutant. Numbering is as follows: full length HGF sequence starting with MWV . . . as numbers 1-3 [chymotrypsinogen numbering is shown in the brackets]. It will be readily apparent that the numbering of amino acids in other isoforms of HGF β may be different than that of the HGF β numbering disclosed herein. The disclosure provides sequential numbering based on sequence only. In embodiments, an isoform may have structural "differences", for example, if it carries insertion(s) or deletion(s) relative to the HGF β reference sequence. The chymotrypsinogen numbering convention may be useful for comparison to workers in the field.

The amino acid sequence of a HGF β is shown in Table 4 (SEQ ID NO:1) and Table 8 (SEQ ID NO:14).

Baculovirus vectors containing the desired inserts were transfected into *Spodoptera frugiperda* (Sf 9) cells on plates in TNM-FH media via the Baculogold™ Expression System according to manufacturer's instructions (Pharmingen, San Diego, Calif.). After 2-4 rounds of virus amplification, 10 mL of viral stock was used to infect 1 L of High Five™ cells (Invitrogen, San Diego, Calif.) in suspension at 5×10$^5$ cells/mL in TNM-FH media. Cultures were incubated at 27° C. for 72 h before harvesting the culture media by centrifugation at 8,000×g for 15 min. Cell culture media was applied to a 4 mL Ni-NTA agarose column (Qiagen, Valencia, Calif.). After washing with 4 column volumes of 50 mM Tris.HCl, pH 8.0, 500 mM NaCl, 5 mM imidazole, HGF β proteins were eluted with 50 mM Tris.HCl pH 8.0, 500 mM NaCl, 500 mM imidazole. The eluate was pooled and applied to a Superdex™-200 column (Amersham Biosciences, Piscataway, N.J.) equilibrated in 10 mM HEPES pH 7.2, 150 mM NaCl, 5 mM CaCl$_2$. Protein peaks were collected and concentrated using a Centriprep™ YM-10 (Millipore, Bedford, Mass.). Fractions were analyzed by 12% SDS-PAGE stained with Coomassie blue.

Met was combined with HGF β-chain in a 1:1.5 ratio and concentrated for loading onto a Superdex S-200 gel filtration column (Amersham Biosciences) equilibrated with 10 mM Tris 8.0, 250 mM NaCl. Elution fractions were assayed with SDS-PAGE, and those containing the complex were pooled. Buffer exchange into 10 mM Tris 8.0, 125 mM NaCl was carried out, and the complex was then concentrated to 10 mg/mL for crystallization trials. Although crystals grew without deglycosylation, diffraction was enhanced after deglycosylating the Met protein. For this, Met, previously purified using Nickel chromatography as described above, was mixed with a combination of PNGase F (Roche) and Endoglycosidase A (Roche) at 1:100 enzyme:Met concentration and incubated at room temperature for 3 hours. Met was then combined with HGF β-chain, concentrated, and loaded onto a gel filtration column as described above for the non-deglycosylated material.

EXAMPLE 2

Crystallization, Data Collection and Refinement

Met/HGF β-chain crystallized at 19° C. in 4 μL hanging drops in a 1:1 ratio of protein to mother liquor, suspended over mother liquor (12-15% PEG 10,000, Tris pH 8.0). Crystals grew to approximately 100 μm×200 μm×200 μm in 3 to 7 days. For data collection, crystals were placed in a solution of mother liquor containing 25% xylitol for 30 seconds, and then flash frozen in liquid $N_2$.

Data were collected at CHESS beamline A1 to 3.2 Å resolution and processed using the HKL package (Otwinowski et al., 1997). The crystals belonged to space group $P2_12_12$ with cell parameters of a=137.1 Å, b=186.4 Å, and c=66.7 Å and contained 1 complex of Met:HGF β-chain in the asymmetric unit and thus have a solvent content of about 75%. The structure was solved by molecular replacement with the program AMoRe (Navaza 1994), with the crystal structure of HGF β-chain alone (structural coordinates available at RCS Protein Databank, Accession No: PDB1UX3) as a search model. Using data from 8 Å to 4 Å yielded a clear solution in the rotation and translation functions and the best solution was subjected to rigid body refinement in program Refmac (CCP4, 1994). Solvent flattening, which due to the high crystal solvent content led to dramatic improvements in the quality of the phases, yielded maps that were of sufficient quality to recognize the β-propeller of the Sema domain and allowed for building the Met receptor without the use of any additional models. Subsequent rounds of model building with program 0 (Jones et al., 1991) and further refinement with program Refmac resulted in the final model with an Rfree and Rcryst of 27.0% and 20.9%, respectively, for all data between 30 Å and 3.2 Å.

TABLE 1

Data Collection and Refinement Statistics for a 1:1 complex of the HGF β-chain with the Sema domain of the Met Receptor.

| Data Collection | |
| --- | --- |
| Resolution (Å) | 50-3.2 (3.3-3.2)[a] |
| $R_{sym}$[b] | 0.058 (0.586)[a] |
| Number of observations | 98,834 |
| Unique reflections | 28,312 |
| Completeness (%) | 99.4 (100.0)[a] |
| Refinement | |
| Resolution (Å) | 30-3.2 |
| Number of reflections | 26830 |
| Final R[c], $R_{free}$ (F > 0) | 0.209, 0.270 |
| Number of residues | 727 |
| Number of solvent molecules | 0 |
| Number of non-H atoms | 5728 |

TABLE 1-continued

Data Collection and Refinement Statistics for a 1:1 complex of the HGF β-chain with the Sema domain of the Met Receptor.

| | |
| --- | --- |
| Rmsd bonds (Å) | 0.013 |
| Rmsd angles (°) | 1.6 |
| Space Group | $P2_12_12$ |

[a]Numbers in parentheses refer to the highest resolution shell.
[b]$R_{sym} = \Sigma |I - <I>|/\Sigma I$. <I> is the average intensity of symmetry related observations of a unique reflection.
[c]$R = \Sigma |F_o - F_c|/\Sigma F_o$. $R_{free}$ is calculated as R, but for 5% of the reflections excluded from all refinement.

Results

The crystal structure of HGFβ: Met was analyzed to identify amino acid positions involved in binding and/or activation of the Met receptor by HGF β.

Structure of HGF β

The β-chain of HGF shares close to 40% sequence identity with the protease domain of plasmin, a trypsin-like serine protease. Structurally, these enzymes can be described as globular proteins composed of two antiparallel β-barrel domains (FIG. 1A). Both of the β-barrels share the same general topology and are formed by six antiparallel β-strands, with the N-terminal four strands folding into a Greek key motif, followed by two strands that form a hairpin. HGF, like serine proteases, is expressed as a zymogen-like precursor. For serine proteases, structural studies have shown that insertion of the N-terminus resulting from the maturation process leads to allosteric rearrangments within the binding site for the protease substrate (Perona and Craig, 1995; Hedstrom 2002). In serine proteases, the newly formed N-terminus forms a salt bridge with a nearby aspartate, which leads to the formation of the oxyanion hole via the backbone NH's of two neighboring residues and the creation of a part of the S1 pocket (FIG. 1). The 'activated' form of the HGF β-chain, as seen in the structure presented here, is very similar to the mature form of serine proteases: superposition with plasmin (pdb-code 1BML) yields an rmsd of about 1.3 Å for 212 $C_\alpha$ pairs. Superposition between HGF β-chain and plasminogen (pdb-code 1QRZ) reveal differences in their 'activation domain' (Freer et al., 1970) and only 198 $C_\alpha$ pairs can be aligned well.

As with serine proteases, the N-terminal amine of Val495 is inserted into the core of the C-terminal β-barrel and forms a salt bridge with the carboxyl group of Asp672, which corresponds to Asp194 in plasmin, presumably leading to similar rearrangements, which have been characterized in serine proteases. The region in HGF corresponding to this so-called 'activation domain', i.e., the loops that undergo conformational changes in serine proteases (Freer et al., 1970; Huber and Bode, 1978), forms part of the binding surface with Met, discussed below. Therefore, proper display of the residues that interact with Met requires maturation of HGF.

After maturation, the α- and β-chains of HGF remain connected via a disulfide bond. Based on alignments of the kringle domains K1 to K4 of HGF and macrophage stimulating protein (MSP), the two cysteine residues responsible for the formation of this disulfide bond were identified as Cys487 on the α-chain of HGF and Cys604 on the β-chain (Donate et al., 1994). The crystal structure, however, raises the possibility of an alternative cysteine residue as the anchor for the HGF β-chain. The HGF β-chain has two (2) cysteine residues that do not have partners for the formation of disulfide bridges within the β-chain. Neither is conserved in plasmin or MSP and both are located on the periphery of the protein and are at least partially solvent exposed; either could be potential partners for the formation of a disulfide bond with the α-chain while the other remains unpaired. The superposition of the plasmin structure that contains part of the α-chain (FIG. 1B), and the HGF β-chain structure presented here, shows that the distance between the C-terminus of the plasmin α-chain and Cys604 of the HGF β-chain is 27 Å and thus only slightly shorter than the respective distance between the plasmin α-chain C-terminus and Cys561 (33 Å) (FIG. 1B). In addition, the sequence alignment between plasmin, MSP, and HGF (FIG. 1C) shows that the α-chain cysteine forming the disulfide bond in plasmin and MSP is 13 and 15 residues away from the cleavage site in those proteins respectively, but there are only 7 residues in HGF to span the distance from Cys487 to the cleavage site. Therefore, due to distance requirements, the C-terminus of the HGF α-chain cannot follow the same path on the surface of the β-chain as it does in plasmin or MSP. Continuing work seeks to clarify which of the two free cysteine residues in HGF β forms the disulfide bond with the α-chain of HGF.

Met Structure

The Sema domain of Met forms 7-bladed β-propeller with a diameter of a little more than 50 Å. The overall shape of the domain resembles a funnel with an inner diameter of about 25 Å between main chain atoms at the wide portion and 10 Å in the narrowest part (FIG. 2). Generally, in β-propellers, each of the blades is formed by 4 antiparallel β-strands with strand A in the center of the propeller followed by strands B and C, and with strand D forming the outermost strand of the blade. The blades are arranged in a circular fashion, with the N-terminal strand forming strand D of the last blade, thus closing the propeller and stabilizing the overall structure (FIG. 2A). The AB and CD loops of each blade of the Met Sema domain form the relatively flat 'bottom' face, and the generally longer BC and DA loops form the 'top' face of the propeller (FIG. 2B). In Met, the position of the 6th and the 7th blade are off-center, with blade 7 being closer to the center of the barrel and blade 6 more distant. This gives the domain an overall oval shape.

The β-propeller of the Met Sema domain is structurally most closely related to the recently reported crystal structures of Sema4D (Love et al., 2003) and Sema3A (Antipenkov et al., 2003). With the exception of the D-strands in blades 3 and 5, the core of Sema4D and the Met Sema domain align well (FIGS. 3 and 4) and the superposition of residues 40 to 519 with the Sema domain of Sema4D results in an mmsd of 1.6 Å for 303 atom pairs (FIG. 4). The residues that form strand D5 in Sema4A are hydrogen bonding to strand D4 in Met, thus the 4th blade of Met contains an extra strand while blade 5 is missing its strand D. While the core of both proteins align well, the loops contain a number of insertions or deletions and generally adopt very different conformations. For example, the Sema domains of Met and of Sema4D both have an insert of about 20 residues following strand D1. In Met, these residues form a short antiparallel two-stranded β-sheet, while Sema4D has an α-helix (FIGS. 3 and 4). Of the 24 loops that connect the various strands, only 3 have no insertions or deletions when comparing Met with Sema4D or Sema3A (FIG. 3). Interestingly, both the Semaphorins and the Met receptor have their largest insertion between strands C5 and A6; however, these inserts are not related in structure or sequence to each other. In Sema3A, this insert is involved in dimer formation and has been shown to be important for neuropilin binding (Antipenko et al., 2003). In the Met Sema domain, some of the residues within the insert are disordered and not included in our model (see FIG. 2). The function of the insert in Met is not known but its proximity to the HGF β-chain binding site, discussed below, suggests that it might be involved in binding to the α-chain of HGF.

The loop containing the cleavage site between the α- and β-chain of Met connects strand D4 to A5; it is disordered in the electron density. After processing of native Met, the α-chain, which forms the N-terminal 4 blades of the Sema domain, and the β-chain remain connected via at least 2 disulfide bonds. One disulfide bond is formed between residues Cys298 on strand D4 and Cys363 on C5, and the second is formed between Cys282 (D3) and Cys409. This last cysteine is positioned in a disordered region of the insert after blade 4. The electron density does not allow tracing of the main chain in this area but there is sufficient density in the area of the Sγ position to suggest that the disulfide bond is at least partially formed. With the exception of the N-terminal Cys26, which is disordered in the presently disclosed crystal structure and has no potential partner in the construct that was used for crystallization, all cysteine residues are engaged in disulfide bonds. It is unclear if Cys26 remains unpaired in the context of full length Met receptor or if it forms a disulfide bond with another cysteine that resides in the IPT domains. Besides the two disulfide bonds that covalently connect the α- and β-chain of the Sema domain, the domain is stabilized by 5 additional disulfide bridges formed between Cys95-Cys101, Cys98-Cys159, Cys133-Cys141, Cys172-Cys175, and Cys385-Cys397 (FIG. 3).

The surface of the Met Sema domain appears to be mostly negatively charged, especially in the center of the bottom face of the Sema domain (FIG. 2C). This surface, which is formed by a 20 residue insertion after strand D in the first blade and includes the rather irregular area of strand D in the third blade, shows clusters of acidic residues. Monomeric, full length Met was shown to bind to heparin (Gherardi et al., 2003). In presently disclosed structure there are no dominant positively charged patches within the Met Sema domain; however, two arginines are located in the vicinity of the disordered furin-cleavage site. Together with the 6 positively charged residues that reside in this loop, these arginines could constitute a potential heparin binding site.

The last strand of the Sema domain (C7) is followed immediately by the PSI domain. This domain, with dimensions of about 20×15 Å, contains four (4) disulfide bridges and is not an integral part of the Sema domain but rather an independent structural module. The small core of the domain is formed by a helix and a short two-stranded antiparallel i-sheet that are connected via a disulfide bond and sandwich the side-chain of Trp540. Superposition of this domain with the PSI domain of Sema4D results in an rmsd of 1.6 Å for 41 $C_\alpha$ pairs. The relative orientation between the Sema and the PSI domains in the Met and the Sema4D structures, however, is different and requires a rotation of about 40° for superposition.

The Interface Between the HGF β-Chain and Met

The HGF β-chain binds to the Sema domain of Met at the bottom face of the propeller, and forms contacts with residues that protrude from blades 2 and 3 (FIGS. 2 and 3). This is unlike other β-propeller containing receptors, such as the integrins, which bind their ligands utilizing the top face of the propeller (Xiong et al., 2002). Other Sema domain containing proteins, such as Sema3A and Sema4D, are also postulated to bind ligands using the top face (Antipenko et al., 2003; Love et al., 2003).

The interface between HGF β-chain and Met buries a total of 1770 Å$^2$ of solvent accessible surface and is dominated by polar or charge-charge interactions. Of the 20 HGF residues that have more that 10 Å$^2$ buried in the interface, 6 are positively charged, 3 carry negative charges, and 3 are aromatic.

Even more dramatic, of the 18 residues contributing more than 10 Å$^2$ of buried surface to the interface on the Met side, 6 carry negative charges, 4 are positively charged and 3 are aromatic. The combined buried surface of the hydrophobic residues Ala, Val, Leu, Ile, Met and Phe amounts to a mere 145 Å$^2$, while the charged residues Asp, Glu, Lys, Arg, and His are responsible for more than 1,000 Å$^2$ of buried surface. The resolution of the presently disclosed structure does not permit a detailed discussion of hydrogen bonds; however, the position of the side chains suggest the presence of at least 7 charged interactions between Met and the HGF β-chain. (See Table 3)

On HGF, the residues analogous to those responsible for substrate binding and catalysis in the related serine proteases form most of the interactions with Met. Serine proteases bind linear peptides to their recognition site and form hydrogen bonds to main chain atoms to position a specific peptide bond for proteolytic cleavage. In contrast, the HGF β-chain binds to a series of protruding polar side chains from Met that originate mainly from 3 separate loops (FIG. 5B). The first of these loops includes residues 124-128 and connects strands A2 and B2 of Met. This loop contains two tyrosines that are in the core of the binding interface and pack against Arg695 of HGF. The second loop of Met that contacts HGF β-chain contains residues Asp190, Arg191, and Phe192 and connects A3 and B3. Asp190 of Met forms charged interactions with Arg533 of HGF. The side chain of Arg191 of Met packs against Val692 and Pro693 of HGF with its hydrophobic portion and in the presently disclosed model is in hydrogen bonding distance to the side chains of Glu656 and Asp578 with its guanidinium group. This Asp578 corresponds to aspartic acid [c102] in the catalytic triad of the related serine proteases. Furthermore, the backbone of this loop forms hydrophilic interactions with Gln534, the residue homologous to the histidine [c57] of the protease catalytic triad.

The third segment contributing to the interface also includes strand D in the third blade of the propeller, an area that deviates from the classical 'propeller fold'. Strand D is interrupted and has a short helical insert within its strand. This unusual conformation presents a number of residues towards the surface of the HGF β-chain. The most prominent interaction formed by this loop involves Glu221 which extends its side chain towards what would be the S1 binding site in serine proteases (FIGS. 5 and 6). The carboxylate of Glu221 forms an extensive network of polar interactions with the side chain of Tyr673 (corresponding to the serine [c195] of the catalytic triad in proteases), as well as the backbone amides of Gly694 and Gly696 (FIG. 6); however, unlike in serine proteases, where the S1 pocket is filled by the specificity determining P1 residue, it does not penetrate deeply into the S1 pocket. As a result of the exchange of Ser to Tyr in position 673 [c195], the entrance of the S1 pocket is much smaller than in the related proteases. Thus, Glu221 projects towards the entrance of the S1 pocket from a different angle when compared to a complex between trypsin and bovine pancreatic trypsin inhibitor (BPTI) and does not fill the pocket (FIG. 6). Therefore, a large cavity, presumably filled with a number of water molecules, remains in HGF β-chain.

Comparison of HGF β-Chain Unbound and Bound to Met

The structures of the HGF β-chain bound to Met and in its unbound state, as disclosed in application U.S. Ser. No. 60/569,301 filed May 6, 2004, which application is hereby incorporated by reference, are very similar and superimpose with an rmsd of less than 0.8 Å for 218 C$_\alpha$-pairs. The only significant differences between the two structures involve residues that are close to the Met binding interface. The backbone of residues 645 to 651 is disordered in unliganded HGF β but well defined in the structure of the complex, where it adopts a conformation that is commonly observed in serine proteases (FIG. 1). The side chains of the basic residues Arg647 and Lys649 are not well defined in the electron density but project towards the Met binding interface and, in presently disclosed model, participate in the formation of the complex. Arg695 also undergoes a change in conformation upon Met binding. This residue, located in the center of the receptor binding interface, packs against Tyr125 of Met, and its backbone forms part of the S1 pocket. In the structure of unliganded HGF β, the conformation of the backbone in this area is different, and the side chain of Arg695 projects toward the disordered region of the structure. It is conceivable that the binding event alters the position of Arg695, which in turn allows residues 645 to 651 to adopt a more stable conformation.

Models for Receptor Activation

In embodiments, a model for HGF mediated Met receptor activation is provided. Little is known about the signaling complex itself, and details of this interaction, such as the stoichiometry between ligand and receptor, have been elusive.

The presently disclosed structure shows unambiguously how Met binds to the β-chain of HGF. However, the exact role this interaction might play in Met activation remains uncertain. Two general models of how HGF can lead to Met dimerization have been suggested (Miller and Leonard, 1998). One of these models, follows the growth hormone paradigm (de Vos et al, 1994) where one HGF molecule binds to two different Met receptors with different affinities to form the 2:1 signaling complex. The other model suggests that two 1:1 complexes of Met and HGF are dimerized either via heparin or an alternative mechanism to form stable 2:2 complexes.

In the present disclosure, complexes of HGF β-chain and the Sema domain of Met were purified from the individual components via size exclusion chromatography. This clearly showed that HGF β and the N-terminal 564 residues of Met form a stable 1:1 complex. If Met activation via HGF indeed entails a 2:1 complex, the present disclosure characterizes the low affinity binding interaction between HGF and Met. The high affinity binding interaction involves the α-chain of HGF, in particular the NK1 domains (Lokker et al., 1992), and a previously uncharacterized binding site on Met. This model is in good agreement with the notion that single chain HGF is able to bind Met via its high affinity binding site which is contained in its N-terminal portion, yet unable to signal. For signaling, maturation of HGF is required. This leads to rearrangements in the activation domain of HGF β, the formation of the low affinity binding site and possibly allows for a reorientation of the β-chain of HGF relative to its α-chain. This model could also be valid for the closely related Ron/MSP system. Like HGF, single chain MSP can bind to its receptor Ron, but is only able to signal in its matured 2-chain form. Interestingly and in contrast to HGF, the high affinity binding site in MSP is contained within its β-chain while the low affinity binding site is harbored by its α-chain (Danilkovitch et al., 1999).

Recent studies employing analytical ultracentrifugation and light scattering experiments indicate that mature HGF and the Met ectodomain form 1:1 complexes that can be stabilized with heparin to form a 1:1 complex (Gherardi et al., 2003). However, in those experiments no higher order complexes or aggregates could be detected.

The present disclosure shows that the low affinity interaction between HGF β and Met is sufficient for 1:1 complex formation. The absence of 2:1 complexes in Gherardi et al, (2003), suggest two possible scenarios. Firstly, it is possible that the high and low affinity binding sites on the receptor overlap. In this case, at a 1:1 molar ratio of ligand and receptor, all high affinity binding sites on the receptor are occupied and none of the low affinity binding sites available thus preventing the formation of 2:1 complexes. An alternative explanation for the absence of 2:1 complexes is that α- and β-chain of a single HGF molecule bind to the same Met receptor and form stable 1:1 complexes. These 1:1 complexes only associate very weakly and require the juxtamembrane or intracellular portion of the receptors or need additional molecules or co-receptors for the assembly of 2:2 or higher order signaling complexes.

Recent crystal structures of dimeric Sema4D and Sema3A have demonstrated how these Sema domains dimerize. Antipenko A, Himanen J P, van Leyen K, Nardi-Dei V, Lesniak J, Barton W A, Rajashankar Kr, Lu M, Hoemme C, Puschel A W, Nikolov D B (2003) Structure of the Semaphorin-3A receptor binding module. *Neuron* 39:589-598 and Love C A, Harlos K, Mavaddat N, Davis S J, Stuart D I, Jones E Y, Esnouf R M (2003). The ligand-binding face of the Semaphorins revealed by the high-resolution crystal structure of Sema4D. *Nat. Struct. Biol.* 10:843-848.

In Sema4D, dimerization of the Sema domains is mediated by four loops that protrude from the core of the propeller. Three of these loops connect strands B4-C4, D4-A5, and B5-C5, and the fourth is part of the insert that follows the 5th blade of the propeller (FIG. 3). In the present crystal structure the interface observed in the Semaphorin structures is not present. The superposition of the complex described here and the dimer of Sema4D shows that none of the regions relevant for dimerization in Sema4D are conserved in the Met structure (FIG. 4B). Thus, it is unlikely that the Met dimerization follows the Semaphorin paradigm. However, since the loop connecting D4-A5 contains the furin cleavage site that was altered in the present construct, the possibility that the dimer seen in Sema4D is similar in the Met receptor system cannot be excluded. A number of characteristics of Met speak against this model. As discussed above, cleavage of Met at the furin cleavage site is not required for signaling. Therefore, it seems unlikely that this loop is involved in crucial interactions in the signaling complex. Furthermore, if Met were to dimerize similarly to the Semaphorins, the β-chains of HGF would be more than 70 Å apart from each other and lie on opposite sides of the Sema domain. Thus, they could not participate in the stabilization of a 2:2 complex, yet it is known that maturation of HGF and the presence of the HGF β-chain are required for the formation of a signaling complex.

Figure 7:
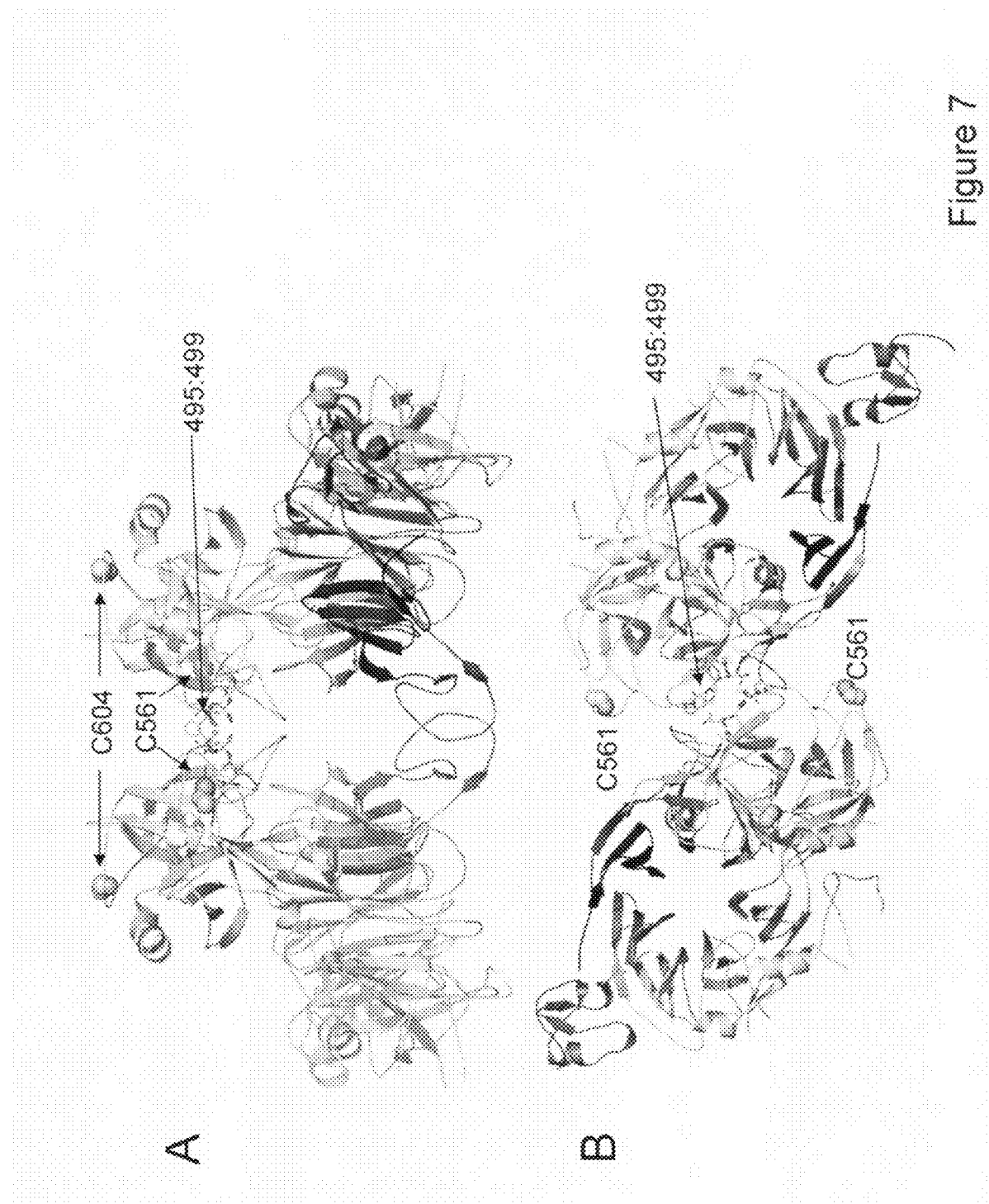
FIGS. 7A and 7B show two different views of two crystallographically related HGF β-chain:Met complexes that may represent a portion of the active signaling complex. Residues 495:499 of both HGF β-chains are shown in stick representation to indicate the position of the HGF β-chain N-termini. Two cysteines (C604 and C561) shown as spheres, are candidates for the formation of the disulfide bond with Cys487 in the HGF α-chain.

A different model for a 2:2 signaling complex is suggested by the crystal packing of the 1:1 complexes in the disclosed crystal structure where two HGF β-chains form a symmetric interface with about 1250 Å$^2$ of total buried surface (FIG. 7). This interface is formed via interactions from 3 loops: the strand immediately following the N-terminus, residues 619-630, and residues 662-665. These 3 loops are part of the so-called 'activation domain' in the related serine proteases and rearrange upon zymogen maturation (Huber and Bode, 1978). As the surface engaged in this interface can only be present if full length HGF is properly cleaved and in its matured form, this dimer can only form after maturation which explains the requirement of HGF maturation for proper signaling. In this model, the C-termini of the Met receptor Sema domains are separated by about 110 Å, a gap that could be easily spanned by the PSI and the 4 IPT domains of the two receptors that connect the Sema domains to the transmembrane helix. Interestingly, while HGF β-chain/β-chain interactions are clearly weak, no oligomers were detected during size exclusion chromatography of the complex and the HGF β-chain is monomeric in solution (data not shown), the same interface is also present in crystals containing only the HGF β-chain and that were derived under different crystallization conditions, see application U.S. Ser. No. 60/569,301 filed May 6, 2004.

Figure 8:
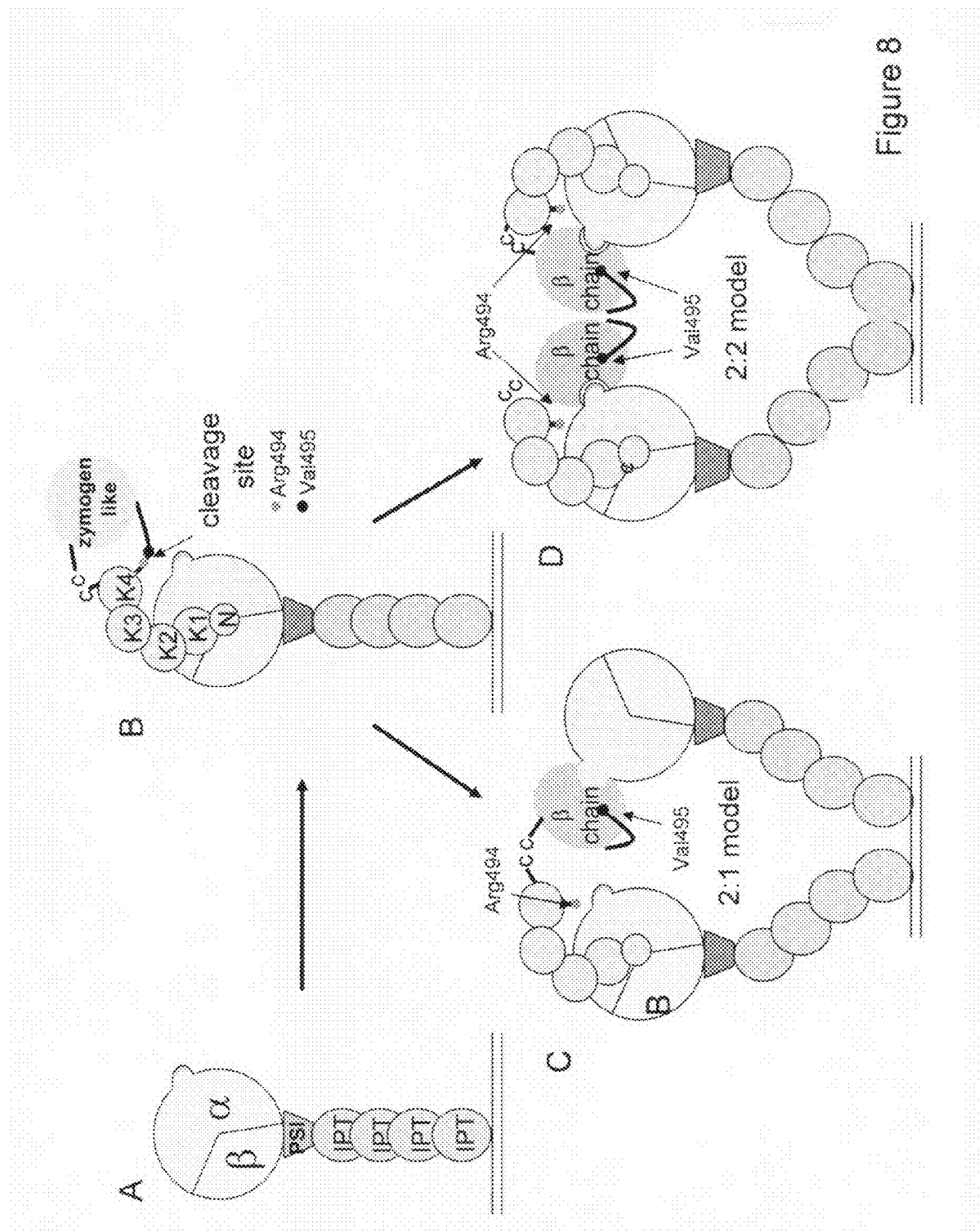
FIG. 8 shows a schematic diagram for Met signaling.

Based on these observations we propose a model in which the α-chain of HGF provides the initial binding event for HGF to Met (FIG. 8). The large, negatively charged patches in the center of the 'bottom' of the Sema domain propeller may represent a potential binding site for the HGF β-chain, allowing for interaction with the positively charged surface region of the NK1 domain (Lokker et al., 1992, Ultsch et al., 1998). Before cleavage of single-chain HGF, the protease-like domain of HGF would be unavailable for binding to Met. Once cleavage occurs, the N-terminus of the newly formed β-chain inserts into the protein and leads to rearrangements in the 'activation domain' creating the Met binding site on HGF β-chain. Now the HGF β-chain can bind to Met, which positions the β-chain dimerization surface for contact with a neighboring HGF/Met complex. The presence of heparin sulfate proteoglycans may serve to strengthen these interactions.

The 2:2 model is supported by the stoichiometry studies mentioned above which show no dimerization of complexes in solution (Gherardi et al., 2003), indicating that the 2:2 complex formation must be very weak. Also, the fact that the α-chain alone (NK4) is not able to mediate dimerization, but instead acts as an antagonist in vivo (Date et al., 1997), further highlights the potential role for the HGF β-chain in dimerization. The disclosed structure of Met lacks the IPT domains, and their role in the signaling of the Met/HGF complex is still unclear. A crystal structure of the full length Met in complex with full length, activated HGF could further resolve these issues.

TABLE 2

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | | Amino Acid Residue | | | X | Y | Z | Occ. | Temp Factor | Atom Type | |
|---|---|---|---|---|---|---|---|---|---|---|---|---|
| ATOM | 1 | N | VAL | A | 495 | 3.648 | 8.257 | 25.688 | 1.00 | 34.05 | A | N |
| ATOM | 2 | CA | VAL | A | 495 | 2.510 | 8.343 | 24.730 | 1.00 | 31.80 | A | C |
| ATOM | 3 | CB | VAL | A | 495 | 2.999 | 8.054 | 23.335 | 1.00 | 34.93 | A | C |
| ATOM | 4 | CG1 | VAL | A | 495 | 1.840 | 7.978 | 22.370 | 1.00 | 33.34 | A | C |
| ATOM | 5 | CG2 | VAL | A | 495 | 4.062 | 9.062 | 22.921 | 1.00 | 39.47 | A | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 6 | C | VAL | A | 495 | 1.486 | 7.274 | 25.046 | 1.00 | 36.19 | A | C |
| ATOM | 7 | O | VAL | A | 495 | 1.814 | 6.071 | 25.187 | 1.00 | 35.83 | A | O |
| ATOM | 8 | N | VAL | A | 496 | 0.231 | 7.684 | 25.129 | 1.00 | 39.53 | A | N |
| ATOM | 9 | CA | VAL | A | 496 | −0.796 | 6.708 | 25.480 | 1.00 | 41.32 | A | C |
| ATOM | 10 | CB | VAL | A | 496 | −1.903 | 7.308 | 26.306 | 1.00 | 39.20 | A | C |
| ATOM | 11 | CG1 | VAL | A | 496 | −3.011 | 6.306 | 26.467 | 1.00 | 36.02 | A | C |
| ATOM | 12 | CG2 | VAL | A | 496 | −1.334 | 7.729 | 27.656 | 1.00 | 40.39 | A | C |
| ATOM | 13 | C | VAL | A | 496 | −1.329 | 5.988 | 24.255 | 1.00 | 41.88 | A | C |
| ATOM | 14 | O | VAL | A | 496 | −1.609 | 6.606 | 23.213 | 1.00 | 43.50 | A | O |
| ATOM | 15 | N | ASN | A | 497 | −1.427 | 4.670 | 24.399 | 1.00 | 35.06 | A | N |
| ATOM | 16 | CA | ASN | A | 497 | −1.803 | 3.780 | 23.313 | 1.00 | 31.56 | A | C |
| ATOM | 17 | CB | ASN | A | 497 | −3.300 | 3.842 | 23.067 | 1.00 | 25.35 | A | C |
| ATOM | 18 | CG | ASN | A | 497 | −4.046 | 3.020 | 24.063 | 1.00 | 34.07 | A | C |
| ATOM | 19 | OD1 | ASN | A | 497 | −3.513 | 2.045 | 24.585 | 1.00 | 39.84 | A | O |
| ATOM | 20 | ND2 | ASN | A | 497 | −5.271 | 3.395 | 24.356 | 1.00 | 41.50 | A | N |
| ATOM | 21 | C | ASN | A | 497 | −0.960 | 3.807 | 22.021 | 1.00 | 33.76 | A | C |
| ATOM | 22 | O | ASN | A | 497 | −1.488 | 3.849 | 20.916 | 1.00 | 37.21 | A | O |
| ATOM | 23 | N | GLY | A | 498 | 0.362 | 3.773 | 22.177 | 1.00 | 34.65 | A | N |
| ATOM | 24 | CA | GLY | A | 498 | 1.265 | 3.585 | 21.052 | 1.00 | 32.53 | A | C |
| ATOM | 25 | C | GLY | A | 498 | 2.206 | 2.425 | 21.294 | 1.00 | 32.73 | A | C |
| ATOM | 26 | O | GLY | A | 498 | 2.168 | 1.802 | 22.361 | 1.00 | 38.63 | A | O |
| ATOM | 27 | N | ILE | A | 499 | 3.058 | 2.128 | 20.318 | 1.00 | 30.60 | A | N |
| ATOM | 28 | CA | ILE | A | 499 | 3.983 | 0.994 | 20.458 | 1.00 | 28.08 | A | C |
| ATOM | 29 | CB | ILE | A | 499 | 3.766 | −0.081 | 19.357 | 1.00 | 26.10 | A | C |
| ATOM | 30 | CG1 | ILE | A | 499 | 4.267 | 0.409 | 18.011 | 1.00 | 30.80 | A | C |
| ATOM | 31 | CD1 | ILE | A | 499 | 3.730 | −0.420 | 16.858 | 1.00 | 41.02 | A | C |
| ATOM | 32 | CG2 | ILE | A | 499 | 2.318 | −0.445 | 19.244 | 1.00 | 24.14 | A | C |
| ATOM | 33 | C | ILE | A | 499 | 5.452 | 1.407 | 20.532 | 1.00 | 26.32 | A | C |
| ATOM | 34 | O | ILE | A | 499 | 5.821 | 2.539 | 20.200 | 1.00 | 29.62 | A | O |
| ATOM | 35 | N | PRO | A | 500 | 6.286 | 0.494 | 21.002 | 1.00 | 22.97 | A | N |
| ATOM | 36 | CA | PRO | A | 500 | 7.734 | 0.707 | 20.994 | 1.00 | 25.27 | A | C |
| ATOM | 37 | CB | PRO | A | 500 | 8.269 | −0.630 | 21.510 | 1.00 | 28.37 | A | C |
| ATOM | 38 | CG | PRO | A | 500 | 7.119 | −1.233 | 22.318 | 1.00 | 23.04 | A | C |
| ATOM | 39 | CD | PRO | A | 500 | 5.906 | −0.804 | 21.591 | 1.00 | 20.18 | A | C |
| ATOM | 40 | C | PRO | A | 500 | 8.229 | 0.950 | 19.570 | 1.00 | 29.77 | A | C |
| ATOM | 41 | O | PRO | A | 500 | 7.752 | 0.311 | 18.614 | 1.00 | 30.70 | A | O |
| ATOM | 42 | N | THR | A | 501 | 9.166 | 1.877 | 19.409 | 1.00 | 32.11 | A | N |
| ATOM | 43 | CA | THR | A | 501 | 9.764 | 2.076 | 18.087 | 1.00 | 32.08 | A | C |
| ATOM | 44 | CB | THR | A | 501 | 10.433 | 3.459 | 17.931 | 1.00 | 30.15 | A | C |
| ATOM | 45 | OG1 | THR | A | 501 | 11.565 | 3.581 | 18.811 | 1.00 | 26.33 | A | O |
| ATOM | 46 | CG2 | THR | A | 501 | 9.475 | 4.579 | 18.353 | 1.00 | 29.78 | A | C |
| ATOM | 47 | C | THR | A | 501 | 10.770 | 0.977 | 17.841 | 1.00 | 36.15 | A | C |
| ATOM | 48 | O | THR | A | 501 | 11.510 | 0.597 | 18.752 | 1.00 | 36.54 | A | O |
| ATOM | 49 | N | ARG | A | 502 | 10.788 | 0.467 | 16.611 | 1.00 | 40.43 | A | N |
| ATOM | 50 | CA | ARG | A | 502 | 11.698 | −0.612 | 16.235 | 1.00 | 36.95 | A | C |
| ATOM | 51 | CB | ARG | A | 502 | 11.661 | −0.825 | 14.734 | 1.00 | 32.79 | A | C |
| ATOM | 52 | CG | ARG | A | 502 | 11.170 | −2.173 | 14.365 | 1.00 | 39.24 | A | C |
| ATOM | 53 | CD | ARG | A | 502 | 10.928 | −2.361 | 12.889 | 1.00 | 51.53 | A | C |
| ATOM | 54 | NE | ARG | A | 502 | 9.667 | −1.765 | 12.471 | 1.00 | 59.18 | A | N |
| ATOM | 55 | CZ | ARG | A | 502 | 9.564 | −0.590 | 11.871 | 1.00 | 65.00 | A | C |
| ATOM | 56 | NH1 | ARG | A | 502 | 10.659 | 0.119 | 11.596 | 1.00 | 67.56 | A | N |
| ATOM | 57 | NH2 | ARG | A | 502 | 8.366 | −0.127 | 11.529 | 1.00 | 68.74 | A | N |
| ATOM | 58 | C | ARG | A | 502 | 13.127 | −0.356 | 16.708 | 1.00 | 41.11 | A | C |
| ATOM | 59 | O | ARG | A | 502 | 13.750 | −1.205 | 17.321 | 1.00 | 46.19 | A | O |
| ATOM | 60 | N | THR | A | 503 | 13.630 | 0.838 | 16.449 | 1.00 | 45.57 | A | N |
| ATOM | 61 | CA | THR | A | 503 | 14.999 | 1.186 | 16.776 | 1.00 | 49.27 | A | C |
| ATOM | 62 | CB | THR | A | 503 | 15.864 | 1.002 | 15.524 | 1.00 | 56.77 | A | C |
| ATOM | 63 | OG1 | THR | A | 503 | 17.186 | 1.495 | 15.774 | 1.00 | 62.39 | A | O |
| ATOM | 64 | CG2 | THR | A | 503 | 15.321 | 1.860 | 14.324 | 1.00 | 56.70 | A | C |
| ATOM | 65 | C | THR | A | 503 | 14.952 | 2.638 | 17.208 | 1.00 | 48.38 | A | C |
| ATOM | 66 | O | THR | A | 503 | 13.856 | 3.193 | 17.333 | 1.00 | 51.69 | A | O |
| ATOM | 67 | N | ASN | A | 504 | 16.091 | 3.286 | 17.427 | 1.00 | 43.12 | A | N |
| ATOM | 68 | CA | ASN | A | 504 | 15.971 | 4.699 | 17.763 | 1.00 | 45.81 | A | C |
| ATOM | 69 | CB | ASN | A | 504 | 17.002 | 5.205 | 18.793 | 1.00 | 51.99 | A | C |
| ATOM | 70 | CG | ASN | A | 504 | 18.415 | 5.244 | 18.278 | 1.00 | 52.58 | A | C |
| ATOM | 71 | OD1 | ASN | A | 504 | 19.003 | 6.329 | 18.154 | 1.00 | 53.21 | A | O |
| ATOM | 72 | ND2 | ASN | A | 504 | 19.003 | 4.069 | 18.055 | 1.00 | 51.18 | A | N |
| ATOM | 73 | C | ASN | A | 504 | 15.719 | 5.618 | 16.573 | 1.00 | 40.80 | A | C |
| ATOM | 74 | O | ASN | A | 504 | 15.688 | 5.153 | 15.447 | 1.00 | 38.18 | A | O |
| ATOM | 75 | N | ILE | A | 505 | 15.469 | 6.899 | 16.847 | 1.00 | 41.30 | A | N |
| ATOM | 76 | CA | ILE | A | 505 | 15.003 | 7.857 | 15.840 | 1.00 | 39.57 | A | C |
| ATOM | 77 | CB | ILE | A | 505 | 13.530 | 8.190 | 16.087 | 1.00 | 35.88 | A | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 78 | CG1 | ILE | A | 505 | 12.662 | 6.955 | 15.901 | 1.00 | 30.11 | A | C |
| ATOM | 79 | CD1 | ILE | A | 505 | 11.804 | 6.992 | 14.674 | 1.00 | 31.81 | A | C |
| ATOM | 80 | CG2 | ILE | A | 505 | 13.099 | 9.344 | 15.213 | 1.00 | 36.92 | A | C |
| ATOM | 81 | C | ILE | A | 505 | 15.840 | 9.139 | 15.865 | 1.00 | 43.61 | A | C |
| ATOM | 82 | O | ILE | A | 505 | 16.022 | 9.761 | 16.915 | 1.00 | 54.35 | A | O |
| ATOM | 83 | N | GLY | A | 506 | 16.315 | 9.549 | 14.700 | 1.00 | 42.54 | A | N |
| ATOM | 84 | CA | GLY | A | 506 | 17.426 | 10.484 | 14.611 | 1.00 | 43.52 | A | C |
| ATOM | 85 | C | GLY | A | 506 | 17.219 | 11.885 | 15.135 | 1.00 | 39.59 | A | C |
| ATOM | 86 | O | GLY | A | 506 | 18.144 | 12.485 | 15.658 | 1.00 | 38.26 | A | O |
| ATOM | 87 | N | TRP | A | 507 | 16.004 | 12.393 | 14.992 | 1.00 | 39.65 | A | N |
| ATOM | 88 | CA | TRP | A | 507 | 15.683 | 13.773 | 15.324 | 1.00 | 43.96 | A | C |
| ATOM | 89 | CB | TRP | A | 507 | 14.541 | 14.257 | 14.448 | 1.00 | 46.87 | A | C |
| ATOM | 90 | CG | TRP | A | 507 | 13.981 | 13.179 | 13.606 | 1.00 | 50.10 | A | C |
| ATOM | 91 | CD1 | TRP | A | 507 | 14.613 | 12.518 | 12.578 | 1.00 | 56.98 | A | C |
| ATOM | 92 | NE1 | TRP | A | 507 | 13.784 | 11.566 | 12.031 | 1.00 | 52.84 | A | N |
| ATOM | 93 | CE2 | TRP | A | 507 | 12.593 | 11.603 | 12.691 | 1.00 | 47.24 | A | C |
| ATOM | 94 | CD2 | TRP | A | 507 | 12.694 | 12.613 | 13.703 | 1.00 | 46.13 | A | C |
| ATOM | 95 | CE3 | TRP | A | 507 | 11.602 | 12.850 | 14.525 | 1.00 | 44.57 | A | C |
| ATOM | 96 | CZ3 | TRP | A | 507 | 10.465 | 12.090 | 14.329 | 1.00 | 53.59 | A | C |
| ATOM | 97 | CH2 | TRP | A | 507 | 10.401 | 11.087 | 13.315 | 1.00 | 52.29 | A | C |
| ATOM | 98 | CZ2 | TRP | A | 507 | 11.459 | 10.842 | 12.490 | 1.00 | 46.18 | A | C |
| ATOM | 99 | C | TRP | A | 507 | 15.247 | 13.868 | 16.763 | 1.00 | 47.81 | A | C |
| ATOM | 100 | O | TRP | A | 507 | 15.144 | 14.975 | 17.322 | 1.00 | 49.41 | A | O |
| ATOM | 101 | N | MET | A | 508 | 14.978 | 12.706 | 17.356 | 1.00 | 43.74 | A | N |
| ATOM | 102 | CA | MET | A | 508 | 14.458 | 12.667 | 18.700 | 1.00 | 42.90 | A | C |
| ATOM | 103 | CB | MET | A | 508 | 13.918 | 11.277 | 19.029 | 1.00 | 45.76 | A | C |
| ATOM | 104 | CG | MET | A | 508 | 12.426 | 11.074 | 18.763 | 1.00 | 46.01 | A | C |
| ATOM | 105 | SD | MET | A | 508 | 11.392 | 12.550 | 18.899 | 1.00 | 46.79 | A | S |
| ATOM | 106 | CE | MET | A | 508 | 10.964 | 12.526 | 20.590 | 1.00 | 46.16 | A | C |
| ATOM | 107 | C | MET | A | 508 | 15.517 | 13.118 | 19.703 | 1.00 | 43.48 | A | C |
| ATOM | 108 | O | MET | A | 508 | 16.665 | 12.640 | 19.687 | 1.00 | 45.57 | A | O |
| ATOM | 109 | N | VAL | A | 509 | 15.101 | 14.062 | 20.546 | 1.00 | 39.27 | A | N |
| ATOM | 110 | CA | VAL | A | 509 | 15.898 | 14.649 | 21.612 | 1.00 | 35.93 | A | C |
| ATOM | 111 | CB | VAL | A | 509 | 16.175 | 16.141 | 21.318 | 1.00 | 34.18 | A | C |
| ATOM | 112 | CG1 | VAL | A | 509 | 16.950 | 16.819 | 22.451 | 1.00 | 30.42 | A | C |
| ATOM | 113 | CG2 | VAL | A | 509 | 16.885 | 16.315 | 19.968 | 1.00 | 35.44 | A | C |
| ATOM | 114 | C | VAL | A | 509 | 15.097 | 14.554 | 22.915 | 1.00 | 41.47 | A | C |
| ATOM | 115 | O | VAL | A | 509 | 13.904 | 14.930 | 22.976 | 1.00 | 40.48 | A | O |
| ATOM | 116 | N | SER | A | 510 | 15.743 | 14.049 | 23.960 | 1.00 | 41.97 | A | N |
| ATOM | 117 | CA | SER | A | 510 | 15.151 | 14.100 | 25.290 | 1.00 | 40.20 | A | C |
| ATOM | 118 | CB | SER | A | 510 | 15.345 | 12.786 | 26.045 | 1.00 | 40.31 | A | C |
| ATOM | 119 | OG | SER | A | 510 | 15.428 | 12.979 | 27.448 | 1.00 | 41.82 | A | O |
| ATOM | 120 | C | SER | A | 510 | 15.799 | 15.267 | 26.009 | 1.00 | 40.83 | A | C |
| ATOM | 121 | O | SER | A | 510 | 17.030 | 15.344 | 26.089 | 1.00 | 37.61 | A | O |
| ATOM | 122 | N | LEU | A | 511 | 14.950 | 16.195 | 26.466 | 1.00 | 42.88 | A | N |
| ATOM | 123 | CA | LEU | A | 511 | 15.348 | 17.347 | 27.263 | 1.00 | 40.77 | A | C |
| ATOM | 124 | CB | LEU | A | 511 | 14.337 | 18.478 | 27.124 | 1.00 | 38.22 | A | C |
| ATOM | 125 | CG | LEU | A | 511 | 14.830 | 19.924 | 27.325 | 1.00 | 41.51 | A | C |
| ATOM | 126 | CD1 | LEU | A | 511 | 14.024 | 20.711 | 28.358 | 1.00 | 39.28 | A | C |
| ATOM | 127 | CD2 | LEU | A | 511 | 16.300 | 19.998 | 27.665 | 1.00 | 43.86 | A | C |
| ATOM | 128 | C | LEU | A | 511 | 15.325 | 16.888 | 28.686 | 1.00 | 43.00 | A | C |
| ATOM | 129 | O | LEU | A | 511 | 14.362 | 16.246 | 29.100 | 1.00 | 42.35 | A | O |
| ATOM | 130 | N | ARG | A | 512 | 16.376 | 17.208 | 29.435 | 1.00 | 43.58 | A | N |
| ATOM | 131 | CA | ARG | A | 512 | 16.405 | 16.838 | 30.838 | 1.00 | 48.38 | A | C |
| ATOM | 132 | CB | ARG | A | 512 | 17.401 | 15.722 | 31.112 | 1.00 | 53.42 | A | C |
| ATOM | 133 | CG | ARG | A | 512 | 18.088 | 15.190 | 29.906 | 1.00 | 61.05 | A | C |
| ATOM | 134 | CD | ARG | A | 512 | 17.820 | 13.739 | 29.651 | 1.00 | 68.73 | A | C |
| ATOM | 135 | NE | ARG | A | 512 | 18.355 | 12.882 | 30.700 | 1.00 | 73.03 | A | N |
| ATOM | 136 | CZ | ARG | A | 512 | 17.944 | 11.640 | 30.889 | 1.00 | 78.60 | A | C |
| ATOM | 137 | NH1 | ARG | A | 512 | 18.477 | 10.916 | 31.875 | 1.00 | 82.59 | A | N |
| ATOM | 138 | NH2 | ARG | A | 512 | 16.990 | 11.128 | 30.092 | 1.00 | 73.30 | A | N |
| ATOM | 139 | C | ARG | A | 512 | 16.676 | 17.990 | 31.769 | 1.00 | 50.34 | A | C |
| ATOM | 140 | O | ARG | A | 512 | 17.745 | 18.598 | 31.723 | 1.00 | 51.89 | A | O |
| ATOM | 141 | N | TYR | A | 513 | 15.683 | 18.266 | 32.613 | 1.00 | 50.28 | A | N |
| ATOM | 142 | CA | TYR | A | 513 | 15.767 | 19.236 | 33.692 | 1.00 | 51.88 | A | C |
| ATOM | 143 | CB | TYR | A | 513 | 14.419 | 19.913 | 33.875 | 1.00 | 51.30 | A | C |
| ATOM | 144 | CG | TYR | A | 513 | 14.306 | 20.769 | 35.110 | 1.00 | 57.87 | A | C |
| ATOM | 145 | CD1 | TYR | A | 513 | 14.988 | 21.981 | 35.210 | 1.00 | 62.28 | A | C |
| ATOM | 146 | CE1 | TYR | A | 513 | 14.875 | 22.779 | 36.339 | 1.00 | 65.67 | A | C |
| ATOM | 147 | CZ | TYR | A | 513 | 14.064 | 22.369 | 37.383 | 1.00 | 70.03 | A | C |
| ATOM | 148 | OH | TYR | A | 513 | 13.945 | 23.147 | 38.514 | 1.00 | 75.63 | A | O |
| ATOM | 149 | CE2 | TYR | A | 513 | 13.376 | 21.170 | 37.304 | 1.00 | 67.53 | A | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 150 | CD2 | TYR | A | 513 | 13.502 | 20.380 | 36.168 | 1.00 | 61.73 | A | C |
| ATOM | 151 | C | TYR | A | 513 | 16.155 | 18.512 | 34.968 | 1.00 | 55.13 | A | C |
| ATOM | 152 | O | TYR | A | 513 | 15.646 | 17.428 | 35.241 | 1.00 | 58.26 | A | O |
| ATOM | 153 | N | ARG | A | 514 | 17.056 | 19.112 | 35.745 | 1.00 | 56.46 | A | N |
| ATOM | 154 | CA | ARG | A | 514 | 17.542 | 18.520 | 36.991 | 1.00 | 55.86 | A | C |
| ATOM | 155 | CB | ARG | A | 514 | 16.650 | 18.929 | 38.173 | 1.00 | 57.14 | A | C |
| ATOM | 156 | CG | ARG | A | 514 | 16.811 | 20.378 | 38.602 | 1.00 | 64.13 | A | C |
| ATOM | 157 | CD | ARG | A | 514 | 16.260 | 20.721 | 39.982 | 1.00 | 68.04 | A | C |
| ATOM | 158 | NE | ARG | A | 514 | 17.340 | 21.090 | 40.889 | 1.00 | 72.92 | A | N |
| ATOM | 159 | CZ | ARG | A | 514 | 17.856 | 20.278 | 41.810 | 1.00 | 78.47 | A | C |
| ATOM | 160 | NH1 | ARG | A | 514 | 17.375 | 19.047 | 41.963 | 1.00 | 78.38 | A | N |
| ATOM | 161 | NH2 | ARG | A | 514 | 18.857 | 20.697 | 42.585 | 1.00 | 81.64 | A | N |
| ATOM | 162 | C | ARG | A | 514 | 17.654 | 16.995 | 36.907 | 1.00 | 54.80 | A | C |
| ATOM | 163 | O | ARG | A | 514 | 17.101 | 16.283 | 37.738 | 1.00 | 57.67 | A | O |
| ATOM | 164 | N | ASN | A | 515 | 18.330 | 16.506 | 35.872 | 1.00 | 52.97 | A | N |
| ATOM | 165 | CA | ASN | A | 515 | 18.721 | 15.090 | 35.760 | 1.00 | 55.78 | A | C |
| ATOM | 166 | CB | ASN | A | 515 | 19.449 | 14.624 | 37.012 | 1.00 | 57.23 | A | C |
| ATOM | 167 | CG | ASN | A | 515 | 20.867 | 15.102 | 37.031 | 1.00 | 62.81 | A | C |
| ATOM | 168 | OD1 | ASN | A | 515 | 21.654 | 14.754 | 36.143 | 1.00 | 63.04 | A | O |
| ATOM | 169 | ND2 | ASN | A | 515 | 21.203 | 15.942 | 38.010 | 1.00 | 65.31 | A | N |
| ATOM | 170 | C | ASN | A | 515 | 17.721 | 14.030 | 35.280 | 1.00 | 57.34 | A | C |
| ATOM | 171 | O | ASN | A | 515 | 18.139 | 13.003 | 34.716 | 1.00 | 59.88 | A | O |
| ATOM | 172 | N | LYS | A | 516 | 16.427 | 14.270 | 35.478 | 1.00 | 53.97 | A | N |
| ATOM | 173 | CA | LYS | A | 516 | 15.409 | 13.383 | 34.924 | 1.00 | 52.63 | A | C |
| ATOM | 174 | CB | LYS | A | 516 | 14.329 | 13.081 | 35.980 | 1.00 | 59.60 | A | C |
| ATOM | 175 | CG | LYS | A | 516 | 13.107 | 13.990 | 36.034 | 1.00 | 71.77 | A | C |
| ATOM | 176 | CD | LYS | A | 516 | 11.887 | 13.206 | 36.610 | 1.00 | 80.27 | A | C |
| ATOM | 177 | CE | LYS | A | 516 | 10.558 | 13.533 | 35.874 | 1.00 | 85.92 | A | C |
| ATOM | 178 | NZ | LYS | A | 516 | 9.889 | 12.372 | 35.163 | 1.00 | 85.07 | A | N |
| ATOM | 179 | C | LYS | A | 516 | 14.866 | 13.943 | 33.600 | 1.00 | 48.79 | A | C |
| ATOM | 180 | O | LYS | A | 516 | 14.991 | 15.139 | 33.364 | 1.00 | 50.31 | A | O |
| ATOM | 181 | N | HIS | A | 517 | 14.308 | 13.100 | 32.724 | 1.00 | 44.58 | A | N |
| ATOM | 182 | CA | HIS | A | 517 | 13.729 | 13.590 | 31.451 | 1.00 | 41.66 | A | C |
| ATOM | 183 | CB | HIS | A | 517 | 13.611 | 12.474 | 30.402 | 1.00 | 45.12 | A | C |
| ATOM | 184 | CG | HIS | A | 517 | 12.438 | 12.613 | 29.463 | 1.00 | 40.15 | A | C |
| ATOM | 185 | ND1 | HIS | A | 517 | 12.534 | 13.226 | 28.231 | 1.00 | 42.52 | A | N |
| ATOM | 186 | CE1 | HIS | A | 517 | 11.364 | 13.175 | 27.618 | 1.00 | 38.84 | A | C |
| ATOM | 187 | NE2 | HIS | A | 517 | 10.515 | 12.548 | 28.405 | 1.00 | 35.65 | A | N |
| ATOM | 188 | CD2 | HIS | A | 517 | 11.163 | 12.175 | 29.558 | 1.00 | 35.82 | A | C |
| ATOM | 189 | C | HIS | A | 517 | 12.383 | 14.244 | 31.644 | 1.00 | 39.70 | A | C |
| ATOM | 190 | O | HIS | A | 517 | 11.574 | 13.779 | 32.439 | 1.00 | 43.99 | A | O |
| ATOM | 191 | N | ILE | A | 518 | 12.134 | 15.282 | 30.859 | 1.00 | 36.76 | A | N |
| ATOM | 192 | CA | ILE | A | 518 | 10.999 | 16.168 | 31.062 | 1.00 | 33.32 | A | C |
| ATOM | 193 | CB | ILE | A | 518 | 11.511 | 17.479 | 31.710 | 1.00 | 30.15 | A | C |
| ATOM | 194 | CG1 | ILE | A | 518 | 10.367 | 18.337 | 32.228 | 1.00 | 33.32 | A | C |
| ATOM | 195 | CD1 | ILE | A | 518 | 10.804 | 19.711 | 32.739 | 1.00 | 30.08 | A | C |
| ATOM | 196 | CG2 | ILE | A | 518 | 12.299 | 18.295 | 30.718 | 1.00 | 29.73 | A | C |
| ATOM | 197 | C | ILE | A | 518 | 10.206 | 16.482 | 29.784 | 1.00 | 33.64 | A | C |
| ATOM | 198 | O | ILE | A | 518 | 9.082 | 16.954 | 29.868 | 1.00 | 36.86 | A | O |
| ATOM | 199 | N | CYS | A | 519 | 10.787 | 16.235 | 28.610 | 1.00 | 36.15 | A | N |
| ATOM | 200 | CA | CYS | A | 519 | 10.261 | 16.799 | 27.363 | 1.00 | 37.62 | A | C |
| ATOM | 201 | CB | CYS | A | 519 | 10.465 | 18.305 | 27.357 | 1.00 | 43.78 | A | C |
| ATOM | 202 | SG | CYS | A | 519 | 8.955 | 19.198 | 27.665 | 1.00 | 53.07 | A | S |
| ATOM | 203 | C | CYS | A | 519 | 10.962 | 16.269 | 26.145 | 1.00 | 36.96 | A | C |
| ATOM | 204 | O | CYS | A | 519 | 12.135 | 15.923 | 26.215 | 1.00 | 44.22 | A | O |
| ATOM | 205 | N | GLY | A | 520 | 10.256 | 16.252 | 25.018 | 1.00 | 33.67 | A | N |
| ATOM | 206 | CA | GLY | A | 520 | 10.824 | 15.825 | 23.750 | 1.00 | 31.07 | A | C |
| ATOM | 207 | C | GLY | A | 520 | 11.312 | 16.997 | 22.941 | 1.00 | 35.19 | A | C |
| ATOM | 208 | O | GLY | A | 520 | 11.103 | 18.162 | 23.307 | 1.00 | 38.25 | A | O |
| ATOM | 209 | N | GLY | A | 521 | 11.975 | 16.699 | 21.835 | 1.00 | 36.29 | A | N |
| ATOM | 210 | CA | GLY | A | 521 | 12.538 | 17.749 | 21.002 | 1.00 | 37.32 | A | C |
| ATOM | 211 | C | GLY | A | 521 | 12.990 | 17.241 | 19.652 | 1.00 | 38.07 | A | C |
| ATOM | 212 | O | GLY | A | 521 | 13.538 | 16.142 | 19.526 | 1.00 | 38.85 | A | O |
| ATOM | 213 | N | SER | A | 522 | 12.745 | 18.041 | 18.626 | 1.00 | 38.93 | A | N |
| ATOM | 214 | CA | SER | A | 522 | 13.114 | 17.658 | 17.271 | 1.00 | 34.80 | A | C |
| ATOM | 215 | CB | SER | A | 522 | 11.988 | 17.977 | 16.271 | 1.00 | 33.89 | A | C |
| ATOM | 216 | OG | SER | A | 522 | 10.701 | 18.060 | 16.889 | 1.00 | 33.28 | A | O |
| ATOM | 217 | C | SER | A | 522 | 14.398 | 18.400 | 16.935 | 1.00 | 34.35 | A | C |
| ATOM | 218 | O | SER | A | 522 | 14.491 | 19.626 | 17.102 | 1.00 | 32.30 | A | O |
| ATOM | 219 | N | LEU | A | 523 | 15.407 | 17.643 | 16.521 | 1.00 | 34.26 | A | N |
| ATOM | 220 | CA | LEU | A | 523 | 16.674 | 18.234 | 16.113 | 1.00 | 34.02 | A | C |
| ATOM | 221 | CB | LEU | A | 523 | 17.818 | 17.221 | 16.278 | 1.00 | 30.65 | A | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 222 | CG | LEU | A | 523 | 19.200 | 17.502 | 15.672 | 1.00 | 30.72 | A | C |
| ATOM | 223 | CD1 | LEU | A | 523 | 19.812 | 18.751 | 16.258 | 1.00 | 34.42 | A | C |
| ATOM | 224 | CD2 | LEU | A | 523 | 20.155 | 16.338 | 15.864 | 1.00 | 25.93 | A | C |
| ATOM | 225 | C | LEU | A | 523 | 16.510 | 18.722 | 14.666 | 1.00 | 35.12 | A | C |
| ATOM | 226 | O | LEU | A | 523 | 16.286 | 17.928 | 13.748 | 1.00 | 34.62 | A | O |
| ATOM | 227 | N | ILE | A | 524 | 16.576 | 20.033 | 14.468 | 1.00 | 34.63 | A | N |
| ATOM | 228 | CA | ILE | A | 524 | 16.254 | 20.582 | 13.157 | 1.00 | 35.75 | A | C |
| ATOM | 229 | CB | ILE | A | 524 | 15.155 | 21.663 | 13.218 | 1.00 | 35.51 | A | C |
| ATOM | 230 | CG1 | ILE | A | 524 | 15.564 | 22.814 | 14.117 | 1.00 | 33.46 | A | C |
| ATOM | 231 | CD1 | ILE | A | 524 | 14.971 | 24.098 | 13.673 | 1.00 | 34.02 | A | C |
| ATOM | 232 | CG2 | ILE | A | 524 | 13.846 | 21.071 | 13.687 | 1.00 | 37.56 | A | C |
| ATOM | 233 | C | ILE | A | 524 | 17.466 | 21.070 | 12.400 | 1.00 | 37.14 | A | C |
| ATOM | 234 | O | ILE | A | 524 | 17.416 | 21.204 | 11.178 | 1.00 | 40.12 | A | O |
| ATOM | 235 | N | LYS | A | 525 | 18.533 | 21.369 | 13.128 | 1.00 | 37.43 | A | N |
| ATOM | 236 | CA | LYS | A | 525 | 19.843 | 21.598 | 12.527 | 1.00 | 38.70 | A | C |
| ATOM | 237 | CB | LYS | A | 525 | 19.997 | 23.024 | 11.995 | 1.00 | 40.01 | A | C |
| ATOM | 238 | CG | LYS | A | 525 | 19.923 | 23.104 | 10.465 | 1.00 | 48.89 | A | C |
| ATOM | 239 | CD | LYS | A | 525 | 20.464 | 24.447 | 9.928 | 1.00 | 58.25 | A | C |
| ATOM | 240 | CE | LYS | A | 525 | 20.461 | 24.504 | 8.394 | 1.00 | 60.68 | A | C |
| ATOM | 241 | NZ | LYS | A | 525 | 19.090 | 24.706 | 7.818 | 1.00 | 59.37 | A | N |
| ATOM | 242 | C | LYS | A | 525 | 20.889 | 21.270 | 13.568 | 1.00 | 38.37 | A | C |
| ATOM | 243 | O | LYS | A | 525 | 20.575 | 21.202 | 14.761 | 1.00 | 40.24 | A | O |
| ATOM | 244 | N | GLU | A | 526 | 22.123 | 21.071 | 13.111 | 1.00 | 36.22 | A | N |
| ATOM | 245 | CA | GLU | A | 526 | 23.226 | 20.562 | 13.931 | 1.00 | 38.49 | A | C |
| ATOM | 246 | CB | GLU | A | 526 | 24.544 | 20.747 | 13.178 | 1.00 | 41.99 | A | C |
| ATOM | 247 | CG | GLU | A | 526 | 24.727 | 19.735 | 12.053 | 1.00 | 49.92 | A | C |
| ATOM | 248 | CD | GLU | A | 526 | 24.503 | 20.305 | 10.651 | 1.00 | 55.90 | A | C |
| ATOM | 249 | OE1 | GLU | A | 526 | 23.479 | 20.986 | 10.403 | 1.00 | 57.40 | A | O |
| ATOM | 250 | OE2 | GLU | A | 526 | 25.358 | 20.049 | 9.772 | 1.00 | 59.44 | A | O |
| ATOM | 251 | C | GLU | A | 526 | 23.323 | 21.129 | 15.364 | 1.00 | 39.56 | A | C |
| ATOM | 252 | O | GLU | A | 526 | 23.780 | 20.444 | 16.288 | 1.00 | 36.08 | A | O |
| ATOM | 253 | N | SER | A | 527 | 22.866 | 22.369 | 15.535 | 1.00 | 41.92 | A | N |
| ATOM | 254 | CA | SER | A | 527 | 22.946 | 23.089 | 16.806 | 1.00 | 39.39 | A | C |
| ATOM | 255 | CB | SER | A | 527 | 23.880 | 24.303 | 16.657 | 1.00 | 37.58 | A | C |
| ATOM | 256 | OG | SER | A | 527 | 25.194 | 24.021 | 17.132 | 1.00 | 37.03 | A | O |
| ATOM | 257 | C | SER | A | 527 | 21.582 | 23.541 | 17.361 | 1.00 | 38.77 | A | C |
| ATOM | 258 | O | SER | A | 527 | 21.530 | 24.361 | 18.296 | 1.00 | 40.76 | A | O |
| ATOM | 259 | N | TRP | A | 528 | 20.485 | 23.011 | 16.810 | 1.00 | 33.24 | A | N |
| ATOM | 260 | CA | TRP | A | 528 | 19.160 | 23.515 | 17.178 | 1.00 | 30.57 | A | C |
| ATOM | 261 | CB | TRP | A | 528 | 18.646 | 24.492 | 16.140 | 1.00 | 29.10 | A | C |
| ATOM | 262 | CG | TRP | A | 528 | 19.412 | 25.747 | 16.114 | 1.00 | 31.01 | A | C |
| ATOM | 263 | CD1 | TRP | A | 528 | 20.396 | 26.075 | 15.243 | 1.00 | 30.54 | A | C |
| ATOM | 264 | NE1 | TRP | A | 528 | 20.886 | 27.325 | 15.527 | 1.00 | 29.07 | A | N |
| ATOM | 265 | CE2 | TRP | A | 528 | 20.215 | 27.832 | 16.605 | 1.00 | 26.11 | A | C |
| ATOM | 266 | CD2 | TRP | A | 528 | 19.278 | 26.860 | 17.004 | 1.00 | 30.79 | A | C |
| ATOM | 267 | CE3 | TRP | A | 528 | 18.454 | 27.142 | 18.096 | 1.00 | 32.09 | A | C |
| ATOM | 268 | CZ3 | TRP | A | 528 | 18.605 | 28.371 | 18.744 | 1.00 | 30.15 | A | C |
| ATOM | 269 | CH2 | TRP | A | 528 | 19.549 | 29.310 | 18.312 | 1.00 | 19.71 | A | C |
| ATOM | 270 | CZ2 | TRP | A | 528 | 20.350 | 29.059 | 17.249 | 1.00 | 21.17 | A | C |
| ATOM | 271 | C | TRP | A | 528 | 18.106 | 22.467 | 17.401 | 1.00 | 32.06 | A | C |
| ATOM | 272 | O | TRP | A | 528 | 17.775 | 21.697 | 16.500 | 1.00 | 37.40 | A | O |
| ATOM | 273 | N | VAL | A | 529 | 17.560 | 22.457 | 18.606 | 1.00 | 29.15 | A | N |
| ATOM | 274 | CA | VAL | A | 529 | 16.450 | 21.588 | 18.887 | 1.00 | 34.38 | A | C |
| ATOM | 275 | CB | VAL | A | 529 | 16.653 | 20.814 | 20.191 | 1.00 | 39.86 | A | C |
| ATOM | 276 | CG1 | VAL | A | 529 | 15.491 | 19.858 | 20.418 | 1.00 | 45.49 | A | C |
| ATOM | 277 | CG2 | VAL | A | 529 | 17.945 | 20.047 | 20.156 | 1.00 | 40.27 | A | C |
| ATOM | 278 | C | VAL | A | 529 | 15.207 | 22.443 | 18.991 | 1.00 | 36.13 | A | C |
| ATOM | 279 | O | VAL | A | 529 | 15.154 | 23.375 | 19.803 | 1.00 | 35.20 | A | O |
| ATOM | 280 | N | LEU | A | 530 | 14.216 | 22.136 | 18.156 | 1.00 | 37.62 | A | N |
| ATOM | 281 | CA | LEU | A | 530 | 12.910 | 22.785 | 18.251 | 1.00 | 36.57 | A | C |
| ATOM | 282 | CB | LEU | A | 530 | 12.191 | 22.760 | 16.909 | 1.00 | 31.08 | A | C |
| ATOM | 283 | CG | LEU | A | 530 | 10.770 | 23.313 | 16.984 | 1.00 | 29.72 | A | C |
| ATOM | 284 | CD1 | LEU | A | 530 | 10.777 | 24.824 | 16.970 | 1.00 | 28.98 | A | C |
| ATOM | 285 | CD2 | LEU | A | 530 | 9.943 | 22.788 | 15.847 | 1.00 | 30.51 | A | C |
| ATOM | 286 | C | LEU | A | 530 | 12.054 | 22.101 | 19.312 | 1.00 | 38.92 | A | C |
| ATOM | 287 | O | LEU | A | 530 | 11.896 | 20.871 | 19.298 | 1.00 | 44.45 | A | O |
| ATOM | 288 | N | THR | A | 531 | 11.496 | 22.891 | 20.224 | 1.00 | 34.89 | A | N |
| ATOM | 289 | CA | THR | A | 531 | 10.706 | 22.315 | 21.313 | 1.00 | 36.51 | A | C |
| ATOM | 290 | CB | THR | A | 531 | 11.655 | 21.749 | 22.382 | 1.00 | 29.03 | A | C |
| ATOM | 291 | OG1 | THR | A | 531 | 10.884 | 21.120 | 23.415 | 1.00 | 26.10 | A | O |
| ATOM | 292 | CG2 | THR | A | 531 | 12.405 | 22.866 | 23.059 | 1.00 | 23.72 | A | C |
| ATOM | 293 | C | THR | A | 531 | 9.608 | 23.230 | 21.905 | 1.00 | 40.20 | A | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 294 | O | THR | A | 531 | 9.405 | 24.338 | 21.426 | 1.00 | 47.18 | A | O |
| ATOM | 295 | N | ALA | A | 532 | 8.885 | 22.770 | 22.921 | 1.00 | 39.47 | A | N |
| ATOM | 296 | CA | ALA | A | 532 | 7.810 | 23.588 | 23.496 | 1.00 | 42.64 | A | C |
| ATOM | 297 | CB | ALA | A | 532 | 6.606 | 22.751 | 23.803 | 1.00 | 47.31 | A | C |
| ATOM | 298 | C | ALA | A | 532 | 8.217 | 24.384 | 24.736 | 1.00 | 42.64 | A | C |
| ATOM | 299 | O | ALA | A | 532 | 9.181 | 24.041 | 25.423 | 1.00 | 38.19 | A | O |
| ATOM | 300 | N | ARG | A | 533 | 7.464 | 25.443 | 25.024 | 1.00 | 44.00 | A | N |
| ATOM | 301 | CA | ARG | A | 533 | 7.873 | 26.378 | 26.058 | 1.00 | 44.35 | A | C |
| ATOM | 302 | CB | ARG | A | 533 | 7.242 | 27.761 | 25.892 | 1.00 | 46.20 | A | C |
| ATOM | 303 | CG | ARG | A | 533 | 5.867 | 27.917 | 26.489 | 1.00 | 53.50 | A | C |
| ATOM | 304 | CD | ARG | A | 533 | 5.162 | 29.162 | 26.000 | 1.00 | 63.95 | A | C |
| ATOM | 305 | NE | ARG | A | 533 | 4.710 | 30.013 | 27.094 | 1.00 | 71.05 | A | N |
| ATOM | 306 | CZ | ARG | A | 533 | 5.460 | 30.932 | 27.695 | 1.00 | 73.73 | A | C |
| ATOM | 307 | NH1 | ARG | A | 533 | 4.948 | 31.652 | 28.685 | 1.00 | 74.71 | A | N |
| ATOM | 308 | NH2 | ARG | A | 533 | 6.718 | 31.133 | 27.315 | 1.00 | 74.31 | A | N |
| ATOM | 309 | C | ARG | A | 533 | 7.573 | 25.802 | 27.401 | 1.00 | 46.11 | A | C |
| ATOM | 310 | O | ARG | A | 533 | 8.343 | 25.999 | 28.329 | 1.00 | 56.79 | A | O |
| ATOM | 311 | N | GLN | A | 534 | 6.477 | 25.062 | 27.497 | 1.00 | 40.40 | A | N |
| ATOM | 312 | CA | GLN | A | 534 | 6.120 | 24.373 | 28.719 | 1.00 | 38.80 | A | C |
| ATOM | 313 | CB | GLN | A | 534 | 4.852 | 23.532 | 28.507 | 1.00 | 42.02 | A | C |
| ATOM | 314 | CG | GLN | A | 534 | 3.522 | 24.276 | 28.352 | 1.00 | 40.73 | A | C |
| ATOM | 315 | CD | GLN | A | 534 | 3.303 | 24.893 | 26.973 | 1.00 | 42.20 | A | C |
| ATOM | 316 | OE1 | GLN | A | 534 | 2.382 | 25.697 | 26.801 | 1.00 | 40.04 | A | O |
| ATOM | 317 | NE2 | GLN | A | 534 | 4.151 | 24.539 | 25.997 | 1.00 | 44.63 | A | N |
| ATOM | 318 | C | GLN | A | 534 | 7.238 | 23.435 | 29.169 | 1.00 | 40.36 | A | C |
| ATOM | 319 | O | GLN | A | 534 | 7.039 | 22.646 | 30.069 | 1.00 | 45.68 | A | O |
| ATOM | 320 | N | CYS | A | 535 | 8.408 | 23.503 | 28.548 | 1.00 | 42.90 | A | N |
| ATOM | 321 | CA | CYS | A | 535 | 9.492 | 22.585 | 28.896 | 1.00 | 45.34 | A | C |
| ATOM | 322 | CB | CYS | A | 535 | 10.138 | 22.036 | 27.640 | 1.00 | 45.96 | A | C |
| ATOM | 323 | SG | CYS | A | 535 | 8.973 | 21.017 | 26.756 | 1.00 | 51.38 | A | S |
| ATOM | 324 | C | CYS | A | 535 | 10.574 | 23.134 | 29.799 | 1.00 | 47.11 | A | C |
| ATOM | 325 | O | CYS | A | 535 | 11.520 | 22.425 | 30.108 | 1.00 | 52.64 | A | O |
| ATOM | 326 | N | PHE | A | 536 | 10.444 | 24.381 | 30.231 | 1.00 | 46.54 | A | N |
| ATOM | 327 | CA | PHE | A | 536 | 11.521 | 25.032 | 30.969 | 1.00 | 40.70 | A | C |
| ATOM | 328 | CB | PHE | A | 536 | 12.183 | 26.086 | 30.082 | 1.00 | 41.52 | A | C |
| ATOM | 329 | CG | PHE | A | 536 | 12.679 | 25.541 | 28.778 | 1.00 | 43.07 | A | C |
| ATOM | 330 | CD1 | PHE | A | 536 | 13.919 | 24.898 | 28.705 | 1.00 | 45.52 | A | C |
| ATOM | 331 | CE1 | PHE | A | 536 | 14.376 | 24.359 | 27.504 | 1.00 | 44.59 | A | C |
| ATOM | 332 | CZ | PHE | A | 536 | 13.592 | 24.472 | 26.365 | 1.00 | 41.06 | A | C |
| ATOM | 333 | CE2 | PHE | A | 536 | 12.356 | 25.121 | 26.437 | 1.00 | 39.09 | A | C |
| ATOM | 334 | CD2 | PHE | A | 536 | 11.905 | 25.641 | 27.632 | 1.00 | 37.71 | A | C |
| ATOM | 335 | C | PHE | A | 536 | 11.056 | 25.645 | 32.287 | 1.00 | 38.93 | A | C |
| ATOM | 336 | O | PHE | A | 536 | 10.680 | 26.792 | 32.339 | 1.00 | 42.14 | A | O |
| ATOM | 337 | N | PRO | A | 537 | 11.082 | 24.878 | 33.358 | 1.00 | 38.38 | A | N |
| ATOM | 338 | CA | PRO | A | 537 | 10.711 | 25.394 | 34.678 | 1.00 | 39.14 | A | C |
| ATOM | 339 | CB | PRO | A | 537 | 10.728 | 24.140 | 35.541 | 1.00 | 44.43 | A | C |
| ATOM | 340 | CG | PRO | A | 537 | 10.593 | 23.029 | 34.540 | 1.00 | 45.79 | A | C |
| ATOM | 341 | CD | PRO | A | 537 | 11.452 | 23.457 | 33.402 | 1.00 | 41.04 | A | C |
| ATOM | 342 | C | PRO | A | 537 | 11.721 | 26.396 | 35.212 | 1.00 | 38.67 | A | C |
| ATOM | 343 | O | PRO | A | 537 | 11.316 | 27.387 | 35.777 | 1.00 | 38.75 | A | O |
| ATOM | 344 | N | SER | A | 538 | 13.008 | 26.119 | 35.038 | 1.00 | 43.61 | A | N |
| ATOM | 345 | CA | SER | A | 538 | 14.095 | 26.998 | 35.444 | 1.00 | 47.01 | A | C |
| ATOM | 346 | CB | SER | A | 538 | 15.383 | 26.191 | 35.550 | 1.00 | 50.27 | A | C |
| ATOM | 347 | OG | SER | A | 538 | 15.968 | 26.280 | 36.836 | 1.00 | 54.13 | A | O |
| ATOM | 348 | C | SER | A | 538 | 14.328 | 28.032 | 34.382 | 1.00 | 53.40 | A | C |
| ATOM | 349 | O | SER | A | 538 | 13.931 | 27.838 | 33.240 | 1.00 | 56.52 | A | O |
| ATOM | 350 | N | ARG | A | 539 | 14.985 | 29.129 | 34.750 | 1.00 | 59.84 | A | N |
| ATOM | 351 | CA | ARG | A | 539 | 15.570 | 30.015 | 33.749 | 1.00 | 62.13 | A | C |
| ATOM | 352 | CB | ARG | A | 539 | 15.334 | 31.495 | 34.072 | 1.00 | 65.44 | A | C |
| ATOM | 353 | CG | ARG | A | 539 | 14.786 | 32.357 | 32.897 | 1.00 | 73.11 | A | C |
| ATOM | 354 | CD | ARG | A | 539 | 14.232 | 31.582 | 31.648 | 1.00 | 79.75 | A | C |
| ATOM | 355 | NE | ARG | A | 539 | 12.759 | 31.550 | 31.546 | 1.00 | 83.84 | A | N |
| ATOM | 356 | CZ | ARG | A | 539 | 11.977 | 32.568 | 31.138 | 1.00 | 85.20 | A | C |
| ATOM | 357 | NH1 | ARG | A | 539 | 10.659 | 32.419 | 31.094 | 1.00 | 85.44 | A | N |
| ATOM | 358 | NH2 | ARG | A | 539 | 12.495 | 33.737 | 30.779 | 1.00 | 86.16 | A | N |
| ATOM | 359 | C | ARG | A | 539 | 17.050 | 29.702 | 33.622 | 1.00 | 61.46 | A | C |
| ATOM | 360 | O | ARG | A | 539 | 17.637 | 29.908 | 32.574 | 1.00 | 63.21 | A | O |
| ATOM | 361 | N | ASP | A | 540 | 17.639 | 29.175 | 34.689 | 1.00 | 63.93 | A | N |
| ATOM | 362 | CA | ASP | A | 540 | 19.062 | 28.855 | 34.718 | 1.00 | 68.12 | A | C |
| ATOM | 363 | CB | ASP | A | 540 | 19.509 | 28.615 | 36.169 | 1.00 | 74.68 | A | C |
| ATOM | 364 | CG | ASP | A | 540 | 20.922 | 28.049 | 36.270 | 1.00 | 82.15 | A | C |
| ATOM | 365 | OD1 | ASP | A | 540 | 21.708 | 28.200 | 35.302 | 1.00 | 83.45 | A | O |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 366 | OD2 | ASP | A | 540 | 21.335 | 27.438 | 37.285 | 1.00 | 86.19 | A | O |
| ATOM | 367 | C | ASP | A | 540 | 19.348 | 27.629 | 33.854 | 1.00 | 66.59 | A | C |
| ATOM | 368 | O | ASP | A | 540 | 18.929 | 26.525 | 34.204 | 1.00 | 71.11 | A | O |
| ATOM | 369 | N | LEU | A | 541 | 20.070 | 27.816 | 32.745 | 1.00 | 60.72 | A | N |
| ATOM | 370 | CA | LEU | A | 541 | 20.310 | 26.722 | 31.782 | 1.00 | 53.13 | A | C |
| ATOM | 371 | CB | LEU | A | 541 | 20.669 | 27.244 | 30.378 | 1.00 | 49.17 | A | C |
| ATOM | 372 | CG | LEU | A | 541 | 19.815 | 28.280 | 29.630 | 1.00 | 44.30 | A | C |
| ATOM | 373 | CD1 | LEU | A | 541 | 20.286 | 28.383 | 28.185 | 1.00 | 41.68 | A | C |
| ATOM | 374 | CD2 | LEU | A | 541 | 18.297 | 28.033 | 29.700 | 1.00 | 38.17 | A | C |
| ATOM | 375 | C | LEU | A | 541 | 21.360 | 25.712 | 32.243 | 1.00 | 49.37 | A | C |
| ATOM | 376 | O | LEU | A | 541 | 21.642 | 24.741 | 31.526 | 1.00 | 46.25 | A | O |
| ATOM | 377 | N | LYS | A | 542 | 21.933 | 25.952 | 33.425 | 1.00 | 47.11 | A | N |
| ATOM | 378 | CA | LYS | A | 542 | 22.772 | 24.973 | 34.106 | 1.00 | 51.16 | A | C |
| ATOM | 379 | CB | LYS | A | 542 | 23.253 | 25.528 | 35.450 | 1.00 | 55.37 | A | C |
| ATOM | 380 | CG | LYS | A | 542 | 24.763 | 25.754 | 35.545 | 1.00 | 63.15 | A | C |
| ATOM | 381 | CD | LYS | A | 542 | 25.122 | 27.183 | 35.986 | 1.00 | 65.17 | A | C |
| ATOM | 382 | CE | LYS | A | 542 | 26.207 | 27.795 | 35.097 | 1.00 | 64.91 | A | C |
| ATOM | 383 | NZ | LYS | A | 542 | 26.907 | 28.922 | 35.774 | 1.00 | 66.28 | A | N |
| ATOM | 384 | C | LYS | A | 542 | 21.985 | 23.678 | 34.333 | 1.00 | 53.42 | A | C |
| ATOM | 385 | O | LYS | A | 542 | 22.470 | 22.578 | 34.054 | 1.00 | 53.95 | A | O |
| ATOM | 386 | N | ASP | A | 543 | 20.751 | 23.830 | 34.808 | 1.00 | 53.44 | A | N |
| ATOM | 387 | CA | ASP | A | 543 | 19.910 | 22.711 | 35.212 | 1.00 | 52.87 | A | C |
| ATOM | 388 | CB | ASP | A | 543 | 18.650 | 23.231 | 35.887 | 1.00 | 56.38 | A | C |
| ATOM | 389 | CG | ASP | A | 543 | 18.942 | 23.964 | 37.176 | 1.00 | 60.48 | A | C |
| ATOM | 390 | OD1 | ASP | A | 543 | 19.775 | 23.488 | 37.994 | 1.00 | 58.01 | A | O |
| ATOM | 391 | OD2 | ASP | A | 543 | 18.364 | 25.033 | 37.450 | 1.00 | 65.01 | A | O |
| ATOM | 392 | C | ASP | A | 543 | 19.512 | 21.753 | 34.099 | 1.00 | 50.26 | A | C |
| ATOM | 393 | O | ASP | A | 543 | 19.065 | 20.637 | 34.380 | 1.00 | 54.20 | A | O |
| ATOM | 394 | N | TYR | A | 544 | 19.672 | 22.174 | 32.848 | 1.00 | 43.23 | A | N |
| ATOM | 395 | CA | TYR | A | 544 | 19.286 | 21.330 | 31.722 | 1.00 | 38.63 | A | C |
| ATOM | 396 | CB | TYR | A | 544 | 18.477 | 22.116 | 30.716 | 1.00 | 29.69 | A | C |
| ATOM | 397 | CG | TYR | A | 544 | 17.306 | 22.885 | 31.238 | 1.00 | 27.52 | A | C |
| ATOM | 398 | CD1 | TYR | A | 544 | 16.008 | 22.363 | 31.143 | 1.00 | 30.21 | A | C |
| ATOM | 399 | CE1 | TYR | A | 544 | 14.893 | 23.090 | 31.571 | 1.00 | 24.62 | A | C |
| ATOM | 400 | CZ | TYR | A | 544 | 15.086 | 24.348 | 32.080 | 1.00 | 24.13 | A | C |
| ATOM | 401 | OH | TYR | A | 544 | 14.019 | 25.055 | 32.497 | 1.00 | 28.35 | A | O |
| ATOM | 402 | CE2 | TYR | A | 544 | 16.350 | 24.900 | 32.182 | 1.00 | 25.18 | A | C |
| ATOM | 403 | CD2 | TYR | A | 544 | 17.461 | 24.166 | 31.746 | 1.00 | 25.99 | A | C |
| ATOM | 404 | C | TYR | A | 544 | 20.452 | 20.632 | 30.985 | 1.00 | 42.29 | A | C |
| ATOM | 405 | O | TYR | A | 544 | 21.630 | 20.955 | 31.192 | 1.00 | 44.90 | A | O |
| ATOM | 406 | N | GLU | A | 545 | 20.083 | 19.710 | 30.093 | 1.00 | 40.12 | A | N |
| ATOM | 407 | CA | GLU | A | 545 | 20.994 | 18.824 | 29.378 | 1.00 | 40.44 | A | C |
| ATOM | 408 | CB | GLU | A | 545 | 21.542 | 17.790 | 30.359 | 1.00 | 46.13 | A | C |
| ATOM | 409 | CG | GLU | A | 545 | 22.580 | 16.830 | 29.811 | 1.00 | 54.99 | A | C |
| ATOM | 410 | CD | GLU | A | 545 | 23.458 | 16.255 | 30.913 | 1.00 | 62.86 | A | C |
| ATOM | 411 | OE1 | GLU | A | 545 | 23.387 | 15.028 | 31.148 | 1.00 | 65.66 | A | O |
| ATOM | 412 | OE2 | GLU | A | 545 | 24.223 | 17.026 | 31.549 | 1.00 | 65.70 | A | O |
| ATOM | 413 | C | GLU | A | 545 | 20.178 | 18.124 | 28.273 | 1.00 | 42.84 | A | C |
| ATOM | 414 | O | GLU | A | 545 | 19.017 | 17.735 | 28.495 | 1.00 | 47.57 | A | O |
| ATOM | 415 | N | ALA | A | 546 | 20.758 | 17.977 | 27.084 | 1.00 | 37.78 | A | N |
| ATOM | 416 | CA | ALA | A | 546 | 20.041 | 17.392 | 25.952 | 1.00 | 31.25 | A | C |
| ATOM | 417 | CB | ALA | A | 546 | 19.925 | 18.396 | 24.825 | 1.00 | 23.18 | A | C |
| ATOM | 418 | C | ALA | A | 546 | 20.722 | 16.119 | 25.469 | 1.00 | 34.99 | A | C |
| ATOM | 419 | O | ALA | A | 546 | 21.838 | 16.161 | 24.959 | 1.00 | 37.39 | A | O |
| ATOM | 420 | N | TRP | A | 547 | 20.044 | 14.988 | 25.633 | 1.00 | 38.48 | A | N |
| ATOM | 421 | CA | TRP | A | 547 | 20.576 | 13.704 | 25.201 | 1.00 | 40.47 | A | C |
| ATOM | 422 | CB | TRP | A | 547 | 20.082 | 12.616 | 26.117 | 1.00 | 40.48 | A | C |
| ATOM | 423 | CG | TRP | A | 547 | 20.618 | 12.697 | 27.487 | 1.00 | 41.31 | A | C |
| ATOM | 424 | CD1 | TRP | A | 547 | 21.048 | 13.810 | 28.139 | 1.00 | 42.51 | A | C |
| ATOM | 425 | NE1 | TRP | A | 547 | 21.456 | 13.480 | 29.407 | 1.00 | 45.89 | A | N |
| ATOM | 426 | CE2 | TRP | A | 547 | 21.294 | 12.130 | 29.586 | 1.00 | 44.69 | A | C |
| ATOM | 427 | CD2 | TRP | A | 547 | 20.771 | 11.610 | 28.398 | 1.00 | 41.64 | A | C |
| ATOM | 428 | CE3 | TRP | A | 547 | 20.515 | 10.237 | 28.327 | 1.00 | 43.81 | A | C |
| ATOM | 429 | CZ3 | TRP | A | 547 | 20.779 | 9.448 | 29.421 | 1.00 | 44.52 | A | C |
| ATOM | 430 | CH2 | TRP | A | 547 | 21.301 | 9.992 | 30.585 | 1.00 | 46.82 | A | C |
| ATOM | 431 | CZ2 | TRP | A | 547 | 21.567 | 11.330 | 30.691 | 1.00 | 48.64 | A | C |
| ATOM | 432 | C | TRP | A | 547 | 20.109 | 13.385 | 23.805 | 1.00 | 44.57 | A | C |
| ATOM | 433 | O | TRP | A | 547 | 18.922 | 13.531 | 23.508 | 1.00 | 50.42 | A | O |
| ATOM | 434 | N | LEU | A | 548 | 21.037 | 12.934 | 22.963 | 1.00 | 43.65 | A | N |
| ATOM | 435 | CA | LEU | A | 548 | 20.772 | 12.711 | 21.544 | 1.00 | 45.06 | A | C |
| ATOM | 436 | CB | LEU | A | 548 | 21.617 | 13.658 | 20.693 | 1.00 | 41.86 | A | C |
| ATOM | 437 | CG | LEU | A | 548 | 21.288 | 15.146 | 20.522 | 1.00 | 39.52 | A | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 438 | CD1 | LEU | A | 548 | 20.574 | 15.345 | 19.210 | 1.00 | 40.81 | A | C |
| ATOM | 439 | CD2 | LEU | A | 548 | 20.487 | 15.769 | 21.662 | 1.00 | 33.92 | A | C |
| ATOM | 440 | C | LEU | A | 548 | 21.096 | 11.278 | 21.163 | 1.00 | 51.45 | A | C |
| ATOM | 441 | O | LEU | A | 548 | 21.915 | 10.626 | 21.816 | 1.00 | 51.74 | A | O |
| ATOM | 442 | N | GLY | A | 549 | 20.455 | 10.797 | 20.099 | 1.00 | 58.34 | A | N |
| ATOM | 443 | CA | GLY | A | 549 | 20.631 | 9.427 | 19.628 | 1.00 | 59.49 | A | C |
| ATOM | 444 | C | GLY | A | 549 | 20.411 | 8.354 | 20.685 | 1.00 | 58.01 | A | C |
| ATOM | 445 | O | GLY | A | 549 | 21.236 | 7.461 | 20.851 | 1.00 | 56.69 | A | O |
| ATOM | 446 | N | ILE | A | 550 | 19.306 | 8.457 | 21.417 | 1.00 | 57.21 | A | N |
| ATOM | 447 | CA | ILE | A | 550 | 18.940 | 7.433 | 22.391 | 1.00 | 56.71 | A | C |
| ATOM | 448 | CB | ILE | A | 550 | 18.836 | 8.022 | 23.803 | 1.00 | 53.72 | A | C |
| ATOM | 449 | CG1 | ILE | A | 550 | 17.671 | 8.994 | 23.892 | 1.00 | 52.36 | A | C |
| ATOM | 450 | CD1 | ILE | A | 550 | 17.114 | 9.109 | 25.269 | 1.00 | 53.68 | A | C |
| ATOM | 451 | CG2 | ILE | A | 550 | 20.107 | 8.729 | 24.165 | 1.00 | 55.94 | A | C |
| ATOM | 452 | C | ILE | A | 550 | 17.637 | 6.729 | 22.001 | 1.00 | 59.34 | A | C |
| ATOM | 453 | O | ILE | A | 550 | 16.900 | 7.194 | 21.116 | 1.00 | 66.68 | A | O |
| ATOM | 454 | N | HIS | A | 551 | 17.373 | 5.604 | 22.658 | 1.00 | 51.80 | A | N |
| ATOM | 455 | CA | HIS | A | 551 | 16.178 | 4.818 | 22.424 | 1.00 | 43.88 | A | C |
| ATOM | 456 | CB | HIS | A | 551 | 16.541 | 3.483 | 21.800 | 1.00 | 40.60 | A | C |
| ATOM | 457 | CG | HIS | A | 551 | 15.387 | 2.764 | 21.175 | 1.00 | 40.32 | A | C |
| ATOM | 458 | ND1 | HIS | A | 551 | 15.490 | 1.472 | 20.698 | 1.00 | 39.93 | A | N |
| ATOM | 459 | CE1 | HIS | A | 551 | 14.326 | 1.097 | 20.200 | 1.00 | 39.40 | A | C |
| ATOM | 460 | NE2 | HIS | A | 551 | 13.473 | 2.098 | 20.331 | 1.00 | 39.45 | A | N |
| ATOM | 461 | CD2 | HIS | A | 551 | 14.112 | 3.154 | 20.935 | 1.00 | 39.43 | A | C |
| ATOM | 462 | C | HIS | A | 551 | 15.542 | 4.583 | 23.769 | 1.00 | 47.12 | A | C |
| ATOM | 463 | O | HIS | A | 551 | 14.323 | 4.661 | 23.893 | 1.00 | 53.18 | A | O |
| ATOM | 464 | N | ASP | A | 552 | 16.369 | 4.283 | 24.775 | 1.00 | 44.11 | A | N |
| ATOM | 465 | CA | ASP | A | 552 | 15.895 | 4.157 | 26.149 | 1.00 | 39.32 | A | C |
| ATOM | 466 | CB | ASP | A | 552 | 16.705 | 3.135 | 26.934 | 1.00 | 38.59 | A | C |
| ATOM | 467 | CG | ASP | A | 552 | 16.098 | 2.862 | 28.304 | 1.00 | 44.48 | A | C |
| ATOM | 468 | OD1 | ASP | A | 552 | 16.576 | 3.424 | 29.316 | 1.00 | 42.47 | A | O |
| ATOM | 469 | OD2 | ASP | A | 552 | 15.104 | 2.118 | 28.459 | 1.00 | 48.70 | A | O |
| ATOM | 470 | C | ASP | A | 552 | 15.955 | 5.494 | 26.879 | 1.00 | 36.72 | A | C |
| ATOM | 471 | O | ASP | A | 552 | 17.018 | 6.031 | 27.078 | 1.00 | 37.41 | A | O |
| ATOM | 472 | N | VAL | A | 553 | 14.810 | 6.017 | 27.295 | 1.00 | 35.32 | A | N |
| ATOM | 473 | CA | VAL | A | 553 | 14.755 | 7.260 | 28.051 | 1.00 | 35.91 | A | C |
| ATOM | 474 | CB | VAL | A | 553 | 13.381 | 7.424 | 28.755 | 1.00 | 32.99 | A | C |
| ATOM | 475 | CG1 | VAL | A | 553 | 13.321 | 6.616 | 30.034 | 1.00 | 30.23 | A | C |
| ATOM | 476 | CG2 | VAL | A | 553 | 13.042 | 8.903 | 28.997 | 1.00 | 26.91 | A | C |
| ATOM | 477 | C | VAL | A | 553 | 15.918 | 7.438 | 29.046 | 1.00 | 43.64 | A | C |
| ATOM | 478 | O | VAL | A | 553 | 16.364 | 8.568 | 29.276 | 1.00 | 52.45 | A | O |
| ATOM | 479 | N | HIS | A | 554 | 16.410 | 6.335 | 29.617 | 1.00 | 45.61 | A | N |
| ATOM | 480 | CA | HIS | A | 554 | 17.535 | 6.367 | 30.556 | 1.00 | 46.89 | A | C |
| ATOM | 481 | CB | HIS | A | 554 | 17.284 | 5.408 | 31.719 | 1.00 | 46.90 | A | C |
| ATOM | 482 | CG | HIS | A | 554 | 16.199 | 5.845 | 32.644 | 1.00 | 49.56 | A | C |
| ATOM | 483 | ND1 | HIS | A | 554 | 14.981 | 5.208 | 32.711 | 1.00 | 52.02 | A | N |
| ATOM | 484 | CE1 | HIS | A | 554 | 14.223 | 5.794 | 33.621 | 1.00 | 53.44 | A | C |
| ATOM | 485 | NE2 | HIS | A | 554 | 14.909 | 6.789 | 34.151 | 1.00 | 56.69 | A | N |
| ATOM | 486 | CD2 | HIS | A | 554 | 16.150 | 6.842 | 33.557 | 1.00 | 55.35 | A | C |
| ATOM | 487 | C | HIS | A | 554 | 18.850 | 5.985 | 29.883 | 1.00 | 46.94 | A | C |
| ATOM | 488 | O | HIS | A | 554 | 19.847 | 5.737 | 30.543 | 1.00 | 51.15 | A | O |
| ATOM | 489 | N | GLY | A | 555 | 18.845 | 5.900 | 28.566 | 1.00 | 48.30 | A | N |
| ATOM | 490 | CA | GLY | A | 555 | 20.049 | 5.588 | 27.816 | 1.00 | 50.65 | A | C |
| ATOM | 491 | C | GLY | A | 555 | 20.513 | 4.149 | 27.921 | 1.00 | 51.26 | A | C |
| ATOM | 492 | O | GLY | A | 555 | 21.633 | 3.828 | 27.492 | 1.00 | 54.15 | A | O |
| ATOM | 493 | N | ARG | A | 556 | 19.652 | 3.282 | 28.455 | 1.00 | 46.93 | A | N |
| ATOM | 494 | CA | ARG | A | 556 | 20.066 | 1.933 | 28.834 | 1.00 | 45.09 | A | C |
| ATOM | 495 | CB | ARG | A | 556 | 18.970 | 1.222 | 29.613 | 1.00 | 40.39 | A | C |
| ATOM | 496 | CG | ARG | A | 556 | 18.843 | 1.746 | 31.027 | 1.00 | 42.37 | A | C |
| ATOM | 497 | CD | ARG | A | 556 | 17.875 | 0.969 | 31.916 | 1.00 | 49.31 | A | C |
| ATOM | 498 | NE | ARG | A | 556 | 16.603 | 1.668 | 32.122 | 1.00 | 51.71 | A | N |
| ATOM | 499 | CZ | ARG | A | 556 | 15.444 | 1.287 | 31.602 | 1.00 | 54.36 | A | C |
| ATOM | 500 | NH1 | ARG | A | 556 | 14.331 | 1.974 | 31.849 | 1.00 | 54.30 | A | N |
| ATOM | 501 | NH2 | ARG | A | 556 | 15.393 | 0.207 | 30.832 | 1.00 | 59.72 | A | N |
| ATOM | 502 | C | ARG | A | 556 | 20.646 | 1.069 | 27.701 | 1.00 | 48.74 | A | C |
| ATOM | 503 | O | ARG | A | 556 | 21.717 | 0.463 | 27.859 | 1.00 | 51.93 | A | O |
| ATOM | 504 | N | GLY | A | 557 | 19.984 | 1.025 | 26.555 | 1.00 | 49.49 | A | N |
| ATOM | 505 | CA | GLY | A | 557 | 20.560 | 0.286 | 25.441 | 1.00 | 53.98 | A | C |
| ATOM | 506 | C | GLY | A | 557 | 21.794 | 0.931 | 24.810 | 1.00 | 54.64 | A | C |
| ATOM | 507 | O | GLY | A | 557 | 22.660 | 0.250 | 24.246 | 1.00 | 47.61 | A | O |
| ATOM | 508 | N | ASP | A | 558 | 21.882 | 2.253 | 24.935 | 1.00 | 59.36 | A | N |
| ATOM | 509 | CA | ASP | A | 558 | 22.565 | 3.049 | 23.925 | 1.00 | 64.13 | A | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 510 | CB  | ASP | A | 558 | 21.577 | 4.015  | 23.225 | 1.00 | 64.08 | A | C |
| ATOM | 511 | CG  | ASP | A | 558 | 20.132 | 3.875  | 23.724 | 1.00 | 63.54 | A | C |
| ATOM | 512 | OD1 | ASP | A | 558 | 19.724 | 4.707  | 24.567 | 1.00 | 63.63 | A | O |
| ATOM | 513 | OD2 | ASP | A | 558 | 19.331 | 2.988  | 23.327 | 1.00 | 60.19 | A | O |
| ATOM | 514 | C   | ASP | A | 558 | 23.806 | 3.784  | 24.411 | 1.00 | 69.82 | A | C |
| ATOM | 515 | O   | ASP | A | 558 | 23.799 | 5.010  | 24.542 | 1.00 | 73.90 | A | O |
| ATOM | 516 | N   | GLU | A | 559 | 24.878 | 3.038  | 24.658 | 1.00 | 72.43 | A | N |
| ATOM | 517 | CA  | GLU | A | 559 | 26.152 | 3.646  | 25.038 | 1.00 | 70.11 | A | C |
| ATOM | 518 | CB  | GLU | A | 559 | 27.004 | 2.694  | 25.886 | 1.00 | 74.85 | A | C |
| ATOM | 519 | CG  | GLU | A | 559 | 26.470 | 1.263  | 26.010 | 1.00 | 82.18 | A | C |
| ATOM | 520 | CD  | GLU | A | 559 | 25.396 | 1.091  | 27.089 | 1.00 | 85.89 | A | C |
| ATOM | 521 | OE1 | GLU | A | 559 | 25.367 | 1.875  | 28.068 | 1.00 | 86.56 | A | O |
| ATOM | 522 | OE2 | GLU | A | 559 | 24.568 | 0.160  | 26.956 | 1.00 | 86.27 | A | O |
| ATOM | 523 | C   | GLU | A | 559 | 26.870 | 4.047  | 23.766 | 1.00 | 65.20 | A | C |
| ATOM | 524 | O   | GLU | A | 559 | 27.501 | 5.090  | 23.699 | 1.00 | 62.09 | A | O |
| ATOM | 525 | N   | LYS | A | 560 | 26.716 | 3.229  | 22.737 | 1.00 | 66.52 | A | N |
| ATOM | 526 | CA  | LYS | A | 560 | 27.395 | 3.455  | 21.473 | 1.00 | 70.54 | A | C |
| ATOM | 527 | CB  | LYS | A | 560 | 27.572 | 2.128  | 20.719 | 1.00 | 78.87 | A | C |
| ATOM | 528 | CG  | LYS | A | 560 | 29.014 | 1.865  | 20.249 | 1.00 | 86.89 | A | C |
| ATOM | 529 | CD  | LYS | A | 560 | 29.280 | 0.382  | 19.952 | 1.00 | 91.41 | A | C |
| ATOM | 530 | CE  | LYS | A | 560 | 29.837 | 0.176  | 18.530 | 1.00 | 94.26 | A | C |
| ATOM | 531 | NZ  | LYS | A | 560 | 31.286 | −0.214 | 18.490 | 1.00 | 93.72 | A | N |
| ATOM | 532 | C   | LYS | A | 560 | 26.745 | 4.512  | 20.569 | 1.00 | 68.03 | A | C |
| ATOM | 533 | O   | LYS | A | 560 | 27.231 | 4.742  | 19.460 | 1.00 | 69.10 | A | O |
| ATOM | 534 | N   | CYS | A | 561 | 25.665 | 5.153  | 21.023 | 1.00 | 65.42 | A | N |
| ATOM | 535 | CA  | CYS | A | 561 | 25.006 | 6.189  | 20.206 | 1.00 | 63.80 | A | C |
| ATOM | 536 | CB  | CYS | A | 561 | 23.696 | 5.687  | 19.592 | 1.00 | 65.05 | A | C |
| ATOM | 537 | SG  | CYS | A | 561 | 23.114 | 4.077  | 20.148 | 1.00 | 71.04 | A | S |
| ATOM | 538 | C   | CYS | A | 561 | 24.779 | 7.541  | 20.900 | 1.00 | 60.62 | A | C |
| ATOM | 539 | O   | CYS | A | 561 | 24.883 | 8.606  | 20.261 | 1.00 | 59.98 | A | O |
| ATOM | 540 | N   | LYS | A | 562 | 24.471 | 7.479  | 22.195 | 1.00 | 55.53 | A | N |
| ATOM | 541 | CA  | LYS | A | 562 | 24.241 | 8.649  | 23.053 | 1.00 | 51.59 | A | C |
| ATOM | 542 | CB  | LYS | A | 562 | 24.284 | 8.204  | 24.517 | 1.00 | 50.33 | A | C |
| ATOM | 543 | CG  | LYS | A | 562 | 23.663 | 9.172  | 25.506 | 1.00 | 50.06 | A | C |
| ATOM | 544 | CD  | LYS | A | 562 | 23.388 | 8.476  | 26.829 | 1.00 | 49.50 | A | C |
| ATOM | 545 | CE  | LYS | A | 562 | 24.453 | 8.784  | 27.862 | 1.00 | 50.51 | A | C |
| ATOM | 546 | NZ  | LYS | A | 562 | 23.950 | 8.466  | 29.219 | 1.00 | 51.61 | A | N |
| ATOM | 547 | C   | LYS | A | 562 | 25.199 | 9.842  | 22.855 | 1.00 | 48.90 | A | C |
| ATOM | 548 | O   | LYS | A | 562 | 26.406 | 9.678  | 22.719 | 1.00 | 48.37 | A | O |
| ATOM | 549 | N   | GLN | A | 563 | 24.635 | 11.041 | 22.856 | 1.00 | 47.04 | A | N |
| ATOM | 550 | CA  | GLN | A | 563 | 25.396 | 12.278 | 22.799 | 1.00 | 43.96 | A | C |
| ATOM | 551 | CB  | GLN | A | 563 | 25.290 | 12.881 | 21.402 | 1.00 | 41.41 | A | C |
| ATOM | 552 | CG  | GLN | A | 563 | 26.214 | 12.301 | 20.363 | 1.00 | 43.30 | A | C |
| ATOM | 553 | CD  | GLN | A | 563 | 26.240 | 13.135 | 19.075 | 1.00 | 47.28 | A | C |
| ATOM | 554 | OE1 | GLN | A | 563 | 26.723 | 14.289 | 19.053 | 1.00 | 48.43 | A | O |
| ATOM | 555 | NE2 | GLN | A | 563 | 25.730 | 12.549 | 17.997 | 1.00 | 45.76 | A | N |
| ATOM | 556 | C   | GLN | A | 563 | 24.738 | 13.231 | 23.792 | 1.00 | 45.34 | A | C |
| ATOM | 557 | O   | GLN | A | 563 | 23.577 | 13.604 | 23.597 | 1.00 | 49.13 | A | O |
| ATOM | 558 | N   | VAL | A | 564 | 25.436 | 13.621 | 24.857 | 1.00 | 41.21 | A | N |
| ATOM | 559 | CA  | VAL | A | 564 | 24.840 | 14.595 | 25.780 | 1.00 | 39.36 | A | C |
| ATOM | 560 | CB  | VAL | A | 564 | 24.832 | 14.133 | 27.272 | 1.00 | 39.41 | A | C |
| ATOM | 561 | CG1 | VAL | A | 564 | 24.330 | 12.699 | 27.395 | 1.00 | 37.33 | A | C |
| ATOM | 562 | CG2 | VAL | A | 564 | 26.203 | 14.301 | 27.936 | 1.00 | 44.32 | A | C |
| ATOM | 563 | C   | VAL | A | 564 | 25.437 | 15.988 | 25.614 | 1.00 | 38.92 | A | C |
| ATOM | 564 | O   | VAL | A | 564 | 26.659 | 16.162 | 25.656 | 1.00 | 44.75 | A | O |
| ATOM | 565 | N   | LEU | A | 565 | 24.567 | 16.972 | 25.414 | 1.00 | 34.38 | A | N |
| ATOM | 566 | CA  | LEU | A | 565 | 25.001 | 18.338 | 25.159 | 1.00 | 34.56 | A | C |
| ATOM | 567 | CB  | LEU | A | 565 | 24.632 | 18.727 | 23.738 | 1.00 | 35.95 | A | C |
| ATOM | 568 | CG  | LEU | A | 565 | 25.329 | 17.895 | 22.669 | 1.00 | 42.59 | A | C |
| ATOM | 569 | CD1 | LEU | A | 565 | 24.769 | 18.194 | 21.290 | 1.00 | 45.02 | A | C |
| ATOM | 570 | CD2 | LEU | A | 565 | 26.853 | 18.128 | 22.703 | 1.00 | 48.14 | A | C |
| ATOM | 571 | C   | LEU | A | 565 | 24.384 | 19.323 | 26.131 | 1.00 | 34.92 | A | C |
| ATOM | 572 | O   | LEU | A | 565 | 23.209 | 19.217 | 26.442 | 1.00 | 39.73 | A | O |
| ATOM | 573 | N   | ASN | A | 566 | 25.169 | 20.281 | 26.610 | 1.00 | 35.34 | A | N |
| ATOM | 574 | CA  | ASN | A | 566 | 24.633 | 21.358 | 27.443 | 1.00 | 39.72 | A | C |
| ATOM | 575 | CB  | ASN | A | 566 | 25.761 | 22.065 | 28.194 | 1.00 | 47.83 | A | C |
| ATOM | 576 | CG  | ASN | A | 566 | 26.303 | 21.245 | 29.356 | 1.00 | 54.40 | A | C |
| ATOM | 577 | OD1 | ASN | A | 566 | 25.550 | 20.864 | 30.252 | 1.00 | 57.20 | A | O |
| ATOM | 578 | ND2 | ASN | A | 566 | 27.620 | 20.980 | 29.353 | 1.00 | 55.33 | A | N |
| ATOM | 579 | C   | ASN | A | 566 | 23.839 | 22.362 | 26.601 | 1.00 | 38.42 | A | C |
| ATOM | 580 | O   | ASN | A | 566 | 24.045 | 22.464 | 25.398 | 1.00 | 40.20 | A | O |
| ATOM | 581 | N   | VAL | A | 567 | 22.928 | 23.099 | 27.217 | 1.00 | 37.71 | A | N |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 582 | CA | VAL | A | 567 | 22.124 | 24.045 | 26.456 | 1.00 | 42.36 | A | C |
| ATOM | 583 | CB | VAL | A | 567 | 20.658 | 24.000 | 26.886 | 1.00 | 44.62 | A | C |
| ATOM | 584 | CG1 | VAL | A | 567 | 19.933 | 25.232 | 26.408 | 1.00 | 45.19 | A | C |
| ATOM | 585 | CG2 | VAL | A | 567 | 19.974 | 22.736 | 26.339 | 1.00 | 47.75 | A | C |
| ATOM | 586 | C | VAL | A | 567 | 22.662 | 25.460 | 26.616 | 1.00 | 48.80 | A | C |
| ATOM | 587 | O | VAL | A | 567 | 22.792 | 25.953 | 27.742 | 1.00 | 56.77 | A | O |
| ATOM | 588 | N | SER | A | 568 | 22.958 | 26.118 | 25.496 | 1.00 | 47.82 | A | N |
| ATOM | 589 | CA | SER | A | 568 | 23.579 | 27.444 | 25.531 | 1.00 | 45.87 | A | C |
| ATOM | 590 | CB | SER | A | 568 | 24.660 | 27.547 | 24.465 | 1.00 | 48.47 | A | C |
| ATOM | 591 | OG | SER | A | 568 | 24.078 | 27.925 | 23.233 | 1.00 | 53.38 | A | O |
| ATOM | 592 | C | SER | A | 568 | 22.613 | 28.622 | 25.378 | 1.00 | 42.18 | A | C |
| ATOM | 593 | O | SER | A | 568 | 22.913 | 29.727 | 25.817 | 1.00 | 43.85 | A | O |
| ATOM | 594 | N | GLN | A | 569 | 21.471 | 28.397 | 24.745 | 1.00 | 38.76 | A | N |
| ATOM | 595 | CA | GLN | A | 569 | 20.524 | 29.476 | 24.495 | 1.00 | 39.06 | A | C |
| ATOM | 596 | CB | GLN | A | 569 | 20.852 | 30.165 | 23.176 | 1.00 | 45.06 | A | C |
| ATOM | 597 | CG | GLN | A | 569 | 21.818 | 31.327 | 23.243 | 1.00 | 50.32 | A | C |
| ATOM | 598 | CD | GLN | A | 569 | 22.452 | 31.614 | 21.888 | 1.00 | 51.10 | A | C |
| ATOM | 599 | OE1 | GLN | A | 569 | 23.693 | 31.665 | 21.757 | 1.00 | 48.40 | A | O |
| ATOM | 600 | NE2 | GLN | A | 569 | 21.603 | 31.787 | 20.870 | 1.00 | 49.35 | A | N |
| ATOM | 601 | C | GLN | A | 569 | 19.086 | 28.985 | 24.391 | 1.00 | 37.54 | A | C |
| ATOM | 602 | O | GLN | A | 569 | 18.804 | 27.889 | 23.871 | 1.00 | 34.48 | A | O |
| ATOM | 603 | N | LEU | A | 570 | 18.175 | 29.826 | 24.855 | 1.00 | 33.79 | A | N |
| ATOM | 604 | CA | LEU | A | 570 | 16.754 | 29.603 | 24.661 | 1.00 | 34.68 | A | C |
| ATOM | 605 | CB | LEU | A | 570 | 16.050 | 29.567 | 26.008 | 1.00 | 31.54 | A | C |
| ATOM | 606 | CG | LEU | A | 570 | 15.741 | 28.169 | 26.504 | 1.00 | 38.19 | A | C |
| ATOM | 607 | CD1 | LEU | A | 570 | 16.987 | 27.329 | 26.642 | 1.00 | 37.37 | A | C |
| ATOM | 608 | CD2 | LEU | A | 570 | 15.009 | 28.238 | 27.826 | 1.00 | 43.38 | A | C |
| ATOM | 609 | C | LEU | A | 570 | 16.227 | 30.764 | 23.838 | 1.00 | 39.24 | A | C |
| ATOM | 610 | O | LEU | A | 570 | 16.413 | 31.928 | 24.209 | 1.00 | 46.68 | A | O |
| ATOM | 611 | N | VAL | A | 571 | 15.605 | 30.490 | 22.700 | 1.00 | 36.53 | A | N |
| ATOM | 612 | CA | VAL | A | 571 | 15.016 | 31.598 | 21.971 | 1.00 | 31.35 | A | C |
| ATOM | 613 | CB | VAL | A | 571 | 15.680 | 31.835 | 20.589 | 1.00 | 26.55 | A | C |
| ATOM | 614 | CG1 | VAL | A | 571 | 15.038 | 33.029 | 19.908 | 1.00 | 25.85 | A | C |
| ATOM | 615 | CG2 | VAL | A | 571 | 17.181 | 32.066 | 20.725 | 1.00 | 16.87 | A | C |
| ATOM | 616 | C | VAL | A | 571 | 13.541 | 31.310 | 21.851 | 1.00 | 32.50 | A | C |
| ATOM | 617 | O | VAL | A | 571 | 13.157 | 30.403 | 21.118 | 1.00 | 37.07 | A | O |
| ATOM | 618 | N | TYR | A | 572 | 12.726 | 32.048 | 22.602 | 1.00 | 34.10 | A | N |
| ATOM | 619 | CA | TYR | A | 572 | 11.272 | 31.849 | 22.600 | 1.00 | 40.89 | A | C |
| ATOM | 620 | CB | TYR | A | 572 | 10.615 | 32.516 | 23.822 | 1.00 | 39.82 | A | C |
| ATOM | 621 | CG | TYR | A | 572 | 10.908 | 31.851 | 25.151 | 1.00 | 42.43 | A | C |
| ATOM | 622 | CD1 | TYR | A | 572 | 12.195 | 31.865 | 25.682 | 1.00 | 47.25 | A | C |
| ATOM | 623 | CE1 | TYR | A | 572 | 12.481 | 31.252 | 26.903 | 1.00 | 47.44 | A | C |
| ATOM | 624 | CZ | TYR | A | 572 | 11.466 | 30.625 | 27.612 | 1.00 | 47.09 | A | C |
| ATOM | 625 | OH | TYR | A | 572 | 11.778 | 30.030 | 28.819 | 1.00 | 49.58 | A | O |
| ATOM | 626 | CE2 | TYR | A | 572 | 10.167 | 30.603 | 27.113 | 1.00 | 44.22 | A | C |
| ATOM | 627 | CD2 | TYR | A | 572 | 9.898 | 31.216 | 25.886 | 1.00 | 43.00 | A | C |
| ATOM | 628 | C | TYR | A | 572 | 10.692 | 32.432 | 21.307 | 1.00 | 46.28 | A | C |
| ATOM | 629 | O | TYR | A | 572 | 11.125 | 33.505 | 20.854 | 1.00 | 48.74 | A | O |
| ATOM | 630 | N | GLY | A | 573 | 9.727 | 31.731 | 20.710 | 1.00 | 43.96 | A | N |
| ATOM | 631 | CA | GLY | A | 573 | 9.081 | 32.215 | 19.500 | 1.00 | 44.58 | A | C |
| ATOM | 632 | C | GLY | A | 573 | 7.976 | 33.201 | 19.824 | 1.00 | 47.16 | A | C |
| ATOM | 633 | O | GLY | A | 573 | 7.668 | 33.398 | 20.991 | 1.00 | 48.67 | A | O |
| ATOM | 634 | N | PRO | A | 574 | 7.371 | 33.793 | 18.793 | 1.00 | 47.15 | A | N |
| ATOM | 635 | CA | PRO | A | 574 | 6.301 | 34.802 | 18.916 | 1.00 | 48.36 | A | C |
| ATOM | 636 | CB | PRO | A | 574 | 5.575 | 34.658 | 17.599 | 1.00 | 44.73 | A | C |
| ATOM | 637 | CG | PRO | A | 574 | 6.678 | 34.358 | 16.654 | 1.00 | 47.04 | A | C |
| ATOM | 638 | CD | PRO | A | 574 | 7.703 | 33.524 | 17.384 | 1.00 | 45.01 | A | C |
| ATOM | 639 | C | PRO | A | 574 | 5.298 | 34.620 | 20.045 | 1.00 | 55.13 | A | C |
| ATOM | 640 | O | PRO | A | 574 | 5.043 | 33.489 | 20.451 | 1.00 | 58.51 | A | O |
| ATOM | 641 | N | GLU | A | 575 | 4.714 | 35.728 | 20.501 | 1.00 | 63.03 | A | N |
| ATOM | 642 | CA | GLU | A | 575 | 3.846 | 35.761 | 21.684 | 1.00 | 72.31 | A | C |
| ATOM | 643 | CB | GLU | A | 575 | 3.172 | 37.131 | 21.825 | 1.00 | 82.86 | A | C |
| ATOM | 644 | CG | GLU | A | 575 | 2.901 | 37.549 | 23.272 | 1.00 | 96.88 | A | C |
| ATOM | 645 | CD | GLU | A | 575 | 1.466 | 38.025 | 23.498 | 1.00 | 106.66 | A | C |
| ATOM | 646 | OE1 | GLU | A | 575 | 1.117 | 39.114 | 22.971 | 1.00 | 110.29 | A | O |
| ATOM | 647 | OE2 | GLU | A | 575 | 0.686 | 37.317 | 24.198 | 1.00 | 108.80 | A | O |
| ATOM | 648 | C | GLU | A | 575 | 2.803 | 34.646 | 21.752 | 1.00 | 73.37 | A | C |
| ATOM | 649 | O | GLU | A | 575 | 2.685 | 33.953 | 22.773 | 1.00 | 75.73 | A | O |
| ATOM | 650 | N | GLY | A | 576 | 2.055 | 34.466 | 20.669 | 1.00 | 72.32 | A | N |
| ATOM | 651 | CA | GLY | A | 576 | 1.073 | 33.397 | 20.599 | 1.00 | 72.86 | A | C |
| ATOM | 652 | C | GLY | A | 576 | 1.612 | 31.997 | 20.886 | 1.00 | 69.25 | A | C |
| ATOM | 653 | O | GLY | A | 576 | 1.072 | 31.285 | 21.730 | 1.00 | 71.38 | A | O |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 654 | N | SER | A | 577 | 2.688 | 31.626 | 20.194 | 1.00 | 64.77 | A | N |
| ATOM | 655 | CA | SER | A | 577 | 3.167 | 30.247 | 20.118 | 1.00 | 59.78 | A | C |
| ATOM | 656 | CB | SER | A | 577 | 4.297 | 30.122 | 19.078 | 1.00 | 55.51 | A | C |
| ATOM | 657 | OG | SER | A | 577 | 5.485 | 30.795 | 19.464 | 1.00 | 45.00 | A | O |
| ATOM | 658 | C | SER | A | 577 | 3.665 | 29.720 | 21.443 | 1.00 | 61.46 | A | C |
| ATOM | 659 | O | SER | A | 577 | 3.946 | 30.494 | 22.368 | 1.00 | 65.82 | A | O |
| ATOM | 660 | N | ASP | A | 578 | 3.774 | 28.397 | 21.530 | 1.00 | 54.85 | A | N |
| ATOM | 661 | CA | ASP | A | 578 | 4.485 | 27.800 | 22.638 | 1.00 | 47.81 | A | C |
| ATOM | 662 | CB | ASP | A | 578 | 3.616 | 26.766 | 23.371 | 1.00 | 50.27 | A | C |
| ATOM | 663 | CG | ASP | A | 578 | 2.324 | 27.373 | 23.933 | 1.00 | 53.63 | A | C |
| ATOM | 664 | OD1 | ASP | A | 578 | 2.383 | 28.234 | 24.849 | 1.00 | 52.49 | A | O |
| ATOM | 665 | OD2 | ASP | A | 578 | 1.197 | 27.053 | 23.501 | 1.00 | 56.11 | A | O |
| ATOM | 666 | C | ASP | A | 578 | 5.784 | 27.212 | 22.119 | 1.00 | 43.41 | A | C |
| ATOM | 667 | O | ASP | A | 578 | 6.335 | 26.294 | 22.707 | 1.00 | 47.68 | A | O |
| ATOM | 668 | N | LEU | A | 579 | 6.273 | 27.751 | 21.010 | 1.00 | 39.96 | A | N |
| ATOM | 669 | CA | LEU | A | 579 | 7.542 | 27.309 | 20.438 | 1.00 | 43.17 | A | C |
| ATOM | 670 | CB | LEU | A | 579 | 7.651 | 27.727 | 18.968 | 1.00 | 40.90 | A | C |
| ATOM | 671 | CG | LEU | A | 579 | 6.831 | 26.942 | 17.947 | 1.00 | 43.06 | A | C |
| ATOM | 672 | CD1 | LEU | A | 579 | 7.406 | 27.120 | 16.571 | 1.00 | 39.25 | A | C |
| ATOM | 673 | CD2 | LEU | A | 579 | 6.717 | 25.446 | 18.311 | 1.00 | 45.29 | A | C |
| ATOM | 674 | C | LEU | A | 579 | 8.716 | 27.910 | 21.188 | 1.00 | 47.30 | A | C |
| ATOM | 675 | O | LEU | A | 579 | 8.645 | 29.065 | 21.622 | 1.00 | 57.38 | A | O |
| ATOM | 676 | N | VAL | A | 580 | 9.794 | 27.142 | 21.342 | 1.00 | 41.85 | A | N |
| ATOM | 677 | CA | VAL | A | 580 | 11.087 | 27.720 | 21.722 | 1.00 | 39.69 | A | C |
| ATOM | 678 | CB | VAL | A | 580 | 11.323 | 27.831 | 23.266 | 1.00 | 38.42 | A | C |
| ATOM | 679 | CG1 | VAL | A | 580 | 10.460 | 26.871 | 24.001 | 1.00 | 37.78 | A | C |
| ATOM | 680 | CG2 | VAL | A | 580 | 12.810 | 27.613 | 23.628 | 1.00 | 38.21 | A | C |
| ATOM | 681 | C | VAL | A | 580 | 12.200 | 26.952 | 21.057 | 1.00 | 37.51 | A | C |
| ATOM | 682 | O | VAL | A | 580 | 12.176 | 25.729 | 21.030 | 1.00 | 40.20 | A | O |
| ATOM | 683 | N | LEU | A | 581 | 13.159 | 27.691 | 20.511 | 1.00 | 35.83 | A | N |
| ATOM | 684 | CA | LEU | A | 581 | 14.315 | 27.111 | 19.859 | 1.00 | 35.33 | A | C |
| ATOM | 685 | CB | LEU | A | 581 | 14.664 | 27.906 | 18.605 | 1.00 | 34.56 | A | C |
| ATOM | 686 | CG | LEU | A | 581 | 13.805 | 27.569 | 17.393 | 1.00 | 34.36 | A | C |
| ATOM | 687 | CD1 | LEU | A | 581 | 13.948 | 28.631 | 16.319 | 1.00 | 34.77 | A | C |
| ATOM | 688 | CD2 | LEU | A | 581 | 14.208 | 26.222 | 16.862 | 1.00 | 34.20 | A | C |
| ATOM | 689 | C | LEU | A | 581 | 15.503 | 27.060 | 20.806 | 1.00 | 36.62 | A | C |
| ATOM | 690 | O | LEU | A | 581 | 15.945 | 28.092 | 21.337 | 1.00 | 37.07 | A | O |
| ATOM | 691 | N | MET | A | 582 | 16.014 | 25.847 | 20.991 | 1.00 | 33.93 | A | N |
| ATOM | 692 | CA | MET | A | 582 | 17.113 | 25.569 | 21.898 | 1.00 | 36.12 | A | C |
| ATOM | 693 | CB | MET | A | 582 | 16.844 | 24.225 | 22.551 | 1.00 | 37.17 | A | C |
| ATOM | 694 | CG | MET | A | 582 | 17.334 | 24.040 | 23.963 | 1.00 | 38.27 | A | C |
| ATOM | 695 | SD | MET | A | 582 | 16.405 | 22.691 | 24.755 | 1.00 | 44.57 | A | S |
| ATOM | 696 | CE | MET | A | 582 | 16.599 | 21.366 | 23.601 | 1.00 | 41.92 | A | C |
| ATOM | 697 | C | MET | A | 582 | 18.433 | 25.486 | 21.139 | 1.00 | 39.39 | A | C |
| ATOM | 698 | O | MET | A | 582 | 18.565 | 24.668 | 20.220 | 1.00 | 41.71 | A | O |
| ATOM | 699 | N | LYS | A | 583 | 19.406 | 26.320 | 21.516 | 1.00 | 40.97 | A | N |
| ATOM | 700 | CA | LYS | A | 583 | 20.788 | 26.203 | 21.001 | 1.00 | 40.86 | A | C |
| ATOM | 701 | CB | LYS | A | 583 | 21.488 | 27.576 | 20.892 | 1.00 | 37.40 | A | C |
| ATOM | 702 | CG | LYS | A | 583 | 22.197 | 27.812 | 19.560 | 1.00 | 39.18 | A | C |
| ATOM | 703 | CD | LYS | A | 583 | 23.728 | 27.624 | 19.622 | 1.00 | 42.16 | A | C |
| ATOM | 704 | CE | LYS | A | 583 | 24.496 | 28.615 | 18.693 | 1.00 | 39.55 | A | C |
| ATOM | 705 | NZ | LYS | A | 583 | 25.333 | 29.620 | 19.428 | 1.00 | 34.06 | A | N |
| ATOM | 706 | C | LYS | A | 583 | 21.601 | 25.311 | 21.925 | 1.00 | 39.35 | A | C |
| ATOM | 707 | O | LYS | A | 583 | 21.647 | 25.552 | 23.140 | 1.00 | 42.05 | A | O |
| ATOM | 708 | N | LEU | A | 584 | 22.238 | 24.284 | 21.377 | 1.00 | 34.24 | A | N |
| ATOM | 709 | CA | LEU | A | 584 | 23.117 | 23.471 | 22.213 | 1.00 | 38.37 | A | C |
| ATOM | 710 | CB | LEU | A | 584 | 22.919 | 21.977 | 21.963 | 1.00 | 35.18 | A | C |
| ATOM | 711 | CG | LEU | A | 584 | 22.189 | 21.527 | 20.706 | 1.00 | 32.63 | A | C |
| ATOM | 712 | CD1 | LEU | A | 584 | 23.174 | 21.472 | 19.551 | 1.00 | 33.30 | A | C |
| ATOM | 713 | CD2 | LEU | A | 584 | 21.544 | 20.166 | 20.929 | 1.00 | 25.36 | A | C |
| ATOM | 714 | C | LEU | A | 584 | 24.591 | 23.883 | 22.092 | 1.00 | 43.10 | A | C |
| ATOM | 715 | O | LEU | A | 584 | 25.049 | 24.272 | 21.014 | 1.00 | 46.68 | A | O |
| ATOM | 716 | N | ALA | A | 585 | 25.317 | 23.809 | 23.208 | 1.00 | 46.13 | A | N |
| ATOM | 717 | CA | ALA | A | 585 | 26.678 | 24.344 | 23.300 | 1.00 | 53.33 | A | C |
| ATOM | 718 | CB | ALA | A | 585 | 27.050 | 24.598 | 24.763 | 1.00 | 54.74 | A | C |
| ATOM | 719 | C | ALA | A | 585 | 27.723 | 23.449 | 22.628 | 1.00 | 57.39 | A | C |
| ATOM | 720 | O | ALA | A | 585 | 28.535 | 22.822 | 23.311 | 1.00 | 62.76 | A | O |
| ATOM | 721 | N | ARG | A | 586 | 27.717 | 23.444 | 21.294 | 1.00 | 55.41 | A | N |
| ATOM | 722 | CA | ARG | A | 586 | 28.465 | 22.506 | 20.456 | 1.00 | 53.60 | A | C |
| ATOM | 723 | CB | ARG | A | 586 | 29.282 | 21.491 | 21.273 | 1.00 | 60.66 | A | C |
| ATOM | 724 | CG | ARG | A | 586 | 29.413 | 20.068 | 20.657 | 1.00 | 69.53 | A | C |
| ATOM | 725 | CD | ARG | A | 586 | 30.358 | 19.105 | 21.403 | 1.00 | 77.97 | A | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 726 | NE | ARG | A | 586 | 31.213 | 19.811 | 22.367 | 1.00 | 86.84 | A | N |
| ATOM | 727 | CZ | ARG | A | 586 | 31.276 | 19.544 | 23.671 | 1.00 | 90.03 | A | C |
| ATOM | 728 | NH1 | ARG | A | 586 | 30.543 | 18.561 | 24.187 | 1.00 | 92.95 | A | N |
| ATOM | 729 | NH2 | ARG | A | 586 | 32.074 | 20.259 | 24.461 | 1.00 | 88.53 | A | N |
| ATOM | 730 | C | ARG | A | 586 | 27.416 | 21.776 | 19.669 | 1.00 | 50.51 | A | C |
| ATOM | 731 | O | ARG | A | 586 | 26.431 | 21.325 | 20.260 | 1.00 | 51.03 | A | O |
| ATOM | 732 | N | PRO | A | 587 | 27.602 | 21.660 | 18.351 | 1.00 | 48.26 | A | N |
| ATOM | 733 | CA | PRO | A | 587 | 26.690 | 20.896 | 17.504 | 1.00 | 51.39 | A | C |
| ATOM | 734 | CB | PRO | A | 587 | 27.310 | 21.057 | 16.113 | 1.00 | 46.83 | A | C |
| ATOM | 735 | CG | PRO | A | 587 | 27.984 | 22.297 | 16.190 | 1.00 | 43.63 | A | C |
| ATOM | 736 | CD | PRO | A | 587 | 28.665 | 22.255 | 17.536 | 1.00 | 46.48 | A | C |
| ATOM | 737 | C | PRO | A | 587 | 26.627 | 19.418 | 17.865 | 1.00 | 53.08 | A | C |
| ATOM | 738 | O | PRO | A | 587 | 27.610 | 18.847 | 18.349 | 1.00 | 58.56 | A | O |
| ATOM | 739 | N | ALA | A | 588 | 25.466 | 18.819 | 17.639 | 1.00 | 48.21 | A | N |
| ATOM | 740 | CA | ALA | A | 588 | 25.363 | 17.377 | 17.609 | 1.00 | 51.17 | A | C |
| ATOM | 741 | CB | ALA | A | 588 | 23.919 | 16.960 | 17.465 | 1.00 | 56.53 | A | C |
| ATOM | 742 | C | ALA | A | 588 | 26.166 | 16.883 | 16.422 | 1.00 | 52.04 | A | C |
| ATOM | 743 | O | ALA | A | 588 | 26.262 | 17.561 | 15.389 | 1.00 | 52.47 | A | O |
| ATOM | 744 | N | VAL | A | 589 | 26.760 | 15.709 | 16.576 | 1.00 | 52.26 | A | N |
| ATOM | 745 | CA | VAL | A | 589 | 27.524 | 15.106 | 15.496 | 1.00 | 51.82 | A | C |
| ATOM | 746 | CB | VAL | A | 589 | 28.839 | 14.523 | 16.031 | 1.00 | 52.02 | A | C |
| ATOM | 747 | CG1 | VAL | A | 589 | 29.159 | 13.154 | 15.413 | 1.00 | 52.14 | A | C |
| ATOM | 748 | CG2 | VAL | A | 589 | 29.965 | 15.527 | 15.798 | 1.00 | 55.27 | A | C |
| ATOM | 749 | C | VAL | A | 589 | 26.626 | 14.065 | 14.848 | 1.00 | 49.96 | A | C |
| ATOM | 750 | O | VAL | A | 589 | 26.070 | 13.211 | 15.540 | 1.00 | 48.25 | A | O |
| ATOM | 751 | N | LEU | A | 590 | 26.451 | 14.151 | 13.532 | 1.00 | 47.38 | A | N |
| ATOM | 752 | CA | LEU | A | 590 | 25.423 | 13.340 | 12.883 | 1.00 | 45.62 | A | C |
| ATOM | 753 | CB | LEU | A | 590 | 24.685 | 14.125 | 11.789 | 1.00 | 41.44 | A | C |
| ATOM | 754 | CG | LEU | A | 590 | 24.303 | 15.586 | 12.053 | 1.00 | 40.18 | A | C |
| ATOM | 755 | CD1 | LEU | A | 590 | 23.703 | 16.257 | 10.818 | 1.00 | 38.93 | A | C |
| ATOM | 756 | CD2 | LEU | A | 590 | 23.344 | 15.693 | 13.217 | 1.00 | 41.47 | A | C |
| ATOM | 757 | C | LEU | A | 590 | 25.933 | 12.006 | 12.351 | 1.00 | 49.38 | A | C |
| ATOM | 758 | O | LEU | A | 590 | 26.514 | 11.935 | 11.270 | 1.00 | 53.92 | A | O |
| ATOM | 759 | N | ASP | A | 591 | 25.731 | 10.948 | 13.124 | 1.00 | 51.83 | A | N |
| ATOM | 760 | CA | ASP | A | 591 | 25.926 | 9.608 | 12.597 | 1.00 | 58.39 | A | C |
| ATOM | 761 | CB | ASP | A | 591 | 26.476 | 8.634 | 13.657 | 1.00 | 61.53 | A | C |
| ATOM | 762 | CG | ASP | A | 591 | 26.002 | 8.950 | 15.068 | 1.00 | 66.29 | A | C |
| ATOM | 763 | OD1 | ASP | A | 591 | 24.841 | 9.389 | 15.249 | 1.00 | 69.83 | A | O |
| ATOM | 764 | OD2 | ASP | A | 591 | 26.728 | 8.769 | 16.068 | 1.00 | 67.55 | A | O |
| ATOM | 765 | C | ASP | A | 591 | 24.608 | 9.112 | 12.009 | 1.00 | 61.73 | A | C |
| ATOM | 766 | O | ASP | A | 591 | 23.817 | 9.898 | 11.466 | 1.00 | 60.56 | A | O |
| ATOM | 767 | N | ASP | A | 592 | 24.385 | 7.806 | 12.120 | 1.00 | 65.41 | A | N |
| ATOM | 768 | CA | ASP | A | 592 | 23.149 | 7.182 | 11.686 | 1.00 | 66.25 | A | C |
| ATOM | 769 | CB | ASP | A | 592 | 23.412 | 5.723 | 11.323 | 1.00 | 70.88 | A | C |
| ATOM | 770 | CG | ASP | A | 592 | 24.441 | 5.578 | 10.196 | 1.00 | 76.70 | A | C |
| ATOM | 771 | OD1 | ASP | A | 592 | 24.462 | 4.512 | 9.539 | 1.00 | 76.48 | A | O |
| ATOM | 772 | OD2 | ASP | A | 592 | 25.270 | 6.475 | 9.893 | 1.00 | 79.23 | A | O |
| ATOM | 773 | C | ASP | A | 592 | 22.115 | 7.295 | 12.790 | 1.00 | 65.00 | A | C |
| ATOM | 774 | O | ASP | A | 592 | 20.915 | 7.302 | 12.529 | 1.00 | 69.47 | A | O |
| ATOM | 775 | N | PHE | A | 593 | 22.591 | 7.416 | 14.023 | 1.00 | 60.82 | A | N |
| ATOM | 776 | CA | PHE | A | 593 | 21.724 | 7.541 | 15.187 | 1.00 | 57.43 | A | C |
| ATOM | 777 | CB | PHE | A | 593 | 22.426 | 6.945 | 16.393 | 1.00 | 58.58 | A | C |
| ATOM | 778 | CG | PHE | A | 593 | 22.879 | 5.555 | 16.160 | 1.00 | 64.33 | A | C |
| ATOM | 779 | CD1 | PHE | A | 593 | 24.232 | 5.255 | 16.095 | 1.00 | 67.61 | A | C |
| ATOM | 780 | CE1 | PHE | A | 593 | 24.658 | 3.949 | 15.847 | 1.00 | 72.30 | A | C |
| ATOM | 781 | CZ | PHE | A | 593 | 23.706 | 2.924 | 15.645 | 1.00 | 73.94 | A | C |
| ATOM | 782 | CE2 | PHE | A | 593 | 22.342 | 3.222 | 15.695 | 1.00 | 71.33 | A | C |
| ATOM | 783 | CD2 | PHE | A | 593 | 21.941 | 4.539 | 15.943 | 1.00 | 68.72 | A | C |
| ATOM | 784 | C | PHE | A | 593 | 21.247 | 8.966 | 15.460 | 1.00 | 55.48 | A | C |
| ATOM | 785 | O | PHE | A | 593 | 20.196 | 9.182 | 16.089 | 1.00 | 58.42 | A | O |
| ATOM | 786 | N | VAL | A | 594 | 22.002 | 9.943 | 14.979 | 1.00 | 46.31 | A | N |
| ATOM | 787 | CA | VAL | A | 594 | 21.563 | 11.314 | 15.107 | 1.00 | 42.48 | A | C |
| ATOM | 788 | CB | VAL | A | 594 | 22.511 | 12.101 | 16.006 | 1.00 | 39.97 | A | C |
| ATOM | 789 | CG1 | VAL | A | 594 | 22.170 | 13.566 | 15.996 | 1.00 | 41.29 | A | C |
| ATOM | 790 | CG2 | VAL | A | 594 | 22.421 | 11.576 | 17.418 | 1.00 | 39.95 | A | C |
| ATOM | 791 | C | VAL | A | 594 | 21.365 | 11.966 | 13.739 | 1.00 | 45.57 | A | C |
| ATOM | 792 | O | VAL | A | 594 | 22.298 | 12.067 | 12.937 | 1.00 | 51.69 | A | O |
| ATOM | 793 | N | SER | A | 595 | 20.130 | 12.382 | 13.473 | 1.00 | 44.40 | A | N |
| ATOM | 794 | CA | SER | A | 595 | 19.777 | 13.041 | 12.214 | 1.00 | 46.13 | A | C |
| ATOM | 795 | CB | SER | A | 595 | 19.079 | 12.046 | 11.258 | 1.00 | 48.36 | A | C |
| ATOM | 796 | OG | SER | A | 595 | 17.667 | 11.921 | 11.450 | 1.00 | 42.75 | A | O |
| ATOM | 797 | C | SER | A | 595 | 18.901 | 14.258 | 12.486 | 1.00 | 46.72 | A | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 798 | O | SER | A | 595 | 18.242 | 14.322 | 13.521 | 1.00 | 53.75 | A | O |
| ATOM | 799 | N | THR | A | 596 | 18.892 | 15.227 | 11.581 | 1.00 | 40.90 | A | N |
| ATOM | 800 | CA | THR | A | 596 | 17.956 | 16.337 | 11.720 | 1.00 | 39.67 | A | C |
| ATOM | 801 | CB | THR | A | 596 | 18.517 | 17.621 | 11.097 | 1.00 | 44.54 | A | C |
| ATOM | 802 | OG1 | THR | A | 596 | 18.456 | 17.514 | 9.664 | 1.00 | 46.83 | A | O |
| ATOM | 803 | CG2 | THR | A | 596 | 20.006 | 17.800 | 11.412 | 1.00 | 44.46 | A | C |
| ATOM | 804 | C | THR | A | 596 | 16.683 | 15.984 | 10.990 | 1.00 | 35.98 | A | C |
| ATOM | 805 | O | THR | A | 596 | 16.735 | 15.238 | 10.024 | 1.00 | 39.34 | A | O |
| ATOM | 806 | N | ILE | A | 597 | 15.550 | 16.533 | 11.421 | 1.00 | 33.54 | A | N |
| ATOM | 807 | CA | ILE | A | 597 | 14.320 | 16.452 | 10.617 | 1.00 | 36.14 | A | C |
| ATOM | 808 | CB | ILE | A | 597 | 13.059 | 16.214 | 11.492 | 1.00 | 34.21 | A | C |
| ATOM | 809 | CG1 | ILE | A | 597 | 11.823 | 16.072 | 10.603 | 1.00 | 37.04 | A | C |
| ATOM | 810 | CD1 | ILE | A | 597 | 10.913 | 14.943 | 10.975 | 1.00 | 41.42 | A | C |
| ATOM | 811 | CG2 | ILE | A | 597 | 12.842 | 17.358 | 12.464 | 1.00 | 32.87 | A | C |
| ATOM | 812 | C | ILE | A | 597 | 14.132 | 17.669 | 9.681 | 1.00 | 36.20 | A | C |
| ATOM | 813 | O | ILE | A | 597 | 14.605 | 18.768 | 9.974 | 1.00 | 39.83 | A | O |
| ATOM | 814 | N | ASP | A | 598 | 13.444 | 17.466 | 8.559 | 1.00 | 33.50 | A | N |
| ATOM | 815 | CA | ASP | A | 598 | 13.169 | 18.555 | 7.632 | 1.00 | 38.28 | A | C |
| ATOM | 816 | CB | ASP | A | 598 | 12.742 | 18.014 | 6.258 | 1.00 | 48.59 | A | C |
| ATOM | 817 | CG | ASP | A | 598 | 13.926 | 17.791 | 5.298 | 1.00 | 57.53 | A | C |
| ATOM | 818 | OD1 | ASP | A | 598 | 15.099 | 17.784 | 5.742 | 1.00 | 62.59 | A | O |
| ATOM | 819 | OD2 | ASP | A | 598 | 13.772 | 17.607 | 4.067 | 1.00 | 60.83 | A | O |
| ATOM | 820 | C | ASP | A | 598 | 12.094 | 19.456 | 8.227 | 1.00 | 35.55 | A | C |
| ATOM | 821 | O | ASP | A | 598 | 11.575 | 19.162 | 9.294 | 1.00 | 35.49 | A | O |
| ATOM | 822 | N | LEU | A | 599 | 11.774 | 20.550 | 7.538 | 1.00 | 34.01 | A | N |
| ATOM | 823 | CA | LEU | A | 599 | 10.771 | 21.514 | 7.981 | 1.00 | 30.60 | A | C |
| ATOM | 824 | CB | LEU | A | 599 | 11.468 | 22.770 | 8.469 | 1.00 | 30.58 | A | C |
| ATOM | 825 | CG | LEU | A | 599 | 11.894 | 23.007 | 9.904 | 1.00 | 31.49 | A | C |
| ATOM | 826 | CD1 | LEU | A | 599 | 12.389 | 24.428 | 9.975 | 1.00 | 33.85 | A | C |
| ATOM | 827 | CD2 | LEU | A | 599 | 10.752 | 22.828 | 10.850 | 1.00 | 34.76 | A | C |
| ATOM | 828 | C | LEU | A | 599 | 9.929 | 21.917 | 6.785 | 1.00 | 31.69 | A | C |
| ATOM | 829 | O | LEU | A | 599 | 10.417 | 21.832 | 5.664 | 1.00 | 36.90 | A | O |
| ATOM | 830 | N | PRO | A | 600 | 8.705 | 22.405 | 7.000 | 1.00 | 31.33 | A | N |
| ATOM | 831 | CA | PRO | A | 600 | 7.858 | 22.898 | 5.906 | 1.00 | 35.28 | A | C |
| ATOM | 832 | CB | PRO | A | 600 | 6.507 | 23.062 | 6.581 | 1.00 | 29.03 | A | C |
| ATOM | 833 | CG | PRO | A | 600 | 6.634 | 22.344 | 7.838 | 1.00 | 29.28 | A | C |
| ATOM | 834 | CD | PRO | A | 600 | 8.019 | 22.535 | 8.290 | 1.00 | 30.60 | A | C |
| ATOM | 835 | C | PRO | A | 600 | 8.289 | 24.265 | 5.340 | 1.00 | 44.44 | A | C |
| ATOM | 836 | O | PRO | A | 600 | 9.114 | 24.967 | 5.946 | 1.00 | 45.45 | A | O |
| ATOM | 837 | N | ASN | A | 601 | 7.740 | 24.626 | 4.176 | 1.00 | 48.63 | A | N |
| ATOM | 838 | CA | ASN | A | 601 | 7.846 | 25.994 | 3.658 | 1.00 | 49.79 | A | C |
| ATOM | 839 | CB | ASN | A | 601 | 7.684 | 26.017 | 2.141 | 1.00 | 54.84 | A | C |
| ATOM | 840 | CG | ASN | A | 601 | 9.009 | 26.081 | 1.424 | 1.00 | 60.02 | A | C |
| ATOM | 841 | OD1 | ASN | A | 601 | 9.924 | 25.301 | 1.715 | 1.00 | 62.59 | A | O |
| ATOM | 842 | ND2 | ASN | A | 601 | 9.132 | 27.017 | 0.485 | 1.00 | 61.65 | A | N |
| ATOM | 843 | C | ASN | A | 601 | 6.797 | 26.881 | 4.316 | 1.00 | 46.76 | A | C |
| ATOM | 844 | O | ASN | A | 601 | 5.729 | 26.396 | 4.691 | 1.00 | 48.29 | A | O |
| ATOM | 845 | N | TYR | A | 602 | 7.089 | 28.172 | 4.453 | 1.00 | 41.68 | A | N |
| ATOM | 846 | CA | TYR | A | 602 | 6.260 | 29.049 | 5.275 | 1.00 | 38.41 | A | C |
| ATOM | 847 | CB | TYR | A | 602 | 6.682 | 30.523 | 5.147 | 1.00 | 38.69 | A | C |
| ATOM | 848 | CG | TYR | A | 602 | 5.668 | 31.503 | 5.700 | 1.00 | 40.48 | A | C |
| ATOM | 849 | CD1 | TYR | A | 602 | 5.116 | 31.332 | 6.968 | 1.00 | 45.45 | A | C |
| ATOM | 850 | CE1 | TYR | A | 602 | 4.169 | 32.218 | 7.469 | 1.00 | 48.45 | A | C |
| ATOM | 851 | CZ | TYR | A | 602 | 3.774 | 33.291 | 6.698 | 1.00 | 48.94 | A | C |
| ATOM | 852 | OH | TYR | A | 602 | 2.842 | 34.166 | 7.192 | 1.00 | 56.21 | A | O |
| ATOM | 853 | CE2 | TYR | A | 602 | 4.305 | 33.487 | 5.443 | 1.00 | 44.43 | A | C |
| ATOM | 854 | CD2 | TYR | A | 602 | 5.246 | 32.591 | 4.950 | 1.00 | 42.93 | A | C |
| ATOM | 855 | C | TYR | A | 602 | 4.752 | 28.872 | 5.055 | 1.00 | 40.51 | A | C |
| ATOM | 856 | O | TYR | A | 602 | 4.026 | 28.531 | 5.988 | 1.00 | 43.26 | A | O |
| ATOM | 857 | N | GLY | A | 603 | 4.277 | 29.079 | 3.833 | 1.00 | 42.23 | A | N |
| ATOM | 858 | CA | GLY | A | 603 | 2.839 | 29.087 | 3.583 | 1.00 | 43.75 | A | C |
| ATOM | 859 | C | GLY | A | 603 | 2.105 | 27.749 | 3.576 | 1.00 | 42.17 | A | C |
| ATOM | 860 | O | GLY | A | 603 | 0.885 | 27.712 | 3.750 | 1.00 | 41.68 | A | O |
| ATOM | 861 | N | SER | A | 604 | 2.860 | 26.666 | 3.399 | 1.00 | 40.29 | A | N |
| ATOM | 862 | CA | SER | A | 604 | 2.350 | 25.319 | 3.121 | 1.00 | 39.35 | A | C |
| ATOM | 863 | CB | SER | A | 604 | 3.489 | 24.308 | 3.264 | 1.00 | 36.47 | A | C |
| ATOM | 864 | OG | SER | A | 604 | 4.073 | 24.379 | 4.548 | 1.00 | 32.06 | A | O |
| ATOM | 865 | C | SER | A | 604 | 1.132 | 24.815 | 3.900 | 1.00 | 43.44 | A | C |
| ATOM | 866 | O | SER | A | 604 | 0.886 | 25.206 | 5.043 | 1.00 | 44.15 | A | O |
| ATOM | 867 | N | THR | A | 605 | 0.376 | 23.933 | 3.249 | 1.00 | 49.57 | A | N |
| ATOM | 868 | CA | THR | A | 605 | −0.707 | 23.190 | 3.891 | 1.00 | 54.12 | A | C |
| ATOM | 869 | CB | THR | A | 605 | −2.016 | 23.296 | 3.074 | 1.00 | 53.99 | A | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | | Amino Acid Residue | | | X | Y | Z | Occ. | Temp Factor | Atom Type | |
|---|---|---|---|---|---|---|---|---|---|---|---|---|
| ATOM | 870 | OG1 | THR | A | 605 | −1.719 | 23.660 | 1.715 | 1.00 | 50.74 | A | O |
| ATOM | 871 | CG2 | THR | A | 605 | −2.905 | 24.422 | 3.618 | 1.00 | 53.92 | A | C |
| ATOM | 872 | C | THR | A | 605 | −0.327 | 21.717 | 4.016 | 1.00 | 55.98 | A | C |
| ATOM | 873 | O | THR | A | 605 | 0.789 | 21.317 | 3.662 | 1.00 | 59.51 | A | O |
| ATOM | 874 | N | ILE | A | 606 | −1.259 | 20.925 | 4.545 | 1.00 | 51.78 | A | N |
| ATOM | 875 | CA | ILE | A | 606 | −1.223 | 19.465 | 4.436 | 1.00 | 46.91 | A | C |
| ATOM | 876 | CB | ILE | A | 606 | −0.730 | 18.770 | 5.719 | 1.00 | 43.94 | A | C |
| ATOM | 877 | CG1 | ILE | A | 606 | −0.568 | 19.764 | 6.889 | 1.00 | 52.16 | A | C |
| ATOM | 878 | CD1 | ILE | A | 606 | −1.883 | 20.487 | 7.367 | 1.00 | 55.17 | A | C |
| ATOM | 879 | CG2 | ILE | A | 606 | 0.531 | 17.972 | 5.410 | 1.00 | 35.80 | A | C |
| ATOM | 880 | C | ILE | A | 606 | −2.621 | 18.970 | 4.105 | 1.00 | 46.21 | A | C |
| ATOM | 881 | O | ILE | A | 606 | −3.602 | 19.485 | 4.653 | 1.00 | 49.11 | A | O |
| ATOM | 882 | N | PRO | A | 607 | −2.721 | 17.976 | 3.224 | 1.00 | 40.22 | A | N |
| ATOM | 883 | CA | PRO | A | 607 | −4.022 | 17.440 | 2.854 | 1.00 | 38.66 | A | C |
| ATOM | 884 | CB | PRO | A | 607 | −3.695 | 16.531 | 1.678 | 1.00 | 40.37 | A | C |
| ATOM | 885 | CG | PRO | A | 607 | −2.274 | 16.854 | 1.306 | 1.00 | 39.77 | A | C |
| ATOM | 886 | CD | PRO | A | 607 | −1.623 | 17.263 | 2.547 | 1.00 | 38.08 | A | C |
| ATOM | 887 | C | PRO | A | 607 | −4.561 | 16.628 | 4.020 | 1.00 | 42.73 | A | C |
| ATOM | 888 | O | PRO | A | 607 | −3.782 | 16.103 | 4.830 | 1.00 | 39.65 | A | O |
| ATOM | 889 | N | GLU | A | 608 | −5.884 | 16.539 | 4.114 | 1.00 | 48.15 | A | N |
| ATOM | 890 | CA | GLU | A | 608 | −6.518 | 15.771 | 5.178 | 1.00 | 50.92 | A | C |
| ATOM | 891 | CB | GLU | A | 608 | −8.026 | 15.990 | 5.172 | 1.00 | 57.50 | A | C |
| ATOM | 892 | CG | GLU | A | 608 | −8.539 | 16.639 | 6.442 | 1.00 | 66.78 | A | C |
| ATOM | 893 | CD | GLU | A | 608 | −9.840 | 17.392 | 6.234 | 1.00 | 75.65 | A | C |
| ATOM | 894 | OE1 | GLU | A | 608 | −10.170 | 17.712 | 5.066 | 1.00 | 77.06 | A | O |
| ATOM | 895 | OE2 | GLU | A | 608 | −10.537 | 17.664 | 7.243 | 1.00 | 80.92 | A | O |
| ATOM | 896 | C | GLU | A | 608 | −6.194 | 14.288 | 5.060 | 1.00 | 46.92 | A | C |
| ATOM | 897 | O | GLU | A | 608 | −5.885 | 13.787 | 3.981 | 1.00 | 45.35 | A | O |
| ATOM | 898 | N | LYS | A | 609 | −6.256 | 13.594 | 6.187 | 1.00 | 45.44 | A | N |
| ATOM | 899 | CA | LYS | A | 609 | −5.980 | 12.165 | 6.245 | 1.00 | 46.36 | A | C |
| ATOM | 900 | CB | LYS | A | 609 | −7.001 | 11.366 | 5.423 | 1.00 | 49.56 | A | C |
| ATOM | 901 | CG | LYS | A | 609 | −8.251 | 10.957 | 6.197 | 1.00 | 57.13 | A | C |
| ATOM | 902 | CD | LYS | A | 609 | −9.444 | 11.878 | 5.894 | 1.00 | 63.83 | A | C |
| ATOM | 903 | CE | LYS | A | 609 | −10.740 | 11.083 | 5.628 | 1.00 | 68.12 | A | C |
| ATOM | 904 | NZ | LYS | A | 609 | −10.818 | 10.437 | 4.264 | 1.00 | 68.00 | A | N |
| ATOM | 905 | C | LYS | A | 609 | −4.559 | 11.829 | 5.823 | 1.00 | 44.97 | A | C |
| ATOM | 906 | O | LYS | A | 609 | −4.269 | 10.687 | 5.485 | 1.00 | 47.16 | A | O |
| ATOM | 907 | N | THR | A | 610 | −3.676 | 12.822 | 5.837 | 1.00 | 45.02 | A | N |
| ATOM | 908 | CA | THR | A | 610 | −2.257 | 12.558 | 5.646 | 1.00 | 45.55 | A | C |
| ATOM | 909 | CB | THR | A | 610 | −1.477 | 13.849 | 5.416 | 1.00 | 44.23 | A | C |
| ATOM | 910 | OG1 | THR | A | 610 | −1.966 | 14.493 | 4.233 | 1.00 | 44.60 | A | O |
| ATOM | 911 | CG2 | THR | A | 610 | −0.043 | 13.519 | 5.053 | 1.00 | 45.14 | A | C |
| ATOM | 912 | C | THR | A | 610 | −1.768 | 11.862 | 6.894 | 1.00 | 45.88 | A | C |
| ATOM | 913 | O | THR | A | 610 | −2.047 | 12.321 | 8.000 | 1.00 | 50.74 | A | O |
| ATOM | 914 | N | SER | A | 611 | −1.064 | 10.749 | 6.730 | 1.00 | 44.73 | A | N |
| ATOM | 915 | CA | SER | A | 611 | −0.715 | 9.928 | 7.885 | 1.00 | 48.38 | A | C |
| ATOM | 916 | CB | SER | A | 611 | −0.485 | 8.475 | 7.476 | 1.00 | 53.73 | A | C |
| ATOM | 917 | OG | SER | A | 611 | 0.802 | 8.291 | 6.929 | 1.00 | 59.49 | A | O |
| ATOM | 918 | C | SER | A | 611 | 0.487 | 10.489 | 8.618 | 1.00 | 46.61 | A | C |
| ATOM | 919 | O | SER | A | 611 | 1.387 | 11.030 | 7.990 | 1.00 | 48.47 | A | O |
| ATOM | 920 | N | CYS | A | 612 | 0.487 | 10.368 | 9.945 | 1.00 | 44.70 | A | N |
| ATOM | 921 | CA | CYS | A | 612 | 1.511 | 10.980 | 10.790 | 1.00 | 42.57 | A | C |
| ATOM | 922 | CB | CYS | A | 612 | 1.011 | 12.319 | 11.297 | 1.00 | 44.39 | A | C |
| ATOM | 923 | SG | CYS | A | 612 | 0.540 | 13.427 | 9.985 | 1.00 | 51.77 | A | S |
| ATOM | 924 | C | CYS | A | 612 | 1.878 | 10.150 | 12.004 | 1.00 | 41.16 | A | C |
| ATOM | 925 | O | CYS | A | 612 | 1.229 | 9.172 | 12.316 | 1.00 | 43.24 | A | O |
| ATOM | 926 | N | SER | A | 613 | 2.909 | 10.577 | 12.717 | 1.00 | 42.06 | A | N |
| ATOM | 927 | CA | SER | A | 613 | 3.273 | 9.956 | 13.985 | 1.00 | 40.39 | A | C |
| ATOM | 928 | CB | SER | A | 613 | 4.427 | 8.982 | 13.785 | 1.00 | 39.56 | A | C |
| ATOM | 929 | OG | SER | A | 613 | 4.162 | 8.149 | 12.669 | 1.00 | 43.63 | A | O |
| ATOM | 930 | C | SER | A | 613 | 3.654 | 10.986 | 15.028 | 1.00 | 38.90 | A | C |
| ATOM | 931 | O | SER | A | 613 | 4.210 | 12.038 | 14.685 | 1.00 | 40.20 | A | O |
| ATOM | 932 | N | VAL | A | 614 | 3.315 | 10.696 | 16.288 | 1.00 | 36.87 | A | N |
| ATOM | 933 | CA | VAL | A | 614 | 3.922 | 11.384 | 17.432 | 1.00 | 35.60 | A | C |
| ATOM | 934 | CB | VAL | A | 614 | 2.895 | 11.967 | 18.458 | 1.00 | 33.11 | A | C |
| ATOM | 935 | CG1 | VAL | A | 614 | 2.072 | 13.070 | 17.828 | 1.00 | 35.92 | A | C |
| ATOM | 936 | CG2 | VAL | A | 614 | 1.993 | 10.919 | 18.999 | 1.00 | 29.73 | A | C |
| ATOM | 937 | C | VAL | A | 614 | 4.904 | 10.424 | 18.092 | 1.00 | 36.63 | A | C |
| ATOM | 938 | O | VAL | A | 614 | 4.769 | 9.195 | 17.954 | 1.00 | 37.34 | A | O |
| ATOM | 939 | N | TYR | A | 615 | 5.907 | 10.981 | 18.770 | 1.00 | 33.21 | A | N |
| ATOM | 940 | CA | TYR | A | 615 | 6.951 | 10.172 | 19.389 | 1.00 | 34.27 | A | C |
| ATOM | 941 | CB | TYR | A | 615 | 8.215 | 10.242 | 18.564 | 1.00 | 33.61 | A | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 942 | CG  | TYR | A | 615 | 8.110  | 9.650  | 17.205 | 1.00 | 33.31 | A | C |
| ATOM | 943 | CD1 | TYR | A | 615 | 8.583  | 8.383  | 16.944 | 1.00 | 37.92 | A | C |
| ATOM | 944 | CE1 | TYR | A | 615 | 8.514  | 7.853  | 15.677 | 1.00 | 40.92 | A | C |
| ATOM | 945 | CZ  | TYR | A | 615 | 7.967  | 8.601  | 14.669 | 1.00 | 39.71 | A | C |
| ATOM | 946 | OH  | TYR | A | 615 | 7.864  | 8.108  | 13.404 | 1.00 | 44.92 | A | O |
| ATOM | 947 | CE2 | TYR | A | 615 | 7.503  | 9.850  | 14.911 | 1.00 | 37.86 | A | C |
| ATOM | 948 | CD2 | TYR | A | 615 | 7.583  | 10.372 | 16.169 | 1.00 | 35.59 | A | C |
| ATOM | 949 | C   | TYR | A | 615 | 7.298  | 10.644 | 20.787 | 1.00 | 35.76 | A | C |
| ATOM | 950 | O   | TYR | A | 615 | 7.390  | 11.852 | 21.038 | 1.00 | 43.10 | A | O |
| ATOM | 951 | N   | GLY | A | 616 | 7.547  | 9.721  | 21.703 | 1.00 | 34.06 | A | N |
| ATOM | 952 | CA  | GLY | A | 616 | 7.847  | 10.190 | 23.040 | 1.00 | 45.60 | A | C |
| ATOM | 953 | C   | GLY | A | 616 | 8.214  | 9.200  | 24.107 | 1.00 | 46.49 | A | C |
| ATOM | 954 | O   | GLY | A | 616 | 7.930  | 8.010  | 23.969 | 1.00 | 55.54 | A | O |
| ATOM | 955 | N   | TRP | A | 617 | 8.862  | 9.709  | 25.158 | 1.00 | 38.09 | A | N |
| ATOM | 956 | CA  | TRP | A | 617 | 9.119  | 8.936  | 26.365 | 1.00 | 33.79 | A | C |
| ATOM | 957 | CB  | TRP | A | 617 | 10.556 | 9.111  | 26.803 | 1.00 | 37.43 | A | C |
| ATOM | 958 | CG  | TRP | A | 617 | 11.561 | 8.530  | 25.883 | 1.00 | 38.24 | A | C |
| ATOM | 959 | CD1 | TRP | A | 617 | 11.946 | 7.242  | 25.830 | 1.00 | 38.92 | A | C |
| ATOM | 960 | NE1 | TRP | A | 617 | 12.920 | 7.077  | 24.877 | 1.00 | 41.68 | A | N |
| ATOM | 961 | CE2 | TRP | A | 617 | 13.179 | 8.283  | 24.288 | 1.00 | 36.78 | A | C |
| ATOM | 962 | CD2 | TRP | A | 617 | 12.349 | 9.227  | 24.905 | 1.00 | 39.06 | A | C |
| ATOM | 963 | CE3 | TRP | A | 617 | 12.431 | 10.559 | 24.480 | 1.00 | 41.65 | A | C |
| ATOM | 964 | CZ3 | TRP | A | 617 | 13.336 | 10.889 | 23.459 | 1.00 | 37.19 | A | C |
| ATOM | 965 | CH2 | TRP | A | 617 | 14.131 | 9.922  | 22.881 | 1.00 | 34.06 | A | C |
| ATOM | 966 | CZ2 | TRP | A | 617 | 14.067 | 8.614  | 23.277 | 1.00 | 33.68 | A | C |
| ATOM | 967 | C   | TRP | A | 617 | 8.194  | 9.320  | 27.523 | 1.00 | 30.56 | A | C |
| ATOM | 968 | O   | TRP | A | 617 | 8.397  | 8.881  | 28.652 | 1.00 | 29.70 | A | O |
| ATOM | 969 | N   | GLY | A | 618 | 7.188  | 10.147 | 27.242 | 1.00 | 29.36 | A | N |
| ATOM | 970 | CA  | GLY | A | 618 | 6.196  | 10.533 | 28.231 | 1.00 | 27.68 | A | C |
| ATOM | 971 | C   | GLY | A | 618 | 5.273  | 9.372  | 28.607 | 1.00 | 32.48 | A | C |
| ATOM | 972 | O   | GLY | A | 618 | 5.533  | 8.204  | 28.256 | 1.00 | 40.20 | A | O |
| ATOM | 973 | N   | TYR | A | 619 | 4.168  | 9.700  | 29.271 | 1.00 | 23.28 | A | N |
| ATOM | 974 | CA  | TYR | A | 619 | 3.399  | 8.745  | 30.055 | 1.00 | 22.13 | A | C |
| ATOM | 975 | CB  | TYR | A | 619 | 2.421  | 9.542  | 30.897 | 1.00 | 26.82 | A | C |
| ATOM | 976 | CG  | TYR | A | 619 | 1.203  | 8.858  | 31.444 | 1.00 | 25.77 | A | C |
| ATOM | 977 | CD1 | TYR | A | 619 | 0.003  | 8.928  | 30.787 | 1.00 | 32.29 | A | C |
| ATOM | 978 | CE1 | TYR | A | 619 | −1.132 | 8.335  | 31.302 | 1.00 | 34.56 | A | C |
| ATOM | 979 | CZ  | TYR | A | 619 | −1.090 | 7.702  | 32.501 | 1.00 | 30.93 | A | C |
| ATOM | 980 | OH  | TYR | A | 619 | −2.224 | 7.110  | 33.002 | 1.00 | 35.53 | A | O |
| ATOM | 981 | CE2 | TYR | A | 619 | 0.079  | 7.645  | 33.189 | 1.00 | 32.42 | A | C |
| ATOM | 982 | CD2 | TYR | A | 619 | 1.225  | 8.242  | 32.659 | 1.00 | 28.30 | A | C |
| ATOM | 983 | C   | TYR | A | 619 | 2.697  | 7.786  | 29.164 | 1.00 | 27.28 | A | C |
| ATOM | 984 | O   | TYR | A | 619 | 2.254  | 8.153  | 28.097 | 1.00 | 35.04 | A | O |
| ATOM | 985 | N   | THR | A | 620 | 2.605  | 6.540  | 29.590 | 1.00 | 33.48 | A | N |
| ATOM | 986 | CA  | THR | A | 620 | 1.992  | 5.508  | 28.751 | 1.00 | 34.79 | A | C |
| ATOM | 987 | CB  | THR | A | 620 | 3.032  | 4.467  | 28.297 | 1.00 | 30.58 | A | C |
| ATOM | 988 | OG1 | THR | A | 620 | 3.603  | 3.826  | 29.446 | 1.00 | 30.46 | A | O |
| ATOM | 989 | CG2 | THR | A | 620 | 4.190  | 5.135  | 27.615 | 1.00 | 30.86 | A | C |
| ATOM | 990 | C   | THR | A | 620 | 0.889  | 4.779  | 29.480 | 1.00 | 36.05 | A | C |
| ATOM | 991 | O   | THR | A | 620 | 0.322  | 3.815  | 28.959 | 1.00 | 37.97 | A | O |
| ATOM | 992 | N   | GLY | A | 621 | 0.623  | 5.217  | 30.700 | 1.00 | 35.69 | A | N |
| ATOM | 993 | CA  | GLY | A | 621 | −0.357 | 4.567  | 31.537 | 1.00 | 35.76 | A | C |
| ATOM | 994 | C   | GLY | A | 621 | −0.083 | 3.100  | 31.810 | 1.00 | 32.89 | A | C |
| ATOM | 995 | O   | GLY | A | 621 | −1.030 | 2.348  | 32.206 | 1.00 | 27.38 | A | O |
| ATOM | 996 | N   | LEU | A | 622 | 1.179  | 2.698  | 31.597 | 1.00 | 27.99 | A | N |
| ATOM | 997 | CA  | LEU | A | 622 | 1.584  | 1.314  | 31.819 | 1.00 | 28.48 | A | C |
| ATOM | 998 | CB  | LEU | A | 622 | 2.693  | 0.921  | 30.869 | 1.00 | 24.30 | A | C |
| ATOM | 999 | CG  | LEU | A | 622 | 2.470  | 0.789  | 29.384 | 1.00 | 26.16 | A | C |
| ATOM | 1000 | CD1 | LEU | A | 622 | 3.849  | 0.846  | 28.758 | 1.00 | 31.43 | A | C |
| ATOM | 1001 | CD2 | LEU | A | 622 | 1.847  | −0.520 | 29.055 | 1.00 | 27.82 | A | C |
| ATOM | 1002 | C   | LEU | A | 622 | 2.098  | 1.130  | 33.240 | 1.00 | 31.75 | A | C |
| ATOM | 1003 | O   | LEU | A | 622 | 2.751  | 2.026  | 33.766 | 1.00 | 36.31 | A | O |
| ATOM | 1004 | N   | ILE | A | 623 | 1.827  | −0.027 | 33.845 | 1.00 | 30.28 | A | N |
| ATOM | 1005 | CA  | ILE | A | 623 | 2.367  | −0.360 | 35.164 | 1.00 | 29.88 | A | C |
| ATOM | 1006 | CB  | ILE | A | 623 | 1.895  | −1.743 | 35.609 | 1.00 | 22.88 | A | C |
| ATOM | 1007 | CG1 | ILE | A | 623 | 0.388  | −1.739 | 35.750 | 1.00 | 21.00 | A | C |
| ATOM | 1008 | CD1 | ILE | A | 623 | −0.217 | −3.082 | 35.588 | 1.00 | 29.56 | A | C |
| ATOM | 1009 | CG2 | ILE | A | 623 | 2.495  | −2.136 | 36.935 | 1.00 | 12.88 | A | C |
| ATOM | 1010 | C   | ILE | A | 623 | 3.892  | −0.258 | 35.222 | 1.00 | 37.02 | A | C |
| ATOM | 1011 | O   | ILE | A | 623 | 4.404  | 0.361  | 36.151 | 1.00 | 41.18 | A | O |
| ATOM | 1012 | N   | ASN | A | 624 | 4.604  | −0.848 | 34.253 | 1.00 | 37.31 | A | N |
| ATOM | 1013 | CA  | ASN | A | 624 | 6.055  | −0.609 | 34.129 | 1.00 | 41.70 | A | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 1014 | CB  | ASN | A | 624 | 6.886  | −1.744 | 34.730 | 1.00 | 47.75 | A | C |
| ATOM | 1015 | CG  | ASN | A | 624 | 6.162  | −2.469 | 35.808 | 1.00 | 57.21 | A | C |
| ATOM | 1016 | OD1 | ASN | A | 624 | 6.429  | −2.271 | 36.996 | 1.00 | 62.72 | A | O |
| ATOM | 1017 | ND2 | ASN | A | 624 | 5.214  | −3.313 | 35.413 | 1.00 | 62.41 | A | N |
| ATOM | 1018 | C   | ASN | A | 624 | 6.583  | −0.302 | 32.729 | 1.00 | 38.62 | A | C |
| ATOM | 1019 | O   | ASN | A | 624 | 7.013  | −1.197 | 31.992 | 1.00 | 39.41 | A | O |
| ATOM | 1020 | N   | TYR | A | 625 | 6.584  | 0.978  | 32.390 | 1.00 | 31.87 | A | N |
| ATOM | 1021 | CA  | TYR | A | 625 | 7.121  | 1.451  | 31.122 | 1.00 | 27.41 | A | C |
| ATOM | 1022 | CB  | TYR | A | 625 | 7.014  | 2.968  | 31.110 | 1.00 | 21.78 | A | C |
| ATOM | 1023 | CG  | TYR | A | 625 | 7.563  | 3.681  | 29.945 | 1.00 | 21.68 | A | C |
| ATOM | 1024 | CD1 | TYR | A | 625 | 7.240  | 3.333  | 28.670 | 1.00 | 38.53 | A | C |
| ATOM | 1025 | CE1 | TYR | A | 625 | 7.773  | 4.041  | 27.580 | 1.00 | 43.92 | A | C |
| ATOM | 1026 | CZ  | TYR | A | 625 | 8.602  | 5.102  | 27.803 | 1.00 | 37.73 | A | C |
| ATOM | 1027 | OH  | TYR | A | 625 | 9.137  | 5.816  | 26.773 | 1.00 | 46.04 | A | O |
| ATOM | 1028 | CE2 | TYR | A | 625 | 8.921  | 5.444  | 29.052 | 1.00 | 32.64 | A | C |
| ATOM | 1029 | CD2 | TYR | A | 625 | 8.393  | 4.736  | 30.117 | 1.00 | 29.30 | A | C |
| ATOM | 1030 | C   | TYR | A | 625 | 8.562  | 1.032  | 31.031 | 1.00 | 32.45 | A | C |
| ATOM | 1031 | O   | TYR | A | 625 | 9.352  | 1.365  | 31.901 | 1.00 | 37.87 | A | O |
| ATOM | 1032 | N   | ASP | A | 626 | 8.911  | 0.284  | 29.993 | 1.00 | 37.23 | A | N |
| ATOM | 1033 | CA  | ASP | A | 626 | 10.295 | −0.174 | 29.824 | 1.00 | 40.95 | A | C |
| ATOM | 1034 | CB  | ASP | A | 626 | 10.359 | −1.346 | 28.850 | 1.00 | 47.19 | A | C |
| ATOM | 1035 | CG  | ASP | A | 626 | 9.714  | −1.028 | 27.515 | 1.00 | 53.70 | A | C |
| ATOM | 1036 | OD1 | ASP | A | 626 | 10.455 | −0.617 | 26.600 | 1.00 | 57.23 | A | O |
| ATOM | 1037 | OD2 | ASP | A | 626 | 8.485  | −1.159 | 27.286 | 1.00 | 55.98 | A | O |
| ATOM | 1038 | C   | ASP | A | 626 | 11.271 | 0.932  | 29.386 | 1.00 | 38.07 | A | C |
| ATOM | 1039 | O   | ASP | A | 626 | 12.470 | 0.712  | 29.359 | 1.00 | 36.48 | A | O |
| ATOM | 1040 | N   | GLY | A | 627 | 10.754 | 2.102  | 29.017 | 1.00 | 36.16 | A | N |
| ATOM | 1041 | CA  | GLY | A | 627 | 11.587 | 3.277  | 28.845 | 1.00 | 33.65 | A | C |
| ATOM | 1042 | C   | GLY | A | 627 | 11.965 | 3.573  | 27.417 | 1.00 | 38.25 | A | C |
| ATOM | 1043 | O   | GLY | A | 627 | 12.599 | 4.584  | 27.143 | 1.00 | 35.77 | A | O |
| ATOM | 1044 | N   | LEU | A | 628 | 11.564 | 2.693  | 26.502 | 1.00 | 44.15 | A | N |
| ATOM | 1045 | CA  | LEU | A | 628 | 11.857 | 2.851  | 25.075 | 1.00 | 39.54 | A | C |
| ATOM | 1046 | CB  | LEU | A | 628 | 11.726 | 1.515  | 24.352 | 1.00 | 40.26 | A | C |
| ATOM | 1047 | CG  | LEU | A | 628 | 12.855 | 0.497  | 24.547 | 1.00 | 39.29 | A | C |
| ATOM | 1048 | CD1 | LEU | A | 628 | 12.568 | −0.741 | 23.718 | 1.00 | 41.84 | A | C |
| ATOM | 1049 | CD2 | LEU | A | 628 | 14.213 | 1.064  | 24.195 | 1.00 | 35.92 | A | C |
| ATOM | 1050 | C   | LEU | A | 628 | 10.947 | 3.851  | 24.396 | 1.00 | 35.47 | A | C |
| ATOM | 1051 | O   | LEU | A | 628 | 9.801  | 4.047  | 24.811 | 1.00 | 33.83 | A | O |
| ATOM | 1052 | N   | LEU | A | 629 | 11.464 | 4.456  | 23.329 | 1.00 | 35.33 | A | N |
| ATOM | 1053 | CA  | LEU | A | 629 | 10.720 | 5.450  | 22.569 | 1.00 | 36.46 | A | C |
| ATOM | 1054 | CB  | LEU | A | 629 | 11.549 | 6.019  | 21.424 | 1.00 | 34.38 | A | C |
| ATOM | 1055 | CG  | LEU | A | 629 | 10.883 | 7.241  | 20.773 | 1.00 | 38.04 | A | C |
| ATOM | 1056 | CD1 | LEU | A | 629 | 11.042 | 8.480  | 21.644 | 1.00 | 37.39 | A | C |
| ATOM | 1057 | CD2 | LEU | A | 629 | 11.357 | 7.509  | 19.315 | 1.00 | 38.24 | A | C |
| ATOM | 1058 | C   | LEU | A | 629 | 9.455  | 4.830  | 22.025 | 1.00 | 39.26 | A | C |
| ATOM | 1059 | O   | LEU | A | 629 | 9.445  | 3.662  | 21.595 | 1.00 | 45.57 | A | O |
| ATOM | 1060 | N   | ARG | A | 630 | 8.379  | 5.602  | 22.067 | 1.00 | 34.06 | A | N |
| ATOM | 1061 | CA  | ARG | A | 630 | 7.099  | 5.076  | 21.652 | 1.00 | 31.59 | A | C |
| ATOM | 1062 | CB  | ARG | A | 630 | 6.155  | 5.029  | 22.833 | 1.00 | 29.16 | A | C |
| ATOM | 1063 | CG  | ARG | A | 630 | 6.130  | 3.639  | 23.386 | 1.00 | 34.00 | A | C |
| ATOM | 1064 | CD  | ARG | A | 630 | 5.512  | 3.490  | 24.722 | 1.00 | 34.33 | A | C |
| ATOM | 1065 | NE  | ARG | A | 630 | 4.554  | 2.392  | 24.764 | 1.00 | 34.81 | A | N |
| ATOM | 1066 | CZ  | ARG | A | 630 | 4.889  | 1.107  | 24.826 | 1.00 | 39.51 | A | C |
| ATOM | 1067 | NH1 | ARG | A | 630 | 6.181  | 0.733  | 24.831 | 1.00 | 42.05 | A | N |
| ATOM | 1068 | NH2 | ARG | A | 630 | 3.921  | 0.194  | 24.881 | 1.00 | 35.27 | A | N |
| ATOM | 1069 | C   | ARG | A | 630 | 6.537  | 5.896  | 20.544 | 1.00 | 37.04 | A | C |
| ATOM | 1070 | O   | ARG | A | 630 | 6.817  | 7.079  | 20.443 | 1.00 | 46.58 | A | O |
| ATOM | 1071 | N   | VAL | A | 631 | 5.755  | 5.274  | 19.689 | 1.00 | 38.91 | A | N |
| ATOM | 1072 | CA  | VAL | A | 631 | 5.213  | 6.000  | 18.555 | 1.00 | 38.59 | A | C |
| ATOM | 1073 | CB  | VAL | A | 631 | 5.961  | 5.652  | 17.271 | 1.00 | 33.71 | A | C |
| ATOM | 1074 | CG1 | VAL | A | 631 | 5.876  | 4.176  | 17.004 | 1.00 | 29.88 | A | C |
| ATOM | 1075 | CG2 | VAL | A | 631 | 5.371  | 6.409  | 16.119 | 1.00 | 39.05 | A | C |
| ATOM | 1076 | C   | VAL | A | 631 | 3.724  | 5.722  | 18.397 | 1.00 | 38.59 | A | C |
| ATOM | 1077 | O   | VAL | A | 631 | 3.280  | 4.575  | 18.524 | 1.00 | 35.78 | A | O |
| ATOM | 1078 | N   | ALA | A | 632 | 2.958  | 6.775  | 18.141 | 1.00 | 36.60 | A | N |
| ATOM | 1079 | CA  | ALA | A | 632 | 1.541  | 6.603  | 17.909 | 1.00 | 41.30 | A | C |
| ATOM | 1080 | CB  | ALA | A | 632 | 0.743  | 7.213  | 19.007 | 1.00 | 44.22 | A | C |
| ATOM | 1081 | C   | ALA | A | 632 | 1.209  | 7.263  | 16.620 | 1.00 | 44.95 | A | C |
| ATOM | 1082 | O   | ALA | A | 632 | 1.681  | 8.369  | 16.363 | 1.00 | 48.50 | A | O |
| ATOM | 1083 | N   | HIS | A | 633 | 0.378  | 6.586  | 15.830 | 1.00 | 47.82 | A | N |
| ATOM | 1084 | CA  | HIS | A | 633 | −0.019 | 7.046  | 14.508 | 1.00 | 47.04 | A | C |
| ATOM | 1085 | CB  | HIS | A | 633 | −0.052 | 5.879  | 13.550 | 1.00 | 49.10 | A | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 1086 | CG | HIS | A | 633 | 1.256 | 5.168 | 13.466 | 1.00 | 58.13 | A | C |
| ATOM | 1087 | ND1 | HIS | A | 633 | 2.312 | 5.644 | 12.719 | 1.00 | 62.57 | A | N |
| ATOM | 1088 | CE1 | HIS | A | 633 | 3.342 | 4.823 | 12.843 | 1.00 | 66.84 | A | C |
| ATOM | 1089 | NE2 | HIS | A | 633 | 2.995 | 3.837 | 13.654 | 1.00 | 68.11 | A | N |
| ATOM | 1090 | CD2 | HIS | A | 633 | 1.697 | 4.036 | 14.065 | 1.00 | 64.36 | A | C |
| ATOM | 1091 | C | HIS | A | 633 | −1.343 | 7.787 | 14.504 | 1.00 | 48.07 | A | C |
| ATOM | 1092 | O | HIS | A | 633 | −2.313 | 7.364 | 15.134 | 1.00 | 52.00 | A | O |
| ATOM | 1093 | N | LEU | A | 634 | −1.346 | 8.919 | 13.809 | 1.00 | 45.09 | A | N |
| ATOM | 1094 | CA | LEU | A | 634 | −2.515 | 9.759 | 13.658 | 1.00 | 42.06 | A | C |
| ATOM | 1095 | CB | LEU | A | 634 | −2.399 | 10.981 | 14.556 | 1.00 | 38.58 | A | C |
| ATOM | 1096 | CG | LEU | A | 634 | −1.778 | 10.717 | 15.927 | 1.00 | 39.62 | A | C |
| ATOM | 1097 | CD1 | LEU | A | 634 | −1.089 | 11.951 | 16.502 | 1.00 | 36.37 | A | C |
| ATOM | 1098 | CD2 | LEU | A | 634 | −2.853 | 10.184 | 16.883 | 1.00 | 44.78 | A | C |
| ATOM | 1099 | C | LEU | A | 634 | −2.618 | 10.199 | 12.209 | 1.00 | 47.99 | A | C |
| ATOM | 1100 | O | LEU | A | 634 | −1.633 | 10.165 | 11.463 | 1.00 | 52.20 | A | O |
| ATOM | 1101 | N | TYR | A | 635 | −3.818 | 10.598 | 11.811 | 1.00 | 48.00 | A | N |
| ATOM | 1102 | CA | TYR | A | 635 | −4.050 | 11.161 | 10.494 | 1.00 | 46.87 | A | C |
| ATOM | 1103 | CB | TYR | A | 635 | −5.218 | 10.448 | 9.828 | 1.00 | 51.37 | A | C |
| ATOM | 1104 | CG | TYR | A | 635 | −4.913 | 8.995 | 9.562 | 1.00 | 58.24 | A | C |
| ATOM | 1105 | CD1 | TYR | A | 635 | −4.363 | 8.592 | 8.353 | 1.00 | 62.45 | A | C |
| ATOM | 1106 | CE1 | TYR | A | 635 | −4.065 | 7.255 | 8.106 | 1.00 | 69.61 | A | C |
| ATOM | 1107 | CZ | TYR | A | 635 | −4.306 | 6.304 | 9.089 | 1.00 | 73.94 | A | C |
| ATOM | 1108 | OH | TYR | A | 635 | −4.007 | 4.972 | 8.853 | 1.00 | 78.01 | A | O |
| ATOM | 1109 | CE2 | TYR | A | 635 | −4.851 | 6.687 | 10.309 | 1.00 | 71.12 | A | C |
| ATOM | 1110 | CD2 | TYR | A | 635 | −5.150 | 8.026 | 10.534 | 1.00 | 64.85 | A | C |
| ATOM | 1111 | C | TYR | A | 635 | −4.349 | 12.622 | 10.727 | 1.00 | 45.01 | A | C |
| ATOM | 1112 | O | TYR | A | 635 | −4.885 | 12.966 | 11.782 | 1.00 | 46.84 | A | O |
| ATOM | 1113 | N | ILE | A | 636 | −3.969 | 13.489 | 9.788 | 1.00 | 40.98 | A | N |
| ATOM | 1114 | CA | ILE | A | 636 | −4.273 | 14.915 | 9.938 | 1.00 | 38.58 | A | C |
| ATOM | 1115 | CB | ILE | A | 636 | −3.433 | 15.808 | 9.011 | 1.00 | 34.96 | A | C |
| ATOM | 1116 | CG1 | ILE | A | 636 | −1.941 | 15.574 | 9.219 | 1.00 | 34.76 | A | C |
| ATOM | 1117 | CD1 | ILE | A | 636 | −1.376 | 16.211 | 10.465 | 1.00 | 35.79 | A | C |
| ATOM | 1118 | CG2 | ILE | A | 636 | −3.771 | 17.269 | 9.246 | 1.00 | 31.89 | A | C |
| ATOM | 1119 | C | ILE | A | 636 | −5.747 | 15.162 | 9.675 | 1.00 | 39.87 | A | C |
| ATOM | 1120 | O | ILE | A | 636 | −6.282 | 14.753 | 8.647 | 1.00 | 40.08 | A | O |
| ATOM | 1121 | N | MET | A | 637 | −6.392 | 15.822 | 10.625 | 1.00 | 39.16 | A | N |
| ATOM | 1122 | CA | MET | A | 637 | −7.769 | 16.225 | 10.488 | 1.00 | 42.04 | A | C |
| ATOM | 1123 | CB | MET | A | 637 | −8.450 | 16.076 | 11.833 | 1.00 | 48.65 | A | C |
| ATOM | 1124 | CG | MET | A | 637 | −9.945 | 15.830 | 11.791 | 1.00 | 55.71 | A | C |
| ATOM | 1125 | SD | MET | A | 637 | −10.473 | 14.993 | 13.305 | 1.00 | 61.14 | A | S |
| ATOM | 1126 | CE | MET | A | 637 | −9.368 | 13.410 | 13.241 | 1.00 | 56.87 | A | C |
| ATOM | 1127 | C | MET | A | 637 | −7.742 | 17.681 | 10.131 | 1.00 | 42.51 | A | C |
| ATOM | 1128 | O | MET | A | 637 | −6.807 | 18.382 | 10.504 | 1.00 | 48.86 | A | O |
| ATOM | 1129 | N | GLY | A | 638 | −8.759 | 18.159 | 9.431 | 1.00 | 41.90 | A | N |
| ATOM | 1130 | CA | GLY | A | 638 | −8.922 | 19.598 | 9.287 | 1.00 | 51.84 | A | C |
| ATOM | 1131 | C | GLY | A | 638 | −9.275 | 20.283 | 10.607 | 1.00 | 56.75 | A | C |
| ATOM | 1132 | O | GLY | A | 638 | −9.833 | 19.642 | 11.496 | 1.00 | 59.32 | A | O |
| ATOM | 1133 | N | ASN | A | 639 | −8.952 | 21.571 | 10.741 | 1.00 | 59.25 | A | N |
| ATOM | 1134 | CA | ASN | A | 639 | −9.334 | 22.343 | 11.933 | 1.00 | 62.23 | A | C |
| ATOM | 1135 | CB | ASN | A | 639 | −8.637 | 23.707 | 11.948 | 1.00 | 62.68 | A | C |
| ATOM | 1136 | CG | ASN | A | 639 | −7.130 | 23.593 | 11.858 | 1.00 | 66.94 | A | C |
| ATOM | 1137 | OD1 | ASN | A | 639 | −6.578 | 22.491 | 11.735 | 1.00 | 71.75 | A | O |
| ATOM | 1138 | ND2 | ASN | A | 639 | −6.451 | 24.732 | 11.909 | 1.00 | 66.88 | A | N |
| ATOM | 1139 | C | ASN | A | 639 | −10.848 | 22.531 | 12.042 | 1.00 | 66.50 | A | C |
| ATOM | 1140 | O | ASN | A | 639 | −11.425 | 22.500 | 13.140 | 1.00 | 58.81 | A | O |
| ATOM | 1141 | N | GLU | A | 640 | −11.471 | 22.721 | 10.873 | 1.00 | 75.25 | A | N |
| ATOM | 1142 | CA | GLU | A | 640 | −12.901 | 22.976 | 10.739 | 1.00 | 76.26 | A | C |
| ATOM | 1143 | CB | GLU | A | 640 | −13.250 | 23.166 | 9.266 | 1.00 | 75.86 | A | C |
| ATOM | 1144 | CG | GLU | A | 640 | −14.457 | 24.057 | 9.006 | 1.00 | 78.64 | A | C |
| ATOM | 1145 | CD | GLU | A | 640 | −15.199 | 23.671 | 7.731 | 1.00 | 78.03 | A | C |
| ATOM | 1146 | OE1 | GLU | A | 640 | −16.091 | 22.796 | 7.805 | 1.00 | 78.97 | A | O |
| ATOM | 1147 | OE2 | GLU | A | 640 | −14.884 | 24.229 | 6.653 | 1.00 | 73.67 | A | O |
| ATOM | 1148 | C | GLU | A | 640 | −13.726 | 21.853 | 11.371 | 1.00 | 78.47 | A | C |
| ATOM | 1149 | O | GLU | A | 640 | −14.683 | 22.124 | 12.101 | 1.00 | 79.05 | A | O |
| ATOM | 1150 | N | LYS | A | 641 | −13.336 | 20.603 | 11.104 | 1.00 | 80.15 | A | N |
| ATOM | 1151 | CA | LYS | A | 641 | −13.935 | 19.431 | 11.758 | 1.00 | 81.49 | A | C |
| ATOM | 1152 | CB | LYS | A | 641 | −13.718 | 18.161 | 10.922 | 1.00 | 82.67 | A | C |
| ATOM | 1153 | CG | LYS | A | 641 | −14.652 | 18.018 | 9.716 | 1.00 | 86.07 | A | C |
| ATOM | 1154 | CD | LYS | A | 641 | −16.120 | 18.376 | 10.035 | 1.00 | 86.82 | A | C |
| ATOM | 1155 | CE | LYS | A | 641 | −16.680 | 19.437 | 9.071 | 1.00 | 85.12 | A | C |
| ATOM | 1156 | NZ | LYS | A | 641 | −17.344 | 18.842 | 7.870 | 1.00 | 82.58 | A | N |
| ATOM | 1157 | C | LYS | A | 641 | −13.381 | 19.233 | 13.172 | 1.00 | 78.08 | A | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

|      | Atom Number |     | Amino Acid Residue | | | X | Y | Z | Occ. | Temp Factor | Atom Type | |
|------|------|------|-----|---|-----|---------|--------|--------|------|--------|---|---|
| ATOM | 1158 | O    | LYS | A | 641 | −14.093 | 18.857 | 14.101 | 1.00 | 77.15  | A | O |
| ATOM | 1159 | N    | CYS | A | 642 | −12.098 | 19.505 | 13.322 | 1.00 | 75.38  | A | N |
| ATOM | 1160 | CA   | CYS | A | 642 | −11.435 | 19.365 | 14.598 | 1.00 | 74.30  | A | C |
| ATOM | 1161 | CB   | CYS | A | 642 | −9.968  | 19.720 | 14.440 | 1.00 | 67.83  | A | C |
| ATOM | 1162 | SG   | CYS | A | 642 | −8.958  | 19.389 | 15.873 | 1.00 | 58.78  | A | S |
| ATOM | 1163 | C    | CYS | A | 642 | −12.067 | 20.240 | 15.667 | 1.00 | 78.61  | A | C |
| ATOM | 1164 | O    | CYS | A | 642 | −12.059 | 19.879 | 16.843 | 1.00 | 79.99  | A | O |
| ATOM | 1165 | N    | SER | A | 643 | −12.601 | 21.391 | 15.254 | 1.00 | 83.11  | A | N |
| ATOM | 1166 | CA   | SER | A | 643 | −13.280 | 22.313 | 16.166 | 1.00 | 86.69  | A | C |
| ATOM | 1167 | CB   | SER | A | 643 | −13.636 | 23.615 | 15.440 | 1.00 | 86.56  | A | C |
| ATOM | 1168 | OG   | SER | A | 643 | −12.862 | 24.710 | 15.903 | 1.00 | 86.24  | A | O |
| ATOM | 1169 | C    | SER | A | 643 | −14.544 | 21.655 | 16.718 | 1.00 | 89.20  | A | C |
| ATOM | 1170 | O    | SER | A | 643 | −14.810 | 21.727 | 17.927 | 1.00 | 84.95  | A | O |
| ATOM | 1171 | N    | GLN | A | 644 | −15.273 | 20.992 | 15.804 | 1.00 | 93.43  | A | N |
| ATOM | 1172 | CA   | GLN | A | 644 | −16.581 | 20.351 | 16.022 | 1.00 | 94.78  | A | C |
| ATOM | 1173 | CB   | GLN | A | 644 | −17.270 | 20.097 | 14.678 | 1.00 | 98.01  | A | C |
| ATOM | 1174 | CG   | GLN | A | 644 | −17.847 | 21.315 | 13.972 | 1.00 | 102.80 | A | C |
| ATOM | 1175 | CD   | GLN | A | 644 | −18.544 | 20.945 | 12.658 | 1.00 | 106.90 | A | C |
| ATOM | 1176 | OE1  | GLN | A | 644 | −18.256 | 19.900 | 12.058 | 1.00 | 105.89 | A | O |
| ATOM | 1177 | NE2  | GLN | A | 644 | −19.464 | 21.798 | 12.216 | 1.00 | 109.02 | A | N |
| ATOM | 1178 | C    | GLN | A | 644 | −16.497 | 19.010 | 16.738 | 1.00 | 94.25  | A | C |
| ATOM | 1179 | O    | GLN | A | 644 | −17.523 | 18.429 | 17.092 | 1.00 | 94.53  | A | O |
| ATOM | 1180 | N    | HIS | A | 645 | −15.278 | 18.507 | 16.905 | 1.00 | 95.16  | A | N |
| ATOM | 1181 | CA   | HIS | A | 645 | −15.015 | 17.264 | 17.626 | 1.00 | 94.75  | A | C |
| ATOM | 1182 | CB   | HIS | A | 645 | −13.754 | 16.611 | 17.059 | 1.00 | 93.02  | A | C |
| ATOM | 1183 | CG   | HIS | A | 645 | −14.000 | 15.605 | 15.978 | 1.00 | 92.95  | A | C |
| ATOM | 1184 | ND1  | HIS | A | 645 | −13.933 | 14.246 | 16.199 | 1.00 | 93.64  | A | N |
| ATOM | 1185 | CE1  | HIS | A | 645 | −14.163 | 13.605 | 15.068 | 1.00 | 93.83  | A | C |
| ATOM | 1186 | NE2  | HIS | A | 645 | −14.362 | 14.499 | 14.116 | 1.00 | 94.05  | A | N |
| ATOM | 1187 | CD2  | HIS | A | 645 | −14.255 | 15.758 | 14.657 | 1.00 | 93.73  | A | C |
| ATOM | 1188 | C    | HIS | A | 645 | −14.773 | 17.552 | 19.115 | 1.00 | 95.54  | A | C |
| ATOM | 1189 | O    | HIS | A | 645 | −14.617 | 16.623 | 19.924 | 1.00 | 95.32  | A | O |
| ATOM | 1190 | N    | HIS | A | 646 | −14.758 | 18.833 | 19.478 | 1.00 | 94.63  | A | N |
| ATOM | 1191 | CA   | HIS | A | 646 | −14.042 | 19.245 | 20.677 | 1.00 | 96.37  | A | C |
| ATOM | 1192 | CB   | HIS | A | 646 | −12.865 | 20.142 | 20.278 | 1.00 | 91.79  | A | C |
| ATOM | 1193 | CG   | HIS | A | 646 | −11.540 | 19.451 | 20.363 | 1.00 | 87.26  | A | C |
| ATOM | 1194 | ND1  | HIS | A | 646 | −10.899 | 19.216 | 21.560 | 1.00 | 82.73  | A | N |
| ATOM | 1195 | CE1  | HIS | A | 646 | −9.768  | 18.574 | 21.333 | 1.00 | 82.76  | A | C |
| ATOM | 1196 | NE2  | HIS | A | 646 | −9.650  | 18.386 | 20.032 | 1.00 | 85.35  | A | N |
| ATOM | 1197 | CD2  | HIS | A | 646 | −10.747 | 18.921 | 19.402 | 1.00 | 87.17  | A | C |
| ATOM | 1198 | C    | HIS | A | 646 | −14.768 | 19.791 | 21.934 | 1.00 | 104.37 | A | C |
| ATOM | 1199 | O    | HIS | A | 646 | −14.130 | 19.909 | 22.978 | 1.00 | 107.00 | A | O |
| ATOM | 1200 | N    | ARG | A | 647 | −16.059 | 20.111 | 21.895 | 1.00 | 110.75 | A | N |
| ATOM | 1201 | CA   | ARG | A | 647 | −16.924 | 20.025 | 20.740 | 1.00 | 116.40 | A | C |
| ATOM | 1202 | CB   | ARG | A | 647 | −18.241 | 19.326 | 21.110 | 1.00 | 122.17 | A | C |
| ATOM | 1203 | CG   | ARG | A | 647 | −18.389 | 18.942 | 22.604 | 1.00 | 128.16 | A | C |
| ATOM | 1204 | CD   | ARG | A | 647 | −18.977 | 17.546 | 22.865 | 1.00 | 131.91 | A | C |
| ATOM | 1205 | NE   | ARG | A | 647 | −20.214 | 17.327 | 22.108 | 1.00 | 135.96 | A | N |
| ATOM | 1206 | CZ   | ARG | A | 647 | −21.245 | 16.587 | 22.514 | 1.00 | 137.12 | A | C |
| ATOM | 1207 | NH1  | ARG | A | 647 | −21.219 | 15.965 | 23.690 | 1.00 | 136.96 | A | N |
| ATOM | 1208 | NH2  | ARG | A | 647 | −22.313 | 16.470 | 21.733 | 1.00 | 137.41 | A | N |
| ATOM | 1209 | C    | ARG | A | 647 | −17.165 | 21.460 | 20.309 | 1.00 | 117.91 | A | C |
| ATOM | 1210 | O    | ARG | A | 647 | −17.190 | 21.766 | 19.120 | 1.00 | 121.75 | A | O |
| ATOM | 1211 | N    | GLY | A | 648 | −17.340 | 22.336 | 21.295 | 1.00 | 115.77 | A | N |
| ATOM | 1212 | CA   | GLY | A | 648 | −17.387 | 23.768 | 21.070 | 1.00 | 112.40 | A | C |
| ATOM | 1213 | C    | GLY | A | 648 | −16.419 | 24.419 | 22.030 | 1.00 | 110.02 | A | C |
| ATOM | 1214 | O    | GLY | A | 648 | −16.299 | 25.645 | 22.075 | 1.00 | 108.47 | A | O |
| ATOM | 1215 | N    | LYS | A | 649 | −15.727 | 23.576 | 22.795 | 1.00 | 109.50 | A | N |
| ATOM | 1216 | CA   | LYS | A | 649 | −14.805 | 24.016 | 23.843 | 1.00 | 109.43 | A | C |
| ATOM | 1217 | CB   | LYS | A | 649 | −14.286 | 22.820 | 24.659 | 1.00 | 110.52 | A | C |
| ATOM | 1218 | CG   | LYS | A | 649 | −15.241 | 22.300 | 25.762 | 1.00 | 109.90 | A | C |
| ATOM | 1219 | CD   | LYS | A | 649 | −14.528 | 21.939 | 27.084 | 1.00 | 105.80 | A | C |
| ATOM | 1220 | CE   | LYS | A | 649 | −13.234 | 21.146 | 26.869 | 1.00 | 104.48 | A | C |
| ATOM | 1221 | NZ   | LYS | A | 649 | −13.217 | 19.855 | 27.607 | 1.00 | 103.67 | A | N |
| ATOM | 1222 | C    | LYS | A | 649 | −13.624 | 24.821 | 23.301 | 1.00 | 108.12 | A | C |
| ATOM | 1223 | O    | LYS | A | 649 | −13.204 | 25.794 | 23.933 | 1.00 | 110.50 | A | O |
| ATOM | 1224 | N    | VAL | A | 650 | −13.092 | 24.416 | 22.144 | 1.00 | 104.25 | A | N |
| ATOM | 1225 | CA   | VAL | A | 650 | −11.940 | 25.091 | 21.528 | 1.00 | 99.47  | A | C |
| ATOM | 1226 | CB   | VAL | A | 650 | −10.672 | 24.186 | 21.496 | 1.00 | 100.20 | A | C |
| ATOM | 1227 | CG1  | VAL | A | 650 | −9.418  | 24.996 | 21.875 | 1.00 | 104.73 | A | C |
| ATOM | 1228 | CG2  | VAL | A | 650 | −10.829 | 22.947 | 22.386 | 1.00 | 97.30  | A | C |
| ATOM | 1229 | C    | VAL | A | 650 | −12.214 | 25.565 | 20.100 | 1.00 | 94.68  | A | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 1230 | O | VAL | A | 650 | −12.916 | 24.882 | 19.346 | 1.00 | 94.84 | A | O |
| ATOM | 1231 | N | THR | A | 651 | −11.676 | 26.734 | 19.743 | 1.00 | 91.93 | A | N |
| ATOM | 1232 | CA | THR | A | 651 | −11.597 | 27.154 | 18.329 | 1.00 | 94.90 | A | C |
| ATOM | 1233 | CB | THR | A | 651 | −12.592 | 28.315 | 17.966 | 1.00 | 97.15 | A | C |
| ATOM | 1234 | OG1 | THR | A | 651 | −13.946 | 27.856 | 18.100 | 1.00 | 98.56 | A | O |
| ATOM | 1235 | CG2 | THR | A | 651 | −12.509 | 28.667 | 16.464 | 1.00 | 94.87 | A | C |
| ATOM | 1236 | C | THR | A | 651 | −10.148 | 27.469 | 17.910 | 1.00 | 90.43 | A | C |
| ATOM | 1237 | O | THR | A | 651 | −9.474 | 28.306 | 18.522 | 1.00 | 92.16 | A | O |
| ATOM | 1238 | N | LEU | A | 652 | −9.695 | 26.803 | 16.850 | 1.00 | 80.36 | A | N |
| ATOM | 1239 | CA | LEU | A | 652 | −8.284 | 26.768 | 16.503 | 1.00 | 72.59 | A | C |
| ATOM | 1240 | CB | LEU | A | 652 | −7.978 | 25.498 | 15.730 | 1.00 | 69.56 | A | C |
| ATOM | 1241 | CG | LEU | A | 652 | −8.464 | 24.209 | 16.374 | 1.00 | 68.21 | A | C |
| ATOM | 1242 | CD1 | LEU | A | 652 | −8.414 | 23.106 | 15.368 | 1.00 | 69.16 | A | C |
| ATOM | 1243 | CD2 | LEU | A | 652 | −7.616 | 23.849 | 17.564 | 1.00 | 70.22 | A | C |
| ATOM | 1244 | C | LEU | A | 652 | −7.817 | 27.950 | 15.693 | 1.00 | 72.26 | A | C |
| ATOM | 1245 | O | LEU | A | 652 | −8.482 | 28.360 | 14.739 | 1.00 | 72.28 | A | O |
| ATOM | 1246 | N | ASN | A | 653 | −6.654 | 28.479 | 16.065 | 1.00 | 73.54 | A | N |
| ATOM | 1247 | CA | ASN | A | 653 | −6.003 | 29.522 | 15.278 | 1.00 | 78.63 | A | C |
| ATOM | 1248 | CB | ASN | A | 653 | −4.964 | 30.257 | 16.123 | 1.00 | 83.81 | A | C |
| ATOM | 1249 | CG | ASN | A | 653 | −5.508 | 31.544 | 16.722 | 1.00 | 88.62 | A | C |
| ATOM | 1250 | OD1 | ASN | A | 653 | −5.377 | 32.625 | 16.132 | 1.00 | 90.14 | A | O |
| ATOM | 1251 | ND2 | ASN | A | 653 | −6.131 | 31.433 | 17.898 | 1.00 | 89.12 | A | N |
| ATOM | 1252 | C | ASN | A | 653 | −5.365 | 28.940 | 14.019 | 1.00 | 75.19 | A | C |
| ATOM | 1253 | O | ASN | A | 653 | −5.153 | 27.734 | 13.938 | 1.00 | 76.29 | A | O |
| ATOM | 1254 | N | GLU | A | 654 | −5.059 | 29.778 | 13.035 | 1.00 | 69.05 | A | N |
| ATOM | 1255 | CA | GLU | A | 654 | −4.385 | 29.274 | 11.841 | 1.00 | 66.11 | A | C |
| ATOM | 1256 | CB | GLU | A | 654 | −4.344 | 30.329 | 10.725 | 1.00 | 74.38 | A | C |
| ATOM | 1257 | CG | GLU | A | 654 | −4.255 | 31.783 | 11.185 | 1.00 | 82.02 | A | C |
| ATOM | 1258 | CD | GLU | A | 654 | −4.063 | 32.762 | 10.029 | 1.00 | 87.39 | A | C |
| ATOM | 1259 | OE1 | GLU | A | 654 | −3.090 | 32.611 | 9.244 | 1.00 | 89.55 | A | O |
| ATOM | 1260 | OE2 | GLU | A | 654 | −4.890 | 33.692 | 9.904 | 1.00 | 89.83 | A | O |
| ATOM | 1261 | C | GLU | A | 654 | −2.981 | 28.749 | 12.169 | 1.00 | 58.30 | A | C |
| ATOM | 1262 | O | GLU | A | 654 | −2.275 | 28.236 | 11.306 | 1.00 | 58.92 | A | O |
| ATOM | 1263 | N | SER | A | 655 | −2.606 | 28.866 | 13.435 | 1.00 | 51.31 | A | N |
| ATOM | 1264 | CA | SER | A | 655 | −1.296 | 28.475 | 13.927 | 1.00 | 49.53 | A | C |
| ATOM | 1265 | CB | SER | A | 655 | −0.827 | 29.544 | 14.892 | 1.00 | 51.93 | A | C |
| ATOM | 1266 | OG | SER | A | 655 | −1.674 | 29.564 | 16.028 | 1.00 | 56.85 | A | O |
| ATOM | 1267 | C | SER | A | 655 | −1.305 | 27.128 | 14.671 | 1.00 | 50.76 | A | C |
| ATOM | 1268 | O | SER | A | 655 | −0.262 | 26.645 | 15.119 | 1.00 | 51.56 | A | O |
| ATOM | 1269 | N | GLU | A | 656 | −2.493 | 26.556 | 14.844 | 1.00 | 49.44 | A | N |
| ATOM | 1270 | CA | GLU | A | 656 | −2.670 | 25.245 | 15.457 | 1.00 | 43.28 | A | C |
| ATOM | 1271 | CB | GLU | A | 656 | −3.763 | 25.316 | 16.542 | 1.00 | 42.82 | A | C |
| ATOM | 1272 | CG | GLU | A | 656 | −3.305 | 25.911 | 17.882 | 1.00 | 50.87 | A | C |
| ATOM | 1273 | CD | GLU | A | 656 | −4.440 | 26.162 | 18.909 | 1.00 | 57.23 | A | C |
| ATOM | 1274 | OE1 | GLU | A | 656 | −5.401 | 26.908 | 18.588 | 1.00 | 63.80 | A | O |
| ATOM | 1275 | OE2 | GLU | A | 656 | −4.375 | 25.651 | 20.064 | 1.00 | 51.97 | A | O |
| ATOM | 1276 | C | GLU | A | 656 | −3.022 | 24.243 | 14.333 | 1.00 | 41.77 | A | C |
| ATOM | 1277 | O | GLU | A | 656 | −3.539 | 24.635 | 13.291 | 1.00 | 41.76 | A | O |
| ATOM | 1278 | N | ILE | A | 657 | −2.728 | 22.960 | 14.533 | 1.00 | 44.22 | A | N |
| ATOM | 1279 | CA | ILE | A | 657 | −2.986 | 21.902 | 13.530 | 1.00 | 43.95 | A | C |
| ATOM | 1280 | CB | ILE | A | 657 | −1.712 | 21.687 | 12.649 | 1.00 | 36.22 | A | C |
| ATOM | 1281 | CG1 | ILE | A | 657 | −1.932 | 20.639 | 11.579 | 1.00 | 33.28 | A | C |
| ATOM | 1282 | CD1 | ILE | A | 657 | −0.616 | 20.125 | 10.975 | 1.00 | 29.39 | A | C |
| ATOM | 1283 | CG2 | ILE | A | 657 | −0.531 | 21.242 | 13.482 | 1.00 | 39.33 | A | C |
| ATOM | 1284 | C | ILE | A | 657 | −3.462 | 20.598 | 14.230 | 1.00 | 48.04 | A | C |
| ATOM | 1285 | O | ILE | A | 657 | −3.043 | 20.321 | 15.356 | 1.00 | 47.63 | A | O |
| ATOM | 1286 | N | CYS | A | 658 | −4.340 | 19.819 | 13.590 | 1.00 | 50.39 | A | N |
| ATOM | 1287 | CA | CYS | A | 658 | −4.901 | 18.611 | 14.236 | 1.00 | 49.95 | A | C |
| ATOM | 1288 | CB | CYS | A | 658 | −6.414 | 18.638 | 14.204 | 1.00 | 51.51 | A | C |
| ATOM | 1289 | SG | CYS | A | 658 | −7.064 | 19.848 | 15.306 | 1.00 | 57.34 | A | S |
| ATOM | 1290 | C | CYS | A | 658 | −4.488 | 17.262 | 13.666 | 1.00 | 50.32 | A | C |
| ATOM | 1291 | O | CYS | A | 658 | −4.323 | 17.090 | 12.445 | 1.00 | 51.27 | A | O |
| ATOM | 1292 | N | ALA | A | 659 | −4.370 | 16.291 | 14.562 | 1.00 | 46.15 | A | N |
| ATOM | 1293 | CA | ALA | A | 659 | −4.202 | 14.908 | 14.150 | 1.00 | 46.32 | A | C |
| ATOM | 1294 | CB | ALA | A | 659 | −2.748 | 14.564 | 13.927 | 1.00 | 47.56 | A | C |
| ATOM | 1295 | C | ALA | A | 659 | −4.800 | 14.004 | 15.188 | 1.00 | 46.76 | A | C |
| ATOM | 1296 | O | ALA | A | 659 | −4.631 | 14.202 | 16.392 | 1.00 | 47.65 | A | O |
| ATOM | 1297 | N | GLY | A | 660 | −5.514 | 13.007 | 14.701 | 1.00 | 47.44 | A | N |
| ATOM | 1298 | CA | GLY | A | 660 | −6.117 | 12.014 | 15.555 | 1.00 | 51.02 | A | C |
| ATOM | 1299 | C | GLY | A | 660 | −6.064 | 10.678 | 14.864 | 1.00 | 52.20 | A | C |
| ATOM | 1300 | O | GLY | A | 660 | −5.707 | 10.590 | 13.693 | 1.00 | 55.62 | A | O |
| ATOM | 1301 | N | ALA | A | 661 | −6.407 | 9.639 | 15.603 | 1.00 | 52.34 | A | N |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 1302 | CA | ALA | A | 661 | −6.515 | 8.312 | 15.044 | 1.00 | 53.28 | A | C |
| ATOM | 1303 | CB | ALA | A | 661 | −5.884 | 7.309 | 15.983 | 1.00 | 55.18 | A | C |
| ATOM | 1304 | C | ALA | A | 661 | −7.995 | 8.062 | 14.894 | 1.00 | 54.47 | A | C |
| ATOM | 1305 | O | ALA | A | 661 | −8.795 | 8.645 | 15.632 | 1.00 | 52.98 | A | O |
| ATOM | 1306 | N | GLU | A | 662 | −8.371 | 7.217 | 13.940 | 1.00 | 58.57 | A | N |
| ATOM | 1307 | CA | GLU | A | 662 | −9.792 | 6.985 | 13.686 | 1.00 | 63.20 | A | C |
| ATOM | 1308 | CB | GLU | A | 662 | −10.015 | 6.298 | 12.329 | 1.00 | 70.71 | A | C |
| ATOM | 1309 | CG | GLU | A | 662 | −11.191 | 6.843 | 11.514 | 1.00 | 77.87 | A | C |
| ATOM | 1310 | CD | GLU | A | 662 | −12.170 | 5.754 | 11.069 | 1.00 | 85.04 | A | C |
| ATOM | 1311 | OE1 | GLU | A | 662 | −11.723 | 4.709 | 10.530 | 1.00 | 86.23 | A | O |
| ATOM | 1312 | OE2 | GLU | A | 662 | −13.399 | 5.937 | 11.256 | 1.00 | 87.81 | A | O |
| ATOM | 1313 | C | GLU | A | 662 | −10.406 | 6.179 | 14.823 | 1.00 | 58.84 | A | C |
| ATOM | 1314 | O | GLU | A | 662 | −9.953 | 5.071 | 15.110 | 1.00 | 58.51 | A | O |
| ATOM | 1315 | N | LYS | A | 663 | −11.394 | 6.779 | 15.490 | 1.00 | 54.07 | A | N |
| ATOM | 1316 | CA | LYS | A | 663 | −12.272 | 6.103 | 16.467 | 1.00 | 52.93 | A | C |
| ATOM | 1317 | CB | LYS | A | 663 | −13.048 | 4.936 | 15.825 | 1.00 | 49.89 | A | C |
| ATOM | 1318 | CG | LYS | A | 663 | −13.993 | 5.349 | 14.726 | 1.00 | 58.71 | A | C |
| ATOM | 1319 | CD | LYS | A | 663 | −15.452 | 5.187 | 15.137 | 1.00 | 69.67 | A | C |
| ATOM | 1320 | CE | LYS | A | 663 | −16.224 | 4.300 | 14.124 | 1.00 | 77.42 | A | C |
| ATOM | 1321 | NZ | LYS | A | 663 | −17.728 | 4.464 | 14.149 | 1.00 | 79.62 | A | N |
| ATOM | 1322 | C | LYS | A | 663 | −11.680 | 5.640 | 17.813 | 1.00 | 49.67 | A | C |
| ATOM | 1323 | O | LYS | A | 663 | −12.417 | 5.121 | 18.649 | 1.00 | 55.81 | A | O |
| ATOM | 1324 | N | ILE | A | 664 | −10.385 | 5.802 | 18.044 | 1.00 | 40.34 | A | N |
| ATOM | 1325 | CA | ILE | A | 664 | −9.809 | 5.244 | 19.270 | 1.00 | 37.17 | A | C |
| ATOM | 1326 | CB | ILE | A | 664 | −8.825 | 4.109 | 18.965 | 1.00 | 28.85 | A | C |
| ATOM | 1327 | CG1 | ILE | A | 664 | −7.553 | 4.627 | 18.315 | 1.00 | 15.23 | A | C |
| ATOM | 1328 | CD1 | ILE | A | 664 | −6.449 | 3.632 | 18.419 | 1.00 | 7.40 | A | C |
| ATOM | 1329 | CG2 | ILE | A | 664 | −9.462 | 3.044 | 18.106 | 1.00 | 36.00 | A | C |
| ATOM | 1330 | C | ILE | A | 664 | −9.114 | 6.285 | 20.118 | 1.00 | 46.28 | A | C |
| ATOM | 1331 | O | ILE | A | 664 | −8.991 | 7.436 | 19.699 | 1.00 | 59.36 | A | O |
| ATOM | 1332 | N | GLY | A | 665 | −8.646 | 5.896 | 21.301 | 1.00 | 39.69 | A | N |
| ATOM | 1333 | CA | GLY | A | 665 | −7.838 | 6.812 | 22.084 | 1.00 | 39.88 | A | C |
| ATOM | 1334 | C | GLY | A | 665 | −6.358 | 6.507 | 21.961 | 1.00 | 41.10 | A | C |
| ATOM | 1335 | O | GLY | A | 665 | −5.905 | 5.472 | 22.422 | 1.00 | 43.92 | A | O |
| ATOM | 1336 | N | SER | A | 666 | −5.590 | 7.388 | 21.338 | 1.00 | 39.79 | A | N |
| ATOM | 1337 | CA | SER | A | 666 | −4.134 | 7.258 | 21.370 | 1.00 | 38.94 | A | C |
| ATOM | 1338 | CB | SER | A | 666 | −3.607 | 6.358 | 20.249 | 1.00 | 44.83 | A | C |
| ATOM | 1339 | OG | SER | A | 666 | −3.617 | 6.986 | 18.973 | 1.00 | 54.44 | A | O |
| ATOM | 1340 | C | SER | A | 666 | −3.617 | 8.650 | 21.253 | 1.00 | 36.61 | A | C |
| ATOM | 1341 | O | SER | A | 666 | −4.401 | 9.530 | 20.919 | 1.00 | 39.14 | A | O |
| ATOM | 1342 | N | GLY | A | 667 | −2.332 | 8.868 | 21.528 | 1.00 | 37.34 | A | N |
| ATOM | 1343 | CA | GLY | A | 667 | −1.785 | 10.227 | 21.528 | 1.00 | 42.52 | A | C |
| ATOM | 1344 | C | GLY | A | 667 | −0.778 | 10.644 | 22.605 | 1.00 | 41.01 | A | C |
| ATOM | 1345 | O | GLY | A | 667 | −0.533 | 9.902 | 23.561 | 1.00 | 44.20 | A | O |
| ATOM | 1346 | N | PRO | A | 668 | −0.158 | 11.813 | 22.434 | 1.00 | 37.69 | A | N |
| ATOM | 1347 | CA | PRO | A | 668 | 0.923 | 12.245 | 23.326 | 1.00 | 39.24 | A | C |
| ATOM | 1348 | CB | PRO | A | 668 | 1.570 | 13.414 | 22.571 | 1.00 | 38.32 | A | C |
| ATOM | 1349 | CG | PRO | A | 668 | 0.507 | 13.949 | 21.695 | 1.00 | 39.02 | A | C |
| ATOM | 1350 | CD | PRO | A | 668 | −0.421 | 12.805 | 21.382 | 1.00 | 39.28 | A | C |
| ATOM | 1351 | C | PRO | A | 668 | 0.345 | 12.711 | 24.642 | 1.00 | 40.63 | A | C |
| ATOM | 1352 | O | PRO | A | 668 | −0.888 | 12.776 | 24.742 | 1.00 | 45.06 | A | O |
| ATOM | 1353 | N | CYS | A | 669 | 1.206 | 13.029 | 25.608 | 1.00 | 35.75 | A | N |
| ATOM | 1354 | CA | CYS | A | 669 | 0.782 | 13.251 | 26.979 | 1.00 | 37.80 | A | C |
| ATOM | 1355 | CB | CYS | A | 669 | 0.477 | 11.911 | 27.611 | 1.00 | 45.73 | A | C |
| ATOM | 1356 | SG | CYS | A | 669 | −0.549 | 12.119 | 29.045 | 1.00 | 59.82 | A | S |
| ATOM | 1357 | C | CYS | A | 669 | 1.854 | 13.936 | 27.821 | 1.00 | 41.35 | A | C |
| ATOM | 1358 | O | CYS | A | 669 | 2.850 | 14.446 | 27.287 | 1.00 | 41.11 | A | O |
| ATOM | 1359 | N | GLU | A | 670 | 1.673 | 13.931 | 29.143 | 1.00 | 40.48 | A | N |
| ATOM | 1360 | CA | GLU | A | 670 | 2.743 | 14.374 | 30.034 | 1.00 | 40.28 | A | C |
| ATOM | 1361 | CB | GLU | A | 670 | 2.453 | 14.003 | 31.486 | 1.00 | 41.30 | A | C |
| ATOM | 1362 | CG | GLU | A | 670 | 1.329 | 14.778 | 32.154 | 1.00 | 43.75 | A | C |
| ATOM | 1363 | CD | GLU | A | 670 | 1.706 | 16.206 | 32.497 | 1.00 | 46.62 | A | C |
| ATOM | 1364 | OE1 | GLU | A | 670 | 2.927 | 16.504 | 32.570 | 1.00 | 46.28 | A | O |
| ATOM | 1365 | OE2 | GLU | A | 670 | 0.767 | 17.032 | 32.682 | 1.00 | 46.89 | A | O |
| ATOM | 1366 | C | GLU | A | 670 | 4.070 | 13.744 | 29.599 | 1.00 | 42.40 | A | C |
| ATOM | 1367 | O | GLU | A | 670 | 4.123 | 12.556 | 29.239 | 1.00 | 38.92 | A | O |
| ATOM | 1368 | N | GLY | A | 671 | 5.132 | 14.549 | 29.607 | 1.00 | 45.96 | A | N |
| ATOM | 1369 | CA | GLY | A | 671 | 6.460 | 14.071 | 29.253 | 1.00 | 46.38 | A | C |
| ATOM | 1370 | C | GLY | A | 671 | 6.701 | 13.918 | 27.760 | 1.00 | 42.28 | A | C |
| ATOM | 1371 | O | GLY | A | 671 | 7.832 | 13.686 | 27.324 | 1.00 | 40.04 | A | O |
| ATOM | 1372 | N | ASP | A | 672 | 5.640 | 14.058 | 26.974 | 1.00 | 42.20 | A | N |
| ATOM | 1373 | CA | ASP | A | 672 | 5.751 | 13.988 | 25.523 | 1.00 | 43.79 | A | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 1374 | CB | ASP | A | 672 | 4.476 | 13.399 | 24.927 | 1.00 | 43.39 | A | C |
| ATOM | 1375 | CG | ASP | A | 672 | 4.373 | 11.896 | 25.095 | 1.00 | 44.59 | A | C |
| ATOM | 1376 | OD1 | ASP | A | 672 | 5.414 | 11.178 | 25.082 | 1.00 | 40.12 | A | O |
| ATOM | 1377 | OD2 | ASP | A | 672 | 3.248 | 11.348 | 25.209 | 1.00 | 46.78 | A | O |
| ATOM | 1378 | C | ASP | A | 672 | 5.998 | 15.346 | 24.853 | 1.00 | 44.68 | A | C |
| ATOM | 1379 | O | ASP | A | 672 | 6.479 | 15.369 | 23.706 | 1.00 | 47.64 | A | O |
| ATOM | 1380 | N | TYR | A | 673 | 5.660 | 16.446 | 25.556 | 1.00 | 38.29 | A | N |
| ATOM | 1381 | CA | TYR | A | 673 | 5.613 | 17.803 | 24.980 | 1.00 | 34.36 | A | C |
| ATOM | 1382 | CB | TYR | A | 673 | 5.162 | 18.849 | 26.016 | 1.00 | 31.83 | A | C |
| ATOM | 1383 | CG | TYR | A | 673 | 3.989 | 18.441 | 26.880 | 1.00 | 30.94 | A | C |
| ATOM | 1384 | CD1 | TYR | A | 673 | 2.898 | 17.812 | 26.343 | 1.00 | 36.19 | A | C |
| ATOM | 1385 | CE1 | TYR | A | 673 | 1.828 | 17.431 | 27.120 | 1.00 | 30.40 | A | C |
| ATOM | 1386 | CZ | TYR | A | 673 | 1.832 | 17.679 | 28.443 | 1.00 | 24.59 | A | C |
| ATOM | 1387 | OH | TYR | A | 673 | 0.744 | 17.259 | 29.186 | 1.00 | 23.65 | A | O |
| ATOM | 1388 | CE2 | TYR | A | 673 | 2.890 | 18.328 | 29.006 | 1.00 | 26.17 | A | C |
| ATOM | 1389 | CD2 | TYR | A | 673 | 3.964 | 18.701 | 28.226 | 1.00 | 28.74 | A | C |
| ATOM | 1390 | C | TYR | A | 673 | 6.945 | 18.243 | 24.395 | 1.00 | 38.55 | A | C |
| ATOM | 1391 | O | TYR | A | 673 | 8.004 | 17.903 | 24.924 | 1.00 | 43.33 | A | O |
| ATOM | 1392 | N | GLY | A | 674 | 6.889 | 19.017 | 23.316 | 1.00 | 35.97 | A | N |
| ATOM | 1393 | CA | GLY | A | 674 | 8.087 | 19.499 | 22.661 | 1.00 | 35.61 | A | C |
| ATOM | 1394 | C | GLY | A | 674 | 8.436 | 18.505 | 21.581 | 1.00 | 42.37 | A | C |
| ATOM | 1395 | O | GLY | A | 674 | 9.177 | 18.807 | 20.630 | 1.00 | 48.06 | A | O |
| ATOM | 1396 | N | GLY | A | 675 | 7.870 | 17.312 | 21.724 | 1.00 | 41.44 | A | N |
| ATOM | 1397 | CA | GLY | A | 675 | 8.025 | 16.261 | 20.738 | 1.00 | 42.59 | A | C |
| ATOM | 1398 | C | GLY | A | 675 | 7.423 | 16.623 | 19.389 | 1.00 | 38.22 | A | C |
| ATOM | 1399 | O | GLY | A | 675 | 6.514 | 17.451 | 19.320 | 1.00 | 36.26 | A | O |
| ATOM | 1400 | N | PRO | A | 676 | 7.927 | 16.000 | 18.323 | 1.00 | 36.98 | A | N |
| ATOM | 1401 | CA | PRO | A | 676 | 7.423 | 16.248 | 16.967 | 1.00 | 36.70 | A | C |
| ATOM | 1402 | CB | PRO | A | 676 | 8.538 | 15.694 | 16.080 | 1.00 | 35.67 | A | C |
| ATOM | 1403 | CG | PRO | A | 676 | 9.134 | 14.564 | 16.903 | 1.00 | 35.15 | A | C |
| ATOM | 1404 | CD | PRO | A | 676 | 9.012 | 14.996 | 18.335 | 1.00 | 34.98 | A | C |
| ATOM | 1405 | C | PRO | A | 676 | 6.135 | 15.490 | 16.668 | 1.00 | 35.69 | A | C |
| ATOM | 1406 | O | PRO | A | 676 | 5.947 | 14.343 | 17.103 | 1.00 | 34.29 | A | O |
| ATOM | 1407 | N | LEU | A | 677 | 5.241 | 16.142 | 15.942 | 1.00 | 34.70 | A | N |
| ATOM | 1408 | CA | LEU | A | 677 | 4.224 | 15.407 | 15.216 | 1.00 | 36.54 | A | C |
| ATOM | 1409 | CB | LEU | A | 677 | 2.928 | 16.198 | 15.123 | 1.00 | 33.41 | A | C |
| ATOM | 1410 | CG | LEU | A | 677 | 2.040 | 15.870 | 13.922 | 1.00 | 29.43 | A | C |
| ATOM | 1411 | CD1 | LEU | A | 677 | 1.051 | 14.802 | 14.282 | 1.00 | 27.30 | A | C |
| ATOM | 1412 | CD2 | LEU | A | 677 | 1.341 | 17.117 | 13.451 | 1.00 | 28.29 | A | C |
| ATOM | 1413 | C | LEU | A | 677 | 4.845 | 15.327 | 13.856 | 1.00 | 37.46 | A | C |
| ATOM | 1414 | O | LEU | A | 677 | 5.168 | 16.367 | 13.280 | 1.00 | 43.56 | A | O |
| ATOM | 1415 | N | VAL | A | 678 | 5.060 | 14.127 | 13.335 | 1.00 | 31.66 | A | N |
| ATOM | 1416 | CA | VAL | A | 678 | 5.706 | 14.085 | 12.035 | 1.00 | 34.44 | A | C |
| ATOM | 1417 | CB | VAL | A | 678 | 7.184 | 13.594 | 12.084 | 1.00 | 28.71 | A | C |
| ATOM | 1418 | CG1 | VAL | A | 678 | 7.496 | 13.062 | 13.435 | 1.00 | 25.66 | A | C |
| ATOM | 1419 | CG2 | VAL | A | 678 | 7.502 | 12.609 | 10.972 | 1.00 | 22.04 | A | C |
| ATOM | 1420 | C | VAL | A | 678 | 4.857 | 13.453 | 10.971 | 1.00 | 39.54 | A | C |
| ATOM | 1421 | O | VAL | A | 678 | 4.256 | 12.409 | 11.198 | 1.00 | 45.36 | A | O |
| ATOM | 1422 | N | CYS | A | 679 | 4.791 | 14.114 | 9.824 | 1.00 | 40.07 | A | N |
| ATOM | 1423 | CA | CYS | A | 679 | 4.026 | 13.622 | 8.708 | 1.00 | 47.18 | A | C |
| ATOM | 1424 | CB | CYS | A | 679 | 2.950 | 14.623 | 8.337 | 1.00 | 46.07 | A | C |
| ATOM | 1425 | SG | CYS | A | 679 | 1.845 | 14.971 | 9.701 | 1.00 | 49.44 | A | S |
| ATOM | 1426 | C | CYS | A | 679 | 4.970 | 13.460 | 7.561 | 1.00 | 56.16 | A | C |
| ATOM | 1427 | O | CYS | A | 679 | 6.137 | 13.818 | 7.680 | 1.00 | 56.93 | A | O |
| ATOM | 1428 | N | GLU | A | 680 | 4.469 | 12.892 | 6.467 | 1.00 | 67.82 | A | N |
| ATOM | 1429 | CA | GLU | A | 680 | 5.146 | 12.959 | 5.182 | 1.00 | 81.24 | A | C |
| ATOM | 1430 | CB | GLU | A | 680 | 6.175 | 11.843 | 5.022 | 1.00 | 90.07 | A | C |
| ATOM | 1431 | CG | GLU | A | 680 | 5.611 | 10.440 | 4.916 | 1.00 | 100.07 | A | C |
| ATOM | 1432 | CD | GLU | A | 680 | 6.680 | 9.394 | 5.158 | 1.00 | 107.31 | A | C |
| ATOM | 1433 | OE1 | GLU | A | 680 | 7.501 | 9.156 | 4.235 | 1.00 | 108.70 | A | O |
| ATOM | 1434 | OE2 | GLU | A | 680 | 6.705 | 8.826 | 6.279 | 1.00 | 110.84 | A | O |
| ATOM | 1435 | C | GLU | A | 680 | 4.144 | 12.929 | 4.050 | 1.00 | 86.73 | A | C |
| ATOM | 1436 | O | GLU | A | 680 | 3.079 | 12.308 | 4.173 | 1.00 | 86.70 | A | O |
| ATOM | 1437 | N | GLN | A | 681 | 4.495 | 13.615 | 2.961 | 1.00 | 94.18 | A | N |
| ATOM | 1438 | CA | GLN | A | 681 | 3.709 | 13.615 | 1.727 | 1.00 | 101.38 | A | C |
| ATOM | 1439 | CB | GLN | A | 681 | 2.642 | 14.742 | 1.706 | 1.00 | 102.61 | A | C |
| ATOM | 1440 | CG | GLN | A | 681 | 3.149 | 16.198 | 1.671 | 1.00 | 103.69 | A | C |
| ATOM | 1441 | CD | GLN | A | 681 | 3.823 | 16.644 | 2.971 | 1.00 | 105.16 | A | C |
| ATOM | 1442 | OE1 | GLN | A | 681 | 3.147 | 16.978 | 3.949 | 1.00 | 104.94 | A | O |
| ATOM | 1443 | NE2 | GLN | A | 681 | 5.154 | 16.653 | 2.977 | 1.00 | 104.44 | A | N |
| ATOM | 1444 | C | GLN | A | 681 | 4.616 | 13.626 | 0.489 | 1.00 | 105.72 | A | C |
| ATOM | 1445 | O | GLN | A | 681 | 4.715 | 12.613 | -0.215 | 1.00 | 105.20 | A | O |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 1446 | N | HIS | A | 682 | 5.293 | 14.761 | 0.266 | 1.00 | 111.00 | A | N |
| ATOM | 1447 | CA | HIS | A | 682 | 6.099 | 15.028 | −0.935 | 1.00 | 113.44 | A | C |
| ATOM | 1448 | CB | HIS | A | 682 | 6.976 | 16.292 | −0.754 | 1.00 | 115.52 | A | C |
| ATOM | 1449 | CG | HIS | A | 682 | 6.211 | 17.583 | −0.599 | 1.00 | 116.80 | A | C |
| ATOM | 1450 | ND1 | HIS | A | 682 | 4.864 | 17.707 | −0.873 | 1.00 | 117.06 | A | N |
| ATOM | 1451 | CE1 | HIS | A | 682 | 4.480 | 18.952 | −0.644 | 1.00 | 115.83 | A | C |
| ATOM | 1452 | NE2 | HIS | A | 682 | 5.530 | 19.645 | −0.240 | 1.00 | 114.65 | A | N |
| ATOM | 1453 | CD2 | HIS | A | 682 | 6.625 | 18.814 | −0.205 | 1.00 | 115.72 | A | C |
| ATOM | 1454 | C | HIS | A | 682 | 6.981 | 13.827 | −1.296 | 1.00 | 112.92 | A | C |
| ATOM | 1455 | O | HIS | A | 682 | 6.840 | 13.250 | −2.381 | 1.00 | 113.10 | A | O |
| ATOM | 1456 | N | LYS | A | 683 | 7.874 | 13.462 | −0.371 | 1.00 | 110.95 | A | N |
| ATOM | 1457 | CA | LYS | A | 683 | 8.774 | 12.317 | −0.510 | 1.00 | 108.18 | A | C |
| ATOM | 1458 | CB | LYS | A | 683 | 9.910 | 12.616 | −1.504 | 1.00 | 113.61 | A | C |
| ATOM | 1459 | CG | LYS | A | 683 | 10.595 | 11.372 | −2.099 | 1.00 | 117.52 | A | C |
| ATOM | 1460 | CD | LYS | A | 683 | 12.004 | 11.679 | −2.634 | 1.00 | 118.90 | A | C |
| ATOM | 1461 | CE | LYS | A | 683 | 12.955 | 10.492 | −2.456 | 1.00 | 119.08 | A | C |
| ATOM | 1462 | NZ | LYS | A | 683 | 13.416 | 10.330 | −1.039 | 1.00 | 118.83 | A | N |
| ATOM | 1463 | C | LYS | A | 683 | 9.359 | 11.953 | 0.847 | 1.00 | 101.80 | A | C |
| ATOM | 1464 | O | LYS | A | 683 | 9.269 | 10.806 | 1.275 | 1.00 | 100.60 | A | O |
| ATOM | 1465 | N | MET | A | 684 | 9.945 | 12.947 | 1.515 | 1.00 | 96.97 | A | N |
| ATOM | 1466 | CA | MET | A | 684 | 10.666 | 12.755 | 2.779 | 1.00 | 93.07 | A | C |
| ATOM | 1467 | CB | MET | A | 684 | 12.014 | 13.500 | 2.750 | 1.00 | 97.15 | A | C |
| ATOM | 1468 | CG | MET | A | 684 | 11.974 | 14.904 | 2.121 | 1.00 | 101.00 | A | C |
| ATOM | 1469 | SD | MET | A | 684 | 12.278 | 14.933 | 0.323 | 1.00 | 103.09 | A | S |
| ATOM | 1470 | CE | MET | A | 684 | 14.014 | 15.513 | 0.260 | 1.00 | 102.46 | A | C |
| ATOM | 1471 | C | MET | A | 684 | 9.839 | 13.143 | 4.021 | 1.00 | 86.11 | A | C |
| ATOM | 1472 | O | MET | A | 684 | 8.650 | 13.447 | 3.904 | 1.00 | 85.56 | A | O |
| ATOM | 1473 | N | ARG | A | 685 | 10.478 | 13.126 | 5.195 | 1.00 | 77.84 | A | N |
| ATOM | 1474 | CA | ARG | A | 685 | 9.821 | 13.363 | 6.492 | 1.00 | 67.29 | A | C |
| ATOM | 1475 | CB | ARG | A | 685 | 10.397 | 12.420 | 7.562 | 1.00 | 67.86 | A | C |
| ATOM | 1476 | CG | ARG | A | 685 | 10.040 | 10.958 | 7.424 | 1.00 | 70.14 | A | C |
| ATOM | 1477 | CD | ARG | A | 685 | 11.245 | 10.039 | 7.195 | 1.00 | 77.65 | A | C |
| ATOM | 1478 | NE | ARG | A | 685 | 11.614 | 9.206 | 8.349 | 1.00 | 86.24 | A | N |
| ATOM | 1479 | CZ | ARG | A | 685 | 10.800 | 8.368 | 9.022 | 1.00 | 92.30 | A | C |
| ATOM | 1480 | NH1 | ARG | A | 685 | 9.515 | 8.224 | 8.698 | 1.00 | 92.95 | A | N |
| ATOM | 1481 | NH2 | ARG | A | 685 | 11.282 | 7.667 | 10.046 | 1.00 | 94.20 | A | N |
| ATOM | 1482 | C | ARG | A | 685 | 10.010 | 14.800 | 6.982 | 1.00 | 59.11 | A | C |
| ATOM | 1483 | O | ARG | A | 685 | 11.136 | 15.288 | 7.042 | 1.00 | 59.70 | A | O |
| ATOM | 1484 | N | MET | A | 686 | 8.918 | 15.457 | 7.363 | 1.00 | 52.07 | A | N |
| ATOM | 1485 | CA | MET | A | 686 | 8.979 | 16.806 | 7.932 | 1.00 | 52.77 | A | C |
| ATOM | 1486 | CB | MET | A | 686 | 8.240 | 17.775 | 7.013 | 1.00 | 56.34 | A | C |
| ATOM | 1487 | CG | MET | A | 686 | 8.911 | 18.076 | 5.693 | 1.00 | 63.29 | A | C |
| ATOM | 1488 | SD | MET | A | 686 | 7.870 | 19.177 | 4.709 | 1.00 | 72.90 | A | S |
| ATOM | 1489 | CE | MET | A | 686 | 9.003 | 19.605 | 3.294 | 1.00 | 73.19 | A | C |
| ATOM | 1490 | C | MET | A | 686 | 8.352 | 16.887 | 9.337 | 1.00 | 50.09 | A | C |
| ATOM | 1491 | O | MET | A | 686 | 7.330 | 16.255 | 9.579 | 1.00 | 57.19 | A | O |
| ATOM | 1492 | N | VAL | A | 687 | 8.930 | 17.658 | 10.261 | 1.00 | 40.20 | A | N |
| ATOM | 1493 | CA | VAL | A | 687 | 8.206 | 17.955 | 11.502 | 1.00 | 35.96 | A | C |
| ATOM | 1494 | CB | VAL | A | 687 | 9.105 | 18.371 | 12.717 | 1.00 | 37.17 | A | C |
| ATOM | 1495 | CG1 | VAL | A | 687 | 10.031 | 19.518 | 12.404 | 1.00 | 31.99 | A | C |
| ATOM | 1496 | CG2 | VAL | A | 687 | 8.223 | 18.743 | 13.901 | 1.00 | 40.76 | A | C |
| ATOM | 1497 | C | VAL | A | 687 | 7.132 | 19.000 | 11.232 | 1.00 | 32.99 | A | C |
| ATOM | 1498 | O | VAL | A | 687 | 7.426 | 20.085 | 10.762 | 1.00 | 35.40 | A | O |
| ATOM | 1499 | N | LEU | A | 688 | 5.886 | 18.670 | 11.531 | 1.00 | 31.53 | A | N |
| ATOM | 1500 | CA | LEU | A | 688 | 4.763 | 19.485 | 11.070 | 1.00 | 35.49 | A | C |
| ATOM | 1501 | CB | LEU | A | 688 | 3.836 | 18.631 | 10.224 | 1.00 | 33.52 | A | C |
| ATOM | 1502 | CG | LEU | A | 688 | 3.871 | 18.865 | 8.727 | 1.00 | 27.94 | A | C |
| ATOM | 1503 | CD1 | LEU | A | 688 | 5.216 | 18.497 | 8.192 | 1.00 | 27.81 | A | C |
| ATOM | 1504 | CD2 | LEU | A | 688 | 2.836 | 17.974 | 8.148 | 1.00 | 27.94 | A | C |
| ATOM | 1505 | C | LEU | A | 688 | 3.943 | 20.123 | 12.174 | 1.00 | 39.83 | A | C |
| ATOM | 1506 | O | LEU | A | 688 | 3.251 | 21.107 | 11.950 | 1.00 | 42.40 | A | O |
| ATOM | 1507 | N | GLY | A | 689 | 3.999 | 19.529 | 13.354 | 1.00 | 42.67 | A | N |
| ATOM | 1508 | CA | GLY | A | 689 | 3.380 | 20.095 | 14.528 | 1.00 | 41.64 | A | C |
| ATOM | 1509 | C | GLY | A | 689 | 4.332 | 19.860 | 15.665 | 1.00 | 39.90 | A | C |
| ATOM | 1510 | O | GLY | A | 689 | 5.215 | 18.992 | 15.557 | 1.00 | 37.02 | A | O |
| ATOM | 1511 | N | VAL | A | 690 | 4.159 | 20.632 | 16.739 | 1.00 | 38.49 | A | N |
| ATOM | 1512 | CA | VAL | A | 690 | 4.974 | 20.486 | 17.944 | 1.00 | 36.23 | A | C |
| ATOM | 1513 | CB | VAL | A | 690 | 5.742 | 21.770 | 18.293 | 1.00 | 33.80 | A | C |
| ATOM | 1514 | CG1 | VAL | A | 690 | 6.504 | 21.581 | 19.575 | 1.00 | 40.76 | A | C |
| ATOM | 1515 | CG2 | VAL | A | 690 | 6.694 | 22.148 | 17.198 | 1.00 | 30.12 | A | C |
| ATOM | 1516 | C | VAL | A | 690 | 4.049 | 20.142 | 19.085 | 1.00 | 36.97 | A | C |
| ATOM | 1517 | O | VAL | A | 690 | 3.064 | 20.828 | 19.302 | 1.00 | 41.25 | A | O |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 1518 | N | ILE | A | 691 | 4.349 | 19.068 | 19.803 | 1.00 | 38.52 | A | N |
| ATOM | 1519 | CA | ILE | A | 691 | 3.470 | 18.613 | 20.873 | 1.00 | 40.23 | A | C |
| ATOM | 1520 | CB | ILE | A | 691 | 3.932 | 17.256 | 21.416 | 1.00 | 39.21 | A | C |
| ATOM | 1521 | CG1 | ILE | A | 691 | 3.816 | 16.178 | 20.341 | 1.00 | 35.12 | A | C |
| ATOM | 1522 | CD1 | ILE | A | 691 | 4.715 | 15.000 | 20.598 | 1.00 | 31.55 | A | C |
| ATOM | 1523 | CG2 | ILE | A | 691 | 3.120 | 16.870 | 22.634 | 1.00 | 40.22 | A | C |
| ATOM | 1524 | C | ILE | A | 691 | 3.458 | 19.642 | 21.993 | 1.00 | 41.66 | A | C |
| ATOM | 1525 | O | ILE | A | 691 | 4.503 | 20.033 | 22.497 | 1.00 | 40.52 | A | O |
| ATOM | 1526 | N | VAL | A | 692 | 2.264 | 20.094 | 22.348 | 1.00 | 43.82 | A | N |
| ATOM | 1527 | CA | VAL | A | 692 | 2.060 | 20.955 | 23.514 | 1.00 | 41.79 | A | C |
| ATOM | 1528 | CB | VAL | A | 692 | 1.644 | 22.399 | 23.113 | 1.00 | 37.14 | A | C |
| ATOM | 1529 | CG1 | VAL | A | 692 | 2.645 | 22.999 | 22.114 | 1.00 | 28.48 | A | C |
| ATOM | 1530 | CG2 | VAL | A | 692 | 0.216 | 22.428 | 22.568 | 1.00 | 38.18 | A | C |
| ATOM | 1531 | C | VAL | A | 692 | 0.986 | 20.293 | 24.378 | 1.00 | 44.75 | A | C |
| ATOM | 1532 | O | VAL | A | 692 | 0.299 | 19.388 | 23.903 | 1.00 | 54.64 | A | O |
| ATOM | 1533 | N | PRO | A | 693 | 0.828 | 20.709 | 25.628 | 1.00 | 41.31 | A | N |
| ATOM | 1534 | CA | PRO | A | 693 | −0.174 | 20.081 | 26.490 | 1.00 | 40.59 | A | C |
| ATOM | 1535 | CB | PRO | A | 693 | −0.069 | 20.890 | 27.786 | 1.00 | 43.86 | A | C |
| ATOM | 1536 | CG | PRO | A | 693 | 1.330 | 21.404 | 27.770 | 1.00 | 43.42 | A | C |
| ATOM | 1537 | CD | PRO | A | 693 | 1.570 | 21.770 | 26.333 | 1.00 | 41.50 | A | C |
| ATOM | 1538 | C | PRO | A | 693 | −1.595 | 20.144 | 25.914 | 1.00 | 42.17 | A | C |
| ATOM | 1539 | O | PRO | A | 693 | −2.014 | 21.132 | 25.259 | 1.00 | 42.65 | A | O |
| ATOM | 1540 | N | GLY | A | 694 | −2.338 | 19.070 | 26.165 | 1.00 | 38.52 | A | N |
| ATOM | 1541 | CA | GLY | A | 694 | −3.699 | 18.979 | 25.684 | 1.00 | 37.62 | A | C |
| ATOM | 1542 | C | GLY | A | 694 | −4.779 | 19.248 | 26.705 | 1.00 | 38.72 | A | C |
| ATOM | 1543 | O | GLY | A | 694 | −4.534 | 19.942 | 27.698 | 1.00 | 48.67 | A | O |
| ATOM | 1544 | N | ARG | A | 695 | −5.970 | 18.692 | 26.447 | 1.00 | 37.38 | A | N |
| ATOM | 1545 | CA | ARG | A | 695 | −7.097 | 18.746 | 27.365 | 1.00 | 34.19 | A | C |
| ATOM | 1546 | CB | ARG | A | 695 | −8.237 | 19.459 | 26.716 | 1.00 | 34.82 | A | C |
| ATOM | 1547 | CG | ARG | A | 695 | −7.918 | 20.935 | 26.594 | 1.00 | 44.94 | A | C |
| ATOM | 1548 | CD | ARG | A | 695 | −8.646 | 21.660 | 25.475 | 1.00 | 47.02 | A | C |
| ATOM | 1549 | NE | ARG | A | 695 | −9.682 | 22.488 | 26.059 | 1.00 | 46.61 | A | N |
| ATOM | 1550 | CZ | ARG | A | 695 | −9.837 | 23.758 | 25.794 | 1.00 | 50.72 | A | C |
| ATOM | 1551 | NH1 | ARG | A | 695 | −9.022 | 24.349 | 24.925 | 1.00 | 49.70 | A | N |
| ATOM | 1552 | NH2 | ARG | A | 695 | −10.818 | 24.438 | 26.390 | 1.00 | 56.06 | A | N |
| ATOM | 1553 | C | ARG | A | 695 | −7.483 | 17.358 | 27.847 | 1.00 | 39.34 | A | C |
| ATOM | 1554 | O | ARG | A | 695 | −8.621 | 17.094 | 28.302 | 1.00 | 42.40 | A | O |
| ATOM | 1555 | N | GLY | A | 696 | −6.482 | 16.485 | 27.793 | 1.00 | 38.78 | A | N |
| ATOM | 1556 | CA | GLY | A | 696 | −6.610 | 15.106 | 28.215 | 1.00 | 43.16 | A | C |
| ATOM | 1557 | C | GLY | A | 696 | −5.873 | 14.210 | 27.250 | 1.00 | 44.55 | A | C |
| ATOM | 1558 | O | GLY | A | 696 | −5.834 | 14.500 | 26.068 | 1.00 | 50.18 | A | O |
| ATOM | 1559 | N | CYS | A | 697 | −5.277 | 13.139 | 27.751 | 1.00 | 44.32 | A | N |
| ATOM | 1560 | CA | CYS | A | 697 | −4.524 | 12.234 | 26.909 | 1.00 | 44.50 | A | C |
| ATOM | 1561 | CB | CYS | A | 697 | −3.426 | 11.595 | 27.744 | 1.00 | 49.09 | A | C |
| ATOM | 1562 | SG | CYS | A | 697 | −2.394 | 12.857 | 28.503 | 1.00 | 56.39 | A | S |
| ATOM | 1563 | C | CYS | A | 697 | −5.429 | 11.178 | 26.286 | 1.00 | 47.38 | A | C |
| ATOM | 1564 | O | CYS | A | 697 | −6.413 | 10.751 | 26.886 | 1.00 | 50.68 | A | O |
| ATOM | 1565 | N | ALA | A | 698 | −5.101 | 10.766 | 25.068 | 1.00 | 52.54 | A | N |
| ATOM | 1566 | CA | ALA | A | 698 | −5.835 | 9.702 | 24.363 | 1.00 | 53.20 | A | C |
| ATOM | 1567 | CB | ALA | A | 698 | −5.124 | 8.372 | 24.560 | 1.00 | 50.25 | A | C |
| ATOM | 1568 | C | ALA | A | 698 | −7.342 | 9.584 | 24.712 | 1.00 | 53.22 | A | C |
| ATOM | 1569 | O | ALA | A | 698 | −7.823 | 8.498 | 25.079 | 1.00 | 55.37 | A | O |
| ATOM | 1570 | N | ILE | A | 699 | −8.074 | 10.698 | 24.608 | 1.00 | 48.34 | A | N |
| ATOM | 1571 | CA | ILE | A | 699 | −9.521 | 10.664 | 24.760 | 1.00 | 41.86 | A | C |
| ATOM | 1572 | CB | ILE | A | 699 | −10.092 | 12.049 | 24.970 | 1.00 | 37.20 | A | C |
| ATOM | 1573 | CG1 | ILE | A | 699 | −10.057 | 12.394 | 26.447 | 1.00 | 44.24 | A | C |
| ATOM | 1574 | CD1 | ILE | A | 699 | −9.181 | 13.547 | 26.806 | 1.00 | 44.51 | A | C |
| ATOM | 1575 | CG2 | ILE | A | 699 | −11.536 | 12.045 | 24.615 | 1.00 | 34.30 | A | C |
| ATOM | 1576 | C | ILE | A | 699 | −10.095 | 10.079 | 23.499 | 1.00 | 44.19 | A | C |
| ATOM | 1577 | O | ILE | A | 699 | −9.861 | 10.609 | 22.417 | 1.00 | 52.15 | A | O |
| ATOM | 1578 | N | PRO | A | 700 | −10.861 | 9.004 | 23.611 | 1.00 | 42.12 | A | N |
| ATOM | 1579 | CA | PRO | A | 700 | −11.352 | 8.323 | 22.422 | 1.00 | 41.31 | A | C |
| ATOM | 1580 | CB | PRO | A | 700 | −12.317 | 7.299 | 22.977 | 1.00 | 38.60 | A | C |
| ATOM | 1581 | CG | PRO | A | 700 | −11.837 | 7.056 | 24.319 | 1.00 | 44.12 | A | C |
| ATOM | 1582 | CD | PRO | A | 700 | −11.357 | 8.377 | 24.842 | 1.00 | 46.01 | A | C |
| ATOM | 1583 | C | PRO | A | 700 | −12.077 | 9.330 | 21.566 | 1.00 | 45.33 | A | C |
| ATOM | 1584 | O | PRO | A | 700 | −12.948 | 10.074 | 22.048 | 1.00 | 43.22 | A | O |
| ATOM | 1585 | N | ASN | A | 701 | −11.635 | 9.385 | 20.315 | 1.00 | 48.30 | A | N |
| ATOM | 1586 | CA | ASN | A | 701 | −12.299 | 10.115 | 19.251 | 1.00 | 52.07 | A | C |
| ATOM | 1587 | CB | ASN | A | 701 | −13.693 | 9.544 | 19.019 | 1.00 | 55.65 | A | C |
| ATOM | 1588 | CG | ASN | A | 701 | −14.174 | 9.804 | 17.641 | 1.00 | 58.03 | A | C |
| ATOM | 1589 | OD1 | ASN | A | 701 | −13.617 | 9.303 | 16.654 | 1.00 | 58.32 | A | O |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 1590 | ND2 | ASN | A | 701 | −15.196 | 10.627 | 17.544 | 1.00 | 61.70 | A | N |
| ATOM | 1591 | C | ASN | A | 701 | −12.321 | 11.647 | 19.348 | 1.00 | 50.08 | A | C |
| ATOM | 1592 | O | ASN | A | 701 | −13.204 | 12.310 | 18.770 | 1.00 | 45.34 | A | O |
| ATOM | 1593 | N | ARG | A | 702 | −11.319 | 12.190 | 20.039 | 1.00 | 46.43 | A | N |
| ATOM | 1594 | CA | ARG | A | 702 | −11.119 | 13.629 | 20.138 | 1.00 | 48.19 | A | C |
| ATOM | 1595 | CB | ARG | A | 702 | −11.374 | 14.045 | 21.579 | 1.00 | 55.76 | A | C |
| ATOM | 1596 | CG | ARG | A | 702 | −11.528 | 15.532 | 21.870 | 1.00 | 65.44 | A | C |
| ATOM | 1597 | CD | ARG | A | 702 | −11.232 | 15.947 | 23.381 | 1.00 | 72.16 | A | C |
| ATOM | 1598 | NE | ARG | A | 702 | −12.249 | 15.637 | 24.415 | 1.00 | 73.97 | A | N |
| ATOM | 1599 | CZ | ARG | A | 702 | −13.488 | 15.134 | 24.213 | 1.00 | 78.19 | A | C |
| ATOM | 1600 | NH1 | ARG | A | 702 | −13.958 | 14.851 | 22.993 | 1.00 | 75.65 | A | N |
| ATOM | 1601 | NH2 | ARG | A | 702 | −14.274 | 14.909 | 25.262 | 1.00 | 80.63 | A | N |
| ATOM | 1602 | C | ARG | A | 702 | −9.674 | 13.913 | 19.723 | 1.00 | 46.23 | A | C |
| ATOM | 1603 | O | ARG | A | 702 | −8.760 | 13.640 | 20.481 | 1.00 | 50.59 | A | O |
| ATOM | 1604 | N | PRO | A | 703 | −9.450 | 14.450 | 18.528 | 1.00 | 45.86 | A | N |
| ATOM | 1605 | CA | PRO | A | 703 | −8.087 | 14.594 | 17.988 | 1.00 | 45.22 | A | C |
| ATOM | 1606 | CB | PRO | A | 703 | −8.318 | 15.221 | 16.608 | 1.00 | 44.09 | A | C |
| ATOM | 1607 | CG | PRO | A | 703 | −9.627 | 15.898 | 16.735 | 1.00 | 43.61 | A | C |
| ATOM | 1608 | CD | PRO | A | 703 | −10.455 | 14.998 | 17.604 | 1.00 | 45.69 | A | C |
| ATOM | 1609 | C | PRO | A | 703 | −7.197 | 15.520 | 18.806 | 1.00 | 43.55 | A | C |
| ATOM | 1610 | O | PRO | A | 703 | −7.688 | 16.336 | 19.584 | 1.00 | 44.36 | A | O |
| ATOM | 1611 | N | GLY | A | 704 | −5.890 | 15.384 | 18.619 | 1.00 | 44.43 | A | N |
| ATOM | 1612 | CA | GLY | A | 704 | −4.928 | 16.256 | 19.268 | 1.00 | 43.96 | A | C |
| ATOM | 1613 | C | GLY | A | 704 | −4.658 | 17.493 | 18.432 | 1.00 | 41.94 | A | C |
| ATOM | 1614 | O | GLY | A | 704 | −4.565 | 17.418 | 17.199 | 1.00 | 47.94 | A | O |
| ATOM | 1615 | N | ILE | A | 705 | −4.560 | 18.637 | 19.094 | 1.00 | 33.42 | A | N |
| ATOM | 1616 | CA | ILE | A | 705 | −4.159 | 19.841 | 18.410 | 1.00 | 28.50 | A | C |
| ATOM | 1617 | CB | ILE | A | 705 | −5.147 | 21.047 | 18.682 | 1.00 | 31.90 | A | C |
| ATOM | 1618 | CG1 | ILE | A | 705 | −4.460 | 22.418 | 18.561 | 1.00 | 36.99 | A | C |
| ATOM | 1619 | CD1 | ILE | A | 705 | −3.332 | 22.737 | 19.529 | 1.00 | 37.47 | A | C |
| ATOM | 1620 | CG2 | ILE | A | 705 | −5.965 | 20.889 | 19.949 | 1.00 | 32.67 | A | C |
| ATOM | 1621 | C | ILE | A | 705 | −2.701 | 20.117 | 18.715 | 1.00 | 27.05 | A | C |
| ATOM | 1622 | O | ILE | A | 705 | −2.281 | 20.125 | 19.865 | 1.00 | 35.29 | A | O |
| ATOM | 1623 | N | PHE | A | 706 | −1.925 | 20.305 | 17.662 | 1.00 | 31.62 | A | N |
| ATOM | 1624 | CA | PHE | A | 706 | −0.487 | 20.540 | 17.772 | 1.00 | 38.59 | A | C |
| ATOM | 1625 | CB | PHE | A | 706 | 0.282 | 19.522 | 16.932 | 1.00 | 34.95 | A | C |
| ATOM | 1626 | CG | PHE | A | 706 | −0.072 | 18.096 | 17.223 | 1.00 | 32.87 | A | C |
| ATOM | 1627 | CD1 | PHE | A | 706 | 0.855 | 17.248 | 17.783 | 1.00 | 37.19 | A | C |
| ATOM | 1628 | CE1 | PHE | A | 706 | 0.542 | 15.911 | 18.024 | 1.00 | 38.47 | A | C |
| ATOM | 1629 | CZ | PHE | A | 706 | −0.714 | 15.424 | 17.711 | 1.00 | 35.32 | A | C |
| ATOM | 1630 | CE2 | PHE | A | 706 | −1.645 | 16.268 | 17.163 | 1.00 | 32.01 | A | C |
| ATOM | 1631 | CD2 | PHE | A | 706 | −1.322 | 17.591 | 16.917 | 1.00 | 32.32 | A | C |
| ATOM | 1632 | C | PHE | A | 706 | −0.203 | 21.944 | 17.258 | 1.00 | 39.92 | A | C |
| ATOM | 1633 | O | PHE | A | 706 | −1.117 | 22.586 | 16.742 | 1.00 | 42.13 | A | O |
| ATOM | 1634 | N | VAL | A | 707 | 1.033 | 22.433 | 17.388 | 1.00 | 35.91 | A | N |
| ATOM | 1635 | CA | VAL | A | 707 | 1.341 | 23.750 | 16.833 | 1.00 | 34.53 | A | C |
| ATOM | 1636 | CB | VAL | A | 707 | 2.227 | 24.638 | 17.760 | 1.00 | 31.70 | A | C |
| ATOM | 1637 | CG1 | VAL | A | 707 | 3.170 | 23.829 | 18.523 | 1.00 | 33.90 | A | C |
| ATOM | 1638 | CG2 | VAL | A | 707 | 3.006 | 25.656 | 16.955 | 1.00 | 34.25 | A | C |
| ATOM | 1639 | C | VAL | A | 707 | 1.880 | 23.645 | 15.400 | 1.00 | 34.97 | A | C |
| ATOM | 1640 | O | VAL | A | 707 | 2.856 | 22.930 | 15.138 | 1.00 | 35.08 | A | O |
| ATOM | 1641 | N | ARG | A | 708 | 1.206 | 24.338 | 14.480 | 1.00 | 35.14 | A | N |
| ATOM | 1642 | CA | ARG | A | 708 | 1.601 | 24.377 | 13.075 | 1.00 | 39.69 | A | C |
| ATOM | 1643 | CB | ARG | A | 708 | 0.639 | 25.237 | 12.251 | 1.00 | 42.35 | A | C |
| ATOM | 1644 | CG | ARG | A | 708 | 0.392 | 24.734 | 10.859 | 1.00 | 46.08 | A | C |
| ATOM | 1645 | CD | ARG | A | 708 | −1.037 | 24.982 | 10.339 | 1.00 | 52.26 | A | C |
| ATOM | 1646 | NE | ARG | A | 708 | −1.026 | 26.025 | 9.318 | 1.00 | 60.83 | A | N |
| ATOM | 1647 | CZ | ARG | A | 708 | −0.483 | 25.893 | 8.097 | 1.00 | 68.01 | A | C |
| ATOM | 1648 | NH1 | ARG | A | 708 | 0.081 | 24.736 | 7.717 | 1.00 | 71.66 | A | N |
| ATOM | 1649 | NH2 | ARG | A | 708 | −0.511 | 26.917 | 7.244 | 1.00 | 65.48 | A | N |
| ATOM | 1650 | C | ARG | A | 708 | 2.984 | 24.972 | 13.008 | 1.00 | 39.97 | A | C |
| ATOM | 1651 | O | ARG | A | 708 | 3.186 | 26.120 | 13.373 | 1.00 | 43.82 | A | O |
| ATOM | 1652 | N | VAL | A | 709 | 3.948 | 24.175 | 12.584 | 1.00 | 37.94 | A | N |
| ATOM | 1653 | CA | VAL | A | 709 | 5.300 | 24.673 | 12.409 | 1.00 | 32.57 | A | C |
| ATOM | 1654 | CB | VAL | A | 709 | 6.281 | 23.524 | 12.228 | 1.00 | 28.96 | A | C |
| ATOM | 1655 | CG1 | VAL | A | 709 | 7.631 | 24.029 | 11.747 | 1.00 | 21.41 | A | C |
| ATOM | 1656 | CG2 | VAL | A | 709 | 6.378 | 22.707 | 13.519 | 1.00 | 28.08 | A | C |
| ATOM | 1657 | C | VAL | A | 709 | 5.315 | 25.563 | 11.178 | 1.00 | 35.08 | A | C |
| ATOM | 1658 | O | VAL | A | 709 | 5.949 | 26.606 | 11.168 | 1.00 | 31.30 | A | O |
| ATOM | 1659 | N | ALA | A | 710 | 4.585 | 25.162 | 10.144 | 1.00 | 41.73 | A | N |
| ATOM | 1660 | CA | ALA | A | 710 | 4.536 | 25.956 | 8.920 | 1.00 | 42.71 | A | C |
| ATOM | 1661 | CB | ALA | A | 710 | 3.512 | 25.382 | 7.952 | 1.00 | 44.89 | A | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 1662 | C | ALA | A | 710 | 4.245 | 27.434 | 9.215 | 1.00 | 40.16 | A | C |
| ATOM | 1663 | O | ALA | A | 710 | 4.770 | 28.317 | 8.549 | 1.00 | 39.48 | A | O |
| ATOM | 1664 | N | TYR | A | 711 | 3.433 | 27.694 | 10.235 | 1.00 | 40.18 | A | N |
| ATOM | 1665 | CA | TYR | A | 711 | 3.038 | 29.055 | 10.577 | 1.00 | 41.47 | A | C |
| ATOM | 1666 | CB | TYR | A | 711 | 1.959 | 29.040 | 11.643 | 1.00 | 39.79 | A | C |
| ATOM | 1667 | CG | TYR | A | 711 | 1.282 | 30.362 | 11.903 | 1.00 | 36.63 | A | C |
| ATOM | 1668 | CD1 | TYR | A | 711 | 0.346 | 30.875 | 11.017 | 1.00 | 42.57 | A | C |
| ATOM | 1669 | CE1 | TYR | A | 711 | −0.301 | 32.087 | 11.266 | 1.00 | 46.47 | A | C |
| ATOM | 1670 | CZ | TYR | A | 711 | −0.022 | 32.781 | 12.430 | 1.00 | 45.43 | A | C |
| ATOM | 1671 | OH | TYR | A | 711 | −0.658 | 33.979 | 12.691 | 1.00 | 45.18 | A | O |
| ATOM | 1672 | CE2 | TYR | A | 711 | 0.901 | 32.274 | 13.324 | 1.00 | 42.37 | A | C |
| ATOM | 1673 | CD2 | TYR | A | 711 | 1.544 | 31.072 | 13.053 | 1.00 | 36.82 | A | C |
| ATOM | 1674 | C | TYR | A | 711 | 4.220 | 29.821 | 11.095 | 1.00 | 44.95 | A | C |
| ATOM | 1675 | O | TYR | A | 711 | 4.275 | 31.040 | 10.974 | 1.00 | 53.00 | A | O |
| ATOM | 1676 | N | TYR | A | 712 | 5.178 | 29.090 | 11.646 | 1.00 | 42.71 | A | N |
| ATOM | 1677 | CA | TYR | A | 712 | 6.345 | 29.695 | 12.266 | 1.00 | 42.49 | A | C |
| ATOM | 1678 | CB | TYR | A | 712 | 6.411 | 29.198 | 13.701 | 1.00 | 31.49 | A | C |
| ATOM | 1679 | CG | TYR | A | 712 | 5.262 | 29.691 | 14.537 | 1.00 | 26.75 | A | C |
| ATOM | 1680 | CD1 | TYR | A | 712 | 5.061 | 31.049 | 14.711 | 1.00 | 28.18 | A | C |
| ATOM | 1681 | CE1 | TYR | A | 712 | 4.027 | 31.532 | 15.503 | 1.00 | 30.60 | A | C |
| ATOM | 1682 | CZ | TYR | A | 712 | 3.161 | 30.659 | 16.121 | 1.00 | 29.77 | A | C |
| ATOM | 1683 | OH | TYR | A | 712 | 2.148 | 31.219 | 16.868 | 1.00 | 34.02 | A | O |
| ATOM | 1684 | CE2 | TYR | A | 712 | 3.325 | 29.284 | 15.973 | 1.00 | 25.70 | A | C |
| ATOM | 1685 | CD2 | TYR | A | 712 | 4.390 | 28.807 | 15.181 | 1.00 | 25.26 | A | C |
| ATOM | 1686 | C | TYR | A | 712 | 7.695 | 29.487 | 11.521 | 1.00 | 48.23 | A | C |
| ATOM | 1687 | O | TYR | A | 712 | 8.754 | 29.901 | 12.003 | 1.00 | 52.43 | A | O |
| ATOM | 1688 | N | ALA | A | 713 | 7.654 | 28.881 | 10.339 | 1.00 | 47.47 | A | N |
| ATOM | 1689 | CA | ALA | A | 713 | 8.875 | 28.421 | 9.692 | 1.00 | 48.61 | A | C |
| ATOM | 1690 | CB | ALA | A | 713 | 8.542 | 27.636 | 8.442 | 1.00 | 49.02 | A | C |
| ATOM | 1691 | C | ALA | A | 713 | 9.837 | 29.565 | 9.380 | 1.00 | 52.52 | A | C |
| ATOM | 1692 | O | ALA | A | 713 | 11.062 | 29.428 | 9.531 | 1.00 | 53.40 | A | O |
| ATOM | 1693 | N | LYS | A | 714 | 9.267 | 30.689 | 8.946 | 1.00 | 54.15 | A | N |
| ATOM | 1694 | CA | LYS | A | 714 | 10.025 | 31.899 | 8.639 | 1.00 | 50.72 | A | C |
| ATOM | 1695 | CB | LYS | A | 714 | 9.072 | 33.069 | 8.372 | 1.00 | 50.32 | A | C |
| ATOM | 1696 | CG | LYS | A | 714 | 9.550 | 34.058 | 7.354 | 1.00 | 49.64 | A | C |
| ATOM | 1697 | CD | LYS | A | 714 | 8.530 | 34.233 | 6.245 | 1.00 | 52.82 | A | C |
| ATOM | 1698 | CE | LYS | A | 714 | 9.107 | 33.779 | 4.892 | 1.00 | 56.98 | A | C |
| ATOM | 1699 | NZ | LYS | A | 714 | 9.283 | 34.895 | 3.904 | 1.00 | 55.47 | A | N |
| ATOM | 1700 | C | LYS | A | 714 | 10.865 | 32.199 | 9.858 | 1.00 | 46.97 | A | C |
| ATOM | 1701 | O | LYS | A | 714 | 12.103 | 32.125 | 9.813 | 1.00 | 43.57 | A | O |
| ATOM | 1702 | N | TRP | A | 715 | 10.170 | 32.477 | 10.963 | 1.00 | 42.31 | A | N |
| ATOM | 1703 | CA | TRP | A | 715 | 10.831 | 32.815 | 12.203 | 1.00 | 36.99 | A | C |
| ATOM | 1704 | CB | TRP | A | 715 | 9.844 | 32.968 | 13.342 | 1.00 | 33.70 | A | C |
| ATOM | 1705 | CG | TRP | A | 715 | 10.556 | 33.022 | 14.636 | 1.00 | 34.96 | A | C |
| ATOM | 1706 | CD1 | TRP | A | 715 | 11.239 | 34.073 | 15.133 | 1.00 | 36.36 | A | C |
| ATOM | 1707 | NE1 | TRP | A | 715 | 11.791 | 33.751 | 16.346 | 1.00 | 37.12 | A | N |
| ATOM | 1708 | CE2 | TRP | A | 715 | 11.469 | 32.459 | 16.649 | 1.00 | 36.71 | A | C |
| ATOM | 1709 | CD2 | TRP | A | 715 | 10.699 | 31.964 | 15.585 | 1.00 | 38.08 | A | C |
| ATOM | 1710 | CE3 | TRP | A | 715 | 10.235 | 30.643 | 15.653 | 1.00 | 42.71 | A | C |
| ATOM | 1711 | CZ3 | TRP | A | 715 | 10.557 | 29.880 | 16.758 | 1.00 | 43.82 | A | C |
| ATOM | 1712 | CH2 | TRP | A | 715 | 11.335 | 30.409 | 17.800 | 1.00 | 42.73 | A | C |
| ATOM | 1713 | CZ2 | TRP | A | 715 | 11.798 | 31.692 | 17.761 | 1.00 | 38.42 | A | C |
| ATOM | 1714 | C | TRP | A | 715 | 11.907 | 31.793 | 12.560 | 1.00 | 35.89 | A | C |
| ATOM | 1715 | O | TRP | A | 715 | 13.046 | 32.171 | 12.830 | 1.00 | 42.05 | A | O |
| ATOM | 1716 | N | ILE | A | 716 | 11.565 | 30.508 | 12.532 | 1.00 | 29.01 | A | N |
| ATOM | 1717 | CA | ILE | A | 716 | 12.551 | 29.472 | 12.818 | 1.00 | 25.70 | A | C |
| ATOM | 1718 | CB | ILE | A | 716 | 12.000 | 28.086 | 12.571 | 1.00 | 19.69 | A | C |
| ATOM | 1719 | CG1 | ILE | A | 716 | 10.683 | 27.889 | 13.333 | 1.00 | 18.28 | A | C |
| ATOM | 1720 | CD1 | ILE | A | 716 | 10.093 | 26.517 | 13.207 | 1.00 | 13.05 | A | C |
| ATOM | 1721 | CG2 | ILE | A | 716 | 13.070 | 27.064 | 12.937 | 1.00 | 13.56 | A | C |
| ATOM | 1722 | C | ILE | A | 716 | 13.793 | 29.631 | 11.963 | 1.00 | 31.34 | A | C |
| ATOM | 1723 | O | ILE | A | 716 | 14.911 | 29.574 | 12.469 | 1.00 | 34.55 | A | O |
| ATOM | 1724 | N | HIS | A | 717 | 13.600 | 29.826 | 10.667 | 1.00 | 34.01 | A | N |
| ATOM | 1725 | CA | HIS | A | 717 | 14.737 | 29.888 | 9.776 | 1.00 | 40.72 | A | C |
| ATOM | 1726 | CB | HIS | A | 717 | 14.288 | 29.962 | 8.326 | 1.00 | 40.20 | A | C |
| ATOM | 1727 | CG | HIS | A | 717 | 13.989 | 28.628 | 7.732 | 1.00 | 38.10 | A | C |
| ATOM | 1728 | ND1 | HIS | A | 717 | 12.706 | 28.210 | 7.458 | 1.00 | 37.66 | A | N |
| ATOM | 1729 | CE1 | HIS | A | 717 | 12.743 | 26.991 | 6.947 | 1.00 | 39.42 | A | C |
| ATOM | 1730 | NE2 | HIS | A | 717 | 14.004 | 26.602 | 6.889 | 1.00 | 39.68 | A | N |
| ATOM | 1731 | CD2 | HIS | A | 717 | 14.804 | 27.608 | 7.374 | 1.00 | 38.80 | A | C |
| ATOM | 1732 | C | HIS | A | 717 | 15.646 | 31.053 | 10.134 | 1.00 | 47.42 | A | C |
| ATOM | 1733 | O | HIS | A | 717 | 16.868 | 30.892 | 10.177 | 1.00 | 50.86 | A | O |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 1734 | N | LYS | A | 718 | 15.048 | 32.211 | 10.421 | 1.00 | 49.56 | A | N |
| ATOM | 1735 | CA | LYS | A | 718 | 15.821 | 33.418 | 10.728 | 1.00 | 50.74 | A | C |
| ATOM | 1736 | CB | LYS | A | 718 | 14.932 | 34.674 | 10.689 | 1.00 | 53.23 | A | C |
| ATOM | 1737 | CG | LYS | A | 718 | 15.153 | 35.710 | 11.785 | 1.00 | 55.66 | A | C |
| ATOM | 1738 | CD | LYS | A | 718 | 13.871 | 35.914 | 12.598 | 1.00 | 60.99 | A | C |
| ATOM | 1739 | CE | LYS | A | 718 | 13.785 | 37.307 | 13.223 | 1.00 | 65.16 | A | C |
| ATOM | 1740 | NZ | LYS | A | 718 | 13.795 | 38.395 | 12.194 | 1.00 | 68.77 | A | N |
| ATOM | 1741 | C | LYS | A | 718 | 16.582 | 33.275 | 12.045 | 1.00 | 48.84 | A | C |
| ATOM | 1742 | O | LYS | A | 718 | 17.526 | 34.015 | 12.300 | 1.00 | 49.48 | A | O |
| ATOM | 1743 | N | ILE | A | 719 | 16.193 | 32.300 | 12.859 | 1.00 | 45.24 | A | N |
| ATOM | 1744 | CA | ILE | A | 719 | 16.927 | 32.002 | 14.080 | 1.00 | 43.16 | A | C |
| ATOM | 1745 | CB | ILE | A | 719 | 15.962 | 31.552 | 15.181 | 1.00 | 42.64 | A | C |
| ATOM | 1746 | CG1 | ILE | A | 719 | 14.993 | 32.684 | 15.542 | 1.00 | 42.75 | A | C |
| ATOM | 1747 | CD1 | ILE | A | 719 | 15.628 | 33.885 | 16.185 | 1.00 | 43.06 | A | C |
| ATOM | 1748 | CG2 | ILE | A | 719 | 16.719 | 31.019 | 16.402 | 1.00 | 42.10 | A | C |
| ATOM | 1749 | C | ILE | A | 719 | 18.019 | 30.960 | 13.865 | 1.00 | 44.68 | A | C |
| ATOM | 1750 | O | ILE | A | 719 | 19.130 | 31.130 | 14.364 | 1.00 | 44.01 | A | O |
| ATOM | 1751 | N | ILE | A | 720 | 17.705 | 29.897 | 13.122 | 1.00 | 47.92 | A | N |
| ATOM | 1752 | CA | ILE | A | 720 | 18.604 | 28.739 | 12.998 | 1.00 | 53.56 | A | C |
| ATOM | 1753 | CB | ILE | A | 720 | 17.823 | 27.406 | 12.880 | 1.00 | 50.50 | A | C |
| ATOM | 1754 | CG1 | ILE | A | 720 | 16.906 | 27.414 | 11.666 | 1.00 | 49.87 | A | C |
| ATOM | 1755 | CD1 | ILE | A | 720 | 17.308 | 26.438 | 10.631 | 1.00 | 52.61 | A | C |
| ATOM | 1756 | CG2 | ILE | A | 720 | 17.007 | 27.149 | 14.121 | 1.00 | 53.14 | A | C |
| ATOM | 1757 | C | ILE | A | 720 | 19.609 | 28.844 | 11.857 | 1.00 | 61.95 | A | C |
| ATOM | 1758 | O | ILE | A | 720 | 20.764 | 28.419 | 11.998 | 1.00 | 64.33 | A | O |
| ATOM | 1759 | N | LEU | A | 721 | 19.160 | 29.372 | 10.719 | 1.00 | 67.80 | A | N |
| ATOM | 1760 | CA | LEU | A | 721 | 20.049 | 29.574 | 9.586 | 1.00 | 70.56 | A | C |
| ATOM | 1761 | CB | LEU | A | 721 | 19.276 | 29.888 | 8.302 | 1.00 | 69.78 | A | C |
| ATOM | 1762 | CG | LEU | A | 721 | 19.365 | 28.816 | 7.207 | 1.00 | 69.35 | A | C |
| ATOM | 1763 | CD1 | LEU | A | 721 | 18.168 | 27.844 | 7.255 | 1.00 | 63.65 | A | C |
| ATOM | 1764 | CD2 | LEU | A | 721 | 19.535 | 29.464 | 5.812 | 1.00 | 69.06 | A | C |
| ATOM | 1765 | C | LEU | A | 721 | 20.980 | 30.700 | 9.969 | 1.00 | 73.23 | A | C |
| ATOM | 1766 | O | LEU | A | 721 | 20.544 | 31.726 | 10.494 | 1.00 | 70.65 | A | O |
| ATOM | 1767 | N | THR | A | 722 | 22.272 | 30.464 | 9.763 | 1.00 | 80.61 | A | N |
| ATOM | 1768 | CA | THR | A | 722 | 23.323 | 31.413 | 10.134 | 1.00 | 87.21 | A | C |
| ATOM | 1769 | CB | THR | A | 722 | 23.375 | 31.652 | 11.695 | 1.00 | 90.25 | A | C |
| ATOM | 1770 | OG1 | THR | A | 722 | 24.652 | 32.191 | 12.076 | 1.00 | 93.38 | A | O |
| ATOM | 1771 | CG2 | THR | A | 722 | 23.270 | 30.337 | 12.491 | 1.00 | 91.06 | A | C |
| ATOM | 1772 | C | THR | A | 722 | 24.686 | 30.991 | 9.567 | 1.00 | 86.57 | A | C |
| ATOM | 1773 | O | THR | A | 722 | 25.245 | 31.668 | 8.697 | 1.00 | 85.09 | A | O |
| ATOM | 1774 | N | LYS | B | 40 | −40.439 | 42.342 | 56.132 | 1.00 | 88.31 | B | N |
| ATOM | 1775 | CA | LYS | B | 40 | −40.314 | 40.869 | 55.911 | 1.00 | 89.08 | B | C |
| ATOM | 1776 | CB | LYS | B | 40 | −41.319 | 40.112 | 56.792 | 1.00 | 91.05 | B | C |
| ATOM | 1777 | CG | LYS | B | 40 | −41.370 | 38.601 | 56.568 | 1.00 | 91.08 | B | C |
| ATOM | 1778 | CD | LYS | B | 40 | −42.788 | 38.072 | 56.744 | 1.00 | 90.84 | B | C |
| ATOM | 1779 | CE | LYS | B | 40 | −43.407 | 37.692 | 55.409 | 1.00 | 90.34 | B | C |
| ATOM | 1780 | NZ | LYS | B | 40 | −44.531 | 38.595 | 55.063 | 1.00 | 90.81 | B | N |
| ATOM | 1781 | C | LYS | B | 40 | −40.506 | 40.510 | 54.433 | 1.00 | 87.17 | B | C |
| ATOM | 1782 | O | LYS | B | 40 | −41.613 | 40.627 | 53.890 | 1.00 | 87.44 | B | O |
| ATOM | 1783 | N | TYR | B | 41 | −39.423 | 40.070 | 53.793 | 1.00 | 82.82 | B | N |
| ATOM | 1784 | CA | TYR | B | 41 | −39.455 | 39.735 | 52.369 | 1.00 | 77.74 | B | C |
| ATOM | 1785 | CB | TYR | B | 41 | −38.214 | 40.264 | 51.652 | 1.00 | 74.81 | B | C |
| ATOM | 1786 | CG | TYR | B | 41 | −38.096 | 41.772 | 51.602 | 1.00 | 73.26 | B | C |
| ATOM | 1787 | CD1 | TYR | B | 41 | −36.962 | 42.402 | 52.091 | 1.00 | 72.23 | B | C |
| ATOM | 1788 | CE1 | TYR | B | 41 | −36.824 | 43.787 | 52.050 | 1.00 | 71.49 | B | C |
| ATOM | 1789 | CZ | TYR | B | 41 | −37.824 | 44.566 | 51.508 | 1.00 | 70.43 | B | C |
| ATOM | 1790 | OH | TYR | B | 41 | −37.644 | 45.935 | 51.482 | 1.00 | 68.52 | B | O |
| ATOM | 1791 | CE2 | TYR | B | 41 | −38.976 | 43.969 | 51.004 | 1.00 | 72.04 | B | C |
| ATOM | 1792 | CD2 | TYR | B | 41 | −39.105 | 42.570 | 51.050 | 1.00 | 73.83 | B | C |
| ATOM | 1793 | C | TYR | B | 41 | −39.609 | 38.240 | 52.108 | 1.00 | 74.94 | B | C |
| ATOM | 1794 | O | TYR | B | 41 | −39.354 | 37.415 | 52.983 | 1.00 | 72.98 | B | O |
| ATOM | 1795 | N | GLN | B | 42 | −40.028 | 37.917 | 50.887 | 1.00 | 73.46 | B | N |
| ATOM | 1796 | CA | GLN | B | 42 | −40.326 | 36.552 | 50.471 | 1.00 | 72.07 | B | C |
| ATOM | 1797 | CB | GLN | B | 42 | −41.851 | 36.391 | 50.273 | 1.00 | 74.52 | B | C |
| ATOM | 1798 | CG | GLN | B | 42 | −42.323 | 35.498 | 49.116 | 1.00 | 76.03 | B | C |
| ATOM | 1799 | CD | GLN | B | 42 | −42.263 | 34.010 | 49.439 | 1.00 | 74.54 | B | C |
| ATOM | 1800 | OE1 | GLN | B | 42 | −43.257 | 33.420 | 49.867 | 1.00 | 72.50 | B | O |
| ATOM | 1801 | NE2 | GLN | B | 42 | −41.100 | 33.402 | 49.222 | 1.00 | 74.77 | B | N |
| ATOM | 1802 | C | GLN | B | 42 | −39.498 | 36.216 | 49.217 | 1.00 | 69.39 | B | C |
| ATOM | 1803 | O | GLN | B | 42 | −39.776 | 36.699 | 48.116 | 1.00 | 70.35 | B | O |
| ATOM | 1804 | N | LEU | B | 43 | −38.467 | 35.395 | 49.406 | 1.00 | 65.67 | B | N |
| ATOM | 1805 | CA | LEU | B | 43 | −37.458 | 35.147 | 48.374 | 1.00 | 60.10 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 1806 | CB | LEU | B | 43 | −36.186 | 35.926 | 48.707 | 1.00 | 55.50 | B | C |
| ATOM | 1807 | CG | LEU | B | 43 | −36.311 | 37.445 | 48.634 | 1.00 | 53.79 | B | C |
| ATOM | 1808 | CD1 | LEU | B | 43 | −35.264 | 38.123 | 49.493 | 1.00 | 51.21 | B | C |
| ATOM | 1809 | CD2 | LEU | B | 43 | −36.236 | 37.931 | 47.187 | 1.00 | 54.63 | B | C |
| ATOM | 1810 | C | LEU | B | 43 | −37.129 | 33.658 | 48.226 | 1.00 | 58.51 | B | C |
| ATOM | 1811 | O | LEU | B | 43 | −37.399 | 32.883 | 49.150 | 1.00 | 59.14 | B | O |
| ATOM | 1812 | N | PRO | B | 44 | −36.578 | 33.255 | 47.070 | 1.00 | 54.41 | B | N |
| ATOM | 1813 | CA | PRO | B | 44 | −36.135 | 31.871 | 46.864 | 1.00 | 52.74 | B | C |
| ATOM | 1814 | CB | PRO | B | 44 | −35.464 | 31.930 | 45.497 | 1.00 | 50.09 | B | C |
| ATOM | 1815 | CG | PRO | B | 44 | −36.199 | 33.016 | 44.788 | 1.00 | 48.95 | B | C |
| ATOM | 1816 | CD | PRO | B | 44 | −36.385 | 34.064 | 45.850 | 1.00 | 52.02 | B | C |
| ATOM | 1817 | C | PRO | B | 44 | −35.164 | 31.437 | 47.956 | 1.00 | 55.95 | B | C |
| ATOM | 1818 | O | PRO | B | 44 | −34.059 | 31.975 | 48.057 | 1.00 | 57.32 | B | O |
| ATOM | 1819 | N | ASN | B | 45 | −35.602 | 30.475 | 48.768 | 1.00 | 57.90 | B | N |
| ATOM | 1820 | CA | ASN | B | 45 | −34.996 | 30.210 | 50.072 | 1.00 | 56.49 | B | C |
| ATOM | 1821 | CB | ASN | B | 45 | −35.896 | 30.734 | 51.251 | 1.00 | 59.73 | B | C |
| ATOM | 1822 | CG | ASN | B | 45 | −37.444 | 30.377 | 51.125 | 1.00 | 61.49 | B | C |
| ATOM | 1823 | OD1 | ASN | B | 45 | −38.318 | 31.134 | 51.606 | 1.00 | 56.31 | B | O |
| ATOM | 1824 | ND2 | ASN | B | 45 | −37.756 | 29.226 | 50.537 | 1.00 | 63.28 | B | N |
| ATOM | 1825 | C | ASN | B | 45 | −34.559 | 28.770 | 50.323 | 1.00 | 55.39 | B | C |
| ATOM | 1826 | O | ASN | B | 45 | −35.290 | 28.037 | 50.995 | 1.00 | 59.64 | B | O |
| ATOM | 1827 | N | PHE | B | 46 | −33.381 | 28.356 | 49.826 | 1.00 | 50.73 | B | N |
| ATOM | 1828 | CA | PHE | B | 46 | −32.858 | 27.004 | 50.170 | 1.00 | 45.86 | B | C |
| ATOM | 1829 | CB | PHE | B | 46 | −32.065 | 26.320 | 49.053 | 1.00 | 45.33 | B | C |
| ATOM | 1830 | CG | PHE | B | 46 | −31.521 | 24.969 | 49.467 | 1.00 | 44.34 | B | C |
| ATOM | 1831 | CD1 | PHE | B | 46 | −32.353 | 23.853 | 49.510 | 1.00 | 46.55 | B | C |
| ATOM | 1832 | CE1 | PHE | B | 46 | −31.859 | 22.600 | 49.920 | 1.00 | 43.16 | B | C |
| ATOM | 1833 | CZ | PHE | B | 46 | −30.542 | 22.476 | 50.304 | 1.00 | 39.14 | B | C |
| ATOM | 1834 | CE2 | PHE | B | 46 | −29.712 | 23.588 | 50.285 | 1.00 | 38.80 | B | C |
| ATOM | 1835 | CD2 | PHE | B | 46 | −30.201 | 24.824 | 49.879 | 1.00 | 41.12 | B | C |
| ATOM | 1836 | C | PHE | B | 46 | −32.060 | 26.841 | 51.473 | 1.00 | 41.12 | B | C |
| ATOM | 1837 | O | PHE | B | 46 | −31.092 | 27.559 | 51.722 | 1.00 | 33.78 | B | O |
| ATOM | 1838 | N | THR | B | 47 | −32.459 | 25.826 | 52.241 | 1.00 | 43.61 | B | N |
| ATOM | 1839 | CA | THR | B | 47 | −31.914 | 25.507 | 53.555 | 1.00 | 47.93 | B | C |
| ATOM | 1840 | CB | THR | B | 47 | −33.049 | 25.533 | 54.579 | 1.00 | 47.66 | B | C |
| ATOM | 1841 | OG1 | THR | B | 47 | −33.753 | 26.778 | 54.498 | 1.00 | 49.67 | B | O |
| ATOM | 1842 | CG2 | THR | B | 47 | −32.499 | 25.486 | 56.003 | 1.00 | 47.43 | B | C |
| ATOM | 1843 | C | THR | B | 47 | −31.297 | 24.104 | 53.588 | 1.00 | 53.53 | B | C |
| ATOM | 1844 | O | THR | B | 47 | −31.994 | 23.105 | 53.386 | 1.00 | 57.56 | B | O |
| ATOM | 1845 | N | ALA | B | 48 | −30.006 | 24.023 | 53.886 | 1.00 | 54.57 | B | N |
| ATOM | 1846 | CA | ALA | B | 48 | −29.338 | 22.731 | 54.009 | 1.00 | 57.41 | B | C |
| ATOM | 1847 | CB | ALA | B | 48 | −27.942 | 22.816 | 53.453 | 1.00 | 61.70 | B | C |
| ATOM | 1848 | C | ALA | B | 48 | −29.291 | 22.235 | 55.446 | 1.00 | 57.95 | B | C |
| ATOM | 1849 | O | ALA | B | 48 | −29.491 | 23.005 | 56.387 | 1.00 | 58.63 | B | O |
| ATOM | 1850 | N | GLU | B | 49 | −28.996 | 20.949 | 55.608 | 1.00 | 59.00 | B | N |
| ATOM | 1851 | CA | GLU | B | 49 | −28.923 | 20.351 | 56.936 | 1.00 | 61.70 | B | C |
| ATOM | 1852 | CB | GLU | B | 49 | −29.316 | 18.860 | 56.902 | 1.00 | 67.90 | B | C |
| ATOM | 1853 | CG | GLU | B | 49 | −30.824 | 18.591 | 56.926 | 1.00 | 72.95 | B | C |
| ATOM | 1854 | CD | GLU | B | 49 | −31.524 | 19.154 | 58.163 | 1.00 | 78.90 | B | C |
| ATOM | 1855 | OE1 | GLU | B | 49 | −31.300 | 18.617 | 59.277 | 1.00 | 81.87 | B | O |
| ATOM | 1856 | OE2 | GLU | B | 49 | −32.302 | 20.133 | 58.027 | 1.00 | 78.86 | B | O |
| ATOM | 1857 | C | GLU | B | 49 | −27.568 | 20.562 | 57.620 | 1.00 | 57.45 | B | C |
| ATOM | 1858 | O | GLU | B | 49 | −27.410 | 20.234 | 58.800 | 1.00 | 60.69 | B | O |
| ATOM | 1859 | N | THR | B | 50 | −26.597 | 21.106 | 56.887 | 1.00 | 50.48 | B | N |
| ATOM | 1860 | CA | THR | B | 50 | −25.287 | 21.443 | 57.459 | 1.00 | 46.07 | B | C |
| ATOM | 1861 | CB | THR | B | 50 | −24.215 | 20.346 | 57.182 | 1.00 | 45.63 | B | C |
| ATOM | 1862 | OG1 | THR | B | 50 | −23.565 | 20.588 | 55.925 | 1.00 | 43.30 | B | O |
| ATOM | 1863 | CG2 | THR | B | 50 | −24.852 | 18.971 | 57.009 | 1.00 | 47.44 | B | C |
| ATOM | 1864 | C | THR | B | 50 | −24.814 | 22.789 | 56.939 | 1.00 | 42.87 | B | C |
| ATOM | 1865 | O | THR | B | 50 | −25.212 | 23.184 | 55.850 | 1.00 | 46.52 | B | O |
| ATOM | 1866 | N | PRO | B | 51 | −23.969 | 23.486 | 57.704 | 1.00 | 39.97 | B | N |
| ATOM | 1867 | CA | PRO | B | 51 | −23.454 | 24.813 | 57.318 | 1.00 | 41.14 | B | C |
| ATOM | 1868 | CB | PRO | B | 51 | −22.417 | 25.100 | 58.402 | 1.00 | 39.83 | B | C |
| ATOM | 1869 | CG | PRO | B | 51 | −22.894 | 24.330 | 59.568 | 1.00 | 39.25 | B | C |
| ATOM | 1870 | CD | PRO | B | 51 | −23.441 | 23.060 | 59.012 | 1.00 | 39.48 | B | C |
| ATOM | 1871 | C | PRO | B | 51 | −22.788 | 24.881 | 55.931 | 1.00 | 43.57 | B | C |
| ATOM | 1872 | O | PRO | B | 51 | −22.138 | 23.917 | 55.502 | 1.00 | 46.80 | B | O |
| ATOM | 1873 | N | ILE | B | 52 | −22.935 | 26.019 | 55.252 | 1.00 | 40.80 | B | N |
| ATOM | 1874 | CA | ILE | B | 52 | −22.419 | 26.180 | 53.889 | 1.00 | 38.35 | B | C |
| ATOM | 1875 | CB | ILE | B | 52 | −23.457 | 26.911 | 53.006 | 1.00 | 39.32 | B | C |
| ATOM | 1876 | CG1 | ILE | B | 52 | −24.813 | 26.203 | 53.092 | 1.00 | 37.65 | B | C |
| ATOM | 1877 | CD1 | ILE | B | 52 | −25.748 | 26.480 | 51.943 | 1.00 | 35.28 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | | Amino Acid Residue | | | X | Y | Z | Occ. | Temp Factor | Atom Type | |
|---|---|---|---|---|---|---|---|---|---|---|---|---|
| ATOM | 1878 | CG2 | ILE | B | 52 | −22.924 | 27.055 | 51.565 | 1.00 | 41.75 | B | C |
| ATOM | 1879 | C | ILE | B | 52 | −21.096 | 26.937 | 53.845 | 1.00 | 34.40 | B | C |
| ATOM | 1880 | O | ILE | B | 52 | −21.038 | 28.113 | 54.165 | 1.00 | 35.36 | B | O |
| ATOM | 1881 | N | GLN | B | 53 | −20.029 | 26.287 | 53.423 | 1.00 | 33.14 | B | N |
| ATOM | 1882 | CA | GLN | B | 53 | −18.770 | 27.009 | 53.342 | 1.00 | 36.41 | B | C |
| ATOM | 1883 | CB | GLN | B | 53 | −17.577 | 26.075 | 53.474 | 1.00 | 35.02 | B | C |
| ATOM | 1884 | CG | GLN | B | 53 | −17.288 | 25.692 | 54.878 | 1.00 | 38.75 | B | C |
| ATOM | 1885 | CD | GLN | B | 53 | −18.283 | 24.685 | 55.393 | 1.00 | 41.87 | B | C |
| ATOM | 1886 | OE1 | GLN | B | 53 | −19.091 | 25.007 | 56.271 | 1.00 | 45.15 | B | O |
| ATOM | 1887 | NE2 | GLN | B | 53 | −18.241 | 23.467 | 54.849 | 1.00 | 38.83 | B | N |
| ATOM | 1888 | C | GLN | B | 53 | −18.627 | 27.820 | 52.068 | 1.00 | 38.87 | B | C |
| ATOM | 1889 | O | GLN | B | 53 | −18.137 | 28.945 | 52.130 | 1.00 | 42.84 | B | O |
| ATOM | 1890 | N | ASN | B | 54 | −19.044 | 27.247 | 50.934 | 1.00 | 34.88 | B | N |
| ATOM | 1891 | CA | ASN | B | 54 | −18.616 | 27.716 | 49.617 | 1.00 | 39.39 | B | C |
| ATOM | 1892 | CB | ASN | B | 54 | −17.328 | 27.018 | 49.209 | 1.00 | 42.49 | B | C |
| ATOM | 1893 | CG | ASN | B | 54 | −16.126 | 27.575 | 49.912 | 1.00 | 46.56 | B | C |
| ATOM | 1894 | OD1 | ASN | B | 54 | −15.962 | 28.787 | 50.023 | 1.00 | 49.88 | B | O |
| ATOM | 1895 | ND2 | ASN | B | 54 | −15.271 | 26.692 | 50.397 | 1.00 | 50.16 | B | N |
| ATOM | 1896 | C | ASN | B | 54 | −19.646 | 27.491 | 48.529 | 1.00 | 43.00 | B | C |
| ATOM | 1897 | O | ASN | B | 54 | −20.502 | 26.607 | 48.660 | 1.00 | 46.24 | B | O |
| ATOM | 1898 | N | VAL | B | 55 | −19.550 | 28.269 | 47.445 | 1.00 | 39.10 | B | N |
| ATOM | 1899 | CA | VAL | B | 55 | −20.634 | 28.306 | 46.466 | 1.00 | 37.57 | B | C |
| ATOM | 1900 | CB | VAL | B | 55 | −21.693 | 29.308 | 46.909 | 1.00 | 30.43 | B | C |
| ATOM | 1901 | CG1 | VAL | B | 55 | −22.337 | 29.978 | 45.755 | 1.00 | 23.21 | B | C |
| ATOM | 1902 | CG2 | VAL | B | 55 | −22.718 | 28.564 | 47.647 | 1.00 | 36.18 | B | C |
| ATOM | 1903 | C | VAL | B | 55 | −20.206 | 28.583 | 45.037 | 1.00 | 44.19 | B | C |
| ATOM | 1904 | O | VAL | B | 55 | −19.450 | 29.517 | 44.778 | 1.00 | 52.60 | B | O |
| ATOM | 1905 | N | ILE | B | 56 | −20.698 | 27.778 | 44.104 | 1.00 | 44.46 | B | N |
| ATOM | 1906 | CA | ILE | B | 56 | −20.324 | 27.934 | 42.704 | 1.00 | 45.81 | B | C |
| ATOM | 1907 | CB | ILE | B | 56 | −19.295 | 26.842 | 42.287 | 1.00 | 46.87 | B | C |
| ATOM | 1908 | CG1 | ILE | B | 56 | −17.892 | 27.376 | 42.446 | 1.00 | 52.08 | B | C |
| ATOM | 1909 | CD1 | ILE | B | 56 | −17.318 | 27.148 | 43.792 | 1.00 | 56.76 | B | C |
| ATOM | 1910 | CG2 | ILE | B | 56 | −19.398 | 26.458 | 40.836 | 1.00 | 45.77 | B | C |
| ATOM | 1911 | C | ILE | B | 56 | −21.570 | 27.873 | 41.858 | 1.00 | 47.28 | B | C |
| ATOM | 1912 | O | ILE | B | 56 | −22.489 | 27.083 | 42.141 | 1.00 | 49.61 | B | O |
| ATOM | 1913 | N | LEU | B | 57 | −21.611 | 28.720 | 40.832 | 1.00 | 43.17 | B | N |
| ATOM | 1914 | CA | LEU | B | 57 | −22.684 | 28.649 | 39.859 | 1.00 | 43.94 | B | C |
| ATOM | 1915 | CB | LEU | B | 57 | −23.326 | 30.017 | 39.659 | 1.00 | 44.30 | B | C |
| ATOM | 1916 | CG | LEU | B | 57 | −24.339 | 30.154 | 38.525 | 1.00 | 41.92 | B | C |
| ATOM | 1917 | CD1 | LEU | B | 57 | −25.656 | 29.469 | 38.866 | 1.00 | 42.10 | B | C |
| ATOM | 1918 | CD2 | LEU | B | 57 | −24.549 | 31.616 | 38.288 | 1.00 | 39.61 | B | C |
| ATOM | 1919 | C | LEU | B | 57 | −22.128 | 28.144 | 38.556 | 1.00 | 46.44 | B | C |
| ATOM | 1920 | O | LEU | B | 57 | −21.215 | 28.748 | 38.011 | 1.00 | 49.16 | B | O |
| ATOM | 1921 | N | HIS | B | 58 | −22.672 | 27.037 | 38.058 | 1.00 | 50.00 | B | N |
| ATOM | 1922 | CA | HIS | B | 58 | −22.206 | 26.468 | 36.797 | 1.00 | 52.04 | B | C |
| ATOM | 1923 | CB | HIS | B | 58 | −21.139 | 25.426 | 37.064 | 1.00 | 52.03 | B | C |
| ATOM | 1924 | CG | HIS | B | 58 | −20.771 | 24.625 | 35.859 | 1.00 | 54.05 | B | C |
| ATOM | 1925 | ND1 | HIS | B | 58 | −20.016 | 25.142 | 34.828 | 1.00 | 51.30 | B | N |
| ATOM | 1926 | CE1 | HIS | B | 58 | −19.848 | 24.205 | 33.909 | 1.00 | 55.00 | B | C |
| ATOM | 1927 | NE2 | HIS | B | 58 | −20.479 | 23.109 | 34.299 | 1.00 | 54.05 | B | N |
| ATOM | 1928 | CD2 | HIS | B | 58 | −21.055 | 23.341 | 35.522 | 1.00 | 53.13 | B | C |
| ATOM | 1929 | C | HIS | B | 58 | −23.331 | 25.874 | 35.954 | 1.00 | 53.48 | B | C |
| ATOM | 1930 | O | HIS | B | 58 | −24.150 | 25.116 | 36.460 | 1.00 | 55.42 | B | O |
| ATOM | 1931 | N | GLU | B | 59 | −23.359 | 26.224 | 34.670 | 1.00 | 55.38 | B | N |
| ATOM | 1932 | CA | GLU | B | 59 | −24.352 | 25.707 | 33.736 | 1.00 | 58.47 | B | C |
| ATOM | 1933 | CB | GLU | B | 59 | −23.874 | 24.385 | 33.133 | 1.00 | 63.90 | B | C |
| ATOM | 1934 | CG | GLU | B | 59 | −24.051 | 24.281 | 31.628 | 1.00 | 72.24 | B | C |
| ATOM | 1935 | CD | GLU | B | 59 | −22.992 | 25.055 | 30.864 | 1.00 | 81.17 | B | C |
| ATOM | 1936 | OE1 | GLU | B | 59 | −23.345 | 26.083 | 30.242 | 1.00 | 85.96 | B | O |
| ATOM | 1937 | OE2 | GLU | B | 59 | −21.805 | 24.643 | 30.885 | 1.00 | 84.29 | B | O |
| ATOM | 1938 | C | GLU | B | 59 | −25.729 | 25.534 | 34.382 | 1.00 | 59.86 | B | C |
| ATOM | 1939 | O | GLU | B | 59 | −26.275 | 24.427 | 34.430 | 1.00 | 61.83 | B | O |
| ATOM | 1940 | N | HIS | B | 60 | −26.275 | 26.635 | 34.893 | 1.00 | 59.00 | B | N |
| ATOM | 1941 | CA | HIS | B | 60 | −27.634 | 26.668 | 35.440 | 1.00 | 57.01 | B | C |
| ATOM | 1942 | CB | HIS | B | 60 | −28.653 | 26.383 | 34.333 | 1.00 | 58.99 | B | C |
| ATOM | 1943 | CG | HIS | B | 60 | −28.442 | 27.210 | 33.104 | 1.00 | 64.85 | B | C |
| ATOM | 1944 | ND1 | HIS | B | 60 | −28.149 | 28.556 | 33.155 | 1.00 | 67.98 | B | N |
| ATOM | 1945 | CE1 | HIS | B | 60 | −28.008 | 29.023 | 31.927 | 1.00 | 69.99 | B | C |
| ATOM | 1946 | NE2 | HIS | B | 60 | −28.192 | 28.025 | 31.080 | 1.00 | 71.81 | B | N |
| ATOM | 1947 | CD2 | HIS | B | 60 | −28.465 | 26.880 | 31.791 | 1.00 | 68.41 | B | C |
| ATOM | 1948 | C | HIS | B | 60 | −27.854 | 25.774 | 36.671 | 1.00 | 54.57 | B | C |
| ATOM | 1949 | O | HIS | B | 60 | −28.965 | 25.348 | 36.960 | 1.00 | 58.35 | B | O |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 1950 | N | HIS | B | 61 | −26.789 | 25.502 | 37.404 | 1.00 | 50.20 | B | N |
| ATOM | 1951 | CA | HIS | B | 61 | −26.920 | 24.835 | 38.682 | 1.00 | 48.51 | B | C |
| ATOM | 1952 | CB | HIS | B | 61 | −26.548 | 23.373 | 38.552 | 1.00 | 53.72 | B | C |
| ATOM | 1953 | CG | HIS | B | 61 | −27.395 | 22.614 | 37.579 | 1.00 | 60.35 | B | C |
| ATOM | 1954 | ND1 | HIS | B | 61 | −28.477 | 21.851 | 37.967 | 1.00 | 63.50 | B | N |
| ATOM | 1955 | CE1 | HIS | B | 61 | −29.019 | 21.284 | 36.904 | 1.00 | 63.17 | B | C |
| ATOM | 1956 | NE2 | HIS | B | 61 | −28.324 | 21.647 | 35.840 | 1.00 | 63.83 | B | N |
| ATOM | 1957 | CD2 | HIS | B | 61 | −27.301 | 22.476 | 36.235 | 1.00 | 62.28 | B | C |
| ATOM | 1958 | C | HIS | B | 61 | −26.055 | 25.520 | 39.738 | 1.00 | 48.02 | B | C |
| ATOM | 1959 | O | HIS | B | 61 | −25.152 | 26.297 | 39.424 | 1.00 | 49.98 | B | O |
| ATOM | 1960 | N | ILE | B | 62 | −26.345 | 25.240 | 40.998 | 1.00 | 43.61 | B | N |
| ATOM | 1961 | CA | ILE | B | 62 | −25.661 | 25.892 | 42.094 | 1.00 | 42.88 | B | C |
| ATOM | 1962 | CB | ILE | B | 62 | −26.681 | 26.718 | 42.903 | 1.00 | 43.14 | B | C |
| ATOM | 1963 | CG1 | ILE | B | 62 | −27.102 | 27.963 | 42.128 | 1.00 | 36.21 | B | C |
| ATOM | 1964 | CD1 | ILE | B | 62 | −27.829 | 28.928 | 42.974 | 1.00 | 32.13 | B | C |
| ATOM | 1965 | CG2 | ILE | B | 62 | −26.133 | 27.093 | 44.292 | 1.00 | 47.65 | B | C |
| ATOM | 1966 | C | ILE | B | 62 | −25.053 | 24.788 | 42.945 | 1.00 | 47.29 | B | C |
| ATOM | 1967 | O | ILE | B | 62 | −25.740 | 23.833 | 43.313 | 1.00 | 53.80 | B | O |
| ATOM | 1968 | N | PHE | B | 63 | −23.769 | 24.901 | 43.254 | 1.00 | 43.54 | B | N |
| ATOM | 1969 | CA | PHE | B | 63 | −23.103 | 23.841 | 43.979 | 1.00 | 41.13 | B | C |
| ATOM | 1970 | CB | PHE | B | 63 | −21.900 | 23.348 | 43.194 | 1.00 | 41.26 | B | C |
| ATOM | 1971 | CG | PHE | B | 63 | −22.238 | 22.800 | 41.832 | 1.00 | 44.61 | B | C |
| ATOM | 1972 | CD1 | PHE | B | 63 | −22.270 | 23.640 | 40.714 | 1.00 | 45.84 | B | C |
| ATOM | 1973 | CE1 | PHE | B | 63 | −22.579 | 23.128 | 39.455 | 1.00 | 46.17 | B | C |
| ATOM | 1974 | CZ | PHE | B | 63 | −22.852 | 21.745 | 39.310 | 1.00 | 46.42 | B | C |
| ATOM | 1975 | CE2 | PHE | B | 63 | −22.815 | 20.906 | 40.412 | 1.00 | 40.65 | B | C |
| ATOM | 1976 | CD2 | PHE | B | 63 | −22.510 | 21.434 | 41.660 | 1.00 | 43.43 | B | C |
| ATOM | 1977 | C | PHE | B | 63 | −22.659 | 24.375 | 45.313 | 1.00 | 45.66 | B | C |
| ATOM | 1978 | O | PHE | B | 63 | −21.739 | 25.196 | 45.389 | 1.00 | 52.04 | B | O |
| ATOM | 1979 | N | LEU | B | 64 | −23.323 | 23.935 | 46.373 | 1.00 | 42.46 | B | N |
| ATOM | 1980 | CA | LEU | B | 64 | −22.908 | 24.347 | 47.706 | 1.00 | 42.09 | B | C |
| ATOM | 1981 | CB | LEU | B | 64 | −24.114 | 24.440 | 48.636 | 1.00 | 41.69 | B | C |
| ATOM | 1982 | CG | LEU | B | 64 | −25.365 | 25.182 | 48.154 | 1.00 | 42.08 | B | C |
| ATOM | 1983 | CD1 | LEU | B | 64 | −26.591 | 24.571 | 48.787 | 1.00 | 44.25 | B | C |
| ATOM | 1984 | CD2 | LEU | B | 64 | −25.321 | 26.644 | 48.511 | 1.00 | 40.96 | B | C |
| ATOM | 1985 | C | LEU | B | 64 | −21.855 | 23.387 | 48.267 | 1.00 | 40.28 | B | C |
| ATOM | 1986 | O | LEU | B | 64 | −22.035 | 22.182 | 48.211 | 1.00 | 44.05 | B | O |
| ATOM | 1987 | N | GLY | B | 65 | −20.755 | 23.920 | 48.791 | 1.00 | 37.34 | B | N |
| ATOM | 1988 | CA | GLY | B | 65 | −19.732 | 23.101 | 49.422 | 1.00 | 37.17 | B | C |
| ATOM | 1989 | C | GLY | B | 65 | −19.905 | 23.231 | 50.914 | 1.00 | 42.05 | B | C |
| ATOM | 1990 | O | GLY | B | 65 | −19.662 | 24.296 | 51.471 | 1.00 | 47.10 | B | O |
| ATOM | 1991 | N | ALA | B | 66 | −20.342 | 22.157 | 51.561 | 1.00 | 44.53 | B | N |
| ATOM | 1992 | CA | ALA | B | 66 | −20.892 | 22.253 | 52.912 | 1.00 | 48.80 | B | C |
| ATOM | 1993 | CB | ALA | B | 66 | −22.389 | 21.972 | 52.888 | 1.00 | 48.72 | B | C |
| ATOM | 1994 | C | ALA | B | 66 | −20.203 | 21.287 | 53.836 | 1.00 | 53.33 | B | C |
| ATOM | 1995 | O | ALA | B | 66 | −19.468 | 20.412 | 53.364 | 1.00 | 58.02 | B | O |
| ATOM | 1996 | N | THR | B | 67 | −20.439 | 21.436 | 55.146 | 1.00 | 54.28 | B | N |
| ATOM | 1997 | CA | THR | B | 67 | −19.855 | 20.522 | 56.139 | 1.00 | 51.15 | B | C |
| ATOM | 1998 | CB | THR | B | 67 | −20.165 | 20.930 | 57.593 | 1.00 | 53.21 | B | C |
| ATOM | 1999 | OG1 | THR | B | 67 | −20.088 | 22.352 | 57.740 | 1.00 | 57.91 | B | O |
| ATOM | 2000 | CG2 | THR | B | 67 | −19.061 | 20.461 | 58.491 | 1.00 | 53.41 | B | C |
| ATOM | 2001 | C | THR | B | 67 | −20.329 | 19.103 | 55.866 | 1.00 | 47.02 | B | C |
| ATOM | 2002 | O | THR | B | 67 | −21.516 | 18.788 | 55.965 | 1.00 | 40.82 | B | O |
| ATOM | 2003 | N | ASN | B | 68 | −19.383 | 18.272 | 55.451 | 1.00 | 50.36 | B | N |
| ATOM | 2004 | CA | ASN | B | 68 | −19.649 | 16.877 | 55.108 | 1.00 | 52.51 | B | C |
| ATOM | 2005 | CB | ASN | B | 68 | −20.235 | 16.140 | 56.331 | 1.00 | 52.59 | B | C |
| ATOM | 2006 | CG | ASN | B | 68 | −19.210 | 15.965 | 57.461 | 1.00 | 51.03 | B | C |
| ATOM | 2007 | OD1 | ASN | B | 68 | −18.111 | 15.446 | 57.243 | 1.00 | 51.42 | B | O |
| ATOM | 2008 | ND2 | ASN | B | 68 | −19.563 | 16.406 | 58.662 | 1.00 | 45.80 | B | N |
| ATOM | 2009 | C | ASN | B | 68 | −20.488 | 16.686 | 53.819 | 1.00 | 50.64 | B | C |
| ATOM | 2010 | O | ASN | B | 68 | −20.866 | 15.565 | 53.458 | 1.00 | 44.48 | B | O |
| ATOM | 2011 | N | TYR | B | 69 | −20.738 | 17.778 | 53.101 | 1.00 | 52.92 | B | N |
| ATOM | 2012 | CA | TYR | B | 69 | −21.653 | 17.721 | 51.967 | 1.00 | 55.27 | B | C |
| ATOM | 2013 | CB | TYR | B | 69 | −23.085 | 18.021 | 52.436 | 1.00 | 60.82 | B | C |
| ATOM | 2014 | CG | TYR | B | 69 | −23.773 | 16.805 | 52.983 | 1.00 | 64.11 | B | C |
| ATOM | 2015 | CD1 | TYR | B | 69 | −23.769 | 16.542 | 54.351 | 1.00 | 66.02 | B | C |
| ATOM | 2016 | CE1 | TYR | B | 69 | −24.382 | 15.408 | 54.863 | 1.00 | 68.88 | B | C |
| ATOM | 2017 | CZ | TYR | B | 69 | −25.006 | 14.521 | 53.997 | 1.00 | 71.22 | B | C |
| ATOM | 2018 | OH | TYR | B | 69 | −25.616 | 13.398 | 54.506 | 1.00 | 75.18 | B | O |
| ATOM | 2019 | CE2 | TYR | B | 69 | −25.017 | 14.757 | 52.627 | 1.00 | 69.32 | B | C |
| ATOM | 2020 | CD2 | TYR | B | 69 | −24.397 | 15.895 | 52.130 | 1.00 | 66.33 | B | C |
| ATOM | 2021 | C | TYR | B | 69 | −21.306 | 18.619 | 50.793 | 1.00 | 51.42 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 2022 | O | TYR | B | 69 | −20.702 | 19.677 | 50.962 | 1.00 | 51.14 | B | O |
| ATOM | 2023 | N | ILE | B | 70 | −21.701 | 18.174 | 49.603 | 1.00 | 46.28 | B | N |
| ATOM | 2024 | CA | ILE | B | 70 | −21.839 | 19.058 | 48.451 | 1.00 | 43.86 | B | C |
| ATOM | 2025 | CB | ILE | B | 70 | −20.843 | 18.667 | 47.346 | 1.00 | 37.93 | B | C |
| ATOM | 2026 | CG1 | ILE | B | 70 | −19.444 | 19.128 | 47.717 | 1.00 | 32.94 | B | C |
| ATOM | 2027 | CD1 | ILE | B | 70 | −18.399 | 18.442 | 46.925 | 1.00 | 34.13 | B | C |
| ATOM | 2028 | CG2 | ILE | B | 70 | −21.259 | 19.241 | 45.989 | 1.00 | 35.59 | B | C |
| ATOM | 2029 | C | ILE | B | 70 | −23.277 | 18.950 | 47.948 | 1.00 | 47.16 | B | C |
| ATOM | 2030 | O | ILE | B | 70 | −23.763 | 17.838 | 47.730 | 1.00 | 53.11 | B | O |
| ATOM | 2031 | N | TYR | B | 71 | −23.961 | 20.086 | 47.794 | 1.00 | 46.45 | B | N |
| ATOM | 2032 | CA | TYR | B | 71 | −25.315 | 20.094 | 47.227 | 1.00 | 47.00 | B | C |
| ATOM | 2033 | CB | TYR | B | 71 | −26.296 | 20.874 | 48.101 | 1.00 | 45.72 | B | C |
| ATOM | 2034 | CG | TYR | B | 71 | −26.279 | 20.473 | 49.539 | 1.00 | 47.73 | B | C |
| ATOM | 2035 | CD1 | TYR | B | 71 | −26.054 | 21.415 | 50.527 | 1.00 | 50.65 | B | C |
| ATOM | 2036 | CE1 | TYR | B | 71 | −26.021 | 21.067 | 51.850 | 1.00 | 54.50 | B | C |
| ATOM | 2037 | CZ | TYR | B | 71 | −26.222 | 19.753 | 52.207 | 1.00 | 60.11 | B | C |
| ATOM | 2038 | OH | TYR | B | 71 | −26.193 | 19.402 | 53.541 | 1.00 | 67.11 | B | O |
| ATOM | 2039 | CE2 | TYR | B | 71 | −26.445 | 18.788 | 51.237 | 1.00 | 57.17 | B | C |
| ATOM | 2040 | CD2 | TYR | B | 71 | −26.476 | 19.157 | 49.912 | 1.00 | 50.73 | B | C |
| ATOM | 2041 | C | TYR | B | 71 | −25.382 | 20.653 | 45.820 | 1.00 | 48.72 | B | C |
| ATOM | 2042 | O | TYR | B | 71 | −24.512 | 21.401 | 45.377 | 1.00 | 53.16 | B | O |
| ATOM | 2043 | N | VAL | B | 72 | −26.445 | 20.289 | 45.124 | 1.00 | 47.30 | B | N |
| ATOM | 2044 | CA | VAL | B | 72 | −26.719 | 20.847 | 43.819 | 1.00 | 47.03 | B | C |
| ATOM | 2045 | CB | VAL | B | 72 | −26.503 | 19.814 | 42.696 | 1.00 | 48.79 | B | C |
| ATOM | 2046 | CG1 | VAL | B | 72 | −26.205 | 20.515 | 41.378 | 1.00 | 48.07 | B | C |
| ATOM | 2047 | CG2 | VAL | B | 72 | −25.368 | 18.860 | 43.059 | 1.00 | 49.23 | B | C |
| ATOM | 2048 | C | VAL | B | 72 | −28.145 | 21.372 | 43.824 | 1.00 | 44.93 | B | C |
| ATOM | 2049 | O | VAL | B | 72 | −29.085 | 20.627 | 44.081 | 1.00 | 46.42 | B | O |
| ATOM | 2050 | N | LEU | B | 73 | −28.288 | 22.667 | 43.571 | 1.00 | 42.05 | B | N |
| ATOM | 2051 | CA | LEU | B | 73 | −29.594 | 23.294 | 43.462 | 1.00 | 40.82 | B | C |
| ATOM | 2052 | CB | LEU | B | 73 | −29.690 | 24.478 | 44.406 | 1.00 | 39.41 | B | C |
| ATOM | 2053 | CG | LEU | B | 73 | −28.964 | 24.390 | 45.744 | 1.00 | 38.24 | B | C |
| ATOM | 2054 | CD1 | LEU | B | 73 | −29.253 | 25.650 | 46.544 | 1.00 | 34.92 | B | C |
| ATOM | 2055 | CD2 | LEU | B | 73 | −29.368 | 23.121 | 46.520 | 1.00 | 36.03 | B | C |
| ATOM | 2056 | C | LEU | B | 73 | −29.810 | 23.782 | 42.052 | 1.00 | 44.28 | B | C |
| ATOM | 2057 | O | LEU | B | 73 | −28.848 | 24.014 | 41.318 | 1.00 | 46.00 | B | O |
| ATOM | 2058 | N | ASN | B | 74 | −31.069 | 23.938 | 41.668 | 1.00 | 47.90 | B | N |
| ATOM | 2059 | CA | ASN | B | 74 | −31.384 | 24.522 | 40.374 | 1.00 | 58.54 | B | C |
| ATOM | 2060 | CB | ASN | B | 74 | −32.808 | 24.161 | 39.984 | 1.00 | 64.84 | B | C |
| ATOM | 2061 | CG | ASN | B | 74 | −32.852 | 23.164 | 38.865 | 1.00 | 72.43 | B | C |
| ATOM | 2062 | OD1 | ASN | B | 74 | −32.112 | 23.291 | 37.881 | 1.00 | 76.53 | B | O |
| ATOM | 2063 | ND2 | ASN | B | 74 | −33.711 | 22.152 | 39.000 | 1.00 | 73.79 | B | N |
| ATOM | 2064 | C | ASN | B | 74 | −31.226 | 26.037 | 40.393 | 1.00 | 62.21 | B | C |
| ATOM | 2065 | O | ASN | B | 74 | −31.793 | 26.691 | 41.265 | 1.00 | 66.91 | B | O |
| ATOM | 2066 | N | GLU | B | 75 | −30.472 | 26.603 | 39.448 | 1.00 | 61.46 | B | N |
| ATOM | 2067 | CA | GLU | B | 75 | −30.289 | 28.065 | 39.404 | 1.00 | 61.67 | B | C |
| ATOM | 2068 | CB | GLU | B | 75 | −29.537 | 28.526 | 38.146 | 1.00 | 60.79 | B | C |
| ATOM | 2069 | CG | GLU | B | 75 | −29.614 | 30.042 | 37.927 | 1.00 | 62.00 | B | C |
| ATOM | 2070 | CD | GLU | B | 75 | −29.076 | 30.516 | 36.586 | 1.00 | 64.68 | B | C |
| ATOM | 2071 | OE1 | GLU | B | 75 | −29.298 | 29.813 | 35.571 | 1.00 | 69.00 | B | O |
| ATOM | 2072 | OE2 | GLU | B | 75 | −28.441 | 31.601 | 36.542 | 1.00 | 60.03 | B | O |
| ATOM | 2073 | C | GLU | B | 75 | −31.621 | 28.817 | 39.490 | 1.00 | 62.54 | B | C |
| ATOM | 2074 | O | GLU | B | 75 | −31.722 | 29.860 | 40.144 | 1.00 | 58.12 | B | O |
| ATOM | 2075 | N | GLU | B | 76 | −32.638 | 28.268 | 38.831 | 1.00 | 66.63 | B | N |
| ATOM | 2076 | CA | GLU | B | 76 | −33.910 | 28.962 | 38.676 | 1.00 | 66.67 | B | C |
| ATOM | 2077 | CB | GLU | B | 76 | −34.747 | 28.336 | 37.562 | 1.00 | 72.43 | B | C |
| ATOM | 2078 | CG | GLU | B | 76 | −35.688 | 29.317 | 36.888 | 1.00 | 75.56 | B | C |
| ATOM | 2079 | CD | GLU | B | 76 | −37.076 | 29.248 | 37.482 | 1.00 | 80.75 | B | C |
| ATOM | 2080 | OE1 | GLU | B | 76 | −37.390 | 28.214 | 38.116 | 1.00 | 82.06 | B | O |
| ATOM | 2081 | OE2 | GLU | B | 76 | −37.850 | 30.222 | 37.324 | 1.00 | 83.79 | B | O |
| ATOM | 2082 | C | GLU | B | 76 | −34.711 | 29.097 | 39.965 | 1.00 | 60.03 | B | C |
| ATOM | 2083 | O | GLU | B | 76 | −35.141 | 30.191 | 40.282 | 1.00 | 59.16 | B | O |
| ATOM | 2084 | N | ASP | B | 77 | −34.892 | 28.018 | 40.718 | 1.00 | 55.97 | B | N |
| ATOM | 2085 | CA | ASP | B | 77 | −35.711 | 28.109 | 41.925 | 1.00 | 56.24 | B | C |
| ATOM | 2086 | CB | ASP | B | 77 | −37.060 | 27.418 | 41.706 | 1.00 | 61.87 | B | C |
| ATOM | 2087 | CG | ASP | B | 77 | −36.977 | 25.912 | 41.842 | 1.00 | 67.33 | B | C |
| ATOM | 2088 | OD1 | ASP | B | 77 | −37.984 | 25.237 | 41.533 | 1.00 | 68.78 | B | O |
| ATOM | 2089 | OD2 | ASP | B | 77 | −35.953 | 25.316 | 42.248 | 1.00 | 69.35 | B | O |
| ATOM | 2090 | C | ASP | B | 77 | −35.058 | 27.642 | 43.231 | 1.00 | 54.59 | B | C |
| ATOM | 2091 | O | ASP | B | 77 | −35.696 | 27.645 | 44.279 | 1.00 | 54.85 | B | O |
| ATOM | 2092 | N | LEU | B | 78 | −33.797 | 27.232 | 43.157 | 1.00 | 55.56 | B | N |
| ATOM | 2093 | CA | LEU | B | 78 | −33.003 | 26.833 | 44.337 | 1.00 | 58.90 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 2094 | CB | LEU | B | 78 | −32.897 | 27.974 | 45.376 | 1.00 | 53.06 | B | C |
| ATOM | 2095 | CG | LEU | B | 78 | −32.152 | 29.307 | 45.162 | 1.00 | 47.82 | B | C |
| ATOM | 2096 | CD1 | LEU | B | 78 | −31.018 | 29.485 | 46.171 | 1.00 | 44.03 | B | C |
| ATOM | 2097 | CD2 | LEU | B | 78 | −31.640 | 29.540 | 43.741 | 1.00 | 46.46 | B | C |
| ATOM | 2098 | C | LEU | B | 78 | −33.450 | 25.516 | 45.012 | 1.00 | 65.07 | B | C |
| ATOM | 2099 | O | LEU | B | 78 | −33.004 | 25.197 | 46.123 | 1.00 | 66.17 | B | O |
| ATOM | 2100 | N | GLN | B | 79 | −34.319 | 24.760 | 44.339 | 1.00 | 67.54 | B | N |
| ATOM | 2101 | CA | GLN | B | 79 | −34.654 | 23.397 | 44.756 | 1.00 | 69.76 | B | C |
| ATOM | 2102 | CB | GLN | B | 79 | −35.741 | 22.814 | 43.850 | 1.00 | 76.35 | B | C |
| ATOM | 2103 | CG | GLN | B | 79 | −36.637 | 21.762 | 44.505 | 1.00 | 80.54 | B | C |
| ATOM | 2104 | CD | GLN | B | 79 | −38.004 | 22.319 | 44.866 | 1.00 | 82.06 | B | C |
| ATOM | 2105 | OE1 | GLN | B | 79 | −38.692 | 22.886 | 44.014 | 1.00 | 82.50 | B | O |
| ATOM | 2106 | NE2 | GLN | B | 79 | −38.394 | 22.170 | 46.128 | 1.00 | 82.37 | B | N |
| ATOM | 2107 | C | GLN | B | 79 | −33.427 | 22.499 | 44.674 | 1.00 | 65.91 | B | C |
| ATOM | 2108 | O | GLN | B | 79 | −32.692 | 22.539 | 43.679 | 1.00 | 65.87 | B | O |
| ATOM | 2109 | N | LYS | B | 80 | −33.214 | 21.695 | 45.717 | 1.00 | 62.42 | B | N |
| ATOM | 2110 | CA | LYS | B | 80 | −32.112 | 20.727 | 45.745 | 1.00 | 58.13 | B | C |
| ATOM | 2111 | CB | LYS | B | 80 | −31.918 | 20.140 | 47.155 | 1.00 | 54.23 | B | C |
| ATOM | 2112 | CG | LYS | B | 80 | −30.826 | 19.091 | 47.281 | 1.00 | 52.77 | B | C |
| ATOM | 2113 | CD | LYS | B | 80 | −31.018 | 18.220 | 48.518 | 1.00 | 55.97 | B | C |
| ATOM | 2114 | CE | LYS | B | 80 | −31.433 | 16.786 | 48.144 | 1.00 | 58.79 | B | C |
| ATOM | 2115 | NZ | LYS | B | 80 | −32.514 | 16.211 | 49.026 | 1.00 | 58.94 | B | N |
| ATOM | 2116 | C | LYS | B | 80 | −32.406 | 19.636 | 44.730 | 1.00 | 56.61 | B | C |
| ATOM | 2117 | O | LYS | B | 80 | −33.469 | 19.024 | 44.760 | 1.00 | 58.06 | B | O |
| ATOM | 2118 | N | VAL | B | 81 | −31.475 | 19.425 | 43.811 | 1.00 | 55.86 | B | N |
| ATOM | 2119 | CA | VAL | B | 81 | −31.624 | 18.392 | 42.805 | 1.00 | 57.02 | B | C |
| ATOM | 2120 | CB | VAL | B | 81 | −31.165 | 18.874 | 41.411 | 1.00 | 57.57 | B | C |
| ATOM | 2121 | CG1 | VAL | B | 81 | −31.286 | 17.752 | 40.378 | 1.00 | 59.42 | B | C |
| ATOM | 2122 | CG2 | VAL | B | 81 | −31.984 | 20.061 | 40.974 | 1.00 | 57.61 | B | C |
| ATOM | 2123 | C | VAL | B | 81 | −30.836 | 17.164 | 43.232 | 1.00 | 58.29 | B | C |
| ATOM | 2124 | O | VAL | B | 81 | −31.331 | 16.044 | 43.138 | 1.00 | 59.22 | B | O |
| ATOM | 2125 | N | ALA | B | 82 | −29.616 | 17.380 | 43.714 | 1.00 | 59.89 | B | N |
| ATOM | 2126 | CA | ALA | B | 82 | −28.717 | 16.274 | 44.032 | 1.00 | 62.94 | B | C |
| ATOM | 2127 | CB | ALA | B | 82 | −27.822 | 15.975 | 42.837 | 1.00 | 63.74 | B | C |
| ATOM | 2128 | C | ALA | B | 82 | −27.864 | 16.550 | 45.261 | 1.00 | 63.09 | B | C |
| ATOM | 2129 | O | ALA | B | 82 | −27.544 | 17.704 | 45.552 | 1.00 | 64.92 | B | O |
| ATOM | 2130 | N | GLU | B | 83 | −27.503 | 15.492 | 45.984 | 1.00 | 60.73 | B | N |
| ATOM | 2131 | CA | GLU | B | 83 | −26.475 | 15.612 | 47.009 | 1.00 | 62.28 | B | C |
| ATOM | 2132 | CB | GLU | B | 83 | −27.023 | 15.376 | 48.419 | 1.00 | 68.08 | B | C |
| ATOM | 2133 | CG | GLU | B | 83 | −27.855 | 14.121 | 48.610 | 1.00 | 76.60 | B | C |
| ATOM | 2134 | CD | GLU | B | 83 | −29.189 | 14.422 | 49.274 | 1.00 | 83.85 | B | C |
| ATOM | 2135 | OE1 | GLU | B | 83 | −29.224 | 15.283 | 50.188 | 1.00 | 84.72 | B | O |
| ATOM | 2136 | OE2 | GLU | B | 83 | −30.211 | 13.809 | 48.878 | 1.00 | 87.29 | B | O |
| ATOM | 2137 | C | GLU | B | 83 | −25.299 | 14.691 | 46.742 | 1.00 | 62.10 | B | C |
| ATOM | 2138 | O | GLU | B | 83 | −25.396 | 13.727 | 45.980 | 1.00 | 67.85 | B | O |
| ATOM | 2139 | N | TYR | B | 84 | −24.171 | 15.015 | 47.349 | 1.00 | 56.36 | B | N |
| ATOM | 2140 | CA | TYR | B | 84 | −23.093 | 14.063 | 47.448 | 1.00 | 54.60 | B | C |
| ATOM | 2141 | CB | TYR | B | 84 | −22.068 | 14.297 | 46.377 | 1.00 | 50.63 | B | C |
| ATOM | 2142 | CG | TYR | B | 84 | −20.818 | 13.464 | 46.515 | 1.00 | 49.86 | B | C |
| ATOM | 2143 | CD1 | TYR | B | 84 | −20.534 | 12.463 | 45.590 | 1.00 | 50.46 | B | C |
| ATOM | 2144 | CE1 | TYR | B | 84 | −19.367 | 11.713 | 45.684 | 1.00 | 53.44 | B | C |
| ATOM | 2145 | CZ | TYR | B | 84 | −18.463 | 11.965 | 46.716 | 1.00 | 51.46 | B | C |
| ATOM | 2146 | OH | TYR | B | 84 | −17.315 | 11.206 | 46.799 | 1.00 | 48.79 | B | O |
| ATOM | 2147 | CE2 | TYR | B | 84 | −18.723 | 12.965 | 47.649 | 1.00 | 48.70 | B | C |
| ATOM | 2148 | CD2 | TYR | B | 84 | −19.892 | 13.708 | 47.540 | 1.00 | 47.48 | B | C |
| ATOM | 2149 | C | TYR | B | 84 | −22.479 | 14.221 | 48.808 | 1.00 | 58.89 | B | C |
| ATOM | 2150 | O | TYR | B | 84 | −22.178 | 15.343 | 49.243 | 1.00 | 61.06 | B | O |
| ATOM | 2151 | N | LYS | B | 85 | −22.298 | 13.081 | 49.465 | 1.00 | 57.68 | B | N |
| ATOM | 2152 | CA | LYS | B | 85 | −21.894 | 13.027 | 50.851 | 1.00 | 60.94 | B | C |
| ATOM | 2153 | CB | LYS | B | 85 | −22.559 | 11.835 | 51.556 | 1.00 | 73.10 | B | C |
| ATOM | 2154 | CG | LYS | B | 85 | −23.450 | 10.931 | 50.661 | 1.00 | 84.97 | B | C |
| ATOM | 2155 | CD | LYS | B | 85 | −22.697 | 10.288 | 49.455 | 1.00 | 90.64 | B | C |
| ATOM | 2156 | CE | LYS | B | 85 | −23.613 | 9.395 | 48.601 | 1.00 | 93.15 | B | C |
| ATOM | 2157 | NZ | LYS | B | 85 | −24.897 | 10.052 | 48.177 | 1.00 | 94.06 | B | N |
| ATOM | 2158 | C | LYS | B | 85 | −20.391 | 12.897 | 50.924 | 1.00 | 59.56 | B | C |
| ATOM | 2159 | O | LYS | B | 85 | −19.839 | 11.833 | 50.633 | 1.00 | 61.16 | B | O |
| ATOM | 2160 | N | THR | B | 86 | −19.730 | 13.994 | 51.289 | 1.00 | 58.76 | B | N |
| ATOM | 2161 | CA | THR | B | 86 | −18.303 | 13.977 | 51.629 | 1.00 | 54.81 | B | C |
| ATOM | 2162 | CB | THR | B | 86 | −17.622 | 15.350 | 51.401 | 1.00 | 52.10 | B | C |
| ATOM | 2163 | OG1 | THR | B | 86 | −17.486 | 16.049 | 52.649 | 1.00 | 49.16 | B | O |
| ATOM | 2164 | CG2 | THR | B | 86 | −18.502 | 16.278 | 50.574 | 1.00 | 53.02 | B | C |
| ATOM | 2165 | C | THR | B | 86 | −18.217 | 13.605 | 53.089 | 1.00 | 55.10 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 2166 | O | THR | B | 86 | −17.123 | 13.520 | 53.637 | 1.00 | 53.13 | B | O |
| ATOM | 2167 | N | GLY | B | 87 | −19.405 | 13.451 | 53.690 | 1.00 | 57.63 | B | N |
| ATOM | 2168 | CA | GLY | B | 87 | −19.688 | 12.920 | 55.024 | 1.00 | 58.47 | B | C |
| ATOM | 2169 | C | GLY | B | 87 | −18.574 | 12.647 | 56.016 | 1.00 | 58.99 | B | C |
| ATOM | 2170 | O | GLY | B | 87 | −17.429 | 12.406 | 55.627 | 1.00 | 66.01 | B | O |
| ATOM | 2171 | N | PRO | B | 88 | −18.912 | 12.634 | 57.303 | 1.00 | 51.01 | B | N |
| ATOM | 2172 | CA | PRO | B | 88 | −17.918 | 12.481 | 58.367 | 1.00 | 45.55 | B | C |
| ATOM | 2173 | CB | PRO | B | 88 | −18.756 | 11.997 | 59.527 | 1.00 | 47.72 | B | C |
| ATOM | 2174 | CG | PRO | B | 88 | −20.084 | 11.695 | 58.912 | 1.00 | 50.77 | B | C |
| ATOM | 2175 | CD | PRO | B | 88 | −20.273 | 12.703 | 57.841 | 1.00 | 48.75 | B | C |
| ATOM | 2176 | C | PRO | B | 88 | −16.898 | 11.426 | 57.981 | 1.00 | 44.01 | B | C |
| ATOM | 2177 | O | PRO | B | 88 | −17.287 | 10.397 | 57.432 | 1.00 | 40.96 | B | O |
| ATOM | 2178 | N | VAL | B | 89 | −15.622 | 11.696 | 58.249 | 1.00 | 47.96 | B | N |
| ATOM | 2179 | CA | VAL | B | 89 | −14.507 | 10.857 | 57.790 | 1.00 | 54.42 | B | C |
| ATOM | 2180 | CB | VAL | B | 89 | −13.786 | 11.555 | 56.641 | 1.00 | 51.16 | B | C |
| ATOM | 2181 | CG1 | VAL | B | 89 | −12.286 | 11.281 | 56.664 | 1.00 | 49.32 | B | C |
| ATOM | 2182 | CG2 | VAL | B | 89 | −14.409 | 11.150 | 55.323 | 1.00 | 53.87 | B | C |
| ATOM | 2183 | C | VAL | B | 89 | −13.506 | 10.542 | 58.913 | 1.00 | 63.96 | B | C |
| ATOM | 2184 | O | VAL | B | 89 | −13.316 | 11.368 | 59.808 | 1.00 | 69.59 | B | O |
| ATOM | 2185 | N | LEU | B | 90 | −12.855 | 9.372 | 58.854 | 1.00 | 66.84 | B | N |
| ATOM | 2186 | CA | LEU | B | 90 | −11.980 | 8.900 | 59.943 | 1.00 | 70.30 | B | C |
| ATOM | 2187 | CB | LEU | B | 90 | −12.246 | 7.420 | 60.203 | 1.00 | 72.52 | B | C |
| ATOM | 2188 | CG | LEU | B | 90 | −11.263 | 6.685 | 61.110 | 1.00 | 73.28 | B | C |
| ATOM | 2189 | CD1 | LEU | B | 90 | −11.986 | 6.110 | 62.309 | 1.00 | 72.75 | B | C |
| ATOM | 2190 | CD2 | LEU | B | 90 | −10.545 | 5.599 | 60.320 | 1.00 | 74.60 | B | C |
| ATOM | 2191 | C | LEU | B | 90 | −10.459 | 9.144 | 59.791 | 1.00 | 73.50 | B | C |
| ATOM | 2192 | O | LEU | B | 90 | −9.820 | 8.635 | 58.858 | 1.00 | 72.88 | B | O |
| ATOM | 2193 | N | GLU | B | 91 | −9.892 | 9.905 | 60.734 | 1.00 | 77.68 | B | N |
| ATOM | 2194 | CA | GLU | B | 91 | −8.464 | 10.260 | 60.730 | 1.00 | 83.04 | B | C |
| ATOM | 2195 | CB | GLU | B | 91 | −8.196 | 11.607 | 61.431 | 1.00 | 83.67 | B | C |
| ATOM | 2196 | CG | GLU | B | 91 | −9.029 | 12.788 | 60.952 | 1.00 | 87.14 | B | C |
| ATOM | 2197 | CD | GLU | B | 91 | −8.398 | 13.569 | 59.802 | 1.00 | 90.79 | B | C |
| ATOM | 2198 | OE1 | GLU | B | 91 | −7.634 | 12.980 | 59.000 | 1.00 | 91.75 | B | O |
| ATOM | 2199 | OE2 | GLU | B | 91 | −8.683 | 14.786 | 59.690 | 1.00 | 91.43 | B | O |
| ATOM | 2200 | C | GLU | B | 91 | −7.622 | 9.184 | 61.398 | 1.00 | 85.64 | B | C |
| ATOM | 2201 | O | GLU | B | 91 | −8.017 | 8.612 | 62.414 | 1.00 | 83.23 | B | O |
| ATOM | 2202 | N | HIS | B | 92 | −6.447 | 8.934 | 60.831 | 1.00 | 90.71 | B | N |
| ATOM | 2203 | CA | HIS | B | 92 | −5.544 | 7.910 | 61.347 | 1.00 | 93.48 | B | C |
| ATOM | 2204 | CB | HIS | B | 92 | −6.044 | 6.525 | 60.945 | 1.00 | 93.96 | B | C |
| ATOM | 2205 | CG | HIS | B | 92 | −5.654 | 5.448 | 61.902 | 1.00 | 95.14 | B | C |
| ATOM | 2206 | ND1 | HIS | B | 92 | −4.667 | 4.530 | 61.624 | 1.00 | 95.64 | B | N |
| ATOM | 2207 | CE1 | HIS | B | 92 | −4.531 | 3.709 | 62.649 | 1.00 | 95.43 | B | C |
| ATOM | 2208 | NE2 | HIS | B | 92 | −5.392 | 4.066 | 63.584 | 1.00 | 96.05 | B | N |
| ATOM | 2209 | CD2 | HIS | B | 92 | −6.106 | 5.152 | 63.143 | 1.00 | 95.04 | B | C |
| ATOM | 2210 | C | HIS | B | 92 | −4.102 | 8.100 | 60.865 | 1.00 | 94.62 | B | C |
| ATOM | 2211 | O | HIS | B | 92 | −3.879 | 8.569 | 59.742 | 1.00 | 96.12 | B | O |
| ATOM | 2212 | N | PRO | B | 93 | −3.125 | 7.753 | 61.710 | 1.00 | 93.29 | B | N |
| ATOM | 2213 | CA | PRO | B | 93 | −1.720 | 7.761 | 61.287 | 1.00 | 92.34 | B | C |
| ATOM | 2214 | CB | PRO | B | 93 | −0.966 | 7.348 | 62.558 | 1.00 | 91.96 | B | C |
| ATOM | 2215 | CG | PRO | B | 93 | −1.913 | 7.623 | 63.683 | 1.00 | 91.22 | B | C |
| ATOM | 2216 | CD | PRO | B | 93 | −3.270 | 7.355 | 63.216 | 1.00 | 91.62 | B | C |
| ATOM | 2217 | C | PRO | B | 93 | −1.503 | 6.732 | 60.185 | 1.00 | 91.87 | B | C |
| ATOM | 2218 | O | PRO | B | 93 | −0.830 | 7.029 | 59.194 | 1.00 | 89.55 | B | O |
| ATOM | 2219 | N | ASP | B | 94 | −2.096 | 5.552 | 60.367 | 1.00 | 93.42 | B | N |
| ATOM | 2220 | CA | ASP | B | 94 | −1.970 | 4.434 | 59.436 | 1.00 | 95.65 | B | C |
| ATOM | 2221 | CB | ASP | B | 94 | −2.314 | 3.099 | 60.124 | 1.00 | 95.17 | B | C |
| ATOM | 2222 | CG | ASP | B | 94 | −1.314 | 2.705 | 61.219 | 1.00 | 94.05 | B | C |
| ATOM | 2223 | OD1 | ASP | B | 94 | −0.971 | 3.553 | 62.073 | 1.00 | 93.69 | B | O |
| ATOM | 2224 | OD2 | ASP | B | 94 | −0.832 | 1.555 | 61.312 | 1.00 | 92.70 | B | O |
| ATOM | 2225 | C | ASP | B | 94 | −2.840 | 4.620 | 58.190 | 1.00 | 97.92 | B | C |
| ATOM | 2226 | O | ASP | B | 94 | −2.438 | 4.222 | 57.091 | 1.00 | 98.07 | B | O |
| ATOM | 2227 | N | CYS | B | 95 | −4.021 | 5.217 | 58.353 | 1.00 | 100.21 | B | N |
| ATOM | 2228 | CA | CYS | B | 95 | −4.911 | 5.449 | 57.210 | 1.00 | 103.84 | B | C |
| ATOM | 2229 | CB | CYS | B | 95 | −6.373 | 5.586 | 57.641 | 1.00 | 104.67 | B | C |
| ATOM | 2230 | SG | CYS | B | 95 | −7.538 | 5.098 | 56.347 | 1.00 | 106.67 | B | S |
| ATOM | 2231 | C | CYS | B | 95 | −4.472 | 6.639 | 56.354 | 1.00 | 105.37 | B | C |
| ATOM | 2232 | O | CYS | B | 95 | −4.582 | 7.798 | 56.769 | 1.00 | 104.25 | B | O |
| ATOM | 2233 | N | PHE | B | 96 | −3.988 | 6.332 | 55.152 | 1.00 | 108.74 | B | N |
| ATOM | 2234 | CA | PHE | B | 96 | −3.347 | 7.320 | 54.279 | 1.00 | 111.75 | B | C |
| ATOM | 2235 | CB | PHE | B | 96 | −2.229 | 6.655 | 53.453 | 1.00 | 116.20 | B | C |
| ATOM | 2236 | CG | PHE | B | 96 | −0.862 | 6.684 | 54.124 | 1.00 | 120.68 | B | C |
| ATOM | 2237 | CD1 | PHE | B | 96 | 0.300 | 6.806 | 53.359 | 1.00 | 123.52 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 2238 | CE1 | PHE | B | 96 | 1.566 | 6.828 | 53.970 | 1.00 | 124.46 | B | C |
| ATOM | 2239 | CZ | PHE | B | 96 | 1.673 | 6.727 | 55.360 | 1.00 | 122.54 | B | C |
| ATOM | 2240 | CE2 | PHE | B | 96 | 0.524 | 6.601 | 56.132 | 1.00 | 120.99 | B | C |
| ATOM | 2241 | CD2 | PHE | B | 96 | −0.734 | 6.577 | 55.514 | 1.00 | 120.92 | B | C |
| ATOM | 2242 | C | PHE | B | 96 | −4.353 | 8.137 | 53.420 | 1.00 | 109.63 | B | C |
| ATOM | 2243 | O | PHE | B | 96 | −5.543 | 7.804 | 53.372 | 1.00 | 110.42 | B | O |
| ATOM | 2244 | N | PRO | B | 97 | −3.878 | 9.193 | 52.752 | 1.00 | 104.75 | B | N |
| ATOM | 2245 | CA | PRO | B | 97 | −4.741 | 10.310 | 52.366 | 1.00 | 100.12 | B | C |
| ATOM | 2246 | CB | PRO | B | 97 | −3.738 | 11.441 | 52.102 | 1.00 | 101.09 | B | C |
| ATOM | 2247 | CG | PRO | B | 97 | −2.433 | 10.910 | 52.577 | 1.00 | 103.80 | B | C |
| ATOM | 2248 | CD | PRO | B | 97 | −2.493 | 9.440 | 52.323 | 1.00 | 104.87 | B | C |
| ATOM | 2249 | C | PRO | B | 97 | −5.700 | 10.152 | 51.179 | 1.00 | 96.19 | B | C |
| ATOM | 2250 | O | PRO | B | 97 | −6.636 | 10.957 | 51.112 | 1.00 | 100.40 | B | O |
| ATOM | 2251 | N | CYS | B | 98 | −5.520 | 9.208 | 50.266 | 1.00 | 87.61 | B | N |
| ATOM | 2252 | CA | CYS | B | 98 | −6.560 | 9.081 | 49.241 | 1.00 | 84.10 | B | C |
| ATOM | 2253 | CB | CYS | B | 98 | −6.045 | 9.392 | 47.830 | 1.00 | 80.73 | B | C |
| ATOM | 2254 | SG | CYS | B | 98 | −6.621 | 10.975 | 47.108 | 1.00 | 71.77 | B | S |
| ATOM | 2255 | C | CYS | B | 98 | −7.287 | 7.753 | 49.302 | 1.00 | 87.62 | B | C |
| ATOM | 2256 | O | CYS | B | 98 | −8.265 | 7.540 | 48.576 | 1.00 | 85.32 | B | O |
| ATOM | 2257 | N | GLN | B | 99 | −6.812 | 6.876 | 50.187 | 1.00 | 95.06 | B | N |
| ATOM | 2258 | CA | GLN | B | 99 | −7.485 | 5.607 | 50.489 | 1.00 | 99.82 | B | C |
| ATOM | 2259 | CB | GLN | B | 99 | −6.482 | 4.452 | 50.640 | 1.00 | 101.05 | B | C |
| ATOM | 2260 | CG | GLN | B | 99 | −5.259 | 4.753 | 51.502 | 1.00 | 103.61 | B | C |
| ATOM | 2261 | CD | GLN | B | 99 | −4.905 | 3.601 | 52.425 | 1.00 | 105.79 | B | C |
| ATOM | 2262 | OE1 | GLN | B | 99 | −5.161 | 3.659 | 53.631 | 1.00 | 104.51 | B | O |
| ATOM | 2263 | NE2 | GLN | B | 99 | −4.322 | 2.546 | 51.860 | 1.00 | 107.30 | B | N |
| ATOM | 2264 | C | GLN | B | 99 | −8.364 | 5.743 | 51.730 | 1.00 | 101.30 | B | C |
| ATOM | 2265 | O | GLN | B | 99 | −7.971 | 6.381 | 52.711 | 1.00 | 97.88 | B | O |
| ATOM | 2266 | N | ASP | B | 100 | −9.560 | 5.158 | 51.669 | 1.00 | 107.39 | B | N |
| ATOM | 2267 | CA | ASP | B | 100 | −10.548 | 5.309 | 52.745 | 1.00 | 114.11 | B | C |
| ATOM | 2268 | CB | ASP | B | 100 | −11.900 | 5.864 | 52.210 | 1.00 | 121.61 | B | C |
| ATOM | 2269 | CG | ASP | B | 100 | −12.948 | 4.773 | 51.925 | 1.00 | 126.01 | B | C |
| ATOM | 2270 | OD1 | ASP | B | 100 | −13.378 | 4.662 | 50.752 | 1.00 | 127.43 | B | O |
| ATOM | 2271 | OD2 | ASP | B | 100 | −13.428 | 4.013 | 52.803 | 1.00 | 126.52 | B | O |
| ATOM | 2272 | C | ASP | B | 100 | −10.695 | 4.054 | 53.609 | 1.00 | 110.78 | B | C |
| ATOM | 2273 | O | ASP | B | 100 | −10.300 | 2.963 | 53.201 | 1.00 | 110.09 | B | O |
| ATOM | 2274 | N | CYS | B | 101 | −11.256 | 4.214 | 54.804 | 1.00 | 109.34 | B | N |
| ATOM | 2275 | CA | CYS | B | 101 | −11.262 | 3.124 | 55.771 | 1.00 | 110.92 | B | C |
| ATOM | 2276 | CB | CYS | B | 101 | −9.951 | 3.117 | 56.568 | 1.00 | 109.38 | B | C |
| ATOM | 2277 | SG | CYS | B | 101 | −9.389 | 4.750 | 57.104 | 1.00 | 107.17 | B | S |
| ATOM | 2278 | C | CYS | B | 101 | −12.452 | 3.054 | 56.735 | 1.00 | 113.41 | B | C |
| ATOM | 2279 | O | CYS | B | 101 | −12.663 | 3.945 | 57.567 | 1.00 | 111.59 | B | O |
| ATOM | 2280 | N | SER | B | 102 | −13.234 | 1.987 | 56.579 | 1.00 | 116.32 | B | N |
| ATOM | 2281 | CA | SER | B | 102 | −13.985 | 1.389 | 57.683 | 1.00 | 116.98 | B | C |
| ATOM | 2282 | CB | SER | B | 102 | −15.427 | 1.033 | 57.284 | 1.00 | 119.06 | B | C |
| ATOM | 2283 | OG | SER | B | 102 | −15.554 | 0.767 | 55.894 | 1.00 | 121.46 | B | O |
| ATOM | 2284 | C | SER | B | 102 | −13.181 | 0.145 | 58.076 | 1.00 | 114.30 | B | C |
| ATOM | 2285 | O | SER | B | 102 | −13.592 | −0.653 | 58.925 | 1.00 | 112.54 | B | O |
| ATOM | 2286 | N | SER | B | 103 | −12.020 | 0.015 | 57.429 | 1.00 | 112.80 | B | N |
| ATOM | 2287 | CA | SER | B | 103 | −11.023 | −1.010 | 57.723 | 1.00 | 112.40 | B | C |
| ATOM | 2288 | CB | SER | B | 103 | −10.246 | −1.382 | 56.446 | 1.00 | 113.52 | B | C |
| ATOM | 2289 | OG | SER | B | 103 | −8.915 | −0.889 | 56.457 | 1.00 | 113.78 | B | O |
| ATOM | 2290 | C | SER | B | 103 | −10.080 | −0.556 | 58.847 | 1.00 | 110.28 | B | C |
| ATOM | 2291 | O | SER | B | 103 | −8.990 | −1.112 | 59.025 | 1.00 | 110.84 | B | O |
| ATOM | 2292 | N | LYS | B | 104 | −10.510 | 0.469 | 59.583 | 1.00 | 107.08 | B | N |
| ATOM | 2293 | CA | LYS | B | 104 | −9.869 | 0.886 | 60.832 | 1.00 | 104.77 | B | C |
| ATOM | 2294 | CB | LYS | B | 104 | −8.674 | 1.814 | 60.569 | 1.00 | 102.55 | B | C |
| ATOM | 2295 | CG | LYS | B | 104 | −7.350 | 1.277 | 61.118 | 1.00 | 102.04 | B | C |
| ATOM | 2296 | CD | LYS | B | 104 | −7.255 | 1.436 | 62.647 | 1.00 | 102.16 | B | C |
| ATOM | 2297 | CE | LYS | B | 104 | −7.226 | 0.095 | 63.414 | 1.00 | 97.37 | B | C |
| ATOM | 2298 | NZ | LYS | B | 104 | −7.273 | 0.328 | 64.885 | 1.00 | 90.84 | B | N |
| ATOM | 2299 | C | LYS | B | 104 | −10.873 | 1.536 | 61.796 | 1.00 | 103.99 | B | C |
| ATOM | 2300 | O | LYS | B | 104 | −10.492 | 2.078 | 62.840 | 1.00 | 102.61 | B | O |
| ATOM | 2301 | N | ALA | B | 105 | −12.157 | 1.443 | 61.446 | 1.00 | 104.09 | B | N |
| ATOM | 2302 | CA | ALA | B | 105 | −13.239 | 2.100 | 62.181 | 1.00 | 104.10 | B | C |
| ATOM | 2303 | CB | ALA | B | 105 | −14.590 | 1.774 | 61.543 | 1.00 | 101.87 | B | C |
| ATOM | 2304 | C | ALA | B | 105 | −13.252 | 1.768 | 63.673 | 1.00 | 106.64 | B | C |
| ATOM | 2305 | O | ALA | B | 105 | −13.732 | 2.566 | 64.484 | 1.00 | 105.54 | B | O |
| ATOM | 2306 | N | ASN | B | 106 | −12.711 | 0.598 | 64.020 | 1.00 | 110.83 | B | N |
| ATOM | 2307 | CA | ASN | B | 106 | −12.686 | 0.104 | 65.402 | 1.00 | 112.90 | B | C |
| ATOM | 2308 | CB | ASN | B | 106 | −12.560 | −1.419 | 65.419 | 1.00 | 112.61 | B | C |
| ATOM | 2309 | CG | ASN | B | 106 | −13.662 | −2.099 | 64.628 | 1.00 | 112.48 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 2310 | OD1 | ASN | B | 106 | −14.782 | −2.268 | 65.117 | 1.00 | 112.22 | B | O |
| ATOM | 2311 | ND2 | ASN | B | 106 | −13.353 | −2.476 | 63.391 | 1.00 | 111.53 | B | N |
| ATOM | 2312 | C | ASN | B | 106 | −11.624 | 0.767 | 66.287 | 1.00 | 114.33 | B | C |
| ATOM | 2313 | O | ASN | B | 106 | −11.708 | 0.697 | 67.516 | 1.00 | 112.37 | B | O |
| ATOM | 2314 | N | LEU | B | 107 | −10.638 | 1.397 | 65.638 | 1.00 | 116.71 | B | N |
| ATOM | 2315 | CA | LEU | B | 107 | −9.740 | 2.421 | 66.219 | 1.00 | 117.65 | B | C |
| ATOM | 2316 | CB | LEU | B | 107 | −10.501 | 3.735 | 66.558 | 1.00 | 118.18 | B | C |
| ATOM | 2317 | CG | LEU | B | 107 | −11.825 | 3.803 | 67.349 | 1.00 | 117.62 | B | C |
| ATOM | 2318 | CD1 | LEU | B | 107 | −11.611 | 3.881 | 68.860 | 1.00 | 116.54 | B | C |
| ATOM | 2319 | CD2 | LEU | B | 107 | −12.698 | 4.964 | 66.876 | 1.00 | 116.79 | B | C |
| ATOM | 2320 | C | LEU | B | 107 | −8.830 | 2.026 | 67.386 | 1.00 | 117.14 | B | C |
| ATOM | 2321 | O | LEU | B | 107 | −9.295 | 1.490 | 68.392 | 1.00 | 118.13 | B | O |
| ATOM | 2322 | N | SER | B | 108 | −7.532 | 2.304 | 67.243 | 1.00 | 116.38 | B | N |
| ATOM | 2323 | CA | SER | B | 108 | −6.592 | 2.207 | 68.368 | 1.00 | 117.71 | B | C |
| ATOM | 2324 | CB | SER | B | 108 | −5.433 | 1.245 | 68.066 | 1.00 | 118.45 | B | C |
| ATOM | 2325 | OG | SER | B | 108 | −5.151 | 0.407 | 69.185 | 1.00 | 114.88 | B | O |
| ATOM | 2326 | C | SER | B | 108 | −6.067 | 3.590 | 68.752 | 1.00 | 116.80 | B | C |
| ATOM | 2327 | O | SER | B | 108 | −5.739 | 3.847 | 69.916 | 1.00 | 116.90 | B | O |
| ATOM | 2328 | N | GLY | B | 109 | −5.991 | 4.470 | 67.757 | 1.00 | 115.23 | B | N |
| ATOM | 2329 | CA | GLY | B | 109 | −5.668 | 5.870 | 67.965 | 1.00 | 114.60 | B | C |
| ATOM | 2330 | C | GLY | B | 109 | −6.196 | 6.711 | 66.816 | 1.00 | 113.83 | B | C |
| ATOM | 2331 | O | GLY | B | 109 | −5.471 | 7.544 | 66.262 | 1.00 | 115.22 | B | O |
| ATOM | 2332 | N | GLY | B | 110 | −7.460 | 6.487 | 66.4586 | 1.00 | 110.69 | B | N |
| ATOM | 2333 | CA | GLY | B | 110 | −8.067 | 7.131 | 65.304 | 1.00 | 106.40 | B | C |
| ATOM | 2334 | C | GLY | B | 110 | −9.356 | 7.848 | 65.640 | 1.00 | 103.85 | B | C |
| ATOM | 2335 | O | GLY | B | 110 | −10.210 | 7.297 | 66.340 | 1.00 | 105.05 | B | O |
| ATOM | 2336 | N | VAL | B | 111 | −9.495 | 9.074 | 65.135 | 1.00 | 99.89 | B | N |
| ATOM | 2337 | CA | VAL | B | 111 | −10.651 | 9.922 | 65.442 | 1.00 | 97.25 | B | C |
| ATOM | 2338 | CB | VAL | B | 111 | −10.219 | 11.257 | 66.141 | 1.00 | 97.47 | B | C |
| ATOM | 2339 | CG1 | VAL | B | 111 | −9.412 | 12.155 | 65.206 | 1.00 | 97.24 | B | C |
| ATOM | 2340 | CG2 | VAL | B | 111 | −11.424 | 12.001 | 66.734 | 1.00 | 97.90 | B | C |
| ATOM | 2341 | C | VAL | B | 111 | −11.551 | 10.183 | 64.225 | 1.00 | 95.04 | B | C |
| ATOM | 2342 | O | VAL | B | 111 | −11.072 | 10.317 | 63.102 | 1.00 | 96.37 | B | O |
| ATOM | 2343 | N | TRP | B | 112 | −12.859 | 10.229 | 64.468 | 1.00 | 92.55 | B | N |
| ATOM | 2344 | CA | TRP | B | 112 | −13.851 | 10.530 | 63.442 | 1.00 | 90.06 | B | C |
| ATOM | 2345 | CB | TRP | B | 112 | −15.193 | 9.946 | 63.862 | 1.00 | 100.15 | B | C |
| ATOM | 2346 | CG | TRP | B | 112 | −15.775 | 8.890 | 62.958 | 1.00 | 108.23 | B | C |
| ATOM | 2347 | CD1 | TRP | B | 112 | −15.115 | 8.104 | 62.042 | 1.00 | 107.69 | B | C |
| ATOM | 2348 | NE1 | TRP | B | 112 | −16.002 | 7.257 | 61.419 | 1.00 | 109.43 | B | N |
| ATOM | 2349 | CE2 | TRP | B | 112 | −17.260 | 7.476 | 61.926 | 1.00 | 114.91 | B | C |
| ATOM | 2350 | CD2 | TRP | B | 112 | −17.152 | 8.497 | 62.901 | 1.00 | 113.79 | B | C |
| ATOM | 2351 | CE3 | TRP | B | 112 | −18.319 | 8.912 | 63.578 | 1.00 | 114.66 | B | C |
| ATOM | 2352 | CZ3 | TRP | B | 112 | −19.538 | 8.306 | 63.268 | 1.00 | 115.28 | B | C |
| ATOM | 2353 | CH2 | TRP | B | 112 | −19.612 | 7.294 | 62.295 | 1.00 | 117.95 | B | C |
| ATOM | 2354 | CZ2 | TRP | B | 112 | −18.488 | 6.865 | 61.612 | 1.00 | 118.19 | B | C |
| ATOM | 2355 | C | TRP | B | 112 | −13.964 | 12.047 | 63.285 | 1.00 | 80.41 | B | C |
| ATOM | 2356 | O | TRP | B | 112 | −14.092 | 12.772 | 64.274 | 1.00 | 77.18 | B | O |
| ATOM | 2357 | N | LYS | B | 113 | −13.921 | 12.525 | 62.044 | 1.00 | 72.68 | B | N |
| ATOM | 2358 | CA | LYS | B | 113 | −13.757 | 13.959 | 61.785 | 1.00 | 65.54 | B | C |
| ATOM | 2359 | CB | LYS | B | 113 | −12.296 | 14.273 | 61.423 | 1.00 | 64.56 | B | C |
| ATOM | 2360 | CG | LYS | B | 113 | −11.738 | 15.565 | 62.025 | 1.00 | 66.31 | B | C |
| ATOM | 2361 | CD | LYS | B | 113 | −11.284 | 15.412 | 63.479 | 1.00 | 70.15 | B | C |
| ATOM | 2362 | CE | LYS | B | 113 | −11.922 | 16.489 | 64.389 | 1.00 | 73.85 | B | C |
| ATOM | 2363 | NZ | LYS | B | 113 | −12.001 | 16.101 | 65.850 | 1.00 | 72.65 | B | N |
| ATOM | 2364 | C | LYS | B | 113 | −14.731 | 14.574 | 60.761 | 1.00 | 59.44 | B | C |
| ATOM | 2365 | O | LYS | B | 113 | −15.106 | 13.949 | 59.763 | 1.00 | 52.74 | B | O |
| ATOM | 2366 | N | ASP | B | 114 | −15.139 | 15.807 | 61.055 | 1.00 | 56.80 | B | N |
| ATOM | 2367 | CA | ASP | B | 114 | −16.058 | 16.573 | 60.230 | 1.00 | 52.56 | B | C |
| ATOM | 2368 | CB | ASP | B | 114 | −16.678 | 17.707 | 61.046 | 1.00 | 55.24 | B | C |
| ATOM | 2369 | CG | ASP | B | 114 | −18.062 | 17.386 | 61.523 | 1.00 | 55.57 | B | C |
| ATOM | 2370 | OD1 | ASP | B | 114 | −18.499 | 16.231 | 61.321 | 1.00 | 56.68 | B | O |
| ATOM | 2371 | OD2 | ASP | B | 114 | −18.779 | 18.228 | 62.111 | 1.00 | 54.42 | B | O |
| ATOM | 2372 | C | ASP | B | 114 | −15.306 | 17.169 | 59.068 | 1.00 | 47.86 | B | C |
| ATOM | 2373 | O | ASP | B | 114 | −14.254 | 17.788 | 59.250 | 1.00 | 46.73 | B | O |
| ATOM | 2374 | N | ASN | B | 115 | −15.873 | 17.001 | 57.880 | 1.00 | 44.76 | B | N |
| ATOM | 2375 | CA | ASN | B | 115 | −15.207 | 17.356 | 56.639 | 1.00 | 42.15 | B | C |
| ATOM | 2376 | CB | ASN | B | 115 | −15.489 | 16.275 | 55.585 | 1.00 | 41.27 | B | C |
| ATOM | 2377 | CG | ASN | B | 115 | −14.563 | 16.362 | 54.379 | 1.00 | 40.72 | B | C |
| ATOM | 2378 | OD1 | ASN | B | 115 | −13.708 | 17.245 | 54.284 | 1.00 | 41.54 | B | O |
| ATOM | 2379 | ND2 | ASN | B | 115 | −14.746 | 15.444 | 53.440 | 1.00 | 38.72 | B | N |
| ATOM | 2380 | C | ASN | B | 115 | −15.596 | 18.735 | 56.118 | 1.00 | 40.63 | B | C |
| ATOM | 2381 | O | ASN | B | 115 | −16.400 | 18.841 | 55.172 | 1.00 | 43.96 | B | O |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 2382 | N | ILE | B | 116 | −15.020 | 19.784 | 56.711 | 1.00 | 36.29 | B | N |
| ATOM | 2383 | CA | ILE | B | 116 | −15.301 | 21.157 | 56.255 | 1.00 | 42.57 | B | C |
| ATOM | 2384 | CB | ILE | B | 116 | −14.724 | 22.206 | 57.236 | 1.00 | 41.18 | B | C |
| ATOM | 2385 | CG1 | ILE | B | 116 | −15.416 | 22.117 | 58.577 | 1.00 | 42.73 | B | C |
| ATOM | 2386 | CD1 | ILE | B | 116 | −14.515 | 21.560 | 59.639 | 1.00 | 52.68 | B | C |
| ATOM | 2387 | CG2 | ILE | B | 116 | −14.927 | 23.600 | 56.719 | 1.00 | 39.91 | B | C |
| ATOM | 2388 | C | ILE | B | 116 | −14.817 | 21.430 | 54.810 | 1.00 | 41.86 | B | C |
| ATOM | 2389 | O | ILE | B | 116 | −13.661 | 21.185 | 54.479 | 1.00 | 40.94 | B | O |
| ATOM | 2390 | N | ASN | B | 117 | −15.711 | 21.918 | 53.955 | 1.00 | 41.50 | B | N |
| ATOM | 2391 | CA | ASN | B | 117 | −15.304 | 22.323 | 52.622 | 1.00 | 44.19 | B | C |
| ATOM | 2392 | CB | ASN | B | 117 | −16.480 | 22.617 | 51.715 | 1.00 | 46.40 | B | C |
| ATOM | 2393 | CG | ASN | B | 117 | −16.035 | 22.856 | 50.298 | 1.00 | 50.38 | B | C |
| ATOM | 2394 | OD1 | ASN | B | 117 | −16.001 | 23.987 | 49.810 | 1.00 | 49.26 | B | O |
| ATOM | 2395 | ND2 | ASN | B | 117 | −15.632 | 21.778 | 49.635 | 1.00 | 57.83 | B | N |
| ATOM | 2396 | C | ASN | B | 117 | −14.459 | 23.565 | 52.660 | 1.00 | 46.47 | B | C |
| ATOM | 2397 | O | ASN | B | 117 | −14.845 | 24.573 | 53.239 | 1.00 | 54.75 | B | O |
| ATOM | 2398 | N | MET | B | 118 | −13.315 | 23.510 | 52.006 | 1.00 | 43.70 | B | N |
| ATOM | 2399 | CA | MET | B | 118 | −12.406 | 24.633 | 52.022 | 1.00 | 39.66 | B | C |
| ATOM | 2400 | CB | MET | B | 118 | −11.039 | 24.186 | 52.479 | 1.00 | 31.69 | B | C |
| ATOM | 2401 | CG | MET | B | 118 | −11.139 | 23.407 | 53.748 | 1.00 | 33.38 | B | C |
| ATOM | 2402 | SD | MET | B | 118 | −10.931 | 24.407 | 55.204 | 1.00 | 31.79 | B | S |
| ATOM | 2403 | CE | MET | B | 118 | −12.315 | 25.652 | 55.009 | 1.00 | 44.44 | B | C |
| ATOM | 2404 | C | MET | B | 118 | −12.332 | 25.294 | 50.682 | 1.00 | 42.98 | B | C |
| ATOM | 2405 | O | MET | B | 118 | −12.171 | 26.508 | 50.598 | 1.00 | 55.86 | B | O |
| ATOM | 2406 | N | ALA | B | 119 | −12.468 | 24.509 | 49.629 | 1.00 | 35.90 | B | N |
| ATOM | 2407 | CA | ALA | B | 119 | −12.353 | 25.057 | 48.304 | 1.00 | 37.59 | B | C |
| ATOM | 2408 | CB | ALA | B | 119 | −10.947 | 24.869 | 47.801 | 1.00 | 37.93 | B | C |
| ATOM | 2409 | C | ALA | B | 119 | −13.355 | 24.379 | 47.394 | 1.00 | 41.21 | B | C |
| ATOM | 2410 | O | ALA | B | 119 | −13.808 | 23.271 | 47.675 | 1.00 | 44.45 | B | O |
| ATOM | 2411 | N | LEU | B | 120 | −13.705 | 25.052 | 46.305 | 1.00 | 40.87 | B | N |
| ATOM | 2412 | CA | LEU | B | 120 | −14.646 | 24.504 | 45.343 | 1.00 | 38.31 | B | C |
| ATOM | 2413 | CB | LEU | B | 120 | −16.065 | 24.657 | 45.876 | 1.00 | 35.61 | B | C |
| ATOM | 2414 | CG | LEU | B | 120 | −17.214 | 23.947 | 45.194 | 1.00 | 34.31 | B | C |
| ATOM | 2415 | CD1 | LEU | B | 120 | −16.986 | 22.455 | 45.139 | 1.00 | 36.68 | B | C |
| ATOM | 2416 | CD2 | LEU | B | 120 | −18.456 | 24.243 | 45.994 | 1.00 | 37.88 | B | C |
| ATOM | 2417 | C | LEU | B | 120 | −14.456 | 25.243 | 44.041 | 1.00 | 39.32 | B | C |
| ATOM | 2418 | O | LEU | B | 120 | −14.624 | 26.448 | 43.994 | 1.00 | 46.51 | B | O |
| ATOM | 2419 | N | VAL | B | 121 | −14.057 | 24.512 | 43.005 | 1.00 | 40.71 | B | N |
| ATOM | 2420 | CA | VAL | B | 121 | −13.658 | 25.055 | 41.703 | 1.00 | 38.95 | B | C |
| ATOM | 2421 | CB | VAL | B | 121 | −12.125 | 24.890 | 41.486 | 1.00 | 38.21 | B | C |
| ATOM | 2422 | CG1 | VAL | B | 121 | −11.725 | 25.174 | 40.048 | 1.00 | 44.46 | B | C |
| ATOM | 2423 | CG2 | VAL | B | 121 | −11.353 | 25.784 | 42.382 | 1.00 | 37.18 | B | C |
| ATOM | 2424 | C | VAL | B | 121 | −14.325 | 24.201 | 40.635 | 1.00 | 41.66 | B | C |
| ATOM | 2425 | O | VAL | B | 121 | −14.182 | 22.971 | 40.636 | 1.00 | 43.10 | B | O |
| ATOM | 2426 | N | VAL | B | 122 | −15.055 | 24.838 | 39.726 | 1.00 | 43.07 | B | N |
| ATOM | 2427 | CA | VAL | B | 122 | −15.458 | 24.156 | 38.494 | 1.00 | 41.96 | B | C |
| ATOM | 2428 | CB | VAL | B | 122 | −16.767 | 24.713 | 37.940 | 1.00 | 35.78 | B | C |
| ATOM | 2429 | CG1 | VAL | B | 122 | −16.605 | 25.113 | 36.525 | 1.00 | 34.77 | B | C |
| ATOM | 2430 | CG2 | VAL | B | 122 | −17.808 | 23.676 | 38.003 | 1.00 | 38.83 | B | C |
| ATOM | 2431 | C | VAL | B | 122 | −14.333 | 24.362 | 37.489 | 1.00 | 43.26 | B | C |
| ATOM | 2432 | O | VAL | B | 122 | −13.808 | 25.467 | 37.392 | 1.00 | 46.50 | B | O |
| ATOM | 2433 | N | ASP | B | 123 | −13.928 | 23.308 | 36.785 | 1.00 | 44.35 | B | N |
| ATOM | 2434 | CA | ASP | B | 123 | −12.900 | 23.451 | 35.752 | 1.00 | 51.92 | B | C |
| ATOM | 2435 | CB | ASP | B | 123 | −11.695 | 22.544 | 35.963 | 1.00 | 61.96 | B | C |
| ATOM | 2436 | CG | ASP | B | 123 | −11.083 | 22.086 | 34.628 | 1.00 | 64.45 | B | C |
| ATOM | 2437 | OD1 | ASP | B | 123 | −10.597 | 22.975 | 33.879 | 1.00 | 65.02 | B | O |
| ATOM | 2438 | OD2 | ASP | B | 123 | −11.090 | 20.887 | 34.242 | 1.00 | 61.38 | B | O |
| ATOM | 2439 | C | ASP | B | 123 | −13.475 | 23.038 | 34.451 | 1.00 | 48.41 | B | C |
| ATOM | 2440 | O | ASP | B | 123 | −14.202 | 22.060 | 34.379 | 1.00 | 53.22 | B | O |
| ATOM | 2441 | N | THR | B | 124 | −13.080 | 23.730 | 33.400 | 1.00 | 47.40 | B | N |
| ATOM | 2442 | CA | THR | B | 124 | −13.768 | 23.538 | 32.145 | 1.00 | 47.40 | B | C |
| ATOM | 2443 | CB | THR | B | 124 | −14.883 | 24.554 | 32.038 | 1.00 | 43.24 | B | C |
| ATOM | 2444 | OG1 | THR | B | 124 | −16.097 | 23.823 | 31.851 | 1.00 | 47.08 | B | O |
| ATOM | 2445 | CG2 | THR | B | 124 | −14.727 | 25.442 | 30.816 | 1.00 | 37.20 | B | C |
| ATOM | 2446 | C | THR | B | 124 | −12.882 | 23.507 | 30.928 | 1.00 | 49.31 | B | C |
| ATOM | 2447 | O | THR | B | 124 | −13.375 | 23.395 | 29.813 | 1.00 | 52.93 | B | O |
| ATOM | 2448 | N | TYR | B | 125 | −11.581 | 23.627 | 31.179 | 1.00 | 50.42 | B | N |
| ATOM | 2449 | CA | TYR | B | 125 | −10.528 | 23.488 | 30.195 | 1.00 | 45.77 | B | C |
| ATOM | 2450 | CB | TYR | B | 125 | −9.194 | 23.956 | 30.785 | 1.00 | 44.67 | B | C |
| ATOM | 2451 | CG | TYR | B | 125 | −8.074 | 23.995 | 29.795 | 1.00 | 42.53 | B | C |
| ATOM | 2452 | CD1 | TYR | B | 125 | −8.168 | 24.795 | 28.667 | 1.00 | 44.26 | B | C |
| ATOM | 2453 | CE1 | TYR | B | 125 | −7.156 | 24.853 | 27.726 | 1.00 | 46.25 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 2454 | CZ | TYR | B | 125 | −6.021 | 24.100 | 27.902 | 1.00 | 50.62 | B | C |
| ATOM | 2455 | OH | TYR | B | 125 | −5.040 | 24.192 | 26.926 | 1.00 | 57.46 | B | O |
| ATOM | 2456 | CE2 | TYR | B | 125 | −5.888 | 23.281 | 29.033 | 1.00 | 45.35 | B | C |
| ATOM | 2457 | CD2 | TYR | B | 125 | −6.925 | 23.234 | 29.972 | 1.00 | 41.33 | B | C |
| ATOM | 2458 | C | TYR | B | 125 | −10.466 | 22.011 | 29.883 | 1.00 | 47.99 | B | C |
| ATOM | 2459 | O | TYR | B | 125 | −10.520 | 21.620 | 28.719 | 1.00 | 55.63 | B | O |
| ATOM | 2460 | N | TYR | B | 126 | −10.382 | 21.179 | 30.915 | 1.00 | 42.77 | B | N |
| ATOM | 2461 | CA | TYR | B | 126 | −10.505 | 19.748 | 30.689 | 1.00 | 48.14 | B | C |
| ATOM | 2462 | CB | TYR | B | 126 | −9.865 | 18.943 | 31.822 | 1.00 | 45.89 | B | C |
| ATOM | 2463 | CG | TYR | B | 126 | −8.368 | 19.056 | 31.814 | 1.00 | 41.38 | B | C |
| ATOM | 2464 | CD1 | TYR | B | 126 | −7.611 | 18.680 | 32.893 | 1.00 | 34.20 | B | C |
| ATOM | 2465 | CE1 | TYR | B | 126 | −6.248 | 18.811 | 32.863 | 1.00 | 33.38 | B | C |
| ATOM | 2466 | CZ | TYR | B | 126 | −5.642 | 19.304 | 31.750 | 1.00 | 37.54 | B | C |
| ATOM | 2467 | OH | TYR | B | 126 | −4.290 | 19.467 | 31.673 | 1.00 | 48.33 | B | O |
| ATOM | 2468 | CE2 | TYR | B | 126 | −6.370 | 19.683 | 30.674 | 1.00 | 41.80 | B | C |
| ATOM | 2469 | CD2 | TYR | B | 126 | −7.714 | 19.567 | 30.707 | 1.00 | 44.40 | B | C |
| ATOM | 2470 | C | TYR | B | 126 | −11.975 | 19.453 | 30.563 | 1.00 | 56.46 | B | C |
| ATOM | 2471 | O | TYR | B | 126 | −12.779 | 20.380 | 30.560 | 1.00 | 64.10 | B | O |
| ATOM | 2472 | N | ASP | B | 127 | −12.335 | 18.178 | 30.449 | 1.00 | 59.78 | B | N |
| ATOM | 2473 | CA | ASP | B | 127 | −13.740 | 17.787 | 30.427 | 1.00 | 57.64 | B | C |
| ATOM | 2474 | CB | ASP | B | 127 | −13.866 | 16.284 | 30.170 | 1.00 | 66.23 | B | C |
| ATOM | 2475 | CG | ASP | B | 127 | −13.341 | 15.897 | 28.785 | 1.00 | 73.41 | B | C |
| ATOM | 2476 | OD1 | ASP | B | 127 | −14.141 | 15.903 | 27.817 | 1.00 | 72.62 | B | O |
| ATOM | 2477 | OD2 | ASP | B | 127 | −12.132 | 15.624 | 28.564 | 1.00 | 78.10 | B | O |
| ATOM | 2478 | C | ASP | B | 127 | −14.364 | 18.224 | 31.739 | 1.00 | 50.09 | B | C |
| ATOM | 2479 | O | ASP | B | 127 | −13.779 | 17.969 | 32.791 | 1.00 | 44.38 | B | O |
| ATOM | 2480 | N | ASP | B | 128 | −15.511 | 18.920 | 31.639 | 1.00 | 50.03 | B | N |
| ATOM | 2481 | CA | ASP | B | 128 | −16.159 | 19.689 | 32.725 | 1.00 | 46.93 | B | C |
| ATOM | 2482 | CB | ASP | B | 128 | −17.615 | 20.032 | 32.395 | 1.00 | 57.55 | B | C |
| ATOM | 2483 | CG | ASP | B | 128 | −17.778 | 20.854 | 31.128 | 1.00 | 66.78 | B | C |
| ATOM | 2484 | OD1 | ASP | B | 128 | −18.857 | 21.478 | 30.984 | 1.00 | 66.39 | B | O |
| ATOM | 2485 | OD2 | ASP | B | 128 | −16.917 | 20.927 | 30.218 | 1.00 | 75.20 | B | O |
| ATOM | 2486 | C | ASP | B | 128 | −16.195 | 18.882 | 33.980 | 1.00 | 41.66 | B | C |
| ATOM | 2487 | O | ASP | B | 128 | −16.663 | 17.741 | 33.967 | 1.00 | 47.23 | B | O |
| ATOM | 2488 | N | GLN | B | 129 | −15.700 | 19.463 | 35.060 | 1.00 | 35.06 | B | N |
| ATOM | 2489 | CA | GLN | B | 129 | −15.570 | 18.743 | 36.314 | 1.00 | 40.83 | B | C |
| ATOM | 2490 | CB | GLN | B | 129 | −14.255 | 17.965 | 36.389 | 1.00 | 42.79 | B | C |
| ATOM | 2491 | CG | GLN | B | 129 | −13.027 | 18.697 | 35.836 | 1.00 | 52.65 | B | C |
| ATOM | 2492 | CD | GLN | B | 129 | −11.706 | 17.927 | 36.035 | 1.00 | 58.28 | B | C |
| ATOM | 2493 | OE1 | GLN | B | 129 | −10.651 | 18.548 | 36.212 | 1.00 | 56.96 | B | O |
| ATOM | 2494 | NE2 | GLN | B | 129 | −11.762 | 16.584 | 35.993 | 1.00 | 58.06 | B | N |
| ATOM | 2495 | C | GLN | B | 129 | −15.664 | 19.675 | 37.495 | 1.00 | 45.17 | B | C |
| ATOM | 2496 | O | GLN | B | 129 | −15.241 | 20.824 | 37.420 | 1.00 | 51.51 | B | O |
| ATOM | 2497 | N | LEU | B | 130 | −16.241 | 19.183 | 38.581 | 1.00 | 43.79 | B | N |
| ATOM | 2498 | CA | LEU | B | 130 | −16.167 | 19.872 | 39.845 | 1.00 | 43.88 | B | C |
| ATOM | 2499 | CB | LEU | B | 130 | −17.454 | 19.661 | 40.627 | 1.00 | 42.37 | B | C |
| ATOM | 2500 | CG | LEU | B | 130 | −17.573 | 20.644 | 41.785 | 1.00 | 43.44 | B | C |
| ATOM | 2501 | CD1 | LEU | B | 130 | −17.291 | 22.057 | 41.272 | 1.00 | 43.17 | B | C |
| ATOM | 2502 | CD2 | LEU | B | 130 | −18.938 | 20.554 | 42.438 | 1.00 | 40.31 | B | C |
| ATOM | 2503 | C | LEU | B | 130 | −14.958 | 19.369 | 40.650 | 1.00 | 47.73 | B | C |
| ATOM | 2504 | O | LEU | B | 130 | −14.846 | 18.181 | 40.939 | 1.00 | 54.37 | B | O |
| ATOM | 2505 | N | ILE | B | 131 | −14.058 | 20.278 | 41.006 | 1.00 | 42.98 | B | N |
| ATOM | 2506 | CA | ILE | B | 131 | −12.927 | 19.958 | 41.863 | 1.00 | 37.29 | B | C |
| ATOM | 2507 | CB | ILE | B | 131 | −11.652 | 20.609 | 41.290 | 1.00 | 33.48 | B | C |
| ATOM | 2508 | CG1 | ILE | B | 131 | −11.204 | 19.859 | 40.043 | 1.00 | 36.20 | B | C |
| ATOM | 2509 | CD1 | ILE | B | 131 | −10.173 | 20.596 | 39.219 | 1.00 | 35.22 | B | C |
| ATOM | 2510 | CG2 | ILE | B | 131 | −10.527 | 20.572 | 42.282 | 1.00 | 31.94 | B | C |
| ATOM | 2511 | C | ILE | B | 131 | −13.250 | 20.511 | 43.247 | 1.00 | 38.31 | B | C |
| ATOM | 2512 | O | ILE | B | 131 | −13.578 | 21.683 | 43.371 | 1.00 | 42.71 | B | O |
| ATOM | 2513 | N | SER | B | 132 | −13.178 | 19.687 | 44.285 | 1.00 | 35.31 | B | N |
| ATOM | 2514 | CA | SER | B | 132 | −13.474 | 20.173 | 45.634 | 1.00 | 36.79 | B | C |
| ATOM | 2515 | CB | SER | B | 132 | −14.862 | 19.710 | 46.084 | 1.00 | 36.06 | B | C |
| ATOM | 2516 | OG | SER | B | 132 | −14.900 | 18.309 | 46.322 | 1.00 | 35.94 | B | O |
| ATOM | 2517 | C | SER | B | 132 | −12.426 | 19.735 | 46.643 | 1.00 | 43.95 | B | C |
| ATOM | 2518 | O | SER | B | 132 | −11.915 | 18.609 | 46.584 | 1.00 | 51.56 | B | O |
| ATOM | 2519 | N | CYS | B | 133 | −12.122 | 20.604 | 47.595 | 1.00 | 42.29 | B | N |
| ATOM | 2520 | CA | CYS | B | 133 | −11.007 | 20.333 | 48.478 | 1.00 | 43.14 | B | C |
| ATOM | 2521 | CB | CYS | B | 133 | −9.878 | 21.294 | 48.169 | 1.00 | 46.61 | B | C |
| ATOM | 2522 | SG | CYS | B | 133 | −9.498 | 21.339 | 46.411 | 1.00 | 49.26 | B | S |
| ATOM | 2523 | C | CYS | B | 133 | −11.407 | 20.486 | 49.903 | 1.00 | 45.17 | B | C |
| ATOM | 2524 | O | CYS | B | 133 | −11.608 | 21.596 | 50.371 | 1.00 | 48.43 | B | O |
| ATOM | 2525 | N | GLY | B | 134 | −11.493 | 19.356 | 50.595 | 1.00 | 50.96 | B | N |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 2526 | CA  | GLY | B | 134 | −11.880 | 19.303 | 52.002 | 1.00 | 47.23 | B | C |
| ATOM | 2527 | C   | GLY | B | 134 | −10.753 | 19.528 | 52.986 | 1.00 | 39.00 | B | C |
| ATOM | 2528 | O   | GLY | B | 134 | −9.589  | 19.518 | 52.619 | 1.00 | 40.38 | B | O |
| ATOM | 2529 | N   | SER | B | 135 | −11.111 | 19.714 | 54.247 | 1.00 | 34.97 | B | N |
| ATOM | 2530 | CA  | SER | B | 135 | −10.146 | 20.011 | 55.299 | 1.00 | 40.38 | B | C |
| ATOM | 2531 | CB  | SER | B | 135 | −10.912 | 20.575 | 56.468 | 1.00 | 41.02 | B | C |
| ATOM | 2532 | OG  | SER | B | 135 | −11.915 | 19.643 | 56.838 | 1.00 | 43.62 | B | O |
| ATOM | 2533 | C   | SER | B | 135 | −9.425  | 18.783 | 55.840 | 1.00 | 48.34 | B | C |
| ATOM | 2534 | O   | SER | B | 135 | −8.572  | 18.894 | 56.711 | 1.00 | 55.69 | B | O |
| ATOM | 2535 | N   | VAL | B | 136 | −9.765  | 17.609 | 55.344 | 1.00 | 49.73 | B | N |
| ATOM | 2536 | CA  | VAL | B | 136 | −9.730  | 16.472 | 56.224 | 1.00 | 47.33 | B | C |
| ATOM | 2537 | CB  | VAL | B | 136 | −11.157 | 15.856 | 56.374 | 1.00 | 38.19 | B | C |
| ATOM | 2538 | CG1 | VAL | B | 136 | −11.435 | 14.768 | 55.351 | 1.00 | 32.38 | B | C |
| ATOM | 2539 | CG2 | VAL | B | 136 | −11.380 | 15.387 | 57.789 | 1.00 | 39.28 | B | C |
| ATOM | 2540 | C   | VAL | B | 136 | −8.586  | 15.485 | 55.993 | 1.00 | 58.89 | B | C |
| ATOM | 2541 | O   | VAL | B | 136 | −7.891  | 15.100 | 56.950 | 1.00 | 66.03 | B | O |
| ATOM | 2542 | N   | ASN | B | 137 | −8.351  | 15.083 | 54.752 | 1.00 | 63.66 | B | N |
| ATOM | 2543 | CA  | ASN | B | 137 | −7.286  | 14.102 | 54.531 | 1.00 | 66.38 | B | C |
| ATOM | 2544 | CB  | ASN | B | 137 | −7.739  | 12.971 | 53.616 | 1.00 | 70.31 | B | C |
| ATOM | 2545 | CG  | ASN | B | 137 | −8.170  | 11.750 | 54.398 | 1.00 | 74.06 | B | C |
| ATOM | 2546 | OD1 | ASN | B | 137 | −7.363  | 11.122 | 55.102 | 1.00 | 74.99 | B | O |
| ATOM | 2547 | ND2 | ASN | B | 137 | −9.450  | 11.411 | 54.295 | 1.00 | 75.95 | B | N |
| ATOM | 2548 | C   | ASN | B | 137 | −5.985  | 14.742 | 54.085 | 1.00 | 64.84 | B | C |
| ATOM | 2549 | O   | ASN | B | 137 | −5.452  | 14.451 | 53.019 | 1.00 | 62.52 | B | O |
| ATOM | 2550 | N   | ARG | B | 138 | −5.486  | 15.607 | 54.961 | 1.00 | 66.90 | B | N |
| ATOM | 2551 | CA  | ARG | B | 138 | −4.336  | 16.464 | 54.717 | 1.00 | 65.01 | B | C |
| ATOM | 2552 | CB  | ARG | B | 138 | −3.047  | 15.654 | 54.503 | 1.00 | 71.48 | B | C |
| ATOM | 2553 | CG  | ARG | B | 138 | −1.956  | 15.954 | 55.529 | 1.00 | 79.03 | B | C |
| ATOM | 2554 | CD  | ARG | B | 138 | −1.753  | 17.448 | 55.823 | 1.00 | 85.21 | B | C |
| ATOM | 2555 | NE  | ARG | B | 138 | −1.583  | 17.732 | 57.252 | 1.00 | 90.48 | B | N |
| ATOM | 2556 | CZ  | ARG | B | 138 | −2.579  | 17.968 | 58.109 | 1.00 | 92.99 | B | C |
| ATOM | 2557 | NH1 | ARG | B | 138 | −3.844  | 17.956 | 57.701 | 1.00 | 92.99 | B | N |
| ATOM | 2558 | NH2 | ARG | B | 138 | −2.306  | 18.218 | 59.387 | 1.00 | 94.36 | B | N |
| ATOM | 2559 | C   | ARG | B | 138 | −4.580  | 17.428 | 53.580 | 1.00 | 58.68 | B | C |
| ATOM | 2560 | O   | ARG | B | 138 | −3.652  | 17.754 | 52.855 | 1.00 | 57.43 | B | O |
| ATOM | 2561 | N   | GLY | B | 139 | −5.827  | 17.881 | 53.436 | 1.00 | 56.99 | B | N |
| ATOM | 2562 | CA  | GLY | B | 139 | −6.186  | 18.869 | 52.419 | 1.00 | 60.31 | B | C |
| ATOM | 2563 | C   | GLY | B | 139 | −6.125  | 18.413 | 50.959 | 1.00 | 56.23 | B | C |
| ATOM | 2564 | O   | GLY | B | 139 | −5.474  | 19.025 | 50.107 | 1.00 | 53.01 | B | O |
| ATOM | 2565 | N   | THR | B | 140 | −6.892  | 17.374 | 50.677 | 1.00 | 51.49 | B | N |
| ATOM | 2566 | CA  | THR | B | 140 | −6.708  | 16.542 | 49.523 | 1.00 | 44.96 | B | C |
| ATOM | 2567 | CB  | THR | B | 140 | −6.359  | 15.144 | 50.079 | 1.00 | 40.88 | B | C |
| ATOM | 2568 | OG1 | THR | B | 140 | −5.543  | 14.445 | 49.159 | 1.00 | 42.11 | B | O |
| ATOM | 2569 | CG2 | THR | B | 140 | −7.570  | 14.236 | 50.258 | 1.00 | 39.68 | B | C |
| ATOM | 2570 | C   | THR | B | 140 | −7.969  | 16.581 | 48.635 | 1.00 | 49.45 | B | C |
| ATOM | 2571 | O   | THR | B | 140 | −9.023  | 16.049 | 49.005 | 1.00 | 52.07 | B | O |
| ATOM | 2572 | N   | CYS | B | 141 | −7.860  | 17.234 | 47.475 | 1.00 | 51.13 | B | N |
| ATOM | 2573 | CA  | CYS | B | 141 | −9.010  | 17.478 | 46.577 | 1.00 | 50.29 | B | C |
| ATOM | 2574 | CB  | CYS | B | 141 | −8.664  | 18.515 | 45.512 | 1.00 | 47.76 | B | C |
| ATOM | 2575 | SG  | CYS | B | 141 | −7.972  | 20.064 | 46.098 | 1.00 | 47.46 | B | S |
| ATOM | 2576 | C   | CYS | B | 141 | −9.505  | 16.256 | 45.814 | 1.00 | 49.65 | B | C |
| ATOM | 2577 | O   | CYS | B | 141 | −8.722  | 15.377 | 45.478 | 1.00 | 54.28 | B | O |
| ATOM | 2578 | N   | GLN | B | 142 | −10.796 | 16.226 | 45.508 | 1.00 | 44.81 | B | N |
| ATOM | 2579 | CA  | GLN | B | 142 | −11.312 | 15.252 | 44.556 | 1.00 | 45.82 | B | C |
| ATOM | 2580 | CB  | GLN | B | 142 | −12.224 | 14.230 | 45.229 | 1.00 | 50.74 | B | C |
| ATOM | 2581 | CG  | GLN | B | 142 | −13.118 | 14.773 | 46.300 | 1.00 | 61.11 | B | C |
| ATOM | 2582 | CD  | GLN | B | 142 | −13.706 | 13.667 | 47.164 | 1.00 | 69.68 | B | C |
| ATOM | 2583 | OE1 | GLN | B | 142 | −14.920 | 13.650 | 47.414 | 1.00 | 73.98 | B | O |
| ATOM | 2584 | NE2 | GLN | B | 142 | −12.852 | 12.745 | 47.629 | 1.00 | 69.82 | B | N |
| ATOM | 2585 | C   | GLN | B | 142 | −12.032 | 15.898 | 43.371 | 1.00 | 45.42 | B | C |
| ATOM | 2586 | O   | GLN | B | 142 | −12.597 | 16.996 | 43.491 | 1.00 | 46.11 | B | O |
| ATOM | 2587 | N   | ARG | B | 143 | −12.007 | 15.216 | 42.227 | 1.00 | 40.44 | B | N |
| ATOM | 2588 | CA  | ARG | B | 143 | −12.773 | 15.673 | 41.079 | 1.00 | 42.36 | B | C |
| ATOM | 2589 | CB  | ARG | B | 143 | −11.916 | 15.712 | 39.821 | 1.00 | 43.64 | B | C |
| ATOM | 2590 | CG  | ARG | B | 143 | −10.693 | 14.855 | 39.870 | 1.00 | 46.96 | B | C |
| ATOM | 2591 | CD  | ARG | B | 143 | −9.746  | 15.107 | 38.695 | 1.00 | 52.05 | B | C |
| ATOM | 2592 | NE  | ARG | B | 143 | −10.263 | 14.581 | 37.430 | 1.00 | 53.03 | B | N |
| ATOM | 2593 | CZ  | ARG | B | 143 | −10.090 | 13.331 | 37.013 | 1.00 | 52.65 | B | C |
| ATOM | 2594 | NH1 | ARG | B | 143 | −9.405  | 12.456 | 37.758 | 1.00 | 50.91 | B | N |
| ATOM | 2595 | NH2 | ARG | B | 143 | −10.612 | 12.954 | 35.852 | 1.00 | 53.00 | B | N |
| ATOM | 2596 | C   | ARG | B | 143 | −14.063 | 14.872 | 40.836 | 1.00 | 42.84 | B | C |
| ATOM | 2597 | O   | ARG | B | 143 | −14.048 | 13.656 | 40.824 | 1.00 | 46.36 | B | O |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 2598 | N | HIS | B | 144 | −15.175 | 15.575 | 40.664 | 1.00 | 37.53 | B | N |
| ATOM | 2599 | CA | HIS | B | 144 | −16.422 | 14.988 | 40.232 | 1.00 | 35.23 | B | C |
| ATOM | 2600 | CB | HIS | B | 144 | −17.549 | 15.616 | 41.028 | 1.00 | 37.05 | B | C |
| ATOM | 2601 | CG | HIS | B | 144 | −17.291 | 15.651 | 42.499 | 1.00 | 43.08 | B | C |
| ATOM | 2602 | ND1 | HIS | B | 144 | −17.933 | 14.811 | 43.390 | 1.00 | 45.29 | B | N |
| ATOM | 2603 | CE1 | HIS | B | 144 | −17.513 | 15.068 | 44.617 | 1.00 | 44.50 | B | C |
| ATOM | 2604 | NE2 | HIS | B | 144 | −16.616 | 16.037 | 44.554 | 1.00 | 45.75 | B | N |
| ATOM | 2605 | CD2 | HIS | B | 144 | −16.460 | 16.421 | 43.240 | 1.00 | 43.81 | B | C |
| ATOM | 2606 | C | HIS | B | 144 | −16.598 | 15.311 | 38.753 | 1.00 | 37.70 | B | C |
| ATOM | 2607 | O | HIS | B | 144 | −16.655 | 16.476 | 38.387 | 1.00 | 43.32 | B | O |
| ATOM | 2608 | N | VAL | B | 145 | −16.678 | 14.301 | 37.893 | 1.00 | 36.97 | B | N |
| ATOM | 2609 | CA | VAL | B | 145 | −16.786 | 14.561 | 36.457 | 1.00 | 36.81 | B | C |
| ATOM | 2610 | CB | VAL | B | 145 | −15.956 | 13.579 | 35.611 | 1.00 | 34.75 | B | C |
| ATOM | 2611 | CG1 | VAL | B | 145 | −15.910 | 14.054 | 34.189 | 1.00 | 35.76 | B | C |
| ATOM | 2612 | CG2 | VAL | B | 145 | −14.556 | 13.416 | 36.148 | 1.00 | 32.94 | B | C |
| ATOM | 2613 | C | VAL | B | 145 | −18.223 | 14.441 | 35.995 | 1.00 | 43.42 | B | C |
| ATOM | 2614 | O | VAL | B | 145 | −18.809 | 13.342 | 36.043 | 1.00 | 47.84 | B | O |
| ATOM | 2615 | N | PHE | B | 146 | −18.785 | 15.564 | 35.543 | 1.00 | 43.72 | B | N |
| ATOM | 2616 | CA | PHE | B | 146 | −20.146 | 15.592 | 35.018 | 1.00 | 44.43 | B | C |
| ATOM | 2617 | CB | PHE | B | 146 | −20.522 | 16.990 | 34.570 | 1.00 | 45.43 | B | C |
| ATOM | 2618 | CG | PHE | B | 146 | −20.341 | 18.050 | 35.610 | 1.00 | 49.30 | B | C |
| ATOM | 2619 | CD1 | PHE | B | 146 | −19.604 | 19.191 | 35.324 | 1.00 | 52.90 | B | C |
| ATOM | 2620 | CE1 | PHE | B | 146 | −19.451 | 20.197 | 36.271 | 1.00 | 54.03 | B | C |
| ATOM | 2621 | CZ | PHE | B | 146 | −20.053 | 20.080 | 37.502 | 1.00 | 51.89 | B | C |
| ATOM | 2622 | CE2 | PHE | B | 146 | −20.808 | 18.963 | 37.786 | 1.00 | 50.76 | B | C |
| ATOM | 2623 | CD2 | PHE | B | 146 | −20.949 | 17.950 | 36.846 | 1.00 | 48.78 | B | C |
| ATOM | 2624 | C | PHE | B | 146 | −20.233 | 14.726 | 33.787 | 1.00 | 49.11 | B | C |
| ATOM | 2625 | O | PHE | B | 146 | −19.447 | 14.904 | 32.878 | 1.00 | 56.47 | B | O |
| ATOM | 2626 | N | PRO | B | 147 | −21.176 | 13.793 | 33.751 | 1.00 | 52.30 | B | N |
| ATOM | 2627 | CA | PRO | B | 147 | −21.520 | 13.069 | 32.523 | 1.00 | 55.83 | B | C |
| ATOM | 2628 | CB | PRO | B | 147 | −22.685 | 12.195 | 32.959 | 1.00 | 54.10 | B | C |
| ATOM | 2629 | CG | PRO | B | 147 | −22.490 | 12.025 | 34.405 | 1.00 | 55.02 | B | C |
| ATOM | 2630 | CD | PRO | B | 147 | −21.968 | 13.337 | 34.901 | 1.00 | 53.64 | B | C |
| ATOM | 2631 | C | PRO | B | 147 | −22.001 | 14.027 | 31.456 | 1.00 | 64.29 | B | C |
| ATOM | 2632 | O | PRO | B | 147 | −22.433 | 15.127 | 31.786 | 1.00 | 64.18 | B | O |
| ATOM | 2633 | N | HIS | B | 148 | −21.954 | 13.612 | 30.196 | 1.00 | 78.08 | B | N |
| ATOM | 2634 | CA | HIS | B | 148 | −22.141 | 14.555 | 29.092 | 1.00 | 92.40 | B | C |
| ATOM | 2635 | CB | HIS | B | 148 | −21.535 | 14.011 | 27.783 | 1.00 | 101.33 | B | C |
| ATOM | 2636 | CG | HIS | B | 148 | −20.107 | 14.429 | 27.550 | 1.00 | 107.97 | B | C |
| ATOM | 2637 | ND1 | HIS | B | 148 | −19.759 | 15.689 | 27.106 | 1.00 | 111.16 | B | N |
| ATOM | 2638 | CE1 | HIS | B | 148 | −18.444 | 15.765 | 26.988 | 1.00 | 112.02 | B | C |
| ATOM | 2639 | NE2 | HIS | B | 148 | −17.926 | 14.601 | 27.338 | 1.00 | 110.28 | B | N |
| ATOM | 2640 | CD2 | HIS | B | 148 | −18.943 | 13.748 | 27.694 | 1.00 | 109.07 | B | C |
| ATOM | 2641 | C | HIS | B | 148 | −23.572 | 15.096 | 28.892 | 1.00 | 94.82 | B | C |
| ATOM | 2642 | O | HIS | B | 148 | −23.874 | 15.676 | 27.847 | 1.00 | 95.71 | B | O |
| ATOM | 2643 | N | ASN | B | 149 | −24.438 | 14.908 | 29.888 | 1.00 | 97.59 | B | N |
| ATOM | 2644 | CA | ASN | B | 149 | −25.715 | 15.626 | 29.928 | 1.00 | 101.83 | B | C |
| ATOM | 2645 | CB | ASN | B | 149 | −26.774 | 14.995 | 29.018 | 1.00 | 108.36 | B | C |
| ATOM | 2646 | CG | ASN | B | 149 | −27.356 | 16.003 | 28.019 | 1.00 | 114.29 | B | C |
| ATOM | 2647 | OD1 | ASN | B | 149 | −26.613 | 16.720 | 27.338 | 1.00 | 115.73 | B | O |
| ATOM | 2648 | ND2 | ASN | B | 149 | −28.689 | 16.066 | 27.937 | 1.00 | 116.16 | B | N |
| ATOM | 2649 | C | ASN | B | 149 | −26.294 | 15.944 | 31.310 | 1.00 | 101.43 | B | C |
| ATOM | 2650 | O | ASN | B | 149 | −26.712 | 17.082 | 31.546 | 1.00 | 103.14 | B | O |
| ATOM | 2651 | N | HIS | B | 150 | −26.343 | 14.966 | 32.214 | 1.00 | 98.98 | B | N |
| ATOM | 2652 | CA | HIS | B | 150 | −26.765 | 15.262 | 33.586 | 1.00 | 96.40 | B | C |
| ATOM | 2653 | CB | HIS | B | 150 | −27.117 | 13.984 | 34.375 | 1.00 | 103.90 | B | C |
| ATOM | 2654 | CG | HIS | B | 150 | −28.007 | 14.226 | 35.566 | 1.00 | 112.70 | B | C |
| ATOM | 2655 | ND1 | HIS | B | 150 | −28.322 | 13.236 | 36.477 | 1.00 | 115.18 | B | N |
| ATOM | 2656 | CE1 | HIS | B | 150 | −29.116 | 13.732 | 37.412 | 1.00 | 115.57 | B | C |
| ATOM | 2657 | NE2 | HIS | B | 150 | −29.329 | 15.008 | 37.143 | 1.00 | 116.22 | B | N |
| ATOM | 2658 | CD2 | HIS | B | 150 | −28.648 | 15.343 | 35.995 | 1.00 | 114.87 | B | C |
| ATOM | 2659 | C | HIS | B | 150 | −25.678 | 16.092 | 34.283 | 1.00 | 86.18 | B | C |
| ATOM | 2660 | O | HIS | B | 150 | −24.553 | 15.636 | 34.441 | 1.00 | 83.39 | B | O |
| ATOM | 2661 | N | THR | B | 151 | −26.017 | 17.321 | 34.661 | 1.00 | 77.85 | B | N |
| ATOM | 2662 | CA | THR | B | 151 | −25.064 | 18.239 | 35.284 | 1.00 | 71.05 | B | C |
| ATOM | 2663 | CB | THR | B | 151 | −25.316 | 19.678 | 34.800 | 1.00 | 71.38 | B | C |
| ATOM | 2664 | OG1 | THR | B | 151 | −25.137 | 19.740 | 33.385 | 1.00 | 74.39 | B | O |
| ATOM | 2665 | CG2 | THR | B | 151 | −24.253 | 20.638 | 35.318 | 1.00 | 67.68 | B | C |
| ATOM | 2666 | C | THR | B | 151 | −25.147 | 18.193 | 36.802 | 1.00 | 68.37 | B | C |
| ATOM | 2667 | O | THR | B | 151 | −24.286 | 18.726 | 37.494 | 1.00 | 69.11 | B | O |
| ATOM | 2668 | N | ALA | B | 152 | −26.188 | 17.569 | 37.328 | 1.00 | 65.26 | B | N |
| ATOM | 2669 | CA | ALA | B | 152 | −26.322 | 17.475 | 38.766 | 1.00 | 66.60 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 2670 | CB  | ALA | B | 152 | −27.775 | 17.454 | 39.151 | 1.00 | 70.48 | B | C |
| ATOM | 2671 | C   | ALA | B | 152 | −25.613 | 16.226 | 39.267 | 1.00 | 68.90 | B | C |
| ATOM | 2672 | O   | ALA | B | 152 | −25.715 | 15.868 | 40.450 | 1.00 | 73.24 | B | O |
| ATOM | 2673 | N   | ASP | B | 153 | −24.885 | 15.569 | 38.368 | 1.00 | 65.99 | B | N |
| ATOM | 2674 | CA  | ASP | B | 153 | −24.266 | 14.294 | 38.690 | 1.00 | 64.22 | B | C |
| ATOM | 2675 | CB  | ASP | B | 153 | −24.356 | 13.338 | 37.507 | 1.00 | 67.82 | B | C |
| ATOM | 2676 | CG  | ASP | B | 153 | −24.270 | 11.886 | 37.927 | 1.00 | 72.99 | B | C |
| ATOM | 2677 | OD1 | ASP | B | 153 | −23.834 | 11.619 | 39.070 | 1.00 | 77.73 | B | O |
| ATOM | 2678 | OD2 | ASP | B | 153 | −24.607 | 10.940 | 37.180 | 1.00 | 72.88 | B | O |
| ATOM | 2679 | C   | ASP | B | 153 | −22.836 | 14.427 | 39.205 | 1.00 | 61.94 | B | C |
| ATOM | 2680 | O   | ASP | B | 153 | −21.872 | 14.052 | 38.541 | 1.00 | 64.99 | B | O |
| ATOM | 2681 | N   | ILE | B | 154 | −22.743 | 14.962 | 40.415 | 1.00 | 59.23 | B | N |
| ATOM | 2682 | CA  | ILE | B | 154 | −21.538 | 15.035 | 41.245 | 1.00 | 57.56 | B | C |
| ATOM | 2683 | CB  | ILE | B | 154 | −21.912 | 15.942 | 42.471 | 1.00 | 55.70 | B | C |
| ATOM | 2684 | CG1 | ILE | B | 154 | −22.096 | 17.368 | 42.013 | 1.00 | 54.79 | B | C |
| ATOM | 2685 | CD1 | ILE | B | 154 | −21.086 | 17.754 | 40.980 | 1.00 | 57.56 | B | C |
| ATOM | 2686 | CG2 | ILE | B | 154 | −20.876 | 15.932 | 43.576 | 1.00 | 57.05 | B | C |
| ATOM | 2687 | C   | ILE | B | 154 | −21.074 | 13.635 | 41.729 | 1.00 | 58.25 | B | C |
| ATOM | 2688 | O   | ILE | B | 154 | −20.039 | 13.496 | 42.403 | 1.00 | 46.30 | B | O |
| ATOM | 2689 | N   | GLN | B | 155 | −21.846 | 12.612 | 41.359 | 1.00 | 63.86 | B | N |
| ATOM | 2690 | CA  | GLN | B | 155 | −21.941 | 11.372 | 42.127 | 1.00 | 67.23 | B | C |
| ATOM | 2691 | CB  | GLN | B | 155 | −23.412 | 11.112 | 42.485 | 1.00 | 75.19 | B | C |
| ATOM | 2692 | CG  | GLN | B | 155 | −23.688 | 9.775  | 43.154 | 1.00 | 82.02 | B | C |
| ATOM | 2693 | CD  | GLN | B | 155 | −23.728 | 9.870  | 44.673 | 1.00 | 86.58 | B | C |
| ATOM | 2694 | OE1 | GLN | B | 155 | −22.981 | 9.164  | 45.366 | 1.00 | 86.57 | B | O |
| ATOM | 2695 | NE2 | GLN | B | 155 | −24.603 | 10.737 | 45.194 | 1.00 | 87.11 | B | N |
| ATOM | 2696 | C   | GLN | B | 155 | −21.365 | 10.167 | 41.416 | 1.00 | 65.06 | B | C |
| ATOM | 2697 | O   | GLN | B | 155 | −20.639 | 9.377  | 42.023 | 1.00 | 66.82 | B | O |
| ATOM | 2698 | N   | SER | B | 156 | −21.684 | 10.025 | 40.135 | 1.00 | 61.98 | B | N |
| ATOM | 2699 | CA  | SER | B | 156 | −21.338 | 8.809  | 39.408 | 1.00 | 62.24 | B | C |
| ATOM | 2700 | CB  | SER | B | 156 | −22.242 | 8.638  | 38.183 | 1.00 | 62.44 | B | C |
| ATOM | 2701 | OG  | SER | B | 156 | −21.611 | 9.101  | 37.007 | 1.00 | 66.58 | B | O |
| ATOM | 2702 | C   | SER | B | 156 | −19.827 | 8.614  | 39.093 | 1.00 | 61.49 | B | C |
| ATOM | 2703 | O   | SER | B | 156 | −19.299 | 7.526  | 39.271 | 1.00 | 63.76 | B | O |
| ATOM | 2704 | N   | GLU | B | 157 | −19.126 | 9.654  | 38.658 | 1.00 | 63.78 | B | N |
| ATOM | 2705 | CA  | GLU | B | 157 | −17.672 | 9.542  | 38.424 | 1.00 | 60.36 | B | C |
| ATOM | 2706 | CB  | GLU | B | 157 | −17.346 | 9.605  | 36.933 | 1.00 | 61.77 | B | C |
| ATOM | 2707 | CG  | GLU | B | 157 | −15.858 | 9.657  | 36.659 | 1.00 | 62.96 | B | C |
| ATOM | 2708 | CD  | GLU | B | 157 | −15.568 | 9.856  | 35.201 | 1.00 | 69.04 | B | C |
| ATOM | 2709 | OE1 | GLU | B | 157 | −16.515 | 10.214 | 34.461 | 1.00 | 71.13 | B | O |
| ATOM | 2710 | OE2 | GLU | B | 157 | −14.399 | 9.656  | 34.799 | 1.00 | 72.81 | B | O |
| ATOM | 2711 | C   | GLU | B | 157 | −16.831 | 10.569 | 39.207 | 1.00 | 52.41 | B | C |
| ATOM | 2712 | O   | GLU | B | 157 | −16.754 | 11.743 | 38.834 | 1.00 | 50.81 | B | O |
| ATOM | 2713 | N   | VAL | B | 158 | −16.212 | 10.095 | 40.286 | 1.00 | 44.97 | B | N |
| ATOM | 2714 | CA  | VAL | B | 158 | −15.491 | 10.926 | 41.235 | 1.00 | 41.41 | B | C |
| ATOM | 2715 | CB  | VAL | B | 158 | −16.212 | 11.004 | 42.585 | 1.00 | 38.90 | B | C |
| ATOM | 2716 | CG1 | VAL | B | 158 | −15.343 | 11.713 | 43.606 | 1.00 | 41.55 | B | C |
| ATOM | 2717 | CG2 | VAL | B | 158 | −17.523 | 11.684 | 42.462 | 1.00 | 38.40 | B | C |
| ATOM | 2718 | C   | VAL | B | 158 | −14.181 | 10.246 | 41.544 | 1.00 | 44.87 | B | C |
| ATOM | 2719 | O   | VAL | B | 158 | −14.190 | 9.158  | 42.091 | 1.00 | 48.33 | B | O |
| ATOM | 2720 | N   | HIS | B | 159 | −13.066 | 10.897 | 41.220 | 1.00 | 48.81 | B | N |
| ATOM | 2721 | CA  | HIS | B | 159 | −11.728 | 10.413 | 41.558 | 1.00 | 49.97 | B | C |
| ATOM | 2722 | CB  | HIS | B | 159 | −10.822 | 10.456 | 40.334 | 1.00 | 55.24 | B | C |
| ATOM | 2723 | CG  | HIS | B | 159 | −11.455 | 9.934  | 39.092 | 1.00 | 57.18 | B | C |
| ATOM | 2724 | ND1 | HIS | B | 159 | −11.255 | 8.649  | 38.645 | 1.00 | 61.70 | B | N |
| ATOM | 2725 | CE1 | HIS | B | 159 | −11.921 | 8.472  | 37.518 | 1.00 | 66.34 | B | C |
| ATOM | 2726 | NE2 | HIS | B | 159 | −12.549 | 9.596  | 37.224 | 1.00 | 64.77 | B | N |
| ATOM | 2727 | CD2 | HIS | B | 159 | −12.266 | 10.528 | 38.190 | 1.00 | 59.87 | B | C |
| ATOM | 2728 | C   | HIS | B | 159 | −11.079 | 11.289 | 42.603 | 1.00 | 45.65 | B | C |
| ATOM | 2729 | O   | HIS | B | 159 | −11.085 | 12.512 | 42.465 | 1.00 | 46.99 | B | O |
| ATOM | 2730 | N   | CYS | B | 160 | −10.486 | 10.667 | 43.617 | 1.00 | 43.49 | B | N |
| ATOM | 2731 | CA  | CYS | B | 160 | −9.662  | 11.386 | 44.589 | 1.00 | 50.24 | B | C |
| ATOM | 2732 | CB  | CYS | B | 160 | −9.462  | 10.511 | 45.829 | 1.00 | 56.49 | B | C |
| ATOM | 2733 | SG  | CYS | B | 160 | −8.633  | 11.276 | 47.239 | 1.00 | 63.33 | B | S |
| ATOM | 2734 | C   | CYS | B | 160 | −8.319  | 11.773 | 43.936 | 1.00 | 50.29 | B | C |
| ATOM | 2735 | O   | CYS | B | 160 | −7.827  | 11.040 | 43.081 | 1.00 | 55.87 | B | O |
| ATOM | 2736 | N   | ILE | B | 161 | −7.741  | 12.924 | 44.286 | 1.00 | 47.03 | B | N |
| ATOM | 2737 | CA  | ILE | B | 161 | −6.490  | 13.348 | 43.632 | 1.00 | 46.63 | B | C |
| ATOM | 2738 | CB  | ILE | B | 161 | −6.543  | 14.777 | 43.026 | 1.00 | 38.65 | B | C |
| ATOM | 2739 | CG1 | ILE | B | 161 | −7.751  | 14.997 | 42.127 | 1.00 | 34.38 | B | C |
| ATOM | 2740 | CD1 | ILE | B | 161 | −7.701  | 16.338 | 41.444 | 1.00 | 34.32 | B | C |
| ATOM | 2741 | CG2 | ILE | B | 161 | −5.260  | 15.053 | 42.246 | 1.00 | 34.37 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 2742 | C | ILE | B | 161 | −5.317 | 13.324 | 44.583 | 1.00 | 56.92 | B | C |
| ATOM | 2743 | O | ILE | B | 161 | −5.078 | 14.321 | 45.300 | 1.00 | 62.39 | B | O |
| ATOM | 2744 | N | PHE | B | 162 | −4.580 | 12.209 | 44.556 | 1.00 | 60.69 | B | N |
| ATOM | 2745 | CA | PHE | B | 162 | −3.338 | 12.051 | 45.300 | 1.00 | 61.03 | B | C |
| ATOM | 2746 | CB | PHE | B | 162 | −3.620 | 11.632 | 46.745 | 1.00 | 59.23 | B | C |
| ATOM | 2747 | CG | PHE | B | 162 | −2.393 | 11.330 | 47.547 | 1.00 | 66.31 | B | C |
| ATOM | 2748 | CD1 | PHE | B | 162 | −2.396 | 11.515 | 48.917 | 1.00 | 69.32 | B | C |
| ATOM | 2749 | CE1 | PHE | B | 162 | −1.268 | 11.236 | 49.679 | 1.00 | 71.72 | B | C |
| ATOM | 2750 | CZ | PHE | B | 162 | −0.118 | 10.759 | 49.067 | 1.00 | 76.67 | B | C |
| ATOM | 2751 | CE2 | PHE | B | 162 | −0.102 | 10.560 | 47.681 | 1.00 | 75.24 | B | C |
| ATOM | 2752 | CD2 | PHE | B | 162 | −1.234 | 10.844 | 46.940 | 1.00 | 71.12 | B | C |
| ATOM | 2753 | C | PHE | B | 162 | −2.451 | 11.023 | 44.616 | 1.00 | 64.46 | B | C |
| ATOM | 2754 | O | PHE | B | 162 | −2.581 | 9.832 | 44.862 | 1.00 | 69.15 | B | O |
| ATOM | 2755 | N | SER | B | 163 | −1.543 | 11.491 | 43.771 | 1.00 | 67.84 | B | N |
| ATOM | 2756 | CA | SER | B | 163 | −0.518 | 10.642 | 43.167 | 1.00 | 72.18 | B | C |
| ATOM | 2757 | CB | SER | B | 163 | −0.001 | 11.298 | 41.887 | 1.00 | 76.28 | B | C |
| ATOM | 2758 | OG | SER | B | 163 | 0.847 | 10.416 | 41.184 | 1.00 | 81.52 | B | O |
| ATOM | 2759 | C | SER | B | 163 | 0.645 | 10.423 | 44.137 | 1.00 | 72.44 | B | C |
| ATOM | 2760 | O | SER | B | 163 | 1.159 | 11.390 | 44.684 | 1.00 | 69.21 | B | O |
| ATOM | 2761 | N | PRO | B | 164 | 1.074 | 9.173 | 44.344 | 1.00 | 79.41 | B | N |
| ATOM | 2762 | CA | PRO | B | 164 | 2.144 | 8.879 | 45.318 | 1.00 | 83.15 | B | C |
| ATOM | 2763 | CB | PRO | B | 164 | 2.208 | 7.348 | 45.330 | 1.00 | 82.50 | B | C |
| ATOM | 2764 | CG | PRO | B | 164 | 1.633 | 6.927 | 44.023 | 1.00 | 81.14 | B | C |
| ATOM | 2765 | CD | PRO | B | 164 | 0.598 | 7.954 | 43.664 | 1.00 | 81.00 | B | C |
| ATOM | 2766 | C | PRO | B | 164 | 3.490 | 9.499 | 44.913 | 1.00 | 82.80 | B | C |
| ATOM | 2767 | O | PRO | B | 164 | 3.808 | 9.545 | 43.729 | 1.00 | 81.17 | B | O |
| ATOM | 2768 | N | GLN | B | 165 | 4.252 | 9.975 | 45.893 | 1.00 | 85.72 | B | N |
| ATOM | 2769 | CA | GLN | B | 165 | 5.390 | 10.850 | 45.629 | 1.00 | 91.50 | B | C |
| ATOM | 2770 | CB | GLN | B | 165 | 5.401 | 11.986 | 46.649 | 1.00 | 89.42 | B | C |
| ATOM | 2771 | CG | GLN | B | 165 | 5.925 | 13.312 | 46.096 | 1.00 | 87.88 | B | C |
| ATOM | 2772 | CD | GLN | B | 165 | 5.147 | 13.843 | 44.892 | 1.00 | 83.64 | B | C |
| ATOM | 2773 | OE1 | GLN | B | 165 | 4.042 | 13.382 | 44.587 | 1.00 | 81.23 | B | O |
| ATOM | 2774 | NE2 | GLN | B | 165 | 5.729 | 14.820 | 44.212 | 1.00 | 81.96 | B | N |
| ATOM | 2775 | C | GLN | B | 165 | 6.735 | 10.129 | 45.608 | 1.00 | 99.59 | B | C |
| ATOM | 2776 | O | GLN | B | 165 | 7.138 | 9.544 | 46.613 | 1.00 | 103.36 | B | O |
| ATOM | 2777 | N | ILE | B | 166 | 7.440 | 10.189 | 44.476 | 1.00 | 106.48 | B | N |
| ATOM | 2778 | CA | ILE | B | 166 | 8.581 | 9.286 | 44.246 | 1.00 | 113.53 | B | C |
| ATOM | 2779 | CB | ILE | B | 166 | 8.212 | 8.200 | 43.163 | 1.00 | 114.08 | B | C |
| ATOM | 2780 | CG1 | ILE | B | 166 | 8.067 | 6.820 | 43.825 | 1.00 | 114.36 | B | C |
| ATOM | 2781 | CD1 | ILE | B | 166 | 6.653 | 6.505 | 44.350 | 1.00 | 113.22 | B | C |
| ATOM | 2782 | CG2 | ILE | B | 166 | 9.192 | 8.178 | 41.965 | 1.00 | 112.30 | B | C |
| ATOM | 2783 | C | ILE | B | 166 | 9.953 | 9.945 | 44.014 | 1.00 | 118.30 | B | C |
| ATOM | 2784 | O | ILE | B | 166 | 10.966 | 9.458 | 44.533 | 1.00 | 114.87 | B | O |
| ATOM | 2785 | N | GLU | B | 167 | 9.980 | 11.045 | 43.257 | 1.00 | 126.36 | B | N |
| ATOM | 2786 | CA | GLU | B | 167 | 11.223 | 11.788 | 43.003 | 1.00 | 131.46 | B | C |
| ATOM | 2787 | CB | GLU | B | 167 | 11.053 | 12.807 | 41.859 | 1.00 | 135.17 | B | C |
| ATOM | 2788 | CG | GLU | B | 167 | 10.514 | 12.245 | 40.540 | 1.00 | 138.96 | B | C |
| ATOM | 2789 | CD | GLU | B | 167 | 11.389 | 11.154 | 39.931 | 1.00 | 140.44 | B | C |
| ATOM | 2790 | OE1 | GLU | B | 167 | 12.610 | 11.380 | 39.754 | 1.00 | 139.92 | B | O |
| ATOM | 2791 | OE2 | GLU | B | 167 | 10.848 | 10.067 | 39.624 | 1.00 | 140.86 | B | O |
| ATOM | 2792 | C | GLU | B | 167 | 11.708 | 12.478 | 44.286 | 1.00 | 131.99 | B | C |
| ATOM | 2793 | O | GLU | B | 167 | 12.810 | 12.199 | 44.771 | 1.00 | 132.18 | B | O |
| ATOM | 2794 | N | GLU | B | 168 | 10.872 | 13.365 | 44.829 | 1.00 | 131.33 | B | N |
| ATOM | 2795 | CA | GLU | B | 168 | 11.119 | 13.991 | 46.126 | 1.00 | 128.96 | B | C |
| ATOM | 2796 | CB | GLU | B | 168 | 11.189 | 15.524 | 45.986 | 1.00 | 132.26 | B | C |
| ATOM | 2797 | CG | GLU | B | 168 | 12.602 | 16.105 | 45.894 | 1.00 | 136.32 | B | C |
| ATOM | 2798 | CD | GLU | B | 168 | 13.399 | 16.025 | 47.200 | 1.00 | 138.39 | B | C |
| ATOM | 2799 | OE1 | GLU | B | 168 | 12.797 | 16.080 | 48.299 | 1.00 | 138.49 | B | O |
| ATOM | 2800 | OE2 | GLU | B | 168 | 14.645 | 15.914 | 47.129 | 1.00 | 138.47 | B | O |
| ATOM | 2801 | C | GLU | B | 168 | 10.026 | 13.583 | 47.128 | 1.00 | 123.48 | B | C |
| ATOM | 2802 | O | GLU | B | 168 | 9.061 | 14.326 | 47.314 | 1.00 | 125.00 | B | O |
| ATOM | 2803 | N | PRO | B | 169 | 10.174 | 12.415 | 47.770 | 1.00 | 117.59 | B | N |
| ATOM | 2804 | CA | PRO | B | 169 | 9.169 | 11.894 | 48.718 | 1.00 | 112.28 | B | C |
| ATOM | 2805 | CB | PRO | B | 169 | 9.774 | 10.558 | 49.172 | 1.00 | 113.47 | B | C |
| ATOM | 2806 | CG | PRO | B | 169 | 10.708 | 10.189 | 48.084 | 1.00 | 115.63 | B | C |
| ATOM | 2807 | CD | PRO | B | 169 | 11.312 | 11.488 | 47.632 | 1.00 | 116.96 | B | C |
| ATOM | 2808 | C | PRO | B | 169 | 8.912 | 12.782 | 49.938 | 1.00 | 105.68 | B | C |
| ATOM | 2809 | O | PRO | B | 169 | 8.082 | 12.436 | 50.783 | 1.00 | 101.38 | B | O |
| ATOM | 2810 | N | SER | B | 170 | 9.621 | 13.905 | 50.011 | 1.00 | 102.05 | B | N |
| ATOM | 2811 | CA | SER | B | 170 | 9.467 | 14.878 | 51.087 | 1.00 | 97.82 | B | C |
| ATOM | 2812 | CB | SER | B | 170 | 10.746 | 15.715 | 51.247 | 1.00 | 99.30 | B | C |
| ATOM | 2813 | OG | SER | B | 170 | 11.837 | 15.150 | 50.530 | 1.00 | 100.06 | B | O |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 2814 | C | SER | B | 170 | 8.279 | 15.796 | 50.826 | 1.00 | 91.37 | B | C |
| ATOM | 2815 | O | SER | B | 170 | 7.655 | 16.293 | 51.766 | 1.00 | 91.05 | B | O |
| ATOM | 2816 | N | GLN | B | 171 | 7.976 | 16.008 | 49.547 | 1.00 | 83.23 | B | N |
| ATOM | 2817 | CA | GLN | B | 171 | 6.943 | 16.955 | 49.132 | 1.00 | 78.78 | B | C |
| ATOM | 2818 | CB | GLN | B | 171 | 7.286 | 17.565 | 47.768 | 1.00 | 82.89 | B | C |
| ATOM | 2819 | CG | GLN | B | 171 | 8.143 | 18.836 | 47.832 | 1.00 | 84.78 | B | C |
| ATOM | 2820 | CD | GLN | B | 171 | 7.735 | 19.785 | 48.947 | 1.00 | 85.40 | B | C |
| ATOM | 2821 | OE1 | GLN | B | 171 | 8.498 | 19.992 | 49.901 | 1.00 | 87.87 | B | O |
| ATOM | 2822 | NE2 | GLN | B | 171 | 6.535 | 20.362 | 48.837 | 1.00 | 82.96 | B | N |
| ATOM | 2823 | C | GLN | B | 171 | 5.544 | 16.347 | 49.096 | 1.00 | 72.27 | B | C |
| ATOM | 2824 | O | GLN | B | 171 | 5.398 | 15.122 | 49.101 | 1.00 | 73.45 | B | O |
| ATOM | 2825 | N | CYS | B | 172 | 4.525 | 17.211 | 49.084 | 1.00 | 62.06 | B | N |
| ATOM | 2826 | CA | CYS | B | 172 | 3.137 | 16.774 | 49.018 | 1.00 | 54.69 | B | C |
| ATOM | 2827 | CB | CYS | B | 172 | 2.534 | 16.578 | 50.395 | 1.00 | 52.71 | B | C |
| ATOM | 2828 | SG | CYS | B | 172 | 0.962 | 15.724 | 50.194 | 1.00 | 58.58 | B | S |
| ATOM | 2829 | C | CYS | B | 172 | 2.262 | 17.745 | 48.256 | 1.00 | 53.37 | B | C |
| ATOM | 2830 | O | CYS | B | 172 | 1.546 | 18.567 | 48.852 | 1.00 | 58.82 | B | O |
| ATOM | 2831 | N | PRO | B | 173 | 2.286 | 17.643 | 46.940 | 1.00 | 43.62 | B | N |
| ATOM | 2832 | CA | PRO | B | 173 | 1.628 | 18.638 | 46.099 | 1.00 | 40.98 | B | C |
| ATOM | 2833 | CB | PRO | B | 173 | 2.383 | 18.530 | 44.780 | 1.00 | 34.49 | B | C |
| ATOM | 2834 | CG | PRO | B | 173 | 3.372 | 17.483 | 45.011 | 1.00 | 38.66 | B | C |
| ATOM | 2835 | CD | PRO | B | 173 | 2.918 | 16.594 | 46.144 | 1.00 | 37.31 | B | C |
| ATOM | 2836 | C | PRO | B | 173 | 0.165 | 18.283 | 45.914 | 1.00 | 43.04 | B | C |
| ATOM | 2837 | O | PRO | B | 173 | −0.543 | 18.973 | 45.190 | 1.00 | 48.61 | B | O |
| ATOM | 2838 | N | ASP | B | 174 | −0.292 | 17.214 | 46.545 | 1.00 | 39.17 | B | N |
| ATOM | 2839 | CA | ASP | B | 174 | −1.687 | 16.864 | 46.402 | 1.00 | 40.82 | B | C |
| ATOM | 2840 | CB | ASP | B | 174 | −1.864 | 15.373 | 46.099 | 1.00 | 43.79 | B | C |
| ATOM | 2841 | CG | ASP | B | 174 | −1.166 | 14.936 | 44.828 | 1.00 | 45.66 | B | C |
| ATOM | 2842 | OD1 | ASP | B | 174 | −1.259 | 15.623 | 43.779 | 1.00 | 46.41 | B | O |
| ATOM | 2843 | OD2 | ASP | B | 174 | −0.500 | 13.890 | 44.796 | 1.00 | 48.95 | B | O |
| ATOM | 2844 | C | ASP | B | 174 | −2.379 | 17.257 | 47.692 | 1.00 | 42.23 | B | C |
| ATOM | 2845 | O | ASP | B | 174 | −3.600 | 17.080 | 47.851 | 1.00 | 46.03 | B | O |
| ATOM | 2846 | N | CYS | B | 175 | −1.574 | 17.773 | 48.614 | 1.00 | 38.28 | B | N |
| ATOM | 2847 | CA | CYS | B | 175 | −2.068 | 18.295 | 49.860 | 1.00 | 42.16 | B | C |
| ATOM | 2848 | CB | CYS | B | 175 | −1.022 | 18.087 | 50.935 | 1.00 | 47.27 | B | C |
| ATOM | 2849 | SG | CYS | B | 175 | −0.658 | 16.364 | 51.258 | 1.00 | 53.13 | B | S |
| ATOM | 2850 | C | CYS | B | 175 | −2.297 | 19.784 | 49.650 | 1.00 | 44.67 | B | C |
| ATOM | 2851 | O | CYS | B | 175 | −1.408 | 20.606 | 49.901 | 1.00 | 54.11 | B | O |
| ATOM | 2852 | N | VAL | B | 176 | −3.482 | 20.140 | 49.180 | 1.00 | 37.73 | B | N |
| ATOM | 2853 | CA | VAL | B | 176 | −3.695 | 21.490 | 48.729 | 1.00 | 37.04 | B | C |
| ATOM | 2854 | CB | VAL | B | 176 | −4.755 | 21.583 | 47.637 | 1.00 | 34.29 | B | C |
| ATOM | 2855 | CG1 | VAL | B | 176 | −4.717 | 22.976 | 47.038 | 1.00 | 36.64 | B | C |
| ATOM | 2856 | CG2 | VAL | B | 176 | −4.550 | 20.534 | 46.565 | 1.00 | 26.75 | B | C |
| ATOM | 2857 | C | VAL | B | 176 | −4.146 | 22.382 | 49.855 | 1.00 | 45.28 | B | C |
| ATOM | 2858 | O | VAL | B | 176 | −3.530 | 23.396 | 50.115 | 1.00 | 54.88 | B | O |
| ATOM | 2859 | N | VAL | B | 177 | −5.224 | 22.006 | 50.523 | 1.00 | 44.67 | B | N |
| ATOM | 2860 | CA | VAL | B | 177 | −5.956 | 22.942 | 51.359 | 1.00 | 41.51 | B | C |
| ATOM | 2861 | CB | VAL | B | 177 | −7.431 | 22.706 | 51.098 | 1.00 | 39.22 | B | C |
| ATOM | 2862 | CG1 | VAL | B | 177 | −8.169 | 22.253 | 52.331 | 1.00 | 35.75 | B | C |
| ATOM | 2863 | CG2 | VAL | B | 177 | −8.037 | 23.920 | 50.460 | 1.00 | 42.41 | B | C |
| ATOM | 2864 | C | VAL | B | 177 | −5.591 | 22.820 | 52.851 | 1.00 | 48.49 | B | C |
| ATOM | 2865 | O | VAL | B | 177 | −5.154 | 21.755 | 53.307 | 1.00 | 55.50 | B | O |
| ATOM | 2866 | N | SER | B | 178 | −5.731 | 23.902 | 53.617 | 1.00 | 45.01 | B | N |
| ATOM | 2867 | CA | SER | B | 178 | −5.509 | 23.797 | 55.065 | 1.00 | 39.42 | B | C |
| ATOM | 2868 | CB | SER | B | 178 | −4.477 | 24.797 | 55.579 | 1.00 | 36.20 | B | C |
| ATOM | 2869 | OG | SER | B | 178 | −4.842 | 25.259 | 56.871 | 1.00 | 38.11 | B | O |
| ATOM | 2870 | C | SER | B | 178 | −6.788 | 23.898 | 55.892 | 1.00 | 40.49 | B | C |
| ATOM | 2871 | O | SER | B | 178 | −7.555 | 24.883 | 55.817 | 1.00 | 37.91 | B | O |
| ATOM | 2872 | N | ALA | B | 179 | −6.974 | 22.855 | 56.695 | 1.00 | 39.49 | B | N |
| ATOM | 2873 | CA | ALA | B | 179 | −8.061 | 22.723 | 57.648 | 1.00 | 31.63 | B | C |
| ATOM | 2874 | CB | ALA | B | 179 | −7.722 | 21.632 | 58.655 | 1.00 | 37.29 | B | C |
| ATOM | 2875 | C | ALA | B | 179 | −8.317 | 24.010 | 58.378 | 1.00 | 28.72 | B | C |
| ATOM | 2876 | O | ALA | B | 179 | −9.466 | 24.300 | 58.740 | 1.00 | 30.40 | B | O |
| ATOM | 2877 | N | LEU | B | 180 | −7.261 | 24.782 | 58.618 | 1.00 | 26.42 | B | N |
| ATOM | 2878 | CA | LEU | B | 180 | −7.440 | 25.993 | 59.412 | 1.00 | 36.32 | B | C |
| ATOM | 2879 | CB | LEU | B | 180 | −6.543 | 26.006 | 60.657 | 1.00 | 37.97 | B | C |
| ATOM | 2880 | CG | LEU | B | 180 | −5.100 | 25.527 | 60.601 | 1.00 | 33.91 | B | C |
| ATOM | 2881 | CD1 | LEU | B | 180 | −4.212 | 26.631 | 60.098 | 1.00 | 34.16 | B | C |
| ATOM | 2882 | CD2 | LEU | B | 180 | −4.722 | 25.159 | 61.992 | 1.00 | 30.99 | B | C |
| ATOM | 2883 | C | LEU | B | 180 | −7.329 | 27.285 | 58.632 | 1.00 | 40.07 | B | C |
| ATOM | 2884 | O | LEU | B | 180 | −6.853 | 28.295 | 59.161 | 1.00 | 39.73 | B | O |
| ATOM | 2885 | N | GLY | B | 181 | −7.786 | 27.238 | 57.379 | 1.00 | 45.44 | B | N |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 2886 | CA | GLY | B | 181 | −7.998 | 28.425 | 56.567 | 1.00 | 44.24 | B | C |
| ATOM | 2887 | C | GLY | B | 181 | −7.245 | 28.363 | 55.268 | 1.00 | 41.77 | B | C |
| ATOM | 2888 | O | GLY | B | 181 | −6.011 | 28.299 | 55.287 | 1.00 | 40.12 | B | O |
| ATOM | 2889 | N | ALA | B | 182 | −7.990 | 28.386 | 54.155 | 1.00 | 42.59 | B | N |
| ATOM | 2890 | CA | ALA | B | 182 | −7.435 | 28.343 | 52.783 | 1.00 | 33.05 | B | C |
| ATOM | 2891 | CB | ALA | B | 182 | −7.517 | 26.957 | 52.252 | 1.00 | 25.62 | B | C |
| ATOM | 2892 | C | ALA | B | 182 | −8.184 | 29.261 | 51.846 | 1.00 | 34.56 | B | C |
| ATOM | 2893 | O | ALA | B | 182 | −9.386 | 29.476 | 52.023 | 1.00 | 44.68 | B | O |
| ATOM | 2894 | N | LYS | B | 183 | −7.490 | 29.813 | 50.859 | 1.00 | 33.14 | B | N |
| ATOM | 2895 | CA | LYS | B | 183 | −8.171 | 30.373 | 49.678 | 1.00 | 36.30 | B | C |
| ATOM | 2896 | CB | LYS | B | 183 | −8.171 | 31.896 | 49.646 | 1.00 | 39.28 | B | C |
| ATOM | 2897 | CG | LYS | B | 183 | −9.279 | 32.532 | 50.470 | 1.00 | 49.30 | B | C |
| ATOM | 2898 | CD | LYS | B | 183 | −10.623 | 32.584 | 49.732 | 1.00 | 58.73 | B | C |
| ATOM | 2899 | CE | LYS | B | 183 | −11.785 | 32.976 | 50.668 | 1.00 | 61.53 | B | C |
| ATOM | 2900 | NZ | LYS | B | 183 | −11.672 | 32.401 | 52.056 | 1.00 | 62.38 | B | N |
| ATOM | 2901 | C | LYS | B | 183 | −7.520 | 29.845 | 48.426 | 1.00 | 35.29 | B | C |
| ATOM | 2902 | O | LYS | B | 183 | −6.299 | 29.836 | 48.290 | 1.00 | 36.47 | B | O |
| ATOM | 2903 | N | VAL | B | 184 | −8.348 | 29.379 | 47.514 | 1.00 | 33.14 | B | N |
| ATOM | 2904 | CA | VAL | B | 184 | −7.855 | 28.698 | 46.337 | 1.00 | 27.03 | B | C |
| ATOM | 2905 | CB | VAL | B | 184 | −8.357 | 27.264 | 46.296 | 1.00 | 24.13 | B | C |
| ATOM | 2906 | CG1 | VAL | B | 184 | −8.210 | 26.679 | 44.889 | 1.00 | 16.54 | B | C |
| ATOM | 2907 | CG2 | VAL | B | 184 | −7.609 | 26.438 | 47.354 | 1.00 | 23.45 | B | C |
| ATOM | 2908 | C | VAL | B | 184 | −8.371 | 29.406 | 45.143 | 1.00 | 25.71 | B | C |
| ATOM | 2909 | O | VAL | B | 184 | −9.561 | 29.648 | 45.032 | 1.00 | 31.46 | B | O |
| ATOM | 2910 | N | LEU | B | 185 | −7.478 | 29.742 | 44.239 | 1.00 | 29.38 | B | N |
| ATOM | 2911 | CA | LEU | B | 185 | −7.882 | 30.436 | 43.041 | 1.00 | 36.04 | B | C |
| ATOM | 2912 | CB | LEU | B | 185 | −7.410 | 31.880 | 43.129 | 1.00 | 33.81 | B | C |
| ATOM | 2913 | CG | LEU | B | 185 | −7.123 | 32.673 | 41.874 | 1.00 | 41.23 | B | C |
| ATOM | 2914 | CD1 | LEU | B | 185 | −8.215 | 32.469 | 40.836 | 1.00 | 52.79 | B | C |
| ATOM | 2915 | CD2 | LEU | B | 185 | −7.011 | 34.133 | 42.222 | 1.00 | 41.51 | B | C |
| ATOM | 2916 | C | LEU | B | 185 | −7.276 | 29.681 | 41.879 | 1.00 | 40.80 | B | C |
| ATOM | 2917 | O | LEU | B | 185 | −6.076 | 29.432 | 41.876 | 1.00 | 49.60 | B | O |
| ATOM | 2918 | N | SER | B | 186 | −8.097 | 29.275 | 40.916 | 1.00 | 41.06 | B | N |
| ATOM | 2919 | CA | SER | B | 186 | −7.589 | 28.435 | 39.828 | 1.00 | 48.57 | B | C |
| ATOM | 2920 | CB | SER | B | 186 | −8.332 | 27.076 | 39.747 | 1.00 | 55.01 | B | C |
| ATOM | 2921 | OG | SER | B | 186 | −8.931 | 26.835 | 38.468 | 1.00 | 54.97 | B | O |
| ATOM | 2922 | C | SER | B | 186 | −7.712 | 29.173 | 38.536 | 1.00 | 46.06 | B | C |
| ATOM | 2923 | O | SER | B | 186 | −8.736 | 29.782 | 38.294 | 1.00 | 55.39 | B | O |
| ATOM | 2924 | N | SER | B | 187 | −6.687 | 29.108 | 37.703 | 1.00 | 42.07 | B | N |
| ATOM | 2925 | CA | SER | B | 187 | −6.729 | 29.786 | 36.412 | 1.00 | 46.72 | B | C |
| ATOM | 2926 | CB | SER | B | 187 | −6.203 | 31.218 | 36.557 | 1.00 | 49.29 | B | C |
| ATOM | 2927 | OG | SER | B | 187 | −4.809 | 31.325 | 36.265 | 1.00 | 54.33 | B | O |
| ATOM | 2928 | C | SER | B | 187 | −5.955 | 29.025 | 35.334 | 1.00 | 49.35 | B | C |
| ATOM | 2929 | O | SER | B | 187 | −4.938 | 28.385 | 35.628 | 1.00 | 54.65 | B | O |
| ATOM | 2930 | N | VAL | B | 188 | −6.424 | 29.089 | 34.090 | 1.00 | 44.80 | B | N |
| ATOM | 2931 | CA | VAL | B | 188 | −5.719 | 28.408 | 33.005 | 1.00 | 45.35 | B | C |
| ATOM | 2932 | CB | VAL | B | 188 | −6.627 | 28.078 | 31.861 | 1.00 | 44.43 | B | C |
| ATOM | 2933 | CG1 | VAL | B | 188 | −6.399 | 26.680 | 31.421 | 1.00 | 45.45 | B | C |
| ATOM | 2934 | CG2 | VAL | B | 188 | −8.064 | 28.268 | 32.285 | 1.00 | 53.50 | B | C |
| ATOM | 2935 | C | VAL | B | 188 | −4.623 | 29.292 | 32.474 | 1.00 | 49.38 | B | C |
| ATOM | 2936 | O | VAL | B | 188 | −4.833 | 30.475 | 32.252 | 1.00 | 52.76 | B | O |
| ATOM | 2937 | N | LYS | B | 189 | −3.446 | 28.718 | 32.290 | 1.00 | 55.20 | B | N |
| ATOM | 2938 | CA | LYS | B | 189 | −2.282 | 29.477 | 31.849 | 1.00 | 61.71 | B | C |
| ATOM | 2939 | CB | LYS | B | 189 | −1.688 | 30.298 | 33.006 | 1.00 | 68.93 | B | C |
| ATOM | 2940 | CG | LYS | B | 189 | −0.918 | 31.531 | 32.551 | 1.00 | 78.03 | B | C |
| ATOM | 2941 | CD | LYS | B | 189 | −1.587 | 32.825 | 33.019 | 1.00 | 85.92 | B | C |
| ATOM | 2942 | CE | LYS | B | 189 | −1.457 | 33.948 | 31.964 | 1.00 | 88.26 | B | C |
| ATOM | 2943 | NZ | LYS | B | 189 | −0.885 | 35.223 | 32.509 | 1.00 | 87.34 | B | N |
| ATOM | 2944 | C | LYS | B | 189 | −1.240 | 28.541 | 31.221 | 1.00 | 60.86 | B | C |
| ATOM | 2945 | O | LYS | B | 189 | −0.802 | 27.544 | 31.834 | 1.00 | 61.91 | B | O |
| ATOM | 2946 | N | ASP | B | 190 | −0.862 | 28.871 | 29.990 | 1.00 | 53.49 | B | N |
| ATOM | 2947 | CA | ASP | B | 190 | 0.075 | 28.068 | 29.222 | 1.00 | 48.50 | B | C |
| ATOM | 2948 | CB | ASP | B | 190 | 1.451 | 28.083 | 29.886 | 1.00 | 48.87 | B | C |
| ATOM | 2949 | CG | ASP | B | 190 | 2.270 | 29.280 | 29.461 | 1.00 | 54.63 | B | C |
| ATOM | 2950 | OD1 | ASP | B | 190 | 1.731 | 30.121 | 28.695 | 1.00 | 53.84 | B | O |
| ATOM | 2951 | OD2 | ASP | B | 190 | 3.456 | 29.469 | 29.832 | 1.00 | 59.09 | B | O |
| ATOM | 2952 | C | ASP | B | 190 | −0.403 | 26.646 | 28.931 | 1.00 | 45.42 | B | C |
| ATOM | 2953 | O | ASP | B | 190 | 0.397 | 25.728 | 28.833 | 1.00 | 45.42 | B | O |
| ATOM | 2954 | N | ARG | B | 191 | −1.709 | 26.484 | 28.754 | 1.00 | 43.30 | B | N |
| ATOM | 2955 | CA | ARG | B | 191 | −2.339 | 25.176 | 28.510 | 1.00 | 38.92 | B | C |
| ATOM | 2956 | CB | ARG | B | 191 | −1.695 | 24.424 | 27.338 | 1.00 | 34.43 | B | C |
| ATOM | 2957 | CG | ARG | B | 191 | −1.910 | 25.039 | 26.008 | 1.00 | 35.89 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 2958 | CD | ARG | B | 191 | −0.698 | 24.935 | 25.096 | 1.00 | 43.60 | B | C |
| ATOM | 2959 | NE | ARG | B | 191 | −0.925 | 25.495 | 23.757 | 1.00 | 45.85 | B | N |
| ATOM | 2960 | CZ | ARG | B | 191 | −1.912 | 25.130 | 22.943 | 1.00 | 43.18 | B | C |
| ATOM | 2961 | NH1 | ARG | B | 191 | −2.774 | 24.186 | 23.326 | 1.00 | 46.90 | B | N |
| ATOM | 2962 | NH2 | ARG | B | 191 | −2.043 | 25.713 | 21.758 | 1.00 | 36.04 | B | N |
| ATOM | 2963 | C | ARG | B | 191 | −2.367 | 24.276 | 29.731 | 1.00 | 40.27 | B | C |
| ATOM | 2964 | O | ARG | B | 191 | −2.762 | 23.103 | 29.627 | 1.00 | 49.44 | B | O |
| ATOM | 2965 | N | PHE | B | 192 | −1.928 | 24.799 | 30.876 | 1.00 | 37.02 | B | N |
| ATOM | 2966 | CA | PHE | B | 192 | −2.050 | 24.071 | 32.144 | 1.00 | 36.02 | B | C |
| ATOM | 2967 | CB | PHE | B | 192 | −0.697 | 24.004 | 32.864 | 1.00 | 38.65 | B | C |
| ATOM | 2968 | CG | PHE | B | 192 | 0.289 | 23.041 | 32.248 | 1.00 | 40.43 | B | C |
| ATOM | 2969 | CD1 | PHE | B | 192 | 1.555 | 23.467 | 31.890 | 1.00 | 45.65 | B | C |
| ATOM | 2970 | CE1 | PHE | B | 192 | 2.458 | 22.603 | 31.313 | 1.00 | 46.19 | B | C |
| ATOM | 2971 | CZ | PHE | B | 192 | 2.098 | 21.282 | 31.110 | 1.00 | 47.84 | B | C |
| ATOM | 2972 | CE2 | PHE | B | 192 | 0.863 | 20.841 | 31.484 | 1.00 | 42.36 | B | C |
| ATOM | 2973 | CD2 | PHE | B | 192 | −0.036 | 21.719 | 32.051 | 1.00 | 42.76 | B | C |
| ATOM | 2974 | C | PHE | B | 192 | −3.102 | 24.700 | 33.067 | 1.00 | 34.90 | B | C |
| ATOM | 2975 | O | PHE | B | 192 | −3.181 | 25.926 | 33.177 | 1.00 | 38.45 | B | O |
| ATOM | 2976 | N | ILE | B | 193 | −3.907 | 23.882 | 33.737 | 1.00 | 31.74 | B | N |
| ATOM | 2977 | CA | ILE | B | 193 | −4.689 | 24.404 | 34.873 | 1.00 | 36.25 | B | C |
| ATOM | 2978 | CB | ILE | B | 193 | −5.808 | 23.415 | 35.237 | 1.00 | 31.14 | B | C |
| ATOM | 2979 | CG1 | ILE | B | 193 | −6.790 | 23.305 | 34.079 | 1.00 | 34.97 | B | C |
| ATOM | 2980 | CD1 | ILE | B | 193 | −7.471 | 21.956 | 33.991 | 1.00 | 36.83 | B | C |
| ATOM | 2981 | CG2 | ILE | B | 193 | −6.500 | 23.822 | 36.511 | 1.00 | 20.62 | B | C |
| ATOM | 2982 | C | ILE | B | 193 | −3.787 | 24.730 | 36.120 | 1.00 | 42.24 | B | C |
| ATOM | 2983 | O | ILE | B | 193 | −3.135 | 23.840 | 36.702 | 1.00 | 40.91 | B | O |
| ATOM | 2984 | N | ASN | B | 194 | −3.738 | 26.002 | 36.516 | 1.00 | 42.02 | B | N |
| ATOM | 2985 | CA | ASN | B | 194 | −2.909 | 26.409 | 37.652 | 1.00 | 42.83 | B | C |
| ATOM | 2986 | CB | ASN | B | 194 | −2.082 | 27.642 | 37.304 | 1.00 | 48.68 | B | C |
| ATOM | 2987 | CG | ASN | B | 194 | −1.103 | 27.389 | 36.187 | 1.00 | 55.84 | B | C |
| ATOM | 2988 | OD1 | ASN | B | 194 | −0.970 | 26.269 | 35.705 | 1.00 | 57.27 | B | O |
| ATOM | 2989 | ND2 | ASN | B | 194 | −0.410 | 28.440 | 35.760 | 1.00 | 61.82 | B | N |
| ATOM | 2990 | C | ASN | B | 194 | −3.715 | 26.709 | 38.903 | 1.00 | 42.86 | B | C |
| ATOM | 2991 | O | ASN | B | 194 | −4.787 | 27.324 | 38.830 | 1.00 | 46.24 | B | O |
| ATOM | 2992 | N | PHE | B | 195 | −3.187 | 26.291 | 40.049 | 1.00 | 35.15 | B | N |
| ATOM | 2993 | CA | PHE | B | 195 | −3.822 | 26.562 | 41.315 | 1.00 | 32.96 | B | C |
| ATOM | 2994 | CB | PHE | B | 195 | −4.081 | 25.255 | 42.030 | 1.00 | 35.85 | B | C |
| ATOM | 2995 | CG | PHE | B | 195 | −5.338 | 24.580 | 41.616 | 1.00 | 43.13 | B | C |
| ATOM | 2996 | CD1 | PHE | B | 195 | −5.585 | 24.281 | 40.269 | 1.00 | 44.31 | B | C |
| ATOM | 2997 | CE1 | PHE | B | 195 | −6.752 | 23.637 | 39.882 | 1.00 | 40.86 | B | C |
| ATOM | 2998 | CZ | PHE | B | 195 | −7.688 | 23.277 | 40.837 | 1.00 | 41.96 | B | C |
| ATOM | 2999 | CE2 | PHE | B | 195 | −7.455 | 23.559 | 42.189 | 1.00 | 44.66 | B | C |
| ATOM | 3000 | CD2 | PHE | B | 195 | −6.279 | 24.212 | 42.571 | 1.00 | 44.66 | B | C |
| ATOM | 3001 | C | PHE | B | 195 | −2.944 | 27.435 | 42.182 | 1.00 | 36.69 | B | C |
| ATOM | 3002 | O | PHE | B | 195 | −1.861 | 27.012 | 42.615 | 1.00 | 46.03 | B | O |
| ATOM | 3003 | N | PHE | B | 196 | −3.411 | 28.646 | 42.453 | 1.00 | 35.16 | B | N |
| ATOM | 3004 | CA | PHE | B | 196 | −2.778 | 29.532 | 43.434 | 1.00 | 34.28 | B | C |
| ATOM | 3005 | CB | PHE | B | 196 | −2.859 | 30.958 | 42.956 | 1.00 | 32.45 | B | C |
| ATOM | 3006 | CG | PHE | B | 196 | −2.313 | 31.131 | 41.592 | 1.00 | 38.26 | B | C |
| ATOM | 3007 | CD1 | PHE | B | 196 | −3.085 | 30.853 | 40.487 | 1.00 | 36.46 | B | C |
| ATOM | 3008 | CE1 | PHE | B | 196 | −2.575 | 30.991 | 39.225 | 1.00 | 35.74 | B | C |
| ATOM | 3009 | CZ | PHE | B | 196 | −1.284 | 31.407 | 39.044 | 1.00 | 38.69 | B | C |
| ATOM | 3010 | CE2 | PHE | B | 196 | −0.493 | 31.692 | 40.128 | 1.00 | 41.38 | B | C |
| ATOM | 3011 | CD2 | PHE | B | 196 | −1.005 | 31.537 | 41.405 | 1.00 | 42.89 | B | C |
| ATOM | 3012 | C | PHE | B | 196 | −3.505 | 29.387 | 44.741 | 1.00 | 34.55 | B | C |
| ATOM | 3013 | O | PHE | B | 196 | −4.728 | 29.351 | 44.751 | 1.00 | 40.48 | B | O |
| ATOM | 3014 | N | VAL | B | 197 | −2.768 | 29.294 | 45.841 | 1.00 | 32.43 | B | N |
| ATOM | 3015 | CA | VAL | B | 197 | −3.370 | 28.869 | 47.102 | 1.00 | 34.63 | B | C |
| ATOM | 3016 | CB | VAL | B | 197 | −3.238 | 27.343 | 47.287 | 1.00 | 35.94 | B | C |
| ATOM | 3017 | CG1 | VAL | B | 197 | −3.680 | 26.939 | 48.697 | 1.00 | 34.44 | B | C |
| ATOM | 3018 | CG2 | VAL | B | 197 | −3.983 | 26.585 | 46.213 | 1.00 | 32.05 | B | C |
| ATOM | 3019 | C | VAL | B | 197 | −2.785 | 29.509 | 48.363 | 1.00 | 37.15 | B | C |
| ATOM | 3020 | O | VAL | B | 197 | −1.611 | 29.267 | 48.738 | 1.00 | 41.19 | B | O |
| ATOM | 3021 | N | GLY | B | 198 | −3.631 | 30.281 | 49.039 | 1.00 | 34.43 | B | N |
| ATOM | 3022 | CA | GLY | B | 198 | −3.318 | 30.808 | 50.360 | 1.00 | 34.89 | B | C |
| ATOM | 3023 | C | GLY | B | 198 | −3.738 | 29.863 | 51.478 | 1.00 | 31.71 | B | C |
| ATOM | 3024 | O | GLY | B | 198 | −4.881 | 29.383 | 51.514 | 1.00 | 30.34 | B | O |
| ATOM | 3025 | N | ASN | B | 199 | −2.824 | 29.609 | 52.406 | 1.00 | 28.72 | B | N |
| ATOM | 3026 | CA | ASN | B | 199 | −3.102 | 28.668 | 53.473 | 1.00 | 33.64 | B | C |
| ATOM | 3027 | CB | ASN | B | 199 | −2.558 | 27.282 | 53.117 | 1.00 | 32.78 | B | C |
| ATOM | 3028 | CG | ASN | B | 199 | −3.633 | 26.337 | 52.613 | 1.00 | 29.87 | B | C |
| ATOM | 3029 | OD1 | ASN | B | 199 | −4.780 | 26.423 | 53.010 | 1.00 | 31.50 | B | O |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 3030 ND2 | ASN | B | 199 | −3.254 | 25.417 | 51.756 | 1.00 | 26.99 | B | N |
| ATOM | 3031 C | ASN | B | 199 | −2.536 | 29.117 | 54.804 | 1.00 | 40.81 | B | C |
| ATOM | 3032 O | ASN | B | 199 | −1.316 | 29.309 | 54.934 | 1.00 | 45.86 | B | O |
| ATOM | 3033 N | THR | B | 200 | −3.430 | 29.295 | 55.781 | 1.00 | 41.96 | B | N |
| ATOM | 3034 CA | THR | B | 200 | −3.038 | 29.525 | 57.172 | 1.00 | 45.39 | B | C |
| ATOM | 3035 CB | THR | B | 200 | −4.233 | 29.913 | 58.008 | 1.00 | 47.52 | B | C |
| ATOM | 3036 OG1 | THR | B | 200 | −5.152 | 30.661 | 57.188 | 1.00 | 58.61 | B | O |
| ATOM | 3037 CG2 | THR | B | 200 | −3.811 | 30.890 | 59.076 | 1.00 | 39.80 | B | C |
| ATOM | 3038 C | THR | B | 200 | −2.456 | 28.243 | 57.701 | 1.00 | 47.44 | B | C |
| ATOM | 3039 O | THR | B | 200 | −2.978 | 27.164 | 57.436 | 1.00 | 50.95 | B | O |
| ATOM | 3040 N | ILE | B | 201 | −1.373 | 28.363 | 58.454 | 1.00 | 47.30 | B | N |
| ATOM | 3041 CA | ILE | B | 201 | −0.518 | 27.220 | 58.734 | 1.00 | 46.34 | B | C |
| ATOM | 3042 CB | ILE | B | 201 | 0.588 | 27.217 | 57.680 | 1.00 | 39.76 | B | C |
| ATOM | 3043 CG1 | ILE | B | 201 | 0.408 | 26.018 | 56.782 | 1.00 | 39.93 | B | C |
| ATOM | 3044 CD1 | ILE | B | 201 | 1.659 | 25.680 | 56.053 | 1.00 | 45.00 | B | C |
| ATOM | 3045 CG2 | ILE | B | 201 | 1.989 | 27.282 | 58.274 | 1.00 | 39.70 | B | C |
| ATOM | 3046 C | ILE | B | 201 | −0.011 | 27.238 | 60.189 | 1.00 | 56.10 | B | C |
| ATOM | 3047 O | ILE | B | 201 | 0.285 | 28.317 | 60.734 | 1.00 | 61.66 | B | O |
| ATOM | 3048 N | ASN | B | 202 | 0.057 | 26.066 | 60.832 | 1.00 | 58.28 | B | N |
| ATOM | 3049 CA | ASN | B | 202 | 0.121 | 26.055 | 62.299 | 1.00 | 60.14 | B | C |
| ATOM | 3050 CB | ASN | B | 202 | −1.312 | 26.021 | 62.917 | 1.00 | 59.83 | B | C |
| ATOM | 3051 CG | ASN | B | 202 | −1.615 | 24.758 | 63.742 | 1.00 | 58.90 | B | C |
| ATOM | 3052 OD1 | ASN | B | 202 | −1.394 | 23.622 | 63.302 | 1.00 | 56.49 | B | O |
| ATOM | 3053 ND2 | ASN | B | 202 | −2.175 | 24.968 | 64.938 | 1.00 | 58.00 | B | N |
| ATOM | 3054 C | ASN | B | 202 | 1.150 | 25.162 | 62.990 | 1.00 | 63.14 | B | C |
| ATOM | 3055 O | ASN | B | 202 | 1.034 | 24.872 | 64.185 | 1.00 | 67.58 | B | O |
| ATOM | 3056 N | SER | B | 203 | 2.175 | 24.754 | 62.246 | 1.00 | 63.26 | B | N |
| ATOM | 3057 CA | SER | B | 203 | 3.317 | 24.005 | 62.820 | 1.00 | 62.77 | B | C |
| ATOM | 3058 CB | SER | B | 203 | 4.094 | 24.825 | 63.884 | 1.00 | 59.71 | B | C |
| ATOM | 3059 OG | SER | B | 203 | 4.057 | 24.247 | 65.182 | 1.00 | 52.81 | B | O |
| ATOM | 3060 C | SER | B | 203 | 3.024 | 22.603 | 63.340 | 1.00 | 60.77 | B | C |
| ATOM | 3061 O | SER | B | 203 | 3.886 | 22.003 | 63.963 | 1.00 | 60.35 | B | O |
| ATOM | 3062 N | SER | B | 204 | 1.828 | 22.082 | 63.095 | 1.00 | 64.29 | B | N |
| ATOM | 3063 CA | SER | B | 204 | 1.629 | 20.645 | 63.172 | 1.00 | 72.70 | B | C |
| ATOM | 3064 CB | SER | B | 204 | 0.170 | 20.260 | 62.914 | 1.00 | 70.92 | B | C |
| ATOM | 3065 OG | SER | B | 204 | −0.727 | 21.224 | 63.436 | 1.00 | 68.03 | B | O |
| ATOM | 3066 C | SER | B | 204 | 2.581 | 20.019 | 62.136 | 1.00 | 84.48 | B | C |
| ATOM | 3067 O | SER | B | 204 | 2.212 | 19.746 | 60.982 | 1.00 | 85.81 | B | O |
| ATOM | 3068 N | TYR | B | 205 | 3.832 | 19.864 | 62.566 | 1.00 | 95.91 | B | N |
| ATOM | 3069 CA | TYR | B | 205 | 4.895 | 19.220 | 61.807 | 1.00 | 106.72 | B | C |
| ATOM | 3070 CB | TYR | B | 205 | 6.069 | 18.915 | 62.756 | 1.00 | 109.83 | B | C |
| ATOM | 3071 CG | TYR | B | 205 | 7.343 | 18.333 | 62.153 | 1.00 | 112.86 | B | C |
| ATOM | 3072 CD1 | TYR | B | 205 | 8.575 | 18.553 | 62.772 | 1.00 | 114.06 | B | C |
| ATOM | 3073 CE1 | TYR | B | 205 | 9.751 | 18.026 | 62.250 | 1.00 | 116.83 | B | C |
| ATOM | 3074 CZ | TYR | B | 205 | 9.705 | 17.260 | 61.091 | 1.00 | 118.54 | B | C |
| ATOM | 3075 OH | TYR | B | 205 | 10.874 | 16.739 | 60.576 | 1.00 | 120.05 | B | O |
| ATOM | 3076 CE2 | TYR | B | 205 | 8.492 | 17.021 | 60.453 | 1.00 | 116.68 | B | C |
| ATOM | 3077 CD2 | TYR | B | 205 | 7.322 | 17.551 | 60.989 | 1.00 | 114.93 | B | C |
| ATOM | 3078 C | TYR | B | 205 | 4.341 | 17.935 | 61.217 | 1.00 | 112.90 | B | C |
| ATOM | 3079 O | TYR | B | 205 | 4.270 | 16.905 | 61.896 | 1.00 | 115.51 | B | O |
| ATOM | 3080 N | PHE | B | 206 | 3.919 | 18.008 | 59.961 | 1.00 | 117.30 | B | N |
| ATOM | 3081 CA | PHE | B | 206 | 3.410 | 16.828 | 59.285 | 1.00 | 121.57 | B | C |
| ATOM | 3082 CB | PHE | B | 206 | 2.037 | 17.095 | 58.643 | 1.00 | 123.14 | B | C |
| ATOM | 3083 CG | PHE | B | 206 | 1.039 | 15.987 | 58.866 | 1.00 | 125.12 | B | C |
| ATOM | 3084 CD1 | PHE | B | 206 | −0.091 | 16.199 | 59.645 | 1.00 | 125.23 | B | C |
| ATOM | 3085 CE1 | PHE | B | 206 | −1.021 | 15.174 | 59.859 | 1.00 | 125.71 | B | C |
| ATOM | 3086 CZ | PHE | B | 206 | −0.813 | 13.916 | 59.297 | 1.00 | 126.53 | B | C |
| ATOM | 3087 CE2 | PHE | B | 206 | 0.320 | 13.686 | 58.522 | 1.00 | 127.26 | B | C |
| ATOM | 3088 CD2 | PHE | B | 206 | 1.239 | 14.721 | 58.311 | 1.00 | 126.85 | B | C |
| ATOM | 3089 C | PHE | B | 206 | 4.423 | 16.269 | 58.276 | 1.00 | 122.66 | B | C |
| ATOM | 3090 O | PHE | B | 206 | 4.653 | 16.856 | 57.213 | 1.00 | 124.48 | B | O |
| ATOM | 3091 N | PRO | B | 207 | 5.070 | 15.165 | 58.637 | 1.00 | 121.91 | B | N |
| ATOM | 3092 CA | PRO | B | 207 | 5.781 | 14.346 | 57.654 | 1.00 | 121.85 | B | C |
| ATOM | 3093 CB | PRO | B | 207 | 6.900 | 13.697 | 58.481 | 1.00 | 122.51 | B | C |
| ATOM | 3094 CG | PRO | B | 207 | 6.437 | 13.761 | 59.928 | 1.00 | 122.28 | B | C |
| ATOM | 3095 CD | PRO | B | 207 | 5.209 | 14.630 | 60.004 | 1.00 | 121.65 | B | C |
| ATOM | 3096 C | PRO | B | 207 | 4.837 | 13.279 | 57.071 | 1.00 | 120.05 | B | C |
| ATOM | 3097 O | PRO | B | 207 | 3.991 | 12.766 | 57.809 | 1.00 | 123.06 | B | O |
| ATOM | 3098 N | ASP | B | 208 | 4.919 | 12.989 | 55.774 | 1.00 | 113.77 | B | N |
| ATOM | 3099 CA | ASP | B | 208 | 5.694 | 13.766 | 54.818 | 1.00 | 107.36 | B | C |
| ATOM | 3100 CB | ASP | B | 208 | 6.502 | 12.826 | 53.907 | 1.00 | 109.81 | B | C |
| ATOM | 3101 CG | ASP | B | 208 | 7.957 | 12.657 | 54.354 | 1.00 | 109.55 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 3102 | OD1 | ASP | B | 208 | 8.743 | 13.626 | 54.253 | 1.00 | 109.43 | B | O |
| ATOM | 3103 | OD2 | ASP | B | 208 | 8.413 | 11.579 | 54.792 | 1.00 | 109.72 | B | O |
| ATOM | 3104 | C | ASP | B | 208 | 4.712 | 14.613 | 53.996 | 1.00 | 99.67 | B | C |
| ATOM | 3105 | O | ASP | B | 208 | 4.823 | 14.687 | 52.766 | 1.00 | 95.43 | B | O |
| ATOM | 3106 | N | HIS | B | 209 | 3.752 | 15.236 | 54.693 | 1.00 | 93.92 | B | N |
| ATOM | 3107 | CA | HIS | B | 209 | 2.711 | 16.084 | 54.078 | 1.00 | 87.26 | B | C |
| ATOM | 3108 | CB | HIS | B | 209 | 1.319 | 15.433 | 54.174 | 1.00 | 90.82 | B | C |
| ATOM | 3109 | CG | HIS | B | 209 | 1.304 | 13.957 | 53.923 | 1.00 | 94.92 | B | C |
| ATOM | 3110 | ND1 | HIS | B | 209 | 1.835 | 13.386 | 52.786 | 1.00 | 96.15 | B | N |
| ATOM | 3111 | CE1 | HIS | B | 209 | 1.675 | 12.076 | 52.837 | 1.00 | 99.11 | B | C |
| ATOM | 3112 | NE2 | HIS | B | 209 | 1.053 | 11.776 | 53.964 | 1.00 | 100.69 | B | N |
| ATOM | 3113 | CD2 | HIS | B | 209 | 0.807 | 12.936 | 54.660 | 1.00 | 97.75 | B | C |
| ATOM | 3114 | C | HIS | B | 209 | 2.629 | 17.493 | 54.684 | 1.00 | 76.18 | B | C |
| ATOM | 3115 | O | HIS | B | 209 | 1.686 | 17.796 | 55.418 | 1.00 | 70.71 | B | O |
| ATOM | 3116 | N | PRO | B | 210 | 3.580 | 18.372 | 54.372 | 1.00 | 71.36 | B | N |
| ATOM | 3117 | CA | PRO | B | 210 | 3.530 | 19.709 | 54.951 | 1.00 | 68.49 | B | C |
| ATOM | 3118 | CB | PRO | B | 210 | 4.960 | 20.231 | 54.763 | 1.00 | 67.93 | B | C |
| ATOM | 3119 | CG | PRO | B | 210 | 5.432 | 19.566 | 53.498 | 1.00 | 68.51 | B | C |
| ATOM | 3120 | CD | PRO | B | 210 | 4.711 | 18.230 | 53.430 | 1.00 | 70.48 | B | C |
| ATOM | 3121 | C | PRO | B | 210 | 2.541 | 20.492 | 54.105 | 1.00 | 67.58 | B | C |
| ATOM | 3122 | O | PRO | B | 210 | 2.049 | 20.000 | 53.077 | 1.00 | 69.65 | B | O |
| ATOM | 3123 | N | LEU | B | 211 | 2.231 | 21.697 | 54.548 | 1.00 | 59.38 | B | N |
| ATOM | 3124 | CA | LEU | B | 211 | 1.387 | 22.567 | 53.776 | 1.00 | 45.84 | B | C |
| ATOM | 3125 | CB | LEU | B | 211 | 0.122 | 22.858 | 54.570 | 1.00 | 37.57 | B | C |
| ATOM | 3126 | CG | LEU | B | 211 | −0.797 | 21.639 | 54.710 | 1.00 | 36.06 | B | C |
| ATOM | 3127 | CD1 | LEU | B | 211 | −2.121 | 22.022 | 55.306 | 1.00 | 41.90 | B | C |
| ATOM | 3128 | CD2 | LEU | B | 211 | −1.040 | 20.937 | 53.389 | 1.00 | 34.99 | B | C |
| ATOM | 3129 | C | LEU | B | 211 | 2.217 | 23.805 | 53.467 | 1.00 | 45.29 | B | C |
| ATOM | 3130 | O | LEU | B | 211 | 3.272 | 23.996 | 54.054 | 1.00 | 51.36 | B | O |
| ATOM | 3131 | N | HIS | B | 212 | 1.790 | 24.626 | 52.523 | 1.00 | 41.89 | B | N |
| ATOM | 3132 | CA | HIS | B | 212 | 2.529 | 25.838 | 52.252 | 1.00 | 40.20 | B | C |
| ATOM | 3133 | CB | HIS | B | 212 | 3.059 | 25.814 | 50.832 | 1.00 | 39.63 | B | C |
| ATOM | 3134 | CG | HIS | B | 212 | 3.964 | 24.671 | 50.553 | 1.00 | 37.59 | B | C |
| ATOM | 3135 | ND1 | HIS | B | 212 | 5.163 | 24.504 | 51.203 | 1.00 | 38.64 | B | N |
| ATOM | 3136 | CE1 | HIS | B | 212 | 5.752 | 23.408 | 50.758 | 1.00 | 41.59 | B | C |
| ATOM | 3137 | NE2 | HIS | B | 212 | 4.975 | 22.860 | 49.842 | 1.00 | 42.57 | B | N |
| ATOM | 3138 | CD2 | HIS | B | 212 | 3.847 | 23.631 | 49.698 | 1.00 | 40.72 | B | C |
| ATOM | 3139 | C | HIS | B | 212 | 1.644 | 27.056 | 52.444 | 1.00 | 45.66 | B | C |
| ATOM | 3140 | O | HIS | B | 212 | 0.419 | 26.959 | 52.320 | 1.00 | 50.32 | B | O |
| ATOM | 3141 | N | SER | B | 213 | 2.264 | 28.203 | 52.716 | 1.00 | 41.75 | B | N |
| ATOM | 3142 | CA | SER | B | 213 | 1.514 | 29.429 | 52.891 | 1.00 | 40.69 | B | C |
| ATOM | 3143 | CB | SER | B | 213 | 2.307 | 30.392 | 53.756 | 1.00 | 46.44 | B | C |
| ATOM | 3144 | OG | SER | B | 213 | 1.855 | 30.299 | 55.102 | 1.00 | 51.16 | B | O |
| ATOM | 3145 | C | SER | B | 213 | 0.983 | 30.071 | 51.585 | 1.00 | 39.99 | B | C |
| ATOM | 3146 | O | SER | B | 213 | −0.173 | 30.478 | 51.532 | 1.00 | 41.81 | B | O |
| ATOM | 3147 | N | ILE | B | 214 | 1.816 | 30.180 | 50.553 | 1.00 | 38.33 | B | N |
| ATOM | 3148 | CA | ILE | B | 214 | 1.346 | 30.452 | 49.180 | 1.00 | 37.83 | B | C |
| ATOM | 3149 | CB | ILE | B | 214 | 1.530 | 31.936 | 48.676 | 1.00 | 34.62 | B | C |
| ATOM | 3150 | CG1 | ILE | B | 214 | 2.868 | 32.534 | 49.139 | 1.00 | 42.04 | B | C |
| ATOM | 3151 | CD1 | ILE | B | 214 | 2.996 | 32.857 | 50.671 | 1.00 | 49.36 | B | C |
| ATOM | 3152 | CG2 | ILE | B | 214 | 0.270 | 32.808 | 48.863 | 1.00 | 25.30 | B | C |
| ATOM | 3153 | C | ILE | B | 214 | 2.169 | 29.595 | 48.260 | 1.00 | 40.06 | B | C |
| ATOM | 3154 | O | ILE | B | 214 | 3.331 | 29.282 | 48.547 | 1.00 | 39.53 | B | O |
| ATOM | 3155 | N | SER | B | 215 | 1.587 | 29.283 | 47.115 | 1.00 | 38.26 | B | N |
| ATOM | 3156 | CA | SER | B | 215 | 2.152 | 28.297 | 46.242 | 1.00 | 40.18 | B | C |
| ATOM | 3157 | CB | SER | B | 215 | 1.945 | 26.909 | 46.852 | 1.00 | 50.01 | B | C |
| ATOM | 3158 | OG | SER | B | 215 | 0.656 | 26.796 | 47.458 | 1.00 | 56.98 | B | O |
| ATOM | 3159 | C | SER | B | 215 | 1.434 | 28.339 | 44.923 | 1.00 | 40.51 | B | C |
| ATOM | 3160 | O | SER | B | 215 | 0.294 | 28.814 | 44.835 | 1.00 | 37.50 | B | O |
| ATOM | 3161 | N | VAL | B | 216 | 2.110 | 27.813 | 43.904 | 1.00 | 40.40 | B | N |
| ATOM | 3162 | CA | VAL | B | 216 | 1.500 | 27.562 | 42.607 | 1.00 | 37.18 | B | C |
| ATOM | 3163 | CB | VAL | B | 216 | 2.091 | 28.423 | 41.502 | 1.00 | 29.19 | B | C |
| ATOM | 3164 | CG1 | VAL | B | 216 | 0.998 | 29.064 | 40.731 | 1.00 | 32.27 | B | C |
| ATOM | 3165 | CG2 | VAL | B | 216 | 3.027 | 29.430 | 42.052 | 1.00 | 25.24 | B | C |
| ATOM | 3166 | C | VAL | B | 216 | 1.780 | 26.149 | 42.191 | 1.00 | 40.74 | B | C |
| ATOM | 3167 | O | VAL | B | 216 | 2.950 | 25.784 | 41.971 | 1.00 | 51.27 | B | O |
| ATOM | 3168 | N | ARG | B | 217 | 0.733 | 25.343 | 42.073 | 1.00 | 32.18 | B | N |
| ATOM | 3169 | CA | ARG | B | 217 | 0.923 | 24.045 | 41.450 | 1.00 | 29.02 | B | C |
| ATOM | 3170 | CB | ARG | B | 217 | 0.840 | 22.871 | 42.456 | 1.00 | 27.36 | B | C |
| ATOM | 3171 | CG | ARG | B | 217 | −0.516 | 22.508 | 43.036 | 1.00 | 26.02 | B | C |
| ATOM | 3172 | CD | ARG | B | 217 | −1.169 | 23.610 | 43.835 | 1.00 | 38.67 | B | C |
| ATOM | 3173 | NE | ARG | B | 217 | −0.632 | 23.876 | 45.189 | 1.00 | 44.65 | B | N |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 3174 | CZ | ARG | B | 217 | −0.536 | 22.985 | 46.183 | 1.00 | 36.92 | B | C |
| ATOM | 3175 | NH1 | ARG | B | 217 | −0.882 | 21.719 | 45.998 | 1.00 | 29.77 | B | N |
| ATOM | 3176 | NH2 | ARG | B | 217 | −0.068 | 23.368 | 47.360 | 1.00 | 33.63 | B | N |
| ATOM | 3177 | C | ARG | B | 217 | −0.036 | 23.923 | 40.307 | 1.00 | 27.19 | B | C |
| ATOM | 3178 | O | ARG | B | 217 | −1.095 | 24.556 | 40.329 | 1.00 | 30.77 | B | O |
| ATOM | 3179 | N | ARG | B | 218 | 0.347 | 23.140 | 39.300 | 1.00 | 24.74 | B | N |
| ATOM | 3180 | CA | ARG | B | 218 | −0.562 | 22.817 | 38.205 | 1.00 | 29.88 | B | C |
| ATOM | 3181 | CB | ARG | B | 218 | 0.120 | 23.006 | 36.872 | 1.00 | 26.23 | B | C |
| ATOM | 3182 | CG | ARG | B | 218 | 1.227 | 22.044 | 36.596 | 1.00 | 28.59 | B | C |
| ATOM | 3183 | CD | ARG | B | 218 | 1.831 | 22.250 | 35.228 | 1.00 | 35.20 | B | C |
| ATOM | 3184 | NE | ARG | B | 218 | 2.799 | 21.210 | 34.902 | 1.00 | 43.71 | B | N |
| ATOM | 3185 | CZ | ARG | B | 218 | 2.482 | 20.043 | 34.355 | 1.00 | 43.88 | B | C |
| ATOM | 3186 | NH1 | ARG | B | 218 | 1.219 | 19.765 | 34.058 | 1.00 | 47.77 | B | N |
| ATOM | 3187 | NH2 | ARG | B | 218 | 3.427 | 19.160 | 34.090 | 1.00 | 37.51 | B | N |
| ATOM | 3188 | C | ARG | B | 218 | −1.076 | 21.393 | 38.323 | 1.00 | 39.55 | B | C |
| ATOM | 3189 | O | ARG | B | 218 | −0.468 | 20.584 | 39.017 | 1.00 | 46.37 | B | O |
| ATOM | 3190 | N | LEU | B | 219 | −2.205 | 21.094 | 37.671 | 1.00 | 44.95 | B | N |
| ATOM | 3191 | CA | LEU | B | 219 | −2.702 | 19.714 | 37.544 | 1.00 | 43.41 | B | C |
| ATOM | 3192 | CB | LEU | B | 219 | −4.139 | 19.692 | 37.017 | 1.00 | 44.18 | B | C |
| ATOM | 3193 | CG | LEU | B | 219 | −5.316 | 19.154 | 37.844 | 1.00 | 42.53 | B | C |
| ATOM | 3194 | CD1 | LEU | B | 219 | −6.467 | 18.699 | 36.936 | 1.00 | 37.24 | B | C |
| ATOM | 3195 | CD2 | LEU | B | 219 | −4.901 | 18.032 | 38.782 | 1.00 | 41.80 | B | C |
| ATOM | 3196 | C | LEU | B | 219 | −1.821 | 18.982 | 36.552 | 1.00 | 42.76 | B | C |
| ATOM | 3197 | O | LEU | B | 219 | −1.108 | 19.603 | 35.761 | 1.00 | 45.42 | B | O |
| ATOM | 3198 | N | LYS | B | 220 | −1.846 | 17.663 | 36.593 | 1.00 | 41.24 | B | N |
| ATOM | 3199 | CA | LYS | B | 220 | −1.169 | 16.914 | 35.556 | 1.00 | 42.17 | B | C |
| ATOM | 3200 | CB | LYS | B | 220 | −0.670 | 15.590 | 36.110 | 1.00 | 40.03 | B | C |
| ATOM | 3201 | CG | LYS | B | 220 | 0.472 | 15.693 | 37.135 | 1.00 | 46.15 | B | C |
| ATOM | 3202 | CD | LYS | B | 220 | 1.435 | 14.475 | 37.057 | 1.00 | 53.99 | B | C |
| ATOM | 3203 | CE | LYS | B | 220 | 2.144 | 14.165 | 38.368 | 1.00 | 56.43 | B | C |
| ATOM | 3204 | NZ | LYS | B | 220 | 1.285 | 13.328 | 39.285 | 1.00 | 62.88 | B | N |
| ATOM | 3205 | C | LYS | B | 220 | −2.245 | 16.717 | 34.480 | 1.00 | 46.84 | B | C |
| ATOM | 3206 | O | LYS | B | 220 | −3.448 | 16.683 | 34.811 | 1.00 | 44.45 | B | O |
| ATOM | 3207 | N | GLU | B | 221 | −1.848 | 16.639 | 33.204 | 1.00 | 43.21 | B | N |
| ATOM | 3208 | CA | GLU | B | 221 | −2.829 | 16.369 | 32.153 | 1.00 | 37.91 | B | C |
| ATOM | 3209 | CB | GLU | B | 221 | −2.249 | 16.485 | 30.733 | 1.00 | 42.50 | B | C |
| ATOM | 3210 | CG | GLU | B | 221 | −3.320 | 16.757 | 29.669 | 1.00 | 51.31 | B | C |
| ATOM | 3211 | CD | GLU | B | 221 | −2.817 | 16.628 | 28.238 | 1.00 | 58.55 | B | C |
| ATOM | 3212 | OE1 | GLU | B | 221 | −3.634 | 16.511 | 27.284 | 1.00 | 54.22 | B | O |
| ATOM | 3213 | OE2 | GLU | B | 221 | −1.588 | 16.651 | 28.058 | 1.00 | 68.04 | B | O |
| ATOM | 3214 | C | GLU | B | 221 | −3.370 | 14.986 | 32.386 | 1.00 | 37.57 | B | C |
| ATOM | 3215 | O | GLU | B | 221 | −4.433 | 14.627 | 31.867 | 1.00 | 46.72 | B | O |
| ATOM | 3216 | N | THR | B | 222 | −2.652 | 14.194 | 33.176 | 1.00 | 31.96 | B | N |
| ATOM | 3217 | CA | THR | B | 222 | −3.203 | 12.908 | 33.554 | 1.00 | 35.83 | B | C |
| ATOM | 3218 | CB | THR | B | 222 | −2.117 | 11.873 | 33.864 | 1.00 | 40.54 | B | C |
| ATOM | 3219 | OG1 | THR | B | 222 | −1.116 | 12.463 | 34.688 | 1.00 | 46.68 | B | O |
| ATOM | 3220 | CG2 | THR | B | 222 | −1.331 | 11.529 | 32.615 | 1.00 | 42.02 | B | C |
| ATOM | 3221 | C | THR | B | 222 | −4.240 | 13.027 | 34.663 | 1.00 | 36.10 | B | C |
| ATOM | 3222 | O | THR | B | 222 | −4.816 | 12.036 | 35.064 | 1.00 | 41.48 | B | O |
| ATOM | 3223 | N | LYS | B | 223 | −4.495 | 14.246 | 35.132 | 1.00 | 39.96 | B | N |
| ATOM | 3224 | CA | LYS | B | 223 | −5.643 | 14.546 | 36.008 | 1.00 | 43.76 | B | C |
| ATOM | 3225 | CB | LYS | B | 223 | −6.954 | 14.218 | 35.298 | 1.00 | 41.79 | B | C |
| ATOM | 3226 | CG | LYS | B | 223 | −7.411 | 15.256 | 34.327 | 1.00 | 46.07 | B | C |
| ATOM | 3227 | CD | LYS | B | 223 | −8.660 | 14.790 | 33.637 | 1.00 | 54.35 | B | C |
| ATOM | 3228 | CE | LYS | B | 223 | −8.359 | 14.301 | 32.244 | 1.00 | 62.18 | B | C |
| ATOM | 3229 | NZ | LYS | B | 223 | −9.324 | 14.941 | 31.302 | 1.00 | 74.28 | B | N |
| ATOM | 3230 | C | LYS | B | 223 | −5.610 | 13.827 | 37.362 | 1.00 | 45.88 | B | C |
| ATOM | 3231 | O | LYS | B | 223 | −6.627 | 13.747 | 38.078 | 1.00 | 46.67 | B | O |
| ATOM | 3232 | N | ASP | B | 224 | −4.440 | 13.316 | 37.711 | 1.00 | 42.42 | B | N |
| ATOM | 3233 | CA | ASP | B | 224 | −4.335 | 12.401 | 38.816 | 1.00 | 46.20 | B | C |
| ATOM | 3234 | CB | ASP | B | 224 | −3.913 | 11.035 | 38.300 | 1.00 | 48.69 | B | C |
| ATOM | 3235 | CG | ASP | B | 224 | −2.558 | 11.071 | 37.675 | 1.00 | 53.56 | B | C |
| ATOM | 3236 | OD1 | ASP | B | 224 | −1.751 | 10.146 | 37.880 | 1.00 | 57.92 | B | O |
| ATOM | 3237 | OD2 | ASP | B | 224 | −2.203 | 12.028 | 36.972 | 1.00 | 59.52 | B | O |
| ATOM | 3238 | C | ASP | B | 224 | −3.293 | 12.916 | 39.773 | 1.00 | 49.82 | B | C |
| ATOM | 3239 | O | ASP | B | 224 | −2.750 | 12.149 | 40.579 | 1.00 | 57.22 | B | O |
| ATOM | 3240 | N | GLY | B | 225 | −2.995 | 14.207 | 39.682 | 1.00 | 45.94 | B | N |
| ATOM | 3241 | CA | GLY | B | 225 | −2.039 | 14.799 | 40.595 | 1.00 | 44.41 | B | C |
| ATOM | 3242 | C | GLY | B | 225 | −1.607 | 16.202 | 40.257 | 1.00 | 41.32 | B | C |
| ATOM | 3243 | O | GLY | B | 225 | −1.470 | 16.567 | 39.093 | 1.00 | 37.54 | B | O |
| ATOM | 3244 | N | PHE | B | 226 | −1.405 | 16.990 | 41.301 | 1.00 | 40.89 | B | N |
| ATOM | 3245 | CA | PHE | B | 226 | −0.805 | 18.301 | 41.162 | 1.00 | 38.23 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 3246 | CB | PHE | B | 226 | −1.305 | 19.190 | 42.285 | 1.00 | 34.25 | B | C |
| ATOM | 3247 | CG | PHE | B | 226 | −2.770 | 19.432 | 42.247 | 1.00 | 36.48 | B | C |
| ATOM | 3248 | CD1 | PHE | B | 226 | −3.645 | 18.568 | 42.875 | 1.00 | 34.58 | B | C |
| ATOM | 3249 | CE1 | PHE | B | 226 | −5.027 | 18.800 | 42.847 | 1.00 | 29.74 | B | C |
| ATOM | 3250 | CZ | PHE | B | 226 | −5.532 | 19.891 | 42.187 | 1.00 | 29.66 | B | C |
| ATOM | 3251 | CE2 | PHE | B | 226 | −4.677 | 20.759 | 41.537 | 1.00 | 36.03 | B | C |
| ATOM | 3252 | CD2 | PHE | B | 226 | −3.292 | 20.529 | 41.571 | 1.00 | 40.84 | B | C |
| ATOM | 3253 | C | PHE | B | 226 | 0.724 | 18.201 | 41.225 | 1.00 | 38.49 | B | C |
| ATOM | 3254 | O | PHE | B | 226 | 1.272 | 17.294 | 41.883 | 1.00 | 43.61 | B | O |
| ATOM | 3255 | N | MET | B | 227 | 1.407 | 19.129 | 40.559 | 1.00 | 31.84 | B | N |
| ATOM | 3256 | CA | MET | B | 227 | 2.843 | 19.247 | 40.714 | 1.00 | 36.84 | B | C |
| ATOM | 3257 | CB | MET | B | 227 | 3.539 | 18.522 | 39.577 | 1.00 | 43.03 | B | C |
| ATOM | 3258 | CG | MET | B | 227 | 3.554 | 19.217 | 38.246 | 1.00 | 51.35 | B | C |
| ATOM | 3259 | SD | MET | B | 227 | 4.875 | 18.500 | 37.239 | 1.00 | 56.42 | B | S |
| ATOM | 3260 | CE | MET | B | 227 | 4.193 | 16.873 | 36.930 | 1.00 | 58.19 | B | C |
| ATOM | 3261 | C | MET | B | 227 | 3.372 | 20.680 | 40.906 | 1.00 | 40.56 | B | C |
| ATOM | 3262 | O | MET | B | 227 | 2.886 | 21.620 | 40.255 | 1.00 | 33.62 | B | O |
| ATOM | 3263 | N | PHE | B | 228 | 4.344 | 20.831 | 41.825 | 1.00 | 46.58 | B | N |
| ATOM | 3264 | CA | PHE | B | 228 | 5.021 | 22.119 | 42.060 | 1.00 | 47.51 | B | C |
| ATOM | 3265 | CB | PHE | B | 228 | 5.661 | 22.216 | 43.435 | 1.00 | 38.62 | B | C |
| ATOM | 3266 | CG | PHE | B | 228 | 4.692 | 22.332 | 44.543 | 1.00 | 37.82 | B | C |
| ATOM | 3267 | CD1 | PHE | B | 228 | 4.846 | 21.567 | 45.683 | 1.00 | 36.64 | B | C |
| ATOM | 3268 | CE1 | PHE | B | 228 | 3.963 | 21.652 | 46.709 | 1.00 | 41.22 | B | C |
| ATOM | 3269 | CZ | PHE | B | 228 | 2.888 | 22.515 | 46.617 | 1.00 | 46.15 | B | C |
| ATOM | 3270 | CE2 | PHE | B | 228 | 2.720 | 23.294 | 45.490 | 1.00 | 45.56 | B | C |
| ATOM | 3271 | CD2 | PHE | B | 228 | 3.624 | 23.197 | 44.456 | 1.00 | 42.25 | B | C |
| ATOM | 3272 | C | PHE | B | 228 | 6.137 | 22.183 | 41.075 | 1.00 | 56.71 | B | C |
| ATOM | 3273 | O | PHE | B | 228 | 6.926 | 21.243 | 40.998 | 1.00 | 58.54 | B | O |
| ATOM | 3274 | N | LEU | B | 229 | 6.223 | 23.287 | 40.337 | 1.00 | 62.47 | B | N |
| ATOM | 3275 | CA | LEU | B | 229 | 7.131 | 23.335 | 39.200 | 1.00 | 62.53 | B | C |
| ATOM | 3276 | CB | LEU | B | 229 | 6.693 | 24.393 | 38.200 | 1.00 | 69.25 | B | C |
| ATOM | 3277 | CG | LEU | B | 229 | 6.466 | 23.730 | 36.843 | 1.00 | 73.88 | B | C |
| ATOM | 3278 | CD1 | LEU | B | 229 | 4.989 | 23.436 | 36.553 | 1.00 | 71.88 | B | C |
| ATOM | 3279 | CD2 | LEU | B | 229 | 7.079 | 24.585 | 35.754 | 1.00 | 79.85 | B | C |
| ATOM | 3280 | C | LEU | B | 229 | 8.611 | 23.448 | 39.552 | 1.00 | 58.82 | B | C |
| ATOM | 3281 | O | LEU | B | 229 | 9.440 | 22.852 | 38.868 | 1.00 | 60.51 | B | O |
| ATOM | 3282 | N | THR | B | 230 | 8.928 | 24.226 | 40.590 | 1.00 | 54.11 | B | N |
| ATOM | 3283 | CA | THR | B | 230 | 10.273 | 24.310 | 41.166 | 1.00 | 56.90 | B | C |
| ATOM | 3284 | CB | THR | B | 230 | 11.124 | 25.377 | 40.502 | 1.00 | 56.66 | B | C |
| ATOM | 3285 | OG1 | THR | B | 230 | 10.567 | 26.667 | 40.800 | 1.00 | 56.72 | B | O |
| ATOM | 3286 | CG2 | THR | B | 230 | 11.095 | 25.267 | 38.981 | 1.00 | 57.50 | B | C |
| ATOM | 3287 | C | THR | B | 230 | 10.146 | 24.708 | 42.623 | 1.00 | 62.33 | B | C |
| ATOM | 3288 | O | THR | B | 230 | 9.046 | 25.052 | 43.066 | 1.00 | 64.63 | B | O |
| ATOM | 3289 | N | ASP | B | 231 | 11.272 | 24.705 | 43.352 | 1.00 | 62.30 | B | N |
| ATOM | 3290 | CA | ASP | B | 231 | 11.273 | 24.977 | 44.791 | 1.00 | 61.19 | B | C |
| ATOM | 3291 | CB | ASP | B | 231 | 12.584 | 24.512 | 45.455 | 1.00 | 68.70 | B | C |
| ATOM | 3292 | CG | ASP | B | 231 | 13.787 | 25.423 | 45.145 | 1.00 | 77.39 | B | C |
| ATOM | 3293 | OD1 | ASP | B | 231 | 14.765 | 25.428 | 45.942 | 1.00 | 76.12 | B | O |
| ATOM | 3294 | OD2 | ASP | B | 231 | 13.857 | 26.155 | 44.130 | 1.00 | 83.28 | B | O |
| ATOM | 3295 | C | ASP | B | 231 | 10.961 | 26.441 | 45.074 | 1.00 | 60.67 | B | C |
| ATOM | 3296 | O | ASP | B | 231 | 10.769 | 26.845 | 46.226 | 1.00 | 60.08 | B | O |
| ATOM | 3297 | N | GLN | B | 232 | 10.889 | 27.225 | 44.002 | 1.00 | 61.02 | B | N |
| ATOM | 3298 | CA | GLN | B | 232 | 10.543 | 28.635 | 44.084 | 1.00 | 63.06 | B | C |
| ATOM | 3299 | CB | GLN | B | 232 | 11.277 | 29.402 | 42.991 | 1.00 | 70.00 | B | C |
| ATOM | 3300 | CG | GLN | B | 232 | 12.295 | 30.405 | 43.507 | 1.00 | 80.47 | B | C |
| ATOM | 3301 | CD | GLN | B | 232 | 13.141 | 31.010 | 42.388 | 1.00 | 89.22 | B | C |
| ATOM | 3302 | OE1 | GLN | B | 232 | 12.682 | 31.123 | 41.238 | 1.00 | 92.67 | B | O |
| ATOM | 3303 | NE2 | GLN | B | 232 | 14.380 | 31.400 | 42.719 | 1.00 | 91.85 | B | N |
| ATOM | 3304 | C | GLN | B | 232 | 9.039 | 28.858 | 43.954 | 1.00 | 59.86 | B | C |
| ATOM | 3305 | O | GLN | B | 232 | 8.584 | 29.992 | 43.855 | 1.00 | 65.25 | B | O |
| ATOM | 3306 | N | SER | B | 233 | 8.271 | 27.774 | 43.958 | 1.00 | 54.46 | B | N |
| ATOM | 3307 | CA | SER | B | 233 | 6.841 | 27.840 | 43.706 | 1.00 | 46.84 | B | C |
| ATOM | 3308 | CB | SER | B | 233 | 6.379 | 26.632 | 42.892 | 1.00 | 50.64 | B | C |
| ATOM | 3309 | OG | SER | B | 233 | 7.127 | 26.481 | 41.699 | 1.00 | 53.85 | B | O |
| ATOM | 3310 | C | SER | B | 233 | 6.041 | 27.900 | 44.983 | 1.00 | 42.79 | B | C |
| ATOM | 3311 | O | SER | B | 233 | 4.824 | 27.930 | 44.933 | 1.00 | 46.51 | B | O |
| ATOM | 3312 | N | TYR | B | 234 | 6.702 | 27.884 | 46.131 | 1.00 | 40.06 | B | N |
| ATOM | 3313 | CA | TYR | B | 234 | 6.006 | 28.200 | 47.377 | 1.00 | 45.71 | B | C |
| ATOM | 3314 | CB | TYR | B | 234 | 5.705 | 26.967 | 48.225 | 1.00 | 48.88 | B | C |
| ATOM | 3315 | CG | TYR | B | 234 | 6.706 | 25.874 | 48.058 | 1.00 | 51.32 | B | C |
| ATOM | 3316 | CD1 | TYR | B | 234 | 7.882 | 25.852 | 48.797 | 1.00 | 48.29 | B | C |
| ATOM | 3317 | CE1 | TYR | B | 234 | 8.813 | 24.826 | 48.628 | 1.00 | 49.61 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 3318 | CZ | TYR | B | 234 | 8.560 | 23.827 | 47.707 | 1.00 | 52.52 | B | C |
| ATOM | 3319 | OH | TYR | B | 234 | 9.439 | 22.802 | 47.494 | 1.00 | 53.66 | B | O |
| ATOM | 3320 | CE2 | TYR | B | 234 | 7.397 | 23.837 | 46.964 | 1.00 | 57.47 | B | C |
| ATOM | 3321 | CD2 | TYR | B | 234 | 6.479 | 24.854 | 47.142 | 1.00 | 55.92 | B | C |
| ATOM | 3322 | C | TYR | B | 234 | 6.832 | 29.142 | 48.196 | 1.00 | 46.38 | B | C |
| ATOM | 3323 | O | TYR | B | 234 | 8.058 | 29.132 | 48.098 | 1.00 | 49.19 | B | O |
| ATOM | 3324 | N | ILE | B | 235 | 6.145 | 29.957 | 48.990 | 1.00 | 43.14 | B | N |
| ATOM | 3325 | CA | ILE | B | 235 | 6.781 | 30.758 | 50.019 | 1.00 | 44.98 | B | C |
| ATOM | 3326 | CB | ILE | B | 235 | 6.577 | 32.254 | 49.738 | 1.00 | 42.96 | B | C |
| ATOM | 3327 | CG1 | ILE | B | 235 | 7.321 | 32.660 | 48.458 | 1.00 | 41.25 | B | C |
| ATOM | 3328 | CD1 | ILE | B | 235 | 6.708 | 33.807 | 47.709 | 1.00 | 39.31 | B | C |
| ATOM | 3329 | CG2 | ILE | B | 235 | 6.989 | 33.094 | 50.953 | 1.00 | 39.46 | B | C |
| ATOM | 3330 | C | ILE | B | 235 | 6.146 | 30.368 | 51.337 | 1.00 | 49.83 | B | C |
| ATOM | 3331 | O | ILE | B | 235 | 4.916 | 30.407 | 51.474 | 1.00 | 54.64 | B | O |
| ATOM | 3332 | N | ASP | B | 236 | 6.971 | 29.990 | 52.306 | 1.00 | 49.31 | B | N |
| ATOM | 3333 | CA | ASP | B | 236 | 6.438 | 29.503 | 53.575 | 1.00 | 52.33 | B | C |
| ATOM | 3334 | CB | ASP | B | 236 | 6.869 | 28.058 | 53.785 | 1.00 | 57.78 | B | C |
| ATOM | 3335 | CG | ASP | B | 236 | 5.985 | 27.079 | 53.061 | 1.00 | 63.72 | B | C |
| ATOM | 3336 | OD1 | ASP | B | 236 | 6.243 | 25.860 | 53.159 | 1.00 | 66.98 | B | O |
| ATOM | 3337 | OD2 | ASP | B | 236 | 5.008 | 27.433 | 52.375 | 1.00 | 67.67 | B | O |
| ATOM | 3338 | C | ASP | B | 236 | 6.856 | 30.311 | 54.789 | 1.00 | 51.93 | B | C |
| ATOM | 3339 | O | ASP | B | 236 | 8.025 | 30.657 | 54.933 | 1.00 | 57.61 | B | O |
| ATOM | 3340 | N | VAL | B | 237 | 5.908 | 30.591 | 55.677 | 1.00 | 48.39 | B | N |
| ATOM | 3341 | CA | VAL | B | 237 | 6.255 | 31.044 | 57.029 | 1.00 | 45.95 | B | C |
| ATOM | 3342 | CB | VAL | B | 237 | 5.010 | 31.037 | 57.967 | 1.00 | 41.63 | B | C |
| ATOM | 3343 | CG1 | VAL | B | 237 | 5.405 | 31.113 | 59.418 | 1.00 | 35.80 | B | C |
| ATOM | 3344 | CG2 | VAL | B | 237 | 4.094 | 32.180 | 57.629 | 1.00 | 41.77 | B | C |
| ATOM | 3345 | C | VAL | B | 237 | 7.380 | 30.148 | 57.596 | 1.00 | 44.14 | B | C |
| ATOM | 3346 | O | VAL | B | 237 | 7.327 | 28.918 | 57.478 | 1.00 | 42.65 | B | O |
| ATOM | 3347 | N | LEU | B | 238 | 8.407 | 30.769 | 58.172 | 1.00 | 42.83 | B | N |
| ATOM | 3348 | CA | LEU | B | 238 | 9.515 | 30.015 | 58.751 | 1.00 | 43.08 | B | C |
| ATOM | 3349 | CB | LEU | B | 238 | 10.627 | 30.946 | 59.237 | 1.00 | 40.25 | B | C |
| ATOM | 3350 | CG | LEU | B | 238 | 11.641 | 31.454 | 58.215 | 1.00 | 41.13 | B | C |
| ATOM | 3351 | CD1 | LEU | B | 238 | 12.642 | 32.352 | 58.880 | 1.00 | 40.12 | B | C |
| ATOM | 3352 | CD2 | LEU | B | 238 | 12.369 | 30.309 | 57.517 | 1.00 | 45.90 | B | C |
| ATOM | 3353 | C | LEU | B | 238 | 9.026 | 29.143 | 59.902 | 1.00 | 46.38 | B | C |
| ATOM | 3354 | O | LEU | B | 238 | 8.185 | 29.575 | 60.692 | 1.00 | 51.15 | B | O |
| ATOM | 3355 | N | PRO | B | 239 | 9.538 | 27.917 | 59.988 | 1.00 | 46.41 | B | N |
| ATOM | 3356 | CA | PRO | B | 239 | 9.187 | 26.993 | 61.070 | 1.00 | 48.37 | B | C |
| ATOM | 3357 | CB | PRO | B | 239 | 10.328 | 25.986 | 61.028 | 1.00 | 47.70 | B | C |
| ATOM | 3358 | CG | PRO | B | 239 | 10.751 | 25.957 | 59.600 | 1.00 | 44.52 | B | C |
| ATOM | 3359 | CD | PRO | B | 239 | 10.486 | 27.307 | 59.039 | 1.00 | 45.44 | B | C |
| ATOM | 3360 | C | PRO | B | 239 | 9.108 | 27.648 | 62.457 | 1.00 | 51.15 | B | C |
| ATOM | 3361 | O | PRO | B | 239 | 8.221 | 27.305 | 63.234 | 1.00 | 51.28 | B | O |
| ATOM | 3362 | N | GLU | B | 240 | 10.006 | 28.586 | 62.741 | 1.00 | 54.22 | B | N |
| ATOM | 3363 | CA | GLU | B | 240 | 10.055 | 29.271 | 64.035 | 1.00 | 59.88 | B | C |
| ATOM | 3364 | CB | GLU | B | 240 | 11.323 | 30.137 | 64.140 | 1.00 | 67.63 | B | C |
| ATOM | 3365 | CG | GLU | B | 240 | 12.212 | 30.100 | 62.893 | 1.00 | 73.77 | B | C |
| ATOM | 3366 | CD | GLU | B | 240 | 13.507 | 30.897 | 63.023 | 1.00 | 76.92 | B | C |
| ATOM | 3367 | OE1 | GLU | B | 240 | 13.725 | 31.559 | 64.076 | 1.00 | 78.28 | B | O |
| ATOM | 3368 | OE2 | GLU | B | 240 | 14.308 | 30.854 | 62.054 | 1.00 | 75.94 | B | O |
| ATOM | 3369 | C | GLU | B | 240 | 8.813 | 30.117 | 64.334 | 1.00 | 57.36 | B | C |
| ATOM | 3370 | O | GLU | B | 240 | 8.355 | 30.166 | 65.481 | 1.00 | 57.03 | B | O |
| ATOM | 3371 | N | PHE | B | 241 | 8.276 | 30.773 | 63.306 | 1.00 | 53.58 | B | N |
| ATOM | 3372 | CA | PHE | B | 241 | 7.129 | 31.678 | 63.472 | 1.00 | 52.07 | B | C |
| ATOM | 3373 | CB | PHE | B | 241 | 7.345 | 32.976 | 62.693 | 1.00 | 52.16 | B | C |
| ATOM | 3374 | CG | PHE | B | 241 | 8.762 | 33.443 | 62.690 | 1.00 | 52.22 | B | C |
| ATOM | 3375 | CD1 | PHE | B | 241 | 9.564 | 33.243 | 61.581 | 1.00 | 50.50 | B | C |
| ATOM | 3376 | CE1 | PHE | B | 241 | 10.875 | 33.671 | 61.569 | 1.00 | 51.40 | B | C |
| ATOM | 3377 | CZ | PHE | B | 241 | 11.410 | 34.298 | 62.679 | 1.00 | 54.59 | B | C |
| ATOM | 3378 | CE2 | PHE | B | 241 | 10.620 | 34.500 | 63.804 | 1.00 | 55.99 | B | C |
| ATOM | 3379 | CD2 | PHE | B | 241 | 9.300 | 34.071 | 63.803 | 1.00 | 54.67 | B | C |
| ATOM | 3380 | C | PHE | B | 241 | 5.787 | 31.062 | 63.090 | 1.00 | 48.67 | B | C |
| ATOM | 3381 | O | PHE | B | 241 | 4.731 | 31.679 | 63.293 | 1.00 | 45.77 | B | O |
| ATOM | 3382 | N | ARG | B | 242 | 5.852 | 29.844 | 62.550 | 1.00 | 48.21 | B | N |
| ATOM | 3383 | CA | ARG | B | 242 | 4.694 | 29.048 | 62.135 | 1.00 | 50.12 | B | C |
| ATOM | 3384 | CB | ARG | B | 242 | 5.146 | 27.617 | 61.852 | 1.00 | 49.18 | B | C |
| ATOM | 3385 | CG | ARG | B | 242 | 4.870 | 27.113 | 60.463 | 1.00 | 48.17 | B | C |
| ATOM | 3386 | CD | ARG | B | 242 | 5.936 | 26.151 | 59.964 | 1.00 | 48.47 | B | C |
| ATOM | 3387 | NE | ARG | B | 242 | 6.231 | 26.331 | 58.546 | 1.00 | 47.70 | B | N |
| ATOM | 3388 | CZ | ARG | B | 242 | 7.220 | 25.726 | 57.902 | 1.00 | 49.41 | B | C |
| ATOM | 3389 | NH1 | ARG | B | 242 | 8.036 | 24.893 | 58.542 | 1.00 | 48.09 | B | N |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 3390 | NH2 | ARG | B | 242 | 7.397 | 25.956 | 56.608 | 1.00 | 51.25 | B | N |
| ATOM | 3391 | C | ARG | B | 242 | 3.557 | 29.021 | 63.158 | 1.00 | 52.31 | B | C |
| ATOM | 3392 | O | ARG | B | 242 | 2.426 | 28.663 | 62.831 | 1.00 | 55.05 | B | O |
| ATOM | 3393 | N | ASP | B | 243 | 3.876 | 29.382 | 64.394 | 1.00 | 53.59 | B | N |
| ATOM | 3394 | CA | ASP | B | 243 | 2.893 | 29.471 | 65.458 | 1.00 | 56.95 | B | C |
| ATOM | 3395 | CB | ASP | B | 243 | 3.286 | 28.560 | 66.632 | 1.00 | 56.30 | B | C |
| ATOM | 3396 | CG | ASP | B | 243 | 2.700 | 27.157 | 66.520 | 1.00 | 55.00 | B | C |
| ATOM | 3397 | OD1 | ASP | B | 243 | 1.457 | 27.031 | 66.439 | 1.00 | 56.52 | B | O |
| ATOM | 3398 | OD2 | ASP | B | 243 | 3.403 | 26.122 | 66.525 | 1.00 | 51.18 | B | O |
| ATOM | 3399 | C | ASP | B | 243 | 2.789 | 30.924 | 65.914 | 1.00 | 59.72 | B | C |
| ATOM | 3400 | O | ASP | B | 243 | 1.684 | 31.461 | 65.989 | 1.00 | 55.22 | B | O |
| ATOM | 3401 | N | SER | B | 244 | 3.951 | 31.541 | 66.185 | 1.00 | 66.19 | B | N |
| ATOM | 3402 | CA | SER | B | 244 | 4.089 | 32.898 | 66.761 | 1.00 | 68.87 | B | C |
| ATOM | 3403 | CB | SER | B | 244 | 5.300 | 33.633 | 66.167 | 1.00 | 70.26 | B | C |
| ATOM | 3404 | OG | SER | B | 244 | 6.500 | 32.916 | 66.410 | 1.00 | 70.08 | B | O |
| ATOM | 3405 | C | SER | B | 244 | 2.821 | 33.713 | 66.583 | 1.00 | 67.72 | B | C |
| ATOM | 3406 | O | SER | B | 244 | 2.127 | 34.020 | 67.556 | 1.00 | 72.14 | B | O |
| ATOM | 3407 | N | TYR | B | 245 | 2.545 | 34.082 | 65.340 | 1.00 | 62.87 | B | N |
| ATOM | 3408 | CA | TYR | B | 245 | 1.158 | 34.146 | 64.880 | 1.00 | 62.23 | B | C |
| ATOM | 3409 | CB | TYR | B | 245 | 0.174 | 34.918 | 65.820 | 1.00 | 64.16 | B | C |
| ATOM | 3410 | CG | TYR | B | 245 | 0.485 | 36.342 | 66.238 | 1.00 | 65.78 | B | C |
| ATOM | 3411 | CD1 | TYR | B | 245 | 0.083 | 36.798 | 67.486 | 1.00 | 67.36 | B | C |
| ATOM | 3412 | CE1 | TYR | B | 245 | 0.324 | 38.092 | 67.881 | 1.00 | 70.36 | B | C |
| ATOM | 3413 | CZ | TYR | B | 245 | 0.962 | 38.960 | 67.014 | 1.00 | 71.24 | B | C |
| ATOM | 3414 | OH | TYR | B | 245 | 1.202 | 40.246 | 67.422 | 1.00 | 75.50 | B | O |
| ATOM | 3415 | CE2 | TYR | B | 245 | 1.356 | 38.549 | 65.758 | 1.00 | 67.14 | B | C |
| ATOM | 3416 | CD2 | TYR | B | 245 | 1.112 | 37.247 | 65.376 | 1.00 | 67.51 | B | C |
| ATOM | 3417 | C | TYR | B | 245 | 0.912 | 34.247 | 63.344 | 1.00 | 54.35 | B | C |
| ATOM | 3418 | O | TYR | B | 245 | 1.823 | 34.500 | 62.555 | 1.00 | 51.13 | B | O |
| ATOM | 3419 | N | PRO | B | 246 | −0.313 | 33.978 | 62.933 | 1.00 | 46.72 | B | N |
| ATOM | 3420 | CA | PRO | B | 246 | −0.530 | 33.443 | 61.613 | 1.00 | 47.43 | B | C |
| ATOM | 3421 | CB | PRO | B | 246 | −1.565 | 32.361 | 61.902 | 1.00 | 50.33 | B | C |
| ATOM | 3422 | CG | PRO | B | 246 | −2.277 | 32.831 | 63.208 | 1.00 | 46.80 | B | C |
| ATOM | 3423 | CD | PRO | B | 246 | −1.590 | 34.091 | 63.654 | 1.00 | 46.95 | B | C |
| ATOM | 3424 | C | PRO | B | 246 | −1.074 | 34.470 | 60.626 | 1.00 | 46.80 | B | C |
| ATOM | 3425 | O | PRO | B | 246 | −1.158 | 35.675 | 60.968 | 1.00 | 47.31 | B | O |
| ATOM | 3426 | N | ILE | B | 247 | −1.436 | 33.959 | 59.436 | 1.00 | 38.47 | B | N |
| ATOM | 3427 | CA | ILE | B | 247 | −1.840 | 34.741 | 58.278 | 1.00 | 36.07 | B | C |
| ATOM | 3428 | CB | ILE | B | 247 | −0.774 | 34.623 | 57.179 | 1.00 | 35.40 | B | C |
| ATOM | 3429 | CG1 | ILE | B | 247 | 0.612 | 34.986 | 57.710 | 1.00 | 34.70 | B | C |
| ATOM | 3430 | CD1 | ILE | B | 247 | 1.738 | 34.674 | 56.747 | 1.00 | 36.11 | B | C |
| ATOM | 3431 | CG2 | ILE | B | 247 | −1.127 | 35.506 | 55.990 | 1.00 | 37.67 | B | C |
| ATOM | 3432 | C | ILE | B | 247 | −3.187 | 34.279 | 57.717 | 1.00 | 39.08 | B | C |
| ATOM | 3433 | O | ILE | B | 247 | −3.243 | 33.338 | 56.941 | 1.00 | 42.52 | B | O |
| ATOM | 3434 | N | LYS | B | 248 | −4.269 | 34.949 | 58.097 | 1.00 | 41.51 | B | N |
| ATOM | 3435 | CA | LYS | B | 248 | −5.576 | 34.640 | 57.539 | 1.00 | 47.33 | B | C |
| ATOM | 3436 | CB | LYS | B | 248 | −6.707 | 35.325 | 58.344 | 1.00 | 54.93 | B | C |
| ATOM | 3437 | CG | LYS | B | 248 | −7.774 | 34.372 | 58.969 | 1.00 | 62.42 | B | C |
| ATOM | 3438 | CD | LYS | B | 248 | −7.130 | 33.130 | 59.696 | 1.00 | 65.56 | B | C |
| ATOM | 3439 | CE | LYS | B | 248 | −7.609 | 32.961 | 61.161 | 1.00 | 67.44 | B | C |
| ATOM | 3440 | NZ | LYS | B | 248 | −6.536 | 33.198 | 62.185 | 1.00 | 66.17 | B | N |
| ATOM | 3441 | C | LYS | B | 248 | −5.594 | 35.099 | 56.086 | 1.00 | 47.12 | B | C |
| ATOM | 3442 | O | LYS | B | 248 | −5.103 | 36.186 | 55.770 | 1.00 | 50.24 | B | O |
| ATOM | 3443 | N | TYR | B | 249 | −6.146 | 34.271 | 55.204 | 1.00 | 44.18 | B | N |
| ATOM | 3444 | CA | TYR | B | 249 | −6.320 | 34.666 | 53.807 | 1.00 | 41.12 | B | C |
| ATOM | 3445 | CB | TYR | B | 249 | −5.694 | 33.610 | 52.873 | 1.00 | 39.51 | B | C |
| ATOM | 3446 | CG | TYR | B | 249 | −4.179 | 33.494 | 53.061 | 1.00 | 39.99 | B | C |
| ATOM | 3447 | CD1 | TYR | B | 249 | −3.623 | 32.520 | 53.899 | 1.00 | 39.32 | B | C |
| ATOM | 3448 | CE1 | TYR | B | 249 | −2.252 | 32.420 | 54.084 | 1.00 | 37.22 | B | C |
| ATOM | 3449 | CZ | TYR | B | 249 | −1.414 | 33.310 | 53.445 | 1.00 | 40.31 | B | C |
| ATOM | 3450 | OH | TYR | B | 249 | −0.041 | 33.235 | 53.623 | 1.00 | 39.21 | B | O |
| ATOM | 3451 | CE2 | TYR | B | 249 | −1.944 | 34.294 | 52.624 | 1.00 | 40.32 | B | C |
| ATOM | 3452 | CD2 | TYR | B | 249 | −3.313 | 34.377 | 52.433 | 1.00 | 38.21 | B | C |
| ATOM | 3453 | C | TYR | B | 249 | −7.797 | 34.965 | 53.497 | 1.00 | 41.07 | B | C |
| ATOM | 3454 | O | TYR | B | 249 | −8.624 | 34.065 | 53.431 | 1.00 | 46.67 | B | O |
| ATOM | 3455 | N | VAL | B | 250 | −8.132 | 36.237 | 53.330 | 1.00 | 40.04 | B | N |
| ATOM | 3456 | CA | VAL | B | 250 | −9.531 | 36.646 | 53.156 | 1.00 | 41.00 | B | C |
| ATOM | 3457 | CB | VAL | B | 250 | −9.740 | 38.102 | 53.563 | 1.00 | 39.09 | B | C |
| ATOM | 3458 | CG1 | VAL | B | 250 | −11.214 | 38.394 | 53.745 | 1.00 | 39.71 | B | C |
| ATOM | 3459 | CG2 | VAL | B | 250 | −9.000 | 38.388 | 54.839 | 1.00 | 44.78 | B | C |
| ATOM | 3460 | C | VAL | B | 250 | −10.049 | 36.496 | 51.726 | 1.00 | 42.79 | B | C |
| ATOM | 3461 | O | VAL | B | 250 | −11.206 | 36.126 | 51.501 | 1.00 | 44.52 | B | O |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 3462 | N | HIS | B | 251 | −9.199 | 36.804 | 50.760 | 1.00 | 40.74 | B | N |
| ATOM | 3463 | CA | HIS | B | 251 | −9.636 | 36.852 | 49.386 | 1.00 | 41.24 | B | C |
| ATOM | 3464 | CB | HIS | B | 251 | −10.375 | 38.164 | 49.135 | 1.00 | 41.80 | B | C |
| ATOM | 3465 | CG | HIS | B | 251 | −11.170 | 38.176 | 47.874 | 1.00 | 43.37 | B | C |
| ATOM | 3466 | ND1 | HIS | B | 251 | −11.037 | 39.164 | 46.925 | 1.00 | 46.38 | B | N |
| ATOM | 3467 | CE1 | HIS | B | 251 | −11.859 | 38.925 | 45.919 | 1.00 | 50.12 | B | C |
| ATOM | 3468 | NE2 | HIS | B | 251 | −12.518 | 37.812 | 46.183 | 1.00 | 52.95 | B | N |
| ATOM | 3469 | CD2 | HIS | B | 251 | −12.103 | 37.322 | 47.398 | 1.00 | 47.36 | B | C |
| ATOM | 3470 | C | HIS | B | 251 | −8.459 | 36.747 | 48.444 | 1.00 | 42.18 | B | C |
| ATOM | 3471 | O | HIS | B | 251 | −7.345 | 37.159 | 48.776 | 1.00 | 40.54 | B | O |
| ATOM | 3472 | N | ALA | B | 252 | −8.713 | 36.184 | 47.268 | 1.00 | 42.50 | B | N |
| ATOM | 3473 | CA | ALA | B | 252 | −7.744 | 36.220 | 46.184 | 1.00 | 39.62 | B | C |
| ATOM | 3474 | CB | ALA | B | 252 | −6.959 | 34.920 | 46.122 | 1.00 | 34.04 | B | C |
| ATOM | 3475 | C | ALA | B | 252 | −8.460 | 36.489 | 44.872 | 1.00 | 38.17 | B | C |
| ATOM | 3476 | O | ALA | B | 252 | −9.628 | 36.158 | 44.727 | 1.00 | 40.85 | B | O |
| ATOM | 3477 | N | PHE | B | 253 | −7.758 | 37.102 | 43.927 | 1.00 | 37.56 | B | N |
| ATOM | 3478 | CA | PHE | B | 253 | −8.280 | 37.319 | 42.583 | 1.00 | 37.97 | B | C |
| ATOM | 3479 | CB | PHE | B | 253 | −9.274 | 38.467 | 42.593 | 1.00 | 39.09 | B | C |
| ATOM | 3480 | CG | PHE | B | 253 | −8.661 | 39.775 | 42.991 | 1.00 | 37.16 | B | C |
| ATOM | 3481 | CD1 | PHE | B | 253 | −8.132 | 40.634 | 42.024 | 1.00 | 35.82 | B | C |
| ATOM | 3482 | CE1 | PHE | B | 253 | −7.548 | 41.831 | 42.382 | 1.00 | 34.32 | B | C |
| ATOM | 3483 | CZ | PHE | B | 253 | −7.481 | 42.184 | 43.711 | 1.00 | 35.35 | B | C |
| ATOM | 3484 | CE2 | PHE | B | 253 | −8.002 | 41.333 | 44.688 | 1.00 | 35.47 | B | C |
| ATOM | 3485 | CD2 | PHE | B | 253 | −8.585 | 40.137 | 44.325 | 1.00 | 35.03 | B | C |
| ATOM | 3486 | C | PHE | B | 253 | −7.155 | 37.627 | 41.590 | 1.00 | 40.06 | B | C |
| ATOM | 3487 | O | PHE | B | 253 | −6.099 | 38.144 | 41.954 | 1.00 | 38.73 | B | O |
| ATOM | 3488 | N | GLU | B | 254 | −7.405 | 37.317 | 40.329 | 1.00 | 44.48 | B | N |
| ATOM | 3489 | CA | GLU | B | 254 | −6.440 | 37.554 | 39.273 | 1.00 | 48.19 | B | C |
| ATOM | 3490 | CB | GLU | B | 254 | −6.511 | 36.392 | 38.295 | 1.00 | 56.38 | B | C |
| ATOM | 3491 | CG | GLU | B | 254 | −5.384 | 36.257 | 37.277 | 1.00 | 60.98 | B | C |
| ATOM | 3492 | CD | GLU | B | 254 | −5.461 | 34.907 | 36.578 | 1.00 | 66.37 | B | C |
| ATOM | 3493 | OE1 | GLU | B | 254 | −6.409 | 34.140 | 36.883 | 1.00 | 68.84 | B | O |
| ATOM | 3494 | OE2 | GLU | B | 254 | −4.587 | 34.597 | 35.737 | 1.00 | 69.66 | B | O |
| ATOM | 3495 | C | GLU | B | 254 | −6.909 | 38.781 | 38.573 | 1.00 | 44.37 | B | C |
| ATOM | 3496 | O | GLU | B | 254 | −8.077 | 38.886 | 38.300 | 1.00 | 49.37 | B | O |
| ATOM | 3497 | N | SER | B | 255 | −6.017 | 39.711 | 38.278 | 1.00 | 46.27 | B | N |
| ATOM | 3498 | CA | SER | B | 255 | −6.357 | 40.842 | 37.418 | 1.00 | 53.56 | B | C |
| ATOM | 3499 | CB | SER | B | 255 | −7.166 | 41.910 | 38.164 | 1.00 | 52.55 | B | C |
| ATOM | 3500 | OG | SER | B | 255 | −6.783 | 43.221 | 37.762 | 1.00 | 47.80 | B | O |
| ATOM | 3501 | C | SER | B | 255 | −5.106 | 41.472 | 36.856 | 1.00 | 62.94 | B | C |
| ATOM | 3502 | O | SER | B | 255 | −4.139 | 41.714 | 37.592 | 1.00 | 64.63 | B | O |
| ATOM | 3503 | N | ASN | B | 256 | −5.146 | 41.749 | 35.552 | 1.00 | 71.08 | B | N |
| ATOM | 3504 | CA | ASN | B | 256 | −4.093 | 42.499 | 34.861 | 1.00 | 75.79 | B | C |
| ATOM | 3505 | CB | ASN | B | 256 | −3.778 | 43.816 | 35.594 | 1.00 | 82.60 | B | C |
| ATOM | 3506 | CG | ASN | B | 256 | −4.344 | 45.022 | 34.884 | 1.00 | 89.10 | B | C |
| ATOM | 3507 | OD1 | ASN | B | 256 | −4.107 | 45.224 | 33.691 | 1.00 | 92.54 | B | O |
| ATOM | 3508 | ND2 | ASN | B | 256 | −5.106 | 45.832 | 35.610 | 1.00 | 91.19 | B | N |
| ATOM | 3509 | C | ASN | B | 256 | −2.816 | 41.706 | 34.685 | 1.00 | 70.33 | B | C |
| ATOM | 3510 | O | ASN | B | 256 | −1.765 | 42.279 | 34.421 | 1.00 | 70.32 | B | O |
| ATOM | 3511 | N | ASN | B | 257 | −2.916 | 40.393 | 34.846 | 1.00 | 66.90 | B | N |
| ATOM | 3512 | CA | ASN | B | 257 | −1.759 | 39.509 | 34.750 | 1.00 | 72.76 | B | C |
| ATOM | 3513 | CB | ASN | B | 257 | −0.871 | 39.894 | 33.564 | 1.00 | 82.20 | B | C |
| ATOM | 3514 | CG | ASN | B | 257 | −1.003 | 38.933 | 32.403 | 1.00 | 89.28 | B | C |
| ATOM | 3515 | OD1 | ASN | B | 257 | −1.889 | 38.062 | 32.383 | 1.00 | 91.61 | B | O |
| ATOM | 3516 | ND2 | ASN | B | 257 | −0.113 | 39.079 | 31.424 | 1.00 | 91.54 | B | N |
| ATOM | 3517 | C | ASN | B | 257 | −0.922 | 39.327 | 36.029 | 1.00 | 66.57 | B | C |
| ATOM | 3518 | O | ASN | B | 257 | 0.134 | 38.689 | 36.001 | 1.00 | 65.77 | B | O |
| ATOM | 3519 | N | PHE | B | 258 | −1.406 | 39.874 | 37.140 | 1.00 | 59.48 | B | N |
| ATOM | 3520 | CA | PHE | B | 258 | −0.951 | 39.446 | 38.457 | 1.00 | 53.56 | B | C |
| ATOM | 3521 | CB | PHE | B | 258 | −0.515 | 40.635 | 39.283 | 1.00 | 56.13 | B | C |
| ATOM | 3522 | CG | PHE | B | 258 | 0.517 | 41.470 | 38.623 | 1.00 | 62.69 | B | C |
| ATOM | 3523 | CD1 | PHE | B | 258 | 0.176 | 42.684 | 38.044 | 1.00 | 67.09 | B | C |
| ATOM | 3524 | CE1 | PHE | B | 258 | 1.135 | 43.480 | 37.424 | 1.00 | 67.82 | B | C |
| ATOM | 3525 | CZ | PHE | B | 258 | 2.443 | 43.061 | 37.384 | 1.00 | 68.92 | B | C |
| ATOM | 3526 | CE2 | PHE | B | 258 | 2.798 | 41.841 | 37.965 | 1.00 | 69.58 | B | C |
| ATOM | 3527 | CD2 | PHE | B | 258 | 1.834 | 41.055 | 38.579 | 1.00 | 66.62 | B | C |
| ATOM | 3528 | C | PHE | B | 258 | −2.018 | 38.648 | 39.221 | 1.00 | 48.68 | B | C |
| ATOM | 3529 | O | PHE | B | 258 | −3.206 | 38.672 | 38.896 | 1.00 | 48.22 | B | O |
| ATOM | 3530 | N | ILE | B | 259 | −1.573 | 37.912 | 40.224 | 1.00 | 40.91 | B | N |
| ATOM | 3531 | CA | ILE | B | 259 | −2.485 | 37.301 | 41.153 | 1.00 | 39.53 | B | C |
| ATOM | 3532 | CB | ILE | B | 259 | −2.055 | 35.890 | 41.478 | 1.00 | 40.17 | B | C |
| ATOM | 3533 | CG1 | ILE | B | 259 | −1.652 | 35.134 | 40.209 | 1.00 | 39.96 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 3534 | CD1 | ILE | B | 259 | −2.786 | 34.790 | 39.319 | 1.00 | 45.11 | B | C |
| ATOM | 3535 | CG2 | ILE | B | 259 | −3.134 | 35.196 | 42.289 | 1.00 | 40.75 | B | C |
| ATOM | 3536 | C | ILE | B | 259 | −2.386 | 38.128 | 42.408 | 1.00 | 44.07 | B | C |
| ATOM | 3537 | O | ILE | B | 259 | −1.284 | 38.523 | 42.817 | 1.00 | 47.98 | B | O |
| ATOM | 3538 | N | TYR | B | 260 | −3.533 | 38.385 | 43.026 | 1.00 | 42.44 | B | N |
| ATOM | 3539 | CA | TYR | B | 260 | −3.574 | 39.155 | 44.257 | 1.00 | 39.09 | B | C |
| ATOM | 3540 | CB | TYR | B | 260 | −4.389 | 40.432 | 44.059 | 1.00 | 38.57 | B | C |
| ATOM | 3541 | CG | TYR | B | 260 | −3.826 | 41.372 | 43.025 | 1.00 | 37.97 | B | C |
| ATOM | 3542 | CD1 | TYR | B | 260 | −4.002 | 41.132 | 41.668 | 1.00 | 39.75 | B | C |
| ATOM | 3543 | CE1 | TYR | B | 260 | −3.479 | 41.993 | 40.708 | 1.00 | 38.56 | B | C |
| ATOM | 3544 | CZ | TYR | B | 260 | −2.785 | 43.113 | 41.109 | 1.00 | 39.14 | B | C |
| ATOM | 3545 | OH | TYR | B | 260 | −2.280 | 43.967 | 40.159 | 1.00 | 45.15 | B | O |
| ATOM | 3546 | CE2 | TYR | B | 260 | −2.603 | 43.378 | 42.448 | 1.00 | 36.98 | B | C |
| ATOM | 3547 | CD2 | TYR | B | 260 | −3.119 | 42.503 | 43.399 | 1.00 | 37.90 | B | C |
| ATOM | 3548 | C | TYR | B | 260 | −4.162 | 38.337 | 45.398 | 1.00 | 36.34 | B | C |
| ATOM | 3549 | O | TYR | B | 260 | −5.162 | 37.643 | 45.234 | 1.00 | 35.00 | B | O |
| ATOM | 3550 | N | PHE | B | 261 | −3.536 | 38.421 | 46.559 | 1.00 | 33.91 | B | N |
| ATOM | 3551 | CA | PHE | B | 261 | −4.176 | 37.919 | 47.754 | 1.00 | 34.52 | B | C |
| ATOM | 3552 | CB | PHE | B | 261 | −3.360 | 36.804 | 48.363 | 1.00 | 32.25 | B | C |
| ATOM | 3553 | CG | PHE | B | 261 | −3.601 | 35.472 | 47.728 | 1.00 | 32.31 | B | C |
| ATOM | 3554 | CD1 | PHE | B | 261 | −3.017 | 35.153 | 46.506 | 1.00 | 32.46 | B | C |
| ATOM | 3555 | CE1 | PHE | B | 261 | −3.226 | 33.916 | 45.917 | 1.00 | 28.63 | B | C |
| ATOM | 3556 | CZ | PHE | B | 261 | −4.024 | 32.996 | 46.539 | 1.00 | 26.50 | B | C |
| ATOM | 3557 | CE2 | PHE | B | 261 | −4.615 | 33.299 | 47.759 | 1.00 | 29.46 | B | C |
| ATOM | 3558 | CD2 | PHE | B | 261 | −4.403 | 34.532 | 48.349 | 1.00 | 30.29 | B | C |
| ATOM | 3559 | C | PHE | B | 261 | −4.442 | 39.011 | 48.771 | 1.00 | 38.12 | B | C |
| ATOM | 3560 | O | PHE | B | 261 | −3.664 | 39.958 | 48.914 | 1.00 | 39.60 | B | O |
| ATOM | 3561 | N | LEU | B | 262 | −5.571 | 38.883 | 49.457 | 1.00 | 39.87 | B | N |
| ATOM | 3562 | CA | LEU | B | 262 | −5.890 | 39.764 | 50.566 | 1.00 | 40.14 | B | C |
| ATOM | 3563 | CB | LEU | B | 262 | −7.258 | 40.378 | 50.377 | 1.00 | 42.28 | B | C |
| ATOM | 3564 | CG | LEU | B | 262 | −7.193 | 41.526 | 49.367 | 1.00 | 44.27 | B | C |
| ATOM | 3565 | CD1 | LEU | B | 262 | −8.595 | 42.027 | 49.064 | 1.00 | 41.80 | B | C |
| ATOM | 3566 | CD2 | LEU | B | 262 | −6.289 | 42.667 | 49.862 | 1.00 | 44.80 | B | C |
| ATOM | 3567 | C | LEU | B | 262 | −5.759 | 39.050 | 51.904 | 1.00 | 39.04 | B | C |
| ATOM | 3568 | O | LEU | B | 262 | −6.107 | 37.879 | 52.049 | 1.00 | 37.11 | B | O |
| ATOM | 3569 | N | THR | B | 263 | −5.226 | 39.760 | 52.883 | 1.00 | 40.23 | B | N |
| ATOM | 3570 | CA | THR | B | 263 | −4.630 | 39.078 | 54.013 | 1.00 | 38.36 | B | C |
| ATOM | 3571 | CB | THR | B | 263 | −3.201 | 38.746 | 53.650 | 1.00 | 36.92 | B | C |
| ATOM | 3572 | OG1 | THR | B | 263 | −2.786 | 37.650 | 54.448 | 1.00 | 46.37 | B | O |
| ATOM | 3573 | CG2 | THR | B | 263 | −2.249 | 39.871 | 54.055 | 1.00 | 32.81 | B | C |
| ATOM | 3574 | C | THR | B | 263 | −4.693 | 39.833 | 55.338 | 1.00 | 38.68 | B | C |
| ATOM | 3575 | O | THR | B | 263 | −4.705 | 41.067 | 55.356 | 1.00 | 42.54 | B | O |
| ATOM | 3576 | N | VAL | B | 264 | −4.738 | 39.092 | 56.440 | 1.00 | 35.16 | B | N |
| ATOM | 3577 | CA | VAL | B | 264 | −4.763 | 39.707 | 57.768 | 1.00 | 37.34 | B | C |
| ATOM | 3578 | CB | VAL | B | 264 | −6.172 | 39.626 | 58.415 | 1.00 | 33.52 | B | C |
| ATOM | 3579 | CG1 | VAL | B | 264 | −6.117 | 39.809 | 59.939 | 1.00 | 23.23 | B | C |
| ATOM | 3580 | CG2 | VAL | B | 264 | −7.112 | 40.650 | 57.769 | 1.00 | 33.16 | B | C |
| ATOM | 3581 | C | VAL | B | 264 | −3.695 | 39.080 | 58.654 | 1.00 | 41.03 | B | C |
| ATOM | 3582 | O | VAL | B | 264 | −3.749 | 37.883 | 58.932 | 1.00 | 43.04 | B | O |
| ATOM | 3583 | N | GLN | B | 265 | −2.724 | 39.892 | 59.083 | 1.00 | 43.99 | B | N |
| ATOM | 3584 | CA | GLN | B | 265 | −1.511 | 39.378 | 59.723 | 1.00 | 46.02 | B | C |
| ATOM | 3585 | CB | GLN | B | 265 | −0.705 | 38.512 | 58.739 | 1.00 | 45.87 | B | C |
| ATOM | 3586 | CG | GLN | B | 265 | −0.727 | 38.986 | 57.265 | 1.00 | 46.68 | B | C |
| ATOM | 3587 | CD | GLN | B | 265 | 0.663 | 39.172 | 56.658 | 1.00 | 47.96 | B | C |
| ATOM | 3588 | OE1 | GLN | B | 265 | 1.650 | 39.339 | 57.385 | 1.00 | 54.67 | B | O |
| ATOM | 3589 | NE2 | GLN | B | 265 | 0.740 | 39.157 | 55.328 | 1.00 | 41.34 | B | N |
| ATOM | 3590 | C | GLN | B | 265 | −0.573 | 40.442 | 60.261 | 1.00 | 49.72 | B | C |
| ATOM | 3591 | O | GLN | B | 265 | −0.152 | 41.324 | 59.517 | 1.00 | 49.81 | B | O |
| ATOM | 3592 | N | ARG | B | 266 | −0.283 | 40.345 | 61.565 | 1.00 | 56.89 | B | N |
| ATOM | 3593 | CA | ARG | B | 266 | 0.990 | 40.764 | 62.207 | 1.00 | 56.47 | B | C |
| ATOM | 3594 | CB | ARG | B | 266 | 1.979 | 39.575 | 62.168 | 1.00 | 58.34 | B | C |
| ATOM | 3595 | CG | ARG | B | 266 | 2.075 | 38.835 | 60.766 | 1.00 | 55.22 | B | C |
| ATOM | 3596 | CD | ARG | B | 266 | 3.450 | 38.296 | 60.372 | 1.00 | 49.40 | B | C |
| ATOM | 3597 | NE | ARG | B | 266 | 3.966 | 37.380 | 61.392 | 1.00 | 47.15 | B | N |
| ATOM | 3598 | CZ | ARG | B | 266 | 3.725 | 36.070 | 61.436 | 1.00 | 47.63 | B | C |
| ATOM | 3599 | NH1 | ARG | B | 266 | 2.974 | 35.488 | 60.506 | 1.00 | 48.62 | B | N |
| ATOM | 3600 | NH2 | ARG | B | 266 | 4.244 | 35.331 | 62.415 | 1.00 | 45.83 | B | N |
| ATOM | 3601 | C | ARG | B | 266 | 1.700 | 41.995 | 61.636 | 1.00 | 56.19 | B | C |
| ATOM | 3602 | O | ARG | B | 266 | 2.615 | 41.853 | 60.819 | 1.00 | 60.41 | B | O |
| ATOM | 3603 | N | GLU | B | 267 | 1.307 | 43.194 | 62.055 | 1.00 | 52.91 | B | N |
| ATOM | 3604 | CA | GLU | B | 267 | 1.960 | 44.403 | 61.549 | 1.00 | 52.98 | B | C |
| ATOM | 3605 | CB | GLU | B | 267 | 1.706 | 45.578 | 62.484 | 1.00 | 56.71 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

|      | Atom Number |     | Amino Acid Residue | | | X | Y | Z | Occ. | Temp Factor | Atom Type | |
|------|------|-----|-----|---|-----|--------|--------|--------|------|-------|---|---|
| ATOM | 3606 | CG  | GLU | B | 267 | 1.691  | 46.934 | 61.805 | 1.00 | 58.19 | B | C |
| ATOM | 3607 | CD  | GLU | B | 267 | 0.987  | 47.961 | 62.657 | 1.00 | 59.65 | B | C |
| ATOM | 3608 | OE1 | GLU | B | 267 | −0.256 | 48.072 | 62.543 | 1.00 | 58.53 | B | O |
| ATOM | 3609 | OE2 | GLU | B | 267 | 1.675  | 48.636 | 63.456 | 1.00 | 61.07 | B | O |
| ATOM | 3610 | C   | GLU | B | 267 | 3.460  | 44.152 | 61.410 | 1.00 | 51.15 | B | C |
| ATOM | 3611 | O   | GLU | B | 267 | 4.090  | 44.565 | 60.435 | 1.00 | 46.09 | B | O |
| ATOM | 3612 | N   | THR | B | 268 | 4.005  | 43.481 | 62.421 | 1.00 | 54.84 | B | N |
| ATOM | 3613 | CA  | THR | B | 268 | 5.303  | 42.813 | 62.358 | 1.00 | 62.31 | B | C |
| ATOM | 3614 | CB  | THR | B | 268 | 6.458  | 43.752 | 62.743 | 1.00 | 64.85 | B | C |
| ATOM | 3615 | OG1 | THR | B | 268 | 5.939  | 44.927 | 63.383 | 1.00 | 65.50 | B | O |
| ATOM | 3616 | CG2 | THR | B | 268 | 7.146  | 44.279 | 61.483 | 1.00 | 66.37 | B | C |
| ATOM | 3617 | C   | THR | B | 268 | 5.263  | 41.587 | 63.275 | 1.00 | 64.01 | B | C |
| ATOM | 3618 | O   | THR | B | 268 | 4.324  | 41.435 | 64.065 | 1.00 | 67.03 | B | O |
| ATOM | 3619 | N   | LEU | B | 269 | 6.259  | 40.710 | 63.160 | 1.00 | 60.92 | B | N |
| ATOM | 3620 | CA  | LEU | B | 269 | 6.266  | 39.470 | 63.929 | 1.00 | 60.85 | B | C |
| ATOM | 3621 | CB  | LEU | B | 269 | 7.294  | 38.473 | 63.395 | 1.00 | 61.11 | B | C |
| ATOM | 3622 | CG  | LEU | B | 269 | 8.696  | 38.888 | 62.946 | 1.00 | 62.75 | B | C |
| ATOM | 3623 | CD1 | LEU | B | 269 | 9.146  | 37.935 | 61.854 | 1.00 | 61.57 | B | C |
| ATOM | 3624 | CD2 | LEU | B | 269 | 8.792  | 40.346 | 62.475 | 1.00 | 63.50 | B | C |
| ATOM | 3625 | C   | LEU | B | 269 | 6.490  | 39.772 | 65.397 | 1.00 | 63.03 | B | C |
| ATOM | 3626 | O   | LEU | B | 269 | 7.050  | 40.821 | 65.733 | 1.00 | 65.56 | B | O |
| ATOM | 3627 | N   | ASP | B | 270 | 6.046  | 38.851 | 66.256 | 1.00 | 64.16 | B | N |
| ATOM | 3628 | CA  | ASP | B | 270 | 5.834  | 39.100 | 67.702 | 1.00 | 64.38 | B | C |
| ATOM | 3629 | CB  | ASP | B | 270 | 6.965  | 38.532 | 68.616 | 1.00 | 63.72 | B | C |
| ATOM | 3630 | CG  | ASP | B | 270 | 8.367  | 39.029 | 68.250 | 1.00 | 61.18 | B | C |
| ATOM | 3631 | OD1 | ASP | B | 270 | 8.591  | 40.254 | 68.181 | 1.00 | 59.90 | B | O |
| ATOM | 3632 | OD2 | ASP | B | 270 | 9.322  | 38.249 | 68.048 | 1.00 | 59.89 | B | O |
| ATOM | 3633 | C   | ASP | B | 270 | 5.451  | 40.538 | 68.070 | 1.00 | 61.42 | B | C |
| ATOM | 3634 | O   | ASP | B | 270 | 5.716  | 40.999 | 69.187 | 1.00 | 62.01 | B | O |
| ATOM | 3635 | N   | ALA | B | 271 | 4.806  | 41.225 | 67.127 | 1.00 | 56.80 | B | N |
| ATOM | 3636 | CA  | ALA | B | 271 | 4.461  | 42.626 | 67.293 | 1.00 | 55.54 | B | C |
| ATOM | 3637 | CB  | ALA | B | 271 | 5.014  | 43.451 | 66.146 | 1.00 | 53.22 | B | C |
| ATOM | 3638 | C   | ALA | B | 271 | 2.961  | 42.858 | 67.467 | 1.00 | 56.34 | B | C |
| ATOM | 3639 | O   | ALA | B | 271 | 2.306  | 43.436 | 66.599 | 1.00 | 55.44 | B | O |
| ATOM | 3640 | N   | GLN | B | 272 | 2.437  | 42.365 | 68.590 | 1.00 | 58.23 | B | N |
| ATOM | 3641 | CA  | GLN | B | 272 | 1.131  | 42.749 | 69.154 | 1.00 | 60.29 | B | C |
| ATOM | 3642 | CB  | GLN | B | 272 | 1.311  | 43.941 | 70.109 | 1.00 | 62.16 | B | C |
| ATOM | 3643 | CG  | GLN | B | 272 | 2.416  | 43.749 | 71.142 | 1.00 | 66.34 | B | C |
| ATOM | 3644 | CD  | GLN | B | 272 | 1.937  | 43.049 | 72.408 | 1.00 | 68.87 | B | C |
| ATOM | 3645 | OE1 | GLN | B | 272 | 1.965  | 43.634 | 73.500 | 1.00 | 67.92 | B | O |
| ATOM | 3646 | NE2 | GLN | B | 272 | 1.506  | 41.793 | 72.269 | 1.00 | 69.10 | B | N |
| ATOM | 3647 | C   | GLN | B | 272 | −0.061 | 43.009 | 68.206 | 1.00 | 58.84 | B | C |
| ATOM | 3648 | O   | GLN | B | 272 | −1.054 | 42.277 | 68.252 | 1.00 | 57.37 | B | O |
| ATOM | 3649 | N   | THR | B | 273 | 0.049  | 44.044 | 67.368 | 1.00 | 57.66 | B | N |
| ATOM | 3650 | CA  | THR | B | 273 | −1.083 | 44.609 | 66.621 | 1.00 | 56.42 | B | C |
| ATOM | 3651 | CB  | THR | B | 273 | −1.024 | 46.172 | 66.636 | 1.00 | 57.29 | B | C |
| ATOM | 3652 | OG1 | THR | B | 273 | −1.629 | 46.695 | 65.447 | 1.00 | 61.32 | B | O |
| ATOM | 3653 | CG2 | THR | B | 273 | 0.415  | 46.685 | 66.545 | 1.00 | 55.99 | B | C |
| ATOM | 3654 | C   | THR | B | 273 | −1.246 | 44.077 | 65.186 | 1.00 | 53.53 | B | C |
| ATOM | 3655 | O   | THR | B | 273 | −0.263 | 43.824 | 64.494 | 1.00 | 50.75 | B | O |
| ATOM | 3656 | N   | PHE | B | 274 | −2.503 | 43.944 | 64.751 | 1.00 | 52.92 | B | N |
| ATOM | 3657 | CA  | PHE | B | 274 | −2.839 | 43.377 | 63.438 | 1.00 | 51.47 | B | C |
| ATOM | 3658 | CB  | PHE | B | 274 | −3.888 | 42.275 | 63.569 | 1.00 | 46.97 | B | C |
| ATOM | 3659 | CG  | PHE | B | 274 | −3.333 | 40.979 | 64.073 | 1.00 | 42.64 | B | C |
| ATOM | 3660 | CD1 | PHE | B | 274 | −2.904 | 40.855 | 65.390 | 1.00 | 39.44 | B | C |
| ATOM | 3661 | CE1 | PHE | B | 274 | −2.388 | 39.657 | 65.869 | 1.00 | 37.37 | B | C |
| ATOM | 3662 | CZ  | PHE | B | 274 | −2.300 | 38.570 | 65.043 | 1.00 | 37.12 | B | C |
| ATOM | 3663 | CE2 | PHE | B | 274 | −2.732 | 38.671 | 63.717 | 1.00 | 42.55 | B | C |
| ATOM | 3664 | CD2 | PHE | B | 274 | −3.237 | 39.880 | 63.237 | 1.00 | 42.40 | B | C |
| ATOM | 3665 | C   | PHE | B | 274 | −3.232 | 44.419 | 62.374 | 1.00 | 53.87 | B | C |
| ATOM | 3666 | O   | PHE | B | 274 | −3.213 | 45.628 | 62.654 | 1.00 | 57.55 | B | O |
| ATOM | 3667 | N   | HIS | B | 275 | −3.637 | 43.940 | 61.189 | 1.00 | 49.35 | B | N |
| ATOM | 3668 | CA  | HIS | B | 275 | −3.129 | 44.498 | 59.942 | 1.00 | 44.95 | B | C |
| ATOM | 3669 | CB  | HIS | B | 275 | −1.634 | 44.213 | 60.011 | 1.00 | 49.77 | B | C |
| ATOM | 3670 | CG  | HIS | B | 275 | −0.802 | 44.995 | 59.060 | 1.00 | 54.02 | B | C |
| ATOM | 3671 | ND1 | HIS | B | 275 | −1.104 | 46.287 | 58.691 | 1.00 | 56.86 | B | N |
| ATOM | 3672 | CE1 | HIS | B | 275 | −0.177 | 46.724 | 57.857 | 1.00 | 59.62 | B | C |
| ATOM | 3673 | NE2 | HIS | B | 275 | 0.712  | 45.762 | 57.676 | 1.00 | 58.82 | B | N |
| ATOM | 3674 | CD2 | HIS | B | 275 | 0.349  | 44.673 | 58.425 | 1.00 | 54.88 | B | C |
| ATOM | 3675 | C   | HIS | B | 275 | −3.663 | 43.778 | 58.699 | 1.00 | 44.44 | B | C |
| ATOM | 3676 | O   | HIS | B | 275 | −3.753 | 42.552 | 58.678 | 1.00 | 44.99 | B | O |
| ATOM | 3677 | N   | THR | B | 276 | −3.975 | 44.528 | 57.644 | 1.00 | 42.61 | B | N |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 3678 | CA | THR | B | 276 | −4.378 | 43.933 | 56.358 | 1.00 | 38.29 | B | C |
| ATOM | 3679 | CB | THR | B | 276 | −5.746 | 44.500 | 55.911 | 1.00 | 35.81 | B | C |
| ATOM | 3680 | OG1 | THR | B | 276 | −6.786 | 43.962 | 56.728 | 1.00 | 39.39 | B | O |
| ATOM | 3681 | CG2 | THR | B | 276 | −6.127 | 44.011 | 54.527 | 1.00 | 34.00 | B | C |
| ATOM | 3682 | C | THR | B | 276 | −3.352 | 44.264 | 55.286 | 1.00 | 39.94 | B | C |
| ATOM | 3683 | O | THR | B | 276 | −2.967 | 45.424 | 55.157 | 1.00 | 45.44 | B | O |
| ATOM | 3684 | N | ARG | B | 277 | −2.919 | 43.277 | 54.501 | 1.00 | 37.62 | B | N |
| ATOM | 3685 | CA | ARG | B | 277 | −2.063 | 43.577 | 53.346 | 1.00 | 38.46 | B | C |
| ATOM | 3686 | CB | ARG | B | 277 | −0.673 | 42.971 | 53.509 | 1.00 | 42.89 | B | C |
| ATOM | 3687 | CG | ARG | B | 277 | 0.089 | 43.397 | 54.743 | 1.00 | 48.14 | B | C |
| ATOM | 3688 | CD | ARG | B | 277 | 0.853 | 42.246 | 55.360 | 1.00 | 50.64 | B | C |
| ATOM | 3689 | NE | ARG | B | 277 | 1.732 | 42.636 | 56.460 | 1.00 | 51.88 | B | N |
| ATOM | 3690 | CZ | ARG | B | 277 | 2.995 | 42.246 | 56.562 | 1.00 | 51.75 | B | C |
| ATOM | 3691 | NH1 | ARG | B | 277 | 3.517 | 41.462 | 55.618 | 1.00 | 50.20 | B | N |
| ATOM | 3692 | NH2 | ARG | B | 277 | 3.735 | 42.636 | 57.598 | 1.00 | 49.27 | B | N |
| ATOM | 3693 | C | ARG | B | 277 | −2.643 | 43.092 | 52.025 | 1.00 | 39.50 | B | C |
| ATOM | 3694 | O | ARG | B | 277 | −3.572 | 42.278 | 52.010 | 1.00 | 38.59 | B | O |
| ATOM | 3695 | N | ILE | B | 278 | −2.107 | 43.616 | 50.918 | 1.00 | 40.77 | B | N |
| ATOM | 3696 | CA | ILE | B | 278 | −2.204 | 42.931 | 49.633 | 1.00 | 43.35 | B | C |
| ATOM | 3697 | CB | ILE | B | 278 | −2.365 | 43.879 | 48.429 | 1.00 | 46.48 | B | C |
| ATOM | 3698 | CG1 | ILE | B | 278 | −3.534 | 44.833 | 48.611 | 1.00 | 53.74 | b | C |
| ATOM | 3699 | CD1 | ILE | B | 278 | −4.565 | 44.776 | 47.457 | 1.00 | 56.04 | B | C |
| ATOM | 3700 | CG2 | ILE | B | 278 | −2.626 | 43.059 | 47.159 | 1.00 | 45.36 | B | C |
| ATOM | 3701 | C | ILE | B | 278 | −0.934 | 42.125 | 49.428 | 1.00 | 45.96 | B | C |
| ATOM | 3702 | O | ILE | B | 278 | 0.150 | 42.505 | 49.881 | 1.00 | 47.89 | B | O |
| ATOM | 3703 | N | ILE | B | 279 | −1.086 | 41.003 | 48.740 | 1.00 | 45.37 | B | N |
| ATOM | 3704 | CA | ILE | B | 279 | 0.028 | 40.239 | 48.243 | 1.00 | 42.10 | B | C |
| ATOM | 3705 | CB | ILE | B | 279 | −0.010 | 38.859 | 48.862 | 1.00 | 46.45 | B | C |
| ATOM | 3706 | CG1 | ILE | B | 279 | 0.560 | 38.922 | 50.277 | 1.00 | 53.46 | B | C |
| ATOM | 3707 | CD1 | ILE | B | 279 | −0.234 | 38.137 | 51.300 | 1.00 | 58.89 | B | C |
| ATOM | 3708 | CG2 | ILE | B | 279 | 0.786 | 37.873 | 48.043 | 1.00 | 48.44 | B | C |
| ATOM | 3709 | C | ILE | B | 279 | −0.158 | 40.180 | 46.747 | 1.00 | 41.15 | B | C |
| ATOM | 3710 | O | ILE | B | 279 | −1.258 | 39.945 | 46.256 | 1.00 | 43.82 | B | O |
| ATOM | 3711 | N | ARG | B | 280 | 0.910 | 40.421 | 46.012 | 1.00 | 41.34 | B | N |
| ATOM | 3712 | CA | ARG | B | 280 | 0.824 | 40.424 | 44.563 | 1.00 | 45.85 | B | C |
| ATOM | 3713 | CB | ARG | B | 280 | 0.811 | 41.869 | 44.068 | 1.00 | 51.26 | B | C |
| ATOM | 3714 | CG | ARG | B | 280 | 0.662 | 42.049 | 42.584 | 1.00 | 55.05 | B | C |
| ATOM | 3715 | CD | ARG | B | 280 | 1.913 | 42.550 | 41.938 | 1.00 | 60.03 | B | C |
| ATOM | 3716 | NE | ARG | B | 280 | 1.758 | 43.887 | 41.382 | 1.00 | 63.67 | B | N |
| ATOM | 3717 | CZ | ARG | B | 280 | 2.748 | 44.569 | 40.814 | 1.00 | 69.54 | B | C |
| ATOM | 3718 | NH1 | ARG | B | 280 | 3.970 | 44.046 | 40.730 | 1.00 | 71.74 | B | N |
| ATOM | 3719 | NH2 | ARG | B | 280 | 2.522 | 45.780 | 40.325 | 1.00 | 72.83 | B | N |
| ATOM | 3720 | C | ARG | B | 280 | 2.013 | 39.666 | 44.003 | 1.00 | 47.40 | B | C |
| ATOM | 3721 | O | ARG | B | 280 | 3.123 | 39.783 | 44.527 | 1.00 | 50.74 | B | O |
| ATOM | 3722 | N | PHE | B | 281 | 1.778 | 38.855 | 42.975 | 1.00 | 46.60 | B | N |
| ATOM | 3723 | CA | PHE | B | 281 | 2.872 | 38.195 | 42.258 | 1.00 | 45.38 | B | C |
| ATOM | 3724 | CB | PHE | B | 281 | 3.370 | 36.936 | 42.965 | 1.00 | 39.87 | B | C |
| ATOM | 3725 | CG | PHE | B | 281 | 2.282 | 36.035 | 43.438 | 1.00 | 37.45 | B | C |
| ATOM | 3726 | CD1 | PHE | B | 281 | 1.625 | 35.184 | 42.549 | 1.00 | 39.49 | B | C |
| ATOM | 3727 | CE1 | PHE | B | 281 | 0.595 | 34.323 | 42.983 | 1.00 | 37.51 | B | C |
| ATOM | 3728 | CZ | PHE | B | 281 | 0.229 | 34.318 | 44.309 | 1.00 | 37.59 | B | C |
| ATOM | 3729 | CE2 | PHE | B | 281 | 0.905 | 35.157 | 45.220 | 1.00 | 40.03 | B | C |
| ATOM | 3730 | CD2 | PHE | B | 281 | 1.925 | 36.010 | 44.776 | 1.00 | 36.13 | B | C |
| ATOM | 3731 | C | PHE | B | 281 | 2.474 | 37.862 | 40.845 | 1.00 | 49.53 | B | C |
| ATOM | 3732 | O | PHE | B | 281 | 1.286 | 37.795 | 40.527 | 1.00 | 47.11 | B | O |
| ATOM | 3733 | N | CYS | B | 282 | 3.490 | 37.663 | 40.011 | 1.00 | 56.23 | B | N |
| ATOM | 3734 | CA | CYS | B | 282 | 3.315 | 37.412 | 38.596 | 1.00 | 57.99 | B | C |
| ATOM | 3735 | CB | CYS | B | 282 | 4.663 | 37.392 | 37.899 | 1.00 | 65.24 | B | C |
| ATOM | 3736 | SG | CYS | B | 282 | 4.825 | 38.675 | 36.652 | 1.00 | 78.83 | B | S |
| ATOM | 3737 | C | CYS | B | 282 | 2.629 | 36.094 | 38.412 | 1.00 | 59.66 | B | C |
| ATOM | 3738 | O | CYS | B | 282 | 2.938 | 35.121 | 39.097 | 1.00 | 60.32 | B | O |
| ATOM | 3739 | N | SER | B | 283 | 1.681 | 36.086 | 37.484 | 1.00 | 67.93 | B | N |
| ATOM | 3740 | CA | SER | B | 283 | 0.865 | 34.913 | 37.149 | 1.00 | 72.78 | B | C |
| ATOM | 3741 | CB | SER | B | 283 | −0.389 | 35.376 | 36.361 | 1.00 | 70.36 | B | C |
| ATOM | 3742 | OG | SER | B | 283 | −1.117 | 34.287 | 35.803 | 1.00 | 72.53 | B | O |
| ATOM | 3743 | C | SER | B | 283 | 1.675 | 33.833 | 36.380 | 1.00 | 73.87 | B | C |
| ATOM | 3744 | O | SER | B | 283 | 1.633 | 33.762 | 35.146 | 1.00 | 77.97 | B | O |
| ATOM | 3745 | N | ILE | B | 284 | 2.430 | 33.007 | 37.094 | 1.00 | 70.60 | B | N |
| ATOM | 3746 | CA | ILE | B | 284 | 3.182 | 31.973 | 36.404 | 1.00 | 76.76 | B | C |
| ATOM | 3747 | CB | ILE | B | 284 | 4.622 | 32.445 | 35.992 | 1.00 | 76.61 | B | C |
| ATOM | 3748 | CG1 | ILE | B | 284 | 4.722 | 33.963 | 35.880 | 1.00 | 75.68 | B | C |
| ATOM | 3749 | CD1 | ILE | B | 284 | 5.398 | 34.456 | 34.599 | 1.00 | 78.40 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 3750 | CG2 | ILE | B | 284 | 5.028 | 31.806 | 34.660 | 1.00 | 80.65 | B | C |
| ATOM | 3751 | C | ILE | B | 284 | 3.239 | 30.618 | 37.122 | 1.00 | 83.89 | B | C |
| ATOM | 3752 | O | ILE | B | 284 | 3.513 | 30.530 | 38.330 | 1.00 | 83.74 | B | O |
| ATOM | 3753 | N | ASN | B | 285 | 2.964 | 29.574 | 36.333 | 1.00 | 86.69 | B | N |
| ATOM | 3754 | CA | ASN | B | 285 | 3.291 | 28.179 | 36.629 | 1.00 | 84.66 | B | C |
| ATOM | 3755 | CB | ASN | B | 285 | 3.435 | 27.449 | 35.306 | 1.00 | 87.10 | B | C |
| ATOM | 3756 | CG | ASN | B | 285 | 2.370 | 26.442 | 35.099 | 1.00 | 90.93 | B | C |
| ATOM | 3757 | OD1 | ASN | B | 285 | 2.008 | 25.724 | 36.025 | 1.00 | 88.91 | B | O |
| ATOM | 3758 | ND2 | ASN | B | 285 | 1.835 | 26.380 | 33.875 | 1.00 | 94.17 | B | N |
| ATOM | 3759 | C | ASN | B | 285 | 4.614 | 28.002 | 37.324 | 1.00 | 82.64 | B | C |
| ATOM | 3760 | O | ASN | B | 285 | 4.709 | 27.384 | 38.384 | 1.00 | 80.16 | B | O |
| ATOM | 3761 | N | SER | B | 286 | 5.629 | 28.566 | 36.673 | 1.00 | 84.00 | B | N |
| ATOM | 3762 | CA | SER | B | 286 | 7.039 | 28.312 | 36.927 | 1.00 | 85.66 | B | C |
| ATOM | 3763 | CB | SER | B | 286 | 7.896 | 29.115 | 35.934 | 1.00 | 88.63 | B | C |
| ATOM | 3764 | OG | SER | B | 286 | 7.581 | 30.505 | 35.951 | 1.00 | 88.36 | B | O |
| ATOM | 3765 | C | SER | B | 286 | 7.447 | 28.636 | 38.349 | 1.00 | 85.35 | B | C |
| ATOM | 3766 | O | SER | B | 286 | 8.517 | 28.211 | 38.807 | 1.00 | 88.05 | B | O |
| ATOM | 3767 | N | GLY | B | 287 | 6.595 | 29.390 | 39.038 | 1.00 | 79.54 | B | N |
| ATOM | 3768 | CA | GLY | B | 287 | 6.879 | 29.803 | 40.398 | 1.00 | 74.83 | B | C |
| ATOM | 3769 | C | GLY | B | 287 | 6.294 | 31.157 | 40.722 | 1.00 | 70.55 | B | C |
| ATOM | 3770 | O | GLY | B | 287 | 5.763 | 31.857 | 39.847 | 1.00 | 72.26 | B | O |
| ATOM | 3771 | N | LEU | B | 288 | 6.371 | 31.521 | 41.995 | 1.00 | 62.57 | B | N |
| ATOM | 3772 | CA | LEU | B | 288 | 5.925 | 32.830 | 42.422 | 1.00 | 56.34 | B | C |
| ATOM | 3773 | CB | LEU | B | 288 | 5.698 | 32.833 | 43.913 | 1.00 | 48.19 | B | C |
| ATOM | 3774 | CG | LEU | B | 288 | 4.757 | 31.729 | 44.318 | 1.00 | 44.46 | B | C |
| ATOM | 3775 | CD1 | LEU | B | 288 | 5.230 | 31.232 | 45.641 | 1.00 | 50.30 | B | C |
| ATOM | 3776 | CD2 | LEU | B | 288 | 3.331 | 32.254 | 44.391 | 1.00 | 41.40 | B | C |
| ATOM | 3777 | C | LEU | B | 288 | 7.022 | 33.798 | 42.087 | 1.00 | 58.68 | B | C |
| ATOM | 3778 | O | LEU | B | 288 | 8.149 | 33.631 | 42.564 | 1.00 | 55.28 | B | O |
| ATOM | 3779 | N | HIS | B | 289 | 6.713 | 34.806 | 41.273 | 1.00 | 62.56 | B | N |
| ATOM | 3780 | CA | HIS | B | 289 | 7.792 | 35.643 | 40.771 | 1.00 | 67.70 | B | C |
| ATOM | 3781 | CB | HIS | B | 289 | 7.951 | 35.543 | 39.242 | 1.00 | 69.53 | B | C |
| ATOM | 3782 | CG | HIS | B | 289 | 8.564 | 34.241 | 38.806 | 1.00 | 71.32 | B | C |
| ATOM | 3783 | ND1 | HIS | B | 289 | 9.708 | 33.731 | 39.383 | 1.00 | 70.97 | B | N |
| ATOM | 3784 | CE1 | HIS | B | 289 | 9.993 | 32.560 | 38.839 | 1.00 | 72.47 | B | C |
| ATOM | 3785 | NE2 | HIS | B | 289 | 9.073 | 32.288 | 37.932 | 1.00 | 72.64 | B | N |
| ATOM | 3786 | CD2 | HIS | B | 289 | 8.163 | 33.319 | 37.896 | 1.00 | 73.23 | B | C |
| ATOM | 3787 | C | HIS | B | 289 | 7.973 | 37.039 | 41.376 | 1.00 | 70.32 | B | C |
| ATOM | 3788 | O | HIS | B | 289 | 8.902 | 37.242 | 42.179 | 1.00 | 78.40 | B | O |
| ATOM | 3789 | N | SER | B | 290 | 7.142 | 38.010 | 41.053 | 1.00 | 63.75 | B | N |
| ATOM | 3790 | CA | SER | B | 290 | 7.478 | 39.304 | 41.628 | 1.00 | 62.91 | B | C |
| ATOM | 3791 | CB | SER | B | 290 | 7.361 | 40.425 | 40.605 | 1.00 | 68.79 | B | C |
| ATOM | 3792 | OG | SER | B | 290 | 8.626 | 40.636 | 40.007 | 1.00 | 70.89 | B | O |
| ATOM | 3793 | C | SER | B | 290 | 6.737 | 39.585 | 42.928 | 1.00 | 58.08 | B | C |
| ATOM | 3794 | O | SER | B | 290 | 5.916 | 40.503 | 43.015 | 1.00 | 63.24 | B | O |
| ATOM | 3795 | N | TYR | B | 291 | 7.069 | 38.791 | 43.941 | 1.00 | 47.39 | B | N |
| ATOM | 3796 | CA | TYR | B | 291 | 6.309 | 38.736 | 45.180 | 1.00 | 41.83 | B | C |
| ATOM | 3797 | CB | TYR | B | 291 | 6.660 | 37.456 | 45.927 | 1.00 | 37.48 | B | C |
| ATOM | 3798 | CG | TYR | B | 291 | 5.744 | 37.182 | 47.084 | 1.00 | 36.21 | B | C |
| ATOM | 3799 | CD1 | TYR | B | 291 | 4.686 | 36.281 | 46.961 | 1.00 | 33.62 | B | C |
| ATOM | 3800 | CE1 | TYR | B | 291 | 3.840 | 36.030 | 48.034 | 1.00 | 34.80 | B | C |
| ATOM | 3801 | CZ | TYR | B | 291 | 4.047 | 36.696 | 49.248 | 1.00 | 36.53 | B | C |
| ATOM | 3802 | OH | TYR | B | 291 | 3.213 | 36.478 | 50.320 | 1.00 | 36.69 | B | O |
| ATOM | 3803 | CE2 | TYR | B | 291 | 5.089 | 37.600 | 49.387 | 1.00 | 36.23 | B | C |
| ATOM | 3804 | CD2 | TYR | B | 291 | 5.927 | 37.836 | 48.309 | 1.00 | 35.98 | B | C |
| ATOM | 3805 | C | TYR | B | 291 | 6.536 | 39.944 | 46.085 | 1.00 | 45.26 | B | C |
| ATOM | 3806 | O | TYR | B | 291 | 7.676 | 40.338 | 46.333 | 1.00 | 49.90 | B | O |
| ATOM | 3807 | N | MET | B | 292 | 5.449 | 40.532 | 46.578 | 1.00 | 43.80 | B | N |
| ATOM | 3808 | CA | MET | B | 292 | 5.515 | 41.703 | 47.458 | 1.00 | 44.36 | B | C |
| ATOM | 3809 | CB | MET | B | 292 | 5.717 | 43.014 | 46.672 | 1.00 | 47.97 | B | C |
| ATOM | 3810 | CG | MET | B | 292 | 6.627 | 42.930 | 45.445 | 1.00 | 53.67 | B | C |
| ATOM | 3811 | SD | MET | B | 292 | 6.460 | 44.262 | 44.234 | 1.00 | 57.70 | B | S |
| ATOM | 3812 | CE | MET | B | 292 | 7.795 | 45.383 | 44.800 | 1.00 | 54.66 | B | C |
| ATOM | 3813 | C | MET | B | 292 | 4.227 | 41.812 | 48.250 | 1.00 | 44.44 | B | C |
| ATOM | 3814 | O | MET | B | 292 | 3.139 | 41.710 | 47.689 | 1.00 | 51.08 | B | O |
| ATOM | 3815 | N | GLU | B | 293 | 4.333 | 42.024 | 49.550 | 1.00 | 40.31 | B | N |
| ATOM | 3816 | CA | GLU | B | 293 | 3.143 | 42.289 | 50.339 | 1.00 | 38.64 | B | C |
| ATOM | 3817 | CB | GLU | B | 293 | 3.098 | 41.424 | 51.594 | 1.00 | 39.59 | B | C |
| ATOM | 3818 | CG | GLU | B | 293 | 3.923 | 40.150 | 51.552 | 1.00 | 38.35 | B | C |
| ATOM | 3819 | CD | GLU | B | 293 | 3.505 | 39.163 | 52.627 | 1.00 | 38.12 | B | C |
| ATOM | 3820 | OE1 | GLU | B | 293 | 3.526 | 39.536 | 53.834 | 1.00 | 37.86 | B | O |
| ATOM | 3821 | OE2 | GLU | B | 293 | 3.142 | 38.021 | 52.263 | 1.00 | 35.21 | B | O |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 3822 | C | GLU | B | 293 | 3.142 | 43.747 | 50.740 | 1.00 | 40.30 | B | C |
| ATOM | 3823 | O | GLU | B | 293 | 4.114 | 44.233 | 51.301 | 1.00 | 43.67 | B | O |
| ATOM | 3824 | N | MET | B | 294 | 2.060 | 44.454 | 50.460 | 1.00 | 39.60 | B | N |
| ATOM | 3825 | CA | MET | B | 294 | 1.975 | 45.843 | 50.866 | 1.00 | 41.04 | B | C |
| ATOM | 3826 | CB | MET | B | 294 | 2.044 | 46.749 | 49.639 | 1.00 | 44.09 | B | C |
| ATOM | 3827 | CG | MET | B | 294 | 1.049 | 47.881 | 49.546 | 1.00 | 48.48 | B | C |
| ATOM | 3828 | SD | MET | B | 294 | 0.858 | 48.261 | 47.786 | 1.00 | 56.51 | B | S |
| ATOM | 3829 | CE | MET | B | 294 | −0.751 | 48.941 | 47.750 | 1.00 | 57.49 | B | C |
| ATOM | 3830 | C | MET | B | 294 | 0.733 | 46.079 | 51.708 | 1.00 | 43.27 | B | C |
| ATOM | 3831 | O | MET | B | 294 | −0.370 | 45.731 | 51.289 | 1.00 | 48.54 | B | O |
| ATOM | 3832 | N | PRO | B | 295 | 0.933 | 46.610 | 52.917 | 1.00 | 42.18 | B | N |
| ATOM | 3833 | CA | PRO | B | 295 | −0.154 | 46.989 | 53.833 | 1.00 | 39.90 | B | C |
| ATOM | 3834 | CB | PRO | B | 295 | 0.575 | 47.748 | 54.935 | 1.00 | 38.78 | B | C |
| ATOM | 3835 | CG | PRO | B | 295 | 1.934 | 48.002 | 54.398 | 1.00 | 41.92 | B | C |
| ATOM | 3836 | CD | PRO | B | 295 | 2.252 | 46.842 | 53.524 | 1.00 | 42.28 | B | C |
| ATOM | 3837 | C | PRO | B | 295 | −1.218 | 47.899 | 53.233 | 1.00 | 40.13 | B | C |
| ATOM | 3838 | O | PRO | B | 295 | −0.902 | 48.692 | 52.344 | 1.00 | 38.20 | B | O |
| ATOM | 3839 | N | LEU | B | 296 | −2.451 | 47.757 | 53.731 | 1.00 | 41.86 | B | N |
| ATOM | 3840 | CA | LEU | B | 296 | −3.620 | 48.548 | 53.334 | 1.00 | 41.65 | B | C |
| ATOM | 3841 | CB | LEU | B | 296 | −4.625 | 47.670 | 52.598 | 1.00 | 36.91 | B | C |
| ATOM | 3842 | CG | LEU | B | 296 | −4.347 | 47.267 | 51.149 | 1.00 | 38.16 | B | C |
| ATOM | 3843 | CD1 | LEU | B | 296 | −5.656 | 47.151 | 50.378 | 1.00 | 38.38 | B | C |
| ATOM | 3844 | CD2 | LEU | B | 296 | −3.432 | 48.251 | 50.447 | 1.00 | 39.97 | B | C |
| ATOM | 3845 | C | LEU | B | 296 | −4.294 | 49.163 | 54.569 | 1.00 | 48.76 | B | C |
| ATOM | 3846 | O | LEU | B | 296 | −4.422 | 48.509 | 55.610 | 1.00 | 51.59 | B | O |
| ATOM | 3847 | N | GLU | B | 297 | −4.725 | 50.417 | 54.450 | 1.00 | 52.95 | B | N |
| ATOM | 3848 | CA | GLU | B | 297 | −5.309 | 51.155 | 55.568 | 1.00 | 54.84 | B | C |
| ATOM | 3849 | CB | GLU | B | 297 | −4.375 | 52.302 | 55.978 | 1.00 | 57.43 | B | C |
| ATOM | 3850 | CG | GLU | B | 297 | −3.502 | 52.030 | 57.198 | 1.00 | 62.42 | B | C |
| ATOM | 3851 | CD | GLU | B | 297 | −2.773 | 53.269 | 57.724 | 1.00 | 66.04 | 8 | C |
| ATOM | 3852 | OE1 | GLU | B | 297 | −3.095 | 54.411 | 57.309 | 1.00 | 67.50 | B | O |
| ATOM | 3853 | OE2 | GLU | B | 297 | −1.865 | 53.102 | 58.570 | 1.00 | 66.40 | B | O |
| ATOM | 3854 | C | GLU | B | 297 | −6.669 | 51.730 | 55.184 | 1.00 | 56.60 | B | C |
| ATOM | 3855 | O | GLU | B | 297 | −6.782 | 52.451 | 54.188 | 1.00 | 57.35 | B | O |
| ATOM | 3856 | N | CYS | B | 298 | −7.701 | 51.403 | 55.957 | 1.00 | 56.57 | B | N |
| ATOM | 3857 | CA | CYS | B | 298 | −8.980 | 52.111 | 55.851 | 1.00 | 55.08 | B | C |
| ATOM | 3858 | CB | CYS | B | 298 | −10.152 | 51.153 | 55.764 | 1.00 | 52.43 | B | C |
| ATOM | 3859 | SG | CYS | B | 298 | −11.578 | 51.921 | 54.988 | 1.00 | 53.14 | B | S |
| ATOM | 3860 | C | CYS | B | 298 | −9.179 | 53.008 | 57.056 | 1.00 | 57.69 | B | C |
| ATOM | 3861 | O | CYS | B | 298 | −8.995 | 52.570 | 58.186 | 1.00 | 59.46 | B | O |
| ATOM | 3862 | N | ILE | B | 299 | −9.564 | 54.258 | 56.817 | 1.00 | 59.66 | B | N |
| ATOM | 3863 | CA | ILE | B | 299 | −9.727 | 55.230 | 57.899 | 1.00 | 59.53 | B | C |
| ATOM | 3864 | CB | ILE | B | 299 | −8.511 | 56.184 | 57.967 | 1.00 | 59.74 | B | C |
| ATOM | 3865 | CG1 | ILE | B | 299 | −8.095 | 56.653 | 56.565 | 1.00 | 61.08 | B | C |
| ATOM | 3866 | CD1 | ILE | B | 299 | −7.489 | 58.053 | 56.521 | 1.00 | 60.66 | B | C |
| ATOM | 3867 | CG2 | ILE | B | 299 | −7.354 | 55.506 | 58.679 | 1.00 | 59.40 | B | C |
| ATOM | 3868 | C | ILE | B | 299 | −11.044 | 56.014 | 57.851 | 1.00 | 62.03 | B | C |
| ATOM | 3869 | O | ILE | B | 299 | −11.657 | 56.170 | 56.785 | 1.00 | 58.16 | B | O |
| ATOM | 3870 | N | LEU | B | 300 | −11.459 | 56.501 | 59.024 | 1.00 | 68.13 | B | N |
| ATOM | 3871 | CA | LEU | B | 300 | −12.708 | 57.258 | 59.199 | 1.00 | 71.33 | B | C |
| ATOM | 3872 | CB | LEU | B | 300 | −13.269 | 57.057 | 60.616 | 1.00 | 70.08 | B | C |
| ATOM | 3873 | CG | LEU | B | 300 | −14.760 | 57.356 | 60.821 | 1.00 | 70.36 | B | C |
| ATOM | 3874 | CD1 | LEU | B | 300 | −15.630 | 56.190 | 60.371 | 1.00 | 69.76 | B | C |
| ATOM | 3875 | CD2 | LEU | B | 300 | −15.061 | 57.724 | 62.273 | 1.00 | 71.69 | B | C |
| ATOM | 3876 | C | LEU | B | 300 | −12.603 | 58.760 | 58.883 | 1.00 | 73.92 | B | C |
| ATOM | 3877 | O | LEU | B | 300 | −13.527 | 59.322 | 58.290 | 1.00 | 75.89 | B | O |
| ATOM | 3878 | N | THR | B | 301 | −11.491 | 59.391 | 59.284 | 1.00 | 74.85 | B | N |
| ATOM | 3879 | CA | THR | B | 301 | −11.243 | 60.839 | 59.111 | 1.00 | 73.74 | B | C |
| ATOM | 3880 | CB | THR | B | 301 | −11.152 | 61.239 | 57.600 | 1.00 | 73.95 | B | C |
| ATOM | 3881 | OG1 | THR | B | 301 | −9.890 | 61.867 | 57.339 | 1.00 | 74.72 | B | O |
| ATOM | 3882 | CG2 | THR | B | 301 | −12.183 | 62.316 | 57.225 | 1.00 | 71.77 | B | C |
| ATOM | 3883 | C | THR | B | 301 | −12.250 | 61.708 | 59.867 | 1.00 | 71.57 | B | C |
| ATOM | 3884 | O | THR | B | 301 | −12.473 | 61.512 | 61.061 | 1.00 | 69.93 | B | O |
| ATOM | 3885 | N | LYS | B | 311 | −5.981 | 59.549 | 63.217 | 1.00 | 75.59 | B | N |
| ATOM | 3886 | CA | LYS | B | 311 | −6.434 | 58.536 | 62.267 | 1.00 | 76.17 | B | C |
| ATOM | 3887 | CB | LYS | B | 311 | −5.240 | 57.941 | 61.505 | 1.00 | 78.74 | B | C |
| ATOM | 3888 | CG | LYS | B | 311 | −4.699 | 58.809 | 60.371 | 1.00 | 81.19 | B | C |
| ATOM | 3889 | CD | LYS | B | 311 | −3.521 | 58.136 | 59.662 | 1.00 | 81.72 | B | C |
| ATOM | 3890 | CE | LYS | B | 311 | −2.818 | 59.103 | 58.711 | 1.00 | 81.77 | B | C |
| ATOM | 3891 | NZ | LYS | B | 311 | −1.672 | 58.467 | 57.997 | 1.00 | 80.78 | B | N |
| ATOM | 3892 | C | LYS | B | 311 | −7.197 | 57.416 | 62.973 | 1.00 | 73.12 | B | C |
| ATOM | 3893 | O | LYS | B | 311 | −6.675 | 56.793 | 63.895 | 1.00 | 73.93 | B | O |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 3894 | N | GLU | B | 312 | −8.431 | 57.172 | 62.546 | 1.00 | 70.40 | B | N |
| ATOM | 3895 | CA | GLU | B | 312 | −9.203 | 56.030 | 63.036 | 1.00 | 70.15 | B | C |
| ATOM | 3896 | CB | GLU | B | 312 | −10.627 | 56.461 | 63.418 | 1.00 | 71.10 | B | C |
| ATOM | 3897 | CG | GLU | B | 312 | −11.398 | 55.423 | 64.225 | 1.00 | 72.95 | B | C |
| ATOM | 3898 | CD | GLU | B | 312 | −11.576 | 55.806 | 65.684 | 1.00 | 73.81 | B | C |
| ATOM | 3899 | OE1 | GLU | B | 312 | −12.398 | 56.701 | 65.961 | 1.00 | 75.52 | B | O |
| ATOM | 3900 | OE2 | GLU | B | 312 | −10.907 | 55.209 | 66.559 | 1.00 | 73.04 | B | O |
| ATOM | 3901 | C | GLU | B | 312 | −9.206 | 54.897 | 61.989 | 1.00 | 69.21 | B | C |
| ATOM | 3902 | O | GLU | B | 312 | −9.962 | 54.938 | 61.011 | 1.00 | 68.31 | B | O |
| ATOM | 3903 | N | VAL | B | 313 | −8.363 | 53.887 | 62.217 | 1.00 | 66.47 | B | N |
| ATOM | 3904 | CA | VAL | B | 313 | −8.036 | 52.878 | 61.199 | 1.00 | 63.03 | B | C |
| ATOM | 3905 | CB | VAL | B | 313 | −6.518 | 52.572 | 61.167 | 1.00 | 64.23 | B | C |
| ATOM | 3906 | CG1 | VAL | B | 313 | −6.090 | 52.118 | 59.787 | 1.00 | 65.00 | B | C |
| ATOM | 3907 | CG2 | VAL | B | 313 | −5.699 | 53.786 | 61.602 | 1.00 | 66.29 | B | C |
| ATOM | 3908 | C | VAL | B | 313 | −8.790 | 51.558 | 61.344 | 1.00 | 60.30 | B | C |
| ATOM | 3909 | O | VAL | B | 313 | −8.998 | 51.068 | 62.445 | 1.00 | 60.55 | B | O |
| ATOM | 3910 | N | PHE | B | 314 | −9.178 | 50.985 | 60.211 | 1.00 | 60.20 | B | N |
| ATOM | 3911 | CA | PHE | B | 314 | −9.881 | 49.708 | 60.177 | 1.00 | 63.28 | B | C |
| ATOM | 3912 | CB | PHE | B | 314 | −11.215 | 49.846 | 59.443 | 1.00 | 68.40 | B | C |
| ATOM | 3913 | CG | PHE | B | 314 | −12.164 | 50.797 | 60.111 | 1.00 | 72.13 | B | C |
| ATOM | 3914 | CD1 | PHE | B | 314 | −13.025 | 50.354 | 61.110 | 1.00 | 73.60 | B | C |
| ATOM | 3915 | CE1 | PHE | B | 314 | −13.900 | 51.235 | 61.743 | 1.00 | 73.55 | B | C |
| ATOM | 3916 | CZ | PHE | B | 314 | −13.912 | 52.576 | 61.382 | 1.00 | 73.29 | B | C |
| ATOM | 3917 | CE2 | PHE | B | 314 | −13.048 | 53.034 | 60.393 | 1.00 | 73.17 | B | C |
| ATOM | 3918 | CD2 | PHE | B | 314 | −12.180 | 52.143 | 59.762 | 1.00 | 73.47 | B | C |
| ATOM | 3919 | C | PHE | B | 314 | −8.980 | 48.623 | 59.585 | 1.00 | 62.17 | B | C |
| ATOM | 3920 | O | PHE | B | 314 | −8.934 | 48.370 | 58.372 | 1.00 | 60.61 | B | O |
| ATOM | 3921 | N | ASN | B | 315 | −8.262 | 47.985 | 60.492 | 1.00 | 60.37 | B | N |
| ATOM | 3922 | CA | ASN | B | 315 | −7.112 | 47.181 | 60.146 | 1.00 | 59.51 | B | C |
| ATOM | 3923 | CB | ASN | B | 315 | −6.130 | 47.235 | 61.306 | 1.00 | 59.70 | B | C |
| ATOM | 3924 | CG | ASN | B | 315 | −6.766 | 46.820 | 62.609 | 1.00 | 59.13 | B | C |
| ATOM | 3925 | OD1 | ASN | B | 315 | −7.854 | 47.282 | 62.958 | 1.00 | 56.72 | B | O |
| ATOM | 3926 | ND2 | ASN | B | 315 | −6.102 | 45.925 | 63.328 | 1.00 | 61.68 | B | N |
| ATOM | 3927 | C | ASN | B | 315 | −7.452 | 45.734 | 59.832 | 1.00 | 56.95 | B | C |
| ATOM | 3928 | O | ASN | B | 315 | −6.575 | 44.968 | 59.423 | 1.00 | 57.41 | B | O |
| ATOM | 3929 | N | ILE | B | 316 | −8.709 | 45.351 | 60.041 | 1.00 | 52.39 | B | N |
| ATOM | 3930 | CA | ILE | B | 316 | −9.113 | 43.981 | 59.749 | 1.00 | 49.80 | B | C |
| ATOM | 3931 | CB | ILE | B | 316 | −9.503 | 43.217 | 61.022 | 1.00 | 48.77 | B | C |
| ATOM | 3932 | CG1 | ILE | B | 316 | −8.296 | 43.127 | 61.947 | 1.00 | 49.54 | B | C |
| ATOM | 3933 | CD1 | ILE | B | 316 | −8.646 | 43.083 | 63.388 | 1.00 | 52.82 | B | C |
| ATOM | 3934 | CG2 | ILE | B | 316 | −9.924 | 41.790 | 60.676 | 1.00 | 51.23 | B | C |
| ATOM | 3935 | C | ILE | B | 316 | −10.167 | 43.864 | 58.642 | 1.00 | 48.52 | B | C |
| ATOM | 3936 | O | ILE | B | 316 | −11.376 | 44.011 | 58.879 | 1.00 | 50.06 | B | O |
| ATOM | 3937 | N | LEU | B | 317 | −9.666 | 43.604 | 57.434 | 1.00 | 42.09 | B | N |
| ATOM | 3938 | CA | LEU | B | 317 | −10.481 | 43.320 | 56.270 | 1.00 | 34.53 | B | C |
| ATOM | 3939 | CB | LEU | B | 317 | −9.591 | 43.078 | 55.073 | 1.00 | 30.31 | B | C |
| ATOM | 3940 | CG | LEU | B | 317 | −10.287 | 42.652 | 53.796 | 1.00 | 32.72 | B | C |
| ATOM | 3941 | CD1 | LEU | B | 317 | −10.778 | 43.860 | 53.020 | 1.00 | 33.80 | B | C |
| ATOM | 3942 | CD2 | LEU | B | 317 | −9.311 | 41.873 | 52.979 | 1.00 | 36.29 | B | C |
| ATOM | 3943 | C | LEU | B | 317 | −11.340 | 42.102 | 56.533 | 1.00 | 36.99 | B | C |
| ATOM | 3944 | O | LEU | B | 317 | −10.852 | 41.085 | 57.040 | 1.00 | 37.81 | B | O |
| ATOM | 3945 | N | GLN | B | 318 | −12.622 | 42.232 | 56.190 | 1.00 | 39.38 | B | N |
| ATOM | 3946 | CA | GLN | B | 318 | −13.667 | 41.275 | 56.559 | 1.00 | 38.34 | B | C |
| ATOM | 3947 | CB | GLN | B | 318 | −14.842 | 42.008 | 57.198 | 1.00 | 35.95 | B | C |
| ATOM | 3948 | CG | GLN | B | 318 | −14.550 | 42.550 | 58.560 | 1.00 | 34.95 | B | C |
| ATOM | 3949 | CD | GLN | B | 318 | −14.256 | 41.448 | 59.549 | 1.00 | 34.71 | B | C |
| ATOM | 3950 | OE1 | GLN | B | 318 | −14.998 | 40.466 | 59.635 | 1.00 | 32.68 | B | O |
| ATOM | 3951 | NE2 | GLN | B | 318 | −13.169 | 41.598 | 60.290 | 1.00 | 35.89 | B | N |
| ATOM | 3952 | C | GLN | B | 318 | −14.191 | 40.515 | 55.366 | 1.00 | 39.89 | B | C |
| ATOM | 3953 | O | GLN | B | 318 | −14.563 | 39.350 | 55.482 | 1.00 | 43.86 | B | O |
| ATOM | 3954 | N | ALA | B | 319 | −14.264 | 41.208 | 54.237 | 1.00 | 38.76 | B | N |
| ATOM | 3955 | CA | ALA | B | 319 | −14.702 | 40.634 | 52.980 | 1.00 | 42.20 | B | C |
| ATOM | 3956 | CB | ALA | B | 319 | −16.206 | 40.436 | 52.970 | 1.00 | 43.13 | B | C |
| ATOM | 3957 | C | ALA | B | 319 | −14.296 | 41.631 | 51.919 | 1.00 | 45.19 | B | C |
| ATOM | 3958 | O | ALA | B | 319 | −13.906 | 42.754 | 52.259 | 1.00 | 47.84 | B | O |
| ATOM | 3959 | N | ALA | B | 320 | −14.397 | 41.224 | 50.648 | 1.00 | 43.30 | B | N |
| ATOM | 3960 | CA | ALA | B | 320 | −14.019 | 42.068 | 49.516 | 1.00 | 38.82 | B | C |
| ATOM | 3961 | CB | ALA | B | 320 | −12.515 | 42.188 | 49.442 | 1.00 | 39.16 | B | C |
| ATOM | 3962 | C | ALA | B | 320 | −14.545 | 41.508 | 48.215 | 1.00 | 37.73 | B | C |
| ATOM | 3963 | O | ALA | B | 320 | −14.533 | 40.290 | 48.028 | 1.00 | 42.20 | B | O |
| ATOM | 3964 | N | ALA | B | 321 | −15.032 | 42.390 | 47.340 | 1.00 | 36.21 | B | N |
| ATOM | 3965 | CA | ALA | B | 321 | −15.285 | 42.055 | 45.930 | 1.00 | 38.81 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 3966 | CB  | ALA | B | 321 | −16.828 | 42.041 | 45.531 | 1.00 | 33.42 | B | C |
| ATOM | 3967 | C   | ALA | B | 321 | −14.496 | 42.994 | 45.032 | 1.00 | 41.25 | B | C |
| ATOM | 3968 | O   | ALA | B | 321 | −14.039 | 44.063 | 45.472 | 1.00 | 41.88 | B | O |
| ATOM | 3969 | N   | VAL | B | 322 | −14.346 | 42.573 | 43.775 | 1.00 | 42.72 | B | N |
| ATOM | 3970 | CA  | VAL | B | 322 | −13.604 | 43.306 | 42.759 | 1.00 | 43.41 | B | C |
| ATOM | 3971 | CB  | VAL | B | 322 | −12.337 | 42.565 | 42.360 | 1.00 | 45.20 | B | C |
| ATOM | 3972 | CG1 | VAL | B | 322 | −11.598 | 43.339 | 41.310 | 1.00 | 45.05 | B | C |
| ATOM | 3973 | CG2 | VAL | B | 322 | −11.448 | 42.329 | 43.572 | 1.00 | 49.72 | B | C |
| ATOM | 3974 | C   | VAL | B | 322 | −14.475 | 43.471 | 41.527 | 1.00 | 43.73 | B | C |
| ATOM | 3975 | O   | VAL | B | 322 | −14.951 | 42.514 | 40.965 | 1.00 | 47.79 | B | O |
| ATOM | 3976 | N   | SER | B | 323 | −14.695 | 44.699 | 41.105 | 1.00 | 47.05 | B | N |
| ATOM | 3977 | CA  | SER | B | 323 | −15.589 | 44.931 | 39.988 | 1.00 | 48.01 | B | C |
| ATOM | 3978 | CB  | SER | B | 323 | −17.061 | 44.989 | 40.444 | 1.00 | 47.16 | B | C |
| ATOM | 3979 | OG  | SER | B | 323 | −17.377 | 46.210 | 41.095 | 1.00 | 42.34 | B | O |
| ATOM | 3980 | C   | SER | B | 323 | −15.197 | 46.216 | 39.309 | 1.00 | 49.32 | B | C |
| ATOM | 3981 | O   | SER | B | 323 | −14.264 | 46.924 | 39.744 | 1.00 | 50.83 | B | O |
| ATOM | 3982 | N   | LYS | B | 324 | −15.914 | 46.509 | 38.234 | 1.00 | 42.95 | B | N |
| ATOM | 3983 | CA  | LYS | B | 324 | −15.702 | 47.733 | 37.528 | 1.00 | 39.54 | B | C |
| ATOM | 3984 | CB  | LYS | B | 324 | −16.078 | 47.489 | 36.082 | 1.00 | 45.40 | B | C |
| ATOM | 3985 | CG  | LYS | B | 324 | −14.884 | 47.335 | 35.169 | 1.00 | 47.01 | B | C |
| ATOM | 3986 | CD  | LYS | B | 324 | −14.282 | 45.960 | 35.203 | 1.00 | 47.97 | B | C |
| ATOM | 3987 | CE  | LYS | B | 324 | −12.862 | 46.016 | 34.666 | 1.00 | 52.58 | B | C |
| ATOM | 3988 | NZ  | LYS | B | 324 | −12.750 | 45.426 | 33.300 | 1.00 | 58.24 | B | N |
| ATOM | 3989 | C   | LYS | B | 324 | −16.589 | 48.768 | 38.212 | 1.00 | 37.81 | B | C |
| ATOM | 3990 | O   | LYS | B | 324 | −17.543 | 48.390 | 38.883 | 1.00 | 37.79 | B | O |
| ATOM | 3991 | N   | PRO | B | 325 | −16.269 | 50.054 | 38.103 | 1.00 | 39.23 | B | N |
| ATOM | 3992 | CA  | PRO | B | 325 | −17.136 | 51.106 | 38.648 | 1.00 | 42.38 | B | C |
| ATOM | 3993 | CB  | PRO | B | 325 | −16.155 | 52.250 | 38.890 | 1.00 | 39.95 | B | C |
| ATOM | 3994 | CG  | PRO | B | 325 | −15.199 | 52.131 | 37.747 | 1.00 | 40.77 | B | C |
| ATOM | 3995 | CD  | PRO | B | 325 | −15.064 | 50.629 | 37.479 | 1.00 | 41.47 | B | C |
| ATOM | 3996 | C   | PRO | B | 325 | −18.209 | 51.583 | 37.659 | 1.00 | 45.95 | B | C |
| ATOM | 3997 | O   | PRO | B | 325 | −18.120 | 51.312 | 36.448 | 1.00 | 49.67 | B | O |
| ATOM | 3998 | N   | GLY | B | 326 | −19.212 | 52.280 | 38.186 | 1.00 | 45.56 | B | N |
| ATOM | 3999 | CA  | GLY | B | 326 | −20.128 | 53.056 | 37.369 | 1.00 | 49.09 | B | C |
| ATOM | 4000 | C   | GLY | B | 326 | −19.605 | 54.476 | 37.241 | 1.00 | 48.35 | B | C |
| ATOM | 4001 | O   | GLY | B | 326 | −18.752 | 54.890 | 38.030 | 1.00 | 50.25 | B | O |
| ATOM | 4002 | N   | ALA | B | 327 | −20.119 | 55.227 | 36.272 | 1.00 | 43.52 | B | N |
| ATOM | 4003 | CA  | ALA | B | 327 | −19.586 | 56.559 | 35.995 | 1.00 | 45.27 | B | C |
| ATOM | 4004 | CB  | ALA | B | 327 | −20.368 | 57.232 | 34.898 | 1.00 | 49.23 | B | C |
| ATOM | 4005 | C   | ALA | B | 327 | −19.471 | 57.483 | 37.206 | 1.00 | 47.02 | B | C |
| ATOM | 4006 | O   | ALA | B | 327 | −18.439 | 58.129 | 37.373 | 1.00 | 49.70 | B | O |
| ATOM | 4007 | N   | GLN | B | 328 | −20.516 | 57.556 | 38.036 | 1.00 | 48.51 | B | N |
| ATOM | 4008 | CA  | GLN | B | 328 | −20.528 | 58.471 | 39.191 | 1.00 | 48.61 | B | C |
| ATOM | 4009 | CB  | GLN | B | 328 | −21.844 | 58.407 | 39.989 | 1.00 | 52.15 | B | C |
| ATOM | 4010 | CG  | GLN | B | 328 | −22.154 | 59.689 | 40.799 | 1.00 | 56.98 | B | C |
| ATOM | 4011 | CD  | GLN | B | 328 | −23.030 | 59.450 | 42.035 | 1.00 | 61.65 | B | C |
| ATOM | 4012 | OE1 | GLN | B | 328 | −22.527 | 59.373 | 43.161 | 1.00 | 63.61 | B | O |
| ATOM | 4013 | NE2 | GLN | B | 328 | −24.340 | 59.356 | 41.826 | 1.00 | 63.51 | B | N |
| ATOM | 4014 | C   | GLN | B | 328 | −19.351 | 58.186 | 40.100 | 1.00 | 47.42 | B | C |
| ATOM | 4015 | O   | GLN | B | 328 | −18.495 | 59.053 | 40.318 | 1.00 | 44.44 | B | O |
| ATOM | 4016 | N   | LEU | B | 329 | −19.294 | 56.958 | 40.608 | 1.00 | 48.25 | B | N |
| ATOM | 4017 | CA  | LEU | B | 329 | −18.167 | 56.568 | 41.431 | 1.00 | 47.42 | B | C |
| ATOM | 4018 | CB  | LEU | B | 329 | −18.294 | 55.129 | 41.906 | 1.00 | 46.47 | B | C |
| ATOM | 4019 | CG  | LEU | B | 329 | −17.867 | 54.835 | 43.349 | 1.00 | 43.93 | B | C |
| ATOM | 4020 | CD1 | LEU | B | 329 | −17.375 | 53.404 | 43.422 | 1.00 | 42.68 | B | C |
| ATOM | 4021 | CD2 | LEU | B | 329 | −16.826 | 55.809 | 43.905 | 1.00 | 39.29 | B | C |
| ATOM | 4022 | C   | LEU | B | 329 | −16.867 | 56.748 | 40.668 | 1.00 | 47.05 | B | C |
| ATOM | 4023 | O   | LEU | B | 329 | −15.892 | 57.231 | 41.236 | 1.00 | 49.30 | B | O |
| ATOM | 4024 | N   | ALA | B | 330 | −16.866 | 56.380 | 39.386 | 1.00 | 43.69 | B | N |
| ATOM | 4025 | CA  | ALA | B | 330 | −15.654 | 56.419 | 38.586 | 1.00 | 42.15 | B | C |
| ATOM | 4026 | CB  | ALA | B | 330 | −15.939 | 56.080 | 37.151 | 1.00 | 41.25 | B | C |
| ATOM | 4027 | C   | ALA | B | 330 | −15.034 | 57.788 | 38.713 | 1.00 | 46.79 | B | C |
| ATOM | 4028 | O   | ALA | B | 330 | −14.026 | 57.940 | 39.397 | 1.00 | 48.86 | B | O |
| ATOM | 4029 | N   | ARG | B | 331 | −15.656 | 58.783 | 38.080 | 1.00 | 52.99 | B | N |
| ATOM | 4030 | CA  | ARG | B | 331 | −15.266 | 60.185 | 38.196 | 1.00 | 54.31 | B | C |
| ATOM | 4031 | CB  | ARG | B | 331 | −16.508 | 61.047 | 38.047 | 1.00 | 57.66 | B | C |
| ATOM | 4032 | CG  | ARG | B | 331 | −16.285 | 62.389 | 37.401 | 1.00 | 66.59 | B | C |
| ATOM | 4033 | CD  | ARG | B | 331 | −17.572 | 63.218 | 37.248 | 1.00 | 74.27 | B | C |
| ATOM | 4034 | NE  | ARG | B | 331 | −18.753 | 62.389 | 36.960 | 1.00 | 78.56 | B | N |
| ATOM | 4035 | CZ  | ARG | B | 331 | −19.128 | 61.980 | 35.741 | 1.00 | 78.96 | B | C |
| ATOM | 4036 | NH1 | ARG | B | 331 | −18.423 | 62.316 | 34.663 | 1.00 | 78.56 | B | N |
| ATOM | 4037 | NH2 | ARG | B | 331 | −20.216 | 61.229 | 35.600 | 1.00 | 77.36 | B | N |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 4038 | C   | ARG | B | 331 | −14.587 | 60.491 | 39.537 | 1.00 | 54.34 | B | C |
| ATOM | 4039 | O   | ARG | B | 331 | −13.501 | 61.068 | 39.571 | 1.00 | 53.46 | B | O |
| ATOM | 4040 | N   | GLN | B | 332 | −15.219 | 60.057 | 40.627 | 1.00 | 54.05 | B | N |
| ATOM | 4041 | CA  | GLN | B | 332 | −14.801 | 60.401 | 41.987 | 1.00 | 56.11 | B | C |
| ATOM | 4042 | CB  | GLN | B | 332 | −15.908 | 60.051 | 42.978 | 1.00 | 56.59 | B | C |
| ATOM | 4043 | CG  | GLN | B | 332 | −17.171 | 60.858 | 42.840 | 1.00 | 57.97 | B | C |
| ATOM | 4044 | CD  | GLN | B | 332 | −18.350 | 60.192 | 43.518 | 1.00 | 60.52 | B | C |
| ATOM | 4045 | OE1 | GLN | B | 332 | −19.471 | 60.259 | 43.021 | 1.00 | 62.43 | B | O |
| ATOM | 4046 | NE2 | GLN | B | 332 | −18.102 | 59.547 | 44.654 | 1.00 | 60.21 | B | N |
| ATOM | 4047 | C   | GLN | B | 332 | −13.487 | 59.802 | 42.511 | 1.00 | 58.78 | B | C |
| ATOM | 4048 | O   | GLN | B | 332 | −12.777 | 60.464 | 43.264 | 1.00 | 61.01 | B | O |
| ATOM | 4049 | N   | ILE | B | 333 | −13.178 | 58.554 | 42.163 | 1.00 | 60.02 | B | N |
| ATOM | 4050 | CA  | ILE | B | 333 | −12.048 | 57.859 | 42.801 | 1.00 | 61.37 | B | C |
| ATOM | 4051 | CB  | ILE | B | 333 | −12.462 | 56.453 | 43.376 | 1.00 | 60.29 | B | C |
| ATOM | 4052 | CG1 | ILE | B | 333 | −13.532 | 55.790 | 42.520 | 1.00 | 57.86 | B | C |
| ATOM | 4053 | CD1 | ILE | B | 333 | −12.967 | 55.019 | 41.368 | 1.00 | 59.06 | B | C |
| ATOM | 4054 | CG2 | ILE | B | 333 | −12.884 | 56.542 | 44.846 | 1.00 | 62.90 | B | C |
| ATOM | 4055 | C   | ILE | B | 333 | −10.803 | 57.692 | 41.930 | 1.00 | 62.41 | B | C |
| ATOM | 4056 | O   | ILE | B | 333 | −9.843  | 57.034 | 42.344 | 1.00 | 65.96 | B | O |
| ATOM | 4057 | N   | GLY | B | 334 | −10.810 | 58.270 | 40.734 | 1.00 | 60.64 | B | N |
| ATOM | 4058 | CA  | GLY | B | 334 | −9.712  | 58.055 | 39.808 | 1.00 | 61.54 | B | C |
| ATOM | 4059 | C   | GLY | B | 334 | −10.127 | 57.351 | 38.531 | 1.00 | 63.72 | B | C |
| ATOM | 4060 | O   | GLY | B | 334 | −9.316  | 57.206 | 37.617 | 1.00 | 65.07 | B | O |
| ATOM | 4061 | N   | ALA | B | 335 | −11.375 | 56.876 | 38.504 | 1.00 | 64.54 | B | N |
| ATOM | 4062 | CA  | ALA | B | 335 | −12.128 | 56.609 | 37.270 | 1.00 | 63.84 | B | C |
| ATOM | 4063 | CB  | ALA | B | 335 | −12.319 | 57.925 | 36.447 | 1.00 | 68.98 | B | C |
| ATOM | 4064 | C   | ALA | B | 335 | −11.620 | 55.487 | 36.381 | 1.00 | 61.10 | B | C |
| ATOM | 4065 | O   | ALA | B | 335 | −10.965 | 54.560 | 36.853 | 1.00 | 60.42 | B | O |
| ATOM | 4066 | N   | SER | B | 336 | −11.920 | 55.627 | 35.087 | 1.00 | 62.19 | B | N |
| ATOM | 4067 | CA  | SER | B | 336 | −11.779 | 54.595 | 34.058 | 1.00 | 66.51 | B | C |
| ATOM | 4068 | CB  | SER | B | 336 | −10.412 | 53.901 | 34.109 | 1.00 | 74.49 | B | C |
| ATOM | 4069 | OG  | SER | B | 336 | −10.411 | 52.686 | 33.371 | 1.00 | 82.14 | B | O |
| ATOM | 4070 | C   | SER | B | 336 | −12.957 | 53.610 | 34.106 | 1.00 | 65.03 | B | C |
| ATOM | 4071 | O   | SER | B | 336 | −12.960 | 52.627 | 34.852 | 1.00 | 62.64 | B | O |
| ATOM | 4072 | N   | LEU | B | 337 | −13.962 | 53.911 | 33.291 | 1.00 | 66.13 | B | N |
| ATOM | 4073 | CA  | LEU | B | 337 | −15.194 | 53.136 | 33.176 | 1.00 | 66.47 | B | C |
| ATOM | 4074 | CB  | LEU | B | 337 | −15.887 | 53.528 | 31.861 | 1.00 | 69.76 | B | C |
| ATOM | 4075 | CG  | LEU | B | 337 | −17.392 | 53.824 | 31.789 | 1.00 | 73.26 | B | C |
| ATOM | 4076 | CD1 | LEU | B | 337 | −18.157 | 52.606 | 31.242 | 1.00 | 76.33 | B | C |
| ATOM | 4077 | CD2 | LEU | B | 337 | −17.982 | 54.285 | 33.126 | 1.00 | 73.40 | B | C |
| ATOM | 4078 | C   | LEU | B | 337 | −14.948 | 51.629 | 33.212 | 1.00 | 63.98 | B | C |
| ATOM | 4079 | O   | LEU | B | 337 | −15.752 | 50.857 | 33.748 | 1.00 | 57.87 | B | O |
| ATOM | 4080 | N   | ASN | B | 338 | −13.815 | 51.239 | 32.638 | 1.00 | 67.61 | B | N |
| ATOM | 4081 | CA  | ASN | B | 338 | −13.431 | 49.852 | 32.468 | 1.00 | 72.58 | B | C |
| ATOM | 4082 | CB  | ASN | B | 338 | −13.182 | 49.583 | 30.978 | 1.00 | 80.29 | B | C |
| ATOM | 4083 | CG  | ASN | B | 338 | −12.809 | 48.137 | 30.695 | 1.00 | 87.12 | B | C |
| ATOM | 4084 | OD1 | ASN | B | 338 | −13.556 | 47.205 | 31.028 | 1.00 | 88.04 | B | O |
| ATOM | 4085 | ND2 | ASN | B | 338 | −11.639 | 47.941 | 30.081 | 1.00 | 89.20 | B | N |
| ATOM | 4086 | C   | ASN | B | 338 | −12.205 | 49.500 | 33.324 | 1.00 | 70.16 | B | C |
| ATOM | 4087 | O   | ASN | B | 338 | −11.214 | 48.963 | 32.834 | 1.00 | 69.51 | B | O |
| ATOM | 4088 | N   | ASP | B | 339 | −12.286 | 49.806 | 34.615 | 1.00 | 69.79 | B | N |
| ATOM | 4089 | CA  | ASP | B | 339 | −11.199 | 49.517 | 35.542 | 1.00 | 67.80 | B | C |
| ATOM | 4090 | CB  | ASP | B | 339 | −10.582 | 50.807 | 36.054 | 1.00 | 70.33 | B | C |
| ATOM | 4091 | CG  | ASP | B | 339 | −9.113  | 50.877 | 35.767 | 1.00 | 77.20 | B | C |
| ATOM | 4092 | OD1 | ASP | B | 339 | −8.389  | 49.949 | 36.218 | 1.00 | 82.67 | B | O |
| ATOM | 4093 | OD2 | ASP | B | 339 | −8.594  | 51.796 | 35.090 | 1.00 | 76.34 | B | O |
| ATOM | 4094 | C   | ASP | B | 339 | −11.593 | 48.636 | 36.720 | 1.00 | 64.34 | B | C |
| ATOM | 4095 | O   | ASP | B | 339 | −12.700 | 48.730 | 37.238 | 1.00 | 64.14 | B | O |
| ATOM | 4096 | N   | ASP | B | 340 | −10.674 | 47.777 | 37.142 | 1.00 | 60.50 | B | N |
| ATOM | 4097 | CA  | ASP | B | 340 | −10.924 | 46.932 | 38.299 | 1.00 | 57.67 | B | C |
| ATOM | 4098 | CB  | ASP | B | 340 | −10.064 | 45.675 | 38.228 | 1.00 | 56.39 | B | C |
| ATOM | 4099 | CG  | ASP | B | 340 | −10.554 | 44.698 | 37.182 | 1.00 | 59.37 | B | C |
| ATOM | 4100 | OD1 | ASP | B | 340 | −11.784 | 44.529 | 37.020 | 1.00 | 58.17 | B | O |
| ATOM | 4101 | OD2 | ASP | B | 340 | −9.774  | 44.030 | 36.481 | 1.00 | 63.66 | B | O |
| ATOM | 4102 | C   | ASP | B | 340 | −10.699 | 47.676 | 39.622 | 1.00 | 57.34 | B | C |
| ATOM | 4103 | O   | ASP | B | 340 | −9.643  | 48.294 | 39.840 | 1.00 | 60.14 | B | O |
| ATOM | 4104 | N   | ILE | B | 341 | −11.708 | 47.635 | 40.491 | 1.00 | 50.94 | B | N |
| ATOM | 4105 | CA  | ILE | B | 341 | −11.584 | 48.209 | 41.822 | 1.00 | 46.54 | B | C |
| ATOM | 4106 | CB  | ILE | B | 341 | −12.555 | 49.357 | 42.014 | 1.00 | 44.72 | B | C |
| ATOM | 4107 | CG1 | ILE | B | 341 | −12.116 | 50.557 | 41.193 | 1.00 | 45.57 | B | C |
| ATOM | 4108 | CD1 | ILE | B | 341 | −12.832 | 50.677 | 39.908 | 1.00 | 44.81 | B | C |
| ATOM | 4109 | CG2 | ILE | B | 341 | −12.599 | 49.757 | 43.473 | 1.00 | 44.54 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 4110 | C | ILE | B | 341 | −11.845 | 47.164 | 42.884 | 1.00 | 49.43 | B | C |
| ATOM | 4111 | O | ILE | B | 341 | −12.760 | 46.351 | 42.775 | 1.00 | 52.41 | B | O |
| ATOM | 4112 | N | LEU | B | 342 | −11.030 | 47.201 | 43.922 | 1.00 | 48.88 | B | N |
| ATOM | 4113 | CA | LEU | B | 342 | −11.190 | 46.319 | 45.055 | 1.00 | 46.16 | B | C |
| ATOM | 4114 | CB | LEU | B | 342 | −9.812 | 45.918 | 45.596 | 1.00 | 42.06 | B | C |
| ATOM | 4115 | CG | LEU | B | 342 | −9.746 | 45.306 | 46.989 | 1.00 | 40.05 | B | C |
| ATOM | 4116 | CD1 | LEU | B | 342 | −10.387 | 43.942 | 46.949 | 1.00 | 41.44 | B | C |
| ATOM | 4117 | CD2 | LEU | B | 342 | −8.314 | 45.213 | 47.477 | 1.00 | 39.40 | 8 | C |
| ATOM | 4118 | C | LEU | B | 342 | −12.034 | 47.033 | 46.116 | 1.00 | 47.55 | B | C |
| ATOM | 4119 | O | LEU | B | 342 | −11.562 | 47.949 | 46.811 | 1.00 | 50.43 | B | O |
| ATOM | 4120 | N | PHE | B | 343 | −13.293 | 46.625 | 46.215 | 1.00 | 41.92 | B | N |
| ATOM | 4121 | CA | PHE | B | 343 | −14.141 | 47.077 | 47.298 | 1.00 | 38.40 | B | C |
| ATOM | 4122 | CB | PHE | B | 343 | −15.596 | 46.984 | 46.878 | 1.00 | 36.63 | B | C |
| ATOM | 4123 | CG | PHE | B | 343 | −15.923 | 47.858 | 45.716 | 1.00 | 34.84 | B | C |
| ATOM | 4124 | CD1 | PHE | B | 343 | −16.015 | 47.326 | 44.440 | 1.00 | 34.47 | B | C |
| ATOM | 4125 | CE1 | PHE | B | 343 | −16.296 | 48.144 | 43.363 | 1.00 | 33.66 | B | C |
| ATOM | 4126 | CZ | PHE | B | 343 | −16.470 | 49.511 | 43.565 | 1.00 | 30.55 | B | C |
| ATOM | 4127 | CE2 | PHE | B | 343 | −16.365 | 50.044 | 44.836 | 1.00 | 26.40 | B | C |
| ATOM | 4128 | CD2 | PHE | B | 343 | −16.100 | 49.225 | 45.893 | 1.00 | 29.75 | B | C |
| ATOM | 4129 | C | PHE | B | 343 | −13.868 | 46.201 | 48.496 | 1.00 | 39.49 | B | C |
| ATOM | 4130 | O | PHE | B | 343 | −14.008 | 44.987 | 48.422 | 1.00 | 43.25 | B | O |
| ATOM | 4131 | N | GLY | B | 344 | −13.452 | 46.815 | 49.594 | 1.00 | 38.93 | B | N |
| ATOM | 4132 | CA | GLY | B | 344 | −13.107 | 46.068 | 50.790 | 1.00 | 41.21 | B | C |
| ATOM | 4133 | C | GLY | B | 344 | −13.843 | 46.525 | 52.032 | 1.00 | 44.97 | B | C |
| ATOM | 4134 | O | GLY | B | 344 | −13.740 | 47.678 | 52.461 | 1.00 | 48.19 | B | O |
| ATOM | 4135 | N | VAL | B | 345 | −14.597 | 45.616 | 52.624 | 1.00 | 45.74 | B | N |
| ATOM | 4136 | CA | VAL | B | 345 | −15.332 | 45.943 | 53.832 | 1.00 | 48.71 | B | C |
| ATOM | 4137 | CB | VAL | B | 345 | −16.716 | 45.237 | 53.825 | 1.00 | 50.32 | B | C |
| ATOM | 4138 | CG1 | VAL | B | 345 | −17.159 | 44.856 | 55.218 | 1.00 | 55.50 | B | C |
| ATOM | 4139 | CG2 | VAL | B | 345 | −17.767 | 46.121 | 53.156 | 1.00 | 45.23 | B | C |
| ATOM | 4140 | C | VAL | B | 345 | −14.451 | 45.610 | 55.052 | 1.00 | 48.69 | B | C |
| ATOM | 4141 | O | VAL | B | 345 | −14.153 | 44.437 | 55.309 | 1.00 | 47.46 | B | O |
| ATOM | 4142 | N | PHE | B | 346 | −14.016 | 46.649 | 55.771 | 1.00 | 48.12 | B | N |
| ATOM | 4143 | CA | PHE | B | 346 | −13.022 | 46.509 | 56.854 | 1.00 | 49.20 | B | C |
| ATOM | 4144 | CB | PHE | B | 346 | −11.926 | 47.575 | 56.748 | 1.00 | 46.30 | B | C |
| ATOM | 4145 | CG | PHE | B | 346 | −11.031 | 47.408 | 55.565 | 1.00 | 45.81 | B | C |
| ATOM | 4146 | CD1 | PHE | B | 346 | −11.440 | 47.830 | 54.302 | 1.00 | 44.17 | B | C |
| ATOM | 4147 | CE1 | PHE | B | 346 | −10.620 | 47.672 | 53.191 | 1.00 | 45.65 | B | C |
| ATOM | 4148 | CZ | PHE | B | 346 | −9.370 | 47.097 | 53.336 | 1.00 | 47.76 | B | C |
| ATOM | 4149 | CE2 | PHE | B | 346 | −8.946 | 46.666 | 54.600 | 1.00 | 49.85 | B | C |
| ATOM | 4150 | CD2 | PHE | B | 346 | −9.779 | 46.829 | 55.707 | 1.00 | 48.05 | B | C |
| ATOM | 4151 | C | PHE | B | 346 | −13.651 | 46.587 | 58.232 | 1.00 | 51.63 | B | C |
| ATOM | 4152 | O | PHE | B | 346 | −14.873 | 46.585 | 58.350 | 1.00 | 59.52 | B | O |
| ATOM | 4153 | N | ALA | B | 347 | −12.811 | 46.667 | 59.265 | 1.00 | 47.44 | B | N |
| ATOM | 4154 | CA | ALA | B | 347 | −13.259 | 46.670 | 60.658 | 1.00 | 45.63 | B | C |
| ATOM | 4155 | CB | ALA | B | 347 | −13.910 | 45.331 | 61.020 | 1.00 | 41.64 | B | C |
| ATOM | 4156 | C | ALA | B | 347 | −12.119 | 46.991 | 61.633 | 1.00 | 48.68 | B | C |
| ATOM | 4157 | O | ALA | B | 347 | −10.939 | 46.742 | 61.340 | 1.00 | 52.11 | B | O |
| ATOM | 4158 | N | GLN | B | 348 | −12.485 | 47.528 | 62.797 | 1.00 | 46.37 | B | N |
| ATOM | 4159 | CA | GLN | B | 348 | −11.523 | 47.935 | 63.812 | 1.00 | 46.50 | B | C |
| ATOM | 4160 | CB | GLN | B | 348 | −12.030 | 49.163 | 64.566 | 1.00 | 51.95 | B | C |
| ATOM | 4161 | CG | GLN | B | 348 | −11.016 | 49.802 | 65.518 | 1.00 | 56.38 | B | C |
| ATOM | 4162 | CD | GLN | B | 348 | −11.488 | 51.143 | 66.055 | 1.00 | 59.58 | B | C |
| ATOM | 4163 | OE1 | GLN | B | 348 | −12.351 | 51.198 | 66.933 | 1.00 | 61.38 | B | O |
| ATOM | 4164 | NE2 | GLN | B | 348 | −10.925 | 52.227 | 65.528 | 1.00 | 60.96 | B | N |
| ATOM | 4165 | C | GLN | B | 348 | −11.204 | 46.810 | 64.789 | 1.00 | 45.95 | B | C |
| ATOM | 4166 | O | GLN | B | 348 | −12.095 | 46.089 | 65.248 | 1.00 | 45.26 | B | O |
| ATOM | 4167 | N | SER | B | 349 | −9.916 | 46.688 | 65.099 | 1.00 | 45.22 | B | N |
| ATOM | 4168 | CA | SER | B | 349 | −9.389 | 45.665 | 65.979 | 1.00 | 42.27 | B | C |
| ATOM | 4169 | CB | SER | B | 349 | −7.881 | 45.644 | 65.851 | 1.00 | 41.04 | B | C |
| ATOM | 4170 | OG | SER | B | 349 | −7.369 | 44.411 | 66.289 | 1.00 | 44.60 | B | O |
| ATOM | 4171 | C | SER | B | 349 | −9.716 | 45.944 | 67.426 | 1.00 | 45.73 | B | C |
| ATOM | 4172 | O | SER | B | 349 | −9.662 | 47.092 | 67.871 | 1.00 | 45.84 | B | O |
| ATOM | 4173 | N | LYS | B | 350 | −10.060 | 44.886 | 68.157 | 1.00 | 49.08 | B | N |
| ATOM | 4174 | CA | LYS | B | 350 | −10.035 | 44.916 | 69.614 | 1.00 | 51.24 | B | C |
| ATOM | 4175 | CB | LYS | B | 350 | −10.611 | 43.627 | 70.201 | 1.00 | 54.70 | B | C |
| ATOM | 4176 | CG | LYS | B | 350 | −12.127 | 43.567 | 70.242 | 1.00 | 59.23 | B | C |
| ATOM | 4177 | CD | LYS | B | 350 | −12.620 | 42.165 | 70.587 | 1.00 | 63.81 | B | C |
| ATOM | 4178 | CE | LYS | B | 350 | −14.036 | 42.200 | 71.153 | 1.00 | 68.32 | B | C |
| ATOM | 4179 | NZ | LYS | B | 350 | −14.042 | 42.442 | 72.637 | 1.00 | 72.71 | B | N |
| ATOM | 4180 | C | LYS | B | 350 | −8.562 | 45.042 | 69.985 | 1.00 | 51.58 | B | C |
| ATOM | 4181 | O | LYS | B | 350 | −7.743 | 44.261 | 69.496 | 1.00 | 50.93 | B | O |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 4182 | N   | PRO | B | 351 | −8.211  | 46.015 | 70.826 | 1.00 | 52.22 | B | N |
| ATOM | 4183 | CA  | PRO | B | 351 | −6.802  | 46.361 | 71.048 | 1.00 | 52.90 | B | C |
| ATOM | 4184 | CB  | PRO | B | 351 | −6.872  | 47.347 | 72.200 | 1.00 | 50.68 | B | C |
| ATOM | 4185 | CG  | PRO | B | 351 | −8.197  | 47.984 | 72.011 | 1.00 | 50.11 | B | C |
| ATOM | 4186 | CD  | PRO | B | 351 | −9.110  | 46.859 | 71.633 | 1.00 | 50.04 | B | C |
| ATOM | 4187 | C   | PRO | B | 351 | −5.928  | 45.154 | 71.384 | 1.00 | 56.85 | B | C |
| ATOM | 4188 | O   | PRO | B | 351 | −6.322  | 44.304 | 72.189 | 1.00 | 55.91 | B | O |
| ATOM | 4189 | N   | ASP | B | 352 | −4.771  | 45.091 | 70.719 | 1.00 | 61.69 | B | N |
| ATOM | 4190 | CA  | ASP | B | 352 | −3.788  | 44.001 | 70.824 | 1.00 | 63.92 | B | C |
| ATOM | 4191 | CB  | ASP | B | 352 | −3.288  | 43.827 | 72.271 | 1.00 | 69.49 | B | C |
| ATOM | 4192 | CG  | ASP | B | 352 | −2.046  | 44.660 | 72.572 | 1.00 | 73.65 | B | C |
| ATOM | 4193 | OD1 | ASP | B | 352 | −2.038  | 45.865 | 72.230 | 1.00 | 75.00 | B | O |
| ATOM | 4194 | OD2 | ASP | B | 352 | −1.033  | 44.199 | 73.155 | 1.00 | 75.16 | B | O |
| ATOM | 4195 | C   | ASP | B | 352 | −4.265  | 42.667 | 70.249 | 1.00 | 60.93 | B | C |
| ATOM | 4196 | O   | ASP | B | 352 | −3.705  | 41.618 | 70.565 | 1.00 | 58.50 | B | O |
| ATOM | 4197 | N   | SER | B | 353 | −5.277  | 42.712 | 69.385 | 1.00 | 61.20 | B | N |
| ATOM | 4198 | CA  | SER | B | 353 | −5.843  | 41.487 | 68.817 | 1.00 | 61.71 | B | C |
| ATOM | 4199 | CB  | SER | B | 353 | −7.135  | 41.103 | 69.553 | 1.00 | 64.07 | B | C |
| ATOM | 4200 | OG  | SER | B | 353 | −8.282  | 41.293 | 68.734 | 1.00 | 64.99 | B | O |
| ATOM | 4201 | C   | SER | B | 353 | −6.077  | 41.526 | 67.301 | 1.00 | 58.70 | B | C |
| ATOM | 4202 | O   | SER | B | 353 | −5.708  | 42.488 | 66.620 | 1.00 | 56.25 | B | O |
| ATOM | 4203 | N   | ALA | B | 354 | −6.695  | 40.455 | 66.805 | 1.00 | 57.57 | B | N |
| ATOM | 4204 | CA  | ALA | B | 354 | −7.019  | 40.273 | 65.397 | 1.00 | 56.61 | B | C |
| ATOM | 4205 | CB  | ALA | B | 354 | −6.290  | 39.073 | 64.876 | 1.00 | 56.85 | B | C |
| ATOM | 4206 | C   | ALA | B | 354 | −8.524  | 40.089 | 65.214 | 1.00 | 56.79 | B | C |
| ATOM | 4207 | O   | ALA | B | 354 | −9.046  | 40.181 | 64.099 | 1.00 | 55.29 | B | O |
| ATOM | 4208 | N   | GLU | B | 355 | −9.200  | 39.810 | 66.323 | 1.00 | 59.16 | B | N |
| ATOM | 4209 | CA  | GLU | B | 355 | −10.652 | 39.736 | 66.385 | 1.00 | 62.50 | B | C |
| ATOM | 4210 | CB  | GLU | B | 355 | −11.094 | 39.174 | 67.741 | 1.00 | 70.39 | B | C |
| ATOM | 4211 | CG  | GLU | B | 355 | −10.388 | 37.885 | 68.155 | 1.00 | 78.56 | B | C |
| ATOM | 4212 | CD  | GLU | B | 355 | −9.384  | 38.086 | 69.291 | 1.00 | 84.21 | B | C |
| ATOM | 4213 | OE1 | GLU | B | 355 | −9.792  | 38.558 | 70.380 | 1.00 | 85.26 | B | O |
| ATOM | 4214 | OE2 | GLU | B | 355 | −8.183  | 37.763 | 69.103 | 1.00 | 86.79 | B | O |
| ATOM | 4215 | C   | GLU | B | 355 | −11.253 | 41.128 | 66.174 | 1.00 | 58.99 | B | C |
| ATOM | 4216 | O   | GLU | B | 355 | −10.697 | 42.127 | 66.640 | 1.00 | 58.55 | B | O |
| ATOM | 4217 | N   | PRO | B | 356 | −12.374 | 41.198 | 65.461 | 1.00 | 55.08 | B | N |
| ATOM | 4218 | CA  | PRO | B | 356 | −12.996 | 42.476 | 65.127 | 1.00 | 52.43 | B | C |
| ATOM | 4219 | CB  | PRO | B | 356 | −13.608 | 42.192 | 63.759 | 1.00 | 51.64 | B | C |
| ATOM | 4220 | CG  | PRO | B | 356 | −13.989 | 40.748 | 63.817 | 1.00 | 52.95 | B | C |
| ATOM | 4221 | CD  | PRO | B | 356 | −13.127 | 40.076 | 64.878 | 1.00 | 55.18 | B | C |
| ATOM | 4222 | C   | PRO | B | 356 | −14.100 | 42.892 | 66.088 | 1.00 | 52.14 | B | C |
| ATOM | 4223 | O   | PRO | B | 356 | −14.894 | 42.060 | 66.535 | 1.00 | 50.25 | B | O |
| ATOM | 4224 | N   | MET | B | 357 | −14.141 | 44.186 | 66.380 | 1.00 | 53.89 | B | N |
| ATOM | 4225 | CA  | MET | B | 357 | −15.249 | 44.794 | 67.102 | 1.00 | 57.79 | B | C |
| ATOM | 4226 | CB  | MET | B | 357 | −14.761 | 46.051 | 67.811 | 1.00 | 61.40 | B | C |
| ATOM | 4227 | CG  | MET | B | 357 | −14.551 | 45.873 | 69.292 | 1.00 | 64.49 | B | C |
| ATOM | 4228 | SD  | MET | B | 357 | −13.841 | 47.351 | 69.981 | 1.00 | 68.87 | B | S |
| ATOM | 4229 | CE  | MET | B | 357 | −15.363 | 48.302 | 70.459 | 1.00 | 67.95 | B | C |
| ATOM | 4230 | C   | MET | B | 357 | −16.375 | 45.139 | 66.126 | 1.00 | 57.94 | B | C |
| ATOM | 4231 | O   | MET | B | 357 | −16.177 | 45.089 | 64.920 | 1.00 | 61.91 | B | O |
| ATOM | 4232 | N   | ASP | B | 358 | −17.548 | 45.501 | 66.632 | 1.00 | 57.25 | B | N |
| ATOM | 4233 | CA  | ASP | B | 358 | −18.677 | 45.819 | 65.759 | 1.00 | 57.76 | B | C |
| ATOM | 4234 | CB  | ASP | B | 358 | −20.000 | 45.655 | 66.519 | 1.00 | 63.05 | B | C |
| ATOM | 4235 | CG  | ASP | B | 358 | −20.349 | 44.196 | 66.788 | 1.00 | 67.73 | B | C |
| ATOM | 4236 | OD1 | ASP | B | 358 | −21.292 | 43.955 | 67.575 | 1.00 | 69.44 | B | O |
| ATOM | 4237 | OD2 | ASP | B | 358 | −19.744 | 43.225 | 66.267 | 1.00 | 69.02 | B | O |
| ATOM | 4238 | C   | ASP | B | 358 | −18.578 | 47.214 | 65.124 | 1.00 | 56.07 | B | C |
| ATOM | 4239 | O   | ASP | B | 358 | −19.547 | 47.966 | 65.108 | 1.00 | 55.88 | B | O |
| ATOM | 4240 | N   | ARG | B | 359 | −17.403 | 47.550 | 64.599 | 1.00 | 55.50 | B | N |
| ATOM | 4241 | CA  | ARG | B | 359 | −17.165 | 48.841 | 63.956 | 1.00 | 57.49 | B | C |
| ATOM | 4242 | CB  | ARG | B | 359 | −16.070 | 49.611 | 64.702 | 1.00 | 58.09 | B | C |
| ATOM | 4243 | CG  | ARG | B | 359 | −16.531 | 50.420 | 65.893 | 1.00 | 59.68 | B | C |
| ATOM | 4244 | CD  | ARG | B | 359 | −15.554 | 51.509 | 66.290 | 1.00 | 62.07 | B | C |
| ATOM | 4245 | NE  | ARG | B | 359 | −16.131 | 52.845 | 66.143 | 1.00 | 66.02 | B | N |
| ATOM | 4246 | CZ  | ARG | B | 359 | −15.538 | 53.872 | 65.536 | 1.00 | 66.88 | B | C |
| ATOM | 4247 | NH1 | ARG | B | 359 | −14.331 | 53.736 | 64.998 | 1.00 | 66.41 | B | N |
| ATOM | 4248 | NH2 | ARG | B | 359 | −16.158 | 55.047 | 65.465 | 1.00 | 67.49 | B | N |
| ATOM | 4249 | C   | ARG | B | 359 | −16.728 | 48.625 | 62.507 | 1.00 | 58.84 | B | C |
| ATOM | 4250 | O   | ARG | B | 359 | −15.655 | 48.081 | 62.255 | 1.00 | 61.46 | B | O |
| ATOM | 4251 | N   | SER | B | 360 | −17.541 | 49.050 | 61.550 | 1.00 | 57.61 | B | N |
| ATOM | 4252 | CA  | SER | B | 360 | −17.193 | 48.821 | 60.158 | 1.00 | 57.19 | B | C |
| ATOM | 4253 | CB  | SER | B | 360 | −18.198 | 47.882 | 59.505 | 1.00 | 57.10 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 4254 | OG | SER | B | 360 | −18.169 | 46.613 | 60.119 | 1.00 | 56.60 | B | O |
| ATOM | 4255 | C | SER | B | 360 | −17.070 | 50.085 | 59.332 | 1.00 | 60.28 | B | C |
| ATOM | 4256 | O | SER | B | 360 | −17.589 | 51.143 | 59.696 | 1.00 | 61.65 | B | O |
| ATOM | 4257 | N | ALA | B | 361 | −16.377 | 49.946 | 58.205 | 1.00 | 63.10 | B | N |
| ATOM | 4258 | CA | ALA | B | 361 | −16.225 | 51.00 | 57.212 | 1.00 | 64.03 | B | C |
| ATOM | 4259 | CB | ALA | B | 361 | −15.295 | 52.077 | 57.727 | 1.00 | 66.25 | B | C |
| ATOM | 4260 | C | ALA | B | 361 | −15.648 | 50.377 | 55.960 | 1.00 | 61.46 | B | C |
| ATOM | 4261 | O | ALA | B | 361 | −14.620 | 49.716 | 56.035 | 1.00 | 66.20 | B | O |
| ATOM | 4262 | N | MET | B | 362 | −16.309 | 50.559 | 54.820 | 1.00 | 56.08 | B | N |
| ATOM | 4263 | CA | MET | B | 362 | −15.803 | 50.023 | 53.559 | 1.00 | 51.84 | B | C |
| ATOM | 4264 | CB | MET | B | 362 | −16.939 | 49.477 | 52.711 | 1.00 | 49.64 | B | C |
| ATOM | 4265 | CG | MET | B | 362 | −16.540 | 49.118 | 51.303 | 1.00 | 47.97 | B | C |
| ATOM | 4266 | SD | MET | B | 362 | −17.156 | 50.314 | 50.155 | 1.00 | 48.28 | B | S |
| ATOM | 4267 | CE | MET | B | 362 | −15.969 | 50.265 | 48.955 | 1.00 | 50.81 | B | C |
| ATOM | 4268 | C | MET | B | 362 | −15.074 | 51.106 | 52.794 | 1.00 | 49.81 | B | C |
| ATOM | 4269 | O | MET | B | 362 | −15.430 | 52.274 | 52.905 | 1.00 | 52.45 | B | O |
| ATOM | 4270 | N | CYS | B | 363 | −14.044 | 50.719 | 52.044 | 1.00 | 45.97 | B | N |
| ATOM | 4271 | CA | CYS | B | 363 | −13.360 | 51.642 | 51.143 | 1.00 | 47.77 | B | C |
| ATOM | 4272 | CB | CYS | B | 363 | −12.450 | 52.634 | 51.889 | 1.00 | 49.60 | B | C |
| ATOM | 4273 | SG | CYS | B | 363 | −11.206 | 51.931 | 52.980 | 1.00 | 56.58 | B | S |
| ATOM | 4274 | C | CYS | B | 363 | −12.653 | 50.921 | 49.997 | 1.00 | 48.50 | B | C |
| ATOM | 4275 | O | CYS | B | 363 | −12.271 | 49.753 | 50.119 | 1.00 | 44.35 | B | O |
| ATOM | 4276 | N | ALA | B | 364 | −12.503 | 51.636 | 48.879 | 1.00 | 50.42 | B | N |
| ATOM | 4277 | CA | ALA | B | 364 | −12.252 | 51.017 | 47.577 | 1.00 | 49.03 | B | C |
| ATOM | 4278 | CB | ALA | B | 364 | −13.368 | 51.371 | 46.627 | 1.00 | 49.45 | B | C |
| ATOM | 4279 | C | ALA | B | 364 | −10.920 | 51.392 | 46.954 | 1.00 | 48.18 | B | C |
| ATOM | 4280 | O | ALA | B | 364 | −10.594 | 52.572 | 46.847 | 1.00 | 51.58 | B | O |
| ATOM | 4281 | N | PHE | B | 365 | −10.175 | 50.382 | 46.515 | 1.00 | 44.80 | B | N |
| ATOM | 4282 | CA | PHE | B | 365 | −8.870 | 50.579 | 45.904 | 1.00 | 41.71 | B | C |
| ATOM | 4283 | CB | PHE | B | 365 | −7.861 | 49.703 | 46.606 | 1.00 | 41.63 | B | C |
| ATOM | 4284 | CG | PHE | B | 365 | −7.780 | 49.938 | 48.067 | 1.00 | 45.47 | B | C |
| ATOM | 4285 | CD1 | PHE | B | 365 | −8.780 | 49.470 | 48.913 | 1.00 | 48.02 | B | C |
| ATOM | 4286 | CE1 | PHE | B | 365 | −8.706 | 49.681 | 50.272 | 1.00 | 48.86 | B | C |
| ATOM | 4287 | CZ | PHE | B | 365 | −7.619 | 50.366 | 50.797 | 1.00 | 49.81 | B | C |
| ATOM | 4288 | CE2 | PHE | B | 365 | −6.612 | 50.836 | 49.956 | 1.00 | 47.81 | B | C |
| ATOM | 4289 | CD2 | PHE | B | 365 | −6.697 | 50.618 | 48.605 | 1.00 | 45.32 | B | C |
| ATOM | 4290 | C | PHE | B | 365 | −8.901 | 50.138 | 44.463 | 1.00 | 43.46 | B | C |
| ATOM | 4291 | O | PHE | B | 365 | −9.124 | 48.964 | 44.205 | 1.00 | 51.12 | B | O |
| ATOM | 4292 | N | PRO | B | 366 | −8.690 | 51.037 | 43.508 | 1.00 | 39.40 | B | N |
| ATOM | 4293 | CA | PRO | B | 366 | −8.539 | 50.607 | 42.121 | 1.00 | 42.33 | B | C |
| ATOM | 4294 | CB | PRO | B | 366 | −8.555 | 51.925 | 41.343 | 1.00 | 35.18 | B | C |
| ATOM | 4295 | CG | PRO | B | 366 | −9.128 | 52.865 | 42.252 | 1.00 | 32.75 | B | C |
| ATOM | 4296 | CD | PRO | B | 366 | −8.598 | 52.494 | 43.612 | 1.00 | 36.60 | B | C |
| ATOM | 4297 | C | PRO | B | 366 | −7.199 | 49.893 | 41.996 | 1.00 | 46.12 | B | C |
| ATOM | 4298 | O | PRO | B | 366 | −6.173 | 50.396 | 42.483 | 1.00 | 44.02 | B | O |
| ATOM | 4299 | N | ILE | B | 367 | −7.211 | 48.714 | 41.382 | 1.00 | 48.74 | B | N |
| ATOM | 4300 | CA | ILE | B | 367 | −5.995 | 47.916 | 41.347 | 1.00 | 50.89 | B | C |
| ATOM | 4301 | CB | ILE | B | 367 | −6.237 | 46.423 | 40.917 | 1.00 | 49.40 | B | C |
| ATOM | 4302 | CG1 | ILE | B | 367 | −6.395 | 46.283 | 39.406 | 1.00 | 55.32 | B | C |
| ATOM | 4303 | CD1 | ILE | B | 367 | −5.207 | 45.601 | 38.745 | 1.00 | 59.97 | B | C |
| ATOM | 4304 | CG2 | ILE | B | 367 | −7.430 | 45.816 | 41.639 | 1.00 | 44.92 | B | C |
| ATOM | 4305 | C | ILE | B | 367 | −4.934 | 48.625 | 40.515 | 1.00 | 51.72 | B | C |
| ATOM | 4306 | O | ILE | B | 367 | −3.738 | 48.383 | 40.690 | 1.00 | 54.19 | B | O |
| ATOM | 4307 | N | LYS | B | 368 | −5.376 | 49.526 | 39.637 | 1.00 | 50.99 | B | N |
| ATOM | 4308 | CA | LYS | B | 368 | −4.440 | 50.293 | 38.828 | 1.00 | 51.13 | B | C |
| ATOM | 4309 | CB | LYS | B | 368 | −5.170 | 51.118 | 37.760 | 1.00 | 50.48 | B | C |
| ATOM | 4310 | CG | LYS | B | 368 | −4.782 | 52.580 | 37.653 | 1.00 | 53.35 | B | C |
| ATOM | 4311 | CD | LYS | B | 368 | −6.001 | 53.489 | 37.860 | 1.00 | 58.19 | B | C |
| ATOM | 4312 | CE | LYS | B | 368 | −6.688 | 53.898 | 36.542 | 1.00 | 60.10 | B | C |
| ATOM | 4313 | NZ | LYS | B | 368 | −6.615 | 55.367 | 36.294 | 1.00 | 61.31 | B | N |
| ATOM | 4314 | C | LYS | B | 368 | −3.515 | 51.116 | 39.726 | 1.00 | 50.15 | B | C |
| ATOM | 4315 | O | LYS | B | 368 | −2.324 | 51.206 | 39.449 | 1.00 | 51.42 | B | O |
| ATOM | 4316 | N | TYR | B | 369 | −4.051 | 51.660 | 40.821 | 1.00 | 49.60 | B | N |
| ATOM | 4317 | CA | TYR | B | 369 | −3.243 | 52.431 | 41.775 | 1.00 | 49.84 | B | C |
| ATOM | 4318 | CB | TYR | B | 369 | −4.095 | 53.424 | 42.574 | 1.00 | 54.03 | B | C |
| ATOM | 4319 | CG | TYR | B | 369 | −4.700 | 54.486 | 41.694 | 1.00 | 58.71 | B | C |
| ATOM | 4320 | CD1 | TYR | B | 369 | −5.959 | 55.017 | 41.963 | 1.00 | 58.12 | B | C |
| ATOM | 4321 | CE1 | TYR | B | 369 | −6.513 | 55.977 | 41.129 | 1.00 | 59.82 | B | C |
| ATOM | 4322 | CZ | TYR | B | 369 | −5.801 | 56.412 | 40.013 | 1.00 | 61.33 | B | C |
| ATOM | 4323 | OH | TYR | B | 369 | −6.323 | 57.357 | 39.169 | 1.00 | 62.86 | B | O |
| ATOM | 4324 | CE2 | TYR | B | 369 | −4.554 | 55.905 | 39.731 | 1.00 | 62.39 | B | C |
| ATOM | 4325 | CD2 | TYR | B | 369 | −4.013 | 54.944 | 40.565 | 1.00 | 62.25 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 4326 | C | TYR | B | 369 | −2.438 | 51.545 | 42.700 | 1.00 | 48.25 | B | C |
| ATOM | 4327 | O | TYR | B | 369 | −1.279 | 51.838 | 42.987 | 1.00 | 49.03 | B | O |
| ATOM | 4328 | N | VAL | B | 370 | −3.051 | 50.460 | 43.160 | 1.00 | 46.31 | B | N |
| ATOM | 4329 | CA | VAL | B | 370 | −2.331 | 49.415 | 43.882 | 1.00 | 44.83 | B | C |
| ATOM | 4330 | CB | VAL | B | 370 | −3.176 | 48.117 | 44.009 | 1.00 | 44.32 | B | C |
| ATOM | 4331 | CG1 | VAL | B | 370 | −2.517 | 47.119 | 44.953 | 1.00 | 43.89 | B | C |
| ATOM | 4332 | CG2 | VAL | B | 370 | −4.592 | 48.429 | 44.475 | 1.00 | 43.16 | B | C |
| ATOM | 4333 | C | VAL | B | 370 | −0.990 | 49.109 | 43.189 | 1.00 | 43.84 | B | C |
| ATOM | 4334 | O | VAL | B | 370 | 0.059 | 49.178 | 43.826 | 1.00 | 44.09 | B | O |
| ATOM | 4335 | N | ASN | B | 371 | −1.033 | 48.799 | 41.891 | 1.00 | 41.71 | B | N |
| ATOM | 4336 | CA | ASN | B | 371 | 0.172 | 48.541 | 41.107 | 1.00 | 43.99 | B | C |
| ATOM | 4337 | CB | ASN | B | 371 | −0.171 | 48.212 | 39.657 | 1.00 | 45.83 | B | C |
| ATOM | 4338 | CG | ASN | B | 371 | −0.936 | 46.929 | 39.522 | 1.00 | 48.53 | B | C |
| ATOM | 4339 | OD1 | ASN | B | 371 | −0.773 | 46.014 | 40.321 | 1.00 | 50.49 | B | O |
| ATOM | 4340 | ND2 | ASN | B | 371 | −1.786 | 46.850 | 38.506 | 1.00 | 51.01 | B | N |
| ATOM | 4341 | C | ASN | B | 371 | 1.160 | 49.694 | 41.125 | 1.00 | 48.30 | B | C |
| ATOM | 4342 | O | ASN | B | 371 | 2.359 | 49.486 | 41.293 | 1.00 | 49.07 | B | O |
| ATOM | 4343 | N | ASP | B | 372 | 0.663 | 50.911 | 40.938 | 1.00 | 52.74 | B | N |
| ATOM | 4344 | CA | ASP | B | 372 | 1.534 | 52.076 | 40.962 | 1.00 | 58.36 | B | C |
| ATOM | 4345 | CB | ASP | B | 372 | 0.731 | 53.373 | 40.807 | 1.00 | 63.81 | B | C |
| ATOM | 4346 | CG | ASP | B | 372 | 0.061 | 53.483 | 39.447 | 1.00 | 67.32 | B | C |
| ATOM | 4347 | OD1 | ASP | B | 372 | 0.402 | 52.669 | 38.553 | 1.00 | 67.14 | B | O |
| ATOM | 4348 | OD2 | ASP | B | 372 | −0.813 | 54.348 | 39.185 | 1.00 | 68.87 | B | O |
| ATOM | 4349 | C | ASP | B | 372 | 2.319 | 52.067 | 42.264 | 1.00 | 57.54 | B | C |
| ATOM | 4350 | O | ASP | B | 372 | 3.553 | 52.110 | 42.254 | 1.00 | 59.02 | B | O |
| ATOM | 4351 | N | PHE | B | 373 | 1.592 | 51.959 | 43.374 | 1.00 | 54.22 | B | N |
| ATOM | 4352 | CA | PHE | B | 373 | 2.191 | 51.901 | 44.695 | 1.00 | 54.15 | B | C |
| ATOM | 4353 | CB | PHE | B | 373 | 1.111 | 51.765 | 45.757 | 1.00 | 53.80 | B | C |
| ATOM | 4354 | CG | PHE | B | 373 | 1.442 | 52.457 | 47.035 | 1.00 | 53.26 | B | C |
| ATOM | 4355 | CD1 | PHE | B | 373 | 1.209 | 53.824 | 47.176 | 1.00 | 54.06 | B | C |
| ATOM | 4356 | CE1 | PHE | B | 373 | 1.520 | 54.477 | 48.359 | 1.00 | 55.19 | B | C |
| ATOM | 4357 | CZ | PHE | B | 373 | 2.072 | 53.754 | 49.416 | 1.00 | 56.46 | B | C |
| ATOM | 4358 | CE2 | PHE | B | 373 | 2.312 | 52.380 | 49.281 | 1.00 | 53.58 | B | C |
| ATOM | 4359 | CD2 | PHE | B | 373 | 1.997 | 51.747 | 48.096 | 1.00 | 51.74 | B | C |
| ATOM | 4360 | C | PHE | B | 373 | 3.197 | 50.765 | 44.829 | 1.00 | 57.41 | B | C |
| ATOM | 4361 | O | PHE | B | 373 | 4.187 | 50.899 | 45.545 | 1.00 | 60.76 | B | O |
| ATOM | 4362 | N | PHE | B | 374 | 2.942 | 49.656 | 44.138 | 1.00 | 58.65 | B | N |
| ATOM | 4363 | CA | PHE | B | 374 | 3.855 | 48.522 | 44.119 | 1.00 | 58.06 | B | C |
| ATOM | 4364 | CB | PHE | B | 374 | 3.154 | 47.283 | 43.576 | 1.00 | 54.16 | B | C |
| ATOM | 4365 | CG | PHE | B | 374 | 2.540 | 46.410 | 44.628 | 1.00 | 52.99 | B | C |
| ATOM | 4366 | CD1 | PHE | B | 374 | 1.197 | 46.080 | 44.568 | 1.00 | 52.81 | B | C |
| ATOM | 4367 | CE1 | PHE | B | 374 | 0.626 | 45.258 | 45.527 | 1.00 | 51.49 | B | C |
| ATOM | 4368 | CZ | PHE | B | 374 | 1.400 | 44.746 | 46.555 | 1.00 | 50.43 | B | C |
| ATOM | 4369 | CE2 | PHE | B | 374 | 2.737 | 45.053 | 46.621 | 1.00 | 50.67 | B | C |
| ATOM | 4370 | CD2 | PHE | B | 374 | 3.305 | 45.879 | 45.655 | 1.00 | 53.35 | B | C |
| ATOM | 4371 | C | PHE | B | 374 | 5.072 | 48.814 | 43.251 | 1.00 | 65.91 | B | C |
| ATOM | 4372 | O | PHE | B | 374 | 6.194 | 48.497 | 43.642 | 1.00 | 69.66 | B | O |
| ATOM | 4373 | N | ASN | B | 375 | 4.850 | 49.420 | 42.083 | 1.00 | 72.20 | B | N |
| ATOM | 4374 | CA | ASN | B | 375 | 5.911 | 49.628 | 41.089 | 1.00 | 79.93 | B | C |
| ATOM | 4375 | CB | ASN | B | 375 | 5.318 | 49.842 | 39.690 | 1.00 | 82.27 | B | C |
| ATOM | 4376 | CG | ASN | B | 375 | 4.508 | 48.657 | 39.204 | 1.00 | 85.14 | B | C |
| ATOM | 4377 | OD1 | ASN | B | 375 | 4.745 | 47.514 | 39.600 | 1.00 | 85.93 | B | O |
| ATOM | 4378 | ND2 | ASN | B | 375 | 3.538 | 48.927 | 38.335 | 1.00 | 86.47 | B | N |
| ATOM | 4379 | C | ASN | B | 375 | 6.882 | 50.771 | 41.388 | 1.00 | 85.35 | B | C |
| ATOM | 4380 | O | ASN | B | 375 | 8.100 | 50.578 | 41.353 | 1.00 | 88.87 | B | O |
| ATOM | 4381 | N | LYS | B | 376 | 6.338 | 51.951 | 41.679 | 1.00 | 86.99 | B | N |
| ATOM | 4382 | CA | LYS | B | 376 | 7.123 | 53.186 | 41.734 | 1.00 | 89.89 | B | C |
| ATOM | 4383 | CB | LYS | B | 376 | 6.193 | 54.394 | 41.939 | 1.00 | 93.49 | B | C |
| ATOM | 4384 | CG | LYS | B | 376 | 6.107 | 55.346 | 40.730 | 1.00 | 96.51 | B | C |
| ATOM | 4385 | CD | LYS | B | 376 | 5.448 | 54.695 | 39.504 | 1.00 | 98.20 | B | C |
| ATOM | 4386 | CE | LYS | B | 376 | 6.358 | 54.745 | 38.270 | 1.00 | 98.62 | B | C |
| ATOM | 4387 | NZ | LYS | B | 376 | 5.665 | 54.286 | 37.025 | 1.00 | 97.72 | B | N |
| ATOM | 4388 | C | LYS | B | 376 | 8.289 | 53.185 | 42.744 | 1.00 | 89.01 | B | C |
| ATOM | 4389 | O | LYS | B | 376 | 8.275 | 52.429 | 43.720 | 1.00 | 86.61 | B | O |
| ATOM | 4390 | N | ALA | B | 377 | 9.290 | 54.033 | 42.473 | 1.00 | 88.95 | B | N |
| ATOM | 4391 | CA | ALA | B | 377 | 10.514 | 54.155 | 43.277 | 1.00 | 86.04 | B | C |
| ATOM | 4392 | CB | ALA | B | 377 | 11.636 | 54.795 | 42.452 | 1.00 | 83.79 | B | C |
| ATOM | 4393 | C | ALA | B | 377 | 10.297 | 54.934 | 44.574 | 1.00 | 83.26 | B | C |
| ATOM | 4394 | O | ALA | B | 377 | 9.772 | 56.046 | 44.566 | 1.00 | 80.21 | B | O |
| ATOM | 4395 | N | ASN | B | 382 | 12.804 | 52.854 | 52.307 | 1.00 | 90.79 | B | N |
| ATOM | 4396 | CA | ASN | B | 382 | 11.818 | 52.620 | 51.256 | 1.00 | 93.43 | B | C |
| ATOM | 4397 | CB | ASN | B | 382 | 12.470 | 52.774 | 49.864 | 1.00 | 95.86 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | Amino Acid Residue | | | X | Y | Z | Occ. | Temp Factor | Atom Type | |
|---|---|---|---|---|---|---|---|---|---|---|---|
| ATOM | 4398 | CG | ASN | B | 382 | 11.509 | 52.453 | 48.697 | 1.00 | 96.25 | B | C |
| ATOM | 4399 | OD1 | ASN | B | 382 | 11.915 | 51.847 | 47.699 | 1.00 | 94.77 | B | O |
| ATOM | 4400 | ND2 | ASN | B | 382 | 10.249 | 52.878 | 48.812 | 1.00 | 95.05 | B | N |
| ATOM | 4401 | C | ASN | B | 382 | 11.112 | 51.263 | 51.392 | 1.00 | 91.79 | B | C |
| ATOM | 4402 | O | ASN | B | 382 | 9.929 | 51.201 | 51.741 | 1.00 | 90.56 | B | O |
| ATOM | 4403 | N | VAL | B | 383 | 11.853 | 50.188 | 51.127 | 1.00 | 90.36 | B | N |
| ATOM | 4404 | CA | VAL | B | 383 | 11.295 | 48.840 | 51.019 | 1.00 | 88.88 | B | C |
| ATOM | 4405 | CB | VAL | B | 383 | 11.441 | 48.311 | 49.569 | 1.00 | 87.27 | B | C |
| ATOM | 4406 | CG1 | VAL | B | 383 | 11.215 | 46.818 | 49.500 | 1.00 | 85.52 | B | C |
| ATOM | 4407 | CG2 | VAL | B | 383 | 10.485 | 49.030 | 48.636 | 1.00 | 88.67 | B | C |
| ATOM | 4408 | C | VAL | B | 383 | 11.986 | 47.870 | 51.980 | 1.00 | 89.70 | B | C |
| ATOM | 4409 | O | VAL | B | 383 | 13.212 | 47.750 | 51.970 | 1.00 | 92.76 | B | O |
| ATOM | 4410 | N | ARG | B | 384 | 11.202 | 47.177 | 52.802 | 1.00 | 87.96 | B | N |
| ATOM | 4411 | CA | ARG | B | 384 | 11.750 | 46.185 | 53.731 | 1.00 | 85.72 | B | C |
| ATOM | 4412 | CB | ARG | B | 384 | 10.849 | 46.045 | 54.964 | 1.00 | 83.28 | B | C |
| ATOM | 4413 | CG | ARG | B | 384 | 11.590 | 46.085 | 56.284 | 1.00 | 80.78 | B | C |
| ATOM | 4414 | CD | ARG | B | 384 | 10.782 | 45.579 | 57.471 | 1.00 | 80.11 | B | C |
| ATOM | 4415 | NE | ARG | B | 384 | 10.595 | 46.597 | 58.506 | 1.00 | 81.51 | B | N |
| ATOM | 4416 | CZ | ARG | B | 384 | 11.545 | 47.036 | 59.340 | 1.00 | 82.35 | B | C |
| ATOM | 4417 | NH1 | ARG | B | 384 | 12.786 | 46.561 | 59.284 | 1.00 | 81.49 | B | N |
| ATOM | 4418 | NH2 | ARG | B | 384 | 11.250 | 47.966 | 60.240 | 1.00 | 82.81 | B | N |
| ATOM | 4419 | C | ARG | B | 384 | 11.964 | 44.825 | 53.047 | 1.00 | 86.09 | B | C |
| ATOM | 4420 | O | ARG | B | 384 | 11.932 | 44.721 | 51.819 | 1.00 | 85.04 | B | O |
| ATOM | 4421 | N | CYS | B | 385 | 12.196 | 43.792 | 53.850 | 1.00 | 86.91 | B | N |
| ATOM | 4422 | CA | CYS | B | 385 | 12.377 | 42.437 | 53.342 | 1.00 | 86.40 | B | C |
| ATOM | 4423 | CB | CYS | B | 385 | 13.867 | 42.059 | 53.361 | 1.00 | 93.48 | B | C |
| ATOM | 4424 | SG | CYS | B | 385 | 14.337 | 40.488 | 54.130 | 1.00 | 101.78 | B | S |
| ATOM | 4425 | C | CYS | B | 385 | 11.491 | 41.475 | 54.140 | 1.00 | 80.84 | B | C |
| ATOM | 4426 | O | CYS | B | 385 | 11.177 | 41.727 | 55.311 | 1.00 | 79.23 | B | O |
| ATOM | 4427 | N | LEU | B | 386 | 11.090 | 40.382 | 53.494 | 1.00 | 75.98 | B | N |
| ATOM | 4428 | CA | LEU | B | 386 | 10.003 | 39.531 | 53.983 | 1.00 | 72.77 | B | C |
| ATOM | 4429 | CB | LEU | B | 386 | 9.596 | 38.520 | 52.914 | 1.00 | 72.03 | B | C |
| ATOM | 4430 | CG | LEU | B | 386 | 8.101 | 38.539 | 52.625 | 1.00 | 70.14 | B | C |
| ATOM | 4431 | CD1 | LEU | B | 386 | 7.773 | 39.669 | 51.661 | 1.00 | 70.58 | B | C |
| ATOM | 4432 | CD2 | LEU | B | 386 | 7.654 | 37.199 | 52.078 | 1.00 | 69.14 | B | C |
| ATOM | 4433 | C | LEU | B | 386 | 10.306 | 38.817 | 55.285 | 1.00 | 70.79 | B | C |
| ATOM | 4434 | O | LEU | B | 386 | 10.760 | 37.674 | 55.285 | 1.00 | 70.38 | B | O |
| ATOM | 4435 | N | GLN | B | 387 | 10.008 | 39.491 | 56.390 | 1.00 | 70.99 | B | N |
| ATOM | 4436 | CA | GLN | B | 387 | 10.450 | 39.070 | 57.719 | 1.00 | 71.21 | B | C |
| ATOM | 4437 | CB | GLN | B | 387 | 10.000 | 40.081 | 58.770 | 1.00 | 76.73 | B | C |
| ATOM | 4438 | CG | GLN | B | 387 | 11.090 | 40.472 | 59.747 | 1.00 | 83.54 | B | C |
| ATOM | 4439 | CD | GLN | B | 387 | 11.192 | 41.970 | 59.922 | 1.00 | 89.26 | B | C |
| ATOM | 4440 | OE1 | GLN | B | 387 | 10.956 | 42.502 | 61.017 | 1.00 | 90.36 | B | O |
| ATOM | 4441 | NE2 | GLN | B | 387 | 11.542 | 42.663 | 58.840 | 1.00 | 92.01 | B | N |
| ATOM | 4442 | C | GLN | B | 387 | 10.031 | 37.666 | 58.147 | 1.00 | 66.69 | B | C |
| ATOM | 4443 | O | GLN | B | 387 | 10.724 | 37.032 | 58.945 | 1.00 | 67.30 | B | O |
| ATOM | 4444 | N | HIS | B | 388 | 8.915 | 37.180 | 57.616 | 1.00 | 61.67 | B | N |
| ATOM | 4445 | CA | HIS | B | 388 | 8.366 | 35.889 | 58.029 | 1.00 | 60.32 | B | C |
| ATOM | 4446 | CB | HIS | B | 388 | 6.842 | 35.962 | 58.010 | 1.00 | 65.91 | B | C |
| ATOM | 4447 | CG | HIS | B | 388 | 6.284 | 36.234 | 56.652 | 1.00 | 75.18 | B | C |
| ATOM | 4448 | ND1 | HIS | B | 388 | 5.974 | 37.506 | 56.219 | 1.00 | 77.75 | B | N |
| ATOM | 4449 | CE1 | HIS | B | 388 | 5.524 | 37.441 | 54.977 | 1.00 | 80.74 | B | C |
| ATOM | 4450 | NE2 | HIS | B | 388 | 5.545 | 36.177 | 54.584 | 1.00 | 78.94 | B | N |
| ATOM | 4451 | CD2 | HIS | B | 388 | 6.024 | 35.403 | 55.612 | 1.00 | 77.60 | B | C |
| ATOM | 4452 | C | HIS | B | 388 | 8.850 | 34.697 | 57.178 | 1.00 | 55.01 | B | C |
| ATOM | 4453 | O | HIS | B | 388 | 8.593 | 33.542 | 57.521 | 1.00 | 50.27 | B | O |
| ATOM | 4454 | N | PHE | B | 389 | 9.544 | 34.986 | 56.080 | 1.00 | 53.61 | B | N |
| ATOM | 4455 | CA | PHE | B | 389 | 9.953 | 33.963 | 55.114 | 1.00 | 55.30 | B | C |
| ATOM | 4456 | CB | PHE | B | 389 | 9.411 | 34.301 | 53.714 | 1.00 | 57.26 | B | C |
| ATOM | 4457 | CG | PHE | B | 389 | 10.279 | 33.799 | 52.569 | 1.00 | 59.85 | B | C |
| ATOM | 4458 | CD1 | PHE | B | 389 | 10.133 | 32.498 | 52.076 | 1.00 | 61.44 | B | C |
| ATOM | 4459 | CE1 | PHE | B | 389 | 10.916 | 32.030 | 51.012 | 1.00 | 60.58 | B | C |
| ATOM | 4460 | CZ | PHE | B | 389 | 11.858 | 32.870 | 50.432 | 1.00 | 60.77 | B | C |
| ATOM | 4461 | CE2 | PHE | B | 389 | 12.015 | 34.169 | 50.914 | 1.00 | 60.24 | B | C |
| ATOM | 4462 | CD2 | PHE | B | 389 | 11.227 | 34.630 | 51.973 | 1.00 | 59.50 | B | C |
| ATOM | 4463 | C | PHE | B | 389 | 11.468 | 33.805 | 55.069 | 1.00 | 53.57 | B | C |
| ATOM | 4464 | O | PHE | B | 389 | 11.984 | 32.686 | 54.991 | 1.00 | 48.22 | B | O |
| ATOM | 4465 | N | TYR | B | 390 | 12.153 | 34.946 | 55.046 | 1.00 | 56.37 | B | N |
| ATOM | 4466 | CA | TYR | B | 390 | 13.584 | 35.028 | 55.271 | 1.00 | 60.65 | B | C |
| ATOM | 4467 | CB | TYR | B | 390 | 14.151 | 36.311 | 54.664 | 1.00 | 60.39 | B | C |
| ATOM | 4468 | CG | TYR | B | 390 | 14.215 | 36.368 | 53.159 | 1.00 | 62.98 | B | C |
| ATOM | 4469 | CD1 | TYR | B | 390 | 13.526 | 37.355 | 52.456 | 1.00 | 65.15 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 4470 | CE1 | TYR | B | 390 | 13.591 | 37.427 | 51.067 | 1.00 | 67.84 | B | C |
| ATOM | 4471 | CZ | TYR | B | 390 | 14.363 | 36.508 | 50.366 | 1.00 | 68.16 | B | C |
| ATOM | 4472 | OH | TYR | B | 390 | 14.427 | 36.572 | 48.991 | 1.00 | 69.28 | B | O |
| ATOM | 4473 | CE2 | TYR | B | 390 | 15.068 | 35.524 | 51.043 | 1.00 | 66.83 | B | C |
| ATOM | 4474 | CD2 | TYR | B | 390 | 14.992 | 35.462 | 52.435 | 1.00 | 65.28 | B | C |
| ATOM | 4475 | C | TYR | B | 390 | 13.731 | 35.137 | 56.769 | 1.00 | 65.50 | B | C |
| ATOM | 4476 | O | TYR | B | 390 | 12.737 | 35.284 | 57.478 | 1.00 | 66.93 | B | O |
| ATOM | 4477 | N | GLY | B | 391 | 14.962 | 35.092 | 57.262 | 1.00 | 70.76 | B | N |
| ATOM | 4478 | CA | GLY | B | 391 | 15.203 | 35.522 | 58.625 | 1.00 | 79.44 | B | C |
| ATOM | 4479 | C | GLY | B | 391 | 14.958 | 37.024 | 58.689 | 1.00 | 85.18 | B | C |
| ATOM | 4480 | O | GLY | B | 391 | 14.863 | 37.674 | 57.641 | 1.00 | 83.68 | B | O |
| ATOM | 4481 | N | PRO | B | 392 | 14.818 | 37.584 | 59.891 | 1.00 | 89.97 | B | N |
| ATOM | 4482 | CA | PRO | B | 392 | 15.016 | 39.027 | 60.065 | 1.00 | 92.05 | B | C |
| ATOM | 4483 | CB | PRO | B | 392 | 14.600 | 39.273 | 61.519 | 1.00 | 91.69 | B | C |
| ATOM | 4484 | CG | PRO | B | 392 | 13.798 | 38.075 | 61.895 | 1.00 | 91.59 | B | C |
| ATOM | 4485 | CD | PRO | B | 392 | 14.429 | 36.928 | 61.153 | 1.00 | 91.23 | B | C |
| ATOM | 4486 | C | PRO | B | 392 | 16.499 | 39.320 | 59.860 | 1.00 | 94.53 | B | C |
| ATOM | 4487 | O | PRO | B | 392 | 16.865 | 40.438 | 59.504 | 1.00 | 94.28 | B | O |
| ATOM | 4488 | N | ASN | B | 393 | 17.330 | 38.299 | 60.064 | 1.00 | 97.98 | B | N |
| ATOM | 4489 | CA | ASN | B | 393 | 18.761 | 38.395 | 59.835 | 1.00 | 103.04 | B | C |
| ATOM | 4490 | CB | ASN | B | 393 | 19.524 | 38.000 | 61.103 | 1.00 | 104.26 | B | C |
| ATOM | 4491 | CG | ASN | B | 393 | 19.878 | 39.199 | 61.973 | 1.00 | 105.22 | B | C |
| ATOM | 4492 | OD1 | ASN | B | 393 | 21.012 | 39.330 | 62.437 | 1.00 | 105.99 | B | O |
| ATOM | 4493 | ND2 | ASN | B | 393 | 18.905 | 40.079 | 62.202 | 1.00 | 104.86 | B | N |
| ATOM | 4494 | C | ASN | B | 393 | 19.214 | 37.556 | 58.641 | 1.00 | 106.92 | B | C |
| ATOM | 4495 | O | ASN | B | 393 | 18.390 | 37.010 | 57.904 | 1.00 | 104.77 | B | O |
| ATOM | 4496 | N | HIS | B | 394 | 20.534 | 37.468 | 58.472 | 1.00 | 114.08 | B | N |
| ATOM | 4497 | CA | HIS | B | 394 | 21.197 | 36.791 | 57.343 | 1.00 | 120.13 | B | C |
| ATOM | 4498 | CB | HIS | B | 394 | 20.898 | 35.274 | 57.299 | 1.00 | 122.25 | B | C |
| ATOM | 4499 | CG | HIS | B | 394 | 22.118 | 34.407 | 57.441 | 1.00 | 123.57 | B | C |
| ATOM | 4500 | ND1 | HIS | B | 394 | 22.990 | 34.510 | 58.507 | 1.00 | 123.45 | B | N |
| ATOM | 4501 | CE1 | HIS | B | 394 | 23.963 | 33.626 | 58.367 | 1.00 | 123.00 | B | C |
| ATOM | 4502 | NE2 | HIS | B | 394 | 23.755 | 32.951 | 57.251 | 1.00 | 123.36 | B | N |
| ATOM | 4503 | CD2 | HIS | B | 394 | 22.608 | 33.419 | 56.653 | 1.00 | 123.77 | B | C |
| ATOM | 4504 | C | HIS | B | 394 | 20.967 | 37.477 | 55.982 | 1.00 | 121.03 | B | C |
| ATOM | 4505 | O | HIS | B | 394 | 20.172 | 38.420 | 55.871 | 1.00 | 120.31 | B | O |
| ATOM | 4506 | N | GLU | B | 395 | 21.685 | 36.987 | 54.967 | 1.00 | 122.26 | B | N |
| ATOM | 4507 | CA | GLU | B | 395 | 21.757 | 37.598 | 53.636 | 1.00 | 124.02 | B | C |
| ATOM | 4508 | CB | GLU | B | 395 | 22.643 | 36.767 | 52.686 | 1.00 | 124.48 | B | C |
| ATOM | 4509 | CG | GLU | B | 395 | 23.282 | 35.525 | 53.293 | 1.00 | 125.18 | B | C |
| ATOM | 4510 | CD | GLU | B | 395 | 24.693 | 35.779 | 53.798 | 1.00 | 125.91 | B | C |
| ATOM | 4511 | OE1 | GLU | B | 395 | 25.650 | 35.595 | 53.017 | 1.00 | 126.50 | B | O |
| ATOM | 4512 | OE2 | GLU | B | 395 | 24.848 | 36.160 | 54.978 | 1.00 | 125.56 | B | O |
| ATOM | 4513 | C | GLU | B | 395 | 20.390 | 37.865 | 52.995 | 1.00 | 125.92 | B | C |
| ATOM | 4514 | O | GLU | B | 395 | 19.347 | 37.484 | 53.544 | 1.00 | 127.28 | B | O |
| ATOM | 4515 | N | HIS | B | 396 | 20.416 | 38.503 | 51.822 | 1.00 | 125.20 | B | N |
| ATOM | 4516 | CA | HIS | B | 396 | 19.221 | 38.992 | 51.121 | 1.00 | 121.60 | B | C |
| ATOM | 4517 | CB | HIS | B | 396 | 18.197 | 37.877 | 50.851 | 1.00 | 121.80 | B | C |
| ATOM | 4518 | CG | HIS | B | 396 | 18.812 | 36.558 | 50.496 | 1.00 | 123.47 | B | C |
| ATOM | 4519 | ND1 | HIS | B | 396 | 19.370 | 36.304 | 49.262 | 1.00 | 124.95 | B | N |
| ATOM | 4520 | CE1 | HIS | B | 396 | 19.831 | 35.066 | 49.235 | 1.00 | 125.85 | B | C |
| ATOM | 4521 | NE2 | HIS | B | 396 | 19.596 | 34.509 | 50.410 | 1.00 | 126.04 | B | N |
| ATOM | 4522 | CD2 | HIS | B | 396 | 18.958 | 35.419 | 51.216 | 1.00 | 124.24 | B | C |
| ATOM | 4523 | C | HIS | B | 396 | 18.583 | 40.158 | 51.880 | 1.00 | 118.72 | B | C |
| ATOM | 4524 | O | HIS | B | 396 | 18.293 | 41.199 | 51.291 | 1.00 | 119.52 | B | O |
| ATOM | 4525 | N | CYS | B | 397 | 18.391 | 39.980 | 53.186 | 1.00 | 114.19 | B | N |
| ATOM | 4526 | CA | CYS | B | 397 | 17.796 | 40.999 | 54.042 | 1.00 | 110.17 | B | C |
| ATOM | 4527 | CB | CYS | B | 397 | 17.284 | 40.371 | 55.338 | 1.00 | 106.64 | B | C |
| ATOM | 4528 | SG | CYS | B | 397 | 15.560 | 40.767 | 55.731 | 1.00 | 102.28 | B | S |
| ATOM | 4529 | C | CYS | B | 397 | 18.761 | 42.148 | 54.341 | 1.00 | 110.73 | B | C |
| ATOM | 4530 | O | CYS | B | 397 | 18.333 | 43.281 | 54.567 | 1.00 | 110.81 | B | O |
| ATOM | 4531 | N | PHE | B | 398 | 20.057 | 41.852 | 54.346 | 1.00 | 111.68 | B | N |
| ATOM | 4532 | CA | PHE | B | 398 | 21.086 | 42.879 | 54.497 | 1.00 | 112.35 | B | C |
| ATOM | 4533 | CB | PHE | B | 398 | 22.096 | 42.466 | 55.579 | 1.00 | 110.38 | B | C |
| ATOM | 4534 | CG | PHE | B | 398 | 22.058 | 43.322 | 56.824 | 1.00 | 110.12 | B | C |
| ATOM | 4535 | CD1 | PHE | B | 398 | 20.857 | 43.849 | 57.302 | 1.00 | 109.64 | B | C |
| ATOM | 4536 | CE1 | PHE | B | 398 | 20.828 | 44.640 | 58.459 | 1.00 | 109.56 | B | C |
| ATOM | 4537 | CZ | PHE | B | 398 | 22.013 | 44.904 | 59.152 | 1.00 | 110.46 | B | C |
| ATOM | 4538 | CE2 | PHE | B | 398 | 23.220 | 44.380 | 58.687 | 1.00 | 110.54 | B | C |
| ATOM | 4539 | CD2 | PHE | B | 398 | 23.235 | 43.592 | 57.528 | 1.00 | 111.21 | B | C |
| ATOM | 4540 | C | PHE | B | 398 | 21.776 | 43.112 | 53.146 | 1.00 | 114.23 | B | C |
| ATOM | 4541 | O | PHE | B | 398 | 23.008 | 43.110 | 53.055 | 1.00 | 114.14 | B | O |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 4542 | N | ASN | B | 399 | 20.969 | 43.318 | 52.101 | 1.00 | 116.16 | B | N |
| ATOM | 4543 | CA | ASN | B | 399 | 21.465 | 43.388 | 50.719 | 1.00 | 116.83 | B | C |
| ATOM | 4544 | CB | ASN | B | 399 | 21.302 | 42.022 | 50.027 | 1.00 | 114.97 | B | C |
| ATOM | 4545 | CG | ASN | B | 399 | 22.618 | 41.273 | 49.877 | 1.00 | 112.37 | B | C |
| ATOM | 4546 | OD1 | ASN | B | 399 | 23.371 | 41.500 | 48.928 | 1.00 | 111.41 | B | O |
| ATOM | 4547 | ND2 | ASN | B | 399 | 22.890 | 40.365 | 50.808 | 1.00 | 110.93 | B | N |
| ATOM | 4548 | C | ASN | B | 399 | 20.875 | 44.521 | 49.840 | 1.00 | 117.60 | B | C |
| ATOM | 4549 | O | ASN | B | 399 | 21.156 | 45.702 | 50.067 | 1.00 | 116.73 | B | O |
| ATOM | 4550 | N | ARG | B | 400 | 20.057 | 44.136 | 48.853 | 1.00 | 118.44 | B | N |
| ATOM | 4551 | CA | ARG | B | 400 | 19.609 | 45.005 | 47.751 | 1.00 | 117.82 | B | C |
| ATOM | 4552 | CB | ARG | B | 400 | 18.609 | 46.074 | 48.216 | 1.00 | 115.30 | B | C |
| ATOM | 4553 | CG | ARG | B | 400 | 17.187 | 45.876 | 47.688 | 1.00 | 113.12 | B | C |
| ATOM | 4554 | CD | ARG | B | 400 | 17.015 | 46.104 | 46.189 | 1.00 | 111.57 | B | C |
| ATOM | 4555 | NE | ARG | B | 400 | 15.717 | 45.618 | 45.717 | 1.00 | 110.25 | B | N |
| ATOM | 4556 | CZ | ARG | B | 400 | 15.384 | 45.448 | 44.438 | 1.00 | 108.16 | B | C |
| ATOM | 4557 | NH1 | ARG | B | 400 | 16.249 | 45.723 | 43.469 | 1.00 | 108.42 | B | N |
| ATOM | 4558 | NH2 | ARG | B | 400 | 14.177 | 45.001 | 44.124 | 1.00 | 105.39 | B | N |
| ATOM | 4559 | C | ARG | B | 400 | 20.775 | 45.638 | 46.987 | 1.00 | 118.38 | B | C |
| ATOM | 4560 | O | ARG | B | 400 | 21.136 | 45.190 | 45.896 | 1.00 | 118.43 | B | O |
| ATOM | 4561 | N | ASP | B | 414 | 11.162 | 37.092 | 40.828 | 1.00 | 118.53 | B | N |
| ATOM | 4562 | CA | ASP | B | 414 | 12.040 | 35.945 | 40.646 | 1.00 | 121.11 | B | C |
| ATOM | 4563 | CB | ASP | B | 414 | 13.014 | 36.193 | 39.474 | 1.00 | 123.45 | B | C |
| ATOM | 4564 | CG | ASP | B | 414 | 13.127 | 34.999 | 38.521 | 1.00 | 124.03 | B | C |
| ATOM | 4565 | OD1 | ASP | B | 414 | 14.022 | 34.149 | 38.731 | 1.00 | 122.65 | B | O |
| ATOM | 4566 | OD2 | ASP | B | 414 | 12.384 | 34.840 | 37.523 | 1.00 | 124.38 | B | O |
| ATOM | 4567 | C | ASP | B | 414 | 12.803 | 35.641 | 41.943 | 1.00 | 121.30 | B | C |
| ATOM | 4568 | O | ASP | B | 414 | 12.532 | 34.639 | 42.607 | 1.00 | 120.92 | B | O |
| ATOM | 4569 | N | GLU | B | 415 | 13.726 | 36.531 | 42.314 | 1.00 | 121.17 | B | N |
| ATOM | 4570 | CA | GLU | B | 415 | 14.741 | 36.237 | 43.332 | 1.00 | 117.56 | B | C |
| ATOM | 4571 | CB | GLU | B | 415 | 16.122 | 36.716 | 42.865 | 1.00 | 118.51 | B | C |
| ATOM | 4572 | CG | GLU | B | 415 | 16.578 | 36.105 | 41.546 | 1.00 | 120.09 | B | C |
| ATOM | 4573 | CD | GLU | B | 415 | 17.038 | 34.664 | 41.688 | 1.00 | 120.61 | B | C |
| ATOM | 4574 | OE1 | GLU | B | 415 | 18.161 | 34.461 | 42.198 | 1.00 | 121.28 | B | O |
| ATOM | 4575 | OE2 | GLU | B | 415 | 16.286 | 33.739 | 41.289 | 1.00 | 119.11 | B | O |
| ATOM | 4576 | C | GLU | B | 415 | 14.441 | 36.780 | 44.730 | 1.00 | 113.94 | B | C |
| ATOM | 4577 | O | GLU | B | 415 | 14.597 | 36.062 | 45.716 | 1.00 | 112.85 | B | O |
| ATOM | 4578 | N | TYR | B | 416 | 14.019 | 38.040 | 44.809 | 1.00 | 111.10 | B | N |
| ATOM | 4579 | CA | TYR | B | 416 | 13.765 | 38.699 | 46.097 | 1.00 | 108.01 | B | C |
| ATOM | 4580 | CB | TYR | B | 416 | 14.486 | 40.060 | 46.204 | 1.00 | 116.70 | B | C |
| ATOM | 4581 | CG | TYR | B | 416 | 15.349 | 40.472 | 45.015 | 1.00 | 125.64 | B | C |
| ATOM | 4582 | CD1 | TYR | B | 416 | 14.876 | 40.373 | 43.691 | 1.00 | 128.98 | B | C |
| ATOM | 4583 | CE1 | TYR | B | 416 | 15.670 | 40.760 | 42.603 | 1.00 | 130.95 | B | C |
| ATOM | 4584 | CZ | TYR | B | 416 | 16.946 | 41.268 | 42.835 | 1.00 | 131.58 | B | C |
| ATOM | 4585 | OH | TYR | B | 416 | 17.732 | 41.657 | 41.774 | 1.00 | 131.74 | B | O |
| ATOM | 4586 | CE2 | TYR | B | 416 | 17.434 | 41.386 | 44.135 | 1.00 | 130.79 | B | C |
| ATOM | 4587 | CD2 | TYR | B | 416 | 16.634 | 40.992 | 45.217 | 1.00 | 128.48 | B | C |
| ATOM | 4588 | C | TYR | B | 416 | 12.270 | 38.849 | 46.436 | 1.00 | 98.37 | B | C |
| ATOM | 4589 | O | TYR | B | 416 | 11.403 | 38.858 | 45.550 | 1.00 | 97.84 | B | O |
| ATOM | 4590 | N | ARG | B | 417 | 11.996 | 38.971 | 47.732 | 1.00 | 86.10 | B | N |
| ATOM | 4591 | CA | ARG | B | 417 | 10.646 | 38.935 | 48.269 | 1.00 | 76.02 | B | C |
| ATOM | 4592 | CB | ARG | B | 417 | 10.423 | 37.608 | 48.995 | 1.00 | 72.99 | B | C |
| ATOM | 4593 | CG | ARG | B | 417 | 9.785 | 36.517 | 48.128 | 1.00 | 70.00 | B | C |
| ATOM | 4594 | CD | ARG | B | 417 | 10.764 | 35.574 | 47.442 | 1.00 | 65.42 | B | C |
| ATOM | 4595 | NE | ARG | B | 417 | 10.280 | 35.179 | 46.122 | 1.00 | 63.02 | B | N |
| ATOM | 4596 | CZ | ARG | B | 417 | 10.061 | 33.922 | 45.754 | 1.00 | 63.41 | B | C |
| ATOM | 4597 | NH1 | ARG | B | 417 | 10.286 | 32.924 | 46.600 | 1.00 | 64.27 | B | N |
| ATOM | 4598 | NH2 | ARG | B | 417 | 9.615 | 33.657 | 44.535 | 1.00 | 61.59 | B | N |
| ATOM | 4599 | C | ARG | B | 417 | 10.437 | 40.107 | 49.216 | 1.00 | 73.44 | B | C |
| ATOM | 4600 | O | ARG | B | 417 | 10.948 | 40.110 | 50.333 | 1.00 | 74.00 | B | O |
| ATOM | 4601 | N | THR | B | 418 | 9.654 | 41.086 | 48.768 | 1.00 | 72.29 | B | N |
| ATOM | 4602 | CA | THR | B | 418 | 9.659 | 42.430 | 49.350 | 1.00 | 71.34 | B | C |
| ATOM | 4603 | CB | THR | B | 418 | 9.921 | 43.475 | 48.234 | 1.00 | 74.11 | B | C |
| ATOM | 4604 | OG1 | THR | B | 418 | 9.420 | 42.981 | 46.983 | 1.00 | 77.18 | B | O |
| ATOM | 4605 | CG2 | THR | B | 418 | 11.413 | 43.622 | 47.967 | 1.00 | 74.10 | B | C |
| ATOM | 4606 | C | THR | B | 418 | 8.418 | 42.837 | 50.152 | 1.00 | 68.83 | B | C |
| ATOM | 4607 | O | THR | B | 418 | 7.307 | 42.872 | 49.640 | 1.00 | 69.50 | B | O |
| ATOM | 4608 | N | GLU | B | 419 | 8.637 | 43.152 | 51.420 | 1.00 | 68.82 | B | N |
| ATOM | 4609 | CA | GLU | B | 419 | 7.639 | 43.798 | 52.263 | 1.00 | 69.08 | B | C |
| ATOM | 4610 | CB | GLU | B | 419 | 7.934 | 43.489 | 53.731 | 1.00 | 71.63 | B | C |
| ATOM | 4611 | CG | GLU | B | 419 | 6.716 | 43.402 | 54.635 | 1.00 | 75.07 | B | C |
| ATOM | 4612 | CD | GLU | B | 419 | 7.003 | 42.674 | 55.942 | 1.00 | 78.09 | B | C |
| ATOM | 4613 | OE1 | GLU | B | 419 | 7.584 | 41.558 | 55.909 | 1.00 | 79.05 | B | O |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 4614 | OE2 | GLU | B | 419 | 6.639 | 43.218 | 57.008 | 1.00 | 79.41 | B | O |
| ATOM | 4615 | C | GLU | B | 419 | 7.699 | 45.313 | 52.040 | 1.00 | 68.22 | B | C |
| ATOM | 4616 | O | GLU | B | 419 | 8.740 | 45.850 | 51.659 | 1.00 | 69.26 | B | O |
| ATOM | 4617 | N | PHE | B | 420 | 6.584 | 45.996 | 52.275 | 1.00 | 66.82 | B | N |
| ATOM | 4618 | CA | PHE | B | 420 | 6.533 | 47.450 | 52.187 | 1.00 | 65.27 | B | C |
| ATOM | 4619 | CB | PHE | B | 420 | 5.407 | 47.905 | 51.254 | 1.00 | 65.84 | B | C |
| ATOM | 4620 | CG | PHE | B | 420 | 5.821 | 48.053 | 49.802 | 1.00 | 65.70 | B | C |
| ATOM | 4621 | CD1 | PHE | B | 420 | 6.559 | 47.058 | 49.154 | 1.00 | 67.04 | B | C |
| ATOM | 4622 | CE1 | PHE | B | 420 | 6.933 | 47.196 | 47.811 | 1.00 | 66.15 | B | C |
| ATOM | 4623 | CZ | PHE | B | 420 | 6.562 | 48.337 | 47.105 | 1.00 | 64.22 | B | C |
| ATOM | 4624 | CE2 | PHE | B | 420 | 5.818 | 49.325 | 47.737 | 1.00 | 63.92 | B | C |
| ATOM | 4625 | CD2 | PHE | B | 420 | 5.448 | 49.179 | 49.075 | 1.00 | 64.43 | B | C |
| ATOM | 4626 | C | PHE | B | 420 | 6.304 | 47.983 | 53.585 | 1.00 | 66.39 | B | C |
| ATOM | 4627 | O | PHE | B | 420 | 5.642 | 47.335 | 54.402 | 1.00 | 64.77 | B | O |
| ATOM | 4628 | N | THR | B | 421 | 6.856 | 49.162 | 53.855 | 1.00 | 68.67 | B | N |
| ATOM | 4629 | CA | THR | B | 421 | 6.843 | 49.736 | 55.198 | 1.00 | 68.95 | B | C |
| ATOM | 4630 | CB | THR | B | 421 | 8.187 | 50.410 | 55.504 | 1.00 | 70.44 | B | C |
| ATOM | 4631 | OG1 | THR | B | 421 | 8.945 | 50.546 | 54.295 | 1.00 | 71.76 | B | O |
| ATOM | 4632 | CG2 | THR | B | 421 | 9.049 | 49.497 | 56.363 | 1.00 | 71.22 | B | C |
| ATOM | 4633 | C | THR | B | 421 | 5.693 | 50.709 | 55.436 | 1.00 | 69.61 | B | C |
| ATOM | 4634 | O | THR | B | 421 | 5.372 | 51.011 | 56.583 | 1.00 | 70.63 | B | O |
| ATOM | 4635 | N | THR | B | 422 | 5.080 | 51.198 | 54.356 | 1.00 | 71.01 | B | N |
| ATOM | 4636 | CA | THR | B | 422 | 3.919 | 52.096 | 54.452 | 1.00 | 70.55 | B | C |
| ATOM | 4637 | CB | THR | B | 422 | 4.256 | 53.523 | 53.958 | 1.00 | 73.13 | B | C |
| ATOM | 4638 | OG1 | THR | B | 422 | 4.820 | 53.458 | 52.640 | 1.00 | 74.02 | B | O |
| ATOM | 4639 | CG2 | THR | B | 422 | 5.350 | 54.168 | 54.819 | 1.00 | 74.37 | B | C |
| ATOM | 4640 | C | THR | B | 422 | 2.705 | 51.584 | 53.681 | 1.00 | 66.95 | B | C |
| ATOM | 4641 | O | THR | B | 422 | 2.830 | 51.012 | 52.590 | 1.00 | 65.46 | B | O |
| ATOM | 4642 | N | ALA | B | 423 | 1.530 | 51.826 | 54.254 | 1.00 | 63.45 | B | N |
| ATOM | 4643 | CA | ALA | B | 423 | 0.263 | 51.413 | 53.655 | 1.00 | 59.07 | B | C |
| ATOM | 4644 | CB | ALA | B | 423 | −0.817 | 51.297 | 54.727 | 1.00 | 58.52 | B | C |
| ATOM | 4645 | C | ALA | B | 423 | −0.205 | 52.347 | 52.549 | 1.00 | 55.58 | B | C |
| ATOM | 4646 | O | ALA | B | 423 | 0.216 | 53.489 | 52.456 | 1.00 | 57.64 | B | O |
| ATOM | 4647 | N | LEU | B | 424 | −1.071 | 51.828 | 51.696 | 1.00 | 55.39 | B | N |
| ATOM | 4648 | CA | LEU | B | 424 | −1.829 | 52.637 | 50.771 | 1.00 | 54.07 | B | C |
| ATOM | 4649 | CB | LEU | B | 424 | −2.076 | 51.854 | 49.481 | 1.00 | 53.16 | B | C |
| ATOM | 4650 | CG | LEU | B | 424 | −2.428 | 52.537 | 48.159 | 1.00 | 53.34 | B | C |
| ATOM | 4651 | CD1 | LEU | B | 424 | −2.975 | 51.496 | 47.196 | 1.00 | 52.78 | B | C |
| ATOM | 4652 | CD2 | LEU | B | 424 | −3.431 | 53.671 | 48.323 | 1.00 | 54.86 | B | C |
| ATOM | 4653 | C | LEU | B | 424 | −3.138 | 52.889 | 51.500 | 1.00 | 54.78 | B | C |
| ATOM | 4654 | O | LEU | B | 424 | −3.909 | 51.956 | 51.758 | 1.00 | 55.38 | B | O |
| ATOM | 4655 | N | GLN | B | 425 | −3.382 | 54.143 | 51.857 | 1.00 | 53.26 | B | N |
| ATOM | 4656 | CA | GLN | B | 425 | −4.586 | 54.469 | 52.605 | 1.00 | 50.56 | B | C |
| ATOM | 4657 | CB | GLN | B | 425 | −4.265 | 55.326 | 53.833 | 1.00 | 57.95 | B | C |
| ATOM | 4658 | CG | GLN | B | 425 | −4.052 | 56.810 | 53.566 | 1.00 | 64.03 | B | C |
| ATOM | 4659 | CD | GLN | B | 425 | −3.515 | 57.523 | 54.783 | 1.00 | 67.46 | B | C |
| ATOM | 4660 | OE1 | GLN | B | 425 | −4.202 | 57.623 | 55.803 | 1.00 | 67.84 | B | O |
| ATOM | 4661 | NE2 | GLN | B | 425 | −2.278 | 58.004 | 54.692 | 1.00 | 70.00 | B | N |
| ATOM | 4662 | C | GLN | B | 425 | −5.661 | 55.115 | 51.751 | 1.00 | 43.53 | B | C |
| ATOM | 4663 | O | GLN | B | 425 | −5.378 | 55.805 | 50.770 | 1.00 | 40.15 | B | O |
| ATOM | 4664 | N | ARG | B | 426 | −6.899 | 54.844 | 52.139 | 1.00 | 40.50 | B | N |
| ATOM | 4665 | CA | ARG | B | 426 | −8.084 | 55.424 | 51.534 | 1.00 | 39.82 | B | C |
| ATOM | 4666 | CB | ARG | B | 426 | −8.641 | 54.524 | 50.435 | 1.00 | 40.11 | B | C |
| ATOM | 4667 | CG | ARG | B | 426 | −7.739 | 54.326 | 49.235 | 1.00 | 41.18 | B | C |
| ATOM | 4668 | CD | ARG | B | 426 | −7.735 | 55.478 | 48.261 | 1.00 | 42.28 | B | C |
| ATOM | 4669 | NE | ARG | B | 426 | −6.378 | 55.792 | 47.829 | 1.00 | 45.34 | B | N |
| ATOM | 4670 | CZ | ARG | B | 426 | −5.993 | 55.870 | 46.559 | 1.00 | 47.98 | B | C |
| ATOM | 4671 | NH1 | ARG | B | 426 | −6.871 | 55.663 | 45.570 | 1.00 | 46.25 | B | N |
| ATOM | 4672 | NH2 | ARG | B | 426 | −4.724 | 56.168 | 46.277 | 1.00 | 49.60 | B | N |
| ATOM | 4673 | C | ARG | B | 426 | −9.122 | 55.581 | 52.631 | 1.00 | 42.57 | B | C |
| ATOM | 4674 | O | ARG | B | 426 | −9.062 | 54.907 | 53.663 | 1.00 | 40.06 | B | O |
| ATOM | 4675 | N | VAL | B | 427 | −10.081 | 56.468 | 52.393 | 1.00 | 48.48 | B | N |
| ATOM | 4676 | CA | VAL | B | 427 | −11.068 | 56.844 | 53.401 | 1.00 | 52.05 | B | C |
| ATOM | 4677 | CB | VAL | B | 427 | −11.393 | 58.346 | 53.327 | 1.00 | 51.13 | B | C |
| ATOM | 4678 | CG1 | VAL | B | 427 | −10.956 | 59.031 | 54.603 | 1.00 | 52.45 | B | C |
| ATOM | 4679 | CG2 | VAL | B | 427 | −10.741 | 58.996 | 52.093 | 1.00 | 50.22 | B | C |
| ATOM | 4680 | C | VAL | B | 427 | −12.363 | 56.063 | 53.243 | 1.00 | 54.73 | B | C |
| ATOM | 4681 | O | VAL | B | 427 | −12.691 | 55.626 | 52.136 | 1.00 | 58.88 | B | O |
| ATOM | 4682 | N | ASP | B | 428 | −13.090 | 55.894 | 54.350 | 1.00 | 52.40 | B | N |
| ATOM | 4683 | CA | ASP | B | 428 | −14.414 | 55.274 | 54.327 | 1.00 | 48.88 | B | C |
| ATOM | 4684 | CB | ASP | B | 428 | −15.051 | 55.293 | 55.727 | 1.00 | 52.09 | B | C |
| ATOM | 4685 | CG | ASP | B | 428 | −16.360 | 54.500 | 55.802 | 1.00 | 53.53 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 4686 | OD1 | ASP | B | 428 | −16.851 | 54.049 | 54.748 | 1.00 | 56.25 | B | O |
| ATOM | 4687 | OD2 | ASP | B | 428 | −16.970 | 54.276 | 56.876 | 1.00 | 50.49 | B | O |
| ATOM | 4688 | C | ASP | B | 428 | −15.304 | 55.986 | 53.305 | 1.00 | 43.23 | B | C |
| ATOM | 4689 | O | ASP | B | 428 | −15.346 | 57.213 | 53.233 | 1.00 | 38.01 | B | O |
| ATOM | 4690 | N | LEU | B | 429 | −15.984 | 55.193 | 52.494 | 1.00 | 41.94 | B | N |
| ATOM | 4691 | CA | LEU | B | 429 | −16.854 | 55.713 | 51.463 | 1.00 | 44.73 | B | C |
| ATOM | 4692 | CB | LEU | B | 429 | −16.849 | 54.772 | 50.266 | 1.00 | 42.69 | B | C |
| ATOM | 4693 | CG | LEU | B | 429 | −15.909 | 55.232 | 49.159 | 1.00 | 45.03 | B | C |
| ATOM | 4694 | CD1 | LEU | B | 429 | −14.963 | 54.120 | 48.741 | 1.00 | 47.96 | B | C |
| ATOM | 4695 | CD2 | LEU | B | 429 | −16.711 | 55.735 | 47.974 | 1.00 | 45.51 | B | C |
| ATOM | 4696 | C | LEU | B | 429 | −18.263 | 55.885 | 52.016 | 1.00 | 48.78 | B | C |
| ATOM | 4697 | O | LEU | B | 429 | −19.132 | 56.509 | 51.383 | 1.00 | 49.46 | B | O |
| ATOM | 4698 | N | PHE | B | 430 | −18.473 | 55.331 | 53.206 | 1.00 | 48.13 | B | N |
| ATOM | 4699 | CA | PHE | B | 430 | −19.757 | 55.397 | 53.874 | 1.00 | 51.15 | B | C |
| ATOM | 4700 | CB | PHE | B | 430 | −20.098 | 54.034 | 54.463 | 1.00 | 47.94 | B | C |
| ATOM | 4701 | CG | PHE | B | 430 | −20.464 | 52.998 | 53.427 | 1.00 | 47.14 | B | C |
| ATOM | 4702 | CD1 | PHE | B | 430 | −19.868 | 51.746 | 53.430 | 1.00 | 46.71 | B | C |
| ATOM | 4703 | CE1 | PHE | B | 430 | −20.219 | 50.777 | 52.479 | 1.00 | 44.76 | B | C |
| ATOM | 4704 | CZ | PHE | B | 430 | −21.160 | 51.056 | 51.520 | 1.00 | 43.07 | B | C |
| ATOM | 4705 | CE2 | PHE | B | 430 | −21.760 | 52.297 | 51.501 | 1.00 | 46.29 | B | C |
| ATOM | 4706 | CD2 | PHE | B | 430 | −21.413 | 53.267 | 52.451 | 1.00 | 47.40 | B | C |
| ATOM | 4707 | C | PHE | B | 430 | −19.749 | 56.486 | 54.939 | 1.00 | 57.21 | B | C |
| ATOM | 4708 | O | PHE | B | 430 | −20.801 | 56.883 | 55.451 | 1.00 | 58.51 | B | O |
| ATOM | 4709 | N | MET | B | 431 | −18.549 | 56.979 | 55.242 | 1.00 | 62.60 | B | N |
| ATOM | 4710 | CA | MET | B | 431 | −18.330 | 58.080 | 56.189 | 1.00 | 66.92 | B | C |
| ATOM | 4711 | CB | MET | B | 431 | −18.965 | 59.387 | 55.685 | 1.00 | 71.06 | B | C |
| ATOM | 4712 | CG | MET | B | 431 | −18.235 | 60.033 | 54.527 | 1.00 | 78.05 | B | C |
| ATOM | 4713 | SD | MET | B | 431 | −19.019 | 59.627 | 52.944 | 1.00 | 86.26 | B | S |
| ATOM | 4714 | CE | MET | B | 431 | −19.859 | 61.190 | 52.582 | 1.00 | 86.91 | B | C |
| ATOM | 4715 | C | MET | B | 431 | −18.804 | 57.769 | 57.611 | 1.00 | 66.59 | B | C |
| ATOM | 4716 | O | MET | B | 431 | −19.202 | 58.664 | 58.348 | 1.00 | 69.83 | B | O |
| ATOM | 4717 | N | GLY | B | 432 | −18.749 | 56.500 | 57.997 | 1.00 | 65.32 | B | N |
| ATOM | 4718 | CA | GLY | B | 432 | −19.175 | 56.097 | 59.324 | 1.00 | 63.07 | B | C |
| ATOM | 4719 | C | GLY | B | 432 | −20.603 | 55.595 | 59.364 | 1.00 | 61.89 | B | C |
| ATOM | 4720 | O | GLY | B | 432 | −21.057 | 55.116 | 60.403 | 1.00 | 61.93 | B | O |
| ATOM | 4721 | N | GLN | B | 433 | −21.307 | 55.699 | 58.237 | 1.00 | 60.80 | B | N |
| ATOM | 4722 | CA | GLN | B | 433 | −22.661 | 55.167 | 58.095 | 1.00 | 60.89 | B | C |
| ATOM | 4723 | CB | GLN | B | 433 | −23.011 | 55.019 | 56.611 | 1.00 | 64.40 | B | C |
| ATOM | 4724 | CG | GLN | B | 433 | −24.331 | 55.642 | 56.186 | 1.00 | 69.58 | B | C |
| ATOM | 4725 | CD | GLN | B | 433 | −25.420 | 55.499 | 57.239 | 1.00 | 74.21 | B | C |
| ATOM | 4726 | OE1 | GLN | B | 433 | −26.012 | 54.429 | 57.383 | 1.00 | 75.27 | B | O |
| ATOM | 4727 | NE2 | GLN | B | 433 | −25.682 | 56.578 | 57.979 | 1.00 | 76.91 | B | N |
| ATOM | 4728 | C | GLN | B | 433 | −22.815 | 53.812 | 58.783 | 1.00 | 59.31 | B | C |
| ATOM | 4729 | O | GLN | B | 433 | −23.914 | 53.425 | 59.184 | 1.00 | 57.45 | B | O |
| ATOM | 4730 | N | PHE | B | 434 | −21.697 | 53.106 | 58.924 | 1.00 | 58.44 | B | N |
| ATOM | 4731 | CA | PHE | B | 434 | −21.698 | 51.738 | 59.410 | 1.00 | 57.23 | B | C |
| ATOM | 4732 | CB | PHE | B | 434 | −21.399 | 50.804 | 58.243 | 1.00 | 51.73 | B | C |
| ATOM | 4733 | CG | PHE | B | 434 | −22.448 | 50.818 | 57.187 | 1.00 | 45.56 | B | C |
| ATOM | 4734 | CD1 | PHE | B | 434 | −22.164 | 51.316 | 55.926 | 1.00 | 44.36 | B | C |
| ATOM | 4735 | CE1 | PHE | B | 434 | −23.132 | 51.333 | 54.930 | 1.00 | 43.99 | B | C |
| ATOM | 4736 | CZ | PHE | B | 434 | −24.409 | 50.862 | 55.207 | 1.00 | 46.41 | B | C |
| ATOM | 4737 | CE2 | PHE | B | 434 | −24.706 | 50.368 | 56.480 | 1.00 | 46.50 | B | C |
| ATOM | 4738 | CD2 | PHE | B | 434 | −23.727 | 50.350 | 57.457 | 1.00 | 43.77 | B | C |
| ATOM | 4739 | C | PHE | B | 434 | −20.710 | 51.495 | 60.546 | 1.00 | 59.69 | B | C |
| ATOM | 4740 | O | PHE | B | 434 | −20.254 | 50.362 | 60.763 | 1.00 | 58.41 | B | O |
| ATOM | 4741 | N | SER | B | 435 | −20.405 | 52.553 | 61.288 | 1.00 | 61.94 | B | N |
| ATOM | 4742 | CA | SER | B | 435 | −19.361 | 52.490 | 62.304 | 1.00 | 64.51 | B | C |
| ATOM | 4743 | CB | SER | B | 435 | −18.734 | 53.869 | 62.507 | 1.00 | 64.60 | B | C |
| ATOM | 4744 | OG | SER | B | 435 | −19.723 | 54.880 | 62.488 | 1.00 | 65.36 | B | O |
| ATOM | 4745 | C | SER | B | 435 | −19.841 | 51.900 | 63.631 | 1.00 | 66.67 | B | C |
| ATOM | 4746 | O | SER | B | 435 | −19.125 | 51.947 | 64.635 | 1.00 | 67.92 | B | O |
| ATOM | 4747 | N | GLU | B | 436 | −21.045 | 51.332 | 63.632 | 1.00 | 68.21 | B | N |
| ATOM | 4748 | CA | GLU | B | 436 | −21.578 | 50.691 | 64.833 | 1.00 | 68.82 | B | C |
| ATOM | 4749 | CB | GLU | B | 436 | −22.713 | 51.525 | 65.412 | 1.00 | 69.36 | B | C |
| ATOM | 4750 | CG | GLU | B | 436 | −22.218 | 52.768 | 66.124 | 1.00 | 71.12 | B | C |
| ATOM | 4751 | CD | GLU | B | 436 | −23.180 | 53.228 | 67.190 | 1.00 | 73.99 | B | C |
| ATOM | 4752 | OE1 | GLU | B | 436 | −24.040 | 54.080 | 66.878 | 1.00 | 75.03 | B | O |
| ATOM | 4753 | OE2 | GLU | B | 436 | −23.079 | 52.731 | 68.333 | 1.00 | 75.48 | B | O |
| ATOM | 4754 | C | GLU | B | 436 | −22.003 | 49.230 | 64.633 | 1.00 | 68.01 | B | C |
| ATOM | 4755 | O | GLU | B | 436 | −22.383 | 48.555 | 65.602 | 1.00 | 67.22 | B | O |
| ATOM | 4756 | N | VAL | B | 437 | −21.904 | 48.750 | 63.386 | 1.00 | 65.67 | B | N |
| ATOM | 4757 | CA | VAL | B | 437 | −22.197 | 47.354 | 63.009 | 1.00 | 60.81 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 4758 | CB  | VAL | B | 437 | −23.421 | 47.248 | 62.059 | 1.00 | 60.54 | B | C |
| ATOM | 4759 | CG1 | VAL | B | 437 | −24.699 | 47.669 | 62.761 | 1.00 | 62.37 | B | C |
| ATOM | 4760 | CG2 | VAL | B | 437 | −23.206 | 48.075 | 60.798 | 1.00 | 60.85 | B | C |
| ATOM | 4761 | C   | VAL | B | 437 | −20.995 | 46.679 | 62.331 | 1.00 | 57.32 | B | C |
| ATOM | 4762 | O   | VAL | B | 437 | −20.110 | 47.370 | 61.812 | 1.00 | 55.78 | B | O |
| ATOM | 4763 | N   | LEU | B | 438 | −20.980 | 45.339 | 62.334 | 1.00 | 52.98 | B | N |
| ATOM | 4764 | CA  | LEU | B | 438 | −19.895 | 44.548 | 61.727 | 1.00 | 49.77 | B | C |
| ATOM | 4765 | CB  | LEU | B | 438 | −19.444 | 43.414 | 62.667 | 1.00 | 49.82 | B | C |
| ATOM | 4766 | CG  | LEU | B | 438 | −18.042 | 42.764 | 62.637 | 1.00 | 49.14 | B | C |
| ATOM | 4767 | CD1 | LEU | B | 438 | −18.127 | 41.240 | 62.819 | 1.00 | 47.45 | B | C |
| ATOM | 4768 | CD2 | LEU | B | 438 | −17.194 | 43.113 | 61.406 | 1.00 | 47.89 | B | C |
| ATOM | 4769 | C   | LEU | B | 438 | −20.257 | 43.975 | 60.347 | 1.00 | 48.76 | B | C |
| ATOM | 4770 | O   | LEU | B | 438 | −20.828 | 42.878 | 60.248 | 1.00 | 47.95 | B | O |
| ATOM | 4771 | N   | LEU | B | 439 | −19.913 | 44.727 | 59.296 | 1.00 | 45.69 | B | N |
| ATOM | 4772 | CA  | LEU | B | 439 | −20.106 | 44.305 | 57.910 | 1.00 | 40.13 | B | C |
| ATOM | 4773 | CB  | LEU | B | 439 | −19.723 | 45.427 | 56.962 | 1.00 | 36.46 | B | C |
| ATOM | 4774 | CG  | LEU | B | 439 | −20.577 | 46.684 | 57.053 | 1.00 | 39.82 | B | C |
| ATOM | 4775 | CD1 | LEU | B | 439 | −19.976 | 47.807 | 56.216 | 1.00 | 38.71 | B | C |
| ATOM | 4776 | CD2 | LEU | B | 439 | −22.007 | 46.400 | 56.625 | 1.00 | 43.44 | B | C |
| ATOM | 4777 | C   | LEU | B | 439 | −19.258 | 43.080 | 57.631 | 1.00 | 40.26 | B | C |
| ATOM | 4778 | O   | LEU | B | 439 | −18.054 | 43.083 | 57.883 | 1.00 | 42.45 | B | O |
| ATOM | 4779 | N   | THR | B | 440 | −19.889 | 42.023 | 57.135 | 1.00 | 37.08 | B | N |
| ATOM | 4780 | CA  | THR | B | 440 | −19.215 | 40.739 | 57.017 | 1.00 | 34.37 | B | C |
| ATOM | 4781 | CB  | THR | B | 440 | −19.895 | 39.677 | 57.883 | 1.00 | 34.54 | B | C |
| ATOM | 4782 | OG1 | THR | B | 440 | −21.305 | 39.699 | 57.643 | 1.00 | 34.99 | B | O |
| ATOM | 4783 | CG2 | THR | B | 440 | −19.766 | 40.012 | 59.361 | 1.00 | 38.15 | B | C |
| ATOM | 4784 | C   | THR | B | 440 | −19.232 | 40.257 | 55.602 | 1.00 | 35.73 | B | C |
| ATOM | 4785 | O   | THR | B | 440 | −18.657 | 39.208 | 55.301 | 1.00 | 38.80 | B | O |
| ATOM | 4786 | N   | SER | B | 441 | −19.900 | 41.006 | 54.732 | 1.00 | 33.65 | B | N |
| ATOM | 4787 | CA  | SER | B | 441 | −19.974 | 40.613 | 53.337 | 1.00 | 36.43 | B | C |
| ATOM | 4788 | CB  | SER | B | 441 | −20.985 | 39.476 | 53.181 | 1.00 | 35.52 | B | C |
| ATOM | 4789 | OG  | SER | B | 441 | −21.583 | 39.526 | 51.900 | 1.00 | 44.41 | B | O |
| ATOM | 4790 | C   | SER | B | 441 | −20.279 | 41.780 | 52.384 | 1.00 | 38.69 | B | C |
| ATOM | 4791 | O   | SER | B | 441 | −21.182 | 42.570 | 52.629 | 1.00 | 44.18 | B | O |
| ATOM | 4792 | N   | ILE | B | 442 | −19.520 | 41.883 | 51.298 | 1.00 | 39.13 | B | N |
| ATOM | 4793 | CA  | ILE | B | 442 | −19.767 | 42.918 | 50.287 | 1.00 | 37.48 | B | C |
| ATOM | 4794 | CB  | ILE | B | 442 | −18.750 | 44.080 | 50.391 | 1.00 | 37.49 | B | C |
| ATOM | 4795 | CG1 | ILE | B | 442 | −18.952 | 45.067 | 49.241 | 1.00 | 36.31 | B | C |
| ATOM | 4796 | CD1 | ILE | B | 442 | −18.239 | 46.385 | 49.411 | 1.00 | 37.95 | B | C |
| ATOM | 4797 | CG2 | ILE | B | 442 | −17.308 | 43.552 | 50.369 | 1.00 | 40.87 | B | C |
| ATOM | 4798 | C   | ILE | B | 442 | −19.741 | 42.353 | 48.875 | 1.00 | 35.99 | B | C |
| ATOM | 4799 | O   | ILE | B | 442 | −19.038 | 41.371 | 48.589 | 1.00 | 41.60 | B | O |
| ATOM | 4800 | N   | SER | B | 443 | −20.496 | 43.011 | 48.007 | 1.00 | 24.89 | B | N |
| ATOM | 4801 | CA  | SER | B | 443 | −20.629 | 42.656 | 46.618 | 1.00 | 24.75 | B | C |
| ATOM | 4802 | CB  | SER | B | 443 | −21.674 | 41.540 | 46.490 | 1.00 | 26.63 | B | C |
| ATOM | 4803 | OG  | SER | B | 443 | −22.647 | 41.816 | 45.507 | 1.00 | 31.94 | B | O |
| ATOM | 4804 | C   | SER | B | 443 | −21.032 | 43.969 | 45.924 | 1.00 | 28.80 | B | C |
| ATOM | 4805 | O   | SER | B | 443 | −21.431 | 44.926 | 46.603 | 1.00 | 33.49 | B | O |
| ATOM | 4806 | N   | THR | B | 444 | −20.930 | 44.045 | 44.597 | 1.00 | 26.26 | B | N |
| ATOM | 4807 | CA  | TER | B | 444 | −21.014 | 45.339 | 43.927 | 1.00 | 29.84 | B | C |
| ATOM | 4808 | CB  | THR | B | 444 | −19.618 | 46.001 | 43.918 | 1.00 | 31.03 | B | C |
| ATOM | 4809 | OG1 | THR | B | 444 | −19.448 | 46.780 | 45.114 | 1.00 | 32.86 | B | O |
| ATOM | 4810 | CG2 | THR | B | 444 | −19.518 | 47.038 | 42.810 | 1.00 | 34.52 | B | C |
| ATOM | 4811 | C   | THR | B | 444 | −21.592 | 45.304 | 42.512 | 1.00 | 35.65 | B | C |
| ATOM | 4812 | O   | THR | B | 444 | −21.283 | 44.406 | 41.723 | 1.00 | 37.14 | B | O |
| ATOM | 4813 | N   | PHE | B | 445 | −22.419 | 46.294 | 42.176 | 1.00 | 39.23 | B | N |
| ATOM | 4814 | CA  | PHE | B | 445 | −22.930 | 46.380 | 40.807 | 1.00 | 43.15 | B | C |
| ATOM | 4815 | CB  | PHE | B | 445 | −24.112 | 45.419 | 40.562 | 1.00 | 41.98 | B | C |
| ATOM | 4816 | CG  | PHE | B | 445 | −25.347 | 45.754 | 41.329 | 1.00 | 44.70 | B | C |
| ATOM | 4817 | CD1 | PHE | B | 445 | −26.443 | 46.316 | 40.687 | 1.00 | 47.35 | B | C |
| ATOM | 4818 | CE1 | PHE | B | 445 | −27.611 | 46.622 | 41.386 | 1.00 | 46.24 | B | C |
| ATOM | 4819 | CZ  | PHE | B | 445 | −27.688 | 46.358 | 42.746 | 1.00 | 47.03 | B | C |
| ATOM | 4820 | CE2 | PHE | B | 445 | −26.603 | 45.793 | 43.401 | 1.00 | 49.40 | B | C |
| ATOM | 4821 | CD2 | PHE | B | 445 | −25.435 | 45.491 | 42.689 | 1.00 | 48.57 | B | C |
| ATOM | 4822 | C   | PHE | B | 445 | −23.256 | 47.778 | 40.320 | 1.00 | 45.35 | B | C |
| ATOM | 4823 | O   | PHE | B | 445 | −23.404 | 48.720 | 41.113 | 1.00 | 43.42 | B | O |
| ATOM | 4824 | N   | ILE | B | 446 | −23.350 | 47.887 | 38.994 | 1.00 | 46.73 | B | N |
| ATOM | 4825 | CA  | ILE | B | 446 | −23.651 | 49.144 | 38.320 | 1.00 | 43.12 | B | C |
| ATOM | 4826 | CB  | ILE | B | 446 | −22.786 | 49.303 | 37.034 | 1.00 | 38.88 | B | C |
| ATOM | 4827 | CG1 | ILE | B | 446 | −21.293 | 49.483 | 37.358 | 1.00 | 34.98 | B | C |
| ATOM | 4828 | CD1 | ILE | B | 446 | −20.344 | 49.107 | 36.186 | 1.00 | 30.34 | B | C |
| ATOM | 4829 | CG2 | ILE | B | 446 | −23.278 | 50.468 | 36.201 | 1.00 | 39.10 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 4830 | C | ILE | B | 446 | −25.120 | 49.151 | 37.944 | 1.00 | 43.23 | B | C |
| ATOM | 4831 | O | ILE | B | 446 | −25.637 | 48.157 | 37.447 | 1.00 | 45.02 | B | O |
| ATOM | 4832 | N | LYS | B | 447 | −25.794 | 50.265 | 38.206 | 1.00 | 47.38 | B | N |
| ATOM | 4833 | CA | LYS | B | 447 | −27.074 | 50.566 | 37.558 | 1.00 | 50.70 | B | C |
| ATOM | 4834 | CB | LYS | B | 447 | −28.255 | 50.536 | 38.543 | 1.00 | 55.97 | B | C |
| ATOM | 4835 | CG | LYS | B | 447 | −29.283 | 49.425 | 38.266 | 1.00 | 60.13 | B | C |
| ATOM | 4836 | CD | LYS | B | 447 | −30.344 | 49.858 | 37.234 | 1.00 | 63.00 | B | C |
| ATOM | 4837 | CE | LYS | B | 447 | −30.918 | 48.661 | 36.457 | 1.00 | 61.30 | B | C |
| ATOM | 4838 | NZ | LYS | B | 447 | −30.831 | 48.836 | 34.979 | 1.00 | 58.41 | B | N |
| ATOM | 4839 | C | LYS | B | 447 | −26.934 | 51.932 | 36.906 | 1.00 | 45.71 | B | C |
| ATOM | 4840 | O | LYS | B | 447 | −26.796 | 52.942 | 37.591 | 1.00 | 42.70 | B | O |
| ATOM | 4841 | N | GLY | B | 448 | −26.926 | 51.941 | 35.579 | 1.00 | 43.97 | B | N |
| ATOM | 4842 | CA | GLY | B | 448 | −26.660 | 53.147 | 34.820 | 1.00 | 47.86 | B | C |
| ATOM | 4843 | C | GLY | B | 448 | −25.401 | 53.871 | 35.255 | 1.00 | 48.53 | B | C |
| ATOM | 4844 | O | GLY | B | 448 | −24.299 | 53.495 | 34.882 | 1.00 | 50.36 | B | O |
| ATOM | 4845 | N | ASP | B | 449 | −25.569 | 54.917 | 36.049 | 1.00 | 51.47 | B | N |
| ATOM | 4846 | CA | ASP | B | 449 | −24.435 | 55.695 | 36.521 | 1.00 | 56.72 | B | C |
| ATOM | 4847 | CB | ASP | B | 449 | −24.756 | 57.187 | 36.451 | 1.00 | 63.14 | B | C |
| ATOM | 4848 | CG | ASP | B | 449 | −24.788 | 57.712 | 35.022 | 1.00 | 69.19 | B | C |
| ATOM | 4849 | OD1 | ASP | B | 449 | −24.985 | 56.905 | 34.079 | 1.00 | 72.01 | B | O |
| ATOM | 4850 | OD2 | ASP | B | 449 | −24.627 | 58.923 | 34.747 | 1.00 | 70.41 | B | O |
| ATOM | 4851 | C | ASP | B | 449 | −24.086 | 55.302 | 37.940 | 1.00 | 56.41 | B | C |
| ATOM | 4852 | O | ASP | B | 449 | −23.024 | 55.644 | 38.458 | 1.00 | 59.77 | B | O |
| ATOM | 4853 | N | LEU | B | 450 | −24.982 | 54.559 | 38.563 | 1.00 | 54.31 | B | N |
| ATOM | 4854 | CA | LEU | B | 450 | −24.849 | 54.265 | 39.970 | 1.00 | 54.00 | B | C |
| ATOM | 4855 | CB | LEU | B | 450 | −26.228 | 54.064 | 40.579 | 1.00 | 49.47 | B | C |
| ATOM | 4856 | CG | LEU | B | 450 | −27.011 | 55.358 | 40.763 | 1.00 | 45.84 | B | C |
| ATOM | 4857 | CD1 | LEU | B | 450 | −28.188 | 55.102 | 41.673 | 1.00 | 45.47 | B | C |
| ATOM | 4858 | CD2 | LEU | B | 450 | −26.113 | 56.458 | 41.319 | 1.00 | 43.49 | B | C |
| ATOM | 4859 | C | LEU | B | 450 | −23.992 | 53.047 | 40.214 | 1.00 | 58.29 | B | C |
| ATOM | 4860 | O | LEU | B | 450 | −24.019 | 52.093 | 39.428 | 1.00 | 60.64 | B | O |
| ATOM | 4861 | N | THR | B | 451 | −23.228 | 53.093 | 41.306 | 1.00 | 59.31 | B | N |
| ATOM | 4862 | CA | THR | B | 451 | −22.509 | 51.918 | 41.813 | 1.00 | 55.51 | B | C |
| ATOM | 4863 | CB | THR | B | 451 | −21.010 | 52.252 | 42.009 | 1.00 | 53.64 | B | C |
| ATOM | 4864 | OG1 | THR | B | 451 | −20.370 | 52.312 | 40.728 | 1.00 | 55.62 | B | O |
| ATOM | 4865 | CG2 | THR | B | 451 | −20.280 | 51.137 | 42.722 | 1.00 | 46.00 | B | C |
| ATOM | 4866 | C | THR | B | 451 | −23.164 | 51.458 | 43.117 | 1.00 | 51.77 | B | C |
| ATOM | 4867 | O | THR | B | 451 | −23.294 | 52.240 | 44.065 | 1.00 | 49.91 | B | O |
| ATOM | 4868 | N | ILE | B | 452 | −23.590 | 50.198 | 43.155 | 1.00 | 49.75 | B | N |
| ATOM | 4869 | CA | ILE | B | 452 | −24.301 | 49.679 | 44.329 | 1.00 | 45.76 | B | C |
| ATOM | 4870 | CB | ILE | B | 452 | −25.751 | 49.322 | 43.975 | 1.00 | 40.39 | B | C |
| ATOM | 4871 | CG1 | ILE | B | 452 | −26.520 | 50.598 | 43.645 | 1.00 | 36.18 | B | C |
| ATOM | 4872 | CD1 | ILE | B | 452 | −27.881 | 50.350 | 43.055 | 1.00 | 37.39 | B | C |
| ATOM | 4873 | CG2 | ILE | B | 452 | −26.415 | 48.592 | 45.137 | 1.00 | 39.83 | B | C |
| ATOM | 4874 | C | ILE | B | 452 | −23.622 | 48.535 | 45.095 | 1.00 | 44.89 | B | C |
| ATOM | 4875 | O | ILE | B | 452 | −23.334 | 47.467 | 44.541 | 1.00 | 43.92 | B | O |
| ATOM | 4876 | N | ALA | B | 453 | −23.387 | 48.786 | 46.379 | 1.00 | 43.54 | B | N |
| ATOM | 4877 | CA | ALA | B | 453 | −22.919 | 47.770 | 47.308 | 1.00 | 44.19 | B | C |
| ATOM | 4878 | CB | ALA | B | 453 | −22.318 | 48.427 | 48.516 | 1.00 | 44.73 | B | C |
| ATOM | 4879 | C | ALA | B | 453 | −24.065 | 46.872 | 47.749 | 1.00 | 44.71 | B | C |
| ATOM | 4880 | O | ALA | B | 453 | −25.180 | 47.348 | 47.990 | 1.00 | 45.36 | B | O |
| ATOM | 4881 | N | ASN | B | 454 | −23.781 | 45.576 | 47.842 | 1.00 | 40.95 | B | N |
| ATOM | 4882 | CA | ASN | B | 454 | −24.655 | 44.623 | 48.514 | 1.00 | 41.90 | B | C |
| ATOM | 4883 | CB | ASN | B | 454 | −24.845 | 43.368 | 47.655 | 1.00 | 42.70 | B | C |
| ATOM | 4884 | CG | ASN | B | 454 | −25.754 | 43.598 | 46.475 | 1.00 | 42.78 | B | C |
| ATOM | 4885 | OD1 | ASN | B | 454 | −26.895 | 44.022 | 46.644 | 1.00 | 48.51 | B | O |
| ATOM | 4886 | ND2 | ASN | B | 454 | −25.264 | 43.308 | 45.269 | 1.00 | 36.52 | B | N |
| ATOM | 4887 | C | ASN | B | 454 | −24.012 | 44.251 | 49.852 | 1.00 | 44.33 | B | C |
| ATOM | 4888 | O | ASN | B | 454 | −22.978 | 43.565 | 49.890 | 1.00 | 52.12 | B | O |
| ATOM | 4889 | N | LEU | B | 455 | −24.604 | 44.687 | 50.952 | 1.00 | 39.41 | B | N |
| ATOM | 4890 | CA | LEU | B | 455 | −23.942 | 44.508 | 52.234 | 1.00 | 41.76 | B | C |
| ATOM | 4891 | CB | LEU | B | 455 | −23.848 | 45.837 | 52.963 | 1.00 | 44.00 | B | C |
| ATOM | 4892 | CG | LEU | B | 455 | −22.929 | 46.833 | 52.269 | 1.00 | 46.17 | B | C |
| ATOM | 4893 | CD1 | LEU | B | 455 | −22.703 | 48.020 | 53.179 | 1.00 | 49.05 | B | C |
| ATOM | 4894 | CD2 | LEU | B | 455 | −21.610 | 46.176 | 51.897 | 1.00 | 47.33 | B | C |
| ATOM | 4895 | C | LEU | B | 455 | −24.575 | 43.459 | 53.125 | 1.00 | 44.02 | B | C |
| ATOM | 4896 | O | LEU | B | 455 | −25.768 | 43.190 | 53.021 | 1.00 | 50.25 | B | O |
| ATOM | 4897 | N | GLY | B | 456 | −23.759 | 42.879 | 54.002 | 1.00 | 41.74 | B | N |
| ATOM | 4898 | CA | GLY | B | 456 | −24.182 | 41.846 | 54.933 | 1.00 | 43.52 | B | C |
| ATOM | 4899 | C | GLY | B | 456 | −23.527 | 42.039 | 56.291 | 1.00 | 48.25 | B | C |
| ATOM | 4900 | O | GLY | B | 456 | −22.424 | 42.592 | 56.390 | 1.00 | 50.51 | B | O |
| ATOM | 4901 | N | THR | B | 457 | −24.195 | 41.556 | 57.335 | 1.00 | 49.52 | B | N |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 4902 | CA  | THR | B | 457 | −23.906 | 41.955 | 58.711 | 1.00 | 51.08 | B | C |
| ATOM | 4903 | CB  | THR | B | 457 | −24.976 | 42.970 | 59.152 | 1.00 | 52.55 | B | C |
| ATOM | 4904 | OG1 | THR | B | 457 | −24.848 | 44.155 | 58.360 | 1.00 | 51.16 | B | O |
| ATOM | 4905 | CG2 | THR | B | 457 | −24.737 | 43.468 | 60.578 | 1.00 | 56.96 | B | C |
| ATOM | 4906 | C   | THR | B | 457 | −23.911 | 40.759 | 59.654 | 1.00 | 50.98 | B | C |
| ATOM | 4907 | O   | THR | B | 457 | −24.577 | 39.765 | 59.388 | 1.00 | 54.42 | B | O |
| ATOM | 4908 | N   | SER | B | 458 | −23.182 | 40.865 | 60.761 | 1.00 | 48.51 | B | N |
| ATOM | 4909 | CA  | SER | B | 458 | −23.175 | 39.810 | 61.764 | 1.00 | 52.73 | B | C |
| ATOM | 4910 | CB  | SER | B | 458 | −22.139 | 40.088 | 62.852 | 1.00 | 55.88 | B | C |
| ATOM | 4911 | OG  | SER | B | 458 | −21.805 | 41.459 | 62.901 | 1.00 | 60.09 | B | O |
| ATOM | 4912 | C   | SER | B | 458 | −24.549 | 39.588 | 62.398 | 1.00 | 56.80 | B | C |
| ATOM | 4913 | O   | SER | B | 458 | −24.846 | 38.479 | 62.858 | 1.00 | 57.21 | B | O |
| ATOM | 4914 | N   | GLU | B | 459 | −25.378 | 40.634 | 62.423 | 1.00 | 60.11 | B | N |
| ATOM | 4915 | CA  | GLU | B | 459 | −26.721 | 40.546 | 63.008 | 1.00 | 62.67 | B | C |
| ATOM | 4916 | CB  | GLU | B | 459 | −27.235 | 41.929 | 63.451 | 1.00 | 69.19 | B | C |
| ATOM | 4917 | CG  | GLU | B | 459 | −28.035 | 41.934 | 64.760 | 1.00 | 77.41 | B | C |
| ATOM | 4918 | CD  | GLU | B | 459 | −28.984 | 43.142 | 64.927 | 1.00 | 83.69 | B | C |
| ATOM | 4919 | OE1 | GLU | B | 459 | −29.075 | 44.007 | 64.014 | 1.00 | 85.31 | B | O |
| ATOM | 4920 | OE2 | GLU | B | 459 | −29.656 | 43.235 | 65.991 | 1.00 | 84.05 | B | O |
| ATOM | 4921 | C   | GLU | B | 459 | −27.701 | 39.850 | 62.049 | 1.00 | 58.99 | B | C |
| ATOM | 4922 | O   | GLU | B | 459 | −28.800 | 39.458 | 62.449 | 1.00 | 61.26 | B | O |
| ATOM | 4923 | N   | GLY | B | 460 | −27.290 | 39.678 | 60.796 | 1.00 | 52.54 | B | N |
| ATOM | 4924 | CA  | GLY | B | 460 | −28.113 | 39.003 | 59.812 | 1.00 | 51.41 | B | C |
| ATOM | 4925 | C   | GLY | B | 460 | −28.703 | 39.949 | 58.779 | 1.00 | 54.46 | B | C |
| ATOM | 4926 | O   | GLY | B | 460 | −29.418 | 39.523 | 57.868 | 1.00 | 56.75 | B | O |
| ATOM | 4927 | N   | ARG | B | 461 | −28.403 | 41.236 | 58.904 | 1.00 | 53.63 | B | N |
| ATOM | 4928 | CA  | ARG | B | 461 | −29.029 | 42.225 | 58.039 | 1.00 | 54.19 | B | C |
| ATOM | 4929 | CB  | ARG | B | 461 | −29.048 | 43.598 | 58.711 | 1.00 | 59.04 | B | C |
| ATOM | 4930 | CG  | ARG | B | 461 | −29.954 | 43.657 | 59.934 | 1.00 | 64.20 | B | C |
| ATOM | 4931 | CD  | ARG | B | 461 | −31.192 | 44.545 | 59.792 | 1.00 | 67.13 | B | C |
| ATOM | 4932 | NE  | ARG | B | 461 | −31.338 | 45.373 | 60.979 | 1.00 | 70.07 | B | N |
| ATOM | 4933 | CZ  | ARG | B | 461 | −30.687 | 46.515 | 61.172 | 1.00 | 74.01 | B | C |
| ATOM | 4934 | NH1 | ARG | B | 461 | −29.858 | 46.972 | 60.238 | 1.00 | 73.29 | B | N |
| ATOM | 4935 | NH2 | ARG | B | 461 | −30.864 | 47.207 | 62.296 | 1.00 | 76.45 | B | N |
| ATOM | 4936 | C   | ARG | B | 461 | −28.367 | 42.289 | 56.668 | 1.00 | 52.80 | B | C |
| ATOM | 4937 | O   | ARG | B | 461 | −27.141 | 42.358 | 56.566 | 1.00 | 52.65 | B | O |
| ATOM | 4938 | N   | PHE | B | 462 | −29.193 | 42.247 | 55.623 | 1.00 | 49.71 | B | N |
| ATOM | 4939 | CA  | PHE | B | 462 | −28.739 | 42.429 | 54.247 | 1.00 | 46.62 | B | C |
| ATOM | 4940 | CB  | PHE | B | 462 | −29.313 | 41.345 | 53.356 | 1.00 | 45.04 | B | C |
| ATOM | 4941 | CG  | PHE | B | 462 | −29.078 | 41.585 | 51.903 | 1.00 | 45.52 | B | C |
| ATOM | 4942 | CD1 | PHE | B | 462 | −27.916 | 41.136 | 51.294 | 1.00 | 46.69 | B | C |
| ATOM | 4943 | CE1 | PHE | B | 462 | −27.679 | 41.357 | 49.946 | 1.00 | 47.63 | B | C |
| ATOM | 4944 | CZ  | PHE | B | 462 | −28.613 | 42.032 | 49.191 | 1.00 | 52.02 | B | C |
| ATOM | 4945 | CE2 | PHE | B | 462 | −29.790 | 42.486 | 49.791 | 1.00 | 52.61 | B | C |
| ATOM | 4946 | CD2 | PHE | B | 462 | −30.012 | 42.260 | 51.141 | 1.00 | 48.34 | B | C |
| ATOM | 4947 | C   | PHE | B | 462 | −29.218 | 43.758 | 53.719 | 1.00 | 48.50 | B | C |
| ATOM | 4948 | O   | PHE | B | 462 | −30.392 | 44.086 | 53.874 | 1.00 | 53.90 | B | O |
| ATOM | 4949 | N   | MET | B | 463 | −28.346 | 44.519 | 53.066 | 1.00 | 48.12 | B | N |
| ATOM | 4950 | CA  | MET | B | 463 | −28.769 | 45.841 | 52.590 | 1.00 | 51.33 | B | C |
| ATOM | 4951 | CB  | MET | B | 463 | −28.715 | 46.868 | 53.723 | 1.00 | 51.90 | B | C |
| ATOM | 4952 | CG  | MET | B | 463 | −27.387 | 46.980 | 54.406 | 1.00 | 52.83 | B | C |
| ATOM | 4953 | SD  | MET | B | 463 | −27.615 | 47.955 | 55.864 | 1.00 | 54.23 | B | S |
| ATOM | 4954 | CE  | MET | B | 463 | −27.473 | 46.667 | 57.089 | 1.00 | 54.31 | B | C |
| ATOM | 4955 | C   | MET | B | 463 | −28.048 | 46.386 | 51.363 | 1.00 | 50.31 | B | C |
| ATOM | 4956 | O   | MET | B | 463 | −26.827 | 46.286 | 51.264 | 1.00 | 56.78 | B | O |
| ATOM | 4957 | N   | GLN | B | 464 | −28.820 | 46.978 | 50.453 | 1.00 | 42.79 | B | N |
| ATOM | 4958 | CA  | GLN | B | 464 | −28.297 | 47.571 | 49.230 | 1.00 | 40.97 | B | C |
| ATOM | 4959 | CB  | GLN | B | 464 | −29.272 | 47.344 | 48.067 | 1.00 | 42.04 | B | C |
| ATOM | 4960 | CG  | GLN | B | 464 | −29.567 | 45.888 | 47.717 | 1.00 | 42.69 | B | C |
| ATOM | 4961 | CD  | GLN | B | 464 | −30.184 | 45.723 | 46.318 | 1.00 | 44.59 | B | C |
| ATOM | 4962 | OE1 | GLN | B | 464 | −31.267 | 46.250 | 46.036 | 1.00 | 43.02 | B | O |
| ATOM | 4963 | NE2 | GLN | B | 464 | −29.492 | 44.985 | 45.446 | 1.00 | 45.35 | B | N |
| ATOM | 4964 | C   | GLN | B | 464 | −28.064 | 49.079 | 49.404 | 1.00 | 41.44 | B | C |
| ATOM | 4965 | O   | GLN | B | 464 | −29.013 | 49.830 | 49.649 | 1.00 | 41.15 | B | O |
| ATOM | 4966 | N   | VAL | B | 465 | −26.808 | 49.517 | 49.262 | 1.00 | 41.53 | B | N |
| ATOM | 4967 | CA  | VAL | B | 465 | −26.453 | 50.947 | 49.310 | 1.00 | 38.42 | B | C |
| ATOM | 4968 | CB  | VAL | B | 465 | −25.397 | 51.267 | 50.379 | 1.00 | 33.77 | B | C |
| ATOM | 4969 | CG1 | VAL | B | 465 | −25.309 | 52.770 | 50.585 | 1.00 | 27.24 | B | C |
| ATOM | 4970 | CG2 | VAL | B | 465 | −25.690 | 50.549 | 51.685 | 1.00 | 35.35 | B | C |
| ATOM | 4971 | C   | VAL | B | 465 | −25.857 | 51.451 | 48.003 | 1.00 | 41.08 | B | C |
| ATOM | 4972 | O   | VAL | B | 465 | −25.300 | 50.672 | 47.225 | 1.00 | 43.64 | B | O |
| ATOM | 4973 | N   | VAL | B | 466 | −25.961 | 52.765 | 47.792 | 1.00 | 40.30 | B | N |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 4974 | CA | VAL | B | 466 | −25.289 | 53.456 | 46.694 | 1.00 | 37.42 | B | C |
| ATOM | 4975 | CB | VAL | B | 466 | −26.139 | 54.619 | 46.132 | 1.00 | 29.50 | B | C |
| ATOM | 4976 | CG1 | VAL | B | 466 | −25.475 | 55.239 | 44.927 | 1.00 | 25.98 | B | C |
| ATOM | 4977 | CG2 | VAL | B | 466 | −27.513 | 54.130 | 45.750 | 1.00 | 28.27 | B | C |
| ATOM | 4978 | C | VAL | B | 466 | −23.938 | 53.983 | 47.168 | 1.00 | 41.60 | B | C |
| ATOM | 4979 | O | VAL | B | 466 | −23.828 | 54.595 | 48.230 | 1.00 | 44.30 | B | O |
| ATOM | 4980 | N | VAL | B | 467 | −22.914 | 53.737 | 46.365 | 1.00 | 44.45 | B | N |
| ATOM | 4981 | CA | VAL | B | 467 | −21.554 | 54.133 | 46.691 | 1.00 | 49.08 | B | C |
| ATOM | 4982 | CB | VAL | B | 467 | −20.561 | 53.127 | 46.097 | 1.00 | 50.63 | B | C |
| ATOM | 4983 | CG1 | VAL | B | 467 | −19.166 | 53.354 | 46.650 | 1.00 | 52.55 | B | C |
| ATOM | 4984 | CG2 | VAL | B | 467 | −21.031 | 51.707 | 46.389 | 1.00 | 51.28 | B | C |
| ATOM | 4985 | C | VAL | B | 467 | −21.252 | 55.533 | 46.169 | 1.00 | 51.76 | B | C |
| ATOM | 4986 | O | VAL | B | 467 | −21.438 | 55.806 | 44.975 | 1.00 | 52.74 | B | O |
| ATOM | 4987 | N | SER | B | 468 | −20.799 | 56.416 | 47.061 | 1.00 | 54.51 | B | N |
| ATOM | 4988 | CA | SER | B | 468 | −20.439 | 57.787 | 46.673 | 1.00 | 58.45 | B | C |
| ATOM | 4989 | CB | SER | B | 468 | −21.689 | 58.621 | 46.372 | 1.00 | 58.52 | B | C |
| ATOM | 4990 | OG | SER | B | 468 | −21.343 | 59.852 | 45.764 | 1.00 | 57.13 | B | O |
| ATOM | 4991 | C | SER | B | 468 | −19.589 | 58.522 | 47.702 | 1.00 | 60.39 | B | C |
| ATOM | 4992 | O | SER | B | 468 | −19.705 | 58.283 | 48.905 | 1.00 | 63.74 | B | O |
| ATOM | 4993 | N | ARG | B | 469 | −18.736 | 59.414 | 47.207 | 1.00 | 60.12 | B | N |
| ATOM | 4994 | CA | ARG | B | 469 | −18.012 | 60.350 | 48.048 | 1.00 | 64.67 | B | C |
| ATOM | 4995 | CB | ARG | B | 469 | −16.757 | 60.861 | 47.334 | 1.00 | 62.58 | B | C |
| ATOM | 4996 | CG | ARG | B | 469 | −15.639 | 59.844 | 47.145 | 1.00 | 61.40 | B | C |
| ATOM | 4997 | CD | ARG | B | 469 | −14.329 | 60.189 | 47.865 | 1.00 | 62.15 | B | C |
| ATOM | 4998 | NE | ARG | B | 469 | −14.371 | 59.832 | 49.286 | 1.00 | 64.27 | B | N |
| ATOM | 4999 | CZ | ARG | B | 469 | −13.932 | 58.678 | 49.802 | 1.00 | 68.65 | B | C |
| ATOM | 5000 | NH1 | ARG | B | 469 | −13.393 | 57.732 | 49.024 | 1.00 | 71.37 | B | N |
| ATOM | 5001 | NH2 | ARG | B | 469 | −14.034 | 58.463 | 51.109 | 1.00 | 67.94 | B | N |
| ATOM | 5002 | C | ARG | B | 469 | −18.964 | 61.508 | 48.311 | 1.00 | 71.94 | B | C |
| ATOM | 5003 | O | ARG | B | 469 | −19.378 | 61.747 | 49.446 | 1.00 | 72.50 | B | O |
| ATOM | 5004 | N | SER | B | 470 | −19.317 | 62.209 | 47.234 | 1.00 | 79.52 | B | N |
| ATOM | 5005 | CA | SER | B | 470 | −20.306 | 63.278 | 47.255 | 1.00 | 84.96 | B | C |
| ATOM | 5006 | CB | SER | B | 470 | −20.197 | 64.117 | 45.977 | 1.00 | 87.60 | B | C |
| ATOM | 5007 | OG | SER | B | 470 | −20.151 | 65.505 | 46.271 | 1.00 | 90.87 | B | O |
| ATOM | 5008 | C | SER | B | 470 | −21.702 | 62.676 | 47.376 | 1.00 | 87.59 | B | C |
| ATOM | 5009 | O | SER | B | 470 | −22.277 | 62.207 | 46.391 | 1.00 | 87.54 | B | O |
| ATOM | 5010 | N | GLY | B | 471 | −22.240 | 62.695 | 48.591 | 1.00 | 91.10 | B | N |
| ATOM | 5011 | CA | GLY | B | 471 | −23.490 | 62.023 | 48.893 | 1.00 | 96.12 | B | C |
| ATOM | 5012 | C | GLY | B | 471 | −23.223 | 60.953 | 49.935 | 1.00 | 100.89 | B | C |
| ATOM | 5013 | O | GLY | B | 471 | −22.493 | 59.993 | 49.663 | 1.00 | 102.51 | B | O |
| ATOM | 5014 | N | PRO | B | 472 | −23.789 | 61.123 | 51.132 | 1.00 | 102.46 | B | N |
| ATOM | 5015 | CA | PRO | B | 472 | −23.551 | 60.202 | 52.252 | 1.00 | 101.06 | B | C |
| ATOM | 5016 | CB | PRO | B | 472 | −23.580 | 61.143 | 53.460 | 1.00 | 102.61 | B | C |
| ATOM | 5017 | CG | PRO | B | 472 | −24.489 | 62.320 | 53.020 | 1.00 | 102.73 | B | C |
| ATOM | 5018 | CD | PRO | B | 472 | −24.699 | 62.219 | 51.518 | 1.00 | 102.43 | B | C |
| ATOM | 5019 | C | PRO | B | 472 | −24.675 | 59.172 | 52.358 | 1.00 | 98.22 | B | C |
| ATOM | 5020 | O | PRO | B | 472 | −25.289 | 59.035 | 53.417 | 1.00 | 100.80 | B | O |
| ATOM | 5021 | N | SER | B | 473 | −24.915 | 58.446 | 51.270 | 1.00 | 92.28 | B | N |
| ATOM | 5022 | CA | SER | B | 473 | −26.193 | 57.768 | 51.055 | 1.00 | 85.23 | B | C |
| ATOM | 5023 | CB | SER | B | 473 | −26.281 | 57.209 | 49.630 | 1.00 | 87.85 | B | C |
| ATOM | 5024 | OG | SER | B | 473 | −26.618 | 58.236 | 48.708 | 1.00 | 89.36 | B | O |
| ATOM | 5025 | C | SER | B | 473 | −26.603 | 56.715 | 52.088 | 1.00 | 76.93 | B | C |
| ATOM | 5026 | O | SER | B | 473 | −25.769 | 56.014 | 52.685 | 1.00 | 71.07 | B | O |
| ATOM | 5027 | N | THR | B | 474 | −27.916 | 56.651 | 52.286 | 1.00 | 71.17 | B | N |
| ATOM | 5028 | CA | THR | B | 474 | −28.548 | 55.708 | 53.189 | 1.00 | 67.45 | B | C |
| ATOM | 5029 | CB | THR | B | 474 | −29.644 | 56.393 | 54.018 | 1.00 | 68.82 | B | C |
| ATOM | 5030 | OG1 | THR | B | 474 | −30.325 | 57.345 | 53.199 | 1.00 | 69.66 | B | O |
| ATOM | 5031 | CG2 | THR | B | 474 | −29.040 | 57.239 | 55.145 | 1.00 | 69.65 | B | C |
| ATOM | 5032 | C | THR | B | 474 | −29.170 | 54.608 | 52.351 | 1.00 | 63.31 | B | C |
| ATOM | 5033 | O | THR | B | 474 | −29.694 | 54.870 | 51.267 | 1.00 | 60.40 | B | O |
| ATOM | 5034 | N | PRO | B | 475 | −29.137 | 53.386 | 52.874 | 1.00 | 61.03 | B | N |
| ATOM | 5035 | CA | PRO | B | 475 | −29.483 | 52.201 | 52.091 | 1.00 | 57.57 | B | C |
| ATOM | 5036 | CB | PRO | B | 475 | −29.198 | 51.048 | 53.062 | 1.00 | 61.28 | B | C |
| ATOM | 5037 | CG | PRO | B | 475 | −28.340 | 51.636 | 54.142 | 1.00 | 61.97 | B | C |
| ATOM | 5038 | CD | PRO | B | 475 | −28.806 | 53.042 | 54.269 | 1.00 | 62.40 | B | C |
| ATOM | 5039 | C | PRO | B | 475 | −30.947 | 52.204 | 51.716 | 1.00 | 52.11 | B | C |
| ATOM | 5040 | O | PRO | B | 475 | −31.784 | 52.514 | 52.556 | 1.00 | 50.78 | B | O |
| ATOM | 5041 | N | HIS | B | 476 | −31.243 | 51.868 | 50.470 | 1.00 | 49.87 | B | N |
| ATOM | 5042 | CA | HIS | B | 476 | −32.625 | 51.779 | 50.025 | 1.00 | 52.15 | B | C |
| ATOM | 5043 | CB | HIS | B | 476 | −32.746 | 52.159 | 48.557 | 1.00 | 56.56 | B | C |
| ATOM | 5044 | CG | HIS | B | 476 | −31.676 | 51.576 | 47.702 | 1.00 | 58.73 | B | C |
| ATOM | 5045 | ND1 | HIS | B | 476 | −31.865 | 50.434 | 46.955 | 1.00 | 61.50 | B | N |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 5046 | CE1 | HIS | B | 476 | −30.752 | 50.148 | 46.306 | 1.00 | 63.67 | B | C |
| ATOM | 5047 | NE2 | HIS | B | 476 | −29.848 | 51.064 | 46.610 | 1.00 | 64.44 | B | N |
| ATOM | 5048 | CD2 | HIS | B | 476 | −30.400 | 51.966 | 47.485 | 1.00 | 59.29 | B | C |
| ATOM | 5049 | C | HIS | B | 476 | −33.226 | 50.399 | 50.259 | 1.00 | 50.23 | B | C |
| ATOM | 5050 | O | HIS | B | 476 | −34.445 | 50.229 | 50.180 | 1.00 | 53.09 | B | O |
| ATOM | 5051 | N | VAL | B | 477 | −32.373 | 49.419 | 50.530 | 1.00 | 46.49 | B | N |
| ATOM | 5052 | CA | VAL | B | 477 | −32.832 | 48.111 | 50.996 | 1.00 | 47.76 | B | C |
| ATOM | 5053 | CB | VAL | B | 477 | −32.606 | 47.006 | 49.934 | 1.00 | 46.95 | B | C |
| ATOM | 5054 | CG1 | VAL | B | 477 | −32.646 | 45.618 | 50.565 | 1.00 | 47.09 | B | C |
| ATOM | 5055 | CG2 | VAL | B | 477 | −33.639 | 47.103 | 48.841 | 1.00 | 45.62 | B | C |
| ATOM | 5056 | C | VAL | B | 477 | −32.144 | 47.758 | 52.326 | 1.00 | 49.84 | B | C |
| ATOM | 5057 | O | VAL | B | 477 | −30.931 | 47.921 | 52.471 | 1.00 | 50.41 | B | O |
| ATOM | 5058 | N | ASN | B | 478 | −32.930 | 47.291 | 53.292 | 1.00 | 49.08 | B | N |
| ATOM | 5059 | CA | ASN | B | 478 | −32.428 | 46.989 | 54.625 | 1.00 | 47.03 | B | C |
| ATOM | 5060 | CB | ASN | B | 478 | −32.276 | 48.274 | 55.430 | 1.00 | 42.47 | B | C |
| ATOM | 5061 | CG | ASN | B | 478 | −31.610 | 48.049 | 56.764 | 1.00 | 42.92 | B | C |
| ATOM | 5062 | OD1 | ASN | B | 478 | −31.747 | 46.985 | 57.390 | 1.00 | 43.55 | B | O |
| ATOM | 5063 | ND2 | ASN | B | 478 | −30.882 | 49.057 | 57.219 | 1.00 | 43.21 | B | N |
| ATOM | 5064 | C | ASN | B | 478 | −33.384 | 46.057 | 55.346 | 1.00 | 50.05 | B | C |
| ATOM | 5065 | O | ASN | B | 478 | −34.540 | 46.422 | 55.584 | 1.00 | 53.51 | B | O |
| ATOM | 5066 | N | PHE | B | 479 | −32.900 | 44.869 | 55.711 | 1.00 | 49.23 | B | N |
| ATOM | 5067 | CA | PHE | B | 479 | −33.753 | 43.845 | 56.312 | 1.00 | 48.17 | B | C |
| ATOM | 5068 | CB | PHE | B | 479 | −34.837 | 43.412 | 55.314 | 1.00 | 46.07 | B | C |
| ATOM | 5069 | CG | PHE | B | 479 | −34.348 | 42.487 | 54.247 | 1.00 | 42.47 | B | C |
| ATOM | 5070 | CD1 | PHE | B | 479 | −34.525 | 41.111 | 54.371 | 1.00 | 44.25 | B | C |
| ATOM | 5071 | CE1 | PHE | B | 479 | −34.072 | 40.238 | 53.387 | 1.00 | 45.91 | B | C |
| ATOM | 5072 | CZ | PHE | B | 479 | −33.447 | 40.747 | 52.254 | 1.00 | 45.90 | B | C |
| ATOM | 5073 | CE2 | PHE | B | 479 | −33.276 | 42.125 | 52.117 | 1.00 | 45.61 | B | C |
| ATOM | 5074 | CD2 | PHE | B | 479 | −33.722 | 42.984 | 53.116 | 1.00 | 42.76 | B | C |
| ATOM | 5075 | C | PHE | B | 479 | −33.015 | 42.608 | 56.846 | 1.00 | 49.08 | B | C |
| ATOM | 5076 | O | PHE | B | 479 | −31.814 | 42.428 | 56.618 | 1.00 | 50.71 | B | O |
| ATOM | 5077 | N | LEU | B | 480 | −33.772 | 41.749 | 57.530 | 1.00 | 46.27 | B | N |
| ATOM | 5078 | CA | LEU | B | 480 | −33.249 | 40.559 | 58.177 | 1.00 | 44.17 | B | C |
| ATOM | 5079 | CB | LEU | B | 480 | −34.053 | 40.279 | 59.445 | 1.00 | 41.95 | B | C |
| ATOM | 5080 | CG | LEU | B | 480 | −33.432 | 40.258 | 60.850 | 1.00 | 41.22 | B | C |
| ATOM | 5081 | CD1 | LEU | B | 480 | −33.112 | 38.820 | 61.275 | 1.00 | 41.81 | B | C |
| ATOM | 5082 | CD2 | LEU | B | 480 | −32.216 | 41.165 | 61.000 | 1.00 | 38.89 | B | C |
| ATOM | 5083 | C | LEU | B | 480 | −33.282 | 39.324 | 57.277 | 1.00 | 49.14 | B | C |
| ATOM | 5084 | O | LEU | B | 480 | −34.350 | 38.875 | 56.853 | 1.00 | 50.31 | B | O |
| ATOM | 5085 | N | LEU | B | 481 | −32.097 | 38.800 | 56.974 | 1.00 | 51.40 | B | N |
| ATOM | 5086 | CA | LEU | B | 481 | −31.942 | 37.423 | 56.533 | 1.00 | 52.20 | B | C |
| ATOM | 5087 | CB | LEU | B | 481 | −30.746 | 37.309 | 55.607 | 1.00 | 51.29 | B | C |
| ATOM | 5088 | CG | LEU | B | 481 | −30.934 | 37.705 | 54.147 | 1.00 | 51.97 | B | C |
| ATOM | 5089 | CD1 | LEU | B | 481 | −29.604 | 37.552 | 53.419 | 1.00 | 49.65 | B | C |
| ATOM | 5090 | CD2 | LEU | B | 481 | −32.024 | 36.870 | 53.474 | 1.00 | 52.97 | B | C |
| ATOM | 5091 | C | LEU | B | 481 | −31.714 | 36.573 | 57.782 | 1.00 | 57.76 | B | C |
| ATOM | 5092 | O | LEU | B | 481 | −31.457 | 37.115 | 58.867 | 1.00 | 58.80 | B | O |
| ATOM | 5093 | N | ASP | B | 482 | −31.784 | 35.251 | 57.638 | 1.00 | 64.02 | B | N |
| ATOM | 5094 | CA | ASP | B | 482 | −31.758 | 34.344 | 58.799 | 1.00 | 72.45 | B | C |
| ATOM | 5095 | CB | ASP | B | 482 | −31.563 | 32.892 | 58.370 | 1.00 | 76.40 | B | C |
| ATOM | 5096 | CG | ASP | B | 482 | −32.823 | 32.303 | 57.791 | 1.00 | 82.98 | B | C |
| ATOM | 5097 | OD1 | ASP | B | 482 | −32.919 | 32.251 | 56.542 | 1.00 | 85.28 | B | O |
| ATOM | 5098 | OD2 | ASP | B | 482 | −33.778 | 31.897 | 58.502 | 1.00 | 84.14 | B | O |
| ATOM | 5099 | C | ASP | B | 482 | −30.771 | 34.709 | 59.896 | 1.00 | 72.93 | B | C |
| ATOM | 5100 | O | ASP | B | 482 | −29.630 | 35.038 | 59.623 | 1.00 | 74.57 | B | O |
| ATOM | 5101 | N | SER | B | 483 | −31.244 | 34.649 | 61.135 | 1.00 | 73.97 | B | N |
| ATOM | 5102 | CA | SER | B | 483 | −30.507 | 35.101 | 62.318 | 1.00 | 74.74 | B | C |
| ATOM | 5103 | CB | SER | B | 483 | −31.111 | 34.477 | 63.577 | 1.00 | 77.91 | B | C |
| ATOM | 5104 | OG | SER | B | 483 | −32.362 | 33.876 | 63.292 | 1.00 | 81.95 | B | O |
| ATOM | 5105 | C | SER | B | 483 | −28.996 | 34.859 | 62.309 | 1.00 | 73.44 | B | C |
| ATOM | 5106 | O | SER | B | 483 | −28.259 | 35.552 | 63.009 | 1.00 | 74.47 | B | O |
| ATOM | 5107 | N | HIS | B | 484 | −28.539 | 33.880 | 61.531 | 1.00 | 69.37 | B | N |
| ATOM | 5108 | CA | HIS | B | 484 | −27.114 | 33.600 | 61.427 | 1.00 | 67.50 | B | C |
| ATOM | 5109 | CB | HIS | B | 484 | −26.894 | 32.195 | 60.857 | 1.00 | 78.88 | B | C |
| ATOM | 5110 | CG | HIS | B | 484 | −27.277 | 31.090 | 61.801 | 1.00 | 89.66 | B | C |
| ATOM | 5111 | ND1 | HIS | B | 484 | −27.930 | 31.316 | 62.999 | 1.00 | 93.08 | B | N |
| ATOM | 5112 | CE1 | HIS | B | 484 | −28.131 | 30.165 | 63.616 | 1.00 | 94.13 | B | C |
| ATOM | 5113 | NE2 | HIS | B | 484 | −27.633 | 29.198 | 62.863 | 1.00 | 95.47 | B | N |
| ATOM | 5114 | CD2 | HIS | B | 484 | −27.093 | 29.749 | 61.723 | 1.00 | 92.90 | B | C |
| ATOM | 5115 | C | HIS | B | 484 | −26.426 | 34.673 | 60.578 | 1.00 | 58.79 | B | C |
| ATOM | 5116 | O | HIS | B | 484 | −27.027 | 35.178 | 59.638 | 1.00 | 56.11 | B | O |
| ATOM | 5117 | N | PRO | B | 485 | −25.175 | 35.022 | 60.893 | 1.00 | 53.92 | B | N |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 5118 | CA | PRO | B | 485 | −24.482 | 36.124 | 60.207 | 1.00 | 49.97 | B | C |
| ATOM | 5119 | CB | PRO | B | 485 | −23.048 | 36.028 | 60.746 | 1.00 | 47.43 | B | C |
| ATOM | 5120 | CG | PRO | B | 485 | −23.162 | 35.349 | 62.017 | 1.00 | 49.05 | B | C |
| ATOM | 5121 | CD | PRO | B | 485 | −24.305 | 34.378 | 61.893 | 1.00 | 53.07 | B | C |
| ATOM | 5122 | C | PRO | B | 485 | −24.464 | 35.955 | 58.692 | 1.00 | 49.45 | B | C |
| ATOM | 5123 | O | PRO | B | 485 | −24.781 | 34.876 | 58.193 | 1.00 | 52.13 | B | O |
| ATOM | 5124 | N | VAL | B | 486 | −24.091 | 37.006 | 57.969 | 1.00 | 49.91 | B | N |
| ATOM | 5125 | CA | VAL | B | 486 | −23.974 | 36.925 | 56.510 | 1.00 | 51.43 | B | C |
| ATOM | 5126 | CB | VAL | B | 486 | −24.359 | 38.252 | 55.823 | 1.00 | 51.96 | B | C |
| ATOM | 5127 | CG1 | VAL | B | 486 | −24.307 | 38.106 | 54.321 | 1.00 | 51.08 | B | C |
| ATOM | 5128 | CG2 | VAL | B | 486 | −25.749 | 38.696 | 56.258 | 1.00 | 53.12 | B | C |
| ATOM | 5129 | C | VAL | B | 486 | −22.562 | 36.498 | 56.106 | 1.00 | 50.68 | B | C |
| ATOM | 5130 | O | VAL | B | 486 | −21.572 | 36.985 | 56.656 | 1.00 | 53.67 | B | O |
| ATOM | 5131 | N | SER | B | 487 | −22.478 | 35.583 | 55.147 | 1.00 | 47.61 | B | N |
| ATOM | 5132 | CA | SER | B | 487 | −21.204 | 34.984 | 54.780 | 1.00 | 42.82 | B | C |
| ATOM | 5133 | CB | SER | B | 487 | −21.408 | 33.541 | 54.319 | 1.00 | 43.71 | B | C |
| ATOM | 5134 | OG | SER | B | 487 | −20.368 | 33.132 | 53.457 | 1.00 | 44.64 | B | O |
| ATOM | 5135 | C | SER | B | 487 | −20.519 | 35.801 | 53.701 | 1.00 | 39.94 | B | C |
| ATOM | 5136 | O | SER | B | 487 | −21.190 | 36.324 | 52.792 | 1.00 | 37.15 | B | O |
| ATOM | 5137 | N | PRO | B | 488 | −19.187 | 35.889 | 53.795 | 1.00 | 38.13 | B | N |
| ATOM | 5138 | CA | PRO | B | 488 | −18.388 | 36.671 | 52.843 | 1.00 | 40.98 | B | C |
| ATOM | 5139 | CB | PRO | B | 488 | −16.990 | 36.684 | 53.481 | 1.00 | 35.56 | B | C |
| ATOM | 5140 | CG | PRO | B | 488 | −16.944 | 35.471 | 54.289 | 1.00 | 32.78 | B | C |
| ATOM | 5141 | CD | PRO | B | 488 | −18.335 | 35.240 | 54.805 | 1.00 | 32.47 | B | C |
| ATOM | 5142 | C | PRO | B | 488 | −18.359 | 36.006 | 51.467 | 1.00 | 44.47 | B | C |
| ATOM | 5143 | O | PRO | B | 488 | −18.133 | 36.692 | 50.465 | 1.00 | 46.31 | B | O |
| ATOM | 5144 | N | GLU | B | 489 | −18.597 | 34.694 | 51.428 | 1.00 | 45.82 | B | N |
| ATOM | 5145 | CA | GLU | B | 489 | −18.694 | 33.967 | 50.171 | 1.00 | 47.70 | B | C |
| ATOM | 5146 | CB | GLU | B | 489 | −18.602 | 32.461 | 50.409 | 1.00 | 50.47 | B | C |
| ATOM | 5147 | CG | GLU | B | 489 | −17.273 | 31.990 | 50.995 | 1.00 | 62.01 | B | C |
| ATOM | 5148 | CD | GLU | B | 489 | −16.042 | 32.659 | 50.383 | 1.00 | 71.18 | B | C |
| ATOM | 5149 | OE1 | GLU | B | 489 | −15.157 | 33.106 | 51.163 | 1.00 | 72.92 | B | O |
| ATOM | 5150 | OE2 | GLU | B | 489 | −15.946 | 32.727 | 49.129 | 1.00 | 75.99 | B | O |
| ATOM | 5151 | C | GLU | B | 489 | −19.991 | 34.336 | 49.467 | 1.00 | 47.82 | B | C |
| ATOM | 5152 | O | GLU | B | 489 | −21.071 | 34.064 | 49.984 | 1.00 | 52.07 | B | O |
| ATOM | 5153 | N | VAL | B | 490 | −19.885 | 34.984 | 48.305 | 1.00 | 44.97 | B | N |
| ATOM | 5154 | CA | VAL | B | 490 | −21.065 | 35.520 | 47.619 | 1.00 | 41.07 | B | C |
| ATOM | 5155 | CB | VAL | B | 490 | −21.256 | 37.023 | 47.926 | 1.00 | 41.20 | B | C |
| ATOM | 5156 | CG1 | VAL | B | 490 | −21.323 | 37.267 | 49.440 | 1.00 | 45.24 | B | C |
| ATOM | 5157 | CG2 | VAL | B | 490 | −20.156 | 37.855 | 47.311 | 1.00 | 36.78 | B | C |
| ATOM | 5158 | C | VAL | B | 490 | −20.991 | 35.353 | 46.117 | 1.00 | 42.15 | B | C |
| ATOM | 5159 | O | VAL | B | 490 | −19.899 | 35.341 | 45.552 | 1.00 | 48.59 | B | O |
| ATOM | 5160 | N | ILE | B | 491 | −22.150 | 35.242 | 45.470 | 1.00 | 40.75 | B | N |
| ATOM | 5161 | CA | ILE | B | 491 | −22.215 | 35.204 | 44.001 | 1.00 | 41.60 | B | C |
| ATOM | 5162 | CB | ILE | B | 491 | −22.684 | 33.818 | 43.526 | 1.00 | 36.63 | B | C |
| ATOM | 5163 | CG1 | ILE | B | 491 | −21.562 | 32.824 | 43.740 | 1.00 | 43.17 | B | C |
| ATOM | 5164 | CD1 | ILE | B | 491 | −21.483 | 31.715 | 42.697 | 1.00 | 53.37 | B | C |
| ATOM | 5165 | CG2 | ILE | B | 491 | −23.050 | 33.833 | 42.066 | 1.00 | 35.14 | B | C |
| ATOM | 5166 | C | ILE | B | 491 | −23.084 | 36.329 | 43.393 | 1.00 | 44.75 | B | C |
| ATOM | 5167 | O | ILE | B | 491 | −24.221 | 36.577 | 43.841 | 1.00 | 43.94 | B | O |
| ATOM | 5168 | N | VAL | B | 492 | −22.544 | 37.007 | 42.380 | 1.00 | 41.70 | B | N |
| ATOM | 5169 | CA | VAL | B | 492 | −23.348 | 37.943 | 41.595 | 1.00 | 43.44 | B | C |
| ATOM | 5170 | CB | VAL | B | 492 | −22.767 | 39.368 | 41.599 | 1.00 | 40.20 | B | C |
| ATOM | 5171 | CG1 | VAL | B | 492 | −23.561 | 40.274 | 40.664 | 1.00 | 38.26 | B | C |
| ATOM | 5172 | CG2 | VAL | B | 492 | −22.761 | 39.937 | 42.984 | 1.00 | 37.76 | B | C |
| ATOM | 5173 | C | VAL | B | 492 | −23.439 | 37.456 | 40.158 | 1.00 | 47.34 | B | C |
| ATOM | 5174 | O | VAL | B | 492 | −22.437 | 37.132 | 39.557 | 1.00 | 52.98 | B | O |
| ATOM | 5175 | N | GLU | B | 493 | −24.633 | 37.390 | 39.599 | 1.00 | 53.09 | B | N |
| ATOM | 5176 | CA | GLU | B | 493 | −24.717 | 37.032 | 38.200 | 1.00 | 62.17 | B | C |
| ATOM | 5177 | CB | GLU | B | 493 | −25.062 | 35.575 | 38.000 | 1.00 | 64.03 | B | C |
| ATOM | 5178 | CG | GLU | B | 493 | −24.305 | 35.007 | 36.815 | 1.00 | 66.27 | B | C |
| ATOM | 5179 | CD | GLU | B | 493 | −25.195 | 34.219 | 35.890 | 1.00 | 66.33 | B | C |
| ATOM | 5180 | OE1 | GLU | B | 493 | −26.290 | 33.805 | 36.332 | 1.00 | 66.86 | B | O |
| ATOM | 5181 | OE2 | GLU | B | 493 | −24.785 | 33.998 | 34.731 | 1.00 | 68.08 | B | O |
| ATOM | 5182 | C | GLU | B | 493 | −25.683 | 37.881 | 37.444 | 1.00 | 68.85 | B | C |
| ATOM | 5183 | O | GLU | B | 493 | −26.852 | 37.964 | 37.794 | 1.00 | 71.46 | B | O |
| ATOM | 5184 | N | HIS | B | 494 | −25.176 | 38.484 | 36.380 | 1.00 | 74.96 | B | N |
| ATOM | 5185 | CA | HIS | B | 494 | −25.947 | 39.409 | 35.583 | 1.00 | 78.80 | B | C |
| ATOM | 5186 | CB | HIS | B | 494 | −25.019 | 40.425 | 34.932 | 1.00 | 78.18 | B | C |
| ATOM | 5187 | CG | HIS | B | 494 | −24.054 | 41.053 | 35.883 | 1.00 | 74.88 | B | C |
| ATOM | 5188 | ND1 | HIS | B | 494 | −24.363 | 42.176 | 36.618 | 1.00 | 72.93 | B | N |
| ATOM | 5189 | CE1 | HIS | B | 494 | −23.325 | 42.502 | 37.367 | 1.00 | 75.94 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 5190 | NE2 | HIS | B | 494 | −22.356 | 41.632 | 37.144 | 1.00 | 76.91 | B | N |
| ATOM | 5191 | CD2 | HIS | B | 494 | −22.787 | 40.715 | 36.218 | 1.00 | 76.17 | B | C |
| ATOM | 5192 | C | HIS | B | 494 | −26.747 | 38.689 | 34.520 | 1.00 | 84.27 | B | C |
| ATOM | 5193 | O | HIS | B | 494 | −26.450 | 37.560 | 34.149 | 1.00 | 85.88 | B | O |
| ATOM | 5194 | N | THR | B | 495 | −27.778 | 39.363 | 34.045 | 1.00 | 93.42 | B | N |
| ATOM | 5195 | CA | THR | B | 495 | −28.557 | 38.892 | 32.922 | 1.00 | 103.57 | B | C |
| ATOM | 5196 | CB | THR | B | 495 | −29.865 | 38.219 | 33.407 | 1.00 | 106.89 | B | C |
| ATOM | 5197 | OG1 | THR | B | 495 | −30.187 | 38.672 | 34.730 | 1.00 | 108.84 | B | O |
| ATOM | 5198 | CG2 | THR | B | 495 | −29.647 | 36.719 | 33.613 | 1.00 | 107.44 | B | C |
| ATOM | 5199 | C | THR | B | 495 | −28.816 | 40.107 | 32.045 | 1.00 | 108.32 | B | C |
| ATOM | 5200 | O | THR | B | 495 | −28.671 | 41.251 | 32.503 | 1.00 | 107.90 | B | O |
| ATOM | 5201 | N | LEU | B | 496 | −29.174 | 39.860 | 30.786 | 1.00 | 113.43 | B | N |
| ATOM | 5202 | CA | LEU | B | 496 | −29.323 | 40.925 | 29.792 | 1.00 | 116.98 | B | C |
| ATOM | 5203 | CB | LEU | B | 496 | −29.878 | 40.365 | 28.478 | 1.00 | 118.11 | B | C |
| ATOM | 5204 | CG | LEU | B | 496 | −29.179 | 40.837 | 27.198 | 1.00 | 119.60 | B | C |
| ATOM | 5205 | CD1 | LEU | B | 496 | −27.997 | 39.932 | 26.825 | 1.00 | 118.19 | B | C |
| ATOM | 5206 | CD2 | LEU | B | 496 | −30.188 | 40.949 | 26.047 | 1.00 | 121.39 | B | C |
| ATOM | 5207 | C | LEU | B | 496 | −30.182 | 42.088 | 30.289 | 1.00 | 117.02 | 8 | C |
| ATOM | 5208 | O | LEU | B | 496 | −31.197 | 41.868 | 30.957 | 1.00 | 117.36 | B | O |
| ATOM | 5209 | N | ASN | B | 497 | −29.740 | 43.310 | 29.968 | 1.00 | 116.73 | B | N |
| ATOM | 5210 | CA | ASN | B | 497 | −30.419 | 44.577 | 30.308 | 1.00 | 116.78 | B | C |
| ATOM | 5211 | CB | ASN | B | 497 | −31.935 | 44.522 | 30.017 | 1.00 | 119.09 | B | C |
| ATOM | 5212 | CG | ASN | B | 497 | −32.275 | 44.789 | 28.551 | 1.00 | 120.22 | B | C |
| ATOM | 5213 | OD1 | ASN | B | 497 | −31.749 | 44.140 | 27.643 | 1.00 | 121.41 | B | O |
| ATOM | 5214 | ND2 | ASN | B | 497 | −33.179 | 45.734 | 28.321 | 1.00 | 120.02 | B | N |
| ATOM | 5215 | C | ASN | B | 497 | −30.144 | 45.112 | 31.728 | 1.00 | 114.89 | B | C |
| ATOM | 5216 | O | ASN | B | 497 | −30.892 | 45.947 | 32.244 | 1.00 | 115.25 | B | O |
| ATOM | 5217 | N | GLN | B | 498 | −29.073 | 44.617 | 32.349 | 1.00 | 112.39 | B | N |
| ATOM | 5218 | CA | GLN | B | 498 | −28.541 | 45.155 | 33.614 | 1.00 | 109.04 | B | C |
| ATOM | 5219 | CB | GLN | B | 498 | −28.317 | 46.680 | 33.522 | 1.00 | 108.39 | B | C |
| ATOM | 5220 | CG | GLN | B | 498 | −27.048 | 47.177 | 34.216 | 1.00 | 108.33 | B | C |
| ATOM | 5221 | CD | GLN | B | 498 | −26.557 | 48.511 | 33.672 | 1.00 | 108.37 | B | C |
| ATOM | 5222 | OE1 | GLN | B | 498 | −26.860 | 49.569 | 34.230 | 1.00 | 108.10 | B | O |
| ATOM | 5223 | NE2 | GLN | B | 498 | −25.794 | 48.464 | 32.586 | 1.00 | 108.25 | B | N |
| ATOM | 5224 | C | GLN | B | 498 | −29.275 | 44.793 | 34.922 | 1.00 | 105.07 | B | C |
| ATOM | 5225 | O | GLN | B | 498 | −29.174 | 45.532 | 35.909 | 1.00 | 104.96 | B | O |
| ATOM | 5226 | N | ASN | B | 499 | −29.996 | 43.668 | 34.941 | 1.00 | 99.22 | B | N |
| ATOM | 5227 | CA | ASN | B | 499 | −30.388 | 43.060 | 36.225 | 1.00 | 93.30 | B | C |
| ATOM | 5228 | CB | ASN | B | 499 | −31.920 | 42.898 | 36.427 | 1.00 | 93.03 | B | C |
| ATOM | 5229 | CG | ASN | B | 499 | −32.640 | 42.347 | 35.210 | 1.00 | 92.94 | B | C |
| ATOM | 5230 | OD1 | ASN | B | 499 | −33.119 | 43.106 | 34.368 | 1.00 | 93.01 | B | O |
| ATOM | 5231 | ND2 | ASN | B | 499 | −32.760 | 41.023 | 35.136 | 1.00 | 91.88 | B | N |
| ATOM | 5232 | C | ASN | B | 499 | −29.579 | 41.797 | 36.559 | 1.00 | 86.53 | B | C |
| ATOM | 5233 | O | ASN | B | 499 | −28.408 | 41.707 | 36.186 | 1.00 | 86.38 | B | O |
| ATOM | 5234 | N | GLY | B | 500 | −30.195 | 40.843 | 37.260 | 1.00 | 78.18 | B | N |
| ATOM | 5235 | CA | GLY | B | 500 | −29.510 | 39.665 | 37.771 | 1.00 | 67.60 | B | C |
| ATOM | 5236 | C | GLY | B | 500 | −29.802 | 39.461 | 39.247 | 1.00 | 61.51 | B | C |
| ATOM | 5237 | O | GLY | B | 500 | −30.786 | 39.989 | 39.748 | 1.00 | 68.61 | B | O |
| ATOM | 5238 | N | TYR | B | 501 | −28.955 | 38.718 | 39.953 | 1.00 | 50.28 | B | N |
| ATOM | 5239 | CA | TYR | B | 501 | −29.215 | 38.388 | 41.347 | 1.00 | 44.13 | B | C |
| ATOM | 5240 | CB | TYR | B | 501 | −30.105 | 37.149 | 41.420 | 1.00 | 43.20 | B | C |
| ATOM | 5241 | CG | TYR | B | 501 | −29.497 | 35.910 | 40.788 | 1.00 | 46.13 | B | C |
| ATOM | 5242 | CD1 | TYR | B | 501 | −28.689 | 35.035 | 41.535 | 1.00 | 50.06 | B | C |
| ATOM | 5243 | CE1 | TYR | B | 501 | −28.121 | 33.889 | 40.960 | 1.00 | 47.10 | B | C |
| ATOM | 5244 | CZ | TYR | B | 501 | −28.360 | 33.610 | 39.628 | 1.00 | 46.87 | B | C |
| ATOM | 5245 | OH | TYR | B | 501 | −27.809 | 32.486 | 39.048 | 1.00 | 43.18 | B | O |
| ATOM | 5246 | CE2 | TYR | B | 501 | −29.163 | 34.459 | 38.871 | 1.00 | 47.16 | B | C |
| ATOM | 5247 | CD2 | TYR | B | 501 | −29.725 | 35.603 | 39.453 | 1.00 | 44.69 | B | C |
| ATOM | 5248 | C | TYR | B | 501 | −27.929 | 38.123 | 42.116 | 1.00 | 46.69 | B | C |
| ATOM | 5249 | O | TYR | B | 501 | −26.900 | 37.838 | 41.518 | 1.00 | 52.06 | B | O |
| ATOM | 5250 | N | THR | B | 502 | −27.992 | 38.208 | 43.443 | 1.00 | 44.56 | B | N |
| ATOM | 5251 | CA | THR | B | 502 | −26.901 | 37.766 | 44.295 | 1.00 | 42.16 | B | C |
| ATOM | 5252 | CB | THR | B | 502 | −26.597 | 38.772 | 45.369 | 1.00 | 43.95 | B | C |
| ATOM | 5253 | OG1 | THR | B | 502 | −26.543 | 40.071 | 44.795 | 1.00 | 51.23 | B | O |
| ATOM | 5254 | CG2 | THR | B | 502 | −25.186 | 38.570 | 45.902 | 1.00 | 45.26 | B | C |
| ATOM | 5255 | C | THR | B | 502 | −27.386 | 36.550 | 45.003 | 1.00 | 46.82 | B | C |
| ATOM | 5256 | O | THR | B | 502 | −28.552 | 36.500 | 45.423 | 1.00 | 47.28 | B | O |
| ATOM | 5257 | N | LEU | B | 503 | −26.494 | 35.573 | 45.145 | 1.00 | 46.91 | B | N |
| ATOM | 5258 | CA | LEU | B | 503 | −26.745 | 34.443 | 46.020 | 1.00 | 41.81 | B | C |
| ATOM | 5259 | CB | LEU | B | 503 | −26.258 | 33.153 | 45.401 | 1.00 | 39.18 | B | C |
| ATOM | 5260 | CG | LEU | B | 503 | −26.990 | 32.801 | 44.116 | 1.00 | 43.11 | B | C |
| ATOM | 5261 | CD1 | LEU | B | 503 | −26.080 | 31.952 | 43.246 | 1.00 | 49.37 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | | Amino Acid Residue | | | X | Y | Z | Occ. | Temp Factor | Atom Type | |
|---|---|---|---|---|---|---|---|---|---|---|---|---|
| ATOM | 5262 | CD2 | LEU | B | 503 | −28.293 | 32.085 | 44.407 | 1.00 | 42.13 | B | C |
| ATOM | 5263 | C | LEU | B | 503 | −26.031 | 34.721 | 47.317 | 1.00 | 43.62 | B | C |
| ATOM | 5264 | O | LEU | B | 503 | −24.846 | 35.060 | 47.323 | 1.00 | 45.71 | B | O |
| ATOM | 5265 | N | VAL | B | 504 | −26.766 | 34.589 | 48.416 | 1.00 | 43.24 | B | N |
| ATOM | 5266 | CA | VAL | B | 504 | −26.293 | 35.037 | 49.714 | 1.00 | 38.51 | B | C |
| ATOM | 5267 | CB | VAL | B | 504 | −26.956 | 36.339 | 50.069 | 1.00 | 30.99 | B | C |
| ATOM | 5268 | CG1 | VAL | B | 504 | −26.314 | 36.928 | 51.274 | 1.00 | 32.01 | B | C |
| ATOM | 5269 | CG2 | VAL | B | 504 | −26.845 | 37.291 | 48.900 | 1.00 | 28.27 | B | C |
| ATOM | 5270 | C | VAL | B | 504 | −26.514 | 34.012 | 50.823 | 1.00 | 44.16 | B | C |
| ATOM | 5271 | O | VAL | B | 504 | −27.659 | 33.706 | 51.195 | 1.00 | 40.91 | B | O |
| ATOM | 5272 | N | ILE | B | 505 | −25.387 | 33.506 | 51.338 | 1.00 | 51.60 | B | N |
| ATOM | 5273 | CA | ILE | B | 505 | −25.326 | 32.444 | 52.357 | 1.00 | 52.85 | B | C |
| ATOM | 5274 | CB | ILE | B | 505 | −24.007 | 31.652 | 52.218 | 1.00 | 55.32 | B | C |
| ATOM | 5275 | CG1 | ILE | B | 505 | −23.946 | 30.935 | 50.872 | 1.00 | 55.99 | B | C |
| ATOM | 5276 | CD1 | ILE | B | 505 | −22.711 | 31.244 | 50.082 | 1.00 | 58.09 | B | C |
| ATOM | 5277 | CG2 | ILE | B | 505 | −23.855 | 30.648 | 53.350 | 1.00 | 58.75 | B | C |
| ATOM | 5278 | C | ILE | B | 505 | −25.432 | 32.974 | 53.789 | 1.00 | 51.35 | B | C |
| ATOM | 5279 | O | ILE | B | 505 | −24.711 | 33.897 | 54.181 | 1.00 | 52.97 | B | O |
| ATOM | 5280 | N | THR | B | 506 | −26.315 | 32.358 | 54.565 | 1.00 | 48.09 | B | N |
| ATOM | 5281 | CA | THR | B | 506 | −26.593 | 32.779 | 55.924 | 1.00 | 47.09 | B | C |
| ATOM | 5282 | CB | THR | B | 506 | −27.931 | 33.526 | 55.950 | 1.00 | 48.13 | B | C |
| ATOM | 5283 | OG1 | THR | B | 506 | −27.697 | 34.939 | 55.863 | 1.00 | 48.97 | B | O |
| ATOM | 5284 | CG2 | THR | B | 506 | −28.595 | 33.374 | 57.292 | 1.00 | 50.75 | B | C |
| ATOM | 5285 | C | THR | B | 506 | −26.671 | 31.519 | 56.766 | 1.00 | 48.75 | B | C |
| ATOM | 5286 | O | THR | B | 506 | −27.584 | 30.719 | 56.585 | 1.00 | 52.12 | B | O |
| ATOM | 5287 | N | GLY | B | 507 | −25.721 | 31.330 | 57.679 | 1.00 | 50.28 | B | N |
| ATOM | 5288 | CA | GLY | B | 507 | −25.621 | 30.075 | 58.412 | 1.00 | 51.01 | B | C |
| ATOM | 5289 | C | GLY | B | 507 | −25.590 | 28.880 | 57.461 | 1.00 | 51.67 | B | C |
| ATOM | 5290 | O | GLY | B | 507 | −24.529 | 28.536 | 56.899 | 1.00 | 51.19 | B | O |
| ATOM | 5291 | N | LYS | B | 508 | −26.758 | 28.261 | 57.271 | 1.00 | 50.11 | B | N |
| ATOM | 5292 | CA | LYS | B | 508 | −26.916 | 27.171 | 56.304 | 1.00 | 51.34 | B | C |
| ATOM | 5293 | CB | LYS | B | 508 | −27.022 | 25.812 | 57.008 | 1.00 | 50.25 | B | C |
| ATOM | 5294 | CG | LYS | B | 508 | −27.934 | 25.776 | 58.225 | 1.00 | 49.54 | B | C |
| ATOM | 5295 | CD | LYS | B | 508 | −27.205 | 25.229 | 59.434 | 1.00 | 50.14 | B | C |
| ATOM | 5296 | CE | LYS | B | 508 | −27.202 | 23.706 | 59.431 | 1.00 | 51.54 | B | C |
| ATOM | 5297 | NZ | LYS | B | 508 | −28.176 | 23.135 | 60.400 | 1.00 | 54.37 | B | N |
| ATOM | 5298 | C | LYS | B | 508 | −28.094 | 27.380 | 55.345 | 1.00 | 53.15 | B | C |
| ATOM | 5299 | O | LYS | B | 508 | −28.794 | 26.431 | 54.990 | 1.00 | 54.71 | B | O |
| ATOM | 5300 | N | LYS | B | 509 | −28.302 | 28.621 | 54.919 | 1.00 | 55.68 | B | N |
| ATOM | 5301 | CA | LYS | B | 509 | −29.359 | 28.947 | 53.960 | 1.00 | 61.78 | B | C |
| ATOM | 5302 | CB | LYS | B | 509 | −30.583 | 29.558 | 54.669 | 1.00 | 68.02 | B | C |
| ATOM | 5303 | CG | LYS | B | 509 | −31.209 | 28.645 | 55.754 | 1.00 | 75.10 | B | C |
| ATOM | 5304 | CD | LYS | B | 509 | −31.956 | 29.428 | 56.867 | 1.00 | 76.79 | B | C |
| ATOM | 5305 | CE | LYS | B | 509 | −32.161 | 28.625 | 58.170 | 1.00 | 73.41 | B | C |
| ATOM | 5306 | NZ | LYS | B | 509 | −31.388 | 29.179 | 59.327 | 1.00 | 70.29 | B | N |
| ATOM | 5307 | C | LYS | B | 509 | −28.845 | 29.884 | 52.861 | 1.00 | 61.33 | B | C |
| ATOM | 5308 | O | LYS | B | 509 | −28.210 | 30.909 | 53.142 | 1.00 | 66.26 | B | O |
| ATOM | 5309 | N | ILE | B | 510 | −29.112 | 29.529 | 51.610 | 1.00 | 53.31 | B | N |
| ATOM | 5310 | CA | ILE | B | 510 | −28.732 | 30.387 | 50.500 | 1.00 | 47.96 | B | C |
| ATOM | 5311 | CB | ILE | B | 510 | −27.847 | 29.621 | 49.486 | 1.00 | 47.05 | B | C |
| ATOM | 5312 | CG1 | ILE | B | 510 | −27.390 | 30.539 | 48.349 | 1.00 | 47.77 | B | C |
| ATOM | 5313 | CD1 | ILE | B | 510 | −25.914 | 30.482 | 48.051 | 1.00 | 43.29 | B | C |
| ATOM | 5314 | CG2 | ILE | B | 510 | −28.569 | 28.418 | 48.943 | 1.00 | 48.55 | B | C |
| ATOM | 5315 | C | ILE | B | 510 | −29.970 | 31.038 | 49.868 | 1.00 | 44.99 | B | C |
| ATOM | 5316 | O | ILE | B | 510 | −30.965 | 30.375 | 49.584 | 1.00 | 46.16 | B | O |
| ATOM | 5317 | N | THR | B | 511 | −29.889 | 32.345 | 49.669 | 1.00 | 40.67 | B | N |
| ATOM | 5318 | CA | THR | B | 511 | −31.032 | 33.160 | 49.292 | 1.00 | 41.47 | B | C |
| ATOM | 5319 | CB | THR | B | 511 | −31.242 | 34.217 | 50.363 | 1.00 | 45.32 | B | C |
| ATOM | 5320 | OG1 | THR | B | 511 | −30.734 | 33.722 | 51.618 | 1.00 | 50.07 | B | O |
| ATOM | 5321 | CG2 | THR | B | 511 | −32.716 | 34.453 | 50.602 | 1.00 | 44.33 | B | C |
| ATOM | 5322 | C | THR | B | 511 | −30.723 | 33.859 | 47.992 | 1.00 | 40.90 | B | C |
| ATOM | 5323 | O | THR | B | 511 | −29.586 | 34.276 | 47.782 | 1.00 | 46.23 | B | O |
| ATOM | 5324 | N | LYS | B | 512 | −31.722 | 34.009 | 47.126 | 1.00 | 35.30 | B | N |
| ATOM | 5325 | CA | LYS | B | 512 | −31.491 | 34.566 | 45.793 | 1.00 | 29.91 | B | C |
| ATOM | 5326 | CB | LYS | B | 512 | −32.092 | 33.665 | 44.723 | 1.00 | 22.89 | B | C |
| ATOM | 5327 | CG | LYS | B | 512 | −31.582 | 33.925 | 43.325 | 1.00 | 23.69 | B | C |
| ATOM | 5328 | CD | LYS | B | 512 | −32.402 | 33.133 | 42.302 | 1.00 | 28.13 | B | C |
| ATOM | 5329 | CE | LYS | B | 512 | −31.796 | 33.207 | 40.901 | 1.00 | 31.45 | B | C |
| ATOM | 5330 | NZ | LYS | B | 512 | −32.717 | 32.728 | 39.823 | 1.00 | 34.26 | B | N |
| ATOM | 5331 | C | LYS | B | 512 | −32.048 | 35.975 | 45.682 | 1.00 | 36.32 | B | C |
| ATOM | 5332 | O | LYS | B | 512 | −33.093 | 36.207 | 45.059 | 1.00 | 42.57 | B | O |
| ATOM | 5333 | N | ILE | B | 513 | −31.340 | 36.920 | 46.287 | 1.00 | 35.43 | B | N |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 5334 | CA | ILE | B | 513 | −31.769 | 38.312 | 46.289 | 1.00 | 31.31 | B | C |
| ATOM | 5335 | CB | ILE | B | 513 | −31.049 | 39.064 | 47.397 | 1.00 | 27.61 | B | C |
| ATOM | 5336 | CG1 | ILE | B | 513 | −31.137 | 38.249 | 48.691 | 1.00 | 25.50 | B | C |
| ATOM | 5337 | CD1 | ILE | B | 513 | −30.231 | 38.744 | 49.771 | 1.00 | 27.33 | B | C |
| ATOM | 5338 | CG2 | ILE | B | 513 | −31.611 | 40.493 | 47.533 | 1.00 | 25.53 | B | C |
| ATOM | 5339 | C | ILE | B | 513 | −31.524 | 38.979 | 44.937 | 1.00 | 33.99 | B | C |
| ATOM | 5340 | O | ILE | B | 513 | −30.373 | 39.099 | 44.510 | 1.00 | 36.24 | B | O |
| ATOM | 5341 | N | PRO | B | 514 | −32.606 | 39.381 | 44.265 | 1.00 | 34.33 | B | N |
| ATOM | 5342 | CA | PRO | B | 514 | −32.527 | 40.131 | 43.007 | 1.00 | 36.56 | B | C |
| ATOM | 5343 | CB | PRO | B | 514 | −33.982 | 40.490 | 42.738 | 1.00 | 35.33 | B | C |
| ATOM | 5344 | CG | PRO | B | 514 | −34.626 | 40.356 | 44.067 | 1.00 | 35.03 | B | C |
| ATOM | 5345 | CD | PRO | B | 514 | −34.003 | 39.138 | 44.647 | 1.00 | 34.41 | B | C |
| ATOM | 5346 | C | PRO | B | 514 | −31.769 | 41.412 | 43.199 | 1.00 | 40.43 | B | C |
| ATOM | 5347 | O | PRO | B | 514 | −31.944 | 42.037 | 44.240 | 1.00 | 46.11 | B | O |
| ATOM | 5348 | N | LEU | B | 515 | −30.968 | 41.807 | 42.217 | 1.00 | 42.57 | B | N |
| ATOM | 5349 | CA | LEU | B | 515 | −30.198 | 43.044 | 42.312 | 1.00 | 45.31 | B | C |
| ATOM | 5350 | CB | LEU | B | 515 | −29.175 | 43.131 | 41.178 | 1.00 | 44.56 | B | C |
| ATOM | 5351 | CG | LEU | B | 515 | −28.031 | 42.114 | 41.142 | 1.00 | 43.12 | B | C |
| ATOM | 5352 | CD1 | LEU | B | 515 | −27.300 | 42.208 | 39.819 | 1.00 | 41.22 | B | C |
| ATOM | 5353 | CD2 | LEU | B | 515 | −27.071 | 42.344 | 42.296 | 1.00 | 42.46 | B | C |
| ATOM | 5354 | C | LEU | B | 515 | −31.052 | 44.311 | 42.310 | 1.00 | 48.69 | B | C |
| ATOM | 5355 | O | LEU | B | 515 | −30.612 | 45.335 | 42.818 | 1.00 | 50.19 | B | O |
| ATOM | 5356 | N | ASN | B | 516 | −32.272 | 44.239 | 41.774 | 1.00 | 51.39 | B | N |
| ATOM | 5357 | CA | ASN | B | 516 | −32.944 | 45.458 | 41.344 | 1.00 | 53.55 | B | C |
| ATOM | 5358 | CB | ASN | B | 516 | −32.905 | 45.545 | 39.822 | 1.00 | 52.30 | B | C |
| ATOM | 5359 | CG | ASN | B | 516 | −31.683 | 46.288 | 39.322 | 1.00 | 53.51 | B | C |
| ATOM | 5360 | OD1 | ASN | B | 516 | −31.298 | 47.325 | 39.867 | 1.00 | 52.78 | B | O |
| ATOM | 5361 | ND2 | ASN | B | 516 | −31.062 | 45.758 | 38.284 | 1.00 | 57.11 | B | N |
| ATOM | 5362 | C | ASN | B | 516 | −34.336 | 45.839 | 41.876 | 1.00 | 58.86 | B | C |
| ATOM | 5363 | O | ASN | B | 516 | −34.521 | 46.936 | 42.433 | 1.00 | 62.39 | B | O |
| ATOM | 5364 | N | GLY | B | 517 | −35.322 | 44.973 | 41.685 | 1.00 | 59.47 | B | N |
| ATOM | 5365 | CA | GLY | B | 517 | −36.691 | 45.350 | 42.011 | 1.00 | 59.33 | B | C |
| ATOM | 5366 | C | GLY | B | 517 | −36.963 | 45.689 | 43.470 | 1.00 | 55.99 | B | C |
| ATOM | 5367 | O | GLY | B | 517 | −37.901 | 46.422 | 43.778 | 1.00 | 56.60 | B | O |
| ATOM | 5368 | N | LEU | B | 518 | −36.109 | 45.178 | 44.353 | 1.00 | 52.22 | B | N |
| ATOM | 5369 | CA | LEU | B | 518 | −36.430 | 45.004 | 45.763 | 1.00 | 46.10 | B | C |
| ATOM | 5370 | CB | LEU | B | 518 | −35.300 | 44.246 | 46.464 | 1.00 | 44.34 | B | C |
| ATOM | 5371 | CG | LEU | B | 518 | −35.765 | 43.451 | 47.683 | 1.00 | 44.94 | B | C |
| ATOM | 5372 | CD1 | LEU | B | 518 | −36.183 | 42.040 | 47.310 | 1.00 | 47.31 | B | C |
| ATOM | 5373 | CD2 | LEU | B | 518 | −34.681 | 43.414 | 48.726 | 1.00 | 44.90 | B | C |
| ATOM | 5374 | C | LEU | B | 518 | −36.784 | 46.268 | 46.532 | 1.00 | 42.67 | B | C |
| ATOM | 5375 | O | LEU | B | 518 | −37.728 | 46.271 | 47.322 | 1.00 | 41.36 | B | O |
| ATOM | 5376 | N | GLY | B | 519 | −36.039 | 47.342 | 46.303 | 1.00 | 40.30 | B | N |
| ATOM | 5377 | CA | GLY | B | 519 | −36.232 | 48.563 | 47.065 | 1.00 | 42.21 | B | C |
| ATOM | 5378 | C | GLY | B | 519 | −37.584 | 49.234 | 46.869 | 1.00 | 42.24 | B | C |
| ATOM | 5379 | O | GLY | B | 519 | −37.761 | 50.411 | 47.203 | 1.00 | 41.48 | B | O |
| ATOM | 5380 | N | CYS | B | 520 | −38.532 | 48.482 | 46.326 | 1.00 | 39.31 | B | N |
| ATOM | 5381 | CA | CYS | B | 520 | −39.857 | 48.996 | 46.045 | 1.00 | 38.82 | B | C |
| ATOM | 5382 | CB | CYS | B | 520 | −40.146 | 48.886 | 44.554 | 1.00 | 37.59 | B | C |
| ATOM | 5383 | SG | CYS | B | 520 | −39.027 | 49.892 | 43.568 | 1.00 | 35.58 | B | S |
| ATOM | 5384 | C | CYS | B | 520 | −40.884 | 48.208 | 46.809 | 1.00 | 40.00 | B | C |
| ATOM | 5385 | O | CYS | B | 520 | −41.929 | 48.736 | 47.170 | 1.00 | 39.24 | B | O |
| ATOM | 5386 | N | ARG | B | 521 | −40.562 | 46.944 | 47.065 | 1.00 | 44.69 | B | N |
| ATOM | 5387 | CA | ARG | B | 521 | −41.533 | 45.968 | 47.537 | 1.00 | 49.98 | B | C |
| ATOM | 5388 | CB | ARG | B | 521 | −40.938 | 44.564 | 47.523 | 1.00 | 55.09 | B | C |
| ATOM | 5389 | CG | ARG | B | 521 | −40.870 | 43.953 | 46.124 | 1.00 | 63.59 | B | C |
| ATOM | 5390 | CD | ARG | B | 521 | −40.265 | 42.554 | 46.079 | 1.00 | 71.10 | B | C |
| ATOM | 5391 | NE | ARG | B | 521 | −40.860 | 41.682 | 47.095 | 1.00 | 75.72 | B | N |
| ATOM | 5392 | CZ | ARG | B | 521 | −40.277 | 40.602 | 47.605 | 1.00 | 76.13 | B | C |
| ATOM | 5393 | NH1 | ARG | B | 521 | −39.067 | 40.230 | 47.193 | 1.00 | 73.32 | B | N |
| ATOM | 5394 | NH2 | ARG | B | 521 | −40.914 | 39.891 | 48.529 | 1.00 | 76.82 | B | N |
| ATOM | 5395 | C | ARG | B | 521 | −42.097 | 46.301 | 48.905 | 1.00 | 51.00 | B | C |
| ATOM | 5396 | O | ARG | B | 521 | −43.202 | 45.869 | 49.243 | 1.00 | 53.86 | B | O |
| ATOM | 5397 | N | HIS | B | 522 | −41.366 | 47.099 | 49.676 | 1.00 | 50.09 | B | N |
| ATOM | 5398 | CA | HIS | B | 522 | −41.825 | 47.444 | 51.021 | 1.00 | 51.92 | B | C |
| ATOM | 5399 | CB | HIS | B | 522 | −40.640 | 47.602 | 51.975 | 1.00 | 53.81 | B | C |
| ATOM | 5400 | CG | HIS | B | 522 | −39.993 | 48.944 | 51.903 | 1.00 | 54.81 | B | C |
| ATOM | 5401 | ND1 | HIS | B | 522 | −38.950 | 49.215 | 51.039 | 1.00 | 56.49 | B | N |
| ATOM | 5402 | CE1 | HIS | B | 522 | −38.588 | 50.479 | 51.188 | 1.00 | 58.86 | B | C |
| ATOM | 5403 | NE2 | HIS | B | 522 | −39.367 | 51.039 | 52.107 | 1.00 | 57.45 | B | N |
| ATOM | 5404 | CD2 | HIS | B | 522 | −40.254 | 50.100 | 52.572 | 1.00 | 54.77 | B | C |
| ATOM | 5405 | C | HIS | B | 522 | −42.758 | 48.664 | 51.124 | 1.00 | 50.26 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 5406 | O | HIS | B | 522 | −43.078 | 49.084 | 52.240 | 1.00 | 53.55 | B | O |
| ATOM | 5407 | N | PHE | B | 523 | −43.181 | 49.240 | 49.992 | 1.00 | 43.87 | B | N |
| ATOM | 5408 | CA | PHE | B | 523 | −44.156 | 50.344 | 50.016 | 1.00 | 34.84 | B | C |
| ATOM | 5409 | CB | PHE | B | 523 | −43.887 | 51.377 | 48.926 | 1.00 | 30.23 | B | C |
| ATOM | 5410 | CG | PHE | B | 523 | −42.620 | 52.145 | 49.132 | 1.00 | 29.35 | B | C |
| ATOM | 5411 | CD1 | PHE | B | 523 | −41.454 | 51.792 | 48.407 | 1.00 | 29.06 | B | C |
| ATOM | 5412 | CE1 | PHE | B | 523 | −40.263 | 52.498 | 48.594 | 1.00 | 25.47 | B | C |
| ATOM | 5413 | CZ | PHE | B | 523 | −40.225 | 53.557 | 49.514 | 1.00 | 24.47 | B | C |
| ATOM | 5414 | CE2 | PHE | B | 523 | −41.381 | 53.918 | 50.245 | 1.00 | 30.23 | B | C |
| ATOM | 5415 | CD2 | PHE | B | 523 | −42.574 | 53.211 | 50.050 | 1.00 | 30.94 | B | C |
| ATOM | 5416 | C | PHE | B | 523 | −45.581 | 49.814 | 49.935 | 1.00 | 34.18 | B | C |
| ATOM | 5417 | O | PHE | B | 523 | −45.994 | 49.215 | 48.929 | 1.00 | 34.09 | B | O |
| ATOM | 5418 | N | GLN | B | 524 | −46.318 | 50.033 | 51.023 | 1.00 | 33.26 | B | N |
| ATOM | 5419 | CA | GLN | B | 524 | −47.561 | 49.326 | 51.259 | 1.00 | 35.86 | B | C |
| ATOM | 5420 | CB | GLN | B | 524 | −47.719 | 49.086 | 52.773 | 1.00 | 39.90 | B | C |
| ATOM | 5421 | CG | GLN | B | 524 | −48.046 | 47.645 | 53.194 | 1.00 | 45.25 | B | C |
| ATOM | 5422 | CD | GLN | B | 524 | −47.197 | 46.574 | 52.485 | 1.00 | 50.10 | B | C |
| ATOM | 5423 | OE1 | GLN | B | 524 | −47.730 | 45.571 | 51.998 | 1.00 | 51.86 | B | O |
| ATOM | 5424 | NE2 | GLN | B | 524 | −45.883 | 46.782 | 52.436 | 1.00 | 52.55 | B | N |
| ATOM | 5425 | C | GLN | B | 524 | −48.758 | 50.081 | 50.682 | 1.00 | 35.92 | B | C |
| ATOM | 5426 | O | GLN | B | 524 | −49.915 | 49.692 | 50.899 | 1.00 | 36.74 | B | O |
| ATOM | 5427 | N | SER | B | 525 | −48.473 | 51.156 | 49.941 | 1.00 | 33.82 | B | N |
| ATOM | 5428 | CA | SER | B | 525 | −49.514 | 52.071 | 49.473 | 1.00 | 30.97 | B | C |
| ATOM | 5429 | CB | SER | B | 525 | −50.004 | 52.943 | 50.632 | 1.00 | 33.70 | B | C |
| ATOM | 5430 | OG | SER | B | 525 | −49.155 | 54.099 | 50.818 | 1.00 | 39.19 | B | O |
| ATOM | 5431 | C | SER | B | 525 | −49.061 | 52.962 | 48.318 | 1.00 | 27.28 | B | C |
| ATOM | 5432 | O | SER | B | 525 | −47.912 | 53.482 | 48.309 | 1.00 | 27.58 | B | O |
| ATOM | 5433 | N | CYS | B | 526 | −49.998 | 53.163 | 47.365 | 1.00 | 24.58 | B | N |
| ATOM | 5434 | CA | CYS | B | 526 | −49.681 | 53.950 | 46.157 | 1.00 | 19.24 | B | C |
| ATOM | 5435 | CB | CYS | B | 526 | −50.960 | 54.320 | 45.354 | 1.00 | 18.73 | B | C |
| ATOM | 5436 | SG | CYS | B | 526 | −50.512 | 55.211 | 43.829 | 1.00 | 15.67 | B | S |
| ATOM | 5437 | C | CYS | B | 526 | −48.893 | 55.216 | 46.465 | 1.00 | 16.28 | B | C |
| ATOM | 5438 | O | CYS | B | 526 | −47.652 | 55.318 | 46.047 | 1.00 | 15.73 | B | O |
| ATOM | 5439 | N | SER | B | 527 | −49.622 | 56.172 | 47.193 | 1.00 | 15.92 | B | N |
| ATOM | 5440 | CA | SER | B | 527 | −48.928 | 57.403 | 47.589 | 1.00 | 15.45 | B | C |
| ATOM | 5441 | CB | SER | B | 527 | −49.640 | 58.093 | 48.735 | 1.00 | 16.48 | B | C |
| ATOM | 5442 | OG | SER | B | 527 | −48.651 | 58.912 | 49.479 | 1.00 | 20.53 | B | O |
| ATOM | 5443 | C | SER | B | 527 | −47.482 | 57.178 | 48.031 | 1.00 | 18.59 | B | C |
| ATOM | 5444 | O | SER | B | 527 | −46.569 | 57.788 | 47.481 | 1.00 | 19.04 | B | O |
| ATOM | 5445 | N | GLN | B | 528 | −47.284 | 56.316 | 49.030 | 1.00 | 22.16 | B | N |
| ATOM | 5446 | CA | GLN | B | 528 | −45.958 | 56.092 | 49.604 | 1.00 | 23.92 | B | C |
| ATOM | 5447 | CB | GLN | B | 528 | −46.029 | 55.001 | 50.669 | 1.00 | 26.41 | B | C |
| ATOM | 5448 | CG | GLN | B | 528 | −45.788 | 55.518 | 52.080 | 1.00 | 29.27 | B | C |
| ATOM | 5449 | CD | GLN | B | 528 | −46.734 | 54.916 | 53.111 | 1.00 | 27.95 | B | C |
| ATOM | 5450 | OE1 | GLN | B | 528 | −46.683 | 53.709 | 53.387 | 1.00 | 27.67 | B | O |
| ATOM | 5451 | NE2 | GLN | B | 528 | −47.589 | 55.756 | 53.691 | 1.00 | 22.48 | B | N |
| ATOM | 5452 | C | GLN | B | 528 | −44.976 | 55.718 | 48.507 | 1.00 | 25.49 | B | C |
| ATOM | 5453 | O | GLN | B | 528 | −43.832 | 56.202 | 48.477 | 1.00 | 28.91 | B | O |
| ATOM | 5454 | N | CYS | B | 529 | −45.460 | 54.875 | 47.597 | 1.00 | 24.45 | B | N |
| ATOM | 5455 | CA | CYS | B | 529 | −44.686 | 54.336 | 46.476 | 1.00 | 21.14 | B | C |
| ATOM | 5456 | CB | CYS | B | 529 | −45.522 | 53.278 | 45.752 | 1.00 | 22.04 | B | C |
| ATOM | 5457 | SG | CYS | B | 529 | −44.724 | 52.460 | 44.370 | 1.00 | 22.10 | B | S |
| ATOM | 5458 | C | CYS | B | 529 | −44.276 | 55.432 | 45.503 | 1.00 | 19.89 | B | C |
| ATOM | 5459 | O | CYS | B | 529 | −43.151 | 55.464 | 45.033 | 1.00 | 21.64 | B | O |
| ATOM | 5460 | N | LEU | B | 530 | −45.175 | 56.349 | 45.204 | 1.00 | 19.23 | B | N |
| ATOM | 5461 | CA | LEU | B | 530 | −44.791 | 57.455 | 44.343 | 1.00 | 23.13 | B | C |
| ATOM | 5462 | CB | LEU | B | 530 | −46.019 | 58.272 | 43.898 | 1.00 | 22.39 | B | C |
| ATOM | 5463 | CG | LEU | B | 530 | −47.106 | 57.578 | 43.083 | 1.00 | 20.21 | B | C |
| ATOM | 5464 | CD1 | LEU | B | 530 | −48.027 | 58.574 | 42.460 | 1.00 | 16.44 | B | C |
| ATOM | 5465 | CD2 | LEU | B | 530 | −46.469 | 56.700 | 42.020 | 1.00 | 22.29 | B | C |
| ATOM | 5466 | C | LEU | B | 530 | −43.775 | 58.374 | 45.020 | 1.00 | 25.56 | B | C |
| ATOM | 5467 | O | LEU | B | 530 | −43.232 | 59.287 | 44.380 | 1.00 | 29.36 | B | O |
| ATOM | 5468 | N | SER | B | 531 | −43.528 | 58.148 | 46.309 | 1.00 | 24.02 | B | N |
| ATOM | 5469 | CA | SER | B | 531 | −42.709 | 59.078 | 47.074 | 1.00 | 29.39 | B | C |
| ATOM | 5470 | CB | SER | B | 531 | −43.379 | 59.424 | 48.410 | 1.00 | 32.04 | B | C |
| ATOM | 5471 | OG | SER | B | 531 | −43.995 | 60.717 | 48.379 | 1.00 | 32.10 | B | O |
| ATOM | 5472 | C | SER | B | 531 | −41.279 | 58.578 | 47.265 | 1.00 | 33.38 | B | C |
| ATOM | 5473 | O | SER | B | 531 | −40.428 | 59.284 | 47.811 | 1.00 | 35.32 | B | O |
| ATOM | 5474 | N | ALA | B | 532 | −41.021 | 57.369 | 46.773 | 1.00 | 35.38 | B | N |
| ATOM | 5475 | CA | ALA | B | 532 | −39.723 | 56.707 | 46.889 | 1.00 | 33.85 | B | C |
| ATOM | 5476 | CB | ALA | B | 532 | −39.824 | 55.287 | 46.347 | 1.00 | 31.65 | B | C |
| ATOM | 5477 | C | ALA | B | 532 | −38.604 | 57.464 | 46.171 | 1.00 | 35.34 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| | Atom Number | | Amino Acid Residue | | | X | Y | Z | Occ. | Temp Factor | Atom Type | |
|---|---|---|---|---|---|---|---|---|---|---|---|---|
| ATOM | 5478 | O | ALA | B | 532 | −38.870 | 58.236 | 45.242 | 1.00 | 35.60 | B | O |
| ATOM | 5479 | N | PRO | B | 533 | −37.359 | 57.234 | 46.597 | 1.00 | 36.25 | B | N |
| ATOM | 5480 | CA | PRO | B | 533 | −36.180 | 57.792 | 45.924 | 1.00 | 35.80 | B | C |
| ATOM | 5481 | CB | PRO | B | 533 | −35.017 | 57.082 | 46.619 | 1.00 | 37.77 | B | C |
| ATOM | 5482 | CG | PRO | B | 533 | −35.640 | 55.914 | 47.337 | 1.00 | 36.66 | B | C |
| ATOM | 5483 | CD | PRO | B | 533 | −36.978 | 56.414 | 47.761 | 1.00 | 36.96 | B | C |
| ATOM | 5484 | C | PRO | B | 533 | −36.177 | 57.452 | 44.437 | 1.00 | 37.92 | B | C |
| ATOM | 5485 | O | PRO | B | 533 | −36.250 | 56.268 | 44.067 | 1.00 | 35.73 | B | O |
| ATOM | 5486 | N | PRO | B | 534 | −36.082 | 58.484 | 43.602 | 1.00 | 40.65 | B | N |
| ATOM | 5487 | CA | PRO | B | 534 | −36.281 | 58.348 | 42.154 | 1.00 | 43.08 | B | C |
| ATOM | 5488 | CB | PRO | B | 534 | −35.967 | 59.749 | 41.622 | 1.00 | 43.53 | B | C |
| ATOM | 5489 | CG | PRO | B | 534 | −35.176 | 60.391 | 42.706 | 1.00 | 44.34 | B | C |
| ATOM | 5490 | CD | PRO | B | 534 | −35.753 | 59.868 | 43.982 | 1.00 | 42.50 | B | C |
| ATOM | 5491 | C | PRO | B | 534 | −35.375 | 57.305 | 41.501 | 1.00 | 43.92 | B | C |
| ATOM | 5492 | O | PRO | B | 534 | −35.866 | 56.544 | 40.667 | 1.00 | 46.13 | B | O |
| ATOM | 5493 | N | PHE | B | 535 | −34.098 | 57.255 | 41.874 | 1.00 | 43.31 | B | N |
| ATOM | 5494 | CA | PHE | B | 535 | −33.171 | 56.293 | 41.260 | 1.00 | 43.87 | B | C |
| ATOM | 5495 | CB | PHE | B | 535 | −31.750 | 56.409 | 41.839 | 1.00 | 43.86 | B | C |
| ATOM | 5496 | CG | PHE | B | 535 | −31.571 | 55.740 | 43.177 | 1.00 | 40.68 | B | C |
| ATOM | 5497 | CD1 | PHE | B | 535 | −31.264 | 54.386 | 43.261 | 1.00 | 42.53 | B | C |
| ATOM | 5498 | CE1 | PHE | B | 535 | −31.099 | 53.777 | 44.497 | 1.00 | 44.40 | B | C |
| ATOM | 5499 | CZ | PHE | B | 535 | −31.237 | 54.537 | 45.664 | 1.00 | 43.40 | B | C |
| ATOM | 5500 | CE2 | PHE | B | 535 | −31.539 | 55.884 | 45.585 | 1.00 | 36.71 | B | C |
| ATOM | 5501 | CD2 | PHE | B | 535 | −31.700 | 56.473 | 44.351 | 1.00 | 38.28 | B | C |
| ATOM | 5502 | C | PHE | B | 535 | −33.658 | 54.841 | 41.302 | 1.00 | 41.68 | B | C |
| ATOM | 5503 | O | PHE | B | 535 | −33.407 | 54.085 | 40.369 | 1.00 | 43.66 | B | O |
| ATOM | 5504 | N | VAL | B | 536 | −34.350 | 54.464 | 42.378 | 1.00 | 37.37 | B | N |
| ATOM | 5505 | CA | VAL | B | 536 | −34.867 | 53.103 | 42.538 | 1.00 | 32.40 | B | C |
| ATOM | 5506 | CB | VAL | B | 536 | −35.492 | 52.886 | 43.936 | 1.00 | 28.07 | B | C |
| ATOM | 5507 | CG1 | VAL | B | 536 | −36.062 | 51.491 | 44.074 | 1.00 | 19.57 | B | C |
| ATOM | 5508 | CG2 | VAL | B | 536 | −34.471 | 53.121 | 45.017 | 1.00 | 28.40 | B | C |
| ATOM | 5509 | C | VAL | B | 536 | −35.905 | 52.789 | 41.461 | 1.00 | 34.29 | B | C |
| ATOM | 5510 | O | VAL | B | 536 | −36.122 | 51.628 | 41.138 | 1.00 | 37.01 | B | O |
| ATOM | 5511 | N | GLN | B | 537 | −36.536 | 53.831 | 40.921 | 1.00 | 34.19 | B | N |
| ATOM | 5512 | CA | GLN | B | 537 | −37.489 | 53.717 | 39.813 | 1.00 | 37.25 | B | C |
| ATOM | 5513 | CB | GLN | B | 537 | −36.781 | 53.359 | 38.491 | 1.00 | 43.61 | B | C |
| ATOM | 5514 | CG | GLN | B | 537 | −35.602 | 54.262 | 38.115 | 1.00 | 50.57 | B | C |
| ATOM | 5515 | CD | GLN | B | 537 | −34.857 | 53.780 | 36.869 | 1.00 | 54.96 | B | C |
| ATOM | 5516 | OE1 | GLN | B | 537 | −35.090 | 54.295 | 35.767 | 1.00 | 55.50 | B | O |
| ATOM | 5517 | NE2 | GLN | B | 537 | −33.961 | 52.793 | 37.040 | 1.00 | 55.50 | B | N |
| ATOM | 5518 | C | GLN | B | 537 | −38.661 | 52.763 | 40.079 | 1.00 | 35.11 | B | C |
| ATOM | 5519 | O | GLN | B | 537 | −38.912 | 51.849 | 39.295 | 1.00 | 33.64 | B | O |
| ATOM | 5520 | N | CYS | B | 538 | −39.378 | 52.994 | 41.178 | 1.00 | 33.99 | B | N |
| ATOM | 5521 | CA | CYS | B | 538 | −40.621 | 52.275 | 41.474 | 1.00 | 30.58 | B | C |
| ATOM | 5522 | CB | CYS | B | 538 | −40.895 | 52.284 | 42.968 | 1.00 | 31.61 | B | C |
| ATOM | 5523 | SG | CYS | B | 538 | −39.461 | 51.843 | 43.916 | 1.00 | 40.00 | B | S |
| ATOM | 5524 | C | CYS | B | 538 | −41.816 | 52.913 | 40.807 | 1.00 | 26.54 | B | C |
| ATOM | 5525 | O | CYS | B | 538 | −41.788 | 54.102 | 40.475 | 1.00 | 21.86 | B | O |
| ATOM | 5526 | N | GLY | B | 539 | −42.874 | 52.120 | 40.648 | 1.00 | 25.92 | B | N |
| ATOM | 5527 | CA | GLY | B | 539 | −44.177 | 52.639 | 40.256 | 1.00 | 29.71 | B | C |
| ATOM | 5528 | C | GLY | B | 539 | −45.343 | 51.874 | 40.855 | 1.00 | 27.62 | B | C |
| ATOM | 5529 | O | GLY | B | 539 | −45.148 | 50.834 | 41.491 | 1.00 | 28.31 | B | O |
| ATOM | 5530 | N | TRP | B | 540 | −46.559 | 52.370 | 40.654 | 1.00 | 22.58 | B | N |
| ATOM | 5531 | CA | TRP | B | 540 | −47.701 | 51.678 | 41.235 | 1.00 | 23.87 | B | C |
| ATOM | 5532 | CB | TRP | B | 540 | −48.631 | 52.656 | 41.935 | 1.00 | 20.61 | B | C |
| ATOM | 5533 | CG | TRP | B | 540 | −49.674 | 51.979 | 42.757 | 1.00 | 18.60 | B | C |
| ATOM | 5534 | CD1 | TRP | B | 540 | −51.011 | 51.861 | 42.458 | 1.00 | 22.67 | B | C |
| ATOM | 5535 | NE1 | TRP | B | 540 | −51.668 | 51.190 | 43.462 | 1.00 | 21.67 | B | N |
| ATOM | 5536 | CE2 | TRP | B | 540 | −50.745 | 50.858 | 44.436 | 1.00 | 16.29 | B | C |
| ATOM | 5537 | CD2 | TRP | B | 540 | −49.478 | 51.343 | 44.024 | 1.00 | 16.67 | B | C |
| ATOM | 5538 | CE3 | TRP | B | 540 | −48.359 | 51.133 | 44.861 | 1.00 | 18.20 | B | C |
| ATOM | 5539 | CZ3 | TRP | B | 540 | −48.541 | 50.457 | 46.055 | 1.00 | 16.38 | B | C |
| ATOM | 5540 | CH2 | TRP | B | 540 | −49.813 | 49.997 | 46.434 | 1.00 | 13.70 | B | C |
| ATOM | 5541 | CZ2 | TRP | B | 540 | −50.924 | 50.189 | 45.640 | 1.00 | 14.20 | B | C |
| ATOM | 5542 | C | TRP | B | 540 | −48.475 | 50.813 | 40.255 | 1.00 | 27.32 | B | C |
| ATOM | 5543 | O | TRP | B | 540 | −49.143 | 51.309 | 39.348 | 1.00 | 31.37 | B | O |
| ATOM | 5544 | N | CYS | B | 541 | −48.392 | 49.507 | 40.472 | 1.00 | 29.65 | B | N |
| ATOM | 5545 | CA | CYS | B | 541 | −49.100 | 48.540 | 39.645 | 1.00 | 34.46 | B | C |
| ATOM | 5546 | CB | CYS | B | 541 | −48.187 | 47.360 | 39.313 | 1.00 | 37.32 | B | C |
| ATOM | 5547 | SG | CYS | B | 541 | −48.608 | 46.580 | 37.747 | 1.00 | 41.09 | B | S |
| ATOM | 5548 | C | CYS | B | 541 | −50.404 | 48.050 | 40.285 | 1.00 | 34.49 | B | C |
| ATOM | 5549 | O | CYS | B | 541 | −50.475 | 46.923 | 40.795 | 1.00 | 34.58 | B | O |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 5550 | N | HIS | B | 542 | −51.423 | 48.910 | 40.249 | 1.00 | 33.21 | B | N |
| ATOM | 5551 | CA | HIS | B | 542 | −52.771 | 48.591 | 40.736 | 1.00 | 35.58 | B | C |
| ATOM | 5552 | CB | HIS | B | 542 | −53.396 | 47.435 | 39.939 | 1.00 | 39.34 | B | C |
| ATOM | 5553 | CG | HIS | B | 542 | −54.803 | 47.117 | 40.343 | 1.00 | 42.34 | B | C |
| ATOM | 5554 | ND1 | HIS | B | 542 | −55.132 | 45.989 | 41.065 | 1.00 | 42.44 | B | N |
| ATOM | 5555 | CE1 | HIS | B | 542 | −56.436 | 45.973 | 41.279 | 1.00 | 43.94 | B | C |
| ATOM | 5556 | NE2 | HIS | B | 542 | −56.964 | 47.050 | 40.722 | 1.00 | 44.40 | B | N |
| ATOM | 5557 | CD2 | HIS | B | 542 | −55.963 | 47.784 | 40.133 | 1.00 | 42.97 | B | C |
| ATOM | 5558 | C | HIS | B | 542 | −52.887 | 48.322 | 42.243 | 1.00 | 34.45 | B | C |
| ATOM | 5559 | O | HIS | B | 542 | −53.626 | 49.028 | 42.943 | 1.00 | 35.13 | B | O |
| ATOM | 5560 | N | ASP | B | 543 | −52.194 | 47.289 | 42.725 | 1.00 | 30.98 | B | N |
| ATOM | 5561 | CA | ASP | B | 543 | −52.203 | 46.954 | 44.147 | 1.00 | 28.77 | B | C |
| ATOM | 5562 | CB | ASP | B | 543 | −52.993 | 45.675 | 44.428 | 1.00 | 30.73 | B | C |
| ATOM | 5563 | CG | ASP | B | 543 | −52.640 | 44.538 | 43.483 | 1.00 | 34.62 | B | C |
| ATOM | 5564 | OD1 | ASP | B | 543 | −53.579 | 44.032 | 42.828 | 1.00 | 35.81 | B | O |
| ATOM | 5565 | OD2 | ASP | B | 543 | −51.480 | 44.071 | 43.335 | 1.00 | 35.65 | B | O |
| ATOM | 5566 | C | ASP | B | 543 | −50.823 | 46.836 | 44.763 | 1.00 | 29.02 | B | C |
| ATOM | 5567 | O | ASP | B | 543 | −50.698 | 46.896 | 45.978 | 1.00 | 33.51 | B | O |
| ATOM | 5568 | N | LYS | B | 544 | −49.792 | 46.672 | 43.940 | 1.00 | 26.83 | B | N |
| ATOM | 5569 | CA | LYS | B | 544 | −48.438 | 46.489 | 44.449 | 1.00 | 25.39 | B | C |
| ATOM | 5570 | CB | LYS | B | 544 | −47.897 | 45.134 | 43.989 | 1.00 | 30.32 | B | C |
| ATOM | 5571 | CG | LYS | B | 544 | −47.894 | 44.934 | 42.472 | 1.00 | 36.12 | B | C |
| ATOM | 5572 | CD | LYS | B | 544 | −48.387 | 43.546 | 42.073 | 1.00 | 41.41 | B | C |
| ATOM | 5573 | CE | LYS | B | 544 | −47.218 | 42.597 | 41.759 | 1.00 | 43.22 | B | C |
| ATOM | 5574 | NZ | LYS | B | 544 | −47.668 | 41.282 | 41.192 | 1.00 | 43.58 | B | N |
| ATOM | 5575 | C | LYS | B | 544 | −47.504 | 47.621 | 44.016 | 1.00 | 24.84 | B | C |
| ATOM | 5576 | O | LYS | B | 544 | −47.849 | 48.419 | 43.159 | 1.00 | 25.15 | B | O |
| ATOM | 5577 | N | CYS | B | 545 | −46.316 | 47.683 | 44.605 | 1.00 | 27.68 | B | N |
| ATOM | 5578 | CA | CYS | B | 545 | −45.302 | 48.665 | 44.212 | 1.00 | 31.24 | B | C |
| ATOM | 5579 | CB | CYS | B | 545 | −44.950 | 49.560 | 45.406 | 1.00 | 27.50 | B | C |
| ATOM | 5580 | SG | CYS | B | 545 | −43.724 | 50.847 | 45.041 | 1.00 | 26.28 | B | S |
| ATOM | 5581 | C | CYS | B | 545 | −44.032 | 47.994 | 43.625 | 1.00 | 37.80 | B | C |
| ATOM | 5582 | O | CYS | B | 545 | −43.457 | 47.089 | 44.236 | 1.00 | 39.35 | B | O |
| ATOM | 5583 | N | VAL | B | 546 | −43.600 | 48.457 | 42.447 | 1.00 | 42.68 | B | N |
| ATOM | 5584 | CA | VAL | B | 546 | −42.500 | 47.838 | 41.694 | 1.00 | 43.63 | B | C |
| ATOM | 5585 | CB | VAL | B | 546 | −42.872 | 46.404 | 41.284 | 1.00 | 42.90 | B | C |
| ATOM | 5586 | CG1 | VAL | B | 546 | −44.193 | 46.366 | 40.499 | 1.00 | 39.68 | B | C |
| ATOM | 5587 | CG2 | VAL | B | 546 | −41.744 | 45.783 | 40.509 | 1.00 | 46.05 | B | C |
| ATOM | 5588 | C | VAL | B | 546 | −42.075 | 48.626 | 40.432 | 1.00 | 47.24 | B | C |
| ATOM | 5589 | O | VAL | B | 546 | −42.790 | 49.548 | 39.997 | 1.00 | 45.55 | B | O |
| ATOM | 5590 | N | ARG | B | 547 | −40.925 | 48.254 | 39.848 | 1.00 | 48.48 | B | N |
| ATOM | 5591 | CA | ARG | B | 547 | −40.461 | 48.861 | 38.588 | 1.00 | 52.40 | B | C |
| ATOM | 5592 | CB | ARG | B | 547 | −38.930 | 48.907 | 38.498 | 1.00 | 55.38 | B | C |
| ATOM | 5593 | CG | ARG | B | 547 | −38.274 | 47.742 | 37.824 | 1.00 | 58.48 | B | C |
| ATOM | 5594 | CD | ARG | B | 547 | −37.139 | 47.148 | 38.619 | 1.00 | 58.66 | B | C |
| ATOM | 5595 | NE | ARG | B | 547 | −37.308 | 45.704 | 38.751 | 1.00 | 59.52 | B | N |
| ATOM | 5596 | CZ | ARG | B | 547 | −36.682 | 44.802 | 38.005 | 1.00 | 59.56 | B | C |
| ATOM | 5597 | NH1 | ARG | B | 547 | −35.830 | 45.185 | 37.057 | 1.00 | 59.35 | B | N |
| ATOM | 5598 | NH2 | ARG | B | 547 | −36.904 | 43.510 | 38.211 | 1.00 | 59.12 | B | N |
| ATOM | 5599 | C | ARG | B | 547 | −41.114 | 48.248 | 37.341 | 1.00 | 50.72 | B | C |
| ATOM | 5600 | O | ARG | B | 547 | −41.588 | 47.115 | 37.389 | 1.00 | 48.52 | B | O |
| ATOM | 5601 | N | SER | B | 548 | −41.138 | 48.999 | 36.237 | 1.00 | 51.45 | B | N |
| ATOM | 5602 | CA | SER | B | 548 | −42.079 | 48.719 | 35.141 | 1.00 | 53.15 | B | C |
| ATOM | 5603 | CB | SER | B | 548 | −42.016 | 49.770 | 34.017 | 1.00 | 53.59 | B | C |
| ATOM | 5604 | OG | SER | B | 548 | −40.685 | 50.128 | 33.704 | 1.00 | 56.77 | B | O |
| ATOM | 5605 | C | SER | B | 548 | −42.002 | 47.297 | 34.589 | 1.00 | 53.91 | B | C |
| ATOM | 5606 | O | SER | B | 548 | −43.027 | 46.611 | 34.509 | 1.00 | 53.72 | B | O |
| ATOM | 5607 | N | GLU | B | 549 | −40.793 | 46.858 | 34.234 | 1.00 | 55.87 | B | N |
| ATOM | 5608 | CA | GLU | B | 549 | −40.573 | 45.504 | 33.700 | 1.00 | 57.44 | B | C |
| ATOM | 5609 | CB | GLU | B | 549 | −39.081 | 45.187 | 33.539 | 1.00 | 53.42 | B | C |
| ATOM | 5610 | CG | GLU | B | 549 | −38.205 | 45.646 | 34.684 | 1.00 | 50.56 | B | C |
| ATOM | 5611 | CD | GLU | B | 549 | −37.353 | 46.841 | 34.307 | 1.00 | 52.88 | B | C |
| ATOM | 5612 | OE1 | GLU | B | 549 | −37.894 | 47.851 | 33.796 | 1.00 | 53.25 | B | O |
| ATOM | 5613 | OE2 | GLU | B | 549 | −36.129 | 46.769 | 34.525 | 1.00 | 55.17 | B | O |
| ATOM | 5614 | C | GLU | B | 549 | −41.233 | 44.415 | 34.543 | 1.00 | 59.78 | B | C |
| ATOM | 5615 | O | GLU | B | 549 | −41.718 | 43.419 | 34.008 | 1.00 | 65.11 | B | O |
| ATOM | 5616 | N | GLU | B | 550 | −41.261 | 44.630 | 35.854 | 1.00 | 56.62 | B | N |
| ATOM | 5617 | CA | GLU | B | 550 | −41.779 | 43.666 | 36.814 | 1.00 | 52.20 | B | C |
| ATOM | 5618 | CB | GLU | B | 550 | −40.971 | 43.811 | 38.095 | 1.00 | 53.08 | B | C |
| ATOM | 5619 | CG | GLU | B | 550 | −40.746 | 42.572 | 38.938 | 1.00 | 55.13 | B | C |
| ATOM | 5620 | CD | GLU | B | 550 | −40.158 | 42.947 | 40.291 | 1.00 | 59.40 | B | C |
| ATOM | 5621 | OE1 | GLU | B | 550 | −40.795 | 42.651 | 41.326 | 1.00 | 61.85 | B | O |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom Number | | Amino Acid Residue | | | X | Y | Z | Occ. | Temp Factor | Atom Type | |
|---|---|---|---|---|---|---|---|---|---|---|---|
| ATOM | 5622 OE2 | GLU | B | 550 | −39.075 | 43.581 | 40.323 | 1.00 | 60.17 | B | O |
| ATOM | 5623 C | GLU | B | 550 | −43.269 | 43.887 | 37.096 | 1.00 | 49.10 | B | C |
| ATOM | 5624 O | GLU | B | 550 | −43.796 | 43.359 | 38.073 | 1.00 | 49.30 | B | O |
| ATOM | 5625 N | CYS | B | 551 | −43.946 | 44.653 | 36.241 | 1.00 | 47.59 | B | N |
| ATOM | 5626 CA | CYS | B | 551 | −45.365 | 44.959 | 36.447 | 1.00 | 49.58 | B | C |
| ATOM | 5627 CB | CYS | B | 551 | −45.576 | 46.471 | 36.598 | 1.00 | 47.57 | B | C |
| ATOM | 5628 SG | CYS | B | 551 | −47.260 | 47.072 | 36.293 | 1.00 | 46.78 | B | S |
| ATOM | 5629 C | CYS | B | 551 | −46.298 | 44.370 | 35.380 | 1.00 | 53.53 | B | C |
| ATOM | 5630 O | CYS | B | 551 | −46.203 | 44.705 | 34.190 | 1.00 | 51.95 | B | O |
| ATOM | 5631 N | LEU | B | 552 | −47.209 | 43.513 | 35.852 | 1.00 | 58.99 | B | N |
| ATOM | 5632 CA | LEU | B | 552 | −48.178 | 42.748 | 35.043 | 1.00 | 64.62 | B | C |
| ATOM | 5633 CB | LEU | B | 552 | −49.131 | 41.961 | 35.976 | 1.00 | 70.91 | B | C |
| ATOM | 5634 CG | LEU | B | 552 | −48.920 | 40.480 | 36.370 | 1.00 | 75.43 | B | C |
| ATOM | 5635 CD1 | LEU | B | 552 | −47.505 | 40.152 | 36.915 | 1.00 | 74.61 | B | C |
| ATOM | 5636 CD2 | LEU | B | 552 | −50.005 | 40.032 | 37.369 | 1.00 | 75.38 | B | C |
| ATOM | 5637 C | LEU | B | 552 | −48.995 | 43.553 | 34.009 | 1.00 | 62.25 | B | C |
| ATOM | 5638 O | LEU | B | 552 | −48.683 | 43.524 | 32.816 | 1.00 | 60.24 | B | O |
| ATOM | 5639 N | SER | B | 553 | −50.026 | 44.263 | 34.480 | 1.00 | 62.45 | B | N |
| ATOM | 5640 CA | SER | B | 553 | −51.006 | 44.956 | 33.622 | 1.00 | 62.32 | B | C |
| ATOM | 5641 CB | SER | B | 553 | −52.275 | 45.291 | 34.423 | 1.00 | 61.74 | B | C |
| ATOM | 5642 OG | SER | B | 553 | −51.974 | 46.123 | 35.528 | 1.00 | 60.96 | B | O |
| ATOM | 5643 C | SER | B | 553 | −50.506 | 46.210 | 32.879 | 1.00 | 61.08 | B | C |
| ATOM | 5644 O | SER | B | 553 | −49.335 | 46.583 | 32.956 | 1.00 | 61.29 | B | O |
| ATOM | 5645 N | GLY | B | 554 | −51.416 | 46.855 | 32.156 | 1.00 | 59.99 | B | N |
| ATOM | 5646 CA | GLY | B | 554 | −51.073 | 47.999 | 31.329 | 1.00 | 59.38 | B | C |
| ATOM | 5647 C | GLY | B | 554 | −50.898 | 49.309 | 32.076 | 1.00 | 56.97 | B | C |
| ATOM | 5648 O | GLY | B | 554 | −50.475 | 50.309 | 31.490 | 1.00 | 58.37 | B | O |
| ATOM | 5649 N | THR | B | 555 | −51.237 | 49.317 | 33.361 | 1.00 | 51.98 | B | N |
| ATOM | 5650 CA | THR | B | 555 | −51.065 | 50.511 | 34.175 | 1.00 | 46.15 | B | C |
| ATOM | 5651 CB | THR | B | 555 | −52.207 | 50.669 | 35.184 | 1.00 | 46.99 | B | C |
| ATOM | 5652 OG1 | THR | B | 555 | −51.844 | 51.675 | 36.136 | 1.00 | 48.11 | B | O |
| ATOM | 5653 CG2 | THR | B | 555 | −52.355 | 49.418 | 36.049 | 1.00 | 47.37 | B | C |
| ATOM | 5654 C | THR | B | 555 | −49.733 | 50.477 | 34.907 | 1.00 | 42.63 | B | C |
| ATOM | 5655 O | THR | B | 555 | −49.145 | 49.408 | 35.096 | 1.00 | 44.37 | B | O |
| ATOM | 5656 N | TRP | B | 556 | −49.280 | 51.658 | 35.318 | 1.00 | 34.63 | B | N |
| ATOM | 5657 CA | TRP | B | 556 | −48.032 | 51.846 | 36.056 | 1.00 | 26.61 | B | C |
| ATOM | 5658 CB | TRP | B | 556 | −46.874 | 51.122 | 35.395 | 1.00 | 13.10 | B | C |
| ATOM | 5659 CG | TRP | B | 556 | −45.634 | 51.046 | 36.208 | 1.00 | 10.94 | B | C |
| ATOM | 5660 CD1 | TRP | B | 556 | −45.329 | 50.103 | 37.159 | 1.00 | 15.04 | B | C |
| ATOM | 5661 NE1 | TRP | B | 556 | −44.068 | 50.317 | 37.676 | 1.00 | 10.32 | B | N |
| ATOM | 5662 CE2 | TRP | B | 556 | −43.517 | 51.408 | 37.056 | 1.00 | 8.38 | B | C |
| ATOM | 5663 CD2 | TRP | B | 556 | −44.477 | 51.896 | 36.120 | 1.00 | 10.63 | B | C |
| ATOM | 5664 CE3 | TRP | B | 556 | −44.147 | 53.026 | 35.354 | 1.00 | 9.06 | B | C |
| ATOM | 5665 CZ3 | TRP | B | 556 | −42.890 | 53.628 | 35.549 | 1.00 | 4.82 | B | C |
| ATOM | 5666 CH2 | TRP | B | 556 | −41.974 | 53.118 | 36.488 | 1.00 | 2.00 | B | C |
| ATOM | 5667 CZ2 | TRP | B | 556 | −42.268 | 52.017 | 37.248 | 1.00 | 2.48 | B | C |
| ATOM | 5668 C | TRP | B | 556 | −47.768 | 53.327 | 35.985 | 1.00 | 28.65 | B | C |
| ATOM | 5669 O | TRP | B | 556 | −47.689 | 53.885 | 34.887 | 1.00 | 32.89 | B | O |
| ATOM | 5670 N | THR | B | 557 | −47.657 | 53.969 | 37.144 | 1.00 | 25.23 | B | N |
| ATOM | 5671 CA | THR | B | 557 | −47.338 | 55.388 | 37.180 | 1.00 | 19.31 | B | C |
| ATOM | 5672 CB | THR | B | 557 | −48.562 | 56.227 | 37.597 | 1.00 | 14.69 | B | C |
| ATOM | 5673 OG1 | THR | B | 557 | −49.483 | 55.370 | 38.312 | 1.00 | 13.85 | B | O |
| ATOM | 5674 CG2 | THR | B | 557 | −49.329 | 56.705 | 36.332 | 1.00 | 14.28 | B | C |
| ATOM | 5675 C | THR | B | 557 | −46.192 | 55.674 | 38.127 | 1.00 | 19.82 | B | C |
| ATOM | 5676 O | THR | B | 557 | −45.692 | 54.781 | 38.849 | 1.00 | 13.19 | B | O |
| ATOM | 5677 N | GLN | B | 558 | −45.774 | 56.939 | 38.069 | 1.00 | 21.06 | B | N |
| ATOM | 5678 CA | GLN | B | 558 | −44.924 | 57.558 | 39.065 | 1.00 | 19.59 | B | C |
| ATOM | 5679 CB | GLN | B | 558 | −43.510 | 57.741 | 38.513 | 1.00 | 23.72 | B | C |
| ATOM | 5680 CG | GLN | B | 558 | −42.499 | 56.735 | 39.040 | 1.00 | 28.82 | B | C |
| ATOM | 5681 CD | GLN | B | 558 | −41.472 | 56.320 | 37.996 | 1.00 | 31.49 | B | C |
| ATOM | 5682 OE1 | GLN | B | 558 | −41.767 | 56.314 | 36.797 | 1.00 | 30.94 | B | O |
| ATOM | 5683 NE2 | GLN | B | 558 | −40.263 | 55.968 | 38.451 | 1.00 | 32.36 | B | N |
| ATOM | 5684 C | GLN | B | 558 | −45.580 | 58.904 | 39.360 | 1.00 | 16.29 | B | C |
| ATOM | 5685 O | GLN | B | 558 | −44.915 | 59.864 | 39.743 | 1.00 | 19.47 | B | O |
| ATOM | 5686 N | GLN | B | 559 | −46.897 | 58.972 | 39.188 | 1.00 | 10.08 | B | N |
| ATOM | 5687 CA | GLN | B | 559 | −47.560 | 60.262 | 39.273 | 1.00 | 9.23 | B | C |
| ATOM | 5688 CB | GLN | B | 559 | −47.447 | 60.967 | 37.925 | 1.00 | 16.38 | B | C |
| ATOM | 5689 CG | GLN | B | 559 | −46.092 | 61.588 | 37.637 | 1.00 | 20.31 | B | C |
| ATOM | 5690 CD | GLN | B | 559 | −45.789 | 61.587 | 36.157 | 1.00 | 23.58 | B | C |
| ATOM | 5691 OE1 | GLN | B | 559 | −46.430 | 62.328 | 35.359 | 1.00 | 18.19 | B | O |
| ATOM | 5692 NE2 | GLN | B | 559 | −44.823 | 60.740 | 35.765 | 1.00 | 23.75 | B | N |
| ATOM | 5693 C | GLN | B | 559 | −49.044 | 60.305 | 39.727 | 1.00 | 8.01 | B | C |

TABLE 2-continued

Atomic Coordinates of Hepatocyte Growth Factor Beta Chain (amino acids 1-228 of SEQ ID NO: 1) with Met Receptor (amino acids 16-277, 287-353, 358-376, and 390-540 of SEQ ID NO: 3)

| Atom | Atom Number | | Amino Acid Residue | | | X | Y | Z | Occ. | Temp Factor | Atom Type | |
|---|---|---|---|---|---|---|---|---|---|---|---|---|
| ATOM | 5694 | O | GLN | B | 559 | −49.539 | 61.359 | 40.270 | 1.00 | 9.84 | B | O |
| ATOM | 5695 | N | ILE | B | 560 | −49.764 | 59.197 | 39.491 | 1.00 | 6.13 | B | N |
| ATOM | 5696 | CA | ILE | B | 560 | −51.221 | 59.261 | 39.713 | 1.00 | 2.72 | B | C |
| ATOM | 5697 | CB | ILE | B | 560 | −51.936 | 59.155 | 38.222 | 1.00 | 3.13 | B | C |
| ATOM | 5698 | CG1 | ILE | B | 560 | −52.238 | 60.671 | 37.707 | 1.00 | 8.67 | B | C |
| ATOM | 5699 | CD1 | ILE | B | 560 | −50.799 | 61.181 | 37.073 | 1.00 | 12.88 | B | C |
| ATOM | 5700 | CG2 | ILE | B | 560 | −53.258 | 58.451 | 38.338 | 1.00 | 4.97 | B | C |
| ATOM | 5701 | C | ILE | B | 560 | −51.760 | 58.170 | 40.639 | 1.00 | 6.20 | B | C |
| ATOM | 5702 | O | ILE | B | 560 | −51.463 | 56.931 | 40.449 | 1.00 | 8.34 | B | O |
| ATOM | 5703 | N | CYS | B | 561 | −52.555 | 58.623 | 41.633 | 1.00 | 6.24 | B | N |
| ATOM | 5704 | CA | CYS | B | 561 | −53.104 | 57.519 | 42.583 | 1.00 | 7.85 | B | C |
| ATOM | 5705 | CB | CYS | B | 561 | −52.670 | 57.845 | 44.061 | 1.00 | 10.20 | B | C |
| ATOM | 5706 | SG | CYS | B | 561 | −50.816 | 57.253 | 44.183 | 1.00 | 12.15 | B | S |
| ATOM | 5707 | C | CYS | B | 561 | −54.639 | 57.583 | 42.382 | 1.00 | 9.24 | B | C |
| ATOM | 5708 | O | CYS | B | 561 | −55.224 | 58.700 | 42.507 | 1.00 | 14.16 | B | O |
| ATOM | 5709 | N | LEU | B | 562 | −55.296 | 56.422 | 42.058 | 1.00 | 9.86 | B | N |
| ATOM | 5710 | CA | LEU | B | 562 | −56.756 | 56.495 | 41.763 | 1.00 | 14.76 | B | C |
| ATOM | 5711 | CB | LEU | B | 562 | −57.163 | 55.407 | 40.696 | 1.00 | 14.45 | B | C |
| ATOM | 5712 | CG | LEU | B | 562 | −56.351 | 55.710 | 39.345 | 1.00 | 10.42 | B | C |
| ATOM | 5713 | CD1 | LEU | B | 562 | −56.207 | 54.397 | 38.579 | 1.00 | 13.65 | B | C |
| ATOM | 5714 | CD2 | LEU | B | 562 | −56.994 | 56.855 | 38.446 | 1.00 | 8.39 | B | C |
| ATOM | 5715 | C | LEU | B | 562 | −57.518 | 56.375 | 43.094 | 1.00 | 17.35 | B | C |
| ATOM | 5716 | O | LEU | B | 562 | −56.964 | 55.809 | 44.055 | 1.00 | 21.25 | B | O |
| ATOM | 5717 | N | PRO | B | 563 | −58.770 | 56.913 | 43.154 | 1.00 | 16.54 | B | N |
| ATOM | 5718 | CA | PRO | B | 563 | −59.567 | 56.864 | 44.396 | 1.00 | 18.87 | B | C |
| ATOM | 5719 | CB | PRO | B | 563 | −60.938 | 57.426 | 43.962 | 1.00 | 22.52 | B | C |
| ATOM | 5720 | CG | PRO | B | 563 | −60.666 | 58.234 | 42.720 | 1.00 | 21.69 | B | C |
| ATOM | 5721 | CD | PRO | B | 563 | −59.525 | 57.553 | 42.038 | 1.00 | 18.04 | B | C |
| ATOM | 5722 | C | PRO | B | 563 | −59.727 | 55.409 | 44.856 | 1.00 | 21.04 | B | C |
| ATOM | 5723 | O | PRO | B | 563 | −60.628 | 54.714 | 44.364 | 1.00 | 24.65 | B | O |
| ATOM | 5724 | N | ALA | B | 564 | −58.855 | 54.941 | 45.745 | 1.00 | 21.91 | B | N |
| ATOM | 5725 | CA | ALA | B | 564 | −59.038 | 53.611 | 46.336 | 1.00 | 21.94 | B | C |
| ATOM | 5726 | CB | ALA | B | 564 | −57.714 | 52.858 | 46.441 | 1.00 | 16.58 | B | C |
| ATOM | 5727 | C | ALA | B | 564 | −59.718 | 53.740 | 47.709 | 1.00 | 24.09 | B | C |
| ATOM | 5728 | O | ALA | B | 564 | −60.674 | 54.518 | 47.881 | 1.00 | 20.73 | B | O |
| END | | | | | | | | | | | | |

TABLE 3

| BURIED RESIDUES IN INTERFACE ON HGF (numbers refer to the amount of buried surface in A2) | |
|---|---|
| TYR A 513 | 24.00 |
| LYS A 516 | 34.00 |
| ARG A 533 | 36.00 |
| GLN A 534 | 48.00 |
| PHE A 536 | 6.00 |
| PRO A 537 | 67.00 |
| SER A 538 | 1.00 |
| ARG A 539 | 10.00 |
| ASP A 578 | 29.00 |
| TYR A 619 | 30.00 |
| ARG A 647 | 39.00 |
| LYS A 649 | 71.00 |
| GLU A 656 | 24.00 |
| PRO A 668 | 2.00 |
| CYS A 669 | 6.00 |
| GLU A 670 | 97.00 |
| TYR A 673 | 20.00 |
| VAL A 692 | 11.00 |
| PRO A 693 | 49.00 |
| GLY A 694 | 36.00 |
| ARG A 695 | 92.00 |
| GLY A 696 | 28.00 |
| CYS A 697 | 24.00 |
| ILE A 699 | 10.00 |
| ARG A 702 | 38.00 |
| ILE A 705 | 8.00 |

TABLE 3-continued

| VAL A 707 | 3.00 |
|---|---|
| BURIED RESIDUES IN INTERFACE ON MET (numbers refer to the amount of buried surface in A2) | |
| THR B 124 | 17.00 |
| TYR B 125 | 77.00 |
| TYR B 126 | 21.00 |
| ASP B 127 | 61.00 |
| ASP B 128 | 11.00 |
| HIS B 148 | 50.00 |
| GLU B 167 | 38.00 |
| ASP B 190 | 69.00 |
| ARG B 191 | 144.00 |
| PHE B 192 | 59.00 |
| ARG B 218 | 15.00 |
| LYS B 220 | 9.00 |
| GLU B 221 | 138.00 |
| THR B 222 | 72.00 |
| LYS B 223 | 18.00 |
| ASP B 224 | 6.00 |
| MET B 227 | 5.00 |
| LEU B 229 | 43.00 |
| THR B 230 | 38.00 |
| ILE B 284 | 1.00 |
| SER B 286 | 23.00 |
| ASP B 414 | 11.00 |

TABLE 4

An Amino Acid Sequence of HGF-β (SEQ ID NO: 1)

```
      495        501        511        521        531
      VVNGIP TRTNIGWMVS LRYRNKHICG GSLIKESWVL TARQCFPSRD 540
541 LKDYEAWLGI HDVHGRGDEK CKQVLNVSQL VYGPEGSDLV LMKLARPAVL 590
591 DDFVSTIDLP NYGSTIPEKT SCSVYGWGYT GLINYDGLLR VAHLYIMGNE 640
641 KCSQHHRGKV TLNESEICAG AEKIGSGPCE GDYGGPLVCE QHKMRMVLGV 690
691 IVPGRGCAIP NRPGIFVRVA YYAKWIHKII LTYKVPQS
```

TABLE 5

An Amino Acid Sequence of the Met Receptor (SEQ ID NO: 2)

```
       1         11         21         31         41
   1 MKAPAVLAPG ILVLLFTLVQ RSNGECKEAL AKSEMNVNMK YQLPNFTAET   50
  51 PIQNVILHEH HIFLGATNYI YVLNEEDLQK VAEYKTGPVL EHPDCFPCQD  100
 101 CSSKANLSGG VWKDNINMAL VVDTYYDDQL ISCGSVNRGT CQRHVFPHNH  150
 151 TADIQSEVHC IFSPQIEEPS QCPDCVVSAL GAKVLSSVKD RFINFFVGNT  200
 201 INSSYFPDHP LHSISVRRLK ETKDGFMFLT DQSYIDVLPE FRDSYPIKYV  250
 251 HAFESNNFIY FLTVQRETLD AQTFHTRIIR FCSINSGLHS YMEMPLECIL  300
 301 TEKRKKRSTK KEVFNILQAA YVSKPGAQLA RQIGASLNDD ILFGVFAQSK  350
 351 PDSAEPMDRS AMCAFPIKYV NDFFNKIVNK NNVRCLQHFY GPNHEHCFNR  400
 401 TLLRNSSGCE ARRDEYRTEF TTALQRVDLF MGQFSEVLLT SISTFIKGDL  450
 451 TIANLGTSEG RFMQVVVSRS GPSTPHVNFL LDSHPVSPEV IVEHTLNQNG  500
 501 YTLVITGKKI TKIPLNGLGC RHFQSCSQCL SAFPPVQCGW CHDKCVRSEE  550
 551 CLSGTWTQQI CLPAIYKVFP NSAPLEGGTR LTICGWDFGF RRNNKFDLKK  600
 601 TRVLLGNESC TLTLSESTMN TLKCTVGPAM NKHFNMSIII SNGHGTTQYS  650
 651 TFSYVDPVIT SISPKYGPMA GGTLLTLTGN YLNSGNSRHI SIGGKTCTLK  700
 701 SVSNSILECY TPAQTISTEF AVKLKIDLAN RETSIFSYRE DPIVYEIHPT  750
 751 KSFISGGSTI TGVGKNLNSV SVPRMVINVH EAGRNFTVAC QHRSNSEIIC  800
 801 CTTPSLQQLN LQLPLKTKAF FMLDGILSKY FDLIYVHNPV FKPFEKPVMI  850
 851 SMGNENVLEI KGNDIDPEAV KGEVLKVGNK SCENIHLHSE AVLCTVPNDL  900
 901 LKLNSELNIE WKQAISSTVL GKVIVQPDQN FTGLIAGVVS ISTALLLLLG  950
 951 FFLWLKKRKQ IKDLGSELVR YDARVHTPHL DRLVSARSVS PTTEMVSNES 1000
1001 VDYRATFPED QFPNSSQNGS CRQVQYPLTD MSPILTSGDS DISSPLLQNT 1050
1051 VHIDLSALNP ELVQAVQHVV IGPSSLIVHF NEVIGRGHFG CVYHGTLLDN 1100
1101 DGKKIHCAVK SLNRITDIGE VSQFLTEGII MKDFSHPNVL SLLGICLRSE 1150
1151 GSPLVVLPYM KHGDLRNFIR NETRNPTVKD LIGFGLQVAK GMKYLASKKF 1200
1201 VHRDLAARNC MLDEKFTVKV ADFGLARDMY DKEYYSVHNK TGAKLPVKWM 1250
1251 ALESLQTQKF TTKSDVWSFG VVLWELMTRG APPYPDVNTF DITVYLLQGR 1300
1301 RLLQPEYCPD PLYEVMLKCW HPKAEMRPSF SELVSRISAI FSTFIGEHYV 1350
1351 HVNATYVNVK CVAPYPSLLS SEDNADDEVD TRPASFWETS
```

TABLE 6

An Amino Acid Sequence of Human Sema Domain 4d and the Psi Domain of Met Receptor. (SEQ ID NO: 3)

```
         25         31         41         51
      ECKEAL     AKSEMNVNMK YQLPNFTAET PIQNVILHEH HIFLGATNYI  70
 71 YVLNEEDLQK VAEYKTGPVL EHPDCFPCQD CSSKANLSGG VWKDNINMAL 120
121 VVDTYYDDQL ISCGSVNRGT CQRHVFPHNH TADIQSEVHC IFSPQIEEPS 170
171 QCPDCVVSAL GAKVLSSVKD RFINFFVGNT INSSYFPDHP LHSISVRRLK 220
221 ETKDGFMFLT DQSYIDVLPE FRDSYPIKYV HAFESNNFIY FLTVQRETLD 270
271 AQTFHTRIIR FCSINSGLHS YMEMPLECIL TELVPRGSTK KEVFNILQAA 320
321 YVSKPGAQLA RQIGASLNDD ILFGVFAQSK PDSAEPMDRS AMCAFPIKYV 370
371 NDFFNKIVNK NNVRCLQHFY GPNHEHCFNR TLLRNSSGCE ARRDEYRTEF 420
421 TTALQRVDLF MGQFSEVLLT SISTFIKGDL TIANLGTSEG RFMQVVVSRS 470
471 GPSTPHVNFL LDSHPVSPEV IVEHTLNQNG YTLVITGKKI TKIPLHGLGC 520
521 RHFQSCSQCL SAPPFVQCGW CHDKCVRSEE CLSGTWTQQI CLPAIYK
```

TABLE 8

An Amino Acid Sequence of Wild-Type HGF β (SEQ ID NO: 14)

VVNGIPTRTNIGWMVSLRYRMCHICGGSLIKESWVLTARQCFPSRDLKDY
EAWLGIHDVHGRGDEKCKQVLNVSQLVYGPEGSDLVLMKLARPAVLDDFV
STIDLPNYGCTIPEKTSCSVYGWGYTGLINYDGLLRVAHLYIMGNEKCSQ
HHRGKVTLNESEICAGAEKIGSGPCEGDYGGPLVCEQHKMRMVLGVIVPG
RGCAIPNRPGIFVRVAYYAKWIHKIILTYKVPQS

TABLE 7

Atomic Coordinates of Hepatocyte Growth Factor Beta Chain with Met Receptor Secondary Structural Features

| Structural Feature | Feature Number | Amino Acid Types | | | | | | Amino Acid Numbers | | | | | | | | |
|---|---|---|---|---|---|---|---|---|---|---|---|---|---|---|---|---|
| HELIX | 1 | 1 | ARG | A | 533 | CYS | A | 535 | 5 | | | | | | | |
| HELIX | 2 | 2 | LEU | A | 541 | ASP | A | 543 | 5 | | | | | | | |
| HELIX | 3 | 3 | ASN | A | 639 | GLN | A | 644 | 1 | | | | | | | |
| HELIX | 4 | 4 | ALA | A | 710 | ILE | A | 720 | 5 | | | | | | | |
| HELIX | 5 | 5 | ASP | B | 231 | SER | B | 233 | 5 | | | | | | | |
| HELIX | 6 | 6 | ALA | B | 327 | ILE | B | 333 | 1 | | | | | | | |
| HELIX | 7 | 7 | ILE | B | 367 | ASN | B | 375 | 1 | | | | | | | |
| HELIX | 8 | 8 | GLY | B | 517 | CYS | B | 520 | 5 | | | | | | | |
| HELIX | 9 | 9 | CYS | B | 526 | SER | B | 531 | 1 | | | | | | | |
| HELIX | 10 | 10 | PRO | B | 534 | VAL | B | 536 | 5 | | | | | | | |
| HELIX | 11 | 11 | SER | B | 548 | GLU | B | 550 | 5 | | | | | | | |
| SHEET | 1 | A7 | GLN | A | 563 | LEU | A | 565 | 0 | | | | | | | |
| SHEET | 2 | A7 | TYR | A | 544 | LEU | A | 548 | -1 | N | LEU | A | 548 | O | GLN | A | 563 |
| SHEET | 3 | A7 | MET | A | 508 | TYR | A | 513 | -1 | N | ARG | A | 512 | O | GLU | A | 545 |
| SHEET | 4 | A7 | LYS | A | 516 | LYS | A | 525 | -1 | N | GLY | A | 521 | O | VAL | A | 509 |
| SHEET | 5 | A7 | TRP | A | 528 | ALA | A | 532 | -1 | N | LEU | A | 530 | O | SER | A | 522 |
| SHEET | 6 | A7 | LEU | A | 579 | LEU | A | 584 | -1 | N | MET | A | 582 | O | VAL | A | 529 |
| SHEET | 7 | A7V | AL | AL | 567 | TYR | A | 572 | -1 | N | VAL | A | 571 | O | LEU | A | 581 |
| SHEET | 1 | B6 | ARG | A | 685 | VAL | A | 690 | 0 | | | | | | | |
| SHEET | 2 | B6 | PRO | A | 676 | GLU | A | 680 | -1 | N | CYS | A | 679 | O | MET | A | 686 |
| SHEET | 3 | B6 | SER | A | 611 | GLY | A | 616 | -1 | N | SER | A | 613 | O | VAL | A | 678 |
| SHEET | 4 | B6 | ARG | A | 630 | MET | A | 637 | -1 | N | LEU | A | 634 | O | CYS | A | 612 |
| SHEET | 5 | B6 | GLU | A | 656 | GLY | A | 660 | -1 | N | GLY | A | 660 | O | TYR | A | 635 |
| SHEET | 6 | B6 | GLY | A | 704 | VAL | A | 707 | -1 | N | PHE | A | 706 | O | ILE | A | 657 |
| SHEET | 1 | C4 | ASN | B | 45 | THR | B | 47 | 0 | | | | | | | |
| SHEET | 2 | C4 | LYS | B | 509 | PRO | B | 514 | -1 | N | ILE | B | 510 | O | PHE | B | 46 |
| SHEET | 3 | C4 | ASN | B | 499 | THR | B | 506 | -1 | N | THR | B | 506 | O | LYS | B | 509 |

TABLE 7-continued

Atomic Coordinates of Hepatocyte Growth Factor Beta Chain with Met Receptor Secondary Structural Features

| Structural Feature | Feature Number | Amino Acid Types | | | | | | | | Amino Acid Numbers | | | | | |
|---|---|---|---|---|---|---|---|---|---|---|---|---|---|---|---|
| SHEET | 4 | C 4 | VAL | B | 490 | THR | B | 495 | −1 | N | THR | B | 495 | O ASN | B | 499 |
| SHEET | 1 | D 4 | ILE | B | 52 | HIS | B | 58 | 0 | | | | | | | |
| SHEET | 2 | D 4 | HIS | B | 61 | ALA | B | 66 | −1 | N | GLY | B | 65 | O GLN | B | 53 |
| SHEET | 3 | D 4 | TYR | B | 69 | ASN | B | 74 | −1 | N | LEU | B | 73 | O ILE | B | 62 |
| SHEET | 4 | D 4 | LYS | B | 80 | LYS | B | 85 | −1 | N | TYR | B | 84 | O ILE | B | 70 |
| SHEET | 1 | E 2 | VAL | B | 89 | GLU | B | 91 | 0 | | | | | | | |
| SHEET | 2 | E 2 | VAL | B | 111 | LYS | B | 113 | −1 | N | LYS | B | 113 | O VAL | B | 89 |
| SHEET | 1 | F 4 | VAL | B | 158 | CYS | B | 160 | 0 | | | | | | | |
| SHEET | 2 | F 4 | CYS | B | 141 | VAL | B | 145 | −1 | N | ARG | B | 143 | O HIS | B | 159 |
| SHEET | 3 | F 4 | GLN | B | 129 | GLY | B | 134 | −1 | N | SER | B | 132 | O GLN | B | 142 |
| SHEET | 4 | F 4 | ASN | B | 117 | ASP | B | 123 | −1 | N | ASP | B | 123 | O GLN | B | 129 |
| SHEET | 1 | G 4 | ALA | B | 182 | LYS | B | 189 | 0 | | | | | | | |
| SHEET | 2 | G 4 | PHE | B | 192 | ASN | B | 199 | −1 | N | GLY | B | 198 | O LYS | B | 183 |
| SHEET | 3 | G 4 | VAL | B | 216 | LEU | B | 219 | −1 | N | ARG | B | 217 | O PHE | B | 195 |
| SHEET | 4 | G 4 | PHE | B | 226 | PHE | B | 228 | −1 | N | MET | B | 227 | O ARG | B | 218 |
| SHEET | 1 | H 5 | LEU | B | 424 | VAL | B | 427 | 0 | | | | | | | |
| SHEET | 2 | H 5 | MET | B | 292 | ILE | B | 299 | 1 | N | GLU | B | 297 | O LEU | B | 424 |
| SHEET | 3 | H 5 | THR | B | 276 | CYS | B | 282 | −1 | N | ARG | B | 280 | O MET | B | 292 |
| SHEET | 4 | H 5 | PHE | B | 258 | VAL | B | 264 | −1 | N | THR | B | 263 | O ARG | B | 277 |
| SHEET | 5 | H 5 | LYS | B | 248 | SER | B | 255 | −1 | N | SER | B | 255 | O PHE | B | 258 |
| SHEET | 1 | I 3 | ALA | B | 319 | LYS | B | 324 | 0 | | | | | | | |
| SHEET | 2 | I 3 | ASP | B | 340 | ALA | B | 347 | −1 | N | VAL | B | 345 | O ALA | B | 319 |
| SHEET | 3 | I 3 | SER | B | 360 | PRO | B | 366 | −1 | N | PHE | B | 365 | O LEU | B | 342 |
| SHEET | 1 | J 4 | VAL | B | 477 | LEU | B | 480 | 0 | | | | | | | |
| SHEET | 2 | J 4 | ARG | B | 461 | VAL | B | 466 | −1 | N | GLN | B | 464 | O VAL | B | 477 |
| SHEET | 3 | J 4 | LEU | B | 450 | THR | B | 457 | −1 | N | LEU | B | 455 | O MET | B | 463 |
| SHEET | 4 | J 4 | LEU | B | 439 | LYS | B | 447 | −1 | N | LYS | B | 447 | O LEU | B | 450 |
| SHEET | 1 | K 2 | GLY | B | 539 | CYS | B | 541 | 0 | | | | | | | |
| SHEET | 2 | K 2 | LYS | B | 544 | VAL | B | 546 | −1 | N | VAL | B | 546 | O GLY | B | 539 |
| SSBOND | 1 | | CYS | A | 519 | CYS | A | 535 | | | | | | | | |
| SSBOND | 2 | | CYS | A | 612 | CYS | A | 679 | | | | | | | | |
| SSBOND | 3 | | CYS | A | 642 | CYS | A | 658 | | | | | | | | |
| SSBOND | 4 | | CYS | A | 669 | CYS | A | 697 | | | | | | | | |
| SSBOND | 5 | | CYS | B | 95 | CYS | B | 101 | | | | | | | | |
| SSBOND | 6 | | CYS | B | 98 | CYS | B | 160 | | | | | | | | |
| SSBOND | 7 | | CYS | B | 133 | CYS | B | 141 | | | | | | | | |
| SSBOND | 8 | | CYS | B | 172 | CYS | B | 175 | | | | | | | | |
| SSBOND | 9 | | CYS | B | 298 | CYS | B | 363 | | | | | | | | |
| SSBOND | 10 | | CYS | B | 385 | CYS | B | 397 | | | | | | | | |
| SSBOND | 11 | | CYS | B | 520 | CYS | B | 538 | | | | | | | | |
| SSBOND | 12 | | CYS | B | 526 | CYS | B | 561 | | | | | | | | |
| SSBOND | 13 | | CYS | B | 529 | CYS | B | 545 | | | | | | | | |
| SSBOND | 14 | | CYS | B | 541 | CYS | B | 551 | | | | | | | | |

LIST OF REFERENCES

Antipenko A, Himanen J P, van Leyen K, Nardi-Dei V, Lesniak J, Barton W A, Rajashankar K R, Lu M, Hoemme C, Puschel A W, Nikolov D B (2003) *Neuron* 39: 589-598.

Bork P, Doerks T, Springer T A, Snel B (1999) *Trends Biochem Sci* 24: 261-263.

Birchmeier C, Birchmeier W, Gherardi E, Vande Woude G F (2003) *Nat Rev Mol Cell Biol* 4: 915-25.

Chan A M, Rubin J S, Bottaro D P, Hirschfield D W, Chedid M, and Aaronson S A (1991) *Science* 254: 1382-1385.

Cioce V, Csaky K G, Chan A M, Bottaro D P, Taylor W G, Jensen R, Aaronson S A, Rubin J S (1996) *J Biol Chem* 271: 13110-13115.

Collaborative Computational Project, N. (1994) Acta Cytstallogr Sect D 50: 760-763.

Comoglio, P M, Boccaccio C (2001). *Semin Cancer Biol* 11: 153-165.

Comoglio P M, Tamagnone L, Boccaccio C (1999) *Experimental Cell Research*, 253: 88-99.

Danilkovitch, A., Miller, M. and Leonard, E. J. (1999) *J Biol. Chem.*, 274, 29937-29943.

Date L, Matsumoto K, Shimura H, Tanaka M, Nakamura T, (1997). *FEBS Letters* 520: 1-8.

DeLano W L (2002) The PyMOL Molecular Graphics System on World Wide Web http://www.pymol.org.

de Vos A M, Ultsch M, Kossiakoff A A (1992) *Science* 255: 306-12.

Donate L E, Gherardi E, Srinivasan N, Sowdhamini R, Aparicio S, Blundell T L (1994) *Protein Sci* 3: 2378-2394.

Freer S T, Kraut J, Robertus J D, Wright H T, Xuong N H (1970). *Biochemistry* 9:1997-2009.

Gherardi E, Youles M E, Miguel R N, Blundell T L, Iamele L, Gough J, Bandyopadhyay A, Hartmann G, Butler P J (2003). *Proc. Natl. Acad. Sci. USA*. 100: 12039-12044.

Hartmann G, Naldini L, Weidner K M, Sachs M, Vigna E, Comoglio P M, Birchmeier W. (1992). *Proc Natl Acad Sci USA*. 89: 11574-11578

Hedstrom L (2002) Serine protease mechanism and specificity. *Chem Rev* 102, 4501-4524.

Huber R, Bode W (1978) *Acc Chem Res* 11: 114-122.

Huff J L, Jelinek M A, Borgman C A, Lansing T J, and Parsons J T (1993). *Proc Natl Acad. Sci. USA* 90: 6140-6144.

Jankowski K, Kucia M, Wysoczynski M, Reca R, Zhao D, Trzyna E, Trent J, Peiper S, Zembala M, Ratajczak J, Houghton P, Janowska-Wieczorek A, Ratajczak M Z (2003) *Cancer Res.* 63: 7926-7935.

Jones T A, Zou J Y, Cowan S W, Kjeldgaard M (1991) *Acta Crystallog. Sect. A* 47: 110-119.

Kataoka H, Miyata S, Uchinokura S, Itoh H (2003) *Cancer Metastasis Rev* 22: 223-236.

Komada M, Hatsuzawa K, Shibamoto S, Ito F, Nakayama K, Kitamura N (1993) *FEBS Lett* 328: 25-29.

Laskowski R A, MacArthur M W, Moss D S, Thornton J M (1993) PROCHECK—a program to check the stereochemical quality of protein structures. *J Appl Crystallogr* 26: 283-291.

Lokker N A, Mark M R, Luis E A, Bennett G L, Robbins K A, Baker J B, Godowski P J (1992) *EMBO J.* 11, 2503-2510.

Love C A, Harlos K, Mavaddat N, Davis S J, Stuart D I, Jones E Y, Esnouf R M (2003) *Nat Struct Biol* 10: 843-848.

Ma P C, Maulik G, Christensen J, and Salgia R (2003) *Cancer Metastasis Rev* 22: 309-325.

Miller M, Leonard E J (1998). *FEBS Lett* 429: 1-3.

Montesano R, Matsumoto K, Nakamura T, Orci L (1991) *Cell* 67:901-908.

Nakamura T, Nishizawa T, Hagiya M, Seki T, Shimonishi M, Sugimura A, Tashiro K, Shimizu S (1989) Nature 342: 440-443.

Navaza J (1994) AMoRe: an Automated Package for Molecular Replacement. Acta Crystallogr. Sect. A 50: 157-163.

Nardone H C, Ziober A F, LiVolsi V A, Mandel S J, Baloch Z W, Weber R S, Mick R, Ziober B L (2003) *Cancer* 98: 1386-1393.

Otwinowski Z, Minor W (1997) Processing of X-Ray Diffraction Data Collected in Oscillation Mode. Methods Enzymol. 276: 307-326.

Perona J J, Craik, C S (1995). *Protein Sci.* 4: 337-360.

Prat M, Crepaldi T, Pennacchietti S, Bussolino F, Comoglio P M (1998). *J Cell Sci* 111: 237-247.

Ronsin C, Muscatelli F, Mattei M G, Breathnach R (1993). *Oncogene* 8: 1195-1202.

Rosen E M, Nigam S K, Goldberg I D (1994) *J Cell Biol* 127: 1783-1787.

Sonnenberg E, Meyer D, Weidner K M, Birchmeier C (1993) *J Cell Biol* 123:223-235.

Takagi S, Murakami Y, Kasuya Y, Tanaka H, Kawakami A, Mizutani A, Ohta K, Fujisawa H (1995) *Neuron* 14: 1189-1199.

Trusolino L, Comoglio P M (2002) *Nature Rev Cancer* 2: 289-300.

Ultsch M, Lokker N A, Godowski P J, de Vos A M (1998). *Structure* 15: 1383-1393.

Winberg M L, Noordermeer J N, Tamagnone L, Comoglio P M, Spriggs M K, Tessier-Lavigne M, Goodman C S (1998). *Cell* 95: 903-916.

Xiong J P, Stehle T, Zhang, R, Joachimiak A, Frech F, Goodman, S L, Arnaout M A (2002) *Science* 296: 151-155.

Zhang Y W, Vande Woude G F (2003) *J Cell Biochem* 88: 408-417.

---

What is claimed is:

1. A crystal of hepatocyte growth factor beta chain (HGF β-chain) complexed with tyrosine kinase Met receptor (Met Receptor) comprising an HGF β-chain comprising an amino acid sequence comprising SEQ ID NO:1 complexed with an extracellular fragment of a Met Receptor, wherein the extracellular fragment of a Met Receptor comprises an amino acid sequence comprising SEQ ID NO:3, and wherein the crystal has a space group symmetry of $P2_12_12$, and comprises a unit cell having the dimensions of a, b, and c, where a is about 137.1 Å, b is about 186.4 Å, and c is about 66.7 Å.

2. The crystal of claim 1, having the structure coordinates of Table 2.

3. The crystal of claim 1, wherein the crystal diffracts X-rays for the determination of atomic coordinates to a resolution of 5 Å or better.

* * * * *